US012746060B2

(12) United States Patent
Azamian et al.

(10) Patent No.: US 12,746,060 B2
(45) Date of Patent: Sep. 29, 2026

(54) MODULATION OF TARGETED NERVE FIBERS

(71) Applicant: Medtronic Ireland Manufacturing Unlimited Company, Dublin (IE)

(72) Inventors: Bobak Robert Azamian, Newport Coast, CA (US); Jonathan Allen Coe, Menlo Park, CA (US); Scott Bradley Vafai, Boston, MA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 189 days.

(21) Appl. No.: 18/609,346

(22) Filed: Mar. 19, 2024

(65) Prior Publication Data

US 2024/0261016 A1 Aug. 8, 2024

Related U.S. Application Data

(63) Continuation of application No. 16/706,468, filed on Dec. 6, 2019, now Pat. No. 12,011,212, which is a (Continued)

(51) Int. Cl.
*A61B 18/14* (2006.01)
*A61N 1/05* (2006.01)
(Continued)

(52) U.S. Cl.
CPC ........ *A61B 18/1492* (2013.01); *A61N 1/0551* (2013.01); *A61N 1/3605* (2013.01); (Continued)

(58) Field of Classification Search
CPC ...... A61B 18/1492; A61B 2018/00005; A61B 2018/00011; A61B 2018/00023; (Continued)

(56) References Cited

U.S. PATENT DOCUMENTS

| | | | |
|---|---|---|---|
| 4,650,466 | A | 3/1987 | Luther |
| 4,983,169 | A | 1/1991 | Furukawa |

(Continued)

FOREIGN PATENT DOCUMENTS

| | | | |
|---|---|---|---|
| EP | 2495012 | A1 | 9/2012 |
| EP | 2561905 | A1 | 2/2013 |

(Continued)

OTHER PUBLICATIONS

Office Action from U.S. Appl. No. 18/609,523 dated Jan. 28, 2026, 13 pp.

(Continued)

*Primary Examiner* — Thomas A Giuliani
(74) *Attorney, Agent, or Firm* — Shumaker & Sieffert, P.A.

(57) ABSTRACT

According to various embodiments, systems, devices and methods for modulating targeted nerve fibers (e.g., hepatic neuromodulation) are provided. The systems may be configured to access tortuous anatomy of or adjacent hepatic vasculature. The systems may be configured to target nerves within a wall of (e.g., within adventitia surrounding a lumen of) an artery or other blood vessel, such as the common hepatic artery.

22 Claims, 117 Drawing Sheets

Related U.S. Application Data continuation of application No. 14/896,063, filed as application No. PCT/US2014/040949 on Jun. 4, 2014, now abandoned.

(60) Provisional application No. 61/906,830, filed on Nov. 20, 2013, provisional application No. 61/831,507, filed on Jun. 5, 2013.

(51) Int. Cl.

| | |
|---|---|
| ***A61N 1/36*** | (2006.01) |
| *A61B 18/00* | (2006.01) |
| *A61B 90/00* | (2016.01) |
| *A61M 25/01* | (2006.01) |
| *A61M 25/10* | (2013.01) |

(52) U.S. Cl.

CPC ............... *A61B 2018/00029* (2013.01); *A61B 2018/00214* (2013.01); *A61B 2018/00279* (2013.01); *A61B 2018/00404* (2013.01); *A61B 2018/00434* (2013.01); *A61B 2018/00529* (2013.01); *A61B 2018/00577* (2013.01); *A61B 2018/1467* (2013.01); *A61B 2090/064* (2016.02); *A61M 25/0138* (2013.01); *A61M 25/0141* (2013.01); *A61M 25/0147* (2013.01); *A61M 2025/1052* (2013.01)

(58) Field of Classification Search

CPC .......... A61B 2018/00029; A61B 2018/00214; A61B 2018/00279; A61B 2018/00404; A61B 2018/00434; A61B 2018/00529; A61B 2018/00577; A61B 2018/0022; A61B 2018/00994; A61B 17/320068; A61B 2017/320069; A61B 2017/320073; A61M 2025/1052

USPC .......... 606/41, 49; 607/96, 98, 99, 104, 105, 607/113, 115, 116

See application file for complete search history.

(56) References Cited

U.S. PATENT DOCUMENTS

| | | | |
|---|---|---|---|
| 5,000,185 | A | 3/1991 | Yock |
| 5,114,423 | A | 5/1992 | Kasprzyk et al. |
| 5,368,591 | A | 11/1994 | Lennox et al. |
| 5,391,197 | A | 2/1995 | Burdette et al. |
| 5,423,811 | A | 6/1995 | Imran et al. |
| 5,558,672 | A | 9/1996 | Edwards et al. |
| 5,620,479 | A | 4/1997 | Diederich |
| 5,688,266 | A | 11/1997 | Edwards et al. |
| 5,800,482 | A | 9/1998 | Pomeranz et al. |
| 6,066,134 | A | 5/2000 | Eggers et al. |
| 6,117,101 | A | 9/2000 | Diederich et al. |
| 6,216,704 | B1 | 4/2001 | Ingle et al. |
| 6,254,598 | B1 | 7/2001 | Edwards et al. |
| 6,292,695 | B1 | 9/2001 | Webster, Jr. et al. |
| 6,296,619 | B1 | 10/2001 | Brisken et al. |
| 6,381,499 | B1 | 4/2002 | Taylor et al. |
| 6,383,151 | B1 | 5/2002 | Diederich et al. |
| 6,514,249 | B1 | 2/2003 | Maguire et al. |
| 6,547,788 | B1 | 4/2003 | Maguire et al. |
| 6,564,096 | B2 | 5/2003 | Mest |
| 6,584,360 | B2 | 6/2003 | Francischelli et al. |
| 6,585,638 | B1 | 7/2003 | Yamamoto |
| 6,605,084 | B2 | 8/2003 | Acker et al. |
| 6,623,736 | B2 | 9/2003 | Tobinick |
| 6,626,855 | B1 | 9/2003 | Weng et al. |
| 6,635,054 | B2 | 10/2003 | Fjield et al. |
| 6,648,883 | B2 | 11/2003 | Francischelli et al. |
| 6,652,515 | B1 | 11/2003 | Maguire et al. |
| 6,669,655 | B1 | 12/2003 | Acker et al. |
| 6,676,675 | B2 | 1/2004 | Mallapragada et al. |
| 6,690,971 | B2 | 2/2004 | Schauerte et al. |
| 6,692,490 | B1 | 2/2004 | Edwards |
| 6,699,242 | B2 | 3/2004 | Heggeness |
| 6,719,694 | B2 | 4/2004 | Weng et al. |
| 6,719,755 | B2 | 4/2004 | Sliwa, Jr. et al. |
| 6,758,847 | B2 | 7/2004 | Maguire |
| 6,763,722 | B2 | 7/2004 | Fjield et al. |
| 6,878,273 | B2 | 4/2005 | Kawaguchi |
| 6,937,896 | B1 | 8/2005 | Kroll |
| 6,954,977 | B2 | 10/2005 | Maguire et al. |
| 7,052,695 | B2 | 5/2006 | Kalish |
| 7,054,689 | B1 | 5/2006 | Whitehurst et al. |
| 7,058,447 | B2 | 6/2006 | Hill et al. |
| 7,063,666 | B2 | 6/2006 | Weng et al. |
| 7,083,614 | B2 | 8/2006 | Fjield et al. |
| 7,149,574 | B2 | 12/2006 | Yun et al. |
| 7,155,278 | B2 | 12/2006 | King et al. |
| 7,155,284 | B1 | 12/2006 | Whitehurst et al. |
| 7,162,303 | B2 | 1/2007 | Levin et al. |
| 7,184,828 | B2 | 2/2007 | Hill et al. |
| 7,277,757 | B2 | 10/2007 | Casavant et al. |
| 7,309,310 | B2 | 12/2007 | Milbocker |
| 7,322,973 | B2 | 1/2008 | Nahon |
| 7,326,201 | B2 | 2/2008 | Fjield et al. |
| 7,340,306 | B2 | 3/2008 | Barrett et al. |
| 7,373,204 | B2 | 5/2008 | Gelfand et al. |
| 7,470,241 | B2 | 12/2008 | Weng et al. |
| 7,477,944 | B1 | 1/2009 | Whitehurst et al. |
| 7,494,661 | B2 | 2/2009 | Sanders |
| 7,540,846 | B2 | 6/2009 | Harhen et al. |
| 7,599,736 | B2 | 10/2009 | DiLorenzo |
| 7,620,454 | B2 | 11/2009 | Dinsmoor et al. |
| 7,630,760 | B2 | 12/2009 | Libbus |
| 7,653,438 | B2 | 1/2010 | Deem et al. |
| 7,653,440 | B1 | 1/2010 | Bornzin et al. |
| 7,660,631 | B2 | 2/2010 | Whitehurst et al. |
| 7,689,276 | B2 | 3/2010 | Dobak |
| 7,706,875 | B2 | 4/2010 | Buras et al. |
| 7,717,948 | B2 | 5/2010 | Demarais et al. |
| 7,738,952 | B2 | 6/2010 | Yun et al. |
| 7,765,007 | B2 | 7/2010 | Martino et al. |
| 7,769,442 | B2 | 8/2010 | Shafer |
| 7,797,050 | B2 | 9/2010 | Libbus et al. |
| 7,837,676 | B2 | 11/2010 | Sinelnikov et al. |
| 7,856,273 | B2 | 12/2010 | Maschino et al. |
| 7,862,563 | B1 | 1/2011 | Cosman et al. |
| 7,865,237 | B2 | 1/2011 | Machado et al. |
| 7,904,175 | B2 | 3/2011 | Scott et al. |
| 7,925,351 | B2 | 4/2011 | Khawaled et al. |
| 7,991,474 | B2 | 8/2011 | Aldrich et al. |
| 8,010,199 | B2 | 8/2011 | Sunagawa et al. |
| 8,021,384 | B2 | 9/2011 | Weiss et al. |
| RE42,961 | E | 11/2011 | Rahme |
| 8,052,672 | B2 | 11/2011 | Laufer et al. |
| 8,060,209 | B2 | 11/2011 | Jaax et al. |
| 8,095,218 | B2 | 1/2012 | Gross et al. |
| 8,116,883 | B2 | 2/2012 | Williams et al. |
| 8,131,362 | B2 | 3/2012 | Moffitt et al. |
| 8,145,316 | B2 | 3/2012 | Deem et al. |
| 8,155,744 | B2 | 4/2012 | Rezai |
| 8,207,138 | B2 | 6/2012 | Thakker et al. |
| 8,216,228 | B2 | 7/2012 | Mateos et al. |
| 8,219,189 | B2 | 7/2012 | Knoblich |
| 8,229,564 | B2 | 7/2012 | Rezai |
| 8,285,374 | B2 | 10/2012 | Hamdan |
| 8,295,912 | B2 | 10/2012 | Gertner |
| 8,295,926 | B2 | 10/2012 | Dobak |
| 8,321,030 | B2 | 11/2012 | Maniak et al. |
| 8,326,428 | B2 | 12/2012 | Wenzel et al. |
| 8,340,772 | B2 | 12/2012 | Vase et al. |
| 8,348,884 | B2 | 1/2013 | Hildebrand et al. |
| 8,352,029 | B2 | 1/2013 | Ternes et al. |
| 8,369,943 | B2 | 2/2013 | Shuros et al. |
| 8,374,674 | B2 | 2/2013 | Gertner |
| 8,386,053 | B2 | 2/2013 | Kornet |
| 8,391,970 | B2 | 3/2013 | Tracey et al. |
| 8,401,641 | B2 | 3/2013 | Peters et al. |
| 8,410,140 | B2 | 4/2013 | Brummett |
| 8,412,350 | B2 | 4/2013 | Bly |

(56) References Cited

U.S. PATENT DOCUMENTS

| | | | |
|---|---|---|---|
| 8,417,354 | B2 | 4/2013 | Zhang et al. |
| 8,447,394 | B2 | 5/2013 | Libbus et al. |
| 8,463,376 | B2 | 6/2013 | Curtis |
| 8,469,904 | B2 | 6/2013 | Gertner |
| 8,492,442 | B2 | 7/2013 | Beppu et al. |
| 8,504,161 | B1 | 8/2013 | Kornet et al. |
| 8,512,262 | B2 | 8/2013 | Gertner |
| 8,512,335 | B2 | 8/2013 | Cheng et al. |
| 8,517,962 | B2 | 8/2013 | Gertner et al. |
| 8,521,291 | B1 | 8/2013 | Cholette et al. |
| 8,556,834 | B2 | 10/2013 | Gertner |
| 8,560,072 | B2 | 10/2013 | Caparso et al. |
| 8,609,082 | B2 | 12/2013 | Ben-David et al. |
| 8,612,022 | B1 | 12/2013 | Morero et al. |
| 8,622,937 | B2 | 1/2014 | Weng et al. |
| 8,634,930 | B2 | 1/2014 | Dalal et al. |
| 8,672,930 | B2 | 3/2014 | Wittenberger |
| 8,676,322 | B2 | 3/2014 | Whitehurst et al. |
| 8,700,161 | B2 | 4/2014 | Harel et al. |
| 8,702,619 | B2 | 4/2014 | Wang |
| 8,715,209 | B2 | 5/2014 | Gertner |
| 8,718,764 | B2 | 5/2014 | Stahmann |
| 8,731,677 | B2 | 5/2014 | Pastore et al. |
| 8,755,907 | B2 | 6/2014 | Kieval et al. |
| 8,792,986 | B2 | 7/2014 | Cigaina |
| 8,818,501 | B2 | 8/2014 | Machado et al. |
| 8,838,231 | B2 | 9/2014 | Dobak |
| 8,838,239 | B2 | 9/2014 | Libbus et al. |
| 8,845,629 | B2 | 9/2014 | Demarais et al. |
| 8,855,778 | B2 | 10/2014 | Rezai |
| 8,868,188 | B2 | 10/2014 | Hershey |
| 8,870,773 | B2 | 10/2014 | Narouze |
| 8,874,216 | B2 | 10/2014 | Kim et al. |
| 8,880,185 | B2 | 11/2014 | Hastings et al. |
| 8,888,699 | B2 | 11/2014 | Buschman et al. |
| 8,897,882 | B2 | 11/2014 | Nakatomi et al. |
| 8,903,501 | B2 | 12/2014 | Perryman |
| 8,909,316 | B2 | 12/2014 | Ng |
| 8,929,990 | B2 | 1/2015 | Moffitt et al. |
| 8,934,968 | B2 | 1/2015 | Whitehurst et al. |
| 8,951,296 | B2 | 2/2015 | Melder et al. |
| 8,974,445 | B2 | 3/2015 | Warnking et al. |
| 8,974,451 | B2 | 3/2015 | Smith |
| 8,983,601 | B2 | 3/2015 | Fukamachi et al. |
| 8,986,211 | B2 | 3/2015 | Gertner et al. |
| 8,986,231 | B2 | 3/2015 | Gertner et al. |
| 8,989,862 | B2 | 3/2015 | Rezai et al. |
| 8,992,447 | B2 | 3/2015 | Gertner et al. |
| 9,002,446 | B2 | 4/2015 | Wenzel et al. |
| 9,005,143 | B2 | 4/2015 | Gertner |
| 9,023,023 | B2 | 5/2015 | Mckay et al. |
| 9,028,391 | B2 | 5/2015 | Gnanashanmugam et al. |
| 9,028,470 | B2 | 5/2015 | Marrouche et al. |
| 9,033,966 | B2 | 5/2015 | Mckay |
| 9,037,244 | B2 | 5/2015 | Sharma |
| 9,050,106 | B2 | 6/2015 | Hill et al. |
| 9,060,761 | B2 | 6/2015 | Hastings et al. |
| 9,067,070 | B2 | 6/2015 | Connor |
| 9,084,609 | B2 | 7/2015 | Smith |
| 9,089,350 | B2 | 7/2015 | Willard |
| 9,095,719 | B2 | 8/2015 | Farazi |
| 9,119,951 | B2 | 9/2015 | Gertner et al. |
| 9,119,952 | B2 | 9/2015 | Gertner |
| 9,125,642 | B2 | 9/2015 | Gertner |
| 9,126,048 | B2 | 9/2015 | Ransbury et al. |
| 9,131,975 | B2 | 9/2015 | Mckay |
| 9,144,678 | B2 | 9/2015 | Marsh et al. |
| 9,155,589 | B2 | 10/2015 | Jenson |
| 9,162,073 | B2 | 10/2015 | Rezai et al. |
| 9,173,696 | B2 | 11/2015 | Schauer et al. |
| 9,174,065 | B2 | 11/2015 | Gertner |
| 9,186,209 | B2 | 11/2015 | Weber et al. |
| 9,186,210 | B2 | 11/2015 | Jenson |
| 9,192,790 | B2 | 11/2015 | Hastings et al. |
| 9,199,097 | B2 | 12/2015 | Gertner |
| 9,216,289 | B2 | 12/2015 | Libbus et al. |
| 9,220,558 | B2 | 12/2015 | Willard |
| 9,220,561 | B2 | 12/2015 | Crow et al. |
| 9,220,899 | B2 | 12/2015 | Cattaneo et al. |
| 9,241,754 | B2 | 1/2016 | McKay |
| 9,259,568 | B2 | 2/2016 | Zhao et al. |
| 9,265,563 | B2 | 2/2016 | Racz et al. |
| 9,283,035 | B2 | 3/2016 | Lanphere |
| 9,314,300 | B2 | 4/2016 | Nabutovsky et al. |
| 9,327,123 | B2 | 5/2016 | Yamasaki et al. |
| 9,345,538 | B2 | 5/2016 | Deem et al. |
| 9,345,880 | B1 | 5/2016 | DiLorenzo |
| 9,352,171 | B2 | 5/2016 | Gertner |
| 9,358,020 | B2 | 6/2016 | Smith |
| 9,358,076 | B2 | 6/2016 | Moll et al. |
| 9,358,401 | B2 | 6/2016 | Gertner et al. |
| 9,364,284 | B2 | 6/2016 | Groff et al. |
| 9,364,668 | B2 | 6/2016 | Marsh et al. |
| 9,364,671 | B2 | 6/2016 | Pless et al. |
| 9,381,063 | B2 | 7/2016 | Gang et al. |
| 9,386,927 | B2 | 7/2016 | Kaiser |
| 9,386,990 | B2 | 7/2016 | Muir et al. |
| 9,403,007 | B2 | 8/2016 | Mokelke et al. |
| 9,427,579 | B2 | 8/2016 | Fain et al. |
| 9,439,598 | B2 | 9/2016 | Shimada et al. |
| 9,446,240 | B2 | 9/2016 | Masson et al. |
| 9,463,062 | B2 | 10/2016 | Smith et al. |
| 9,463,065 | B2 | 10/2016 | Sugimoto et al. |
| 9,511,228 | B2 | 12/2016 | Amurthur et al. |
| 9,526,572 | B2 | 12/2016 | Kunis |
| 9,526,893 | B2 | 12/2016 | Averina et al. |
| 9,554,850 | B2 | 1/2017 | Lee et al. |
| 9,555,020 | B2 | 1/2017 | Pasricha et al. |
| 9,561,370 | B2 | 2/2017 | Rezai et al. |
| 9,572,982 | B2 | 2/2017 | Burnes et al. |
| 9,579,507 | B2 | 2/2017 | Cakmak |
| 9,579,518 | B2 | 2/2017 | Gertner |
| 9,586,046 | B2 | 3/2017 | Knudson et al. |
| 9,616,226 | B2 | 4/2017 | Lockwood et al. |
| 9,616,228 | B2 | 4/2017 | Shuros et al. |
| 9,616,231 | B2 | 4/2017 | Tweden et al. |
| 9,629,675 | B2 | 4/2017 | Kleshinski et al. |
| 9,649,156 | B2 | 5/2017 | Jenson et al. |
| 9,656,080 | B2 | 5/2017 | Chiu et al. |
| 9,662,490 | B2 | 5/2017 | Tracey et al. |
| 9,668,811 | B2 * | 6/2017 | Sogard .................. A61N 5/062 |
| 9,693,821 | B2 | 7/2017 | Hanson et al. |
| 9,700,372 | B2 | 7/2017 | Schaer |
| 9,707,000 | B2 | 7/2017 | Hoke et al. |
| 9,707,034 | B2 | 7/2017 | Schaer |
| 9,707,391 | B2 | 7/2017 | Ahmed |
| 9,750,568 | B2 | 9/2017 | Sobotka |
| 9,789,275 | B2 | 10/2017 | Iyer et al. |
| 9,801,557 | B2 | 10/2017 | Ghaffari et al. |
| 9,808,616 | B2 | 11/2017 | Cederna et al. |
| 9,821,003 | B2 | 11/2017 | Yun |
| 9,833,283 | B2 | 12/2017 | Hanson et al. |
| 9,833,623 | B2 | 12/2017 | Gnanashanmugam et al. |
| 9,844,405 | B2 | 12/2017 | Weber et al. |
| 9,844,668 | B2 | 12/2017 | Ahmed |
| 9,861,504 | B2 | 1/2018 | Abunassar et al. |
| 9,861,547 | B2 | 1/2018 | Crunick et al. |
| 9,872,985 | B2 | 1/2018 | Butera et al. |
| 9,883,909 | B2 | 2/2018 | Brennan |
| 9,895,543 | B2 | 2/2018 | Lian et al. |
| 9,918,822 | B2 | 3/2018 | Abunassar et al. |
| 9,919,144 | B2 | 3/2018 | Meyer |
| 9,925,001 | B2 | 3/2018 | Willard et al. |
| 9,943,354 | B2 | 4/2018 | Yamit et al. |
| 9,943,365 | B2 | 4/2018 | Haverkost et al. |
| 9,943,666 | B2 | 4/2018 | Warnking |
| 9,950,099 | B2 | 4/2018 | Romero-Ortega et al. |
| 9,950,164 | B2 | 4/2018 | Lipani |
| 9,955,892 | B2 | 5/2018 | Arora et al. |
| 9,956,033 | B2 | 5/2018 | Squire et al. |
| 9,956,034 | B2 | 5/2018 | Toth et al. |
| 9,974,477 | B2 | 5/2018 | Cholette et al. |
| 9,981,108 | B2 | 5/2018 | Warnking |
| 9,999,532 | B2 | 6/2018 | Mische |

(56) References Cited

U.S. PATENT DOCUMENTS 10,004,557 B2 6/2018 Gross
10,010,364 B2 7/2018 Harrington
10,022,182 B2 7/2018 Willard et al.
10,022,516 B2 7/2018 Papay
10,039,901 B2 8/2018 Warnking
10,052,495 B2 8/2018 Ben-Haim
10,058,372 B1 8/2018 Shadduck
10,065,037 B2 9/2018 Nelson et al.
10,076,384 B2 9/2018 Kasprzyk et al.
10,085,799 B2 10/2018 Smith
10,092,352 B2 10/2018 Rudie
10,092,756 B2 10/2018 Bonnet et al.
10,123,896 B2 11/2018 Farrugia et al.
10,124,173 B2 11/2018 Bonnet et al.
10,195,467 B2 2/2019 Tran et al.
10,201,705 B2 2/2019 Bharmi et al.
10,201,706 B2 2/2019 Schwab et al.
10,207,110 B1 2/2019 Gelfand et al.
10,230,041 B2 3/2019 Taylor et al.
10,231,778 B2 3/2019 Highsmith et al.
10,232,180 B2 3/2019 Kramer et al.
10,238,875 B2 3/2019 Masiach
10,265,122 B2 4/2019 Wang et al.
10,271,898 B2 4/2019 Cao et al.
10,272,269 B2 4/2019 Garrison et al.
10,292,610 B2 5/2019 Srivastava
10,307,324 B2 6/2019 Osorio
10,321,946 B2 6/2019 Horn et al.
10,328,258 B2 6/2019 Gittard et al.
10,335,280 B2 7/2019 Keogh et al.
10,350,005 B2 7/2019 Mathur et al.
10,350,440 B2 7/2019 Taylor et al.
10,363,362 B2 7/2019 Osorio
10,368,944 B2 8/2019 Schaer
10,376,310 B2 8/2019 Fain et al.
10,376,516 B2 8/2019 Gelfand et al.
10,376,694 B2 8/2019 Sharma
10,383,685 B2 8/2019 Gross et al.
10,390,881 B2 8/2019 Rudie
10,426,956 B2 10/2019 Williamson et al.
10,449,002 B2 10/2019 Wybo
10,456,573 B1 10/2019 Feinstein
10,463,423 B2 11/2019 Sutton et al.
10,463,858 B2 11/2019 Perryman et al.
10,470,837 B2 11/2019 Lin et al.
10,471,257 B2 11/2019 Ahmad et al.
10,478,249 B2 11/2019 Gross et al.
10,478,633 B2 11/2019 Schwarz et al.
10,492,713 B2 12/2019 Haber et al.
10,499,937 B2 12/2019 Warnking
10,512,498 B2 12/2019 Saadat
10,512,504 B2 12/2019 Chang et al.
10,517,672 B2 12/2019 Long
10,518,112 B2 12/2019 Gilad
10,531,913 B2 1/2020 Haverkost
10,543,037 B2 1/2020 Shah
10,543,039 B2 1/2020 Lindquist et al.
10,561,461 B2 2/2020 Panescu et al.
10,561,846 B2 2/2020 Tracey et al.
10,575,893 B2 3/2020 Mayse
10,583,286 B2 3/2020 Swanson et al.
10,583,295 B2 3/2020 Gupte et al.
10,646,710 B2 5/2020 Feinstein
10,646,713 B2 5/2020 Hettrick et al.
10,660,703 B2 5/2020 Rizq et al.
10,674,963 B2 6/2020 Toth
10,675,085 B2 6/2020 Clark et al.
10,695,124 B2 6/2020 Groff et al.
10,702,533 B2 7/2020 Yun et al.
10,709,490 B2 7/2020 Turovskiy
10,716,749 B2 7/2020 Yun et al.
10,722,714 B2 7/2020 Thornton et al.
10,722,716 B2 7/2020 Waldhauser et al.
10,729,365 B2 8/2020 Beasley et al.
10,743,933 B2 8/2020 Smith et al.
10,751,536 B1 8/2020 Heit et al.
10,751,539 B2 8/2020 Zitzewitz et al.
10,765,482 B2 9/2020 Hastings
10,772,681 B2 9/2020 Gertner
10,772,759 B2 9/2020 Khanna
10,786,295 B2 9/2020 Buelna
10,792,098 B2 10/2020 Ku et al.
10,799,289 B2 10/2020 Alas et al.
10,828,090 B2 11/2020 Haverkost et al.
10,828,460 B2 11/2020 Chang
10,828,491 B2 11/2020 Schepis et al.
10,835,305 B2 11/2020 Sutermeister et al.
10,842,494 B2 11/2020 Agarwal et al.
10,842,556 B1 11/2020 Tandri et al.
10,849,685 B2 12/2020 Denison et al.
10,849,879 B2 12/2020 Seward
10,857,352 B2 12/2020 Ransbury et al.
10,869,997 B2 12/2020 Mayse
10,874,454 B2 12/2020 Chen
10,888,377 B2 1/2021 Ben-Oren et al.
10,905,495 B2 2/2021 Toth et al.
10,933,259 B2 3/2021 Sverdlik et al.
10,952,790 B2 3/2021 Haverkost et al.
10,959,669 B2 3/2021 Neidert et al.
10,960,209 B2 3/2021 Sridhar et al.
10,974,041 B2 4/2021 Chew et al.
10,987,163 B2 4/2021 Pike
11,007,001 B1 5/2021 Carignan et al.
11,013,459 B2 5/2021 Toth et al.
11,013,549 B2 5/2021 Barman et al.
11,013,938 B2 5/2021 Konofagou et al.
11,040,197 B2 6/2021 Ludwig et al.
11,052,253 B2 7/2021 Cakmak
11,058,484 B2 7/2021 Asirvatham et al.
11,065,046 B2 7/2021 Edidin
11,083,877 B2 8/2021 Seward
11,103,692 B2 8/2021 Cakmak
11,116,561 B2 9/2021 Melder
11,129,673 B2 9/2021 Barry et al.
11,129,674 B2 9/2021 Naga et al.
11,134,998 B2 10/2021 Cross et al.
11,154,351 B2 10/2021 Rothman et al.
11,154,356 B2 10/2021 Gertner
11,154,547 B2 10/2021 Bright et al.
11,154,712 B2 10/2021 Sullivan et al.
11,160,975 B2 11/2021 Mercanzini et al.
11,179,195 B2 11/2021 Sobotka
11,179,196 B2 11/2021 Cao et al.
11,185,361 B2 11/2021 Toth et al.
11,185,662 B2 11/2021 Warnking
11,185,699 B2 11/2021 Masson et al.
11,202,671 B2 12/2021 Hanson et al.
11,207,070 B2 12/2021 Berman et al.
11,213,340 B2 1/2022 Su et al.
11,213,345 B2 1/2022 Willard
11,213,674 B2 1/2022 Barman et al.
11,235,154 B2 2/2022 Phillips et al.
11,246,654 B2 2/2022 Weber et al.
11,247,057 B1 2/2022 Gliner
11,304,633 B2 4/2022 Koya et al.
11,305,115 B2 4/2022 Caldwell et al.
11,318,310 B1 5/2022 Bradley
11,318,331 B2 5/2022 Shabtay et al.
11,324,408 B2 5/2022 Wang
11,324,673 B2 5/2022 Velis et al.
11,337,748 B2 5/2022 Wang et al.
11,338,120 B2 5/2022 Yun et al.
11,344,364 B2 5/2022 Herth et al.
11,344,731 B2 5/2022 Toth et al.
11,350,992 B2 6/2022 Pilcher et al.
11,357,447 B2 6/2022 Sverdlik et al.
11,382,515 B2 7/2022 Buelna et al.
11,382,689 B2 7/2022 Wang
11,389,534 B2 7/2022 Yun et al.
11,413,090 B2 8/2022 Iranitalab et al.
11,419,681 B2 8/2022 Coates et al.
11,433,235 B2 9/2022 Narayan et al.
11,433,237 B2 9/2022 Lovett
11,439,809 B2 9/2022 Whipple et al.

(56) References Cited

U.S. PATENT DOCUMENTS 11,439,819 B2 9/2022 Imran
11,446,359 B2 9/2022 Bright
11,446,498 B2 9/2022 Schepis et al.
11,446,502 B2 9/2022 Donega et al.
11,457,819 B2 10/2022 Trudel
11,464,971 B2 10/2022 Schepis et al.
11,464,976 B2 10/2022 Hunsberger et al.
11,471,208 B2 10/2022 Waldstreicher et al.
11,471,210 B2 10/2022 Pellegrino et al.
11,478,297 B2 10/2022 Viswanadha et al.
11,478,582 B2 10/2022 Toth et al.
11,490,844 B2 11/2022 Imran et al.
11,497,775 B2 11/2022 Lefer et al.
11,497,915 B2 11/2022 Tehrani
11,504,185 B2 11/2022 Iranitalab et al.
11,510,731 B2 11/2022 Puryear et al.
11,515,029 B2 11/2022 Sullivan et al.
11,517,499 B2 12/2022 Spector
11,517,754 B2 12/2022 Sridhar et al.
11,524,159 B2 12/2022 Caban et al.
11,534,611 B2 12/2022 Baldoni et al.
11,534,631 B2 12/2022 Gilad
11,547,480 B2 1/2023 Weiss
11,559,687 B2 1/2023 Goedeke et al.
11,564,616 B2 1/2023 Toth et al.
11,564,743 B1 1/2023 Ben Oren et al.
11,565,113 B2 1/2023 Curtis
11,589,919 B2 2/2023 Long
11,596,468 B2 3/2023 Pellegrino et al.
11,596,469 B2 3/2023 Nair
11,607,176 B2 3/2023 Brockway et al.
11,607,275 B2 3/2023 Brar et al.
11,622,805 B2 4/2023 Salazar et al.
11,623,093 B2 4/2023 Cuchiara et al.
11,633,601 B2 4/2023 Vervoordeldonk et al.
11,638,745 B2 5/2023 Jackson et al.
11,660,474 B2 5/2023 Puleo et al.
11,672,456 B2 6/2023 Dubhashi
11,672,595 B1 6/2023 Melton et al.
11,672,597 B2 6/2023 Tajima et al.
11,673,006 B2 6/2023 Sobotka et al.
11,691,015 B2 7/2023 Minassian et al.
11,701,172 B2 7/2023 Asirvatham et al.
11,712,283 B2 8/2023 Mayse et al.
11,712,296 B2 8/2023 Panescu et al.
11,723,719 B2 8/2023 Sachs et al.
11,724,102 B2 8/2023 Donega et al.
11,724,108 B2 8/2023 Chew et al.
11,730,506 B2 8/2023 Sverdlik et al.
11,738,196 B2 8/2023 Vervoordeldonk et al.
11,744,640 B2 9/2023 Amaoua et al.
11,759,608 B2 9/2023 Fischell et al.
11,771,497 B2 10/2023 Townley et al.
11,779,392 B2 10/2023 Hezi-Yamit et al.
11,794,001 B2 10/2023 Imran
11,801,092 B2 10/2023 Levin et al.
11,806,070 B2 11/2023 Wright et al.
11,806,072 B2 11/2023 Hakimimehr
11,806,073 B2 11/2023 Bapna et al.
11,826,569 B2 11/2023 Mishra et al.
11,832,965 B2 12/2023 Wang
11,839,766 B2 12/2023 Scheltienne et al.
11,844,558 B2 12/2023 Lazarus et al.
11,844,565 B2 12/2023 Asirvatham et al.
11,844,569 B1 12/2023 Panescu et al.
11,857,249 B2 1/2024 Ku et al.
11,857,778 B2 1/2024 Hamner et al.
11,857,783 B2 1/2024 Lo et al.
11,864,826 B2 1/2024 Levin et al.
11,864,904 B2 1/2024 Dubhashi et al.
11,865,343 B2 1/2024 Gallagher et al.
11,883,087 B2 1/2024 Tunev et al.
11,883,091 B2 1/2024 Townley
11,883,103 B2 1/2024 Toth et al.
11,890,393 B2 2/2024 Bright et al.
11,896,818 B2 2/2024 Townley
11,911,634 B2 2/2024 Puleo et al.
11,918,362 B2 3/2024 Fagin et al.
11,918,595 B2 3/2024 Bright et al.
11,923,063 B2 3/2024 Georgiou et al.
11,937,868 B2 3/2024 Mayse et al.
2002/0002371 A1 1/2002 Acker et al.
2002/0026228 A1 2/2002 Schauerte
2002/0042610 A1 4/2002 Sliwa et al.
2002/0068885 A1 6/2002 Harhen et al.
2002/0122815 A1 9/2002 Peroutka
2002/0165535 A1 11/2002 Lesh et al.
2002/0193681 A1 12/2002 Vitek et al.
2003/0004439 A1 1/2003 Pant et al.
2003/0013968 A1 1/2003 Fjield et al.
2003/0028111 A1 2/2003 Vaczy et al.
2003/0060813 A1 3/2003 Loeb et al.
2003/0069620 A1 4/2003 Li
2003/0144708 A1 7/2003 Starkebaum
2003/0152637 A1 8/2003 Chasin et al.
2003/0181963 A1 9/2003 Pellegrino et al.
2003/0216721 A1 11/2003 Diederich et al.
2003/0216792 A1 11/2003 Levin et al.
2003/0225331 A1 12/2003 Diederich et al.
2004/0082859 A1 4/2004 Schaer
2004/0106880 A1 6/2004 Weng et al.
2004/0176757 A1 9/2004 Sinelnikov et al.
2004/0181178 A1 9/2004 Aldrich et al.
2004/0242999 A1 12/2004 Vitek et al.
2005/0004563 A1 1/2005 Racz et al.
2005/0027328 A1 2/2005 Greenstein
2005/0038340 A1 2/2005 Vaezy et al.
2005/0049293 A1 3/2005 Lautt
2005/0075701 A1 4/2005 Shafer
2005/0113295 A1 5/2005 Dolle
2005/0215990 A1 9/2005 Govari
2005/0240126 A1 10/2005 Foley et al.
2005/0240170 A1 10/2005 Zhang et al.
2005/0261672 A1 11/2005 Deem et al.
2006/0009815 A1 1/2006 Boveja et al.
2006/0034847 A1 2/2006 Yun et al.
2006/0089678 A1 4/2006 Shalev
2006/0121085 A1 6/2006 Warren et al.
2006/0161217 A1 7/2006 Jaax et al.
2006/0217698 A1 9/2006 Starkebaum et al.
2006/0235300 A1 10/2006 Weng et al.
2007/0016274 A1 1/2007 Boveja et al.
2007/0021786 A1 1/2007 Parnis et al.
2007/0027484 A1 2/2007 Guzman et al.
2007/0027497 A1 2/2007 Parnis
2007/0060971 A1 3/2007 Glasberg et al.
2007/0100380 A1 5/2007 Fukui
2007/0106337 A1 5/2007 Errico et al.
2007/0156179 A1 7/2007 S.E.
2007/0197970 A1 8/2007 Shen-Gunther
2007/0208388 A1 9/2007 Jahns et al.
2007/0225781 A1 9/2007 Saadat et al.
2007/0299476 A1 12/2007 Park et al.
2008/0004596 A1 1/2008 Yun et al.
2008/0009917 A1 1/2008 Rossing et al.
2008/0015642 A1 1/2008 Johnson et al.
2008/0027346 A1 1/2008 Litt et al.
2008/0044392 A1 2/2008 Kues et al.
2008/0077165 A1 3/2008 Murphy
2008/0086180 A1 4/2008 Ben-Ezra et al.
2008/0147137 A1 6/2008 Cohen et al.
2008/0161865 A1 7/2008 Hagen
2008/0208305 A1 8/2008 Rezai et al.
2008/0249419 A1 10/2008 Sekins et al.
2008/0275424 A1 11/2008 Doshi et al.
2009/0060873 A1 3/2009 Sporn et al.
2009/0062697 A1 3/2009 Zhang et al.
2009/0118777 A1 5/2009 Iki et al.
2009/0182303 A1 7/2009 Walak et al.
2009/0240306 A1 9/2009 Kapoor
2009/0253974 A1 10/2009 Rahme
2009/0254142 A1 10/2009 Edwards et al.
2009/0275997 A1 11/2009 Faltys et al.
2009/0312690 A1 12/2009 Kim

(56) References Cited

U.S. PATENT DOCUMENTS

2010/0076519 A1 3/2010 Kornet et al.
2010/0114195 A1 5/2010 Burnes et al.
2010/0114244 A1 5/2010 Manda et al.
2010/0211059 A1 8/2010 Deem et al.
2010/0228310 A1 9/2010 Shuros et al.
2010/0255123 A1 10/2010 Lohajoti et al.
2010/0268288 A1 10/2010 Hunter et al.
2010/0303617 A1 12/2010 Chen
2011/0066085 A1 3/2011 Weng et al.
2011/0092880 A1 4/2011 Gertner
2011/0118600 A1 5/2011 Gertner
2011/0118632 A1 5/2011 Sinelnikov et al.
2011/0152855 A1 6/2011 Mayse et al.
2011/0172527 A1 7/2011 Gertner
2011/0172528 A1 7/2011 Gertner
2011/0200171 A1 8/2011 Beetel et al.
2011/0257523 A1* 10/2011 Hastings ............ A61B 18/0206
601/2
2011/0257562 A1 10/2011 Schaer
2011/0263921 A1 10/2011 Vrba et al.
2011/0264086 A1 10/2011 Ingle
2011/0264116 A1 10/2011 Kocur et al.
2011/0270238 A1 11/2011 Rizq et al.
2011/0275891 A1 11/2011 Shemi
2011/0319765 A1 12/2011 Gertner et al.
2012/0016226 A1 1/2012 Gertner
2012/0022409 A1 1/2012 Gertner et al.
2012/0029496 A1 2/2012 Smith
2012/0029505 A1 2/2012 Jenson
2012/0029512 A1 2/2012 Willard et al.
2012/0059286 A1 3/2012 Hastings et al.
2012/0065506 A1 3/2012 Smith
2012/0065554 A1 3/2012 Pikus
2012/0123261 A1 5/2012 Jenson et al.
2012/0130269 A1 5/2012 Rea
2012/0172680 A1 7/2012 Gelfand et al.
2012/0209118 A1 8/2012 Warnking
2012/0238918 A1 9/2012 Gertner
2012/0245494 A1 9/2012 Gertner
2012/0265198 A1 10/2012 Crow et al.
2012/0277781 A1 11/2012 Gertner
2012/0283756 A1 11/2012 Moonly et al.
2012/0316451 A1 12/2012 Province et al.
2013/0035682 A1 2/2013 Weil
2013/0041424 A1 2/2013 Neisz
2013/0053732 A1 2/2013 Heuser
2013/0066308 A1 3/2013 Landman
2013/0090578 A1 4/2013 Smith et al.
2013/0090637 A1 4/2013 Sliwa
2013/0090647 A1 4/2013 Smith
2013/0090649 A1 4/2013 Smith et al.
2013/0096471 A1 4/2013 Slayton et al.
2013/0096550 A1 4/2013 Hill
2013/0110012 A1 5/2013 Gertner
2013/0110106 A1 5/2013 Richardson
2013/0116683 A1 5/2013 Shadduck et al.
2013/0116737 A1 5/2013 Edwards et al.
2013/0144283 A1 6/2013 Barman
2013/0165921 A1 6/2013 Sutermeister et al.
2013/0172877 A1 7/2013 Subramaniam et al.
2013/0172880 A1 7/2013 Willard
2013/0184703 A1 7/2013 Shireman et al.
2013/0184789 A1 7/2013 Stett et al.
2013/0190716 A1 7/2013 Gertner
2013/0197555 A1 8/2013 Schaer
2013/0218029 A1 8/2013 Cholette et al.
2013/0225973 A1 8/2013 Gertner
2013/0231658 A1 9/2013 Wang et al.
2013/0231659 A1 9/2013 Hill et al.
2013/0237948 A1 9/2013 Donders et al.
2013/0245622 A1 9/2013 Wang et al.
2013/0253381 A1 9/2013 Gertner
2013/0253628 A1 9/2013 Smith et al.
2013/0274730 A1 10/2013 Anderson et al.
2013/0274731 A1 10/2013 Anderson et al.
2013/0289678 A1 10/2013 Clark et al.
2013/0296965 A1 11/2013 Mokelke et al.
2013/0331739 A1 12/2013 Gertner
2014/0018794 A1 1/2014 Anderson et al.
2014/0025069 A1 1/2014 Willard et al.
2014/0039479 A1 2/2014 Gertner
2014/0058188 A1 2/2014 Gertner
2014/0058372 A1 2/2014 Belson
2014/0065107 A1 3/2014 Lockwood et al.
2014/0066915 A1 3/2014 Zhou et al.
2014/0067003 A1 3/2014 Vase et al.
2014/0074076 A1 3/2014 Gertner
2014/0081301 A1 3/2014 Tran et al.
2014/0088575 A1 3/2014 Loeb
2014/0088585 A1 3/2014 Hill et al.
2014/0094787 A1 4/2014 Reynolds
2014/0107482 A1 4/2014 Warnking
2014/0114215 A1 4/2014 Melder et al.
2014/0121568 A1 5/2014 Weng et al.
2014/0135715 A1 5/2014 Lambert et al.
2014/0163372 A1 6/2014 Deladi et al.
2014/0163540 A1 6/2014 Iyer et al.
2014/0188103 A1 7/2014 Millett
2014/0194784 A1 7/2014 Gertner
2014/0194785 A1 7/2014 Gertner
2014/0194786 A1 7/2014 Gertner et al.
2014/0200578 A1 7/2014 Groff et al.
2014/0213971 A1 7/2014 Dolan et al.
2014/0214018 A1 7/2014 Behar et al.
2014/0249524 A1 9/2014 Kocur
2014/0271717 A1 9/2014 Goshayeshgar et al.
2014/0275993 A1 9/2014 Ballakur
2014/0276707 A1 9/2014 Jaax
2014/0276756 A1 9/2014 Hill
2014/0277310 A1 9/2014 Beetel et al.
2014/0288015 A1 9/2014 Venkateswara-Rao
2014/0303617 A1 10/2014 Shimada
2014/0316269 A1 10/2014 Zhang et al.
2014/0330068 A1 11/2014 Partsch et al.
2014/0336497 A1 11/2014 Gertner
2014/0350327 A1 11/2014 Poon et al.
2014/0378968 A1 12/2014 Sutermeister et al.
2015/0018817 A1 1/2015 Willard
2015/0018820 A1 1/2015 Cao et al.
2015/0065783 A1 3/2015 Buelna
2015/0065945 A1 3/2015 Zarins et al.
2015/0066118 A1 3/2015 O'Connell
2015/0080926 A1 3/2015 Emery
2015/0094787 A1 4/2015 Madhavan et al.
2015/0112234 A1 4/2015 McCaffrey et al.
2015/0112326 A1 4/2015 Li
2015/0126992 A1 5/2015 Mogul
2015/0126997 A1 5/2015 Beetel et al.
2015/0148794 A1 5/2015 Squire et al.
2015/0151077 A1 6/2015 Harrington
2015/0173830 A1 6/2015 Johnson et al.
2015/0190194 A1 7/2015 Weber et al.
2015/0196783 A1 7/2015 Emery et al.
2015/0202466 A1 7/2015 Gertner
2015/0223877 A1 8/2015 Behar et al.
2015/0224089 A1 8/2015 Saltiel
2015/0230859 A1 8/2015 Mauch
2015/0251008 A1 9/2015 Rezai et al.
2015/0359432 A1 12/2015 Ehrenreich et al.
2015/0359589 A1 12/2015 Mauch et al.
2015/0366608 A1 12/2015 Weber et al.
2016/0008024 A1 1/2016 Payne et al.
2016/0033144 A1 2/2016 Larson
2016/0045121 A1 2/2016 Akingba et al.
2016/0045257 A1 2/2016 Fischell et al.
2016/0058503 A1 3/2016 Tunev et al.
2016/0059044 A1 3/2016 Gertner
2016/0074112 A1 3/2016 Himmelstein et al.
2016/0074677 A1 3/2016 Gertner
2016/0135878 A1 5/2016 Warner et al.
2017/0007157 A1 1/2017 Gross et al.
2017/0049503 A1 2/2017 Cosman
2017/0049989 A1 2/2017 Kapural
2017/0065327 A1 3/2017 Joyner et al.

(56) References Cited

U.S. PATENT DOCUMENTS

| | | | |
|---|---|---|---|
| 2017/0065818 | A1 | 3/2017 | Ransbury et al. |
| 2017/0112564 | A1 | 4/2017 | Joyner et al. |
| 2017/0189642 | A1 | 7/2017 | Masson et al. |
| 2017/0348049 | A1 | 12/2017 | Vrba et al. |
| 2018/0028264 | A1 | 2/2018 | Onik et al. |
| 2018/0056074 | A1 | 3/2018 | Clark et al. |
| 2018/0103992 | A1 | 4/2018 | Guyuron |
| 2018/0153467 | A1 | 6/2018 | Lichtenstein et al. |
| 2018/0154155 | A1 | 6/2018 | Keaveney et al. |
| 2018/0177549 | A1 | 6/2018 | Harrington et al. |
| 2018/0344517 | A1 | 12/2018 | Nofzinger |
| 2019/0053847 | A1 | 2/2019 | Tandri et al. |
| 2019/0175243 | A1 | 6/2019 | Keweloh |
| 2019/0223754 | A1 | 7/2019 | Gunasekaran et al. |
| 2019/0223945 | A1 | 7/2019 | Coates et al. |
| 2019/0329042 | A1 | 10/2019 | DiLorenzo |
| 2019/0343579 | A1 | 11/2019 | Tandri et al. |
| 2019/0366130 | A1 | 12/2019 | Sverdlik et al. |
| 2020/0038096 | A1 | 2/2020 | Schepis et al. |
| 2020/0046552 | A1 | 2/2020 | Velis et al. |
| 2020/0046996 | A1 | 2/2020 | Jo et al. |
| 2020/0069366 | A1 | 3/2020 | Clark et al. |
| 2020/0121357 | A1 | 4/2020 | Gomez et al. |
| 2020/0121961 | A1 | 4/2020 | Taylor et al. |
| 2020/0170702 | A1 | 6/2020 | Warnking |
| 2020/0215266 | A1 | 7/2020 | Koya et al. |
| 2020/0253192 | A1 | 8/2020 | Jiang et al. |
| 2020/0268536 | A1 | 8/2020 | DiLorenzo |
| 2020/0306496 | A1 | 10/2020 | Radha et al. |
| 2020/0315700 | A1 | 10/2020 | Petitpierre et al. |
| 2020/0368528 | A1 | 11/2020 | Sridhar et al. |
| 2020/0368531 | A1 | 11/2020 | Sridhar et al. |
| 2020/0375658 | A1 | 12/2020 | Qian et al. |
| 2020/0397804 | A1 | 12/2020 | Hellstrom |
| 2021/0007799 | A1 | 1/2021 | Tajima et al. |
| 2021/0022948 | A1 | 1/2021 | Musallam |
| 2021/0023375 | A1 | 1/2021 | Holland et al. |
| 2021/0045711 | A1 | 2/2021 | Brattain et al. |
| 2021/0093378 | A1 | 4/2021 | Mori |
| 2021/0128051 | A1 | 5/2021 | Li et al. |
| 2021/0146136 | A1 | 5/2021 | Waataja et al. |
| 2021/0205013 | A1 | 7/2021 | Meyer et al. |
| 2021/0205501 | A1 | 7/2021 | Bright |
| 2021/0275241 | A1 | 9/2021 | Fahey et al. |
| 2021/0301306 | A1 | 9/2021 | Kaplitt et al. |
| 2021/0315638 | A1 | 10/2021 | Townley et al. |
| 2021/0322718 | A1 | 10/2021 | DiLorenzo |
| 2021/0322769 | A1 | 10/2021 | Kim |
| 2021/0330977 | A1 | 10/2021 | Sinha |
| 2021/0346625 | A1 | 11/2021 | Rezai et al. |
| 2021/0369337 | A1 | 12/2021 | Aklog et al. |
| 2021/0370066 | A1 | 12/2021 | Caban et al. |
| 2022/0031389 | A1 | 2/2022 | Fischell et al. |
| 2022/0054163 | A1 | 2/2022 | Mansell |
| 2022/0096318 | A1 | 3/2022 | Harper et al. |
| 2022/0104866 | A1 | 4/2022 | Townley et al. |
| 2022/0126062 | A1 | 4/2022 | Warnking |
| 2022/0151674 | A1 | 5/2022 | Sharma |
| 2022/0152394 | A1 | 5/2022 | Levin |
| 2022/0202483 | A1 | 6/2022 | Gertner |
| 2022/0233856 | A1 | 7/2022 | Gupta et al. |
| 2022/0233860 | A1 | 7/2022 | Hamner et al. |
| 2022/0241590 | A1 | 8/2022 | Gupta et al. |
| 2022/0249840 | A1 | 8/2022 | Gupta et al. |
| 2022/0257298 | A1 | 8/2022 | Fox et al. |
| 2022/0265302 | A1 | 8/2022 | Thirumalai et al. |
| 2022/0265339 | A1 | 8/2022 | Mn et al. |
| 2022/0296884 | A1 | 9/2022 | Jeong et al. |
| 2022/0305259 | A1 | 9/2022 | Gupta et al. |
| 2022/0305268 | A1 | 9/2022 | Hassan et al. |
| 2022/0313995 | A1 | 10/2022 | Cakmak |
| 2022/0347470 | A1 | 11/2022 | Lai et al. |
| 2022/0378461 | A1 | 12/2022 | Cheung et al. |
| 2022/0386935 | A1 | 12/2022 | Yung et al. |
| 2023/0000564 | A1 | 1/2023 | Rapoport et al. |
| 2023/0040877 | A1 | 2/2023 | Reo et al. |
| 2023/0052520 | A1 | 2/2023 | Mattison et al. |
| 2023/0054079 | A1 | 2/2023 | Lakshmi |
| 2023/0062487 | A1 | 3/2023 | Claude et al. |
| 2023/0140990 | A1 | 5/2023 | Puleo et al. |
| 2023/0181245 | A1 | 6/2023 | Cao et al. |
| 2023/0181251 | A1 | 6/2023 | Melder et al. |
| 2023/0200637 | A1 | 6/2023 | Hakimimehr et al. |
| 2023/0203582 | A1 | 6/2023 | Snyder et al. |
| 2023/0218432 | A1 | 7/2023 | Chabal et al. |
| 2023/0225791 | A1 | 7/2023 | van der Horst |
| 2023/0233095 | A1 | 7/2023 | Cezo |
| 2023/0233135 | A1 | 7/2023 | Cezo et al. |
| 2023/0233251 | A1 | 7/2023 | Cezo et al. |
| 2023/0255676 | A1 | 8/2023 | Donovan et al. |
| 2023/0256252 | A1 | 8/2023 | Brandner et al. |
| 2023/0277076 | A1 | 9/2023 | Cezo |
| 2023/0277233 | A1 | 9/2023 | Spranger et al. |
| 2023/0293229 | A1 | 9/2023 | Barman et al. |
| 2023/0301700 | A1 | 9/2023 | Nahama |
| 2023/0302301 | A1 | 9/2023 | Sobotka et al. |
| 2023/0338083 | A1 | 10/2023 | Nollert et al. |
| 2023/0338744 | A1 | 10/2023 | Demazumder et al. |
| 2023/0389852 | A1 | 12/2023 | Zhai |
| 2023/0414160 | A1 | 12/2023 | Zhai et al. |
| 2024/0032801 | A1 | 2/2024 | Coates et al. |
| 2024/0091387 | A1 | 3/2024 | Berman |
| 2024/0099988 | A1 | 3/2024 | Buelna |
| 2024/0261016 | A1 | 8/2024 | Azamian et al. |
| 2024/0261017 | A1 | 8/2024 | Azamian et al. |

FOREIGN PATENT DOCUMENTS

| | | | |
|---|---|---|---|
| EP | 2995350 | A1 | 3/2016 |
| EP | 2995350 | B1 | 8/2016 |
| WO | 9902096 | A1 | 1/1999 |
| WO | 0195820 | A1 | 12/2001 |
| WO | 0205897 | A1 | 1/2002 |
| WO | 0219934 | A1 | 3/2002 |
| WO | 03022167 | A1 | 3/2003 |
| WO | 03051450 | A1 | 6/2003 |
| WO | 2004112883 | A2 | 12/2004 |
| WO | 2006041881 | A2 | 4/2006 |
| WO | 2007121424 | A2 | 10/2007 |
| WO | 2008151001 | A2 | 12/2008 |
| WO | 2010022071 | A2 | 2/2010 |
| WO | 2013111136 | A2 | 8/2013 |
| WO | 2014091401 | A2 | 6/2014 |
| WO | 2014176785 | A1 | 11/2014 |
| WO | 2015119624 | A1 | 8/2015 |
| WO | 2016090175 | A1 | 6/2016 |
| WO | 2017146660 | A1 | 8/2017 |
| WO | 2020046839 | A1 | 3/2020 |
| WO | 2020250417 | A1 | 12/2020 |
| WO | 2021033275 | A1 | 2/2021 |
| WO | 2021097448 | A1 | 5/2021 |
| WO | 2021140421 | A1 | 7/2021 |
| WO | 2021242231 | A1 | 12/2021 |
| WO | 2022011222 | A1 | 1/2022 |
| WO | 2022221452 | A1 | 4/2022 |
| WO | 2022139971 | A1 | 6/2022 |
| WO | 2022169712 | A1 | 8/2022 |
| WO | 2022170275 | A1 | 8/2022 |
| WO | 2022204008 | A1 | 9/2022 |
| WO | 2022215760 | A1 | 10/2022 |
| WO | 2022237233 | A1 | 11/2022 |
| WO | 2022256218 | A1 | 12/2022 |
| WO | 2022266261 | A1 | 12/2022 |
| WO | 2022266327 | A1 | 12/2022 |
| WO | 2022269617 | A2 | 12/2022 |
| WO | 2023282396 | A1 | 1/2023 |
| WO | 2023283568 | A1 | 1/2023 |
| WO | 2023020544 | A1 | 2/2023 |
| WO | 2023025590 | A1 | 3/2023 |
| WO | 2023031056 | A1 | 3/2023 |
| WO | 2023031802 | A1 | 3/2023 |
| WO | 2023070128 | A1 | 4/2023 |
| WO | 2023097261 | A1 | 6/2023 |
| WO | 2023105061 | A1 | 6/2023 |

(56) References Cited

FOREIGN PATENT DOCUMENTS

| | | | |
|---|---|---|---|
| WO | 2023167343 | A1 | 9/2023 |
| WO | 2023187510 | A1 | 10/2023 |
| WO | 2023201415 | A1 | 10/2023 |
| WO | 2023205654 | A2 | 10/2023 |
| WO | 2023221710 | A1 | 11/2023 |
| WO | 2023224382 | A1 | 11/2023 |
| WO | 2023225084 | A1 | 11/2023 |
| WO | 2023235474 | A1 | 12/2023 |
| WO | 2023240154 | A2 | 12/2023 |
| WO | 2023250370 | A1 | 12/2023 |
| WO | 2023250426 | A1 | 12/2023 |
| WO | 2024019391 | A1 | 1/2024 |
| WO | 2024042216 | A1 | 2/2024 |
| WO | 2024046967 | A1 | 3/2024 |
| WO | 2024056505 | A1 | 3/2024 |

OTHER PUBLICATIONS

"Catheter-Based Renal Sympathetic Denervation for Resistant Hypertension Durability of Blood Pressure Reduction Out to 24 Months", Hypertension, vol. 57, No. 5, May 2011, pp. 911-917.

"Medtronic Announces U.S. Renal Denervation Pivotal Trial Fails to Meet Primary Efficacy Endpoint While Meeting Primary Safety Endpoint," Medtronic Press Release, Jan. 9, 2014, 3 pp.

"Meet Recor," retrieved from https://www.recormedical.com/our-story/, on Nov. 4, 2025, 4 pp.

"Pulmonary Hypertension—High Blood Pressure in the Heart-to-Lung System," https://www.heart.org/en/health-topics/high-blood-pressure/the-facts-about-high-blood-pressure/pulmonary-hypertension-high-blood-pressure-in-the-heart-to-lung-system, Oct. 31, 2016, 2 pp.

"Pulsed Radiofrequency", https://en.wikipedia.org/wiki/Pulsed_radiofrequency, Feb. 27, 2024, 4 pp., Retrieved on Feb. 27, 2024.

"Renal Artery Stenosis After Renal Sympathetic Denervation", Journal of the American College of Cardiology, vol. 60, No. 25, Dec. 25, 2012, pp. 2694-2695.

"Zapping Nerves with Ultrasound Lowers Drug-Resistant Blood Pressure," https://www.cuimc.columbia.edu/news/zapping-nerves-ultrasound-lowers-drug-resistant-blood-pressure, May 16, 2021, 4 pp.

Ahmad, BMBS, Phd et al., "Renal Denervation for Hypertension a Systematic Review and Meta-Analysis of Randomized, Blinded, Placebo-Controlled Trials", JACC: Cardiovascular Interventions, vol. 14, No. 23, Dec. 13, 2021, pp. 2614-2624.

Ahmed, BA et al., "Renal Sympathetic! Denervation Using an Irrigated Radiofrequency Ablation Catheter for the Management of Drug-Resistant Hypertension", JACC: Cardiovascular Interventions, vol. 5, No. 7, Jul. 2012, pp. 758-765.

Antz, M.D., et al., "Ablation of Atrial Fibrillation in Humans Using a Balloon-Based Ablation System: Identification of the Site of Phrenic Nerve Damage Using Pacing Maneuvers and CARTO", Journal of Cardiovascular Electrophysiology, vol. 17, No. 11, Nov. 2006, pp. 1242-1245.

Aranzulla, MD, et al., "Successful Endovascular Renal Artery Aneurysm Exclusion Using the Venture, Nc Catheter and Covered Stent Implantation: A Case Repo", Journal of Invasive Cardiology, Aug. 2007, 7 pp.

Ashenburg, MD et al., "Renal Arterial Rupture Complicating Transluminal Angioplasty: Successful Conservative Management", Radiology, vol. 174, No. 3, Mar. 1990, pp. 983-985.

Aytac, MD, et al., "Correlation Between the Diameter of the Main Renal Artery and the Presence of an Accessory Renal Artery", J Ultrasound Med, vol. 22, No. 5, May 2003, pp. 433-439.

Azizi et al., "Ultrasound renal denervation for hypertension resistant to a triple medication pill (Radiance-HTN Trio): a randomised, multicentre, single-blind, sham-controlled trial", The Lancet, vol. 397, Jun. 26, 2021, pp. 2476-2486.

Bailey et al., "Physical Mechanisms of the Therapeutic Effect of Ultrasound (A Review)", Acoustical Physics, vol. 49, No. 4, Jul. 2003, 118 pp.

Bengel et al., "Serial Assessment of Sympathetic Reinnervation After Orthotopic Heart Transplantation A Longitudinal Study Using PET and C-11 Hydroxyephedrine", Circulation, vol. 99, No. 14, Apr. 13, 1999, pp. 1866-1871.

Bergqvist et al., "Complications after percutaneous transluminal angioplasty of peripheral and renal arteries", Acta Radiol, vol. 28, No. 1, Jan. 1987, pp. 3-12.

Bhatt et al., "Long-term outcomes after catheter-based renal artery denervation for resistant hypertension: final follow-up of the randomised Symplicity HTN-3 Trial", The Lancet, vol. 400, Oct. 22, 2022, pp. 1405-1416.

Bhatt, M.D., et al., "A Controlled Trial of Renal Denervation for Resistant Hypertension", The New England Journal of Medicine, vol. 370, No. 15, Apr. 10, 2014, pp. 1393-1401.

Billard et al., "Effects of Physical Parameters on High Temperature Ultrasound Hyperthermia", Ultrasound in Med. & Biol., vol. 16, No. 4, 1990, pp. 409-420, (Applicant points out, in accordance with MPEP 609.04(a), that the year of publication, 1990, is sufficiently earlier than the effective U.S. filing date, so that the particular month of publication is not an issue.).

Bisdas, MD, PHD, et al., "Initial Experience With the 6-F and 8-F Indigo Thrombectomy System for Acute Renovisceral Occlusive Events", Journal of Endovascular Therapy, vol. 24, No. 4, Aug. 2017, 7 pp.

Blankestijn et al., "Sympathetic hyperactivity in chronic kidney disease", Nephrol Dial Transplant, vol. 19, No. 6, Jun. 2004, pp. 1354-1357.

Blum, M.D. et al., "Treatment of ostial renal-artery stenoses with vascular endoprostheses after unsuccessful balloon angioplasty", N Engl J Med, vol. 336, No. 7, Feb. 13, 1997, pp. 459-465.

Bohm et al., "Efficacy of catheter-based renal denervation in the absence of antihypertensive medications (SPYRAL HTN-OFF MED Pivotal): a multicentre, randomised, sham-controlled trial", Lancet, vol. 395, Mar. 29, 2020, pp. 1444-1451.

Bonsignore, "A Decade of Evolution in Stent Design", SMST-2003 Proceedings of the International Conference on Shape Memory and Superelastic Technologies, May 2003, pp. 519-528.

Bradfield, MD, FHRS et al., "Renal denervation as adjunctive therapy to cardiac sympathetic denervation for ablation refractory ventricular tachycardia", vol. 17, Feb. 2020, pp. 220-227.

Bui, MD, et al., "Renal Artery Aneurysm: Treatment with Percutaneous Placement of a Stent-Graft", Radiology, Apr. 1995, pp. 181-183.

Bush et al., "Endovascular revascularization of renal artery stenosis: Technical and clinical results", Journal of Vascular Surgery, vol. 33, No. 5, May 2021, pp. 1041-1049.

Calkins, MD et al., "Temperature Monitoring During Radiofrequency Catheter Ablation Procedures Using Closed Loop Control", Circulation, vol. 90, No. 3, Sep. 1994, pp. 1279-1286.

Camasão et al., "The mechanical characterization of blood vessels and their substitutes in the continuous quest for physiological-relevant performances. A critical review", Materials Today Bio, vol. 10, Jan. 1, 2025, 18 pp.

Carter, MD, et al., "Measurement of Renal Artery Pressures by Catheterization in Patients with and without Renal Artery Stenosis", Circulation, Mar. 1966, pp. 443-449.

Centenera, MD et al., "Wide-necked Saccular Renal Artery Aneurysm: Endovascular Embolization with the Guglielmi Detachable Coil and Temporary Balloon Occlusion of the Aneurysm Neck", JVIR, vol. 9, May 1998, pp. 513-516.

Chapelon et al., "Treatment of localised prostate cancer with transrectal high intensity focused ultrasound", European Journal of Ultrasound, vol. 9, Mar. 1999, pp. 31-38.

Charlesworth, M.B.CH.B., et al., "Renal artery injury from a Fogarty balloon catheter", J Vasc Surg, vol. 1, No. 4, Jul. 1984, pp. 573-576.

Chiesa, MD, et al., "Endovascular Stenting for the Nutcracker Phenomenon", J Endovasc Ther, vol. 8, No. 6, Dec. 2001, pp. 652-655.

(56) References Cited

OTHER PUBLICATIONS

Choe et al., "Anatomic Conformation of Renal Sympathetic Nerve Fibers in Living Human Tissues", Scientific Reports, vol. 9, No. 4831, Mar. 18, 2019, 10 pp.
Coates et al., "Time, temperature, power, and impedance considerations for radiofrequency catheter renal denervation", Cardiovascular Revascularization Medicine, vol. 42, Sep. 2022, pp. 171-177.
Dalecki et al., "Mechanical Bioeffects of Ultrasound", Annu Rev Biomed Eng, vol. 6, 2004, pp. 229-248, (Applicant points out, in accordance with MPEP 609.04(a), that the year of publication, 2004, is sufficiently earlier than the effective U.S. filing date, so that the particular month of publication is not an issue.).
Dangas, MD, PHD, et al., "Intravascular Ultrasound-Guided Renal Artery Stenting", J Endovasc Ther, vol. 8, No. 3, Jun. 2001, pp. 238-247.
Deardorff et al., "Control of interstitial thermal coagulation: Comparative evaluation of microwave and ultrasound applicators", Med. Phys., vol. 28, No. 1, Jan. 2001, pp. 104-117.
Deardorff et al., "Ultrasound applicators with internal cooling for interstitial thermal therapy", SPIE, vol. 3594, Jan. 1999, pp. 36-46.
Deardorff et al., "Ultrasound Applicators with Internal Water-Cooling for High-Powered Interstitial Thermal Therapy", IEEE Transactions on Biomedical Engineering, vol. 47, No. 10, Oct. 2000, pp. 1356-1365.
Dibner-Dunlap, MD, et al., "Control of Sympathetic Nerve Activity by Vagal Mechanoreflexes is Blunted in Heart Failure", Circulation, vol. 86, No. 6, Dec. 1992, pp. 1929-1934.
Dibona et al., "Neural Control of Renal Function", Physiological Reviews, vol. 77, No. 1, Jan. 1997, pp. 75, 132-150.
Dibona et al., "Neural Control of the Kidney: Past, Present, and Future", Hypertension, vol. 41, Mar. 2003, pp. 621-624.
Dibona et al., "Sympathetic nervous system and the kidney in hypertension", Curr Opin Nephrol Hypertens, vol. 11, No. 2, Mar. 2002, pp. 197-200.
Diederich et al., "Catheter-based ultrasound applicators for selective thermal ablation: progress towards MRI-guided applications in prostate", International Journal of Hyperthermia, vol. 20, No. 7, Nov. 2004, pp. 739-756.
Diederich et al., "Transurethral ultrasound applicators with directional heating patterns for prostate thermal therapy: In vivo evaluation using magnetic resonance thermometry", Med. Phys., vol. 31, No. 2, Feb. 2004, pp. 405-413.
Diederich et al., "Ultrasound Catheters for Circumferential Cardiac Ablation", SPIE, vol. 3594, Jan. 1999, pp. 26-34.
Dinerman, M.D. et al., "Temperature Monitoring During Radiofrequency Ablation", Journal of Cardiovascular Electrophysiology, vol. 7, No. 2, Feb. 1996, pp. 163-173.
Douma et al., "Renal sympathetic denervation: the jury is still out", The Lancet, vol. 376, No. 9756, Dec. 4, 2010, pp. 1878-1880.
Draney, PHD, et al., "Three-Dimensional Analysis of Renal Artery Bending Motion During Respiration", J Endovasc Ther, vol. 12, No. 3, Jun. 2005, pp. 380-386.
Dyson et al., "Urinary System", Gray's Anatomy 38th Edition, 1995, pp. 1814-1845, (Applicant points out, in accordance with MPEP 609.04(a), that the year of publication, 1995, is sufficiently earlier than the effective U.S. filing date, so that the particular month of publication is not an issue.).
Erikson et al., "Ultrasound in Medicine—A Review", IEEE Transactions OS Sonics and Ultrasonics, vol. SU-21, No. 3, Jul. 1974, pp. 144-170.
Esler et al., "The future of renal denervation", Autonomic Neuroscience: Basic and Clinical, vol. 204, May 2017, pp. 131-138.
Fan et al., "Control of the necrosed tissue volume during noninvasive ultrasound surgery using a 16-element phased array", Med Phys, vol. 22, No. 3, Mar. 1995, pp. 297-306.
Fender, MD, et al., "Severe Pulmonary Vein Stenosis Resulting From Ablation for Atrial Fibrillation", Circulation, vol. 134, Dec. 6, 2016, pp. 1812-1821.
Feng et al., "Potential mechanism of apoptosis induced by ultrasound in human hepatocarcinoma cells via comparative proteomic analysis", Bio-Medical Materials and Engineering, vol. 26, Feb. 2015, pp. S2083-S2089.
Fengler, MD, et al., "A Three-Arm Randomized Trial of Different Renal Denervation Devices and Techniques in Patients With Resistant Hypertension (RADIOSOUND-HTN)", Circulation, vol. 139, Jan. 29, 2019, pp. 590-600.
Feril Jr. et al., "Apoptosis induced by the sonomechanical effects of low intensity pulsed ultrasound in a human leukemia cell line", Cancer Letters, vol. 221, Apr. 2005, pp. 145-152.
Feyz, "Advances in the workup and treatment for diseases associated with sympathetic overactivity", Erasmus University Rotterdam, 2021, 323 pp., (Applicant points out, in accordance with MPEP 609.04(a), that the year of publication, 2021, is sufficiently earlier than the effective U.S. filing date, so that the particular month of publication is not an issue.).
Foley et al., "Image-Guided HIFU Neurolysis of Peripheral Nerves to Treat Spasticity and Pain", Ultrasound in Medicine and Biology, vol. 30, No. 9, Sep. 2004, pp. 1199-1207.
Fry et al., "Production of Reversible Changes in the Central Nervous System by Ultrasound", Science, vol. 127, Jan. 10, 1958, pp. 83-84.
Gallitto et al., "Renal Artery Orientation Influences the Renal Outcome in Endovascular Thoraco-abdominal Aortic Aneurysm Repair", Eur J Vasc Endovasc Surg, vol. 56, Sep. 2018, pp. 382-390.
Gavrilov et al., "Use of focused ultrasound for stimulation of nerve structures", Ultrasonics, May 1984, pp. 132-138.
Gentry et al., "Catheter Ultrasound Phased-Array Transducers for Thermal Ablation: A Feasibility Study", Ultrasonic Imaging, vol. 27, No. 2, Apr. 2005, pp. 89-100.
Gervais et al., "Radiofrequency Ablation of Renal Cell Carcinoma: Part 2, Lessons Learned with Ablation of 100 Tumors", AJR, vol. 185, Jul. 2005, pp. 72-80.
Goldberg, MD, et al., "EUS-guided radiofrequency ablation in the pancreas: results in a porcine model", Gastrointestinal Endoscopy, vol. 50, No. 3, Sep. 1999, pp. 392-401.
Golwyn, Jr, MD, et al., "Percutaneous Transcatheter Renal Ablation with Absolute Ethanol for Uncontrolled Hypertension or Nephrotic Syndrome: Results in 11 Patients with End-Stage Renal Disease", Journal of Vascular and Interventional Radiology, vol. 8, No. 4, Jul. 1997, 8 pp.
Gorisch, Phd et al., "Heat-Induced Contraction of Blood Vessels", Lasers in Surgery and Medicine, vol. 2, 1982, 13 pp., (Applicant points out, in accordance with MPEP 609.04(a), that the year of publication, 1982, is sufficiently earlier than the effective U.S. filing date, so that the particular month of publication is not an issue.).
Habicht et al., "Sympathische Überaktivität und Niere", Wien Klin Wochenschr, vol. 115, No. 17, Sep. 2003, pp. 634-640.
Haines, M.D. et al., "Biophysics of Ablation: Application to Technology", Journal of Cardiovascular Electrophysiology, vol. 15, No. 10, Oct. 2004, pp. S2-S11.
Hansen et al., "The transplanted human kidney does not achieve functional reinnervation", Clinical Science, vol. 87, Jul. 1994, pp. 13-20.
Harrison et al., "The Urogenital System", Cunningham's Textbook of Anatomy, 11th Edition, 1972, Pages pp. 503-509, (Applicant points out, in accordance with MPEP 609.04(a), that the year of publication, 1972, is sufficiently earlier than the effective U.S. filing date, so that the particular month of publication is not an issue.).
Hawkins, MD, et al., "You can get There From Here! A Novel Virtual 4.5F Guide Facilitates Renal Intervention From Transradial Access", Catheterization and Cardiovascular Interventions, vol. 81, No. 6, May 2013, pp. 1047-1048.
He et al., "Application of ultrasound energy for intracardiac ablation of arrhythmias", European Heart Journal, vol. 16, Jul. 1995, pp. 961-966.
Henegar et al., "Catheter-Based Radiofrequency Renal Denervation: Location Effects on Renal Norepinephrine", American Journal of Hypertension, vol. 28, No. 7, Jul. 2015, pp. 909-914.
Hill et al., "Ultrasonic Biophysics", Physical Principles of Medical Ultrasonics, Second Edition, 2004, pp. 335-389, (Applicant points out, in accordance with MPEP 609.04(a), that the year of publica-

(56) References Cited

OTHER PUBLICATIONS tion, 2004, is sufficiently earlier than the effective U.S. filing date, so that the particular month of publication is not an issue.).
Holmes, Jr, MD, et al., "Pulmonary Vein Stenosis Complicating Ablation for Atrial Fibrillation", JACC Cardiovasc Interv, vol. 2, No. 4, Apr. 2009, pp. 267-276.
Hsu et al., "Radiofrequency Ablation of the Kidney: Acute and Chronic Histology in Porcine Model", Urology, vol. 56, No. 5, Nov. 2000, pp. 872-875.
Huang et al., "Renal Denervation Prevents and Reverses Hyperinsulinemia-Induced Hypertension in Rats", Hypertension, vol. 32, Aug. 1998, pp. 249-254.
Huang, MD et al., "Radiofrequency Catheter Ablation of Cardiac Arrhythmias, Second Edition", 2000, pp. 3-12, (Applicant points out, in accordance with MPEP 609.04(a), that the year of publication, 2000, is sufficiently earlier than the effective U.S. filing date, so that the particular month of publication is not an issue.).
Hynynen et al., "Design of Ultrasonic Transducers for Local Hyperthermia", Ultrasound in Med. & Biol., vol. 7, No. 4, 1981, pp. 397-402., (Applicant points out, in accordance with MPEP 609.04(a), that the year of publication, 1981, is sufficiently earlier than the effective U.S. filing date, so that the particular month of publication is not an issue.).
Hynynen et al., "Temperature measurements during ultrasound hyperthermia", Med. Phys., vol. 16, No. 4, Jul. 1989, pp. 618-626.
Hynynen, "Chapter 12: Ultrasound Heating Technology", Thermoradiotherapy and Thermochemotherapy, 1995, pp. 253-277, (Applicant points out, in accordance with MPEP 609.04(a), that the year of publication, 1995, is sufficiently earlier than the effective U.S. filing date, so that the particular month of publication is not an issue.).
Hypertension and the Symplicity Renal Denervation System, Medtronic, 2011 (Applicant points out, in accordance with MPEP 609.04(a), that the year of publication, 2011, is sufficiently earlier than the effective U.S. filing date, so that the particular month of publication is not in issue.) 5 pp.
Isles et al., "Management of renovascular disease: a review of renal artery stenting in ten studies", QJM, vol. 92, No. 3, Mar. 1999, pp. 159-167.
Janssen et al., "Renal Nerves in Hypertension", Miner Electrolyte Metab, vol. 15, No. 1-2, 1989, pp. 74-82, (Applicant points out, in accordance with MPEP 609.04(a), that the year of publication, 1989, is sufficiently earlier than the effective U.S. filing date, so that the particular month of publication is not an issue.).
Janzen, MD, et al., "Minimally Invasive Ablative Approaches in the Treatment of Renal Cell Carcinoma", vol. 3, No. 1, Feb. 2002, pp. 13-20.
Jolesz, MD et al., "MR Imaging-Controlled Focused Ultrasound Ablation: A Noninvasive Image-Guided Surgery", Magnetic Resonance Imaging Clinics of North America, vol. 13, No. 3, Aug. 2005, pp. 545-560.
Kaltenbach et al., "Renal Artery Stenosis After Renal Sympathetic Denervation", Journal of the American College of Cardiology, vol. 60, No. 5, Dec. 25, 2012, pp. 694-695.
Kapural, MD, PHD et al., "Radiofrequency Ablation for Chronic Pain Control", Current Pain and Headache Reports, vol. 5, Dec. 2001, pp. 517-525.
Katholi, M.D., et al., "Importance of Renal Sympathetic Tone in the Development of DOCA-Salt Hypertension in the Rat", Hypertension, vol. 2, May 1980, pp. 266-273.
Keane et al., "New Catheter Ablation Techniques for the Treatment of Cardiac Arrhythmias", Cardiac Electrophysiology Review, vol. 6, No. 4, Dec. 2002, pp. 341-348.
Kim, MD, et al., "Pulmonary Vein Diameter, Cross-sectional Area, and Shape: CT Analysis", Radiology, vol. 235, Apr. 2005, pp. 43-50.
Kirsh, "Balloon Catheters: What are Some Key Design Considerations?" https://www.medicaldesignandoutsourcing.com/balloon-catheters-key-design-considerations/Dec. 8, 2016. 10 pp.
Kompanowska-Jezierska et al., "Early effects of renal denervation in the anaesthetised rat: natriuresis and increased cortical blood flow", Journal of Physiology, vol. 531, No. 2, Mar. 2001, pp. 527-534.
Koomans et al., "Sympathetic Hyperactivity in Chronic Renal Failure: A Wakeup Call", J Am Soc Nephrol, vol. 15, Mar. 2004, pp. 524-537.
Kuo, MD, et al., "Atrial Fibrillation: New Horizons", Med J, vol. 26, No. 10, Oct. 2003, pp. 712-721.
Lang et al., "Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology", Journal of the American Society of Echocardiography, vol. 18, No. 12, Dec. 2005, pp. 1440-1463.
Lee, MD, et al., "MR Imaging-Histopathologic Correlation of Radiofrequency Thermal Ablation Lesion in a Rabbit Liver Model: Observation during Acute and Chronic Stages", Korean J Radiol, vol. 2, No. 3, Sep. 2001, pp. 151-158.
Leertouwer et al., "In-vitro validation, with histology, of intravascular ultrasound in renal arteries", Journal of Hypertension, vol. 17, No. 2, Feb. 1999, pp. 271-277.
Lele et al., "Effects of Focused Ultrasonic Radiation on Peripheral Nerve, with Observations on Local Heating", Experimental Neurology, vol. 8, Jan. 1963, pp. 47-83.
Lesh et al., "An Anatomic Approach to Prevention of Atrial Fibrillation: Pulmonary Vein Isolation with Through-the-Balloon Ultrasound Ablation (TTB-USA)", Thorac and Cardiovascular Surgeon, vol. 47, Sep. 1999, pp. 347-351.
Levin et al., "ARDIAN: Succeeding Where Drugs Fail—Treating Hypertension in the Cath Lab", In Vivo: the Business & Medicine Report, vol. 27, No. 10, Nov. 2009, 10 pp.
Levin, MD, et al., "Percutaneous Transluminal Angioplasty of the Renal Arteries", JAMA, vol. 251, No. 6, Feb. 10, 1984, pp. 759-763.
Linden, D.A.S.G. et al., "The nature of the atrial receptors responsible for a reflex decrease in activity in renal nerves in the dog", J. Physiol., vol. 300, Mar. 1980, pp. 31-20.
Lohmeier et al., "Baroreflexes prevent neurally induced sodium retention in angiotensin hypertension", Am J Physiol Regulatory Integrative Comp Physiol, vol. 279, Oct. 2000, pp. R1437-R1448.
Longhurst et al., "Cardiac Receptors: Their Function in Health and Disease", Progress in Cardiovascular Diseases, vol. XXVII, No. 3, Nov. 1984, pp. 201-222.
Mabin et al., "First experience with endovascular ultrasound renal denervation for the treatment of resistant hypertension", EuroIntervention, vol. 8, May 2012, pp. 57-61.
Mahfoud, MD, et al., "Catheter-Based Renal Denervation is no Simple Matter", Journal of the American College of Cardiology, vol. 64, No. 7, Aug. 19, 2014, pp. 644-646.
Mahler et al., "Complications in Percutaneous Transluminal Dilatation of Renal Arteries", Nephron, vol. 44, No. 1, 1986, pp. 60-63, (Applicant points out, in accordance with MPEP 609.04(a), that the year of publication, 1986, is sufficiently earlier than the effective U.S. filing date, so that the particular month of publication is not an issue.).
Manousaki et al., "Endovascular Treatment of a Ruptured Profunda Femoral Artery Branch After Fogarty Thrombectomy of a Femoro-Femoral Crossover Arterial Graft: A Case Report and Review of the Literature", Cardiovasc Intervent Radiol, vol. 33, Feb. 2010, pp. 182-186.
Marine, MD, et al., "Catheter Ablation Therapy for Supraventricular Arrhythmias", JAMA, vol. 298, No. 23, Dec. 19, 2007, pp. 2768-2778.
Martin, MD et al., "Long-term Results of Angioplasty in 110 Patients with Renal Artery Stenosis", Journal of Vascular and Interventional Radiology, vol. 3, Nov. 1992, pp. 619-626.
Matsuda, M.D., et al., "Pulmonary Vein Stenosis After Second-Generation Cryoballoon Ablation", J Cardiovasc Electrophysiol, vol. 28, No. 3, Mar. 2017, pp. 298-303.
Matsumoto et al., "Short-Term Efficacy of Temperature-Based Radiofrequency Ablation of Small Renal Tumors", Urology, vol. 65, No. 5, May 2005, pp. 877-881.

(56) References Cited

OTHER PUBLICATIONS

Meyers et al., "Temporary Endovascular Balloon Occlusion of the Internal Carotid Artery with a Nondetachable Silicone Balloon Catheter: Analysis of Technique and Cost", AJNR Am J Neuroradiol, vol. 20, Apr. 1999, pp. 559-564.
Millard et al., "Renal embolization for ablation of function in renal failure and hypertension", Postgraduate Medical Journal, vol. 65, No. 768, Oct. 1989, pp. 729-734.
Morris et al., "Nonsurgical Treatment of Acute Iatrogenic Renal Artery Injuries Occurring After Renal Artery Angioplasty and Stenting", AJR, vol. 177, Dec. 2001, pp. 1353-1357.
Morrissey et al., "Sympathectomy in the Treatment of Hypertension", The Lancet, vol. 1, No. 6757, Feb. 28, 1953, pp. 403-408.
Moubarak et al., "Pulmonary Veins-Left Atrial junction: Anatomic and Histological Study", PACE, vol. 23, Nov. 2000, pp. 1836-1838.
Murat et al., "Hemostatic efficacy of a high-precision collimated ultrasound applicator intensity of partial sub hilar nephrectomy in pigs", Progres en Urologie, vol. 15, No. 4, Sep. 2005, pp. 684-688.
Natale, MD et al., "First Human Experience With Pulmonary Vein Isolation Using a Through-the-Balloon Circumferential Ultrasound Ablation System for Recurrent Atrial Fibrillation", Circulation, Oct. 17, 2000, pp. 1879-1882.
Netter, MD, et al., "Human Anatomy, Third Edition, Plate 159, 160, 330, 331, 332, 333, 334, 335", Jan. 1, 2003, 10 pp., (Applicant points out, in accordance with MPEP 609.04(a), that the year of publication, 2003, is sufficiently earlier than the effective U.S. filing date, so that the particular month of publication is not an issue.).
Neumann et al., "Sympathetic hyperactivity in chronic kidney disease: Pathogenesis, clinical relevance, and treatment", Kidney International, vol. 65, May 2004, pp. 1568-1576.
Neven, MD et al., "Fatal End of a Safety Algorithm for Pulmonary Vein Isolation With use of High-Intensity Focused Ultrasound", Circ Arrhythm Electrophysiol, vol. 3, No. 3, Jun. 2010, pp. 260-265.
Neven, MD, et al., "Two-year clinical follow-up after pulmonary vein isolation using high-intensity focused ultrasound (HIFU) and an esophageal temperature-guided safety algorithm", Heart Rhythm, vol. 9, No. 3, Mar. 2012, pp. 407-413.
Nozawa et al., "Effects of long-term renal sympathetic denervation on heart failure after myocardial infarction in rats", Heart Vessels, vol. 16, Jan. 2002, pp. 51-56.
Oldham et al., "Denervation of the Kidney", Hunterian Lecture delivered at the Royal College of Surgeons of England, Mar. 9, 1950, pp. 222-245.
Oliveira et al., "Renal Denervation Normalizes Pressure and Baroreceptor Reflex in High Renin Hypertension in Conscious Rats", Hypertension, vol. 19, No. 2, Feb. 1992, pp. 17-21.
Page et al., "The Effect of Renal Denervation on Patients Suffering From Nephritis", J Clin Invest, vol. 14, No. 4, Jul. 1935, pp. 443-458.
Page et al., "The Effect of Renal Denervation on the Level of Arterial Blood Pressure and Renal Function in Essential Hypertension", Journal of Clinical Investigation, vol. 14, No. 1, Jan. 1935, pp. 27-30.
Palmaz, MD, et al., "The Current Status of Vascular Intervention in Ischemic Nephropathy", JVIR, vol. 9, No. 4, Jul. 1998, pp. 539-543.
Papademetriou et al.. "Catheter-Based Renal Denervation for Resistant Hypertension", Hypertension, vol. 64, Sep. 2014, pp. 565-572.
Papademetriou et al., "Renal Sympathetic Denervation for the Treatment of Difficult-to-Control or Resistant Hypertension", International Journal of Hypertension, vol. 2011, Mar. 30, 2011, 8 pp.
Pappone, MD, et al., "Atrio-Esophageal Fistula After AF Ablation: Pathophysiology, Prevention & Treatment", Journal of Atrial Fibrillation, vol. 6, No. 3, Oct. 2013, pp. 102-107.
Pappone, MD, PHD; et al., "Circumferential Radiofrequency Ablation of Pulmonary Vein Ostia", Circulation, vol. 102, Nov. 21, 2000, pp. 2619-2628.
Parsons, MD, et al., "Fluoroscopically Assisted Thromboembolectomy: An Improved Method for Treating Acute Arterial Occlusions", Annals of Vascular Surgery, vol. 10, No. 3, May 1996. pp. 201-210.
Peet, M.D. et al., "Hypertension and its surgical treatment by bilateral supradiaphragmatic splanchnicectomy", The American Journal of Surgery, vol. 75, No. 1, Jan. 1948, pp. 46-48.
Perry, M.D., et al., "Intramural dissection mesenteric artery", Journal of Vascular Surgery, vol. 2, No. 3, May 1985, pp. 480-484.
Piorkowski, M.D., et al., "Steerable Sheath Catheter Navigation for Ablation of Atrial Fibrillation: A Case-Control Study", PACE, vol. 31, Jul. 2008, pp. 863-873.
Plouin et al., "Blood Pressure Outcome of Angioplasty in Atherosclerotic Renal Artery Stenosis : A Randomized Trial", Hypertension, vol. 31, Mar. 1998, pp. 823-829.
Prochnau, MD et al., "Catheter-based renal denervation for drug-resistant hypertension by using a standard electrophysiology catheter", EuroIntervention, vol. 7, No. 9, Jan. 2012, pp. 1077-1080.
Pugsley et al., "The vascular system an overview of structure and function", Journal of Pharmacological and Toxicological Methods, vol. 44, No. 2, Sep. 2000, pp. 333-340.
Purerfellner et al., "Pulmonary vein stenosis following catheter ablation of atrial fibrillation", Current Opinion in Cardiology, vol. 20, No. 6, Nov. 2005, pp. 484-490.
Purerfellner, MD, et al., "Incidence, Management, and Outcome in Significant Pulmonary Vein Stenosis Complicating Ablation for Atrial Fibrillation", The American Journal of Cardiology, vol. 93, No. 1, Jun. 1, 2004, pp. 1428-1431.
Qian et al., "Transcatheter non-contact microwave ablation may enable circumferential renal artery denervation while sparing the vessel intima and media", EuroIntervention, vol. 12, No. 15, Dec. 2016, pp. e1907-e1915.
Reddy et al., "Use of a Diode Laser Balloon Ablation Catheter to Generate Circumferential Pulmonary Venous Lesions in an Open-Thoracotomy Caprine Model", PACE, vol. 27, Jan. 2004, pp. 52-57.
Rees, MD, et al., "Palmaz Stent in Atherosclerotic Stenoses Involving the Ostia of the Renal Arteries: Preliminary Report of a Multicenter Study", Radiology, vol. 181, Nov. 1991, pp. 507-514.
Response to Office Action dated Jan. 28, 2026 from U.S. Appl. No. 18/609,523, filed Apr. 7, 2026, 14 pp.
Robbins, MD et al., "Pulmonary Vein Stenosis After Catheter Ablation of Atrial Fibrillation", Circulation, vol. 98, No. 17, Oct. 27, 1998, pp. 1769-1775.
Ross et al., "Highly directional transurethral ultrasound applicators with rotational control for MRI-guided prostatic thermal therapy", Physics in Medicine and Biology, vol. 49, No. 2, Jan. 21, 2004, pp. 189-204.
Rundback, MD, et al., "Percutaneous Stent-Graft Management of Renal Artery Aneurysms", JVIR, vol. 11, Oct. 2000, pp. 1189-1193.
Ryan et al., "Proceedings of Thermal Treatment of Tissue with Image Guidance", Progress in Biomedical Optics, vol. 3594, Jan. 1999, 5 pp.
Ryan, PhD, "What are the Risks Associated with a Pulmonary Vein Ablation Procedure?" https://a-fib.com/risks-associated-with-pulmonary-vein-procedure/, Sep. 11, 2017, 3 pp.
Sakakura, MD et al., "Anatomic Assessment of Sympathetic Peri-Arterial Renal Nerves in Man", Journal of the American College of Cardiology, vol. 64, No. 7, Aug. 19, 2014, pp. 635-643.
Saliba, M.D., et al., "Circumferential Ultrasound Ablation for Pulmonary Vein Isolation: Analysis of Acute and Chronic Failures", Journal of Cardiovascular Electrophysiology, vol. 13, No. 10, Oct. 2002, pp. 957-961.
Sanchez-Quintana, M.D., PH.D., et al., "How Close are the Phrenic Nerves to Cardiac Structures? Implications for Cardiac Interventionalists", Journal of Cardiovascular Electrophysiology, vol. 16, No. 3, Mar. 2005, pp. 309-313.
Schauerte et al., "Catheter Ablation of Cardiac Autonomic Nerves for Prevention of Vagal Atrial Fibrillation", Circulation, vol. 102, Nov. 28, 2000, pp. 2774-2780.
Schmidt, MD et al., "Pulmonary Vein Isolation by High Intensity Focused Ultrasound", Indian Pacing and Electrophysiology Journal, vol. 7, No. 2, 04, Apr. 1, 2007, pp. 126-133.
Schmieder, "Renal denervation in patients with chronic kidney disease: current evidence and future perspectives", Nephrol Dial Transplant, May 25, 2002, 8 pp.
Schneider et al., "Endovascular Skills", 2003, Pages pp. 151-152, 198, 284-286, 290, (Applicant points out, in accordance with MPEP

(56) References Cited

OTHER PUBLICATIONS 609.04(a), that the year of publication, 2003, is sufficiently earlier than the effective U.S. filing date, so that the particular month of publication is not an issue.).
Schneider, M.D., et al., "Endovascular Skills", 1998, Pages pp. 70-71, 101, 188-190, (Applicant points out, in accordance with MPEP 609.04(a), that the year of publication, 1998, is sufficiently earlier than the effective U.S. filing date, so that the particular month of publication is not an issue.).
Shimizu et al., "Sympathetic dysfunction in heart failure", Bailliere's Clinical Endocrinology and Metabolism, vol. 7, No. 2, Apr. 1993, pp. 439-463.
Shonai, MD, et al., "Renal Artery Aneurysm: Evaluation with Color Doppler Ultrasonography Before and After Percutaneous Transarterial Embolization", J Ultrasound Med, vol. 19, Apr. 2000, pp. 277-280.
Smithwick et al., "Splanchnicectomy for essential hypertension; results in 1,266 cases", J Am Med Assoc, vol. 152, No. 16, Aug. 1953, pp. 1501-1504.
Stella et al., "Effects of Reversible Renal Denervation on Haemodynamic and Excretory Functions of the ipsilateral and Contralateral Kidney in the Cat", Journal of Hypertension, vol. 4, Apr. 1986, pp. 181-188.
Stoeckel et al., "A survey of stent designs", vol. 11, No. 4, Jul. 2002, pp. 137-147.
Swartz, MD, et al., "Radiofrequency Endocardial Catheter Ablation of Accessory Atrioventricular Pathway Atrial Insertion Sites", Circulation, vol. 87, No. 2, Feb. 1993, pp. 487-499.
Takeshita, MD, FACC, et al., "Renal Artery Intervention Using a Virtual 4.5-Fr Guiding Catheter", Catheterization and Cardiovascular Interventions, vol. 81, May 2013, pp. 1043-1046.
Tanaka, MD et al., "A New Radio frequency Thermal Balloon Catheter for Pulmonary Vein Isolation", Journal of the American College of Cardiology, vol. 38, No. 7, Dec. 2001, pp. 2079-2086.
Teigen, MD, et al., "Segmental Renal Artery Embolization for Treatment of Pediatric Renovascular Hypertension", Journal of Vascular and Interventional Radiology, vol. 3, No. 1, Feb. 1992, pp. 111-117.
Teitelbaum, M.D., et al., "Regulation of Body Fluid Osmolality", Principles and Practice of Nephrology, 1991, pp. 22-26, (Applicant points out, in accordance with MPEP 609.04(a), that the year of publication, 1991, is sufficiently earlier than the effective U.S. filing date, so that the particular month of publication is not an issue.).
Thatipelli et al., "CT Angiography of Renal Artery Anatomy for Evaluating Embolic Protection Devices", vol. 18, No. 7, Jul. 2007, pp. 842-846.
Tsao et al., "Evaluation of Pulmonary Vein Stenosis after Catheter Ablation of Atrial Fibrillation", Cardiac Electrophysiology Review, vol. 6, No. 4, Dec. 2002, pp. 397-400.
Turagam, MD, et al., "Renal Sympathetic Denervation as Upstream Therapy During Atrial Fibrillation Ablation", JACC: Clinical Electrophysiology, vol. 7, No. 1, Oct. 28, 2020, 15 pp.
Turner, MD, et al., "Initial Experience Using the Palmaz Corinthian Stent for Right Ventricular Outflow Obstruction in Infants and Small Children", Catheterization and Cardiovascular Interventions, vol. 51, No. 4, Dec. 2000, pp. 444-449.
Uchida et al., "Effect of Radiofrequency Catheter Ablation on Parasympathetic Denervation: A Comparison of Three Different Ablation Sites", PACE, vol. 21, Nov. 1998, pp. 2517-2521.
Ulmsten et al., "The safety and efficacy of MenoTreat™, a new balloon device for thermal endometrial ablation", Acta Obstetricia et Gynecologica Scandinavica, vol. 80, Jan. 2001, pp. 52-57.
Vaezy et al., "Image-Guided Acoustic Therapy", Annu Rev Biomed Eng, vol. 3, 2001, pp. 375-390, (Applicant points out, in accordance with MPEP 609.04(a), that the year of publication, 2001, is sufficiently earlier than the effective U.S. filing date, so that the particular month of publication is not an issue.).
Valente et al., "Laparoscopic renal denervation for intractable ADPKD-related pain", Nephrology Dialysis Transplantation, vol. 16, No. 1, Jan. 2001, 1 pp.
Vari, PH.D., et al., "Normal Regulation of Arterial Pressure", Principles and Practice of Nephrology, 1991, pp. 492-500, (Applicant points out, in accordance with MPEP 609.04(a), that the year of publication, 1991, is sufficiently earlier than the effective U.S. filing date, so that the particular month of publication is not an issue.).
Vujaskovic et al., "Effects of intraoperative hyperthermia on canine sciatic nerve: histopathologic and morphometric studies", Int. J. Hyperthermia, vol. 10, No. 6, Nov. 1994, pp. 845-855.
Vuong et al., "Perioperative Arterial Changes", Diseases of the Arterial Wall, 1989, pp. 561-583, (Applicant points out, in accordance with MPEP 609.04(a), that the year of publication, 1989, is sufficiently earlier than the effective U.S. filing date, so that the particular month of publication is not an issue.).
Wanchoo et al., "Medtronic Gets European and Australian Approval for Symplicity Spyral Multi-Electrode Renal Denervation Catheter", Medgadget, Dec. 9, 2013, 3 pp.
Wanhainen et al., "How to define an abdominal aortic aneurysm—influence on epidemiology and clinical practice", Scandinavian Journal of Surgery, vol. 97, 2008, pp. 105-109, (Applicant points out, in accordance with MPEP 609.04(a), that the year of publication, 2008, is sufficiently earlier than the effective U.S. filing date, so that the particular month of publication is not an issue.).
Webster's New World Medical Dictionary, Third Edition, 2008, (Applicant points out, in accordance with MPEP 609.04(a), that the year of publication, 2008, is sufficiently earlier than the effective U.S. filing date, so that the particular month of publication is not in issue.), 13 pp.
Weinberg et al., "Comparison of ASPIRE Mechanical Thrombectomy Versus AngioJet Thrombectomy System in a Porcine Iliac Vein Thrombosis Model", Ann Vasc Surg, vol. 42, Jul. 2017, pp. 254-262.
Weinstock et al., "Renal denervation prevents sodium retention and hypertension in salt-sensitive rabbits with genetic baroreflex impairment", Clinical Science, vol. 90, Apr. 1996, pp. 287-293.
Wong et al., "Anatomic left atrial circumferential ablation to electrically isolate pulmonary veins using a novel focused ultrasound balloon catheter", Heart Rythm, vol. 3, No. 3, Mar. 2006, 2 pp.
Yokoyama, MD, PHD et al., "Canine Model of Esophageal Injury and Atrial-Esophageal Fistula After Applications of Forward-Firing High-Intensity Focused Ultrasound and Side-Firing Unfocused Ultrasound in the Left Atrium and Inside the Pulmonary Vein", Circ Arrhythmia Electrophysiol, Feb. 2009, pp. 41-49.
Zazgornik et al., "Bilateral Nephrectomy: The Best, but Often Overlooked, Treatment for Refractory Hypertension in Hemodialysis Patients", AJH, vol. 11, No. 11, Nov. 1998, pp. 1364-1370.
Ziegler et al., "Sources of urinary catecholamines in renal denervated transplant recipients", Journal of Hypertension, vol. 8, No. 10, Oct. 1990, pp. 927-931.
Notice of Allowance from U.S. Appl. No. 18/609,523 dated Jun. 5, 2026, 9 pp.

* cited by examiner

Liver norepinephrine levels

| | Lobe | Normal content (ng/g) tissue | Denervated content (ng/g) tissue |
|---|---|---|---|
| Dog | Caudate | 248±41 | 0.9±0.4 |
| | Left central | 299±93 | 0.8±0.4 |
| | Left lateral | 376±151 | 0.4±0.2 |
| | Left posterior | 349±110 | 0.4±0.1 |
| | Quadrate | 307±104 | 28.1±12.8 |
| | Right lateral | 394±195 | 7.0±4.0 |
| | Right central | 342±135 | 0.4±0.3 |
| Pig | Left central | *Estimated 72-95% effective denervation compared to dog (Vanderbilt) controls* | 1.2 |
| | Right lateral | | 2.1 |
| | Left lateral | | 173.6 |
| | Right Caudate | | 269.7 |
| | Right central | | 9.5 |

FIG. 66

FIG. 90A
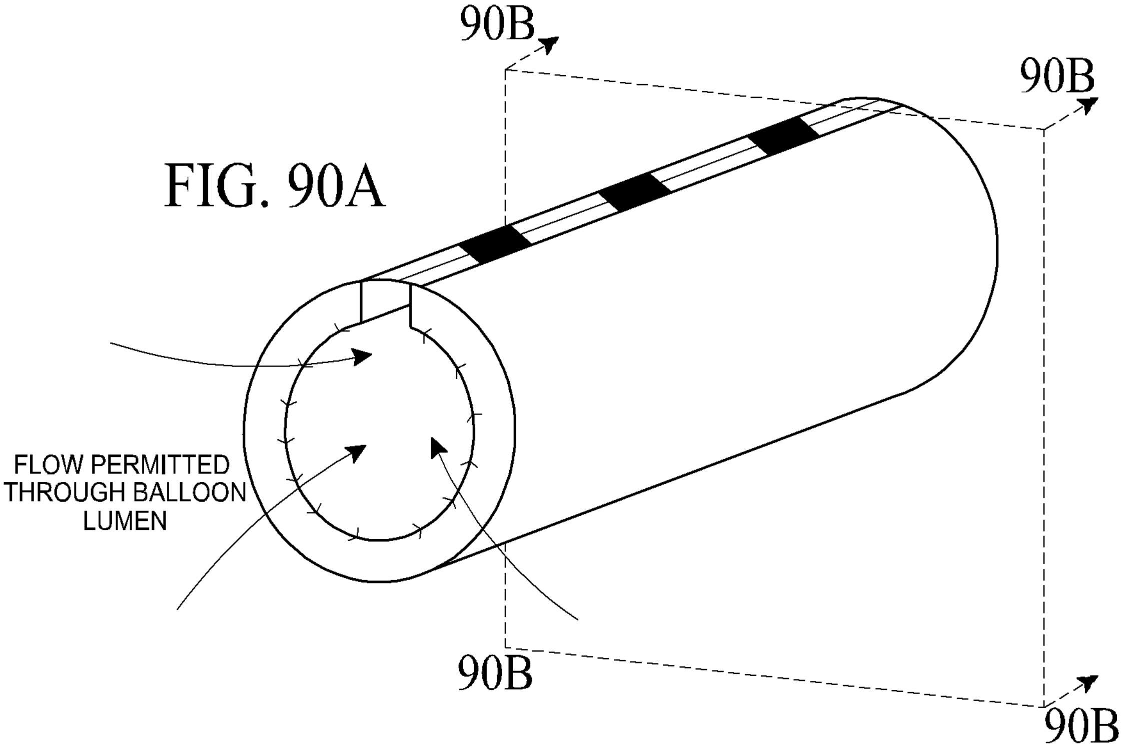
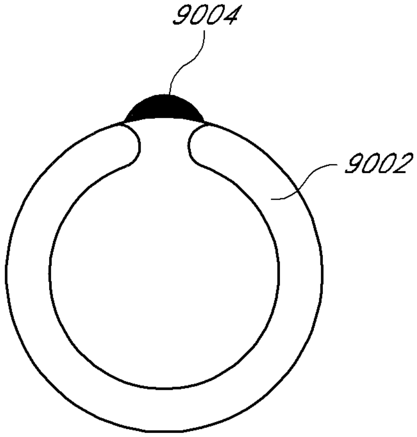
FIG. 90B

MODULATION OF TARGETED NERVE FIBERS

This application is a continuation of U.S. patent application Ser. No. 16/706,468, now U.S. Pat. No. 12,011,212, filed Dec. 6, 2019, which is a continuation of U.S. patent application Ser. No. 14/896,063, filed Dec. 4, 2015, now abandoned, which is a 371 of International Application No. PCT/US2014/040949 filed Jun. 4, 2014, which claims priority to U.S. Provisional Application No. 61/831,507 filed Jun. 5, 2013 and to U.S. Provisional Application No. 61/906,830 filed Nov. 20, 2013, the entire content of each of which is hereby incorporated by reference herein in its entirety.

FIELD

The disclosure relates generally to therapeutic neuromodulation and, more specifically, to embodiments of devices, systems and methods for therapeutically effecting neuromodulation of targeted nerve fibers of, for example, the hepatic system, to treat metabolic diseases or conditions, such as diabetes mellitus.

BACKGROUND

Chronic hyperglycemia is one of the defining characteristics of diabetes mellitus. Hyperglycemia is a condition in which there is an elevated blood glucose concentration. An elevated blood glucose concentration may result from impaired insulin secretion from the pancreas and also, or alternatively, from cells failing to respond to insulin normally. Excessive glucose release from liver is a significant contributor to hyperglycemia. The liver is responsible for approximately 90% of the glucose production and 33% of glucose uptake, and derangements in both in type 2 diabetes contribute to hyperglycemia in the fasting and post-prandial states.

Type 1 diabetes mellitus results from autoimmune destruction of the pancreatic beta cells leading to inadequate insulin production. Type 2 diabetes mellitus is a more complex, chronic metabolic disorder that develops due to a combination of insufficient insulin production as well as cellular resistance to the action of insulin. Insulin promotes glucose uptake into a variety of tissues and also decreases production of glucose by the liver and kidneys; insulin resistance results in reduced peripheral glucose uptake and increased endogenous glucose output, both of which drive blood the glucose concentration above normal levels.

Current estimates are that approximately 26 million people in the United States (over 8% of the population) have some form of diabetes mellitus. Treatments, such as medications, diet, and exercise, seek to control blood glucose levels, which require a patient to closely monitor his or her blood glucose levels. Additionally, patients with type 1 diabetes mellitus, and many patients with type 2 diabetes mellitus, are required to take insulin every day. Insulin is not available in a pill form, however, but must be injected under the skin. Because treatment for diabetes mellitus is self-managed by the patient on a day-to-day basis, compliance or adherence with treatments can be problematic.

SUMMARY

Several embodiments described herein relate generally to devices, systems and methods for therapeutically effecting neuromodulation of targeted nerve fibers to treat various medical conditions, disorders and diseases. In some embodiments, neuromodulation of targeted nerve fibers is used to treat, or reduce the risk of occurrence of symptoms associated with, a variety of metabolic diseases. For example, neuromodulation of targeted nerve fibers can treat, or reduce the risk of occurrence of symptoms associated with, diabetes (e.g., diabetes mellitus) or other diabetes-related diseases. The methods described herein can advantageously treat diabetes without requiring daily insulin injection or constant monitoring of blood glucose levels. The treatment provided by the devices, systems and methods described herein can be permanent or at least semi-permanent (e.g., lasting for several weeks, months or years), thereby reducing the need for continued or periodic treatment. Embodiments of the devices described herein can be temporary or implantable.

In some embodiments, neuromodulation of targeted nerve fibers as described herein can be used for the treatment of insulin resistance, genetic metabolic syndromes, ventricular tachycardia, atrial fibrillation or flutter, arrhythmia, inflammatory diseases, hypertension, obesity, hyperglycemia, hyperlipidemia, eating disorders, and/or endocrine diseases. In some embodiments, neuromodulation of targeted nerve fibers treats any combination of diabetes, insulin resistance, or other metabolic diseases. In some embodiments, temporary or implantable neuromodulators may be used to regulate satiety and appetite. In several embodiments, modulation of nervous tissue that innervates (afferently or efferently) the liver is used to treat hemochromatosis, Wilson's disease, non-alcoholic steatohepatitis (NASH), non-alcoholic fatty liver disease (NAFLD), and/or other conditions affecting the liver and/or liver metabolism. In some embodiments, modulation of nervous tissue that innervates (afferently or efferently) the liver (e.g., hepatic denervation) is effective for reducing whole-body sympathetic tone and resulting conditions such as hypertension, congestive heart failure, atrial fibrillation, obstructive sleep apnea, and/or renal failure, etc.

In some embodiments, sympathetic nerve fibers associated with the liver are selectively disrupted (e.g., ablated, denervated, disabled, severed, blocked, injured, desensitized, removed) to decrease hepatic glucose production and/or increase hepatic glucose uptake, thereby aiding in the treatment of, or reduction in the risk of, diabetes and/or related diseases or disorders. The disruption can be permanent or temporary (e.g., for a matter of several days, weeks or months). In some embodiments, sympathetic nerve fibers in the hepatic plexus are selectively disrupted. In some embodiments, sympathetic nerve fibers surrounding the common hepatic artery proximal to the proper hepatic artery, sympathetic nerve fibers surrounding the proper hepatic artery, sympathetic nerve fibers in the celiac ganglion adjacent the celiac artery, other sympathetic nerve fibers that innervate or surround the liver, sympathetic nerve fibers that innervate the pancreas, sympathetic nerve fibers that innervate fat tissue (e.g., visceral fat), sympathetic nerve fibers that innervate the adrenal glands, sympathetic nerve fibers that innervate the small intestine (e.g., duodenum), sympathetic nerve fibers that innervate the stomach, sympathetic nerve fibers that innervate brown adipose tissue, sympathetic nerve fibers that innervate skeletal muscle, and/or sympathetic nerve fibers that innervate the kidneys are selectively disrupted or modulated (simultaneously or sequentially) to facilitate treatment or reduction of symptoms associated with hypertension, diabetes (e.g., diabetes mellitus), or other metabolic diseases or disorders. In some embodiments, the methods, devices and systems described herein are used to therapeutically modulate autonomic nerves associated with any diabetes-relevant organs or tissues. For example, with respect to the pancreas and duodenum, the nerves that innervate one or both structures can be neuromodulated (e.g., ablated) in addition to or instead of the nerves that innervate the liver, wherein said neuromodulation affects one or more symptoms/characteristics associated with diabetes or other metabolic diseases or disorders. Such symptoms/characteristics include but are not limited to increased blood glucose, cholesterol, lipids, triglycerides, insulin regulation, etc. The devices and methods disclosed herein with respect hepatic modulation can be used for neuromodulating the pancreas, duodenum, or other organs and structures.

In accordance with several embodiments, any nerves containing autonomic fibers are modulated, including, but not limited to, the saphenous nerve, femoral nerves, lumbar nerves, median nerves, ulnar nerves, vagus nerves, and radial nerves. Nerves surrounding arteries or veins other than the hepatic artery may be modulated such as, but not limited to, nerves surrounding the superior mesenteric artery, the inferior mesenteric artery, the femoral artery, the pelvic arteries, the portal vein, pulmonary arteries, pulmonary veins, abdominal aorta, vena cavas, splenic arteries, gastric arteries, the internal carotid artery, the internal jugular vein, the vertebral artery, renal arteries, and renal veins.

In accordance with several embodiments, a therapeutic neuromodulation system is used to selectively disrupt sympathetic nerve fibers. The neuromodulation system can comprise an ablation catheter system and/or a delivery catheter system (e.g., hollow, solid, partially hollow, catheter, probe, shaft or other delivery device with or without a lumen). An ablation catheter system may use radiofrequency (RF) energy to ablate sympathetic nerve fibers to cause neuromodulation or disruption of sympathetic communication. In some embodiments, an ablation catheter system uses ultrasonic energy to ablate sympathetic nerve fibers. In some embodiments, an ablation catheter system uses ultrasound (e.g., high-intensity focused ultrasound or low-intensity focused ultrasound) energy to selectively ablate sympathetic nerve fibers. In other embodiments, an ablation catheter system uses electroporation to modulate sympathetic nerve fibers. An ablation catheter, as used herein, shall not be limited to causing ablation, but also includes devices that facilitate the modulation of nerves (e.g., partial or reversible ablation, blocking without ablation, stimulation). In some embodiments, a delivery catheter system delivers drugs or chemical agents to nerve fibers to modulate the nerve fibers (e.g., via chemoablation). Chemical agents used with chemoablation (or some other form of chemically-mediated neuromodulation) may, for example, include phenol, alcohol, or any other chemical agents that cause chemoablation of nerve fibers. In some embodiments, cryotherapy is used. For example, an ablation catheter system is provided that uses cryoablation to selectively modulate (e.g., ablate) sympathetic nerve fibers. In other embodiments, a delivery catheter system is used with brachytherapy to modulate the nerve fibers. The catheter systems may further utilize any combination of RF energy, ultrasonic energy, focused ultrasound (e.g., HIFU, LIFU) energy, ionizing energy (such as X-ray, proton beam, gamma rays, electron beams, and alpha rays), electroporation, drug delivery, chemoablation, cryoablation, brachytherapy, or any other modality to cause disruption or neuromodulation (e.g., ablation, denervation, stimulation) of autonomic (e.g., sympathetic or parasympathetic) nerve fibers.

In some embodiments, a minimally invasive surgical technique is used to deliver the therapeutic neuromodulation system. For example, a catheter system (e.g., hollow, solid, partially hollow, catheter, probe, shaft or other delivery device with or without a lumen). for the disruption or neuromodulation of sympathetic nerve fibers can be delivered intra-arterially (e.g., via a femoral artery, brachial artery, radial artery). In some embodiments, an ablation catheter system is advanced to the proper hepatic artery to ablate (completely or partially) sympathetic nerve fibers in the hepatic plexus. In other embodiments, the ablation catheter system is advanced to the common hepatic artery to ablate sympathetic nerve fibers surrounding the common hepatic artery. In some embodiments, the ablation catheter system is advanced to the celiac artery or celiac trunk to ablate sympathetic nerve fibers in the celiac ganglion or celiac plexus. An ablation or delivery catheter system can be advanced within other arteries (e.g., left hepatic artery, right hepatic artery, gastroduodenal artery, gastric arteries, splenic artery, renal arteries, etc.) in order to disrupt targeted sympathetic nerve fibers associated with the liver or other organs or tissue (such as the pancreas, fat tissue (e.g., visceral fat of the liver), the adrenal glands, the stomach, the small intestine, gall bladder, bile ducts, brown adipose tissue, skeletal muscle), at least some of which may be clinically relevant to diabetes. In several embodiments, neuromodulation (e.g., denervation, stripping, stimulation) of the celiac ganglion or modulation of celiac ganglion activity facilitates treatment of hypertension.

In some embodiments, a therapeutic neuromodulation or disruption system is delivered intravascularly through the venous system. For example, the therapeutic neuromodulation system may be delivered either through the portal vein or through the inferior vena cava. In some embodiments, the neuromodulation system is delivered percutaneously to the biliary tree to modulate or disrupt sympathetic nerve fibers.

In other embodiments, the neuromodulation system is delivered transluminally or laparoscopically to modulate or disrupt sympathetic nerve fibers. For example, the neuromodulation system may be delivered transluminally either through the stomach, or through the duodenum.

In some embodiments, minimally invasive surgical delivery of the neuromodulation system is accomplished in conjunction with image guidance techniques. For example, a visualization device such as a fiberoptic scope can be used to provide image guidance during minimally invasive surgical delivery of the neuromodulation system. In some embodiments, fluoroscopic, computerized tomography (CT), radiographic, optical coherence tomography (OCT), intravascular ultrasound (IVUS), Doppler, thermography, and/or magnetic resonance (MR) imaging is used in conjunction with minimally invasive surgical delivery of the neuromodulation system. In some embodiments, radiopaque markers are located at a distal end of the neuromodulation system to aid in delivery and alignment of the neuromodulation system.

In some embodiments, an open surgical procedure is used to access the nerve fibers to be modulated. In some embodiments, any of the modalities described herein, including, but not limited to, RF energy, ultrasonic energy, HIFU, thermal energy, light energy, electrical energy other than RF energy, drug delivery, chemoablation, cryoablation, steam or hot-water, ionizing energy (such as X-ray, proton beam, gamma rays, electron beams, and alpha rays) or any other modality are used in conjunction with an open surgical procedure to modulate or disrupt sympathetic nerve fibers. In other embodiments, nerve fibers are surgically cut (e.g., transected) to disrupt conduction of nerve signals or otherwise cause nerve injury.

In some embodiments, a non-invasive (e.g., transcutaneous) procedure is used to modulate or disrupt sympathetic nerve fibers. In some embodiments, any of the modalities described herein, including, but not limited, to RF energy, ultrasonic energy, HIFU energy, radiation therapy, light energy, infrared energy, thermal energy, steam, hot water, magnetic fields, ionizing energy, other forms of electrical or electromagnetic energy or any other modality are used in conjunction with a non-invasive procedure to modulate or disrupt sympathetic nerve fibers.

In accordance with some embodiments, the neuromodulation system is used to modulate or disrupt sympathetic nerve fibers at one or more locations or target sites. For example, an ablation catheter system may perform ablation in a circumferential or radial pattern, and/or the ablation catheter system may perform ablation at a plurality of points linearly spaced apart along a vessel length. In other embodiments, an ablation catheter system performs ablation at one or more locations in any other pattern capable of causing disruption in the communication pathway of sympathetic nerve fibers (e.g., spiral patterns, zig-zag patterns, multiple linear patterns, etc.). The pattern can be continuous or non-continuous (e.g., intermittent). The ablation may be targeted at certain portions of the circumference of the vessels (e.g., half or portions less than half of the circumference). In some embodiments, modulation of the vessel is non-circumferential.

In accordance with embodiments of the invention disclosed herein, therapeutic neuromodulation to treat various medical disorders and diseases includes neural stimulation of targeted nerve fibers. For example, autonomic nerve fibers (e.g., sympathetic nerve fibers, parasympathetic nerve fibers) may be stimulated to treat, or reduce the risk of occurrence of, diabetes (e.g., diabetes mellitus) or other conditions, diseases and disorders.

In some embodiments, parasympathetic nerve fibers that innervate the liver are stimulated. In some embodiments, parasympathetic nerve fibers that innervate the pancreas, fat tissue (e.g., visceral fat of the liver), the adrenal glands, the stomach, the kidneys, brown adipose tissue, skeletal muscle, and/or the small intestine (e.g., duodenum) are stimulated. In accordance with some embodiments, any combination of parasympathetic nerve fibers innervating the liver, the pancreas, fat tissue, the adrenal glands, the stomach, the kidneys, brown adipose tissue, skeletal muscle, and the small intestine are stimulated to treat, or alleviate or reduce the risk of occurrence of the symptoms associated with, diabetes (e.g., diabetes mellitus) or other conditions, diseases, or disorders. In some embodiments, the organs or tissue are stimulated directly either internally or externally.

In some embodiments, a neurostimulator is used to stimulate sympathetic or parasympathetic nerve fibers. In some embodiments, the neurostimulator is implantable. In accordance with some embodiments, the implantable neurostimulator electrically stimulates parasympathetic nerve fibers. In some embodiments, the implantable neurostimulator chemically stimulates parasympathetic nerve fibers. In still other embodiments, the implantable neurostimulator uses any combination of electrical stimulation, chemical stimulation, or any other method capable of stimulating parasympathetic nerve fibers.

In other embodiments, non-invasive neurostimulation is used to effect stimulation of parasympathetic nerve fibers. For example, transcutaneous electrical stimulation may be used to stimulate parasympathetic nerve fibers. Other energy modalities can also be used to affect non-invasive neurostimulation of parasympathetic nerve fibers (e.g., light energy, ultrasound energy).

In some embodiments, neuromodulation of targeted autonomic nerve fibers treats diabetes (e.g., diabetes mellitus) and related conditions by decreasing systemic glucose. For example, therapeutic neuromodulation of targeted nerve fibers can decrease systemic glucose by decreasing hepatic glucose production. In some embodiments, hepatic glucose production is decreased by disruption (e.g., ablation) of sympathetic nerve fibers. In other embodiments, hepatic glucose production is decreased by stimulation of parasympathetic nerve fibers.

In some embodiments, therapeutic neuromodulation of targeted nerve fibers decreases systemic glucose by increasing hepatic glucose uptake. In some embodiments, hepatic glucose uptake is increased by disruption (e.g., ablation) of sympathetic nerve fibers. In other embodiments, hepatic glucose uptake is increased by stimulation of parasympathetic nerve fibers. In some embodiments, triglyceride or cholesterol levels are reduced by the therapeutic neuromodulation.

In some embodiments, disruption or modulation of the sympathetic nerve fibers of the hepatic plexus has no effect on the parasympathetic nerve fibers surrounding the liver. In some embodiments, disruption or modulation (e.g., ablation or denervation) of the sympathetic nerve fibers of the hepatic plexus causes a reduction of very low-density lipoprotein (VLDL) levels, thereby resulting in a beneficial effect on lipid profile. In several embodiments, the invention comprises neuromodulation therapy to affect sympathetic drive and/or triglyceride or cholesterol levels, including high-density lipoprotein (HDL) levels, low-density lipoprotein (LDL) levels, and/or very-low-density lipoprotein (VLDL) levels. In some embodiments, denervation or ablation of sympathetic nerves reduces triglyceride levels, cholesterol levels and/or central sympathetic drive.

In other embodiments, therapeutic neuromodulation of targeted nerve fibers (e.g., hepatic denervation) decreases systemic glucose by increasing insulin secretion. In some embodiments, insulin secretion is increased by disruption (e.g., ablation) of sympathetic nerve fibers (e.g., surrounding branches of the hepatic artery). In other embodiments, insulin secretion is increased by stimulation of parasympathetic nerve fibers. In some embodiments, sympathetic nerve fibers surrounding the pancreas may be modulated to decrease glucagon levels and increase insulin levels. In some embodiments, sympathetic nerve fibers surrounding the adrenal glands are modulated to affect adrenaline or noradrenaline levels. Fatty tissue (e.g., visceral fat) of the liver may be targeted to affect glycerol or free fatty acid levels. In some embodiments, insulin levels remain the same or increase or decrease by less than +5%, less than +10%, less than +2.5%, or overlapping ranges thereof. In some embodiments, insulin levels remain constant or substantially constant when a portion of the pancreas is ablated, either alone or in combination with the common hepatic artery or other hepatic artery branch. In various embodiments, denervation of nerves innervating the liver (e.g., sympathetic nerves surrounding the common hepatic artery) was found not to affect a subject's ability to respond to a hypoglycemic event.

In accordance with several embodiments of the invention, a method of decreasing blood glucose levels within a subject is provided. The method comprises forming an incision in a groin of a subject to access a femoral artery and inserting a neuromodulation device (e.g., catheter) into the incision. In some embodiments, the method comprises advancing the neuromodulation device from the femoral artery through an arterial system to a common or proper hepatic artery and causing a therapeutically effective amount of energy to thermally inhibit neural communication along a sympathetic nerve in a hepatic plexus surrounding the common or proper hepatic artery to be delivered intravascularly by the ablation catheter to the inner wall of the proper hepatic artery, thereby decreasing blood glucose levels within the subject. Other incision or access points may be used as desired or required.

In some embodiments, the neuromodulation device catheter (e.g., hollow, solid, partially hollow, catheter, probe, shaft or other delivery device with or without a lumen), is a radiofrequency (RF) ablation catheter comprising one or more electrodes. In some embodiments, the neuromodulation catheter is a high-intensity focused ultrasound ablation catheter. In some embodiments, the neuromodulation catheter is a cryoablation catheter. The method can further comprise stimulating one or more parasympathetic nerves associated with the liver to decrease hepatic glucose production or increase glucose uptake.

In accordance with several embodiments, a method of treating a subject having diabetes or symptoms associated with diabetes is provided. The method can comprise delivering an RF ablation catheter (e.g., hollow, solid, partially hollow, catheter, probe, shaft or other delivery device with or without a lumen) to a vicinity of a hepatic plexus of a subject and disrupting neural communication along a sympathetic nerve of the hepatic plexus by causing RF energy to be emitted from one or more electrodes of the RF ablation catheter. In some embodiments, the RF ablation catheter is delivered intravascularly through a femoral artery to a location within the proper or common hepatic artery branch. In some embodiments, the RF energy is delivered extravascularly by the RF ablation catheter.

In some embodiments, disrupting neural communication comprises permanently disabling neural communication along the sympathetic nerve of the hepatic plexus. In some embodiments, disrupting neural communication comprises temporarily inhibiting or reducing neural communication along the sympathetic nerve of the hepatic plexus. In some embodiments, disrupting neural communication along a sympathetic nerve of the hepatic plexus comprises disrupting neural communication along a plurality of sympathetic nerves of the hepatic plexus.

The method can further comprise positioning the RF ablation catheter in the vicinity of the celiac plexus of the subject and disrupting neural communication along a sympathetic nerve of the celiac plexus by causing RF energy to be emitted from one or more electrodes of the RF ablation catheter. In some embodiments, the method comprises positioning the RF ablation catheter in the vicinity of sympathetic nerve fibers that innervate the pancreas and disrupting neural communication along the sympathetic nerve fibers by causing RF energy to be emitted from one or more electrodes of the RF ablation catheter, positioning the RF ablation catheter in the vicinity of sympathetic nerve fibers that innervate the stomach and disrupting neural communication along the sympathetic nerve fibers by causing RF energy to be emitted from one or more electrodes of the RF ablation catheter, and/or positioning the RF ablation catheter in the vicinity of sympathetic nerve fibers that innervate the duodenum and disrupting neural communication along the sympathetic nerve fibers by causing RF energy to be emitted from one or more electrodes of the RF ablation catheter. In some embodiments, drugs or therapeutic agents can be delivered to the liver or surrounding organs or tissues.

In accordance with several embodiments, a method of decreasing blood glucose levels within a subject is provided. The method comprises inserting an RF ablation catheter (e.g., hollow, solid, partially hollow, catheter, probe, shaft or other delivery device with or without a lumen) into vasculature of the subject and advancing the RF ablation catheter to a location of a branch of a hepatic artery (e.g., the proper hepatic artery or the common hepatic artery). In one embodiment, the method comprises causing a therapeutically effective amount of RF energy to thermally inhibit neural communication within sympathetic nerves of a hepatic plexus surrounding the common or proper hepatic artery to be delivered intravascularly by the ablation catheter to the inner wall of the proper hepatic artery, thereby decreasing blood glucose levels within the subject. In some embodiments, the delivery of the therapeutically effective amount of RF energy to the common or proper hepatic artery also comprises delivery of energy sufficient to modulate (e.g., ablate, denervate) nerves of the pancreas and/or duodenum, which may provide a synergistic effect. In various embodiments, blood glucose levels decrease by 30-60% (e.g., 40-50%, 30-50%, 35-55%, 45-60% or overlapping ranges thereof) from a baseline level.

In one embodiment, the therapeutically effective amount of RF energy at the location of the inner vessel wall of the target vessel or at the location of the target nerves is in the range of between about 100 J and about 1 KJ (e.g., between about 100 J and about 500 J, between about 250 J and about 750 J, between about 300 J and about 1 kJ, between about 500 J and 1 kJ, or overlapping ranges thereof). In one embodiment, the therapeutically effective amount of RF energy has a power between about 0.1 W and about 14 W (e.g., between about 0.1 W and about 10 W, between about 0.5 W and about 5 W, between about 3 W and about 8 W, between about 2 W and about 6 W, between about 5 W and about 10 W, between about 8 W and about 12 W, between about 10 W and about 14 W, or overlapping ranges thereof). The ranges provided herein can be per electrode, per energy delivery location, or per total energy delivery. The RF energy may be delivered at one location or multiple locations along the target vessel or within multiple different vessels. In some embodiments, the RF energy is delivered sufficient to cause fibrosis of the tissue surrounding the nerves, thereby resulting in nerve dropout.

In one embodiment, the RF ablation catheter (e.g., hollow, solid, partially hollow, catheter, probe, shaft or other delivery device with or without a lumen) comprises at least one ablation electrode. The RF ablation catheter may be configured to cause the at least one ablation electrode to contact the inner wall of the hepatic artery branch and maintain contact against the inner wall with sufficient contact pressure while the RF energy is being delivered. In one embodiment, the RF ablation catheter comprises a balloon catheter configured to maintain sufficient and continuous contact pressure of the at least one electrode against the inner wall of the hepatic artery branch. In one embodiment, the RF ablation catheter comprises an actuatable (e.g., steerable, articulatable, expandable) distal tip configured to maintain sufficient contact pressure of the at least one electrode against the inner wall of the hepatic artery branch. In various embodiments, the sufficient contact pressure may range from about 0.1 g/mm$^2$ to about 100 g/mm$^2$ (e.g., between about 0.1 g/mm$^2$ and about 10 g/mm$^2$). In some embodiments, the RF ablation catheter comprises at least one anchoring member configured to maintain sufficient and continuous contact of the at least one electrode against the inner wall of the hepatic artery branch. The actuatable distal tip and/or anchoring member may comprise one or more flexible portions, one or more expandable members (e.g., balloons, ribbons, wires, struts), one or more steerable or articulatable members, one or more pre-curved shape memory portions, or combinations of the same. Expandable members may be self-expandable, mechanically expandable, pneumatically expandable, inflatable, or otherwise expandable.

In accordance with several embodiments, a method of treating a subject having diabetes or symptoms associated with diabetes is provided. In one embodiment, the method comprises delivering an RF ablation catheter to a vicinity of a hepatic plexus within a hepatic artery branch (e.g., proper hepatic artery, common hepatic artery or adjacent or within a bifurcation between the two). In one embodiment, the RF ablation catheter comprises at least one electrode. The method may comprise positioning the at least one electrode in contact with an inner wall of the hepatic artery branch. In one embodiment, the method comprises disrupting neural communication of sympathetic nerves of the hepatic plexus surrounding the hepatic artery branch by applying an electric signal to the at least one electrode, thereby causing thermal energy to be delivered by the at least one electrode to heat the inner wall of the hepatic artery branch. Non-ablative heating, ablative heating, or combinations thereof, are used in several embodiments.

In one embodiment, disrupting neural communication comprises permanently disabling neural communication of sympathetic nerves of the hepatic plexus. In one embodiment, disrupting neural communication comprises temporarily inhibiting or reducing neural communication along sympathetic nerves of the hepatic plexus. In some embodiments, the method comprises positioning the RF ablation catheter in the vicinity of the celiac plexus of the subject and disrupting neural communication along sympathetic nerves of the celiac plexus, positioning the RF ablation catheter in the vicinity of sympathetic nerve fibers that innervate the pancreas and disrupting neural communication along the sympathetic nerve fibers, positioning the RF ablation catheter in the vicinity of sympathetic nerve fibers that innervate the stomach and disrupting neural communication along the sympathetic nerve fibers, and/or positioning the RF ablation catheter in the vicinity of sympathetic nerve fibers that innervate the duodenum and disrupting neural communication along the sympathetic nerve fibers by causing RF energy to be emitted from the at least one electrode of the RF ablation catheter. In several embodiments, a feedback mechanism is provided to facilitate confirmation of neuromodulation and to allow for adjustment of treatment in real time. In one embodiment, ultrasound elastography, ultrasound sonography, echo decorrelation, Doppler ultrasound, magnetic resonance elastography, and/or computed tomography is used to track progress or status of neuromodulation (e.g., ablation) procedures or methods (such as the methods described herein).

In accordance with several embodiments, a method of treating a subject having diabetes or symptoms associated with diabetes (e.g., high blood glucose or triglyceride levels) is provided. In one embodiment, the method comprises delivering a neuromodulation catheter within a hepatic artery to a vicinity of a hepatic plexus of a subject and modulating nerves of the hepatic plexus by causing RF energy to be emitted from one or more electrodes of the neuromodulation catheter. In one embodiment, the step of modulating the nerves of the hepatic plexus comprises denervating sympathetic nerves of the hepatic plexus and/or stimulating parasympathetic nerves of the hepatic plexus. In one embodiment, the sympathetic denervation and the parasympathetic stimulation are performed simultaneously. In one embodiment, the sympathetic denervation and the parasympathetic stimulation are performed sequentially. In one embodiment, sympathetic nerves are modulated without modulating parasympathetic nerves surrounding the same vessel or tissue.

In accordance with several embodiments, an apparatus configured for hepatic neuromodulation is provided. In one embodiment, the apparatus comprises a balloon catheter configured for intravascular placement within one or more hepatic artery branches or adjacent artery branches. In one embodiment, the balloon catheter comprises at least one expandable balloon and a bipolar electrode pair. In one embodiment, at least one of the bipolar electrode pair is configured to be positioned to be expanded into contact with an inner wall of the hepatic artery branch upon expansion of the at least one expandable balloon. In one embodiment, the bipolar electrode pair is configured to deliver a thermal dose of energy configured to achieve hepatic denervation. The at least one expandable balloon may be configured to maintain sufficient contact pressure (e.g., continuous contact pressure) between the at least one electrode of the bipolar electrode pair and the inner wall of the hepatic artery branch. In some embodiments, the balloon catheter comprises two expandable balloons, each having one electrode of the bipolar electrode pair disposed thereon. In one embodiment, the balloon catheter comprises a single expandable balloon and the bipolar electrode pair is disposed on the expandable balloon. In one embodiment, the balloon comprises a cooling fluid within a lumen of the balloon.

In accordance with several embodiments, an apparatus configured for hepatic neuromodulation is provided. In one embodiment, the apparatus comprises a catheter comprising a lumen and an open distal end and a steerable shaft configured to be slidably received within the lumen of the catheter. In one embodiment, at least a distal portion of the steerable shaft comprises a shape memory material having a pre-formed shape configured to cause the distal portion of the steerable shaft to change in linear shape (e.g., bend) to contact a vessel wall upon advancement of the distal portion of the steerable shaft out of the open distal end of the catheter. In one embodiment, a distal end of the steerable shaft comprises at least one electrode that is configured to be activated to deliver a thermal dose of energy configured to achieve denervation of a branch of a hepatic artery or other target vessel. In one embodiment, the shape memory material of the steerable shaft is sufficiently resilient to maintain sufficient and continuous contact pressure between the at least one electrode and an inner wall of the branch of the hepatic artery during a hepatic denervation procedure. The outside diameter at a distal end of the catheter may be smaller than the outside diameter at a proximal end of the catheter to accommodate insertion within vessels having a small inner diameter. In various embodiments, the outside diameter at the distal end of the catheter is between about 1 mm and about 4 mm (e.g., 1 mm-3 mm, 1 mm, 2 mm, 3 mm, 4 mm, less than or equal to 3 mm). In one embodiment, the at least one electrode comprises a coating having one or more windows. For embodiments to be used in the hepatic arteries, the steerable shaft of the catheter can be actuated to have multiple bends (e.g., two, three, or more bends) configured to conform to two or more bends in the hepatic artery branches or neighboring arteries. In some embodiments, one or more portions of the catheter are pre-curved to have a particular bend shape. In some embodiments, one of the multiple bends is pre-formed and one of the multiple bends is actuated during delivery. In some embodiments, an energy delivery device (e.g., catheter) comprises a distal portion constructed of shape memory material and a lumen configured to receive a guidewire. The shape memory material may be heat- or shape-set so as to cause a distal end of the energy delivery device (which may include an energy delivery element such as an electrode) to contact an inner wall of a target vessel. A guidewire may retain the distal portion of the energy delivery device in a straight or substantially straight alignment until the distal portion is positioned in a desired position within the target vessel. When the guidewire is withdrawn from the lumen of the energy delivery device, the shape-memory distal portion deforms to the heat- or shape-set configuration so as to cause the distal end of the energy delivery device to contact the inner wall of the target vessel.

In accordance with several embodiments, a neuromodulation kit is provided. In one embodiment, the kit comprises a neuromodulation catheter configured to be inserted within a vessel of the hepatic system for modulating nerves surrounding the hepatic artery. In one embodiment, the kit comprises a plurality of energy delivery devices configured to be inserted within the lumen of the neuromodulation catheter. In one embodiment, each of the energy delivery devices comprises at least one modulation element at or near a distal end of the energy delivery device. In one embodiment, each of the energy delivery devices comprises a distal portion comprising a different pre-formed shape memory configuration. The at least one modulation element may be configured to be activated to modulate at least a portion of the nerves surrounding the hepatic artery to treat symptoms associated with diabetes.

In several embodiments, the invention comprises modulation of the nervous system to treat disorders affecting insulin and/or glucose, such as insulin regulation, glucose uptake, metabolism, etc. In some embodiments, nervous system input and/or output is temporarily or permanently modulated (e.g., decreased). Several embodiments are configured to perform one or a combination of the following effects: ablating nerve tissue, heating nerve tissue, cooling the nerve tissue, deactivating nerve tissue, severing nerve tissue, cell lysis, apoptosis, and necrosis. In some embodiments, localized neuromodulation is performed, leaving surrounding tissue unaffected. In other embodiments, the tissue surrounding the targeted nerve(s) is also treated.

In accordance with several embodiments, methods of hepatic denervation are performed with shorter procedural and energy application times than renal denervation procedures. In several embodiments, hepatic denervation is performed without causing pain or mitigates pain to the subject during the treatment. In accordance with several embodiments, neuromodulation (e.g., denervation or ablation) is performed without causing stenosis or thrombosis within the target vessel (e.g., hepatic artery). In embodiments involving thermal treatment, heat lost to the blood stream may be prevented or reduced compared to existing denervation systems and methods, resulting in lower power and shorter treatment times. In various embodiments, the methods of neuromodulation are performed with little or no endothelial damage to the target vessels. In several embodiments, energy delivery is delivered substantially equally in all directions (e.g., omnidirectional delivery). In various embodiments of neuromodulation systems (e.g., catheter-based energy delivery systems described herein), adequate electrode contact with the target vessel walls is maintained, thereby reducing power levels, voltage levels, vessel wall or tissue thermal injury, and treatment times.

In accordance with several embodiments, a method for thermally-induced hepatic neuromodulation is provided. The method comprises inserting a neuromodulation catheter (e.g., RF ablation catheter) into vasculature of a subject. In one embodiment, the neuromodulation catheter is configured to form a first bend to conform to, or be positioned to correspond with, a first anatomical bend of a first hepatic artery portion or a first artery branching into or out from a hepatic artery and is configured to form a second bend to conform to a second anatomical bend of a second hepatic artery portion or a second artery branching into or out from the hepatic artery. The first bend and/or second bend may be formed by mechanical actuation, magnetic actuation, material actuation, pneumatic actuation, hydraulic actuation, inflation, self-expansion, or the like. In one embodiment, the neuromodulation catheter, the first bend and/or second bend is pre-bent or pre-curved. Although several catheters and other access/delivery devices are disclosed herein that are designed (e.g., in shape, size, flexibility, etc.) for the hepatic artery, such catheters and other access/delivery devices can also be used for other arteries and vessels, and in particular, other arteries and vessels that are tortuous.

In some embodiments, the neuromodulation catheter is advanced to a location within a hepatic artery of the vasculature or to a location upstream of the hepatic artery (e.g., within the aorta or celiac trunk or axis). The first bend may be formed and/or aligned with a first anatomical bend (e.g., an acute bend between the aorta or celiac trunk and the common hepatic artery, or a first bend within the common hepatic artery). The second bend may be formed and/or aligned with a second anatomical bend (e.g., an acute bend between the common hepatic artery and the proper hepatic artery or gastroduodenal artery, or a second bend within the common hepatic artery). In some embodiments, the neuromodulation catheter is activated or otherwise caused to intravascularly deliver a therapeutically effective amount of energy (e.g., RF energy, thermal energy, ultrasound energy) to an inner wall of the hepatic artery to modulate (e.g., denervate, ablate, injure, stimulate) one or more sympathetic nerves of a hepatic plexus.

In one embodiment, the neuromodulation catheter comprises an RF ablation catheter having at least one electrode. The RF ablation catheter may advantageously be configured to maintain sufficient contact pressure of the at least one electrode against an inner arterial wall of the hepatic artery while RF energy is being delivered. In one embodiment, the RF ablation catheter comprises a balloon catheter configured to maintain the sufficient contact pressure of the at least one electrode against the inner arterial wall of the hepatic artery. In one embodiment, the RF ablation catheter comprises an actuatable distal portion configured to conform to the first anatomical bend and the second anatomical bend during said advancing of the RF ablation catheter to a location within a hepatic artery. In one embodiment, the actuatable distal portion comprises shape memory material configured to form the first bend and the second bend. In one embodiment, the actuatable distal portion is configured to be mechanically expanded by one or more pull wires to form the first bend and the second bend. In one embodiment, the first bend and the second bend together from an S-shape.

In one embodiment, the sufficient contact pressure is between about 0.1 g/mm$^2$ and about 100 g/mm$^2$ (e.g., between about 0.1 g/mm$^2$ and about 10 g/mm$^2$, between about 5 g/mm$^2$ and about 20 g/mm$^2$, between about 1 g/mm$^2$ and about 50 g/mm$^2$, or overlapping ranges thereof). In one embodiment, the therapeutically effective amount of RF energy is in the range of between about 300 J and about 1.5 kJ (e.g., about 300 J to about 1 kJ) per target location or total for all target locations. The therapeutically effective amount of RF energy may have a power level between about 0.1 W and about 14 W (e.g., between about 0.1 W and about 10 W, between about 3 W and about 8 W, between about 3 W and about 10 W) per target location.

In some embodiments, the method comprises providing cooling to a portion of the common hepatic artery that is or is not being targeted by the RF energy or to the at least one electrode. In one embodiment, cooling comprises infusing saline within the catheter or within the blood flow adjacent the at least one electrode. In one embodiment, cooling comprises obstructing flow upstream of the at least one electrode to increase the arterial flow rate past the at least one electrode, thereby providing convective cooling due to increased blood flow. In some embodiments, flow is diverted or channeled toward the at least one electrode (e.g., from a center of the vessel toward a wall of the vessel).

In accordance with several embodiments, a device for thermally-induced hepatic neuromodulation is provided. The device comprises a catheter body having a proximal end and a distal end and a lumen extending from the proximal end to the distal end. In one embodiment, the catheter body is configured for percutaneous, intravascular placement within a hepatic artery branch. The device may comprise an actuatable portion at the distal end of the catheter body and at least one electrode disposed on the actuatable portion. In some embodiments, the actuatable portion is configured to provide stabilization of the catheter within the hepatic artery branch and to facilitate contact of the at least one electrode with an inner arterial wall of hepatic artery branch. The at least one electrode may be configured to be activated to deliver thermal energy sufficient to achieve modulation (e.g., denervation, ablation, stimulation) of at least a portion of the hepatic artery branch (e.g., a segment of the common hepatic artery having a length of 30 mm or less, 24 mm or less, 20 mm or less, or between 20 m and 30 mm). The at least one electrode may be repositioned and activated at multiple positions along the length of and/or around the circumference of the hepatic artery branch. The at least one electrode may comprise one or more monopolar electrodes or one or more bipolar electrode pairs. In embodiments involving multiple electrodes, modulation at different locations or positions may be performed simultaneously.

In one embodiment, the actuatable portion comprises an inflatable balloon. In one embodiment, the actuatable portion comprises a deflectable bend segment having a pre-formed bend shape such that the distal end of the catheter body bends off-axis relative to a longitudinal axis of the proximal portion of the catheter body. In one embodiment, the actuatable portion comprises shape memory material having one or more pre-formed bend shapes. In one embodiment, the actuatable portion comprises one or more flexible bend segments configured to be actuated by one or more pull wires to form one or more bend shapes to conform to anatomical bends within the hepatic artery branch or to facilitate access to the hepatic artery branch. In one embodiment, the actuatable portion comprises one or more flexible ribbon wires or cables configured to be expanded outward to contact the inner arterial wall of the hepatic artery branch at a target location with the at least one electrode disposed on at least one of said one or more flexible ribbon wires or cables. The actuatable portion may comprise a plurality of independently actuatable members. In various embodiments, the actuatable portion(s) comprises one or more of the following: shape-memory material, flexible bend segments, ribbon wires or cables, expandable members, and inflatable members. In one embodiment, the device comprises an outer sheath and the catheter body (e.g., probe or shaft) is configured to be delivered within a lumen of the outer sheath and is translatable relative to the outer sheath. In one embodiment, the outer sheath is deflectable. In one embodiment, articulation of a first bend segment is controlled by a first pull wire and articulation of a second bend segment is controlled by a second pull wire. In one embodiment, a first flexible bend segment is configured to conform to a first arterial bend upon actuation and a second flexible bend segment is configured to conform to a second arterial bend. The first bend segment and the second segment may together form an S-shape upon actuation. In one embodiment, the device comprises an obstruction element configured to be positioned adjacent the at least one electrode to increase arterial flow past the electrode, thereby facilitating cooling of the at least one electrode. The at least one electrode may comprise a plurality of electrodes configured to deliver thermal energy to multiple locations within the hepatic artery branch simultaneously or sequentially. The target locations may be spaced apart along a length of a target segment of the hepatic artery (e.g., segment of less than 30 mm length, 20 mm to 30 mm length, less than 24 mm length, etc.). In some embodiment, an apparatus for neuromodulation includes an elongate body having a proximal end and a distal end that is configured for percutaneous, intravascular placement within a tortuous artery. The apparatus may also include an actuatable portion at the distal end of the elongate body. The apparatus may include at least one electrode disposed on the actuatable portion that is configured to provide stabilization within the tortuous artery and configured to facilitate contact of the at least one electrode with an inner wall of the tortuous artery. In one embodiment, the at least one electrode is configured to be activated to deliver thermal energy sufficient to achieve denervation of at least a portion of the tortuous artery. The actuatable portion may comprise one or more flexible bend segments configured to be actuated by one or more pull wires to form one or more bend shapes to conform to anatomical bends within the artery or to facilitate access to the tortuous artery, wherein a first flexible bend segment is configured to conform to a first arterial bend upon actuation, and wherein a second flexible bend segment is configured to conform to a second arterial bend upon actuation. In some embodiments, articulation of the first flexible bend segment is controlled by a first pull wire and articulation of the second flexible bend segment is controlled by a second pull wire. The apparatus may further include an outer sheath, wherein the elongate body is configured to be delivered within a lumen of the outer sheath and is translatable relative to the outer sheath. The elongate body may include a lumen configured to track a guidewire to facilitate access. In one embodiment, the elongate body comprises a third and/or fourth bend. In one embodiment, the elongate body further comprises a pre-formed bend shape.

In accordance with several embodiments, a method for thermally-induced hepatic neuromodulation is provided to decrease blood glucose and/or triglyceride levels within a subject. In one embodiment, the method comprises identifying a subject having a metabolic disorder and inserting an RF ablation catheter into vasculature of the subject. In one embodiment, the method comprises advancing the RF ablation catheter to a location within a common hepatic artery of the vasculature. The location may be within the common hepatic artery between a branch of the celiac artery and a branch of the common hepatic artery. In one embodiment, the RF ablation catheter is used to intravascularly deliver a therapeutically effective amount of RF energy to an inner wall of the common hepatic artery to ablate one or more sympathetic nerves of a hepatic plexus, thereby decreasing blood glucose and/or triglyceride levels within the subject. In one embodiment, the RF ablation catheter comprises two electrodes. The RF ablation catheter may advantageously be configured to maintain sufficient contact pressure of at least one of the two electrodes (e.g., an active electrode) against the inner wall of the common hepatic artery while the RF energy is being delivered. In one embodiment, the ablation catheter comprises a balloon catheter configured to maintain the sufficient contact pressure of the at least one electrode against the inner wall of the common hepatic artery. In one embodiment, the ablation catheter comprises a steerable distal tip configured to maintain sufficient contact pressure of the at least one electrode against the inner wall of the common hepatic artery. The sufficient contact pressure may be between about 5 g/mm$^2$ and about 100 g/mm$^2$ or between about 0.1 g/mm$^2$ and about 10 g/mm$^2$. In one embodiment, the RF energy is caused to be delivered to an anterior 180° arc of the inner wall of the common hepatic artery, thereby ablating sympathetic nerves without ablating parasympathetic nerves. In some embodiments, the ablation catheter comprises a force sensor or transducer for measuring the contact force of the at least one electrode against the inner wall of the common hepatic artery.

In one embodiment, a method for thermally-induced hepatic neuromodulation to decrease blood glucose and/or triglyceride levels within a subject is provided. The method comprises delivering an RF ablation catheter comprising two electrodes to a vicinity of a hepatic plexus within a hepatic artery branch, positioning at least one of the two electrodes in contact with an inner wall of the hepatic artery branch and disrupting neural communication of sympathetic nerves of the hepatic plexus surrounding the hepatic artery branch by applying an electric signal to the at least one electrode, thereby causing thermal energy to be delivered by the at least one electrode to heat the inner wall of the hepatic artery branch. The hepatic artery branch may be the proper hepatic artery or the common hepatic artery. In various embodiments, disrupting neural communication comprises permanently disabling neural communication of sympathetic nerves of the hepatic plexus or temporarily inhibiting or reducing neural communication of sympathetic nerves of the hepatic plexus. In one embodiment, the method comprises positioning the RF ablation catheter in the vicinity of the celiac plexus of the subject and disrupting neural communication of sympathetic nerves of the celiac plexus by causing RF energy to be emitted from the at least one electrode of the RF ablation catheter.

In one embodiment, a method for thermally-induced hepatic neuromodulation to decrease blood glucose and/or triglyceride levels within a subject comprises delivering a neuromodulation catheter within a hepatic artery to a vicinity of a hepatic plexus of a subject; and modulating nerves of the hepatic plexus by using said catheter to deliver energy to the hepatic plexus sufficient to modulate one or more nerves within the hepatic plexus to decrease at least one of blood glucose levels or triglyceride levels in said subject. In one embodiment, modulating the nerves of the hepatic plexus comprises denervating sympathetic nerves of the hepatic plexus without denervating parasympathetic nerves of the hepatic plexus. In one embodiment, modulating the nerves of the hepatic plexus comprises denervating sympathetic nerves of the hepatic plexus and stimulating parasympathetic nerves of the hepatic plexus.

In accordance with several embodiments, a device for hepatic neuromodulation is provided. In one embodiment, the device comprises a catheter body having a proximal end and a distal end and a lumen extending from the proximal end to the distal end and the catheter body is configured for percutaneous, intravascular placement within a hepatic artery branch. In one embodiment, the device comprises an articulatable portion at the distal end of the catheter body and at least one articulation member (e.g., wire) extending from the proximal end of the body and being coupled to the articulatable portion. The at least one articulation wire may be configured to bend the articulatable portion at the distal end of the catheter body. In one embodiment, the articulatable portion and/or a region distal to the articulatable portion comprises one or more RF electrodes, wherein at least one of the RF electrodes is configured to be activated to deliver RF energy sufficient to achieve denervation of the hepatic artery branch, thereby decreasing blood glucose and/or triglyceride levels within the subject. In one embodiment, the distal portion of the catheter body comprises a deflectable bend segment having a preformed bend shape such that the distal end of the catheter body bends off-axis relative to a longitudinal axis of the proximal portion of the catheter body such that the articulatable portion and the deflectable bend segment facilitate treatment within variable and tortuous anatomy of the hepatic artery. In one embodiment, the articulatable portion is configured to apply and maintain contact pressure between the at least one active RF electrode and an inner arterial wall of the hepatic artery branch, thereby facilitating continuous contact as the hepatic artery branch moves in response to diaphragm motion. In one embodiment, the contact pressure is between about 5 g/mm$^2$ and about 100 g/mm$^2$ and the RF energy configured to be delivered to achieve denervation of the hepatic artery branch is between about 100 J and about 1 kJ.

In one embodiment, the catheter body has a length sufficient to extend from a radial or femoral artery to the hepatic artery branch and the distal end of the catheter body has an outside diameter sized to fit within the hepatic artery branch. In some embodiments, the catheter body has a length sufficient to extend from a femoral artery or a radial artery to an arterial branch supplying the pancreas, duodenum, stomach, liver, or other gastrointestinal organs. In one embodiment, the device comprises an outer sheath and the catheter body is configured to be delivered within a lumen of the outer sheath and is translatable relative to the outer sheath. In one embodiment, the deflectable bend segment of the catheter body is configured to transition to the preformed bend shape upon retraction of the outer sheath or upon advancement of the distal end of the catheter body out of the outer sheath. In one embodiment, the outer sheath is deflectable. In one embodiment, the device comprises two radiopaque markers positioned along the distal end of the catheter body configured to be used to adjust the contact pressure. In one embodiment, the articulatable portion comprises a plurality of independently controllable bending segments. In one embodiment, the preformed bend shape of the deflectable bend segment is configured to correspond to a bend between a celiac artery or aorta and a common hepatic artery. Various embodiments of RF ablation catheters and methods of use provide decreased ablation times and decreased lumenal injury while providing heat to ablate nerves.

In accordance with several embodiments, a device for hepatic neuromodulation is provided. In one embodiment, the device comprises a catheter body having a proximal end and a distal end and a lumen extending from the proximal end to the distal end and the catheter body is configured for percutaneous, intravascular placement within a hepatic artery branch. In one embodiment, the device comprises an articulatable portion at the distal end of the catheter body comprising two independently controllable bending segments configured to be individually articulated by two articulation members (e.g., wires) extending from the proximal end of the catheter body to the two independently controllable bending segments. In one embodiment, the two independently controllable bending segments together comprise two or more electrodes, wherein at least one of the RF electrodes is configured to be activated to deliver RF energy sufficient to achieve denervation of the hepatic artery branch, thereby decreasing blood glucose and/or triglyceride levels within the subject. In one embodiment, articulation of a first bending segment of the two independently controllable bending segments is controlled by a first articulation wire and wherein articulation of a second bending segment of the two independently controllable bending segments is controlled by a second articulation wire. The first bending segment may be configured to articulate to conform to a first arterial bend, and wherein the second bending segment is configured to conform to a second arterial bend.

In accordance with several embodiments, a device for thermally-induced hepatic neuromodulation is provided. In one embodiment, the device comprises a catheter body having a proximal end and a distal end and a lumen extending from the proximal end to the distal end and the catheter body is configured for percutaneous, intravascular placement within a hepatic artery branch. In one embodiment, the catheter body has a length sufficient to extend from a femoral artery to the hepatic artery branch and the distal end of the catheter body has an outside diameter sized to fit within the hepatic artery branch. The distal end of the catheter body may comprise a deflectable bend segment having a preformed bend shape such that the distal end of the catheter body bends off-axis relative to a longitudinal axis of the proximal portion of the catheter body. The deflectable bend segment and/or a region distal to the bend segment may comprise one or more electrodes, wherein at least one of the RF electrodes is configured to be activated to deliver RF energy sufficient to achieve denervation of the hepatic artery branch. In one embodiment, the deflectable bend segment is configured to apply and maintain contact pressure between the at least one active RF electrode and an inner arterial wall of the hepatic artery branch, thereby facilitating continuous contact as the hepatic artery branch moves in response to diaphragm motion and thereby facilitating treatment within variable and tortuous anatomy of the hepatic artery. In one embodiment, the device comprises an outer sheath and the catheter body is configured to be delivered within a lumen of the outer sheath and is translatable relative to the outer sheath. The deflectable bend segment may be configured to transition to the preformed bend shape upon retraction of the outer sheath or upon advancement of the distal end of the catheter body out of the outer sheath.

In accordance with several embodiments, an apparatus for hepatic neuromodulation is provided that includes a shaft comprising a proximal end, a distal end and a lumen and an electrode positioned at a distal tip of the distal end of the shaft. In one embodiment, the shaft comprises a first region, a second region and a third region. The first region may comprise a resiliently deformable region proximal to the electrode, the second region may comprise an articulatable region proximal to the resiliently deformable region and the third region may comprise a torsionally rigid region proximal to the articulatable region. In some embodiments, at least one of the first region, the second region and the third region is configured to navigate a tortuosity of a hepatic artery. The apparatus may include a pull wire extending from a distal end of the articulatable region to the proximal end of the shaft, the pull wire configured to articulate the electrode at the distal tip toward an inner wall of the hepatic artery and maintain a consistent contact force of the electrode against the inner wall, wherein the electrode is configured to be activated to deliver energy sufficient to achieve denervation of at least a portion of the hepatic artery. In one embodiment, the diameter of the electrode is equal to the length of the electrode. In one embodiment, the torsionally rigid region is flexible and the torsionally rigid region is torsionally rigid in at least one direction. The articulatable region may be configured to provide a cantilever support to facilitate maintenance of the consistent electrode contact force. The length of the articulatable region may be between 0.5 and 2 cm. In one embodiment, the shaft comprises a hypotube and the torsionally rigid region comprises an interrupted spiral cut pattern that varies along a length of the torsionally rigid region. In one embodiment, the articulatable region comprises a spine cut pattern and/or is configured to provide 180-degree articulation.

In accordance with several embodiments, a neuromodulation catheter is provided. The catheter comprises a first end, a second end and a lumen extending from the first end to the second end. In one embodiment, the catheter comprises a balloon disposed at the distal end. The balloon may be disposed about substantially the entire circumference of the catheter (e.g., between 80% and 90%, between 75% and 85%, between 85% and 95%, or overlapping ranges thereof). In one embodiment, the catheter comprises an electrode disposed at a region of the catheter not covered by the balloon. Inflation of the balloon may be effective to occlude a portion of the cross-sectional area of an artery or other vessel into which the catheter is placed, thereby increasing the blood flow velocity around the electrode. In one embodiment, the electrode is configured to deliver energy sufficient to cause denervation of one or more sympathetic nerves surrounding the artery or other vessel. In some embodiments, an apparatus adapted for neuromodulation of nerves surrounding a vessel lumen comprises a tubular shaft comprising a first end, a second end and a lumen extending from the first end to the second end. The apparatus may comprise a balloon positioned at the distal end of the shaft, the balloon configured to transition from a deflated configuration to an inflated configuration through introduction of fluid through the lumen of the shaft. When in the inflated configuration, the balloon may be disposed around between 85% and 95% of a circumference of the shaft. The apparatus may comprise an electrode positioned at a location of the shaft that is not covered by the balloon. In the inflated configuration the balloon may occlude a portion of a cross-sectional area of a vessel, thereby increasing blood flow velocity around the electrode. In one embodiment, the electrode is configured to deliver energy sufficient to cause denervation of one or more sympathetic nerves surrounding the vessel. In some embodiments, the apparatus comprises a plurality of electrodes positioned along a length of the shaft that is not covered by the balloon.

For purposes of summarizing the disclosure, certain aspects, advantages, and novel features of embodiments of the invention have been described herein. It is to be understood that not necessarily all such advantages may be achieved in accordance with any particular embodiment of the invention disclosed herein. Thus, the embodiments disclosed herein may be embodied or carried out in a manner that achieves or optimizes one advantage or group of advantages as taught or suggested herein without necessarily achieving other advantages as may be taught or suggested herein. The methods summarized above and set forth in further detail below describe certain actions taken by a practitioner; however, it should be understood that they can also include the instruction of those actions by another party. Thus, actions such as "delivering a neuromodulation catheter within a hepatic artery" include "instructing the delivery of a neuromodulation catheter within a hepatic artery." With respect to the drawings, elements from one figure may be combined with elements from the other figures.

BRIEF DESCRIPTION OF THE DRAWINGS

FIGS. 14C-1, 14C-2, 14D, 14E, 14F, 14G, 14H-1, 14H-2, 14I-1, 14I-2, 14I-3, 14I-4, 14J-1, 14J-2 and 14K Illustrate various embodiments of energy delivery devices configured to facilitate maintained contact of an energy delivery member (e.g., an electrode) against a vessel wall (e.g., a wall of a common hepatic artery) despite motion due to respiration or blood flow.

FIGS. 64A-1, 64A-2, 64B and 65 illustrate graphs of data from hepatic denervation studies, in accordance with embodiments of the invention.

FIG. 66 illustrates the effect on liver norepinephrine levels following a hepatic denervation procedure during an animal study.

FIGS. 82A-95 illustrate embodiments of catheter systems and associated methods configured to provide catheter stabilization and/or electrode cooling.

DETAILED DESCRIPTION

I. Introduction and Overview

Figure 1:
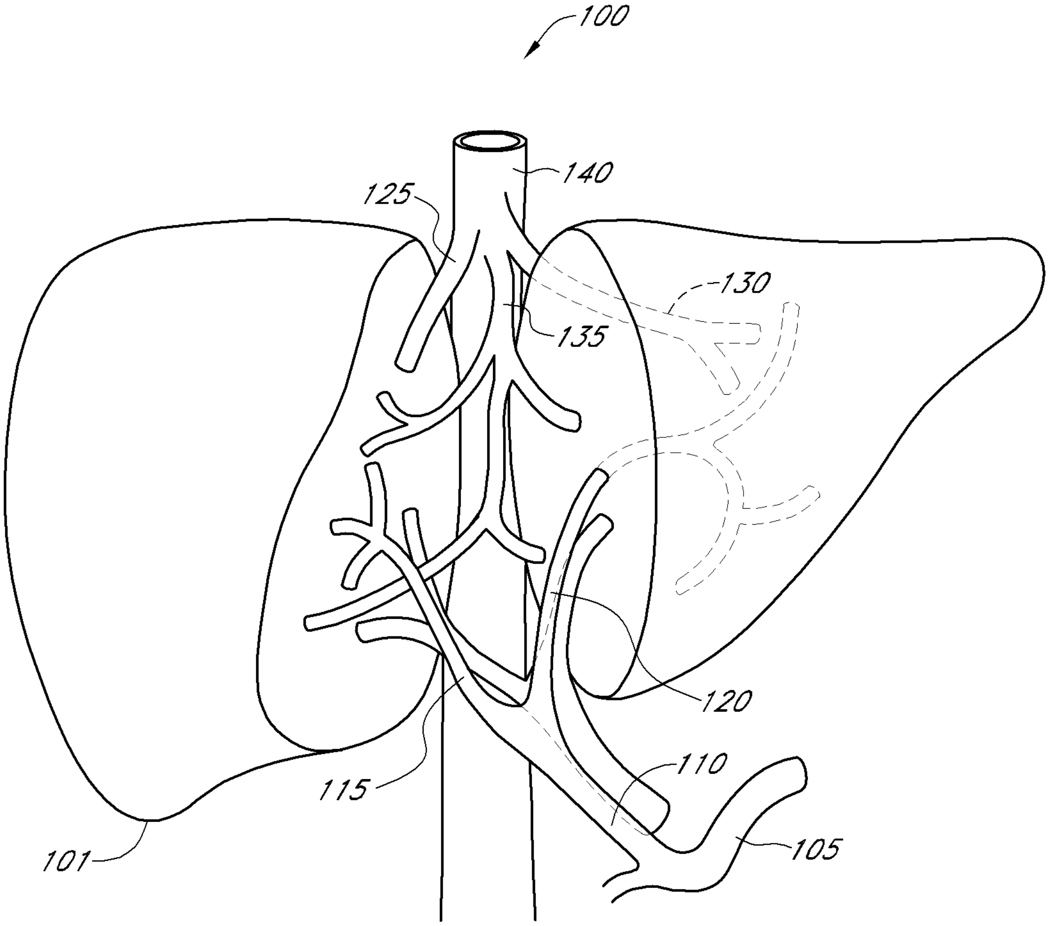
FIG. 1 illustrates the anatomy of a target treatment location including the liver and hepatic blood supply, in accordance with an embodiment of the invention.

Embodiments of the invention described herein are generally directed to therapeutic neuromodulation of targeted nerve fibers to treat, or reduce the risk of occurrence or progression of, various metabolic diseases, conditions, or disorders, including but not limited to diabetes (e.g., diabetes mellitus). While the description sets forth specific details in various embodiments, it will be appreciated that the description is illustrative only and should not be construed in any way as limiting the disclosure. Furthermore, various applications of the disclosed embodiments, and modifications thereto, which may occur to those who are skilled in the art, are also encompassed by the general concepts described herein.

The autonomic nervous system includes the sympathetic and parasympathetic nervous systems. The sympathetic nervous system is the component of the autonomic nervous system that is responsible for the body's "fight or flight" responses, those that can prepare the body for periods of high stress or strenuous physical exertion. One of the functions of the sympathetic nervous system, therefore, is to increase availability of glucose for rapid energy metabolism during periods of excitement or stress, and to decrease insulin secretion.

The liver can play an important role in maintaining a normal blood glucose concentration. For example, the liver can store excess glucose within its cells by forming glycogen, a large polymer of glucose. Then, if the blood glucose concentration begins to decrease too severely, glucose molecules can be separated from the stored glycogen and returned to the blood to be used as energy by other cells. The liver is a highly vascular organ that is supplied by two independent blood supplies, one being the portal vein (as the liver's primary blood supply) and the other being the hepatic artery (being the liver's secondary blood supply).

The process of breaking down glycogen into glucose is known as glycogenolysis, and is one way in which the sympathetic nervous system can increase systemic glucose. In order for glycogenolysis to occur, the enzyme phosphorylase must first be activated in order to cause phosphorylation, which allows individual glucose molecules to separate from branches of the glycogen polymer. One method of activating phosphorylase, for example, is through sympathetic stimulation of the adrenal medulla. By stimulating the sympathetic nerves that innervate the adrenal medulla, epinephrine is released. Epinephrine then promotes the formation of cyclic AMP, which in turn initiates a chemical reaction that activates phosphorylase. An alternative method of activating phosphorylase is through sympathetic stimulation of the pancreas. For example, phosphorylase can be activated through the release of the hormone glucagon by the alpha cells of the pancreas. Similar to epinephrine, glucagon stimulates formation of cyclic AMP, which in turn begins the chemical reaction to activate phosphorylase.

Another way in which the liver functions to maintain a normal blood glucose concentration is through the process of gluconeogenesis. When the blood glucose concentration decreases below normal, the liver will synthesize glucose from various amino acids and glycerol in order to maintain a normal blood glucose concentration. Increased sympathetic activity has been shown to increase gluconeogenesis, thereby resulting in an increased blood glucose concentration.

The parasympathetic nervous system is the second component of the autonomic nervous system and is responsible for the body's "rest and digest" functions. These "rest and digest" functions complement the "fight or flight" responses of the sympathetic nervous system. Stimulation of the parasympathetic nervous system has been associated with decreased blood glucose levels. For example, stimulation of the parasympathetic nervous system has been shown to increase insulin secretion from the beta-cells of the pancreas. Because the rate of glucose transport through cell membranes is greatly enhanced by insulin, increasing the amount of insulin secreted from the pancreas can help to lower blood glucose concentration. In some embodiments, stimulation of the parasympathetic nerves innervating the pancreas is combined with denervation of sympathetic nerves innervating the liver to treat diabetes or the symptoms associated with diabetes (e.g., high blood glucose levels, high triglyceride levels, high cholesterol levels, low insulin secretion levels). Stimulation and/or denervation of sympathetic and/or parasympathetic nerves surrounding other organs or tissues may also be performed in combination.

FIG. 1 illustrates a liver 101 and vasculature of a target hepatic treatment location 100. The vasculature includes the common hepatic artery 105, the proper hepatic artery 110, the right hepatic artery 115, the left hepatic artery 120, the right hepatic vein 125, the left hepatic vein 130, the middle hepatic vein 135, and the inferior vena cava 140. In the hepatic blood supply system, blood enters the liver by coursing through the common hepatic artery 105, the proper hepatic artery 110, and then either of the left hepatic artery 120 or the right hepatic artery 115. The right hepatic artery 115 and the left hepatic artery 120 (as well as the portal vein, not shown) provide blood supply to the liver 101, and directly feed the capillary beds within the hepatic tissue of the liver 101. The liver 101 uses the oxygen provided by the oxygenated blood flow provided by the right hepatic artery 115 and the left hepatic artery 120. Deoxygenated blood from the liver 101 leaves the liver 101 through the right hepatic vein 125, the left hepatic vein 130, and the middle hepatic vein 135, all of which empty into the inferior vena cava 140.

Figure 2:
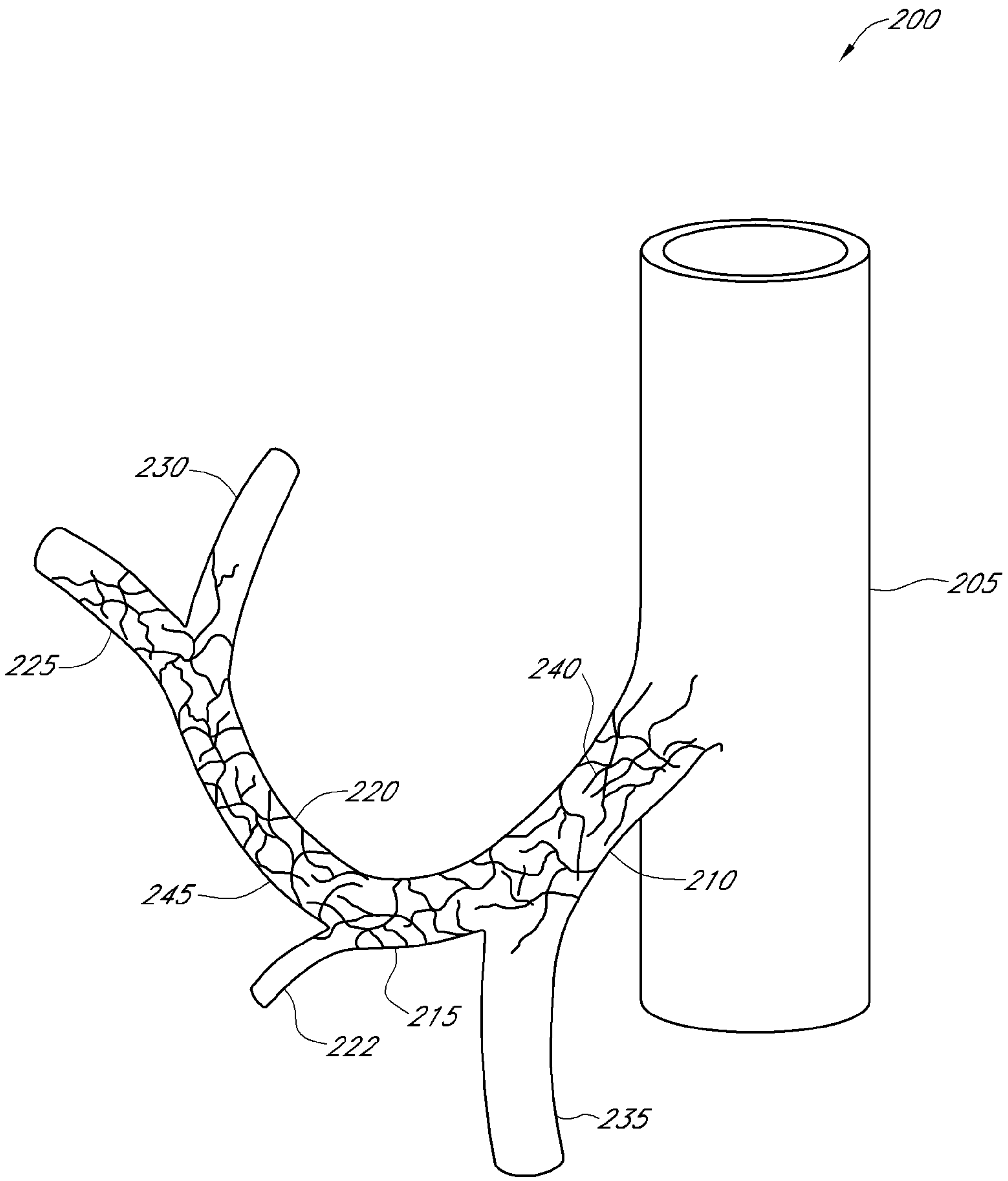
FIG. 2 illustrates various arteries supplying blood to the liver and its surrounding organs and tissues and nerves that innervate the liver and its surrounding organs and tissues.

FIG. 2 illustrates various arteries surrounding the liver and the various nerve systems 200 that innervate the liver and its surrounding organs and tissue. The arteries include the abdominal aorta 205, the celiac artery 210, the common hepatic artery 215, the proper hepatic artery 220, the gastroduodenal artery 222, the right hepatic artery 225, the left hepatic artery 230, and the splenic artery 235. The various nerve systems 200 illustrated include the celiac plexus 240 and the hepatic plexus 245. Blood supply to the liver is pumped from the heart into the aorta and then down through the abdominal aorta 205 and into the celiac artery 210. From the celiac artery 210, the blood travels through the common hepatic artery 215, into the proper hepatic artery 220, then into the liver through the right hepatic artery 225 and the left hepatic artery 230. The common hepatic artery 215 branches off of the celiac trunk, or artery 210. The common hepatic artery 215 gives rise to the gastric and gastroduodenal arteries. The nerves innervating the liver include the celiac plexus 240 and the hepatic plexus 245. The celiac plexus 240 wraps around the celiac artery 210 and continues on into the hepatic plexus 245, which wraps around the proper hepatic artery 220, the common hepatic artery 215, and may continue on to the right hepatic artery 225 and the left hepatic artery 230. In some anatomies, the celiac plexus 240 and hepatic plexus 245 adhere tightly to the walls (and some of the nerves may be embedded in the adventitia) of the arteries supplying the liver with blood, thereby rendering intra-to-extra-vascular neuromodulation particularly advantageous to modulate nerves of the celiac plexus 240 and/or hepatic plexus 245. In several embodiments, the media thickness of the vessel (e.g., hepatic artery) ranges from about 0.1 cm to about 0.25 cm. In some anatomies, at least a substantial portion of nerve fibers of the hepatic artery branches are localized within 0.5 mm to 1 mm from the lumen wall such that modulation (e.g., denervation) using an endovascular approach is effective with reduced power or energy dose requirements. In some embodiments, low-power or low-energy (e.g., less than 10 W of power output and/or less than 1 kJ of energy delivered to the inner wall of the target vessel or to the target nerves) intravascular energy delivery may be used because the nerves are tightly adhered to or within the outer walls of the arteries supplying the liver with blood (e.g., hepatic artery branches).

With continued reference to FIGS. 1 and 2, the hepatic plexus 245 is the largest offset from the celiac plexus 240. The hepatic plexus 245 is believed to carry primarily afferent and efferent sympathetic nerve fibers, the stimulation of which can increase blood glucose levels by a number of mechanisms. For example, stimulation of sympathetic nerve fibers in the hepatic plexus 245 can increase blood glucose levels by increasing hepatic glucose production. Stimulation of sympathetic nerve fibers of the hepatic plexus 245 can also increase blood glucose levels by decreasing hepatic glucose uptake. Therefore, by disrupting sympathetic nerve signaling in the hepatic plexus 245, blood glucose, triglyceride, norepinephrine, lipid (e.g., lipoprotein), and/or cholesterol levels can be decreased or reduced. In some embodiments, blood glucose levels are reduced by 40-50% from baseline.

In several embodiments, any of the regions (e.g., nerves) identified in FIGS. 1 and 2 may be modulated according to embodiments described herein. Alternatively, in one embodiment, localized therapy is provided to the hepatic plexus, while leaving one or more of these other regions unaffected. In some embodiments, multiple regions (e.g., of organs, arteries, nerve systems) shown in FIGS. 1 and 2 may be modulated in combination (simultaneously or sequentially), which may provide one or more synergistic effects. For example, in some embodiments, methods of metabolic neuromodulation treatment involve forming ablation lesions in the common hepatic artery as well as in the celiac, splenic and/or proper hepatic arteries to facilitate denervation of complementary metabolic organs and structures (e.g., pancreas, duodenum) in addition to the liver, even in the instance of a shortened common hepatic artery and/or unusual branch vessel anatomy. In some embodiments, if a subject has a short common hepatic artery (e.g., less than 30 mm), ablation of other vessels may be desired and/or required to achieve an effective treatment. In other embodiments, treatment of complementary metabolic organs and structures by delivering energy in the celiac, splenic and/or proper hepatic arteries may advantageously provide one or more synergistic effects. Although several access/delivery devices are described herein that are configured for (e.g., in shape, size, flexibility, etc.) the hepatic artery, such access/delivery devices can also be used for other arteries and vessels, and in particular, other tortuous vasculature.

Figure 3:
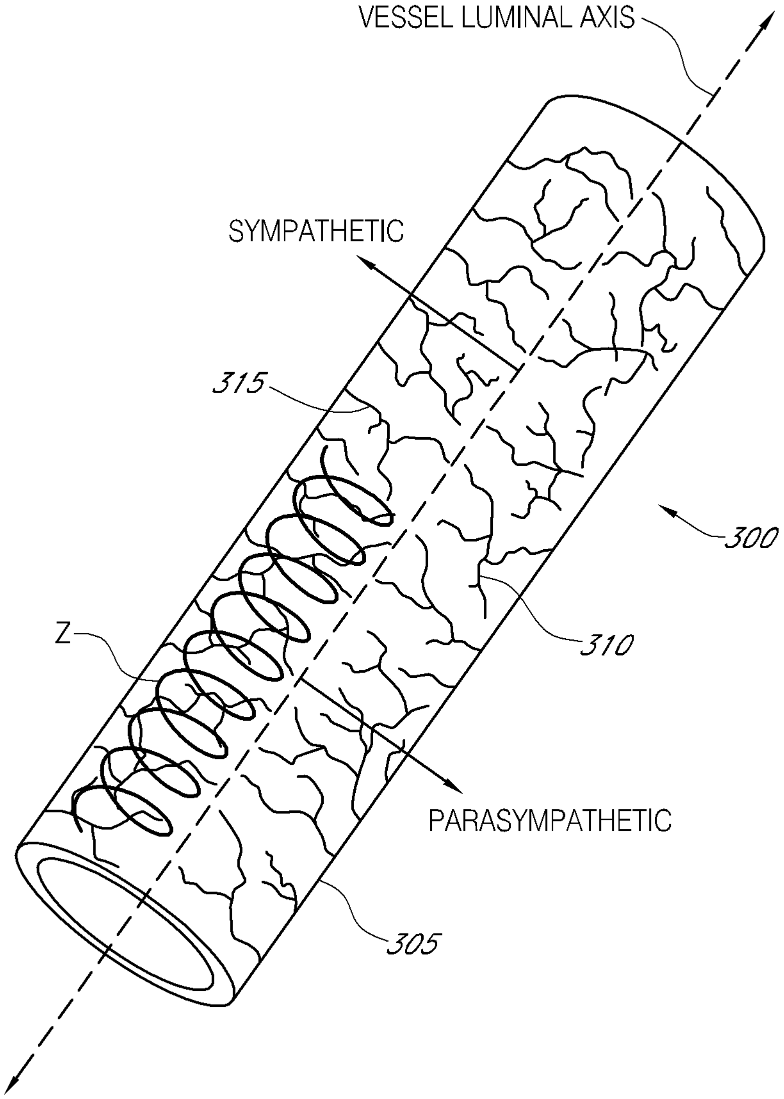
FIG. 3 illustrates a schematic drawing of a common hepatic artery and nerves of the hepatic plexus.

FIG. 3 is a schematic illustration of the nerve fibers of the hepatic plexus 300. A portion of the common hepatic artery 305 (or, alternatively, the proper hepatic artery) is shown with the hepatic plexus 300 wrapping around the artery. Some of the nerve fibers of the hepatic plexus may be embedded within the adventitia of the common hepatic artery 305 (or proper hepatic artery), or at least tightly adhered to or within the outer vascular walls. As shown, there is a vessel lumenal axis that follows the center of the artery lumen. The hepatic plexus 300 is comprised of parasympathetic nerves 310 and sympathetic nerves 315. In some anatomies, the parasympathetic nerves 310 tend to course down one half of the circumference of an artery and the sympathetic nerves 315 tend to course down the other half of the artery.

As shown in FIG. 3, the portion of the common hepatic artery 305 is roughly cylindrical, with parasympathetic nerves 310 innervating approximately a 180° arc of the cylinder, and the sympathetic nerves of the hepatic plexus 315 innervating the opposite approximately 180° arc of the cylinder. In some anatomies, there is very little overlap (if any) between the parasympathetic nerves 310 and the sympathetic nerves 315 of the hepatic plexus. Such discretization may be advantageous in embodiments where only sympathetic nerves 315 or parasympathetic nerves 310 of the hepatic plexus are to be modulated. In some embodiments, modulation of the sympathetic nerves 315 of the hepatic plexus may be desirable while modulation of the parasympathetic nerves 310 of the hepatic plexus may not be desirable (or vice-versa).

In some embodiments, only selective regions of the adventitial layer of target vasculature is modulated. In some subjects, parasympathetic and sympathetic nerves may be distributed distinctly on or within the adventitial layer of blood vessels. For example, using an axis created by the lumen of a blood vessel, parasympathetic nerves of the hepatic plexus may lie in one 180 degree arc of the adventitia while sympathetic nerves may lie in the other 180 degree arc of the adventitia, such as shown in FIG. 3. Generally, the sympathetic nerve fibers tend to run along the anterior surface of the hepatic artery, while the parasympathetic nerve fibers are localized toward the posterior surface of the hepatic artery. In these cases, it may be advantageous to selectively disrupt either the sympathetic or the parasympathetic nerves by modulating nerves in either the anterior region or the posterior region.

In some subjects, sympathetic nerve fibers may run along a significant length of the hepatic artery, while parasympathetic nerve fibers may join toward the distal extent of the hepatic artery. Research has shown that the vagus nerve joins the liver hilus near the liver parenchyma (e.g., in a more distal position than the nerves surrounding the hepatic arterial tree). As the vagal nerves are parasympathetic, the nerves surrounding the hepatic artery proximally may be predominantly sympathetic. In accordance with several embodiments, modulation (e.g., ablation) of the proper hepatic artery towards its proximal extent (e.g., halfway between the first branch of the celiac artery and the first branch of the common hepatic artery) is performed when it is desired to disrupt sympathetic nerves in the hepatic plexus. Ablation of the proximal extent of the hepatic artery could advantageously provide the concomitant benefit of avoiding such critical structures as the bile duct, pancreas and portal vein (which approaches the hepatic artery as it courses distally towards the liver).

In one embodiment, only the anterior regions of the hepatic artery are selectively modulated (e.g., ablated). In one embodiment, approximately 180 degrees of the arterial circumference (which may include the corresponding adventitial layer) is ablated. In some embodiments, it is desirable to ablate in the range of about 60° to about 240°, about 80° to about 220°, about 100° to about 200°, about 120° to about 180°, about 140° to about 160°, or overlapping ranges thereof. In some embodiments, the portion of the vessel wall not being targeted opposite the portion of the vessel wall being targeted is actively cooled during the modulation procedure (e.g., as described, for example, in connection with FIGS. 110A and 110B). Such cooling may decrease collateral injury to the nerve fibers not intended for treatment. In many embodiments, cooling is not used.

In embodiments in which only selective portions of the vessel wall are to be treated, a zig-zag, overlapping semi-circular, spiral, lasso, or other pattern of ablation may be used to treat only selective regions of nerve tissue in the adventitia. An example of a spiral ablation pattern Z, in accordance with one embodiment, is shown in FIG. 3. In some embodiments, one or more ablation electrodes having an inherent zig-zag, spiral or other pattern are used. In some embodiments, a single point ablation electrode (regardless of electrode pattern) is advanced longitudinally and circumferentially about substantially 180 degrees of the vessel circumference to ablate in a zig-zag, spiral or other pattern, thereby selectively ablating only approximately 180 degrees of the vessel wall and the accompanying nerve tissues. In some embodiments, other patterns of electrode configurations are used. In some embodiments, other patterns of ablation electrode movement (regardless of inherent conformation) are used. In some embodiments, lesion zones are created that do not overlap with each other. In various embodiments, lesion zones are spaced apart axially and/or radially.

In some embodiments, where only selective regions of the vessel wall are to be modulated (e.g., ablated or stimulated) it may be helpful to have a high degree of device (e.g., catheter) control, stability and/or precision. To achieve the control necessary for a high degree of precision, a guide catheter may be used to engage the osteum of a nearby branch (e.g., the branch of the common hepatic artery off of the celiac artery, or celiac trunk) to provide a constant reference point from which to position an energy delivery (e.g., ablation) catheter. Alternatively, the catheter (e.g., probe) could also be anchored in other branches, either individually or simultaneously, to further improve control and/or stabilization. Simultaneous anchoring may be achieved by means of a compliant, inflatable balloon (e.g., having a shape and size configured to match an osteum or another portion of a particular vessel), which may substantially occlude the vascular lumen (e.g., osteum), thereby anchoring the catheter and providing increased stability. Such an approach may obviate the need for angiography to map the course of treatment, including the concomitant deleterious contrast agent and x-ray exposure, because treatment guidance can be performed relative to a reference angiogram, with distance of the neuromodulation catheter from the guide catheter measured outside of the patient. In some embodiments, the inflatable balloon may have a size and shape configured to engage multiple ostia or to be anchored in multiple branches (simultaneously or sequentially). In some embodiments, occlusion of a vessel results in increased arterial blood flow at a target location, thereby providing more effective convective cooling. In one embodiment, a balloon catheter is configured to deliver a controlled amount of energy within a defined region of an arterial wall irrespective of low and/or variable flow within the artery (e.g., hepatic artery).

The anatomy of the vascular branches distal of the celiac plexus may be highly disparate between subjects and variations in the course of the sympathetic and parasympathetic nerves tend to be associated predominantly with branches distal of the celiac plexus, rather than being associated with any specific distance distally along the hepatic artery. In some embodiments, a neuromodulation location is selected based on a position relative to the branching anatomy rather than on any fixed distance along the hepatic artery in order to target the sympathetic nerve fibers; for example, within the common hepatic artery and about 1 cm-6 cm (e.g., about 2 cm-3 cm, or substantially at the midpoint of the common hepatic artery) from the branching of the celiac axis.

Parasympathetic and sympathetic nerve fibers tend to have opposing physiologic effects, and therefore, in some embodiments, only the sympathetic nerve fibers and not the parasympathetic nerve fibers are disrupted (e.g., denervated, ablated) in order to achieve the effects of reducing endogenous glucose production and increasing hepatic and peripheral glucose storage. In some embodiments, only the parasympathetic nerve fibers and not the sympathetic nerve fibers are stimulated in order to achieve the effects of reducing endogenous glucose production and increasing hepatic and peripheral glucose storage. In some embodiments, the sympathetic nerve fibers are denervated while the parasympathetic nerve fibers are simultaneously stimulated in order to achieve the effects of reducing endogenous glucose production and increasing hepatic and peripheral glucose storage. In some embodiments, the denervation of the sympathetic nerve fibers and the stimulation of the parasympathetic nerve fibers are performed sequentially.

In accordance with several embodiments, methods of therapeutic neuromodulation for preventing or treating disorders (such as diabetes mellitus) comprise modulation of nerve fibers (e.g., the sympathetic nerve fibers of the hepatic plexus). In one embodiment, neuromodulation decreases hepatic glucose production and/or increases hepatic glucose uptake, which in turn can result in a decrease of blood glucose levels, triglyceride levels, lipid levels, norepinephrine levels, and/or cholesterol levels. Disruption of the nerve fibers can be effected by ablating, denervating, severing, destroying, removing, desensitizing, disabling, reducing, crushing or compression, or inhibiting neural activity through, blocking, or otherwise modulating (permanently or temporarily) the nerve fibers or surrounding regions. In some embodiments, the disruption is carried out using one or more energy modalities. Energy modalities include, but are not limited to, microwave, radiofrequency (RF) energy, thermal energy, electrical energy, ultrasonic energy, focused ultrasound such as high-intensity or low-intensity focused ultrasound, laser energy, phototherapy or photodynamic therapy (e.g., in combination with one or more activation agents), ionizing energy delivery (such as X-ray, proton beam, gamma rays, electron beams, and alpha rays), cryoablation, and chemoablation, or any combination thereof. In some embodiments, the disruption of the sympathetic nerve fibers is carried out by chemicals or therapeutic agents (for example, via drug delivery), either alone or in combination with an energy modality. In some embodiments, ionizing energy is delivered to a target region to prevent regrowth of nerves. In various embodiments different energy modalities may be used in combination (either simultaneously or sequentially).

In accordance with several embodiments disclosed herein, the invention comprises modulation of nerve fibers instead of or in addition to nerve fibers in the hepatic plexus to treat diabetes or other metabolic conditions, disorders, or other diseases. For example, sympathetic nerve fibers surrounding (e.g. within the intima, media and/or adventitial layer of) the common hepatic artery proximal to the proper hepatic artery, sympathetic nerve fibers surrounding the celiac artery (e.g., the celiac ganglion or celiac plexus, which supplies nerve fibers to multiple organs including the pancreas, stomach, and small intestine), sympathetic nerve fibers that innervate the pancreas, sympathetic nerve fibers that innervate fat tissue (e.g., visceral fat), sympathetic nerve fibers that innervate the adrenal glands (e.g., the renal plexus or suprarenal plexus), sympathetic nerve fibers that innervate the gut, stomach or small intestine (e.g., the duodenum), sympathetic nerve fibers that innervate brown adipose tissue, sympathetic nerve fibers that innervate skeletal muscle, the vagal nerves, the phrenic plexus or phrenic ganglion, the gastric plexus, the splenic plexus, the splanchnic nerves, the spermatic plexus, the superior mesenteric ganglion, the lumbar ganglia, the superior or inferior mesenteric plexus, the aortic plexus, or any combination of sympathetic nerve fibers thereof may be modulated in accordance with the embodiments herein disclosed. In some embodiments, instead of being treated, these other tissues are protected from destruction (e.g., ablation or denervation) during localized neuromodulation of the hepatic plexus. In some embodiments, one or more sympathetic nerve fibers (for example, a ganglion) can be removed (for example, pancreatic sympathectomy). The nerves (sympathetic or parasympathetic) surrounding the various organs described above may be modulated in a combined treatment procedure (either simultaneously or sequentially), which may provide one or more synergistic effects.

In some embodiments, modulation of the nerves (e.g., sympathetic denervation) innervating the stomach results in reduction of ghrelin secretion and greater satiety, decreased sympathetic tone leading to increased motility and/or faster food transit time, thereby effecting a "neural gastric bypass." In some embodiments, modulation of the nerves (e.g., sympathetic denervation) innervating the pylorus results in decreased efferent sympathetic tone, leading to faster transit time and effecting a "neural gastric bypass." In some embodiments, modulation of the nerves (e.g., sympathetic denervation) innervating the duodenum results in disrupted afferent sympathetic activity leading to altered signaling of various receptors and hormones (e.g., gut hormones, GLP-1, gastric inhibitory peptide (GIP), cholecystokinin (CCK), peptide YY (PYY), 5-hydroxytryptamine (5-HT)), thereby causing increased insulin secretion and insulin sensitivity, and/or decreased efferent sympathetic tone leading to faster transit time, thereby effecting a "neural duodenal bypass."

In some embodiments, modulation of the nerves (e.g., sympathetic denervation) innervating the pancreas results in decreased efferent sympathetic tone, thereby causing increased beta cell insulin production and beta cell mass, and decreased alpha cell glucagon production. In some embodiments, modulation of the afferent sympathetic nerves innervating the liver results in reflexive decreased sympathetic tone to the pancreas, gastrointestinal tract, and/or muscle. In some embodiments, modulation of the afferent sympathetic nerves innervating the liver results in an increase in a hepatokine hormone with systemic effects (e.g., hepatic insulin sensitizing substance). In some embodiments, stimulation of the common hepatic branch of the vagus nerves could result in similar effects.

II. Types of Neuromodulation

A. Mechanical Neuromodulation

The selective modulation or disruption of nerve fibers may be performed through mechanical or physical disruption, such as, but not limited to, cutting, severing, ripping, tearing, transecting, or crushing. Several embodiments of the invention comprise disrupting cell membranes of nerve tissue. Several embodiments involve selective compression of the nerve tissue and fibers. Nerves being subjected to mechanical pressure, such as, but not limited to, selective compression or crushing forces may experience effects such as, but not limited to, ischemia, impeded neural conduction velocity, and nervous necrosis. Such effects may be due to a plurality of factors, such as decreased blood flow.

In several embodiments, many of the effects due to selective compression or mechanical crushing forces are reversible. Beyond using mechanical compression to selectively and reversibly modulate neural response, mechanical compression may be used to permanently modulate neural response through damage to select myelin sheaths and individual nerve fascicles. In some embodiments, the level of neural modulation is tuned by modulating the mechanical compressive forces applied to the nerve. For example, a large compressive force applied to a nerve may completely inhibit neural response, while a light compressive force applied to the same nerve may only slightly decrease neural response. In some embodiments, a mechanical compressive force or crushing force may be applied to a nerve, such as a sympathetic nerve in the hepatic plexus, with a removable crushing device. In some embodiments, the removable crushing device is removed and replaced with a stronger or weaker removable crushing device depending on the individual needs of the subject (e.g., the strength of the removable crushing device being keyed to the needed neural response levels). The ability of such removable crushing devices to be fine-tuned to selectively modulate neural response is advantageous over the binary (e.g., all or nothing) response of many types of neural ablation.

In various embodiments, the compressive or crushing forces necessary to compress or crush nerves or cause ischemia within the hepatic artery or other vessels may range from about 1 to about 100 g/mm$^2$, from about 1 g/mm$^2$ to about 10 g/mm$^2$, from about 3 g/mm$^2$ to about 5 g/mm$^2$ (e.g., 8 g/mm$^2$), from about 5 g/mm$^2$ to about 20 g/mm$^2$, from about 10 g/mm$^2$ to about 50 g/mm$^2$, from about 20 g/mm$^2$ to about 80 g/mm$^2$, from about 50 g/mm$^2$ to about 100 g/mm$^2$, or overlapping ranges thereof. These compressive forces may be effected by the various embodiments of mechanical neuromodulation devices or members described herein.

Figure 4A:
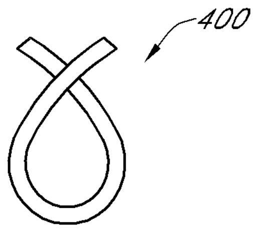
FIGS. 4A-4C, 5A and 5B, 6 and 7 illustrate embodiments of compression members configured to facilitate modulation of nerves.
Figure 4B:
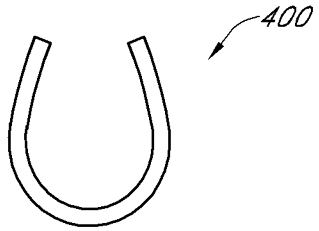
Figure 4C:
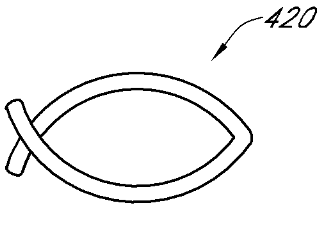

FIGS. 4A-4C, 5A, 5B, 6 and 7 illustrate various embodiments of mechanical neuromodulation devices or members. FIGS. 4A-4C illustrate embodiments of a shape memory compression clip 400. In some embodiments, the shape memory compression clip 400 is used to mechanically compress target nerves. In some embodiments, the shape memory compression clip 400 is removable. FIG. 4A illustrates a resting conformation of the shape memory compression clip 400. FIG. 4B illustrates a strained conformation of the shape memory compression clip 400, which looks like a capital "U" in the illustrated embodiment The shape memory compression clip 400 may be applied to a nerve, such as a nerve of the hepatic plexus by forcibly placing the shape memory compression clip 400 in its strained conformation, placing the target nerve in the bottom well of the shape memory compression clip 400, and then allowing the shape memory compression clip 400 to return to its resting conformation, thereby applying the desired compressive forces to the target nerve by causing it to be crushed or pinched. FIG. 4C illustrates an alternative embodiment of a shape memory compression clip 420 in which the bottom well forms an acute bend instead of being curvate when in a resting shape. The compression clip 400, 420 may be allowed to return to a resting configuration through either removal of external forces biasing the compression clip in a strained configuration (e.g., utilizing superelastic properties of shape memory materials) or heating the compression clip above a transition temperature, thereby allowing the compression clip to assume a native or resting configuration in an austenitic phase above the transition temperature.

In some embodiments, mechanical compressive forces are held at substantially constant levels after application. In some embodiments, the shape memory compression clip 400 may be tailored to the anatomy of different target nerves. In some embodiments, the shape memory compression clip 400 varies in size or shape to compensate for anatomical variance. In some embodiments, varying sizes or shapes of shape memory compression clips may be used, in addition to compensating for anatomical variance, to selectively apply varying levels of compressive stresses to the target nerve (e.g., smaller clip or stronger material for higher forces and larger clip or weaker material for smaller forces). In one embodiment, the shape memory material is nitinol. In various embodiments, the shape memory material is a shape memory polymer or any other appropriate material having shape memory material properties. In some embodiments, compression members comprise simple spring clips or any other devices capable of applying a substantially constant force. In some embodiments, a compression member is configured to clamp the entire artery and the nerves in the adventitial layer, thereby applying the desired compressive forces to both the target nerves and the artery around which the target nerves travel.

Applying compressive, occlusive or collapsing forces to hepatic arteries is uniquely feasible, in some embodiments, because the liver is supplied with blood from both the hepatic arteries, around which many of the target nerves described herein may travel, as well as the portal vein. If at least one of the hepatic arteries is clamped (for the purpose of applying compressive forces to the nerves in its adventitia), the liver would lose the blood supply from that artery, but would be fully supplied by the portal vein, thereby leaving the liver viable and healthy.

In some embodiments, mechanical compressive forces are variable across time following application. In some embodiments, the mechanical compressive forces are varied according to a pre-set duty cycle, thereby titrating the effects of the neuromodulation. One or more embodiments may comprise a transcutaneous delivery of energy to a circuit coupled to a compression member (e.g., a nitinol clip) having a transition between martensitic and austenitic states at a specific temperature induced by a temperature that is substantially different from body temperature. In several embodiments, a variance in temperature is provided through, but is not limited to: a thermocouple (e.g., a Peltier junction) thermally coupled to the compression member to which the circuit may apply power, or a heating element thermally coupled to the compression member to which the circuit may apply resistive power, thereby altering the physical conformation of the compression member and varying (either increasing or decreasing depending on the power applied) the compressive forces generated by the compression member. In one embodiment, the compression member itself acts as a resistive element and the circuit is coupled directly to the compression member to apply resistive power to the compression member, thereby altering the physical conformation of the compression member and varying (either increasing or decreasing depending on the power applied) the compressive forces generated by the compression member. Other embodiments combine the compression member with a thermocouple or other temperature-measurement device to allow the selective application of electric power to vary the compressive stresses created by the compression member.

Figure 5A:
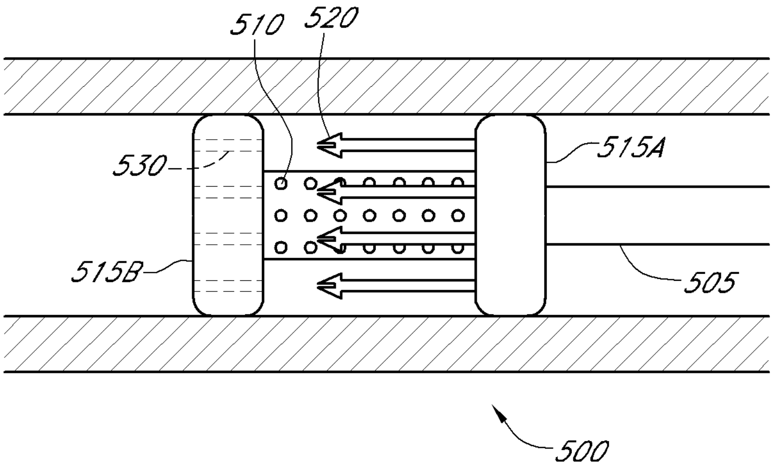
Figure 5B:
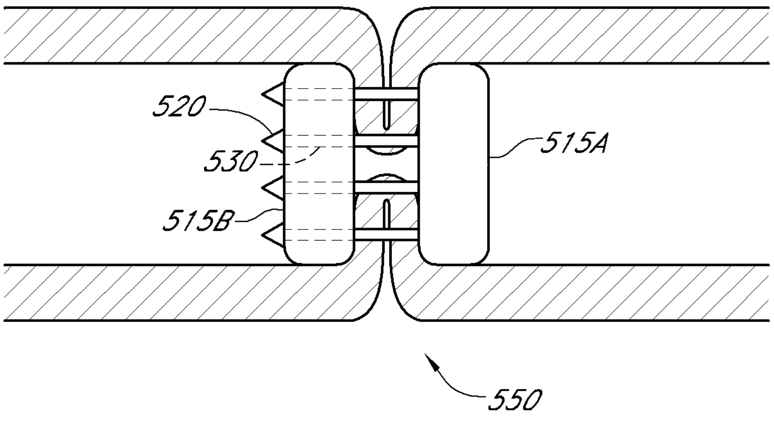

FIGS. 5A and 5B illustrate another embodiment of a compression device. FIG. 5A illustrates a catheter-based vascular wall compression system 500 including a vascular wall clamp 515 in an open conformation. The catheter-based vascular wall compression system 500 includes a detachable insertion catheter 505, suction holes 510, an engagement portion 515A of the vascular wall clamp 515, an anchoring mechanism 520, a receiving portion 515B of the vascular wall clamp, and an anchoring mechanism accepting portion 530. In operation, the vascular wall clamp 515 may be inserted into the target vessel on the distal end of the detachable insertion catheter 505. In one embodiment, the receiving portion 515B of the vascular wall clamp 515 is located at the distal end of the detachable insertion catheter 505, while the engagement portion 515A of the vascular wall clamp 515 is located slightly proximal to the receiving portion 515B. The surface of the detachable insertion catheter 505 between the receiving portion 515B and the engagement portion 515A may include a plurality of suction holes 510.

In further operation, once the vascular wall clamp 515 is placed at the desired target location, the suction holes 510, in one embodiment, create a vacuum, or suction, which brings the walls of the target vessel in substantially direct apposition to the surface of the detachable insertion catheter portion that includes the plurality of suction holes 510. While maintaining suction, and therefore the position of the vessel wall in apposition to the detachable insertion catheter 505, the engagement portion 515A is moved toward the receiving portion 515B (or vice versa), thereby pinching the vascular wall which remained in direct apposition to the detachable insertion catheter between the receiving portion 515B and the engagement portion 515A.

The anchoring mechanism 520, which is attached to the engagement portion 515A engages the anchoring member accepting portion 530 of the receiving portion 515B, thereby securing the receiving portion 515B to the engagement portion 515A and clamping the vascular wall portion that remains in direct apposition to the detachable insertion catheter 505 between the receiving portion 515B and the engagement portion 515A. Once the receiving portion 515B has fully engaged with the engagement portion 515A, the detachable insertion catheter 505 may be disengaged from the vascular wall clamp 515 and removed by the same path it was inserted.

FIG. 5B illustrates the vascular wall clamp 515 in a closed conformation. In FIG. 5B, the anchoring mechanism 520, which is attached to the engagement portion 515A of the vascular wall clamp 515 has engaged the anchoring member accepting portion 530 of the receiving portion 515B of the vascular wall clamp 515, thereby clamping a portion of the vascular wall between the receiving portion 515B and the engagement portion 515A. FIG. 5B shows that the detachable insertion catheter 505 has already been removed.

In some embodiments, the engagement portion 515A and the receiving portion 515B of the vascular wall clamp 525 both include a hollow center. In these embodiments, when the detachable insertion catheter 505 is removed, the hole at the center of the engagement portion 515A of the vascular wall clamp 515 and the hole at the center of the receiving portion 515B of the vascular wall clamp 525 creates a patent lumen between the receiving portion 515B and the engagement portion 515A, thereby allowing continued blood flow from one side to the other. In some embodiments, the detachable insertion catheter 505 is attached to either the engagement portion 515A or the receiving portion 515B of the vascular wall clamp 515 by means of a threaded portion, which may be unthreaded once the receiving portion 515B and engagement portion 515A have engaged, and the detachable insertion catheter 505 is no longer needed.

In some embodiments, the vascular wall clamp 515 is inserted to the target anatomy using an over-the-wire approach. In some embodiments, the detachable insertion catheter 505 is hollow and has suction holes 510 in communication with an internal hollow lumen of the detachable insertion catheter 505. The suction holes 510 may be a series of small openings, a screen, or any other structure which allows a lower pressure area to be created between the receiving portion 515B and the engagement portion 515A of the vascular wall clamp 515 to bring the vessel wall and perivascular tissue in substantially direct apposition with the detachable insertion catheter 505. In some embodiments, the vascular wall clamp 515 is deployed by pulling proximally on the detachable insertion catheter 505, thereby bringing the distal receiving portion 515B of the vascular wall clamp 525 into engagement with the proximal engagement portion 515A of the vascular wall clamp 515, thereby compressing and/or severing arterial and nerve tissue captured therein. In some embodiments, rotation of the catheter 505 is effective to disengage the catheter 505 from the vascular wall clamp 515. In some embodiments, removal of the detachable insertion catheter 505 from the vascular wall clamp 515 leaves a patent lumen permitting blood flow to the liver.

In some embodiments, the engagement mechanism 520 comprises at least one spear-shaped clip and the engagement accepting portion 530 comprises at least one hole aligned to accept the at least one spear shaped clip and to engage the at least one spear shaped clip engagement mechanism 520 as it enters the at least one hole engagement accepting portion 530 and snaps into place. In some embodiments, the engagement mechanism 520 and engagement accepting portion 530 are simply magnets which hold the receiving portion 515B of the vascular wall clamp 515 and the engagement portion 515A of the vascular wall clamp 515 together. In still other embodiments, the engagement mechanism 520 and the engagement accepting portion 530 are any structures that allow the engagement portion 515A to engage the receiving portion 515B and remain in that engaged conformation. In some embodiments, the vascular wall clamp 515 comprises a biologically inert material with decreased thrombogenicity, such as Teflon®.

Figure 6:
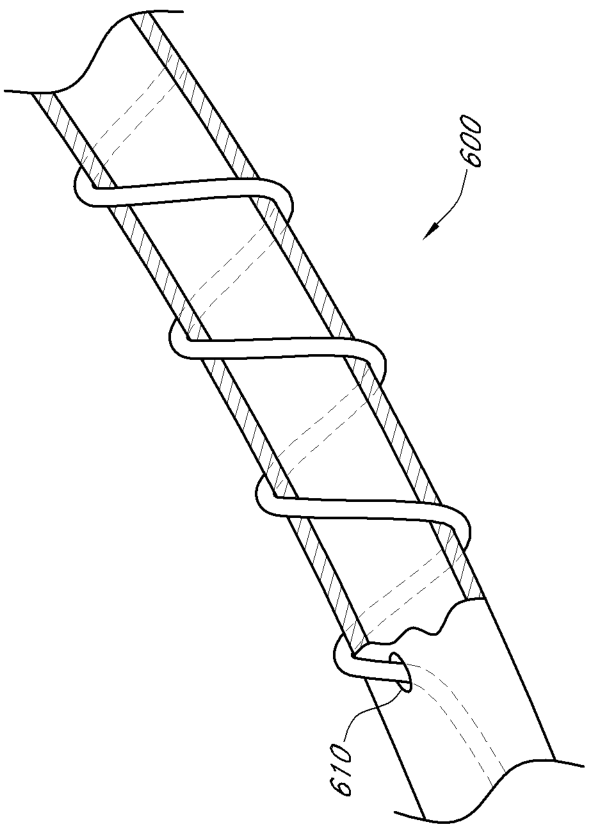

FIG. 6 illustrates an embodiment of an extravascular compression coil 600 inserted within a vessel. In operation, the extravascular compression coil 600 may be advanced through a hole in the vascular wall 610 in a spiraling intra-vascular to extra-vascular manner into the vessel adventitia, thereby placing the extravascular compression coil 600 around the target vessel. In some embodiments, the extravascular compression coil 600 has the effect of compressing the nerves located within the vascular wall of the target vessel. In some embodiments, to prevent occlusion and stenosis, an intravascular stent is subsequently placed within the lumen of the target vessel, thereby both propping open the vessel for continued flow and providing a resilient surface against which the target nerves may be compressed.

In embodiments where stenosis is of particular concern, a stent is placed in the target vessel after treatment to retain patency. In some embodiments, the placement of a stent within the lumen of the target vessel provides the added benefit of compressing the vascular wall to a higher degree, thereby disrupting the target nerves even more. In some embodiments, a stent is placed in the portal vein due to the risk of portal vein stenosis from hepatic arterial ablation procedures. In some embodiments, to protect the portal vein from possible stenosis, anal cooling is used because the gut venous flow travels to the portal system (in some embodiments, anal cooling has the direct result of cooling the portal vein and decreasing the likelihood of stenosis due to treatment of the hepatic artery).

In some embodiments, magnets may be delivered separately into the portal vein and hepatic artery. Upon placement of the two magnets, opposite poles of the two magnets will attract each other and subsequently mate, thereby resulting in substantial compression of the nerves disposed between the two magnets. The force created by the mating of the two magnets may be selectively modulated by increasing or decreasing the strength of magnets used for any given patient morphology, as desired or required.

Figure 7:
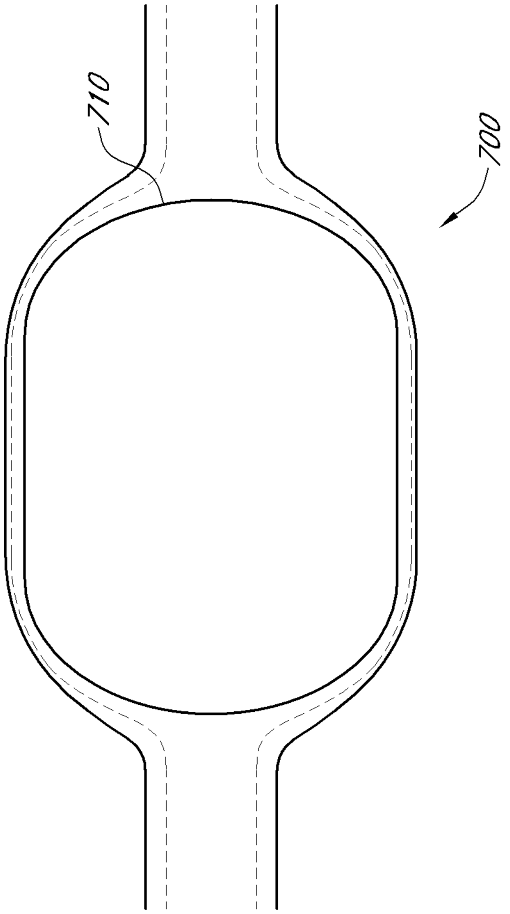

FIG. 7 illustrates an embodiment of a fully occluding balloon 700 inserted within a target blood vessel. In operation, a fully occluding balloon 710 is inserted into a target vessel, inflated and used to expand or stretch the vascular lumen to sufficiently stretch the surrounding nerves to either the point of ischemia or physical disruption. The fully occluding balloon 710 may be removed after physical disruption or after the target nerves have been destroyed due to ischemia. Alternatively, the fully occluding balloon 710 may be left in place permanently because, as discussed previously, the liver is supplied by blood from the portal vein as well, rendering the hepatic artery at least somewhat redundant. In some embodiments, the level of balloon compression is adjusted in an ambulatory fashion, thereby allowing for titration of the neuromodulation effect.

In some embodiments, rather than using a fully occluding balloon 710, a non-occluding balloon or partially occluding balloon is inserted into a target vessel, inflated, and used to expand or stretch the vascular lumen to sufficiently stretch the surrounding nerves to the point of ischemia or physical disruption. The non-occluding or partially occluding balloon may have similar structural features as the fully occluding balloon 710, but may include at least one hollow lumen (e.g., a central lumen) to allow for continued blood flow after placement. In some embodiments, the level of balloon compression can be adjusted in an ambulatory fashion, thereby allowing for titration of the neuromodulation effect.

In some embodiments, similar to the occlusion techniques described above, a balloon catheter may be inserted into the target vessel and then filled with a fluid which is infused and withdrawn at a specific frequency (e.g., pressurized in an oscillating fashion), thereby causing mechanical disruption of the nerve fibers surrounding (e.g. within a wall of, such as within the intima, media or adventitia of) the target vessel (e.g., hepatic artery). In some embodiments, the fluid used to fill the balloon catheter may be a contrast agent to aid in visualization of the arterial structure (and thereby limiting the amount of contrast agent used in the procedure).

In some embodiments, a fluid is injected into the interstitial space surrounding the vasculature around which the target nerve lies, thereby applying compressive forces to the nerve bundle which surrounds the vessel(s). In some embodiments, the fluid is air. In some embodiments, the fluid is any noble gas (e.g., heavy gas), including but not limited to: helium, neon, argon, krypton, and xenon. In some embodiments, the fluid is nitrogen gas. In some embodiments, the fluid is any fluid capable of being injected to apply the desired compressive forces. In some embodiments, the fluid is injected by a catheter inserted transluminally through a blood vessel in substantially close proximity to the target site (e.g., location where nervous compression is desired). In some embodiments, the fluid is injected by a needle or trocar inserted transdermally through the skin and surrounding tissues to the target site. Any method of fluid injection may be used to deliver the requisite amount of fluid to the target site in order to create compressive forces that are applied to the target nerve, such as nerves of the hepatic plexus.

In some embodiments, a target vessel is completely transected, thereby causing a complete and total physical disruption of the vessel wall and the surrounding nerves in the adventitial tissues. The target vessel may then be re-anastamosed, thereby allowing continued perfusion through the vessel. The nerve tissue either does not reconnect, or takes a significant amount of time to do so. Therefore, all neural communication surrounding the transected vessel may temporarily or permanently the disrupted. In some embodiments, a cutting device is advanced in a catheter through the subject's vasculature until it reaches a target vessel. The cutting device may then be twisted along the axis of the target vessel to cut through the target vessel from the inside out. In some embodiments, an expandable element, such as a balloon catheter, is inserted into the vessel to compress the vessel wall and provide a controlled vessel thickness to permit transection. A rotational cutter may then be advanced circumferentially around the expandable element to effect transection of the vessel and the nerves disposed within the adventitia of the vessel. In one embodiment, the target vessel is transected during open surgery.

Re-anastomoses of vessels could be achieved using any of several methods, including laser, RF, microwave, direct thermal, or ultrasonic vessel sealing. In some embodiments, thermal energy may be delivered through an expandable element to effect anastomosis of the vessel under the mechanical pressure provided by the expandable element. The combination of pressure, time, and temperature (e.g., 60° C., 5 seconds, and 120 psi in one embodiment) may be an effective means to seal vessels such as the hepatic arteries.

B. Device-Based Neuromodulation

In accordance with some embodiments, neuromodulation (e.g., the disruption of sympathetic nerve fibers) is performed using a minimally invasive system, such as an ablation catheter system. In some embodiments, an ablation catheter system for ablating nerve fibers is introduced using an intravascular (e.g., intra-arterial) approach. In one embodiment, an ablation catheter system is used to ablate sympathetic nerve fibers in the hepatic plexus and/or nerves innervating the liver. As described above, the hepatic plexus surrounds the common hepatic artery or the proper hepatic artery, where it branches from the common hepatic artery. In some embodiments, the ablation catheter system is introduced via an incision in the groin to access the femoral artery. The ablation catheter system may be advanced from the femoral artery to the proper hepatic artery via the iliac artery, the abdominal aorta, the celiac artery, and the common hepatic artery. In other embodiments, any other suitable percutaneous intravascular incision point or approach is used to introduce the ablation catheter system into the arterial system (e.g., a radial approach via a radial artery or a brachial approach via a brachial artery).

In some embodiments, the catheter (e.g., hollow, solid, partially hollow, catheter, probe, shaft or other delivery device with or without a lumen) may be placed into the target region substantially close to the target nerve through percutaneous injection. Using such a percutaneous placement may allow less destructive, less invasive selective destruction or disruption of the target nerve.

In some embodiments, the catheter system comprises a visualization or other diagnostic device substantially close to the distal end of the catheter. The visualization device may promote nervous visualization, thereby possibly allowing higher levels of precision in targeted nervous disruption. In some embodiments, the catheter system comprises a light source configured to aid in visualization. In some embodiments, a light source and a visualization device (such as a camera) are used in tandem to promote visibility. A diagnostic device may include a temperature-measurement device (e.g., thermistor, thermocouple, radiometer) or one or more ultrasound transducers. In some embodiments, the catheter system comprises a distal opening out of which active elements (such as any camera, light, drug delivery port, and/or cutting device, etc.) are advanced. In some embodiments, the catheter system comprises a side opening out of which the active elements (such as any camera, light, drug delivery port, and/or cutting device, etc.) may be advanced, thereby allowing the user to access the vessel wall in vessels with tortuous curves and thereby allowing nerve destruction with the axis of the catheter aligned parallel to the vessel.

Animal studies have shown that the force of electrode contact against the vessel wall may be a critical parameter for achieving ablative success in some embodiments. Therefore, ablation catheter devices may advantageously not only be small enough to access the target vasculature, but also to incorporate low-profile features for facilitating sufficient electrode contact force or pressure during the length of the treatments.

In some embodiments, the catheter of the neuromodulation catheter system has a diameter in the range of about 2-8 Fr, about 3-7 Fr, about 4-6 Fr (including about 5 Fr), and overlapping ranges thereof. The catheter (e.g., tube, probe or shaft) may have a varying diameter along its length such that the distal portion of the catheter is small enough to fit into progressively smaller vessels as the catheter is advanced within vasculature. In one embodiment, the catheter has an outside diameter sized to fit within the common hepatic artery (which may be as small as about 1 mm in lumenal diameter) or the proper hepatic artery. In some embodiments, the catheter is at least about 150 cm long, at least about 140 cm long, at least about 130 cm long, at least about 120 cm long, at least about 110 cm long, at least about 100 cm long, at least about 75 cm long, or at least about 90 cm long. In some embodiments, the flexibility of the catheter is sufficient to navigate tortuous hepatic arterial anatomy having bend radii of about 10 mm, about 9 mm, about 8 mm, about 7 mm, about 6 mm, about 5 mm, about 4 mm, about 3 mm, about 2 mm, about 1 mm, or about 0.5 mm.

In accordance with several embodiments, devices of the catheter-based systems described herein have actuatable, expandable, steerable, pre-curved, deflectable and/or flexible distal tip components or distal segments. The deflectability or flexibility may advantageously bias an energy applicator against the arterial wall to ensure effective and/or safe delivery of therapy, permit accurate positioning of the energy applicator, maintain contact of an energy delivery element against a vascular wall, maintain sufficient contact force or pressure with a vascular wall, and/or help navigate the catheter to the target anatomy. In some embodiments, devices (e.g., catheters) with steerable, curvable or articulatable distal portions provide the ability to cause articulation, bending, or other deployment of the distal tip (which may contain an ablation element or energy delivery element) even when a substantial portion of the catheter remains within a guide catheter or guide extension catheter. In some embodiments, the neuromodulation catheters provide the ability to be delivered over a guidewire, as placing guide catheters may be unwieldy and time-consuming to navigate. In some embodiments, the neuromodulation catheters are inserted within the vasculature through guide sheaths or guide extension catheters. In some embodiments, guidewires are not used.

Figure 101:
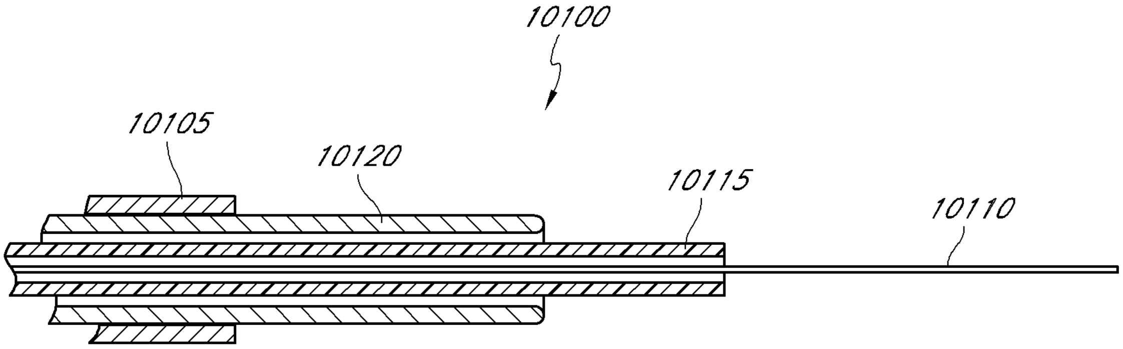
FIG. 101 illustrates an embodiment of a "telescoping" system for facilitating delivery of a low-profile neuromodulation catheter to a hepatic artery branch.

In accordance with several embodiments, catheter-based systems may comprise a guide catheter, a guide extension catheter or support catheter (e.g., a Guidezilla™ catheter or GuideLiner™ catheter), a microcatheter, and/or a guidewire, in addition to a neuromodulation catheter. FIG. 101 illustrates an embodiment of a "telescoping" system 10100 for facilitating delivery of a low-profile neuromodulation catheter to a hepatic artery branch. The "telescoping" system 10100 comprises a guide catheter 10105. In one embodiment, the guide catheter 10105 is a 7 F guide catheter that is configured to engage with the inner wall of the celiac artery to provide a stable anchoring and/or reference point. The system 10100 further comprises a guidewire 10110 (e.g., 0.014" guidewire) that may be configured to be delivered through a lumen of the guide catheter 10105 and advanced to a position beyond a target neuromodulation location within a hepatic artery or other vessel or organ. The system 10100 also comprises a microcatheter 10115 (e.g., 4 Fr or less) and a guide extension catheter 10120 (e.g., a 6 French guide extension catheter). The guide extension catheter 10120 may be configured to fit and be movable within a lumen of the guide catheter 10105 to provide support at a lower profile (e.g., outer diameter) than the guide catheter 10105. The microcatheter 10115 may be configured to fit and be movable within a lumen of the guide extension catheter 10120 and extend beyond a distal end of the guide extension catheter 10120. The microcatheter 10115 may facilitate tracking and advancement of the guide extension catheter 10120 over the guidewire 10110. In some embodiments, the microcatheter 10115 comprises a rapid exchange microcatheter. The guidewire 10110 may provide a "rail" to aid catheter tracking and lessen the risk of vessel damage when advancing a neuromodulation device.

In some embodiments, the guide catheter 10105 and/or the guide extension catheter 10120 comprises an expandable portion that is configured to be advanced to a desired location and then expanded before or during advancement of a neuromodulation device through the guide extension catheter 10120 or the guide catheter 10105. The expandable portion may enable transitory, or temporary, expansion of vessel inner diameters. In one embodiment, the expandable portion may be formed of multiple layers that slide over each other. In one embodiment, the expandable portion may be formed of a cylinder with interrupted longitudinal cuts and encapsulated by an elastic layer that keeps the cuts compressed in an unexpanded state. The expandable portion may provide stabilization or anchoring. Stabilization mechanisms (in addition to or instead of the expandable portion) may be provided at various locations along a length of the guide catheter 10105 and/or the guide extension catheter 10120 (e.g., balloons, ribbons, wires). In some embodiments, portions of the guide catheter 10105 or guide extension catheter 10120 may be stiffened after introduction of the neuromodulation device to provide stability and maintenance of positioning during neuromodulation procedures. In some embodiments, the "telescoping" system 10100 does not comprise a guidewire, as the guide extension catheter 10120 may obviate the need for a guide wire.

In some embodiments, the system 10100 may include a flexible introducer that provides a tapered transition between the guidewire 10110 and the guide catheter 10105 or guide extension catheter 10120, thereby facilitating access to the tortuous hepatic artery vasculature. The flexible introducer may replace the microcatheter 10115 and/or guide extension catheter 10120. In some embodiments, the flexible introducer comprises elastic or shape-memory materials such as nitinol or low durometer PEBAX. The flexible introducer may have a coil cut pattern or a torque converter or flexure cut pattern (e.g., similar to the cut pattern illustrated in FIGS. 98A-98C) or a metallic coil may be encapsulated within the flexible introducer. Portions of the guide catheter 10105, guide extension catheter 10120 and/or microcatheter 10115 may be deflectable and/or steerable. The mechanisms for deflection and/or steering may comprise any of the deflection or steering mechanisms described herein (e.g., tension wire, hydraulics, magnetism, and/or the like). In some embodiments, portions of the guide catheter 10105, guide extension catheter 10120 and/or microcatheter 10115 are plastically deformable and/or shape set to provide deform-ability within vasculature, thereby functioning as accessory devices configured to fit unique and patient-specific anatomy.

Figure 102:
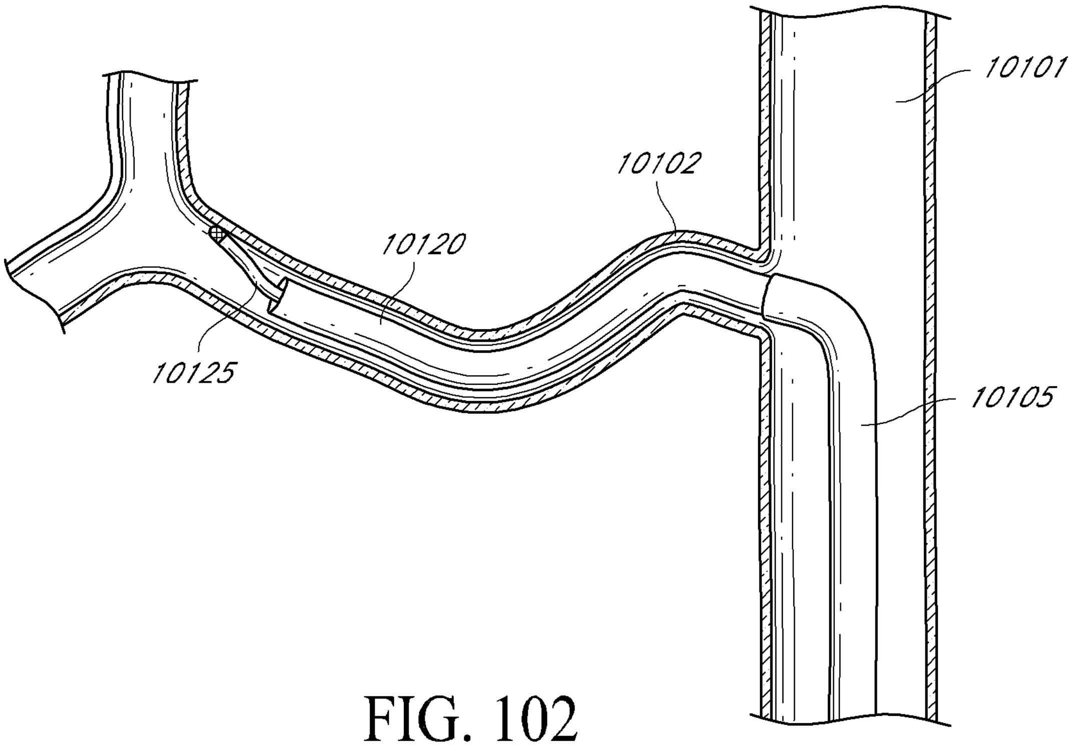
FIG. 102 illustrates an embodiment of use of the system of FIG. 101 to access a target neuromodulation location within a hepatic artery.

FIG. 102 illustrates an embodiment of use of the system of FIG. 101 to access a target neuromodulation location within a hepatic artery. The guide catheter 10105 is advanced to a position within an abdominal aorta 10101 or at an origin of the celiac artery 10102 off the abdominal aorta 10101. In some embodiments, the guidewire 10110 and microcatheter 10115 are then advanced to a position at or adjacent the target neuromodulation location and the guide extension catheter 10120 is advanced over the micro-catheter 10115 to the target neuromodulation location. The guide extension catheter 10120 may be advanced over either the guidewire 10110 alone or over the microcatheter 10115 (which in turn is advanced over the guidewire 10110). FIG. 102 illustrates the system 10100 after the guidewire 10110 and/or microcatheter 10115 have been removed. FIG. 102 also illustrates an embodiment of a neuromodulation device 10125 advanced to the target neuromodulation location within the hepatic artery through the guide extension catheter 10120. In some embodiments, a guidewire 10110 or microcatheter 10115 may not be used and the guide extension catheter 10120 may be advanced beyond the target neuromodulation location and the neuromodulation device 10125 advanced to the target neuromodulation location and then the guide extension catheter 10120 is withdrawn to unsheathe the neuromodulation device 10125. In accordance with several embodiments, the guide extension catheter 10120 may facilitate torqueing of the neuromodulation device 10125 so as to allow for rotation of the neuromodulation device 10125 to multiple or all quadrants of the hepatic artery or other target vessel. In some embodiments, the guide extension catheter 10120 is removed following the initial "deployment" of the neuromodulation device 10125. Fluid (e.g., cooling fluid) may be infused through the guide catheter 10105 or guide extension catheter 10120 during neuromodulation (e.g. ablation).

In some embodiments, the guide extension catheter 10120, or other access device within which the neuromodulation device 10125 is advanced, is configured to maintain a tight clearance between the inner diameter of the guide extension catheter 10120 or other access device and the outer diameter of the neuromodulation device 10125. For example, the inner diameter may have a low friction surface or coating and/or structures (e.g., raised ribs of a compliant material such as silicone) that reduce the number of contact points and provide an inward radial force against the outer surface of the neuromodulation device that run along the length of the guide extension catheter 10120 or other access device and are coated with a low-friction coating, such as a hydrophilic coating. The enhanced support along the flexible length of the neuromodulation device may allow the neuromodulation device to be more accurately flexed and may support increased torque efficiency.

Figure 103A:
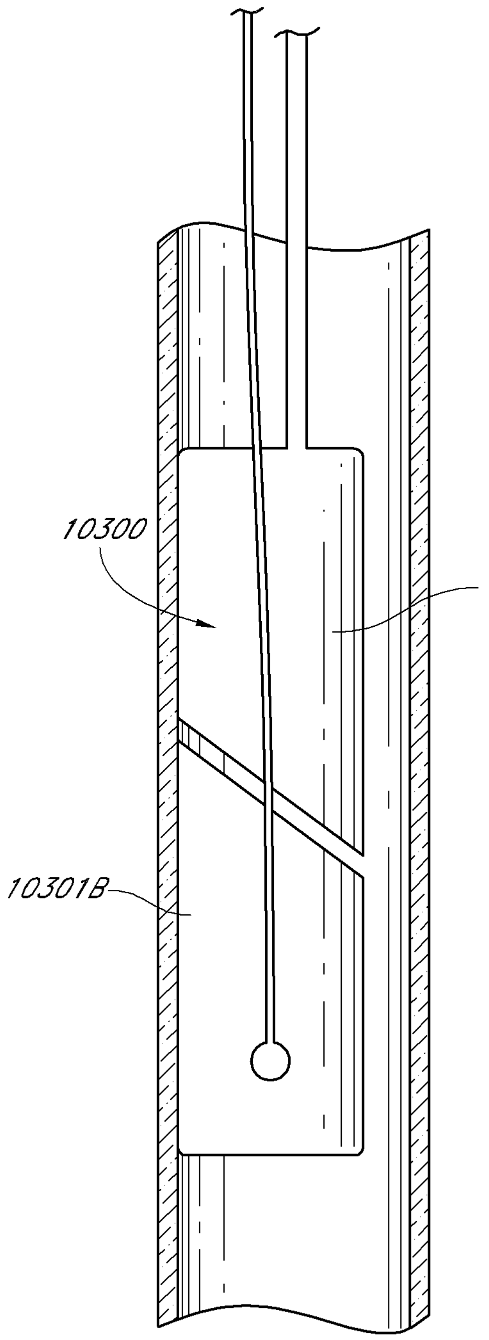
FIGS. 103A and 103B illustrate an embodiment of a wedge-type expanding anchor that can be used to secure a guide catheter or guide extension catheter in place.
Figure 103B:
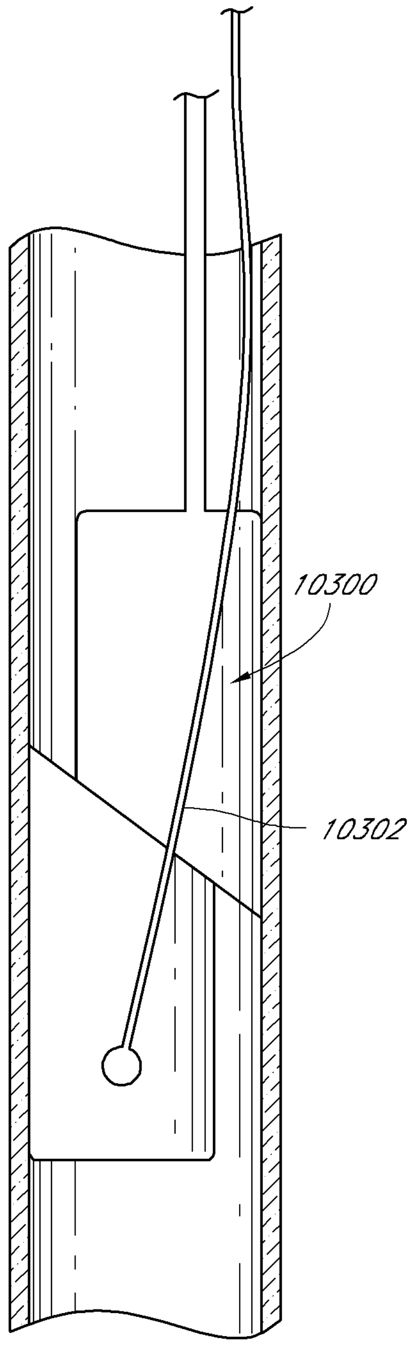

Movement of the guide catheter 10105 or guide extension catheter 10120 may disturb the position of the neuromodulation device. For example, movement of the guide catheter 10105 or guide extension catheter 10120 may cause an electrode of an RF energy delivery device delivered through a lumen of the guide catheter 10105 or guide extension catheter 10120 to move due to friction between the devices. Accordingly, in some embodiments, anchoring the catheter 10105 or guide extension catheter 10120 may advantageously minimize or reduce movement artifacts. FIGS. 103A and 103B illustrate an embodiment of a wedge-type expanding anchor 10300 that can be used to secure a guide catheter 10105 or guide extension catheter 10120 in place. The anchor 10300 may be placed on a distal end of a guide catheter to prevent or reduce the likelihood of movement of the guide catheter or guide extension catheter (e.g., during treatment or during injection of contrast). The anchor 10300 comprises two portions 10301A, 10301B that are cut at a slant and connected by a pull wire 10302 fixed to a joint positioned on portion 10301B. As the two portions 10301 are drawn together (e.g., by pulling the pull wire 10302 and pushing the portion 10301A, the two portions 10301 move sideways and expand into the vessel wall, thereby providing an anchor for the guide catheter, guide extension catheter or guide sheath.

In one embodiment, a neuromodulation catheter (e.g., hollow, solid, partially hollow, catheter, probe, shaft or other delivery device with or without a lumen) is provided that comprises one or more customizable bending or deflection regions. In one embodiment, the neuromodulation catheter facilitates adjustment of multiple articulation or bending regions (collectively or independently). In one embodiment, a method of using the neuromodulation catheter comprises performing a computed tomography (CT) scan, digitizing the CT scan to create a three-dimensional (3D) model of a target anatomical region, determining the location(s) of major arterial or other vascular or anatomical bends and bend radii, and adjusting one or more articulation portions of the catheter to correspond to (e.g., match or line up with) the location(s) of the major arterial bends or other vascular or anatomical bends. In some embodiments, the neuromodulation catheter is configured to have a first bend corresponding to a first anatomical bend (e.g., first bend in a first portion of a hepatic artery or branch off of a hepatic artery) and a second bend corresponding to a second anatomical bend (e.g., second bend in a second portion of the hepatic artery or branch off of a hepatic artery). In some embodiments, the neuromodulation catheter is configured to have three or four bends corresponding to third and/or fourth anatomical bends. The bends may be approximately right angle bends or acute bends ranging from 5 degrees to 90 degrees (e.g., 5-10 degrees, 10-20 degrees, 20-40 degrees, 40-60 degrees, 60-90 degrees, and overlapping ranges thereof). One or more of the bends may be pre-formed and/or one or more of the bends may be formed by movement during delivery (e.g., by expansion, inflation, articulation, actuation, unsheathing).

Figure 95:
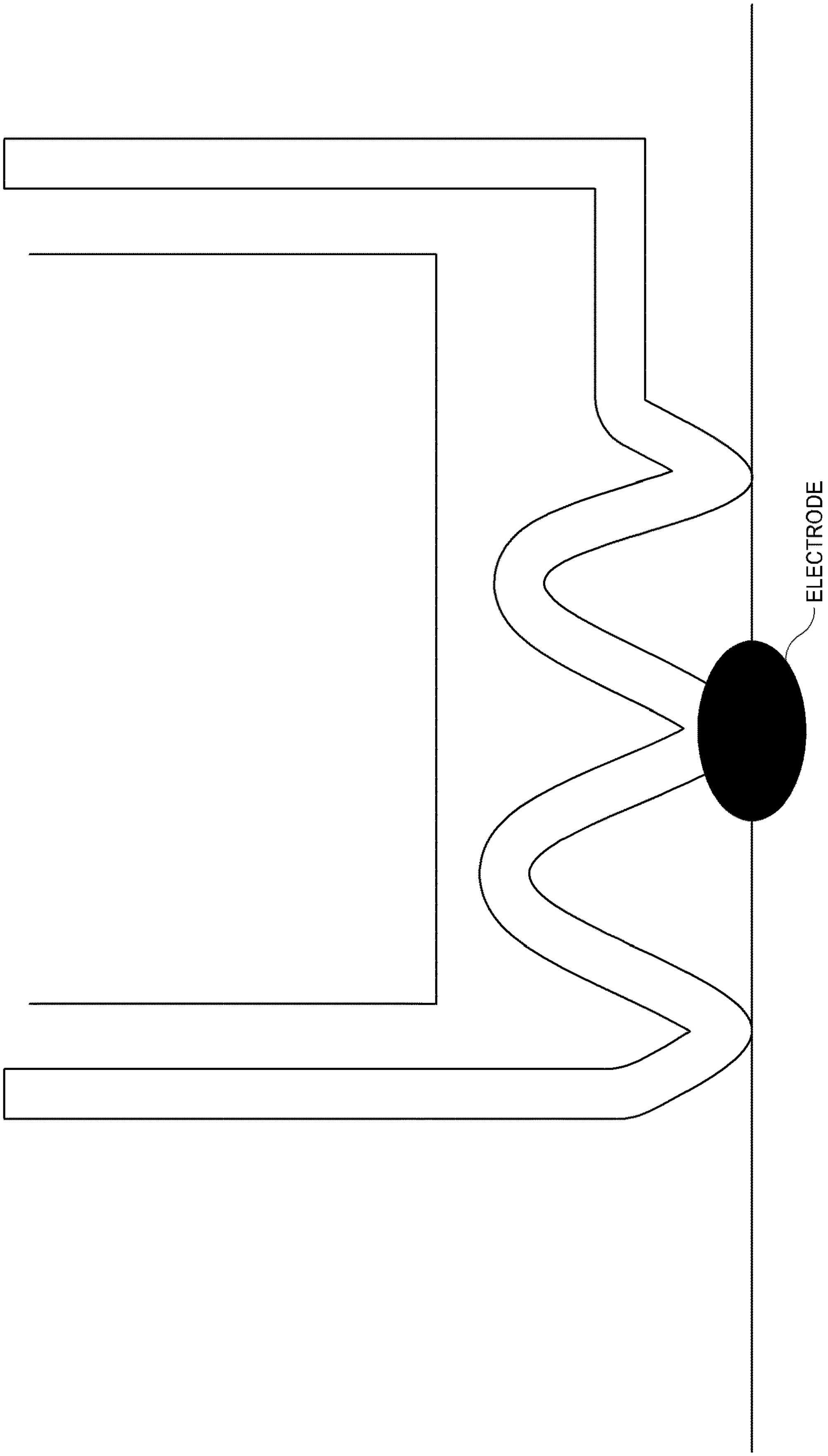

In some embodiments, a first bend is located or formed in the distal 10-40% (e.g., 20%) of the catheter length and a second bend is located or formed in the distal 1-20% (e.g., 5%) of the catheter length. The bends may be partially or wholly pre-formed. In several embodiments, the bends conform to a bend in the vessel wall such that the outer portion of the catheter optionally contacts the interior of the vessel wall. In one embodiment, the catheter bend conforms to the vessel wall but does not touch the vessel wall (e.g., is substantially parallel to the vessel wall but is separated by a distance of 0.1 mm-10 mm, or more). In some embodiments, a first bend is approximately 90° (e.g., 70-110°) in a first plane, about a radius of approximately 0.5 cm (e.g., 0.3 to 0.7 cm), corresponding to the takeoff of the celiac axis from the aorta. In some embodiments, a second bend is approximately 90° (e.g., 70-110°) in a second plane, about a radius of approximately 0.4 cm (e.g., 0.2 to 0.5 cm), the second plane being substantially orthogonal to the first plane, and corresponding to the bifurcation of the common hepatic and splenic arteries. In some embodiments, a third bend is approximately 90° (e.g., 70-110°) in a third plane, about a radius of approximately 0.3 cm (0.2 to 0.4 cm), the third plane being substantially orthogonal to the first and second planes, corresponding to the bend in the common hepatic artery. The bends may be achieved by any of the means described herein, including, but not limited to, hydraulic, pneumatic, pull-wire, resilient deformation, magnetic, and electromagnetic means. In yet another embodiment, a plurality of bends are configured to bias the electrode against the arterial wall, thereby generating an electrode contact force, and further yet provide a defined reaction force to balance the electrode contact force, as illustrated, for example, in FIG. 95. In one embodiment, the catheter comprises one or more spring-like or coil-like members to facilitate electrode contact force.

In various embodiments, the contact force exerted on the vessel wall to maintain sufficient contact pressure is between about 1 g to about 500 g, from about 20 g to about 200 g, from about 10 g to about 100 g, from about 50 g to about 150 g, from about 100 g to about 300 g, from about 200 g to about 400 g, from about 300 g to about 500 g, or overlapping ranges thereof. In some embodiments, the same ranges may be used but expressed as g/mm$^2$ pressure numbers. The contact forces/pressures described above may be achieved by any of the neuromodulation (e.g., ablation) devices and systems described herein.

In accordance with several embodiments, the contact force of the RF electrode against the hepatic arterial wall is a key variable determining ablative success. In various embodiments, devices providing tangential electrode contact through bending regions having bend radii of approximately 0.5 cm (e.g., 0.2 cm-0.8 cm) are provided. In other embodiments, devices having means to exert a controllable reaction force to the electrode contact force are provided. In some embodiment, suction is provided to ensure reliable contact between the electrode(s) and the hepatic arterial wall.

In some embodiments, feedback and/or evaluative measures are provided for assessing the quality and/or magnitude of wall contact. For example, fluoroscopic imaging (e.g., angiography) can be used to assess the magnitude of lumen indentation caused by the contact of an electrode against the arterial wall. The indentation size may be directly correlated to the contact force. Additionally, because there is a significant difference between blood and arterial resistivity, the electrode impedance can be used as an indicator of contact force, with increased impedance generally correlated with improved contact. Prior to initiating an ablation, a test current can be applied to measure the impedance of the tissue immediately surrounding the electrode.

Figure 104:
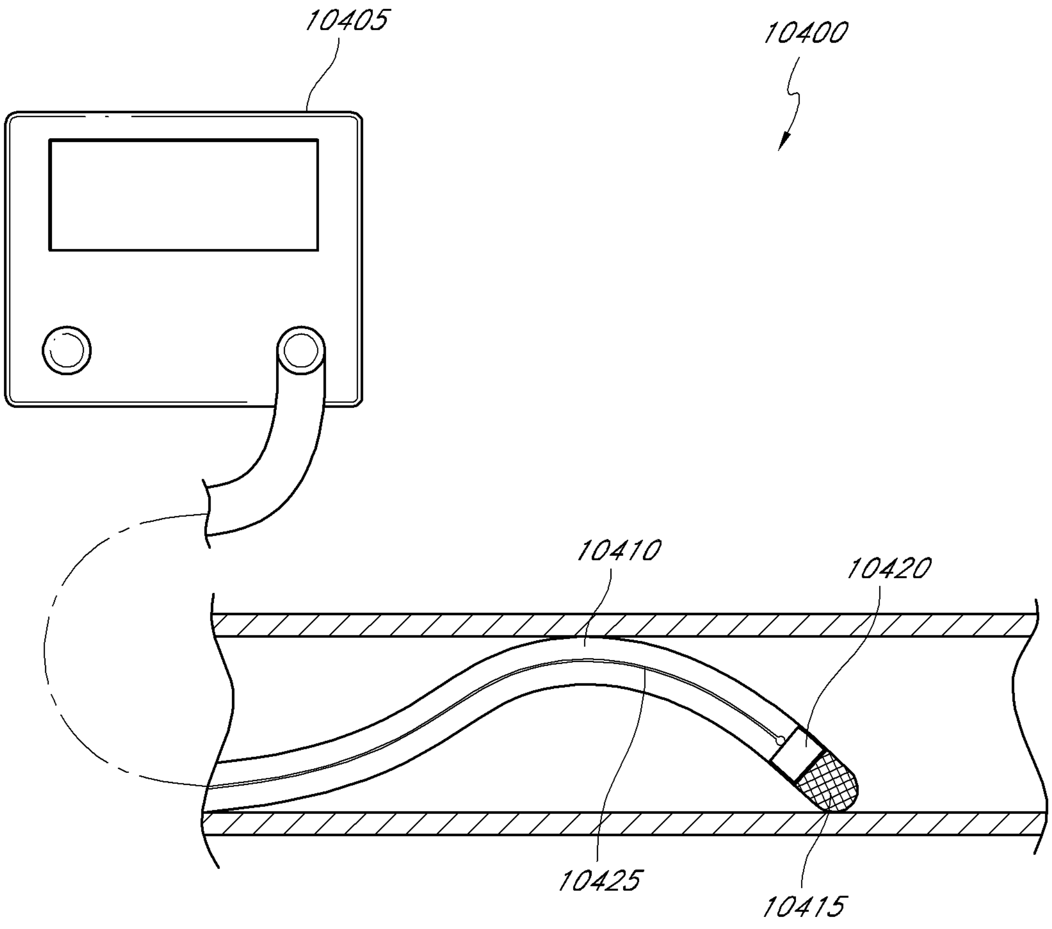
FIG. 104 illustrates an embodiment of a system comprising a controller (e.g., generator) positioned outside of a subject's body that is communicatively coupled (via wired or wireless connection) to an energy delivery device.

In some embodiments, a pressure, force or contact sensor is incorporated directly onto or adjacent the catheter tip, such as the FlexiForce® Force Sensor (Tekscan Inc., South Boston, MA). In some embodiments, the contact force may be displayed on a display of a neuromodulation system (e.g., RF energy delivery) system. In some embodiments, an alert or warning may be provided audibly or visually when the contact force goes above or below a threshold range. Contact of the energy delivery member (e.g., electrode) may be adjusted (manually or automatically) based on feedback (e.g., measurements) received from the sensor. For example, FIG. 104 illustrates an embodiment of a system 10400 comprising a controller 10405 (e.g., generator) positioned outside of a subject's body that is communicatively coupled (via wired or wireless connection) to an energy delivery device 10410. The energy delivery device 10410 includes an energy delivery element 10415 (e.g., electrode) at a distal tip of the energy delivery device 10410 and a force sensor 10420 adjacent the energy delivery element 10415 to sense force exerted by the energy delivery element 10415 on a vessel wall. In the illustrated embodiment, the distal end portion of the energy delivery device 10410 is deflectable via a deflection or actuation wire 10425. A tension force of the wire 10425 may be adjusted based on feedback received from the sensor 10420 in order to maintain a preferred contact force (even during respiration and/or blood flow cycles). The adjustment of the tension force of the wire 10425 may be performed automatically by one or more computing or processing devices of the controller 10405 or manually by an operator. The maintained contact force may advantageously facilitate consistent lesion creation for ablative energy delivery embodiments. The force sensor may also provide real-time feedback of lesion creation due to heat changes resulting from tissue stiffness. The controller 10405 may include a display to display the contact force or temperatures or may cause the contact force or temperature measurements to be displayed on a separate display device.

In some embodiments, a portion of an electrode of an RF energy delivery device is comprised of a deformable membrane, with fluid perfused through this region. In one embodiment, the fluid is coolant fluid circulated within the catheter or delivered to the arterial lumen to cool the electrode. An external controller can be configured to maintain a constant flow rate of the coolant, and the resulting driving pressure required to do so may be directly correlated with the contact pressure along the deformable region of the electrode.

Figure 93:
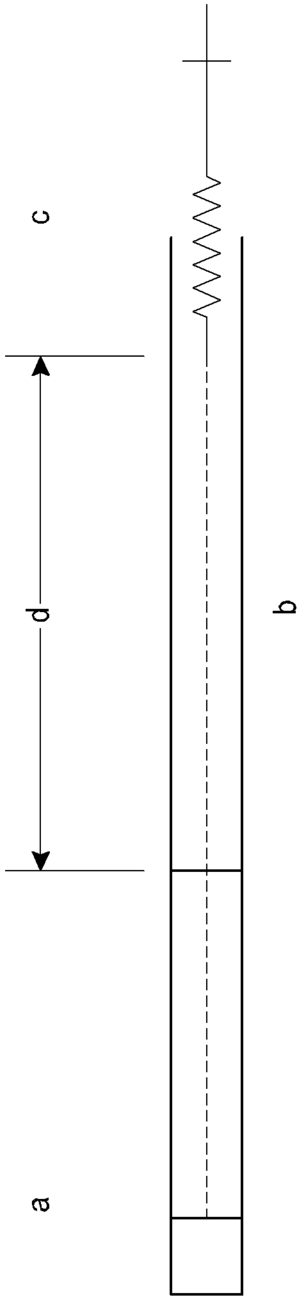

Referring now to FIG. 93, an embodiment of a catheter distal tip design is illustrated having a radiopaque marker disposed within a distal lumen of the catheter and attached to the electrode at one end and an extensible spring anchored at a proximal region of the catheter. The catheter in region A, the flexible region, is configured to be substantially radiopaque, whereas the catheter in region B is configured to be non-radiopaque. Upon contact of the electrode against the arterial wall, which causes deflection of the catheter in region A, the radiopaque marker is urged distally into the radiopaque region A, thereby decreasing the visible length, d, of the radiopaque marker, and thereby providing a visual indicator of the electrode contact force, visible during angiography or other imaging modalities. In some embodiments, the visible length, d, may be indirectly related to the electrode contact force.

Figure 8:
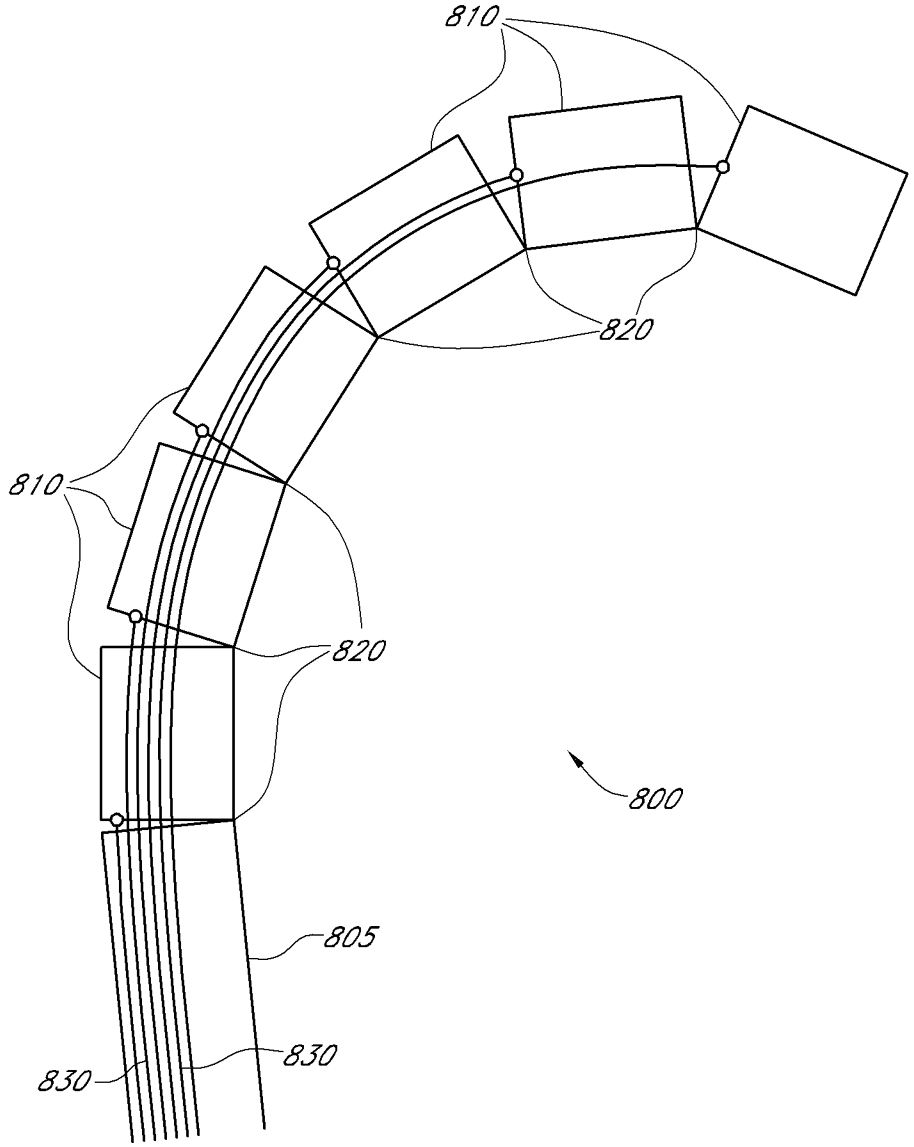
FIGS. 8 and 9 illustrate embodiments of neuromodulation catheters.

FIG. 8 illustrates an embodiment of a steerable neuromodulation catheter 800 having an articulatable tip. The neuromodulation catheter 800 comprises a catheter body 805, multiple segments 810, multiple corresponding hinges 820, and multiple corresponding articulation members (e.g., wires) 830. In some embodiments, the neuromodulation catheter 800 includes fewer than six segments, hinges, and/or articulation wires (e.g., two, three, four, or five). In some embodiments, the neuromodulation catheter 800 includes more than six segments, hinges, and/or articulation wires (e.g., seven, eight, nine, ten, eleven to twenty, or more than twenty). In one embodiment, the segments 810 and the hinges 820 are hollow.

Each of the segments 810 is coupled to adjacent segment(s) by one of the hinges 820. Each of the articulation wires is attached to at least one of the segments and passes from the segment to which it is attached through the other segments toward the catheter body 805. In operation, the articulation members (e.g., wires) may be extended or retracted as desired, thereby pivoting the articulatable tip of the catheter 800. In one embodiment, the steerable neuromodulation catheter comprises an "inchworm" end.

In some embodiments, all of the articulation wires 830 are extended and retracted in combination. In other embodiments, each of the articulation wires 830 is individually actuatable. In such embodiments, each individual segment 810 could be individually actuatable by each corresponding articulation wire 830. For example, even when the third segment, the fourth segment, the fifth segment, and the sixth segment are constrained within a guide catheter, the first segment and the second segment may be articulated by extending or retracting the first articulation wire and/or the second articulation wire, respectively, with sufficient force. The steerable catheter 800 may advantageously permit improved contact pressure between the distal tip of the steerable catheter 800 and the vascular wall of the target vessel, thereby improving treatment efficacy. In various embodiments, a first portion of segments 810 is actuated to have a first bend shape configured to conform to a first anatomical bend (e.g., a first bend of a hepatic artery branch or portion) and a second portion of segments 810 is actuated to have a second bend shape configured to conform to a second anatomical bend (e.g., a second bend of a hepatic artery branch or portion). The first portion of segments 810 and second portion of segments 810 may be actuated by movement of one or more articulation wires 830 (if multiple, collectively or independently). In one embodiment, the steerable catheter 800 substantially locks in a shaped configuration matching the shape of the hepatic artery or other artery or vessel, providing improved stability.

Figure 9:
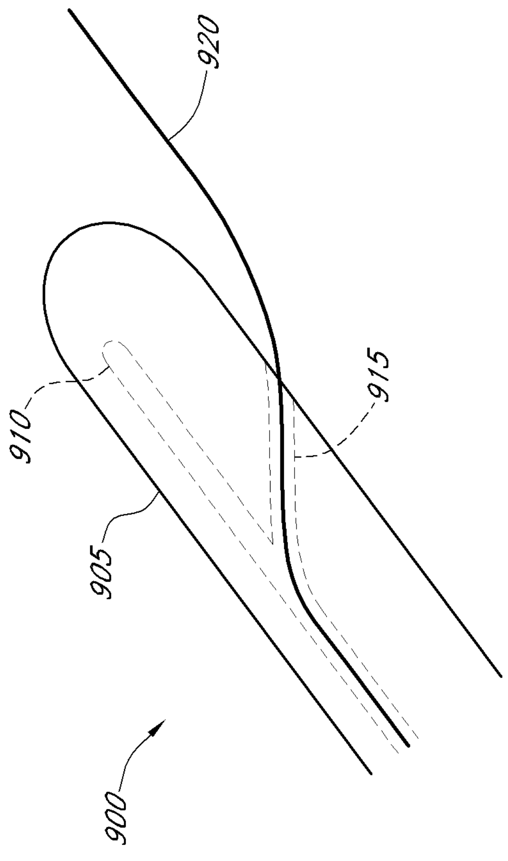

FIG. 9 illustrates an embodiment of a neuromodulation catheter 900 with a deflectable distal tip. The neuromodulation catheter 900 comprises a guidewire configured to facilitate steerability. The neuromodulation catheter 900 includes an ablation catheter tip 905, a guidewire housing 910, a guide wire channel 915, and a guidewire 920. In operation, the guidewire 920 may be extended out through guide wire channel 915 to be used in its guiding capacity to navigate through vasculature. When it is not desirable to use the guidewire 920 in its guiding capacity, the guide wire 920 may be retracted into the ablation catheter tip 905 and then extended into the guide wire housing 910, where it may be stored until needed or desired. In one embodiment, the steerable neuromodulation catheter comprises an "inchworm" end.

In some embodiments, the guidewire 920 is plastically deformable with a permanent bend in the distal tip. In such embodiments, the guidewire 920 may be rotated within the body of the neuromodulation catheter 900 to plastically deform and be pushed into the guide wire housing 910, or may be rotated 180 degrees and regain its bent configuration to exit through the guide wire channel 915. In some embodiments, a thermocouple (e.g., type T thermocouple) temperature sensor may be incorporated into the guidewire 920. The thermocouple may be used to assess thermal loss delivered to target tissue compared to thermal loss convected away by blood. In some embodiments, the guidewire 920 is used to deliver ablative energy (such as RF energy) to at least one electrode. In one embodiment, delivery of the ablative energy is facilitated by disposing a conductive gel between the guidewire 920 and the at least one ablation electrode. In various embodiments, the deflectable distal tip comprises two deflectable, steerable and/or actuatable portions, with a first portion configured to have a first bend shape to conform to a first anatomical bend (e.g., a first bend of a hepatic artery branch) and a second portion configured to have a second bend shape to conform to a second anatomical bend (e.g., a second bend of a hepatic artery branch). In one embodiment, the neuromodulation catheter 900 comprises one or more pre-bent or pre-curved portions. The pre-bent or pre-curved portions may conform to particular anatomical bend shapes (e.g., within the hepatic arteries or neighboring branches upstream or downstream of the hepatic arteries).

Figure 26:
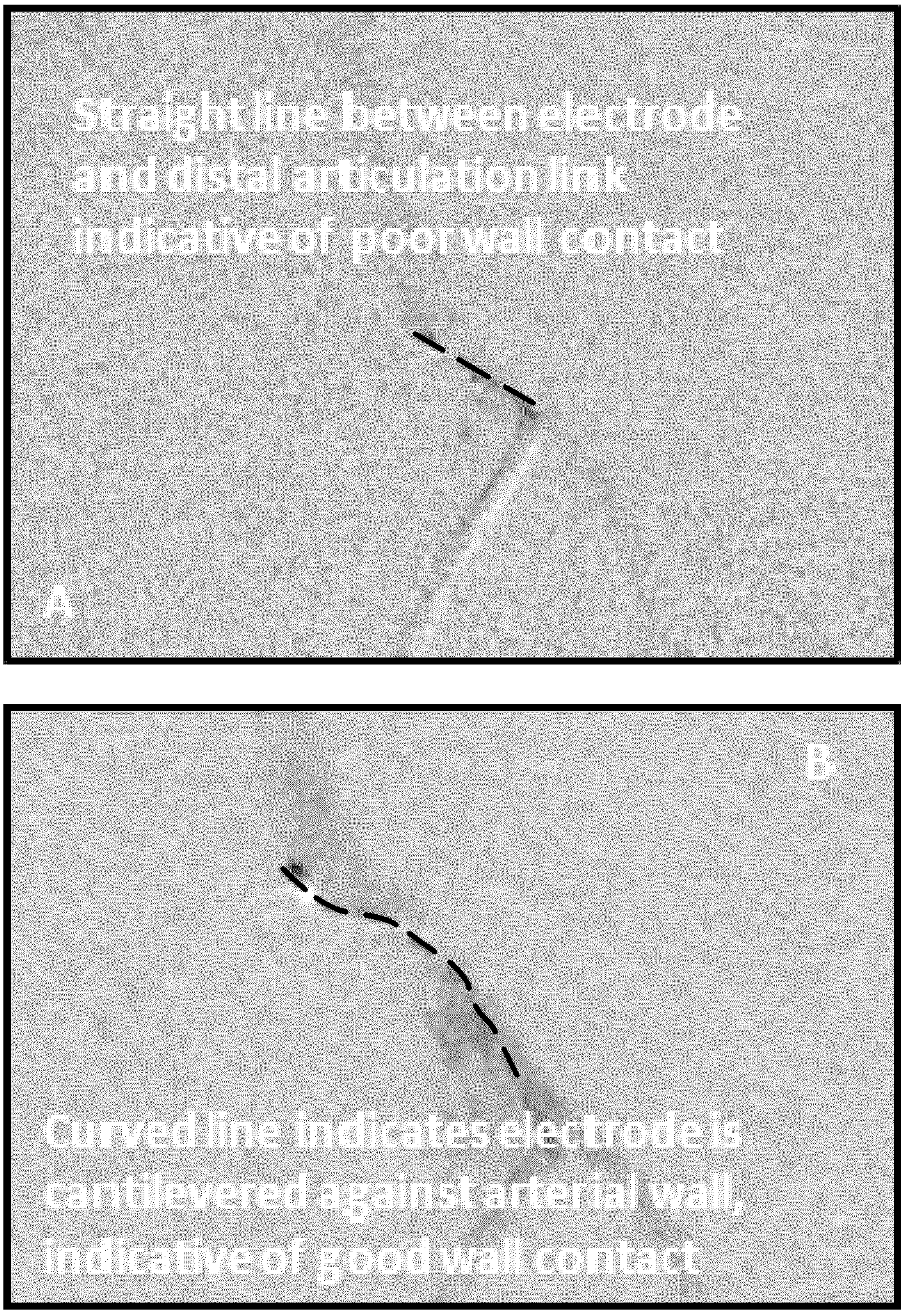
FIG. 26 illustrates an example of poor wall-electrode contact and an example of good wall-electrode contact.
Figure 27B:
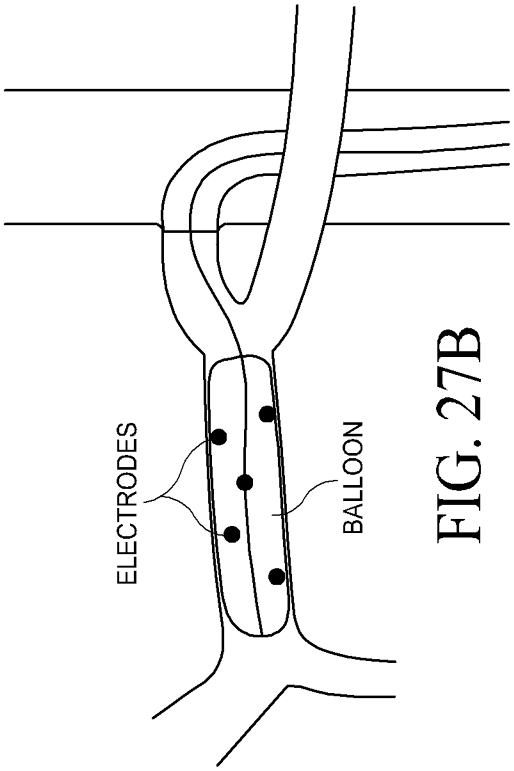
FIGS. 27A, 27B, 28A, 28B, 29, 30A, 30B, 31 and 32 illustrate embodiments of neuromodulation catheters configured to provide catheter stabilization within tortuous vasculature or within vasculature subject to movement during respiration.
Figure 27A:
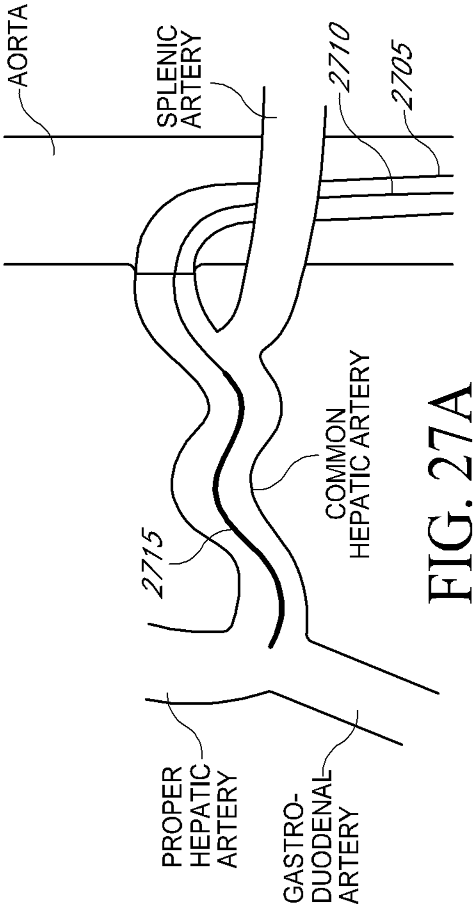
Figure 28A:
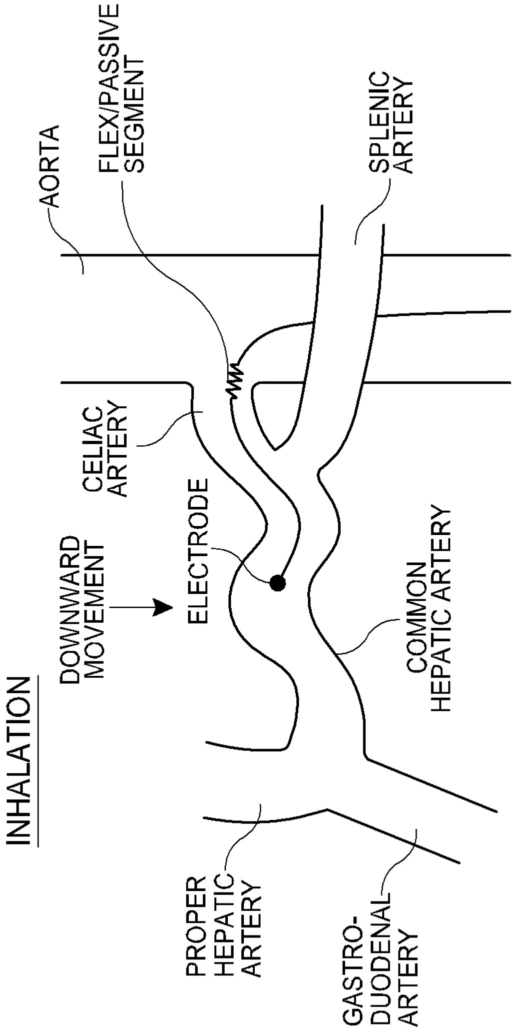

As shown in FIGS. 26, 27A and 28A, the common hepatic artery and celiac trunk can be very tortuous (e.g., can have multiple bends). In some embodiments, accessing this anatomy is performed using a highly flexible catheter with sufficiently strong column strength. In some embodiments, the ablation catheters described herein having a single electrode are configured to make contact with multiple points around the circumference of the target vessel, and have excellent torque transfer through the catheter shaft. In some embodiments, the catheters are flexible enough to navigate a tortuous anatomy without kinking or reduce the likelihood of kinking. Kinking can occur because the cross section of the shaft becomes oval as it is bent. For example, after a critical bend radius is reached, the oval may collapse and a kink may be created. In accordance with several embodiments, the catheters described herein prevent, or reduce the likelihood of, "ovalization" while enabling material on the inner and outer arcs to compress and stretch, respectively.

With a single electrode or limited number of electrodes on an ablation device, rotation of the electrodes and multiple ablation doses may be required to create circumferential ablation of the nerves surrounding a vessel. In the case of denervating the common hepatic artery (CHA), unique vessel tortuosity (multiple acute turns) can make torque transfer more difficult. When a torque is applied at the proximal end of a catheter shaft the torque may first be translated into a distal rotational displacement until the shaft contacts the length of the vessel wall. After the shaft is supported, the torque applied at the proximal end may then cause a rotation of the distal end of the shaft, but may "flip" or otherwise result in uncontrolled rotation of the distal electrode.

Figure 82A:
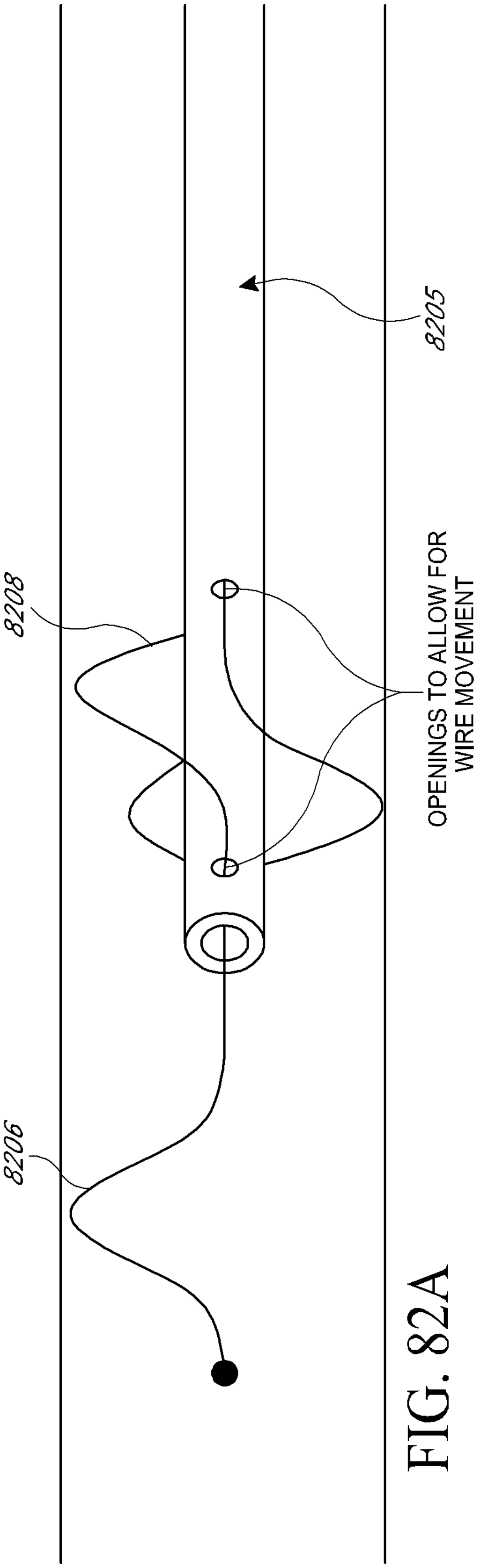
Figure 82B:
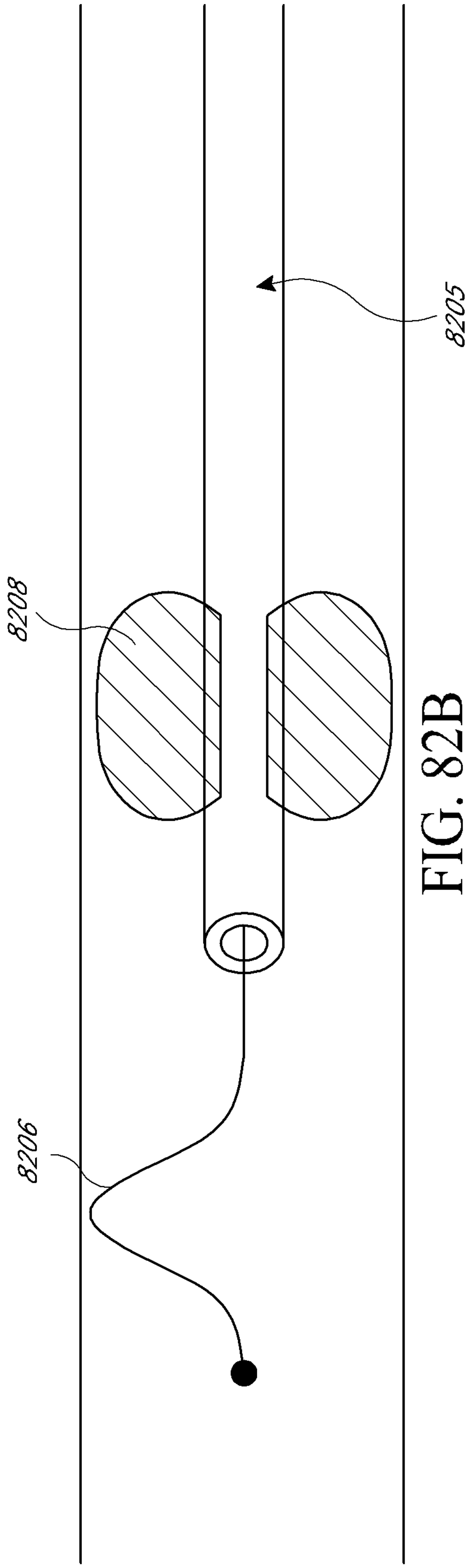

Referring now to FIGS. 82A and 82B, an embodiment of a catheter system configured to support the catheter shaft within the vessel lumen, thereby reducing the translation of the shaft into the vessel wall. The illustrated embodiment may advantageously improve torque efficiency by reducing losses along the length of the arterial lumen and allow the proximally applied torque to result in controlled rotation of a distal electrode at a distal end of the catheter shaft. As illustrated in FIG. 82A, a guide catheter 8205 with a lumen that is just larger than the outer diameter of the ablation device 8206 is able to support itself against a section of the vessel wall by means of a support structure 8208. In one embodiment, the support structure 8208 is comprised of multiple wires or ribbons that are pushed out of a plurality of lumens disposed along a length of the guide catheter and exposed to the arterial or other vessel lumen near (e.g., within 1 cm of, within 2 cm of, within 3 cm of) the distal end of the guide catheter. The wires or ribbons, disposed within the lumens and controlled at the proximal end of the guide catheter 8205, expand outward until they contact the vessel wall. In some embodiment, the wires or ribbons exert a force against the vessel wall at multiple points, thereby providing a reaction force to restrict lateral movement of the guide catheter when the ablation device 8206 is rotated within the guide catheter 8205. The inner lumen of the guide catheter 8205 and outer surface of the ablation device 8206 (e.g., electrode/catheter) can be comprised of materials or coatings having low coefficients of friction (e.g., PTFE or hydrophilic coatings) in order to further reduce the rotational friction between the two devices.

In one embodiment, a plurality of support structures could be used to place the guide catheter 8205 in contact with the vessel wall. Some examples include pressurized support balloons (such as shown in FIG. 82B) that may allow for perfusion, self-expanding stent structures, and basket sections of the guide catheter polymer tube that can be compressed and expanded radially or otherwise deployed.

Figure 83:
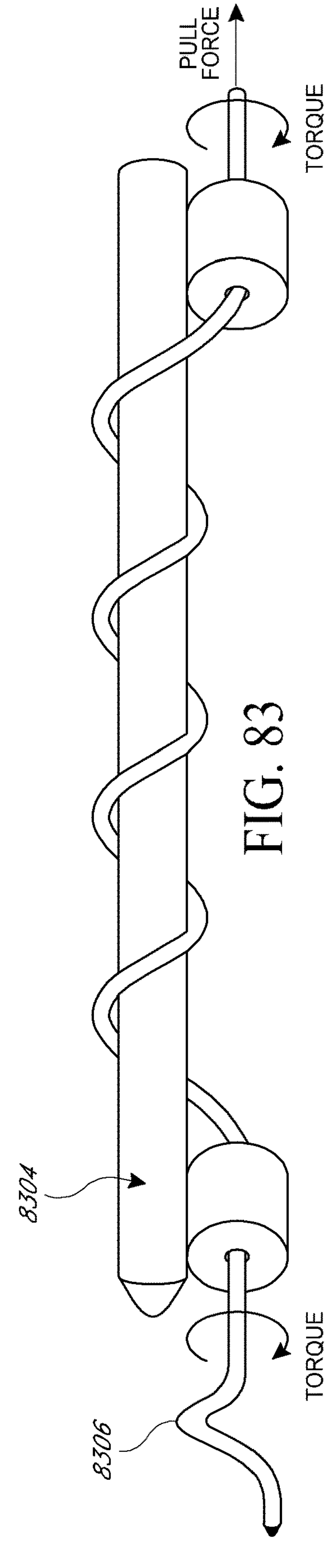

In one embodiment, illustrated in FIG. 83, an inner support member 8304 (e.g., a guidewire) is configured to hold the ablation device. For example, loops 8301 and 8302 can be welded or otherwise fixed or coupled to the inner support member to hold the ablation device. The ablation device may then be passed through the loops and wrapped in a spiral around the inner support member between the loops. When a torque is applied (in one direction) to the ablation device, the ablation device can take up the slack between the inner support member and then transfer the torque to the distal end, "winding" the distal end of the ablation device in one rotational direction. If the torque is applied in the opposite direction, the ablation device wants to "unwind." In one embodiment, this torque improvement mechanism advantageously allows for improved torque efficiency in one direction. In one embodiment, a pull force can be applied to a proximal end of the ablation device, either alone, or in combination with the torque.

Figure 84:
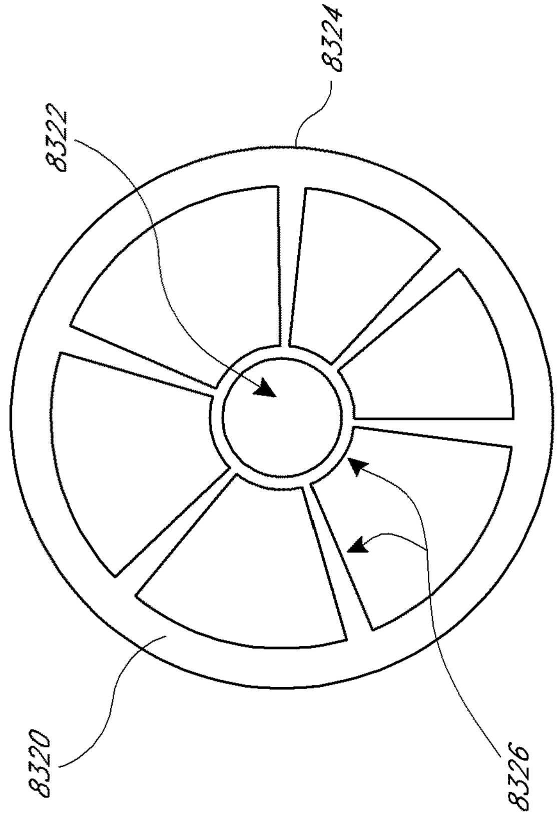

In one embodiment, illustrated in FIG. 84, the guide catheter is comprised of an expandable balloon 8320 having an internal catheter-receiving lumen 8322 and an external, arterial contacting surface 8324, with an external lumen extending between the internal lumen 8322 and the external surface 8324. The internal lumen 8322 and external lumen are connected by a plurality of struts 8326 running along a portion of, or substantially the entire, length of an inflatable guide region of the guide catheter. Upon insertion at the target anatomy (e.g., the celiac axis), the balloon chambers defined by the struts are inflated to maintain the position of the guide catheter and improve navigation and torque response of the ablation catheter inserted within the internal lumen 8322 of the guide catheter.

Figure 94:
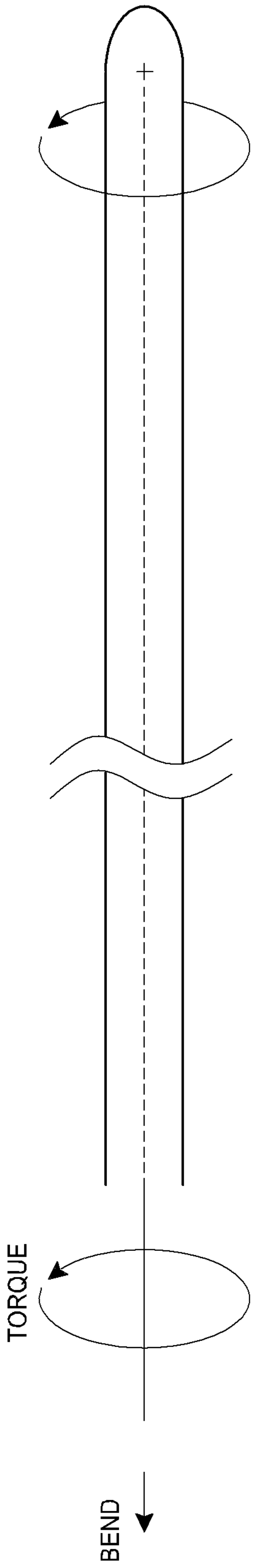

Referring now to FIG. 94, an embodiment of a control mechanism configured to provide precise control of an electrode at the distal end of a catheter by controlling the distal end of the catheter directly is provided. As shown in FIG. 94, the direct control maybe accomplished by applying torque/rotation to a control wire disposed within the catheter shaft and anchored to a distal location of the catheter, such as near the electrode region. In accordance with several embodiments, the challenges associated with torqueing a catheter disposed in tortuous anatomy may altogether be avoided or reduced.

Figure 23:
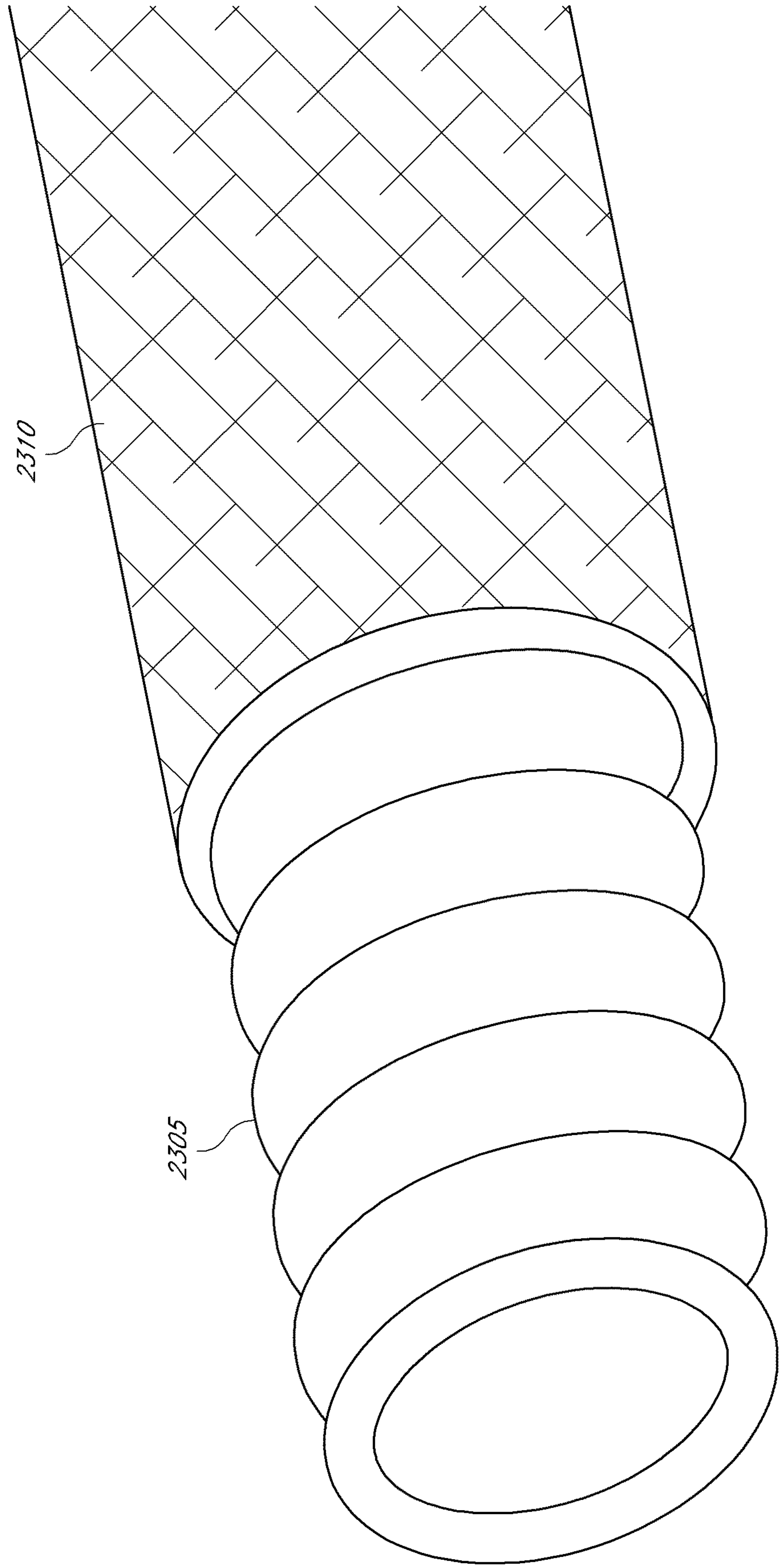
FIGS. 23-25 illustrate embodiments of neuromodulation catheters.

FIG. 23 illustrates one embodiment of a distal portion of a catheter that combines the benefits of a coil 2305 (e.g., kink prevention) and a solid rod 2310 (improved torque transfer for a given diameter constraint). The catheter comprises a hose having a coiled and ribbed polymer inner layer and a braided outer layer that is disposed about the inner layer. The inner layer prevents, or reduces the likelihood of, "ovalization" while the outer layer provides improved column strength and torque transfer properties. In one embodiment, the inner layer comprises a coil (without the ribbed polymer) and the outer layer comprises a braid.

Figure 24B:
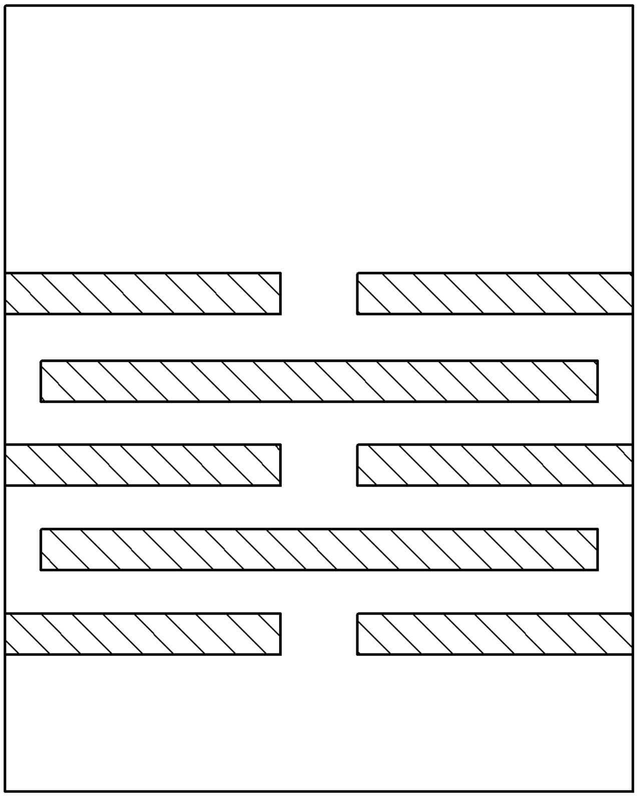
Figure 24A:
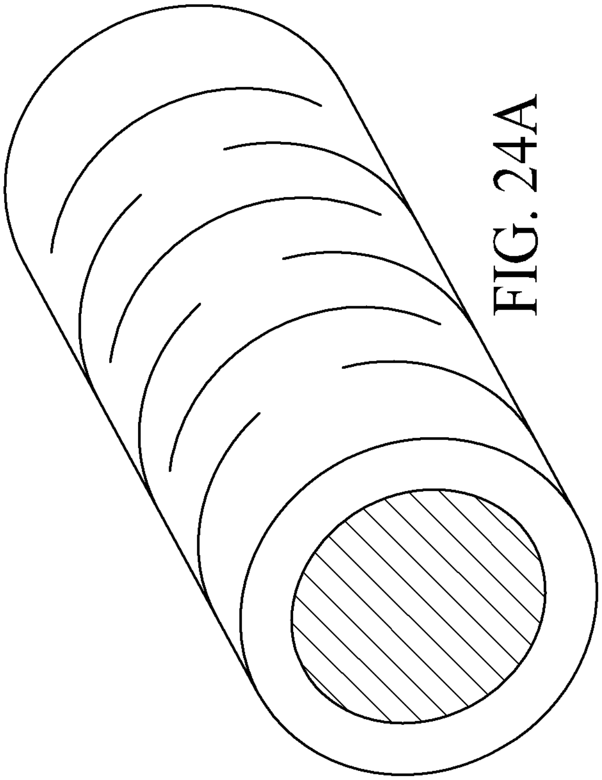

FIGS. 24A and 24B illustrate an embodiment of a hypotube having a cut pattern that advantageously provides bending flexibility, column strength, and torquability. Material may be removed around the circumference of a tube so that only a "peninsula" of material connects one ring or portion of material to another, thereby allowing the rings of material to bend towards each other and move into the empty space. Alternating the position of the rings by 90 degrees or about 90 degrees can enable the ring portions to bend in multiple directions. The cut pattern may be formed by laser or mechanical cutting means.

Figure 25:
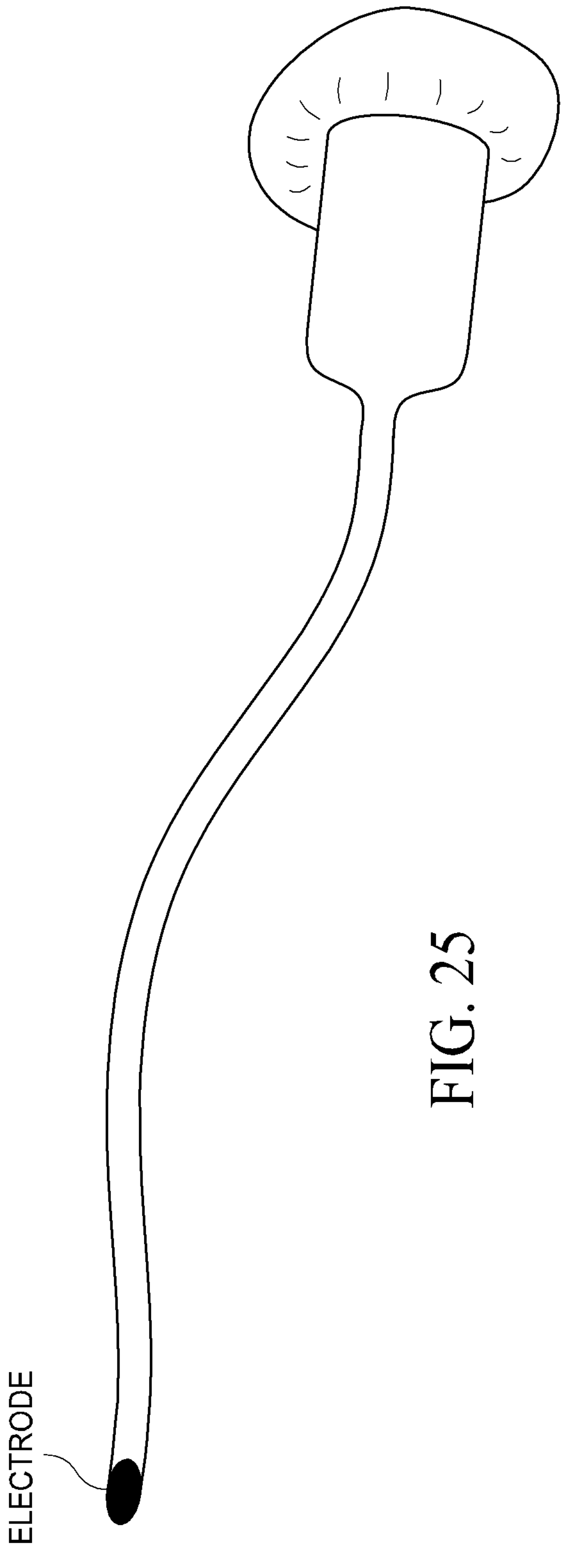

Torquability can be especially advantageous in branches of the hepatic artery or surrounding arteries, where the small size of the arterial lumen may not permit passage of a multi-tip electrode catheter. In accordance with several embodiments, it is particularly advantageous to have fine control of the rotation of an electrode (e.g., to adjust the position of the electrode in subsequent ablations or other procedural actions to cover the area in the proximity of the efferent nerves). One embodiment of a catheter for improving user control of electrode positioning is schematically shown in FIG. 25. As shown, a small-diameter shaft of the catheter may be connected to a larger-diameter cylindrical shaft, thereby providing a physician or other clinician with a larger control surface for adjustment. In one embodiment, the control surface could comprise the ring gear of a planetary gear system, with the catheter shaft forming the sun gear and the ratio of the rotation of the control surface to the rotation of the catheter being determined by the planetary gears. In one embodiment, the ratio is <1:1 (e.g., 1:10, 1:9, 1:8, 1:7, 1:6, 1:5, 1:4, 1:3, 1:2).

Referring now to FIG. 26, the tortuous anatomy of the hepatic artery and surrounding arteries may provide challenges for access and catheter contact (in embodiments where contact with the arterial wall facilitates modulation of nerves, such as RF catheter ablation with one or more electrodes). For example, FIG. 26 illustrates an electrode catheter within a tortuous artery. As shown in FIG. 26A, a straight line formed between an electrode and a distal articulation link of the catheter may be indicative of poor arterial wall contact, whereas a curved line between the electrode and the distal articulation link (as shown in FIG. 26B) may indicate that the electrode is cantilevered against the arterial wall (which may be indicative of sufficient arterial wall contact).

Figure 105A:
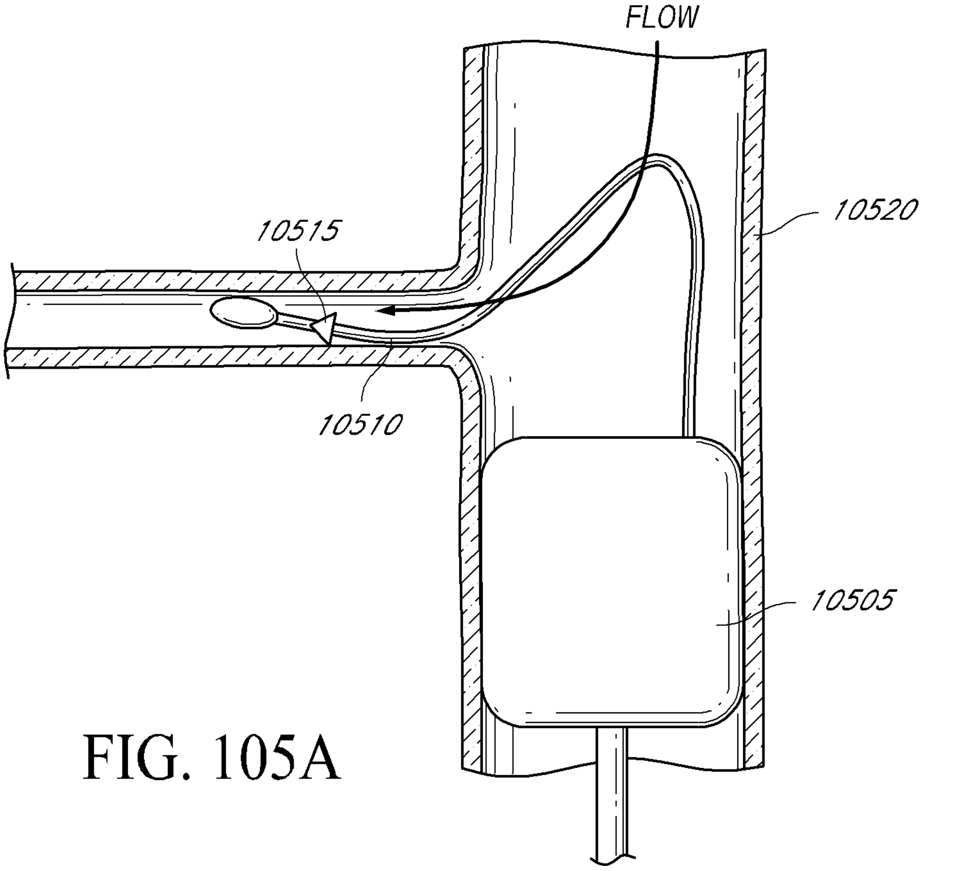
FIGS. 105A and 105B illustrate embodiments of devices (and methods of using such devices) specifically designed to facilitate access to tortuous hepatic vasculature.
Figure 105B:
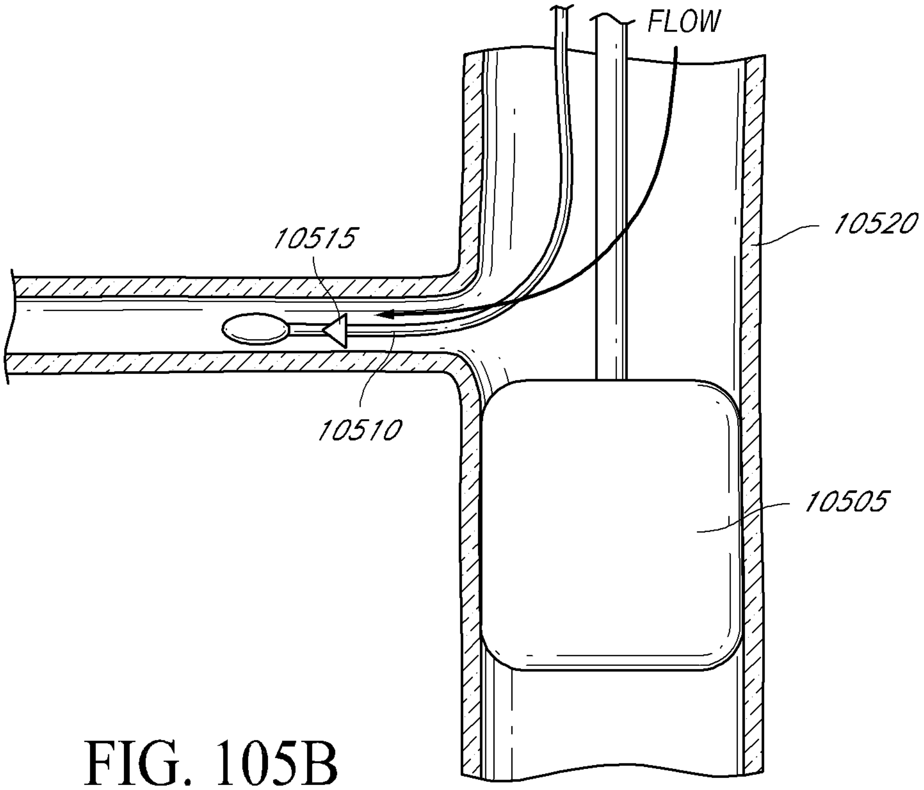

FIGS. 105A and 105B illustrate embodiments of devices (and methods of using such devices) specifically designed to facilitate access to tortuous hepatic vasculature. In certain situations, it may be difficult for a clinician to locate an artery using a guidewire. In accordance with some embodiments, a balloon catheter 10505 may be used to temporarily block distal portions of arteries. An electrode catheter or guidewire 10510 having a very loose, flexible distal portion may be positioned near an origin of a branch vessel where access is desired. The distal portion of the electrode catheter or guidewire may comprise an inflatable or otherwise expandable sail or parachute-like attachment 10515 designed to capture blood flow and drift with the blood flow into a target branch vessel, thereby facilitating access to the target branch vessel. FIG. 105A illustrates advancement of the balloon catheter 10505 and the electrode catheter or guidewire 10510 from a downstream location with respect to a main vessel 10520 and FIG. 105B illustrates advancement of the balloon catheter 10505 and the electrode catheter or guidewire 10510 from an upstream location with respect to the main vessel 10520. In some embodiments, blood flow may facilitate stabilization and maintenance of electrode contact and/or direct the electrode to the wall of the vessel.

In accordance with several embodiments described herein, the electrode catheters advantageously facilitate improved stabilization of the catheter and/or electrode within target vessels, which can lead to more predictable outcomes and more effective procedures. For example, the improved stabilization may prevent or reduce the likelihood of heating, burning or charring of unwanted portions of tissue or of the blood (which may prevent or reduce the likelihood of thrombus formation). Embodiments of catheters described herein may also facilitate access from the origin of the common hepatic artery.

FIGS. 27A and 27B illustrate an embodiment of a catheter system configured to provide improved wall contact and catheter stabilization within tortuous vasculature (e.g., tortuous vasculature of the common hepatic artery). The catheter system comprises a guide catheter 2705 and an expandable element catheter 2710 (e.g. balloon catheter). In the illustrated embodiment, the expandable element catheter 2710 comprises a balloon catheter having a balloon positioned at a distal end of the balloon catheter. The balloon catheter may be inserted within the common hepatic artery in a deflated state (as shown in FIG. 27A) and then inflated to an expanded state (as shown in FIG. 27B). In some embodiments, expansion of the expandable element 2715 (e.g., inflation of a balloon) straightens out a tortuous vessel (e.g., hepatic artery portion) to facilitate wall contact of one or more electrodes or other treatment members (e.g., transducers) disposed in or on the expandable element. If multiple electrodes or other treatment members are used, the multiple members may be spaced at various positions along the length and/or circumference of the expandable element, thereby facilitating treatment at multiple locations (simultaneously or separately). The expanded state may also result in improved catheter stabilization, thereby improving efficiency of the treatment procedure and reducing treatment times.

The expandable element may be self-expandable, mechanically expandable, or pneumatically expandable (e.g., inflatable). In one embodiment, the expandable element comprises shape memory material (e.g., a self-expandable stent-like element). In one embodiment, the catheter system comprises a passive segmented catheter (e.g., shape-lock assembly of one or more nested links) that guides the catheter into and through a tortuous vessel in a flexible state and then transitions to a rigid, shape-locked state. In one embodiment, the catheter enters the tortuous vessel in a curved state and then straightens out the vessel to cause the vessel to form a substantially straight cylindrical shape.

Respiration can cause movement of vessels being targeted for nerve modulation. For example, respiration can cause movement by as much as 2-5 cm in the area of the common hepatic artery, which may result in undesirable motion of a neuromodulation catheter or a treatment element (e.g., electrode or transducer) disposed thereon. The motion caused by respiration may adversely affect continuous and sufficient wall contact of a treatment element (e.g., electrode or transducer) against a vessel wall, and in several embodiments described herein, the adverse effect is reduced or removed.

The hepatic arteries move due to the tidal breathing motions of the hemidiaphragm and the motion of the diaphragm. The vertical motion of the hepatic arteries generally matches that of the right or left hemadiaphragm. In one embodiment, the mean horizontal movement can be up to 1.90 mm. During a porcine study of hepatic arterial ablation, it was observed that the position of a catheter tip post-ablation was consistently up to 1 cm from the initial target location, increasing the variability of the resulting lesion and, correspondingly, the consistency with which hepatic arterial denervation was achieved. In various embodiments, methods and systems aimed at reducing catheter tip and/or electrode motion during the procedure are provided, as breathing suspension may not be feasible for the duration of the procedures (e.g., ablations) required to achieve hepatic denervation or other nerve modulation.

In various embodiments, undesired motion of neuromodulation catheters (e.g., ablation catheters) can be reduced by substantially reducing the friction between the neuromodulation catheter and the guide catheter within which the neuromodulation catheter is inserted. The reduction of friction can be achieved, for example, by means of a hydrophobic (e.g., fluorine-based) lubricant or coating. In some embodiments, the force and/or displacement translation from the proximal end of the catheter (e.g., in contact with an introducer sheath) and the distal end of the catheter (e.g., electrode) can be reduced to address the motion of the catheter. In some embodiments, the friction near the catheter's distal end (e.g., electrode) and the target tissue can be increased to address the motion of the catheter.

Figure 28B:
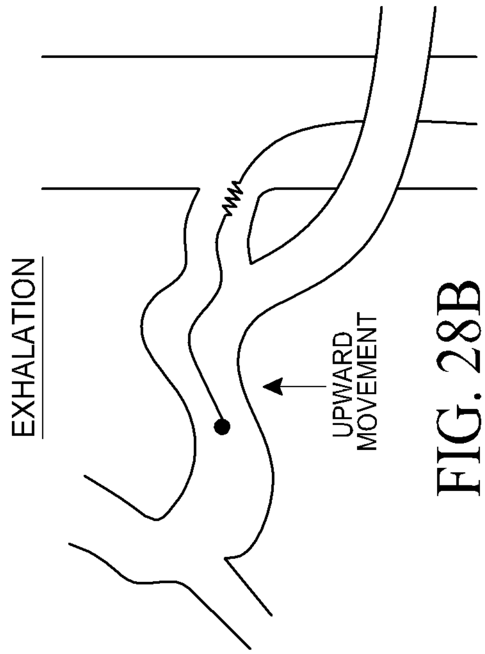

FIGS. 28A and 28B illustrate an embodiment of catheter configured to address the effects of respiratory motion on the hepatic arteries. FIG. 28A illustrates the catheter during an inhalation and FIG. 28B illustrates the catheter during an exhalation. The catheter comprises a disconnection or a flexible and/or passive segment. In some embodiments, the flexible and/or passive segment is positioned at an origin of the common hepatic artery (as shown in FIG. 28A and FIG. 28B).

Figure 29:
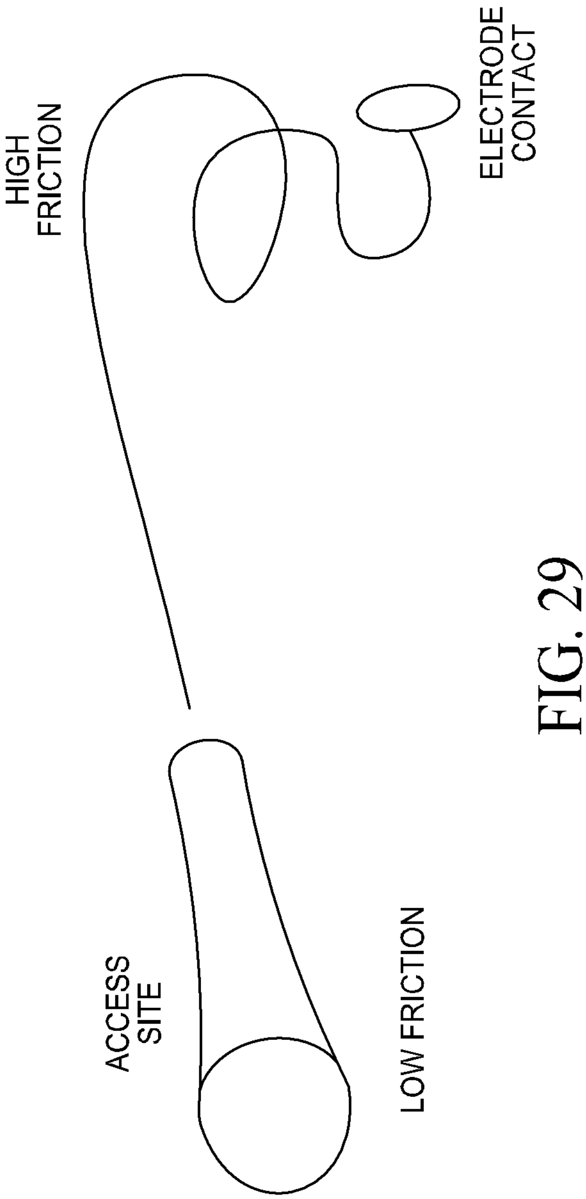

FIG. 29 illustrates an embodiment of a catheter system configured to address motion of the target vessels by reducing the force and/or displacement translation from the proximal end of the catheter and the distal end of the catheter. In methods of using the catheter of FIG. 29, slack can be placed in the catheter system between an access site and a distal end of the catheter (e.g., electrode). In one embodiment, the slack formation is accomplished by fixing the distal end of the catheter and then pushing the flexible catheter forward a few centimeters so additional material lies between the distal end of the catheter and the access site. In one embodiment, any movement of the distal end relative to the access site straightens out the slack in the catheter instead of applying a translational force to the distal end and/or access site.

Figure 30A:
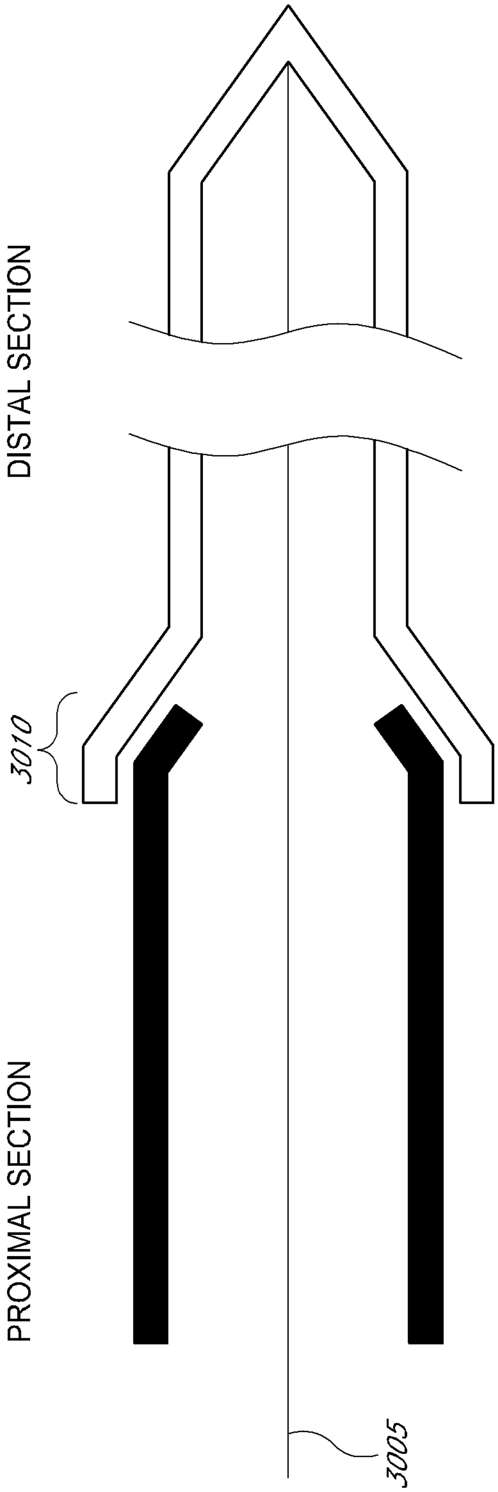
Figure 30B:
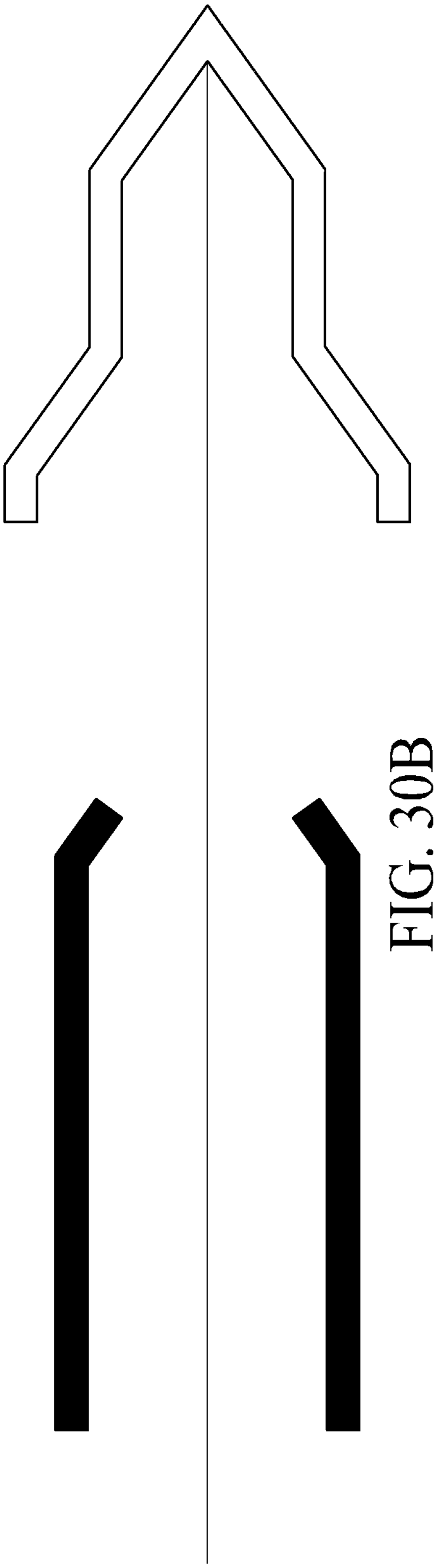

In some embodiments, the catheter could also be designed to selectively create or allow slack between the distal end and proximal end of the catheter. One embodiment of a catheter with a distal segment and a proximal segment is shown in FIGS. 30A and 30B. In one embodiment, a tension wire or tether 3005 runs from the distal segment to the proximal segment. When placed in tension, this wire or tether 3005 can pull the distal segment towards the proximal segment. A mechanical interface 3010 (e.g., a tapered end of the proximal section and a flared end of the distal section), can align the two segments and prevent the distal segment from sliding over the proximal segment. During access and navigation of the catheter, the tension wire or tether 3005 can be placed in tension; however, during treatment (e.g., ablation dosage), the tension can be released and the wire or tether 3005 can act as the tether connecting the two segments. The mechanical interface 3010 may be formed by any corresponding mechanical structures (e.g., notch/protrusion, latches) or adhesive structures.

Figure 31:
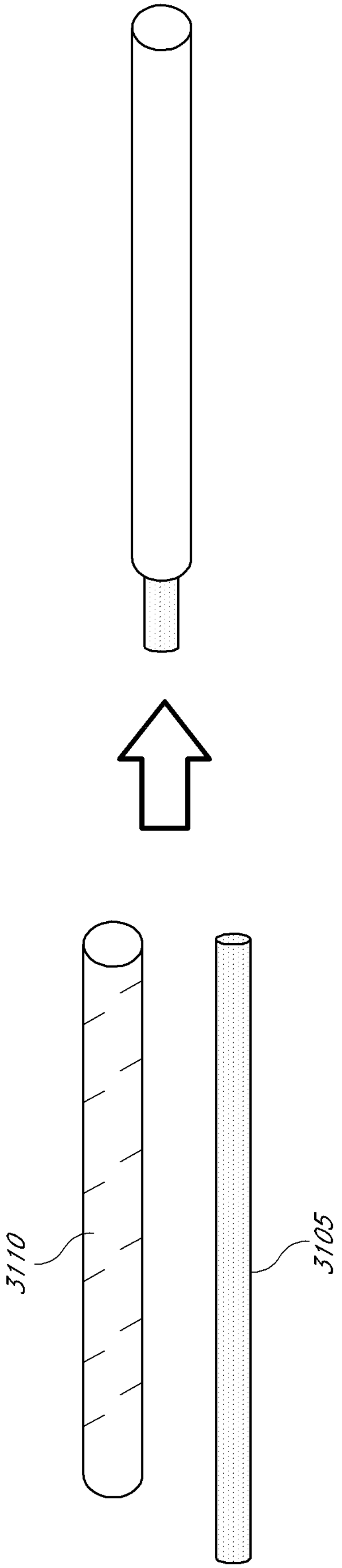

In accordance with some embodiments, flexibility of the catheter allows slack to be added to the system, but also decreases push-efficiency and reduces the catheter's ability to access the hepatic arteries. In some embodiments, a mechanism for switching between a flexible and a stiff configuration is advantageously provided. One embodiment of such a switching mechanism involves moving a stiff member 3105 axially into or out of a nominally flexible catheter shaft 3110, thereby defining a selectably stiff region, as illustrated in FIG. 31. For example, the stiff member could comprise a removable guidewire.

Figure 32:
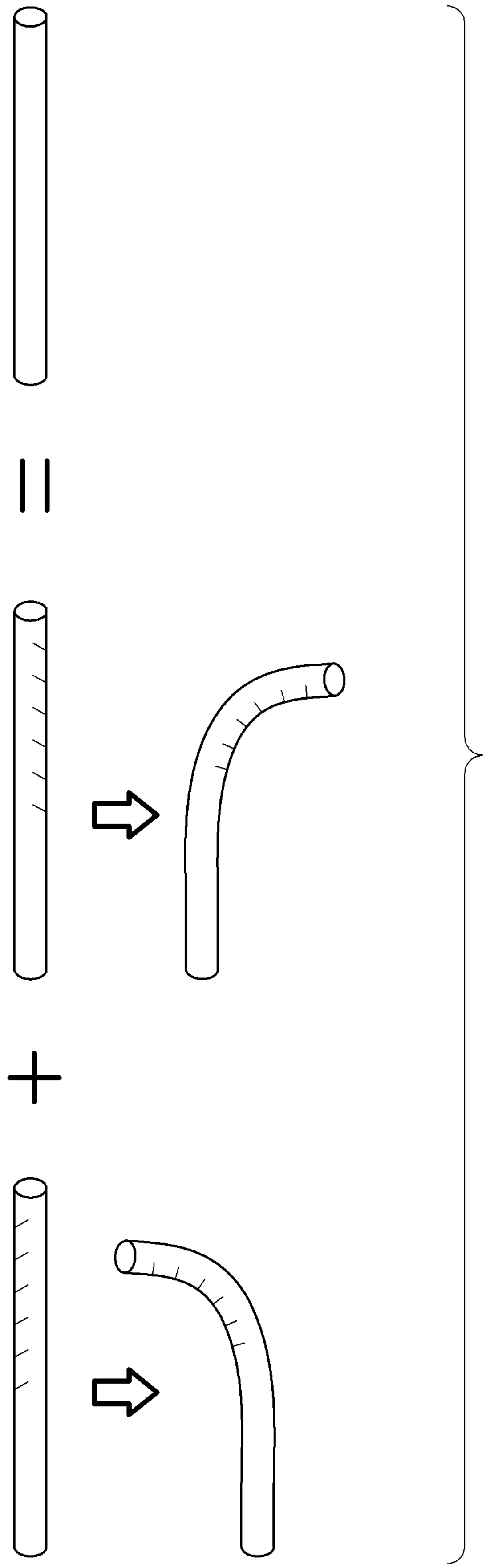

In one embodiment, the switching mechanism involves combining two coaxial members having a flexible region and a singular bending plane, e.g., rotatable members that are flexible in a singular direction, as illustrated in FIG. 32. When the flexible directions of the two rotatable members are aligned, the catheter portion is flexible, and when the rotatable members are rotated relative to each other substantially along their longitudinal axes such that their flexible directions are out of alignment, the catheter portion is stiff or substantially rigid.

Through various studies of the common hepatic artery anatomy, there seems to be greater variation in motion as one proceeds distally down the length of the common hepatic artery, which makes sense physiologically, since more distal points are closer to the diaphragm, which is causing such variation. In some embodiments, catheter stiffness may be varied along its length to compensate for the variation in anticipated motion of the target vessel (e.g., common hepatic artery) due to respiratory motion. One or more portions of the catheter length configured to be positioned in portions of the vessel likely to experience greater movement due to respiration may be constructed to have greater axial compliance, thereby allowing the portion of the catheter to move and stretch with the vessel. In one embodiment, the catheter may have an axial stiffness gradient along the length of the catheter by using alloys that allow for change in stiffness with relative composition of different metals. In one embodiment, the same material (e.g., metal) is used but the thickness of the catheter wall is tapered along its length. In one embodiment, material composition or amount may be changed at discrete locations or "links" along the length of the catheter. In some embodiments, the stiffness of a catheter configured to access and target the common hepatic artery decreases along the length of the catheter from proximal to distal at the portion of the catheter configured to be positioned within the common hepatic artery. In one embodiment, the catheter comprises multiple electrodes positioned at different points along the length of the catheter, and thus at different points of catheter stiffness. The more distal electrodes could track with greater respiratory movement than the more proximal electrodes. Keeping the position of the electrodes stationary may allow for a more consistent spacing between ablations, potentially allowing patients with shorter vessels to achieve more ablations.

In some embodiments, energy delivery may be gated based on respiration using temperature or impedance measurements due to the asymmetric motion of an energy delivery element during a respiratory cycle. The energy delivery element may remain relatively stationary for about two-thirds of the respiratory cycle (expiration) and during this time period the tissue being treated may increase in temperature. When the energy delivery element is in motion during the other third of the respiratory cycle (inspiration), the tissue may cool down. The changes in temperature may be monitored and used to gate the delivery of energy so that energy is only delivered when the energy delivery element is stationary (e.g., during expiration) or power may be increased during the stationary period to maintain a desired average power level (e.g., 10 Watts). Because tissue impedance varies with temperature, impedance measurements could be monitored (either alternatively or in combination with temperature) and used to start and stop the energy delivery. In situations where variation in temperature and/or impedance measurements is not detected, power may be delivered at a constant rate.

In such embodiments in which power output is synchronized with respiration, the ramp of the energy source may be adjusted to achieve an almost instantaneous climb of power. The adjustment may be performed by modifying a ramping algorithm of the energy source. In some embodiments, the energy source may be programmed to ramp up from a power output below 1 W to a peak power output in less than half a second. In accordance with several embodiments, synchronization of power output with respiration takes advantage of the time frame when blood flow in the vessel (e.g., common hepatic artery) is at a maximum, thereby providing enhanced cooling to the energy delivery element and vessel wall, which may reduce charring, notching and vessel spasm.

In some embodiments, a catheter system is configured to extravascularly and selectively disrupt target nerves. In some embodiments, a catheter is advanced through a cardiovascular system, such as described above, to the target site. The catheter may be passed transluminally to the extravascular space or may create a virtual space between the vascular media and adventitia of the vessel. In some embodiments, the catheter, once positioned at the desired location is activated to selectively modulate or disrupt the target nerve or nerves. The selective disruption may be accomplished or performed through chemo-disruption, such as supplying any type of nerve destroying agent, including, but not limited to, neurotoxins or other drugs detrimental to nerve viability. In some embodiments, selective disruption is performed through energy-induced disruption, such as thermal or light ablation (e.g., radiofrequency ablation, ultrasound ablation, or laser ablation). In one embodiment, a camera or other visualization device (e.g., fiberoptic scope) is disposed on a distal end of the catheter to ensure that nerves are targeted and not surrounding tissue. If a target location is adjacent the branch between the common hepatic artery and the proper hepatic artery, a less acute catheter bend may be required due to the angulation between the bifurcation of the common hepatic artery and the proper hepatic artery. In some embodiments, the catheter comprises a side port, opening or window, thereby allowing for delivery of fluid or energy to denervate or ablate nerves with the longitudinal axis of the catheter aligned parallel or substantially parallel to the target vessel portion. In some embodiments, the catheter or probe is inserted percutaneously and advanced to the target location for extravascular delivery of energy or fluid.

C. Energy-Based Neuromodulation

1. Radiofrequency

In some embodiments, a catheter system comprises an ablation device coupled to a pulse-generating device. For example, the ablation device may be an ablation catheter. The ablation catheter may have a proximal end and a distal end. In some embodiments, the distal end of the ablation catheter comprises one or more electrodes. The one or more electrodes can be positioned on an external surface of the ablation catheter or can extend out of the distal end of the ablation catheter. In some embodiments, the electrodes comprise one or more bipolar electrode pairs. In some embodiments, the electrodes comprise one or more active electrodes and one or more return electrodes that cooperate to form electrode pairs. In some embodiments, one or more electrodes are monopolar electrodes. In some embodiments, the distal end of the ablation catheter comprises at least one bipolar electrode pair and at least one monopolar electrode. One or more electrically conductive wires may connect one or more electrodes located at the distal end of the ablation catheter to the pulse-generating device. In some embodiments, multiple electrodes can extend from the ablation catheter on multiple wires to provide multiple energy delivery locations or points within a vessel (e.g., a hepatic artery).

In some embodiments, the pulse-generating device delivers electrical (e.g., radiofrequency (RF)) signals or pulses to the electrodes located at or near the distal end of the ablation catheter. The electrodes may be positioned to deliver RF energy in the direction of sympathetic nerve fibers in the hepatic plexus to cause ablation due to thermal energy. In some embodiments, the electrodes are positioned on top of reflective layers or coatings to facilitate directivity of the RF energy away from the ablation catheter. In some embodiments, the electrodes are curved or flat. The electrodes can be dry electrodes or wet electrodes. In some embodiments, the catheter system comprises one or more probes with one or more electrodes. For example, a first probe can include an active electrode and a second probe can include a return electrode. In some embodiments, the distal ends of the one or more probes are flexible. The ablation catheter can comprise a flexible distal end. Variable regions of flexibility or stiffness are provided in some embodiments. In various embodiments, a first flexible portion is actuated to have a first bend shape configured to conform to a first anatomical bend (e.g., a first bend of a hepatic artery branch) and a second flexible portion is actuated to have a second bend shape configured to conform to a second anatomical bend (e.g., a second bend of a hepatic artery branch).

In one embodiment, a pair of bipolar electrodes is disposed at a location that is substantially tangential to the inner lumen of the hepatic artery, each individual electrode having an arc length of 20 degrees, with an inter-electrode spacing of 10 degrees. In one embodiment, the arc length and electrode spacing are configured to deliver thermal energy to a region within 1-3 mm of a hepatic artery lumen. The edges of the two electrodes may have radii sufficient to reduce current concentrations. In some embodiments, the two electrodes are coated with a thin layer of non-conductive material to reduce current concentrations such that energy is delivered to target tissue via capacitive coupling. The arc length and spacing of the bipolar electrodes may be varied to alter the shape of the energy delivery zones and thermal lesions created by the delivery of energy from the electrodes.

In some embodiments, peripheral active or grounding conductors are used to shape an electric field. In one embodiment, a grounding needle is positioned perivascularly to direct ablative current towards nerves within the perivascular space. In a non-invasive embodiment to accomplish the same effect, high ion content material is infused into the portal vein. In another embodiment, a shaping electrode is positioned within the portal vein using percutaneous techniques such as employed in transjugular intrahepatic portosystemic (TIPS) techniques. In one embodiment, a second shaping electrode is positioned in the biliary tree endoscopically.

In some embodiments, a plurality of electrodes are spaced apart longitudinally with respect to a center axis of the ablation catheter (e.g., along the length of the ablation catheter). In some embodiments, a plurality of electrodes are spaced apart radially around a circumference of the distal end of the ablation catheter. In some embodiments, a plurality of electrodes are spaced apart both longitudinally along a longitudinal axis of the ablation catheter and radially around a circumference of the ablation catheter from each other. In various embodiments, the electrodes are positioned in various other patterns (e.g., spiral patterns, checkered patterns, zig-zag patterns, linear patterns, randomized patterns).

One or more electrodes can be positioned so as to be in contact with the inner walls (e.g., intima) of the blood vessel (e.g., common hepatic artery or proper hepatic artery) at one or more target ablation sites adjacent the autonomic nerves to be disrupted or modulated, thereby providing intravascular energy delivery. In some embodiments, the electrodes are coupled to expandable and collapsible structures (e.g., self-expandable or mechanically expandable) to facilitate contact with an inner vessel wall. The expandable structures can comprise coils, springs, prongs, tines, scaffolds, wires, stents, balloons, and/or the like. The expandable electrodes can be deployed from the distal end of the catheter or from the external circumferential surface of the catheter. The catheter can also include insulation layers adjacent to the electrodes or active cooling elements. In some embodiments, cooling elements are not required. In some embodiments, the electrodes can be needle electrodes configured to penetrate through a wall of a blood vessel (e.g., a hepatic artery) to deliver energy extravascularly to disrupt sympathetic nerve fibers (e.g., the hepatic plexus). For example, the catheter can employ an intra-to-extravascular approach using expandable needle electrodes having piercing elements. The electrodes can be disposable or reusable.

In some embodiments, the ablation catheter includes electrodes having a surface area of about 2 to about 5 $mm^2$, 5 to about 20 $mm^2$, about 7.5 to about 17.5 $mm^2$, about 10 to about 15 $mm^2$, overlapping ranges thereof, less than about 5 $mm^2$, greater than about 20 $mm^2$, 4 $mm^2$, or about 12.5 $mm^2$. In some embodiments, the ablation catheter relies only on direct blood cooling. In some embodiments, the surface area of the electrodes is a function of the cooling available to reduce thrombus formation and endothelial wall damage. In some embodiments, lower temperature cooling is provided. In some embodiments, higher surface areas are used, thereby increasing the amount of energy delivered to the perivascular space, including surface areas of about 5 to about 120 $mm^2$, about 40 to about 110 $mm^2$, about 50 to about 100 $mm^2$, about 60 to about 90 $mm^2$, about 70 to about 80 $mm^2$, overlapping ranges thereof, less than 5 $mm^2$, or greater than 120 $mm^2$. In some embodiments, the electrodes comprise stainless steel, copper, platinum, gold, nickel, nickel-plated steel, magnesium, or any other suitably conductive material. In some embodiments, positive temperature coefficient (PTC) composite polymers having an inverse and highly non-linear relationship between conductivity and temperature are used. In some embodiments, PTC electrodes (such as the PTC electrodes described in U.S. Pat. No. 7,327,951, which is hereby incorporated herein by reference) are used to control the temperature of RF energy delivered to the target tissue. For example, PTC electrodes may provide high conductivity at temperatures below 60° C. and substantially lower conductivity at temperatures above 60° C., thereby limiting the effect of energy delivery to tissue above 60° C.

Figure 10:
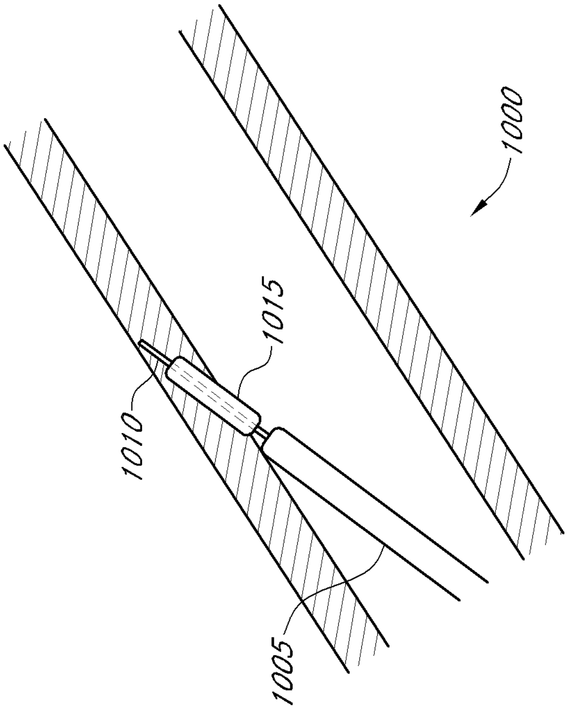
FIGS. 10 and 11 illustrate embodiments of electrode catheters.

FIG. 10 illustrates a self-repairing ablation catheter 1000. The self-repairing ablation catheter 1000 comprises a catheter body 1005, a needle electrode 1010, and a vascular wall plug 1015. In one embodiment, the needle electrode 1010 is placed at or near the distal end of the catheter body 1005 and used to heat tissue (which may result in nerve ablation). The vascular wall plug 1015 may be placed around the needle electrode 1010 such that when the needle electrode 1010 is pushed into or through the vascular wall, the vascular wall plug 1015 is pushed into or through the vascular wall as well. Upon retracting the self-repairing ablation catheter 1000, the needle electrode 1010 fully retracts in some embodiments, leaving the vascular wall plug 1015 behind, and thereby plugging or occluding the hole left by the needle electrode 1010.

In embodiments used to modulate (e.g., ablate) extravascularly, the vascular wall plug 1015 may comprise a hydrogel jacket or coating disposed on the needle electrode 1010. In some embodiments, the vascular wall plug 1015 is glued or otherwise adhered or fixed in a frangible manner at its distal end to the needle electrode 1010, yet may be sufficiently thin so it does not prevent smooth passage of the needle electrode 1010 as it is advanced into the perivascular space. In some embodiments, once the proximal end of the vascular wall plug 1015 passes out of the guiding lumen, it cannot be pulled proximally. Therefore, upon ablation completion, removal of the needle electrode 1010 from the perivascular space places the hydrogel jacket in compression in the hole made by the needle electrode 1010 in the vessel wall, thereby forming a plug which prevents or reduces the likelihood of vessel leakage or rupture. In some embodiments, the vascular wall plug 1015 is made of a hydrogel that swells when exposed to tissues, such as polyvinyl alcohol, or a thrombogenic material, such as those employed during interventional radiology procedures to coil off non-target vessels.

Figure 11:
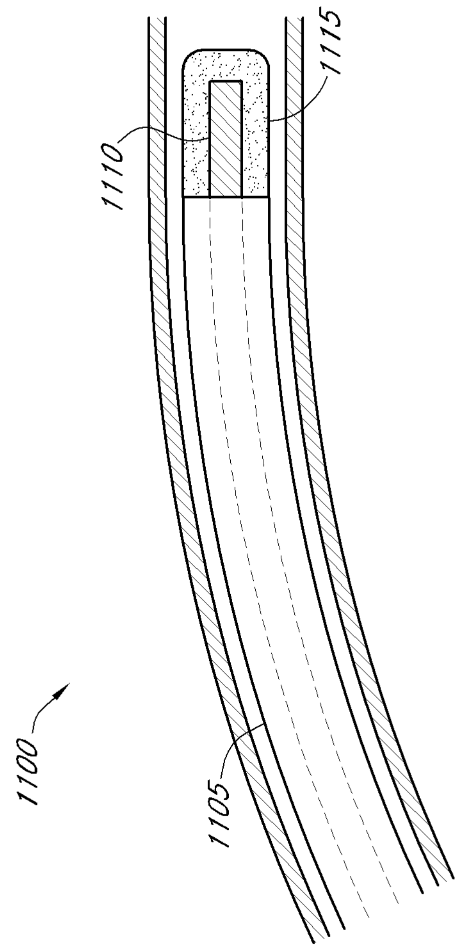

FIG. 11 illustrates an embodiment of a hydrogel-coated electrode catheter 1100. The hydrogel-coated electrode catheter 1100 includes a catheter body 1105, an ablation electrode 1110, and a hydrogel coating 1115. In one embodiment, the ablation electrode 1110 is attached to the distal end of the catheter body 1105 and the hydrogel coating 1115 coats the electrode 1110.

In some embodiments, the hydrogel coating 1115 is a previously-desiccated hydrogel. Upon insertion into the target anatomy, the hydrogel coating 1115 on the ablation electrode 1110 may absorb water from the surrounding tissues and blood. Ions drawn in from the blood (or included a priori in the hydrogel coating 1115) may impart conductive properties to the hydrogel coating 1115, thereby permitting delivery of energy to tissue. In accordance with several embodiments, the hydrogel-coated electrode catheter 1100 requires less cooling during ablation, as the hydrogel coating resists desiccation. A smaller catheter size may also be used, as construction requirements and number of components may be reduced. In some embodiments, the electrode impedance replicates native tissue impedance for better impedance matching. In some embodiments, temperature measurements at the surface of the hydrogel-coated electrode are possible.

In some embodiments, a balloon catheter comprises a catheter body and a distal balloon. The catheter body comprises a lumen configured to continuously infuse saline or other fluid into the balloon. The distal balloon comprises one or more hydrogel portions spaced around the circumference of the distal balloon. In one embodiment, if saline is used, any water that vaporizes from the surface of the distal balloon is replenished by diffusion from the balloon lumen, thereby preventing free saline to travel into the vessel interface and reducing any undesired effects of saline infusion.

In accordance with several embodiments, the branches of the forks between the common hepatic artery, the proper hepatic artery and the gastroduodenal artery are advantageously simultaneously or sequentially targeted (e.g., with RF energy) because sympathetic nerves supplying the liver and pancreas are generally tightly adhered to or within the walls of these arteries. Forks between other arteries or vessels may similarly be simultaneously or sequentially be targeted (e.g., with RF energy). In some embodiments, coiled electrodes opposing the artery walls are used.

Figure 12A:
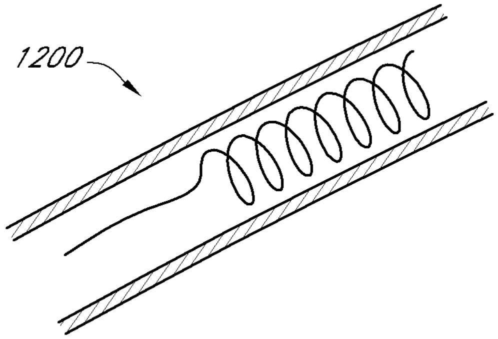
FIGS. 12A and 12B illustrate embodiments of ablation coils.

FIG. 12A illustrates an embodiment of a single ablation coil 1200 device. The single ablation coil device 1200 may be inserted into target vasculature and activated to ablate the nerves within or surrounding the vasculature. To ablate a vascular fork, it may be necessary to insert the single ablation coil 1200 into one branch of the fork (e.g., proper hepatic artery branch) and ablate that branch, then insert the single ablation coil 1200 into the other branch of the fork (e.g., gastroduodenal artery branch or left or right hepatic artery branch) and ablate that branch.

Figure 12B:
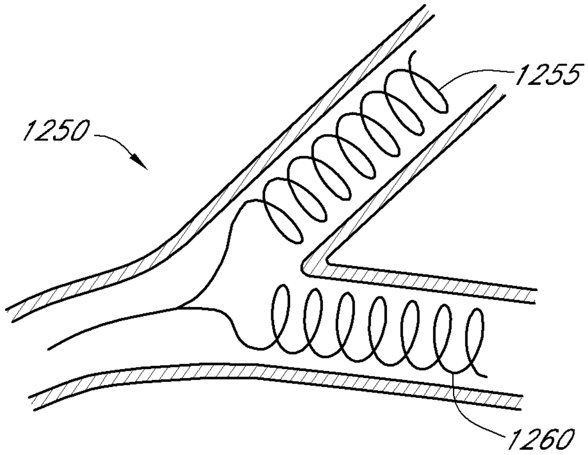

FIG. 12B illustrates a forked ablation coil device 1250. The forked ablation coil device 1250 comprises two ablation coils, a first ablation coil 1255 and a second ablation coil 1260. In accordance with several embodiments, the forked ablation coil device 1250 allows an entire vascular fork to be ablated simultaneously. In operation, the forked ablation coil device 1250 may be inserted to the target vasculature by overlapping the first ablation coil 1255 and the second ablation coil 1260 (effectively creating a single double helix coil). Once the target fork is reached, the first ablation coil 1255 and the second ablation coil 1260 may be separated and the first ablation coil 1255 inserted into a first branch of the target fork and the second ablation coil 1260 inserted into a second branch of the target fork. The branches of the target vessel fork (and the nerves within or surrounding the vessels of the fork branches) may then be simultaneously ablated.

In some embodiments, the coiled electrodes (e.g., ablation coil device 1200 or forked ablation coil device 1250) are created out of a memory material, such as nitinol or any other shape memory material. In some embodiments, energy may be delivered by the one or more coiled electrodes in a manner so as not to cause nerve ablation (temporary or permanent). In some embodiments, the thermal dose delivered may modulate nerves without causing ablation. The ablation coils may be delivered by one or more catheters. The ablation coils may be coupled to a catheter such that the ablation coils may be removed or repositioned following ablation of a target location. Balloon electrodes or other ablation elements may be used instead of ablation coils. In some embodiments, a single balloon with multiple electrodes may be used instead of the coiled electrodes. A portion of the balloon with an electrode may be positioned in each of the branches. In other embodiments, each of the branches may be occluded with an occlusion member and fluid may be infused to create a wet electrode effect for ablation.

In some embodiments, energy is delivered between two ablation elements positioned to span a vessel bifurcation in a bipolar manner, thereby concentrating delivery of energy and denervation between the ablation elements in a bifurcation region where a higher density of nerve fibers may exist.

Figure 13A:
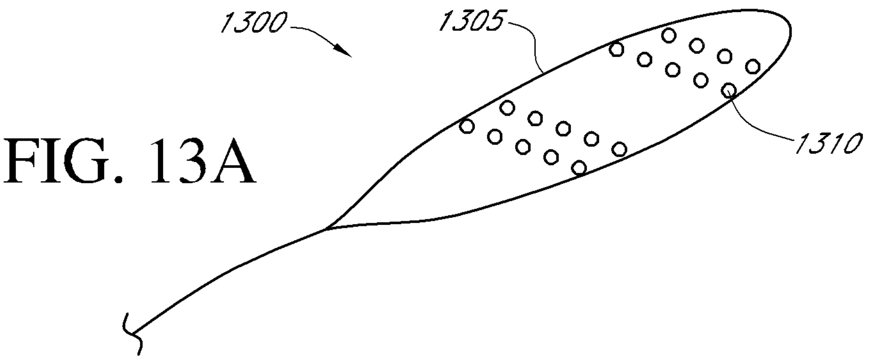
FIGS. 13A-13C, 14A and 14B illustrate embodiments of energy delivery catheters.
Figure 13B:
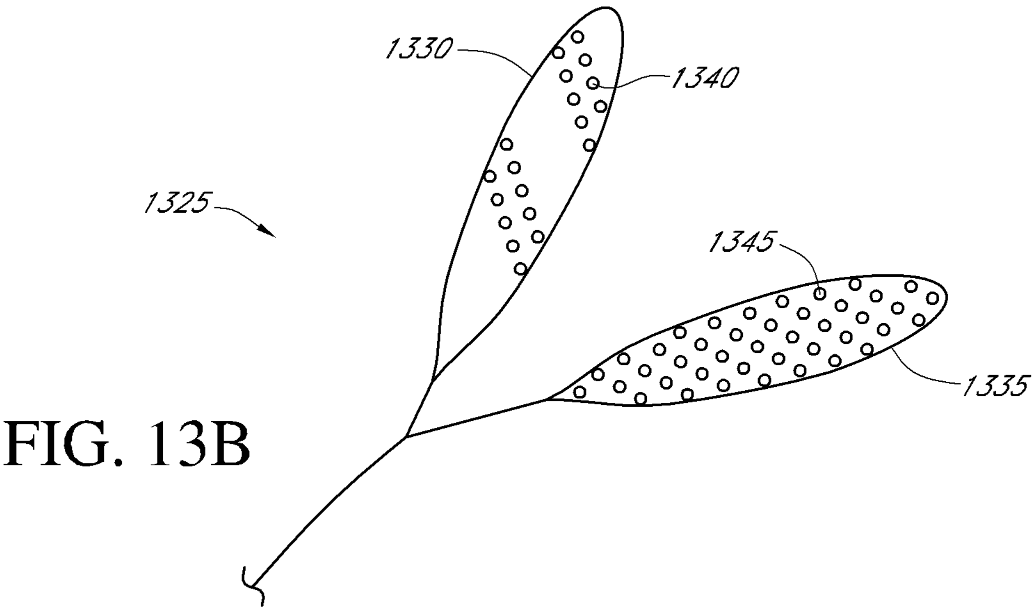
Figure 13C:
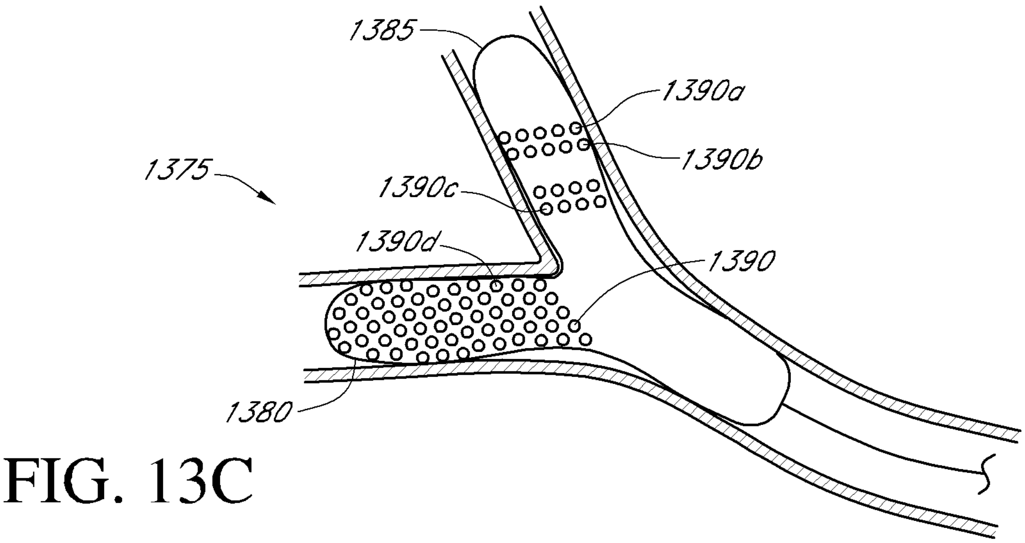

FIGS. 13A-13C illustrate embodiments of balloon ablation catheters. FIG. 13A illustrates an embodiment of a single balloon ablation catheter 1300, FIG. 13B illustrates an embodiment of a forked double balloon ablation catheter 1325, and FIG. 13C illustrates an embodiment of a forked balloon ablation catheter 1375. In various embodiments, a balloon ablation catheter comprises a bipolar balloon catheter.

The single balloon ablation catheter 1300 of FIG. 13A comprises an electrode balloon 1305 having at least one electrode 1310 (e.g., one electrode, two electrodes, three electrodes, four electrodes, five to ten electrodes, ten to twenty electrodes, or more than twenty electrodes). The electrode patterns and configurations shown in FIGS. 13A-13C illustrate various embodiments of electrode patterns and configurations; however, other patterns and configurations may be used as desired or required. In some embodiments, a high dielectric constant material may be used in the place of at least one electrode. The single balloon ablation catheter 1300 may be inserted into target vasculature and then inflated and used to ablate the vasculature (and thereby ablate the nerves within or surrounding the vessel). To ablate a vascular fork, it may be necessary to insert the single balloon ablation catheter 1300 into one branch of the fork and ablate that branch, then retract the single balloon ablation catheter 1300 from that branch and insert the single balloon ablation catheter 1300 into the other branch of the fork and ablate that branch.

The forked two balloon ablation catheter 1325 of FIG. 13B includes a first electrode balloon 1330 and a second electrode balloon 1335. The first electrode balloon 1330 includes at least a first electrode 1340, and the second electrode balloon 1330 includes at least a second electrode 1345. In several embodiments, the forked two balloon ablation catheter 1325 allows an entire vascular fork (e.g., all branches) to be ablated simultaneously. In operation, the forked two balloon ablation catheter 1325 is inserted into the vasculature and advanced to the target fork. Once the target fork is reached, the left electrode balloon 1330 and the right electrode balloon 1335 may be inflated and the left electrode balloon 1330 inserted into the left branch of the target fork and the right electrode balloon 1335 inserted into the right branch of the target fork (or vice versa). The target fork may then be simultaneously ablated. As discussed above, the first balloon and the second balloon can comprise a plurality of electrodes, or in some embodiments, at least one of the electrodes is replaced with a high dielectric constant material. The one or more electrodes may be individually connected to a pulse generator. By selectively and/or sequentially activating one or more electrode pair simultaneously, energy delivery to the surrounding tissue can be uniquely directed toward target anatomy with respect to balloon position. For example, referring now to FIG. 13C, energy could be directed between electrode 1390A and electrode 1390B in order to create a focused lesion within the vessel wall, or between electrode 1390C and 1390D to focus energy delivery at the vessel bifurcation.

The forked balloon ablation catheter 1375 of FIG. 13C includes a single balloon which has a left fork 1380 and a right fork 1385 with at least one balloon electrode 1390. In some embodiments the forked balloon ablation catheter 1375 comprises at least one balloon electrode for each balloon fork. The electrodes can be spaced and distributed along the balloon to facilitate positioning of at least one balloon electrode in each branch of the target fork. The forked balloon ablation catheter 1375 operates in the same manner as the forked double balloon ablation catheter 1325; however, it may advantageously allow for more effective ablation of the crotch of the vascular fork. In some embodiments, the balloon of the forked balloon ablation catheter 1375 is substantially the shape of the target fork or is configured to conform to the shape of the target fork. In some embodiments, the forked balloon ablation catheter 1375 is configured to be used in vessels having forks with three or more branches (such as the fork between the common hepatic artery, proper hepatic artery and the gastroduodenal artery). In some embodiments, each of the branches of the vessel fork may be occluded with an occlusion member and fluid may be infused to form a wet electrode for ablation. In various embodiments, the bifurcation devices described herein are used to modulate nerves at the bifurcation of the common hepatic artery and the gastroduodenal artery or the bifurcation of the proper hepatic artery into the right and left hepatic arteries.

An electrode balloon may be used to ablate (or otherwise modulate) target vasculature. In some embodiments, the electrode balloon is inserted via a catheter and inflated such that the balloon is in contact with substantially all of the fork intimal walls. In some embodiments, the electrode balloon is substantially oval. A two-step approach may be used to ablate the entire surface of the fork: first, the balloon can be put in place in one branch of the fork (e.g., the proper hepatic artery branch), inflated, and then used to ablate; second, the balloon can be retracted and then advanced into the other fork (e.g., the gastroduodenal artery branch or right or left hepatic artery branch), inflated, and then used to ablate. In some embodiments, the electrode balloon comprises ablation electrodes on an external surface in sufficient density that simultaneous ablation of the entire intimal wall in contact with the electrode balloon is possible. In some embodiments, the ablation electrodes on the surface of the electrode balloon are arranged in a predetermined pattern. In some embodiments, the ablation electrodes on the surface of the electrode balloon are activated simultaneously. In some embodiments, the ablation electrodes on the surface of the electrode balloon are individually addressable (e.g., actuatable), thereby allowing selective areas to be ablated as desired. In some embodiments, at least one electrode on the electrode balloon is an ablation electrode and at least one electrode on the electrode balloon is a sensing electrode (used, for example, to sense impedance, temperature, etc.).

In some embodiments, the electrode balloon comprises a proximal electrode and a distal electrode configured to be individually actuatable and configured to be used in a stimulation mode, ablation mode, and/or sensing mode. The proximal electrode and distal electrode may be positioned in two different branches (e.g., the proximal electrode in the proper hepatic artery and the distal electrode in the gastroduodenal artery). The electrode balloon may be deployed from a guide catheter positioned in the common hepatic artery. In one embodiment, the proximal electrode is stimulated and the distal electrode is sensed and if the correct territory is identified (e.g., nerve fibers emanating to the proper hepatic artery but not the gastroduodenal artery), then the proximal electrode may be activated for ablation. The electrode balloon may be used to map and selectively ablate or otherwise treat various vessel portions.

In some embodiments, a round electrode balloon may be used to selectively ablate only a select area. In some embodiments, the round electrode balloon has approximately the same electrode properties as described above, including electrode density, and the presence of at least one ablation electrode. In some embodiments, the round electrode balloon comprises at least one sensor electrode or temperature-measurement device (e.g., thermocouple).

In some embodiments, a dielectric ablating balloon is used. The dielectric ablating balloon may have the same shape characteristics as do the other electrode balloon embodiments described herein. In some embodiments, the dielectric ablating balloon comprises at least one piece of a high conductivity material on its outer surface. In some embodiments, use of the dielectric ablating balloon comprises advancing the dielectric ablating balloon into position in the target vessel through methods described herein and inflating the dielectric ablating balloon so that its outer surface is proximate to the intimal walls of the target vessel. In some embodiments, a microwave generator is then placed near the surface of the body of the subject and microwaves are directed from the microwave generator toward the dielectric ablating balloon within the subject such that the microwaves interact with the at least one piece of a high conductivity material to create heat and such that the heat created thermally ablates the region (e.g., vessel wall surface) proximate to the at least one high permittivity material. In some embodiments, the dielectric ablating balloon comprises a plurality of (e.g., two, three, four or more than four) pieces or portions of high conductivity material on its outer surface.

In some embodiments, lower power and longer duration ablations may be used for ablation procedures involving occlusion within the hepatic arteries than in other arteries. Such treatment may be uniquely possible because of the liver's dual source blood supply (as described above). Balloon ablation of the hepatic artery may employ full occlusion for a substantial period of time, not previously possible or not previously attempted in other locations for safety reasons (e.g., to avoid potential stroke due to ischemia). In some embodiments, balloons may be inflated and used for ablation in the range of about 1 to about 10 minutes, about 10 minutes to about 20 minutes, about 20 minutes to about 60 minutes, about 15 minutes to about 45 minutes, about 10 minutes to about 40 minutes, about 15 minutes, about 20 minutes, about 25 minutes, about 30 minutes, about 35 minutes, about 40 minutes, about 45 minutes, about 50 minutes, about 55 minutes, about 60 minutes. Longer ablation times may have several advantages in accordance with several embodiments. First, longer exposure times mean that lower treatment temperatures may be used because tissue and nerve death is a function of both temperature and time. In some embodiments, temperatures are used in the ranges of about 30° C. to about 80° C., about 40° C. to about 70° C., or about 50° C. to about 60° C. In one embodiment, temperatures greater than 45° C. and less than 60° C. are used.

In some embodiments, the arterial lumen may be simultaneously protected by infusing a low temperature coolant through the balloon cavity (thereby keeping the intima cool) while focusing RF energy and thermal heating at the level of the adventitia (where the target nerves are located). Second, balloon occlusion may facilitate improved contact and contact pressure between the electrodes disposed on the outside of the balloon and the arterial wall. Third, balloon occlusion may compress the tissues of the arterial wall and thereby reduce the distance from the electrode(s) to the target nerves, which improves the efficiency of thermal energy delivery to the target nerves. Fourth, less contrast/imaging agent may be required by using a balloon catheter because an occluding device is reliably and accurately positioned (and maintains that position once in place), and serves as a reliable marker of device and therapy placement. Additionally, when a balloon engages the vascular wall, heating of the blood is avoided entirely (because energy is transferred directly from the electrode(s) to the vessel wall without directly contacting the blood), thereby reducing the risk of vapor bubble formation or thrombosis (e.g., clot formation).

An embodiment of a balloon catheter is illustrated in FIGS. 90A and 90B. The balloon catheter may advantageously be configured to provide flow to cool one or more electrodes without having or without requiring the electrode(s) in contact with blood. In some embodiments, the balloon is a c-shaped balloon as shown in FIGS. 90A and 90B, having an inflatable region 9002 about a substantial portion of the balloon circumference and a small non-inflatable region 9004 (e.g., "webbed region") comprising less than 1/18 (or alternatively, less than 1/10, less than 1/12, less than 1/14, less than 1/16, less than 1/20, less than 1/22, less than 1/24, less than 1/25) of the total circumference of the balloon in order for the balloon to maintain a substantially circular shape upon inflation. A plurality of electrodes may be disposed along the longitudinal axis of the balloon on the non-inflatable webbed region, configured to deliver RF energy to the hepatic artery or other target vessel or tissue. The c-shaped balloon of the design illustrated in FIG. 90 defines a lumen upon inflation that may permit the flow of blood therethrough. In one embodiment, a thin membrane of the webbed region provides electrical isolation to ensure that the applied RF energy is delivered substantially to the target tissue (and hence to the nerves surrounding the hepatic artery or other target vessel or tissue) and not lost to the blood. In one embodiment, the balloon design illustrated in FIGS. 90A and 90B advantageously provides the ability for the blood to cool the electrode by means of the limited thermal insulation offered by the thin membrane of the webbed region, thereby increasing the effective power that can be delivered to the target tissue.

Figure 91:
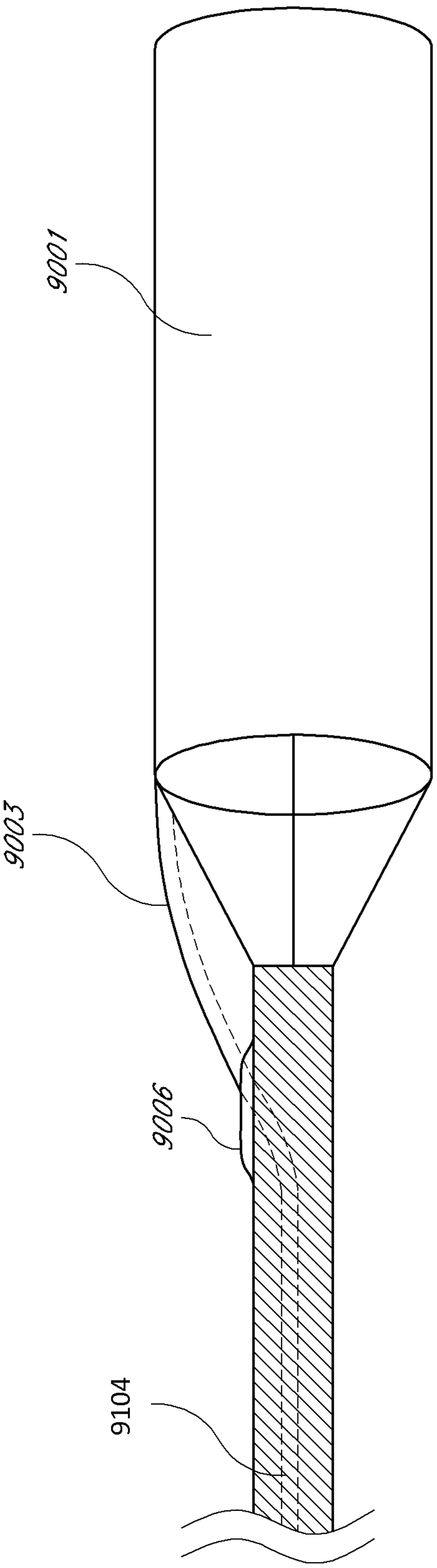

FIG. 91 illustrates how the c-shaped balloon electrode design of FIGS. 90A and 90B could be attached to an interventional catheter. In one embodiment, the inflatable region 9002 of the c-shaped balloon is in fluidic communication with an inflation manifold 9003, which may be disposed proximally toward a shaft of the interventional catheter. The inflation manifold 9003 can define a lumen 9004 terminating in a flange 9006 configured for attachment to the catheter. The flange 9006 of the inflation manifold 9003 may be adhered to a side-exiting lumen disposed along a portion of or substantially the entire length of the catheter using suitable adhesion means (e.g., UV cured adhesives, RF welding, adhesives, heat sealing), thereby permitting fluidic communication between the catheter lumen and the inflatable region of the c-shaped balloon 9001. In order to structurally attach the c-shaped balloon 9001 to the catheter, a plurality of struts may be provided. In one embodiment, the struts are formed of a resilient material such as nitinol and biased towards a position that would tend to expand the balloon into a cylindrical shape. The struts may be joined to the catheter and c-shaped balloon using any suitable means. In one embodiment, the struts are overmolded into the catheter and glued to the balloon 9001.

Figure 92A:
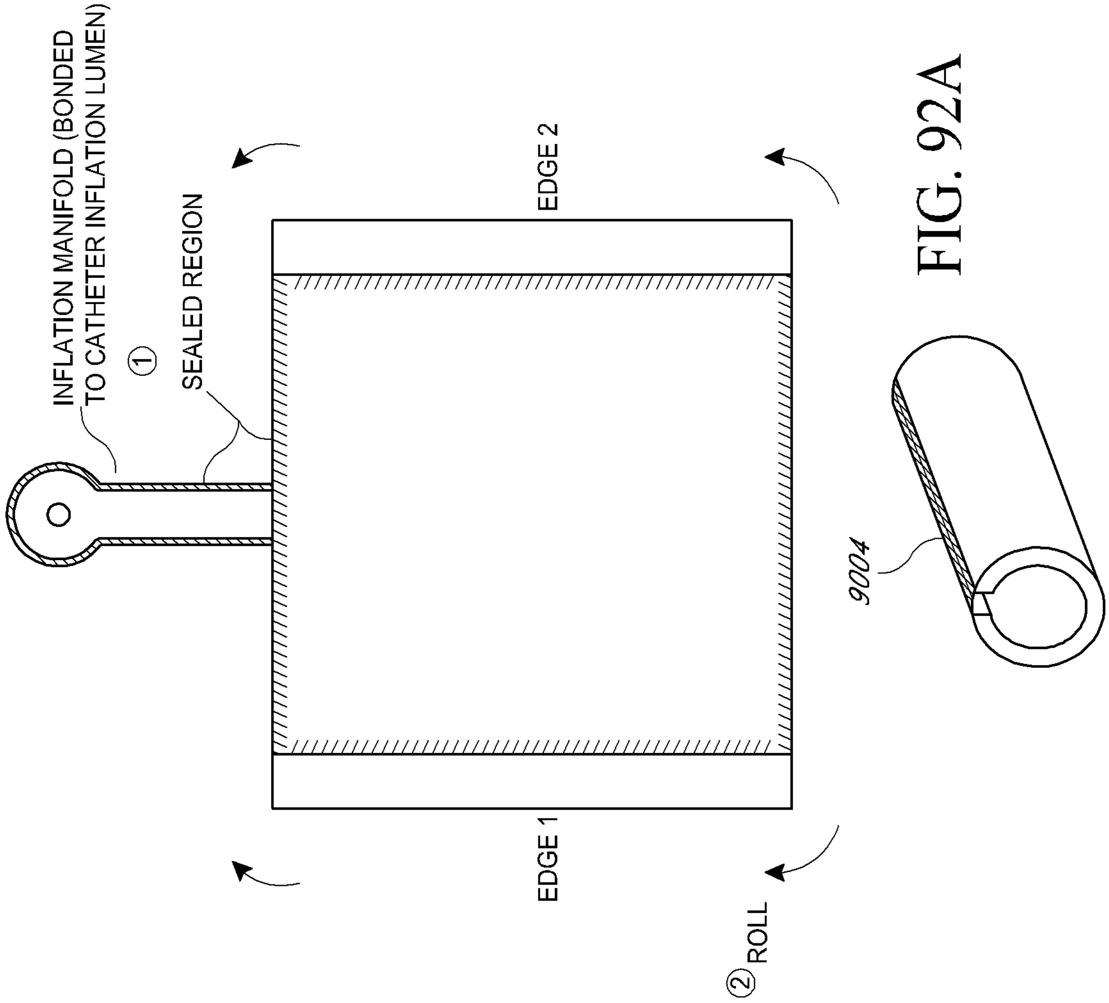
Figure 92B:
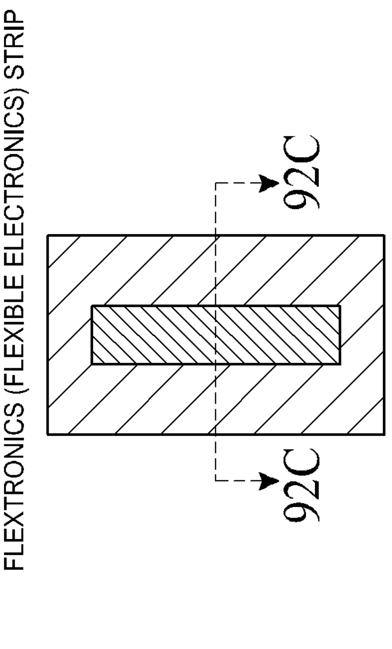
Figure 92C:
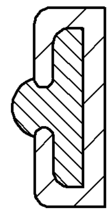

An exemplary method for fabricating the c-shaped balloon and electrode is highlighted in FIGS. 92A-92C. The balloon may be fabricated using two pieces of flat or substantially flat stock material (e.g., polyurethane sheet of about 0.003" in thickness). The two layers may be bonded using suitable techniques in the regions illustrated (e.g., RF welding, adhesives, heat sealing, etc.), and then rolled and sealed into a cylinder to form the non-inflatable webbed region. In one embodiment, the webbed region 9004 is formed using flexible electronics manufacturing techniques (e.g., "Flextronics"), where the electrode is laminated between two dielectric layers, such as polyimide. The Flextronics strip can then be adhered to each edge of the thin film balloon structure to form the cylindrical, c-shaped balloon.

Figure 97B:
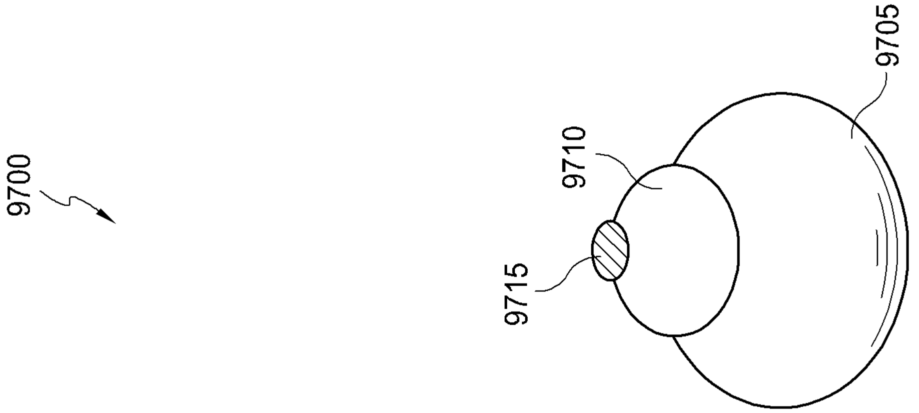
Figure 97A:
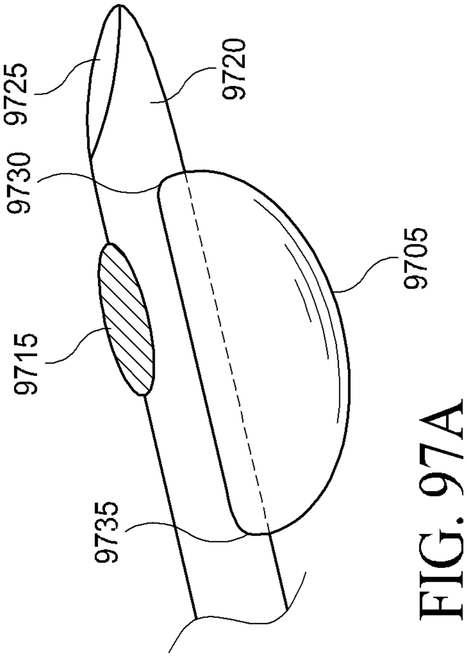

FIGS. 97A and 97B illustrate another arrangement of the balloon catheter of FIGS. 90A and 90B. In one embodiment, an energy delivery catheter 9700 includes a perfusion balloon 9705 enabling occlusion of a vessel lumen and redirection of the blood flow through a perfusion lumen 9710. The perfusion lumen 9710 provides a constant diameter flow pathway which directs the blood flow over an exposed electrode surface within the perfusion lumen 9710, thereby allowing for a more predictable cooling effect. The catheter embodiments described herein may be used in conjunction with an over-the-wire, rapid exchange or steerable catheter approach.

At the distal end of the catheter 9700, an atraumatic, flexible tip 9720 is incorporated on or adjacent to a distal opening 9725 of the perfusion lumen 9710. In one embodiment, proximal to the distal tip 9720 is a balloon attachment region 9730, where the perfusion balloon 9705 is attached to the perfusion lumen 9710. The balloon attachment region 9730 may advantageously be optimized to provide a smooth flexibility transition. In various embodiments, the perfusion balloon 9705 is attached by adhesive or thermal joining or bonding methods and materials. The balloon attachment region 9730 may encompass the full or partial circumference of the perfusion lumen 9710 and/or guide wire lumen. The balloon material may be a compliant or non-compliant type. The balloon 9705 can be made of a single material or incorporate layers of different materials or grades of the same material. Similarly, the balloon 9705 can be formed of a polymer blend.

The shape of the balloon 9705 may be tapered or non-concentric. Cross sectional shapes may range from round to crescent shaped. In accordance with several embodiments, the balloon 9705 is formed and attached to the perfusion lumen 9710 such that it occludes the natural vessel lumen and maintains electrode contact with the vessel wall. The balloon diameter in the expanded state can range from about 2 mm to about 10 mm, (e.g., from 2 mm to 8 mm, from 3 mm to 6 mm, from 4 mm to 10 mm, and overlapping ranges thereof).

In some embodiments, at least one electrode 9715 resides within the length of the perfusion lumen 9710. The electrode 9715 may be placed or positioned such that the exterior side of the electrode 9715 is able to contact the vessel wall and the internal side (e.g., the side exposed within the perfusion lumen 9710) is flush or within the lumen formed by the internal diameter of the perfusion lumen 9710. The one or more electrodes 9715 are connected via conductive wires to an external energy source, such as an RF generator. The electrodes 9715 may be individually controlled or jointly controlled to deliver energy independently or simultaneously at the same or different levels.

Proximal to the electrode location is a second balloon attachment point or region 9735. Materials and joining methods may advantageously be selected to optimize the flexibility transition. Cross-sectionally at the attachment point or region 9735, the balloon 9705, the perfusion lumen 9710, an inflation lumen, a guide wire lumen, and/or conductive wires are contained. Proximal to the second balloon attachment point or region 9735 is a perfusion lumen exit or opening (not shown). The length of the perfusion lumen 9710 can range from about 5 mm to about 80 mm (e.g., 5 mm to 40 mm, 10 mm to 50 mm, 20 mm to 60 mm, 30 mm to 80 mm, 5 mm to 20 mm, or overlapping ranges thereof). The balloon length may generally be shorter than the length of the perfusion lumen 9710. The perfusion lumen 9710 may be insulated from the electrode 9715 by an insulation layer to avoid direct contact of the electrode 9715 with the blood, as described in connection with FIGS. 90A and 90B.

Proximal or corresponding with the perfusion lumen proximal opening the catheter construction may be optimized for flexibility, torque and push force capability while maintaining a lumen or lumens for balloon inflation, guide wire containment, and/or conductive wire pathways.

In some embodiments, a handle or manifold (not shown) is located proximally on the shaft that enables conductive wire connections to the energy source (e.g., RF generator), attachment to a balloon inflation device, and/or access to a guide wire lumen and/or a mechanism to deflect the distal steerable segment.

In a rapid exchange embodiment, a guide wire port may be located 10 to 20 cm proximal of the distal tip. In one embodiment, the guide wire port is constructed to maintain a flexibility transition that is kink resistant while efficiently transferring push force to the distal assembly. Proximal to the guide wire port, the shaft maybe be constructed of a hypotube that is sheathed in polymer and includes an inflation lumen and protects the conductive wires.

In some embodiments, the shaft proximal to the proximal perfusion lumen opening comprises an inflation lumen, a lumen containing the shielded conductive wires, a guide wire lumen, a pull wire, and/or a polymer that encapsulates or sheaths the aforementioned lumens. The polymer encasement or sheath may be an extruded or deposition formed tube or a thermoplastic that has been reflowed to reduce profile. In some embodiments, the catheter is steerable and contains a pull wire assembly that can deflect the distal assembly, as described elsewhere in the disclosure.

Balloon ablation catheter systems may be advantageous for denervating nerves surrounding (e.g. within a wall of, such as within the intima, media or adventitia of) the hepatic artery branches may be advantageous in that the hepatic artery can be occluded by one or more balloons and then coolant can be circulated in the region of the ablation (e.g., through a lumen of a balloon). In various embodiments, balloon ablation catheters advantageously facilitate both higher power net energy through larger electrode surface area (enabled, for example, by large electrode sizes that can be included on a balloon) and increased deposition time (which may be permitted by the ability to occlude flow to the hepatic artery for longer periods of time). In some embodiments, the risk of damage to the endothelial wall is mitigated by the flow of coolant even with an increase in energy density through higher power. Accordingly, higher power energy delivery (e.g., about 40 to 50% higher power) may be used than denervation systems used for denervation of other vessels or organs without risk of damage to the endothelial region of the hepatic artery due to maintained less than hyperthermic temperatures up to 1 mm from the lumen of the hepatic artery.

In some embodiments, an actively-cooled balloon catheter is used to ablate target vasculature. A pump sufficient to deliver high flow coolant to the cooling element may be used to facilitate the active cooling. In several embodiments, the range of drive pressures to deliver an appropriate flow rate (e.g., between about 100 and 500 mL/min) of coolant into a 4 to 6 Fr balloon catheter to maintain an appropriate temperature is between about 25 and about 150 psi. The flow rate may be adjusted on the basis of the actual temperature inside the balloon. In some embodiments, the desired coolant temperature in the balloon is between about 5° C. and about 10° C. In some embodiments, temperature-measurement devices (e.g., thermocouples) are included inside the balloon to constantly monitor the coolant temperature. The pump output may be increased or decreased based on the difference between the desired temperature and the actual temperature of the coolant.

Figure 106:
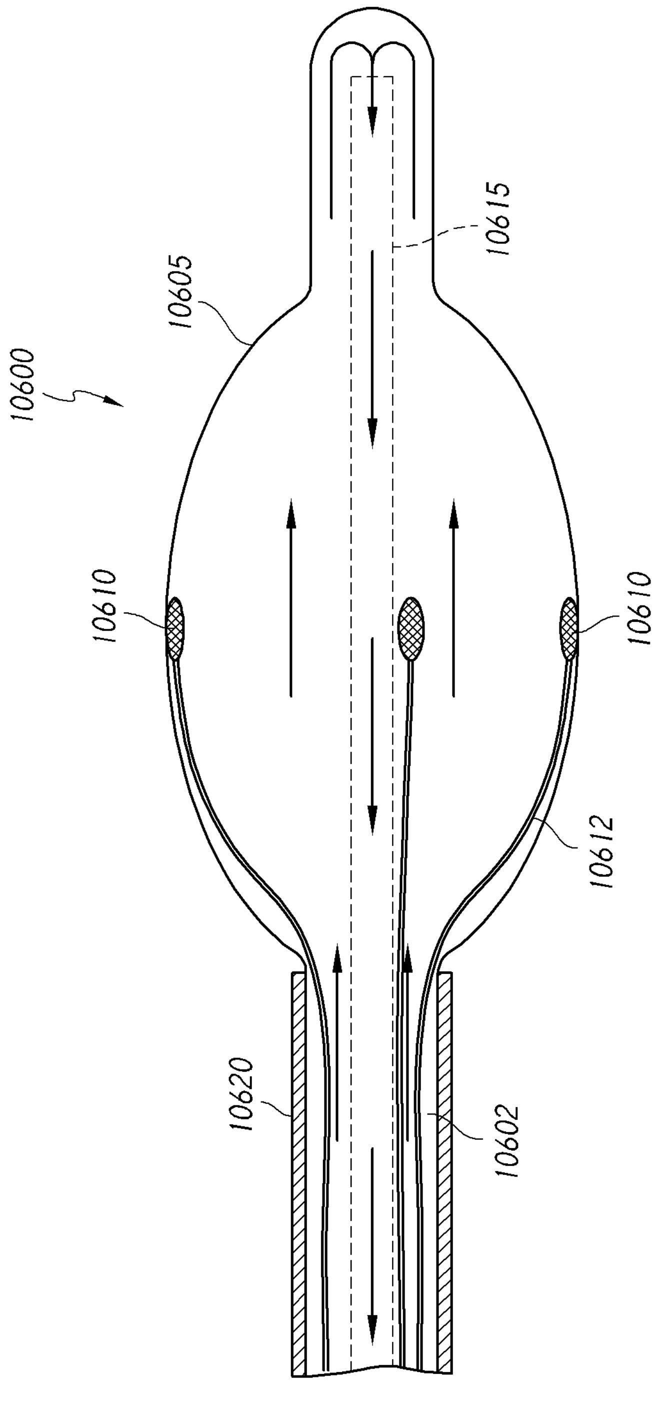
FIGS. 106 and 107A-107C illustrate embodiments of balloon catheters.

FIG. 106 illustrates an embodiment of an actively-cooled balloon catheter 10600. The balloon catheter comprises a main shaft 10602 having a lumen, a balloon 10605 coupled to a distal end of the main shaft 10602 and in fluid communication with the lumen, a plurality of electrodes 10610 disposed around the circumference of the balloon 10605, electrode leads 10612 coupled to the electrodes 10610 and extending to a proximal end of the main shaft 10602, and an outlet tube 10615. Nonconductive coolant solution may be pumped into an inlet of the balloon 10605 by a pump (not shown) and the nonconductive coolant solution may exit the balloon 10605 through the outlet tube 10615. The main shaft 10602 may comprise an insulating sheath or cover 10620 to prevent heat transfer. The nonconductive coolant solution may advantageously provide cooling to the electrodes 10610 on the balloon 10605, while also shielding adjacent tissues from RF energy.

Figures 107A, 107B, 107C:
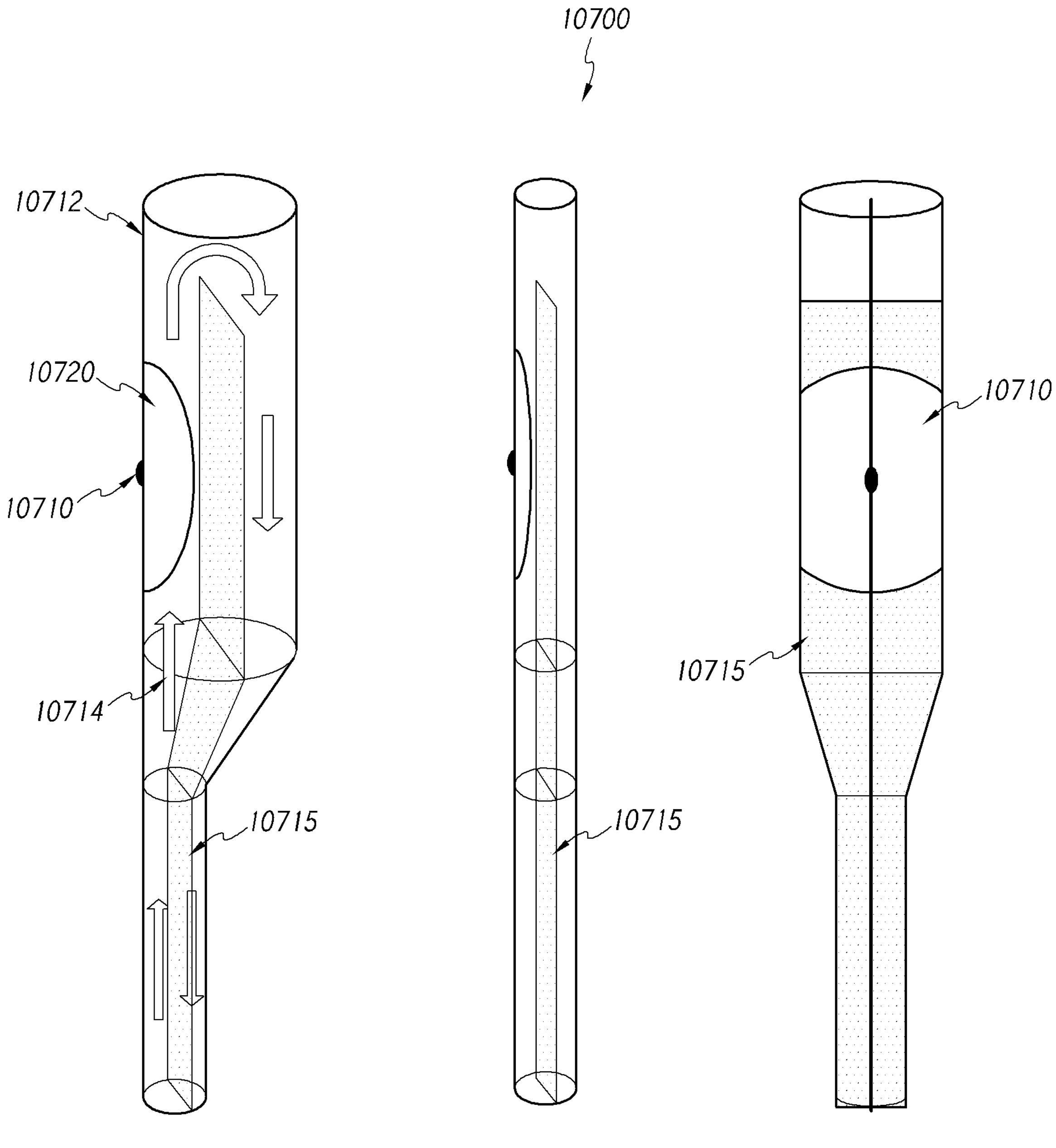

FIGS. 107A-107C illustrate a distal end portion of another embodiment of a balloon catheter 10700 configured to provide cooling to an electrode 10710 of the balloon catheter 10700. In the illustrated embodiment, the balloon catheter 10700 is a tube comprising a balloon 10712 that expands when infused with coolant, pulling taut an internal diaphragm 10715 which directs the flow 10714 (illustrated by arrows) of the coolant from at least one inlet to at least one outlet. A circular surface centered on the electrode 10710 may comprise a heat conducting surface 10720, while the rest of the catheter 1700 may comprise a heat-insulating material configured to prevent warming of the coolant 10714 while traveling to a target ablation area. When the cooling balloon 10712 is infused with coolant, the balloon 10712 expands, thereby pressing the electrode 10710 and the cooling balloon 10712 against the vessel wall. In one embodiment, the coolant cools the vessel wall at the target ablation area, thereby preventing against or reducing the likelihood of excessive vessel wall damage.

Figure 33:
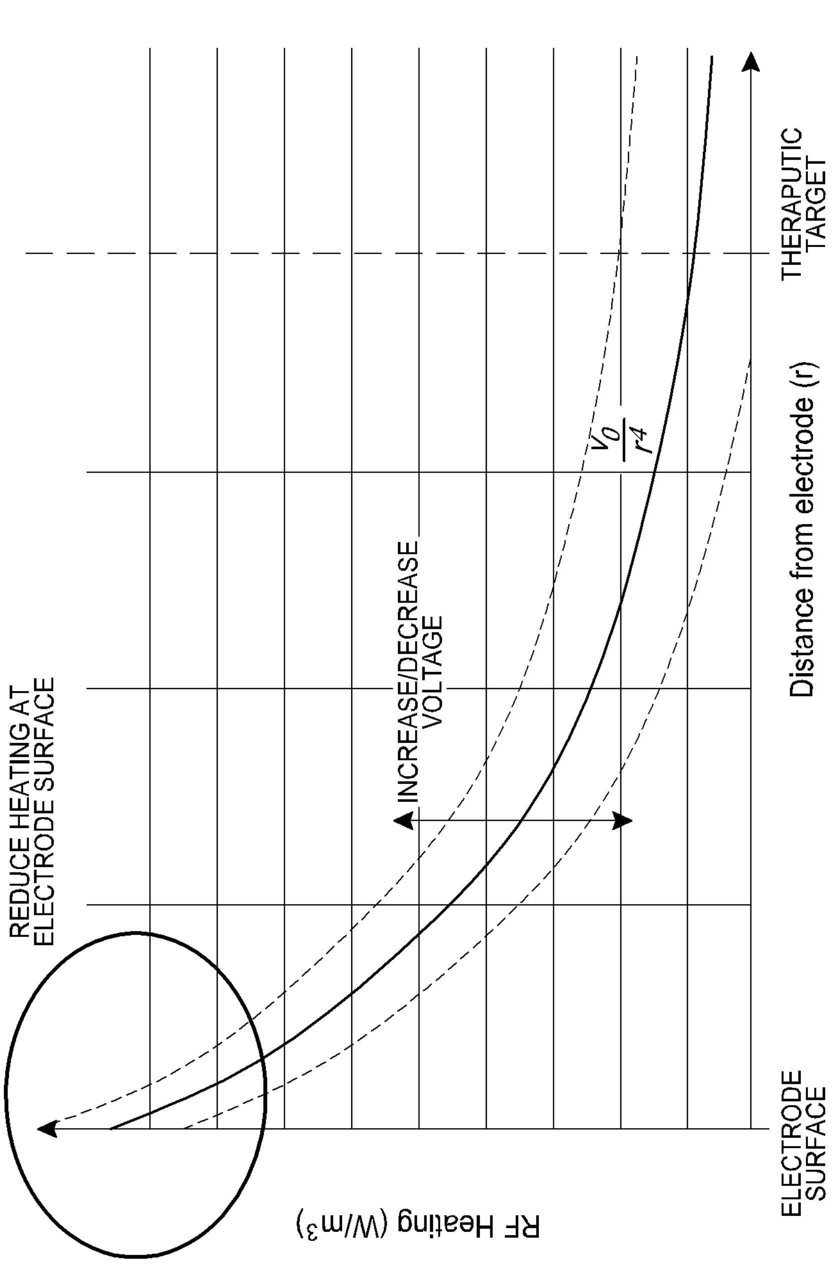
FIG. 33 illustrates a graph of RF heating versus distance from the electrode.

In accordance with several embodiments, electrode and vessel wall temperature are carefully monitored and controlled during vessel ablation. In several embodiments, temperatures at the arterial wall are limited or reduced to avoid vessel spasm, thrombus formation, and stenosis. The ability to affect the convective cooling of the electrode and contacted tissue can be particularly advantageous in various embodiments. Electrode temperature can affect the depth of the lesion. In some embodiments, a main mechanism affecting electrode cooling is convective cooling from blood flow past the electrode and contacted vessel wall. Ablation of the renal artery has a flow rate of 550 mL/min. Flow through the common hepatic artery is ~100-200 mL/min (e.g., 150 mL/min), which is much slower than typical flow rates in renal arteries (~550 mL/min), where ablations have been performed with minimal or no electrode cooling. Because of the low and/or variable flow rate within the hepatic arteries, methods and systems aimed at increasing electrode cooling are provided herein. FIG. 33 illustrates an example of challenges of endovascular ablation given the reduced flow rates in the common hepatic artery. FIG. 33 illustrates a plot of the reduction in RF heating as the distance from the electrode surface increases. In some embodiments, reduced heating at the electrode surface requires a reduction in overall power, which can result in reduced heating at the therapeutic target (e.g., hepatic nerves or other peripheral nerves).

Figure 34A:
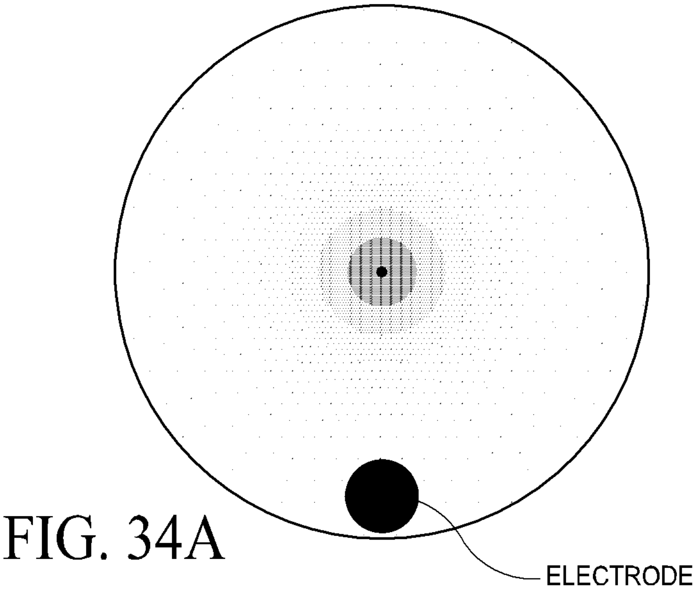
FIGS. 34A-34C, 35A-35C, 36, 37, 38A, 38B and 39 illustrate devices and methods configured to provide increased cooling for electrode catheters.
Figure 34B:
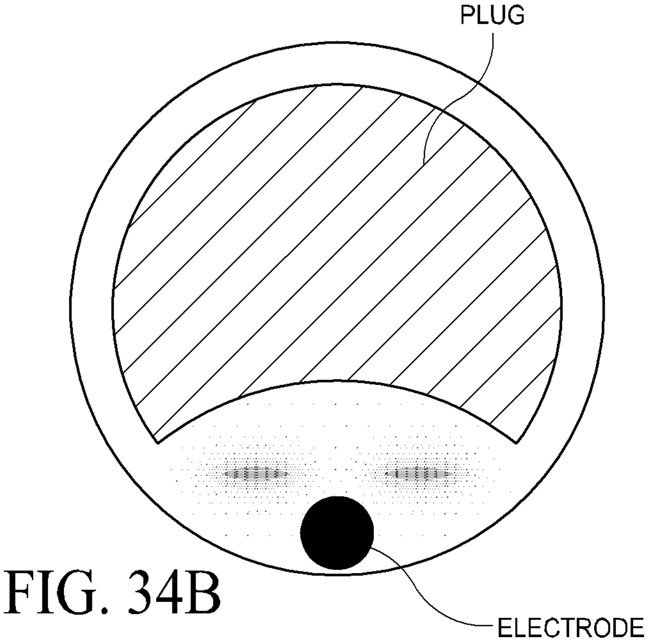
Figure 34C:
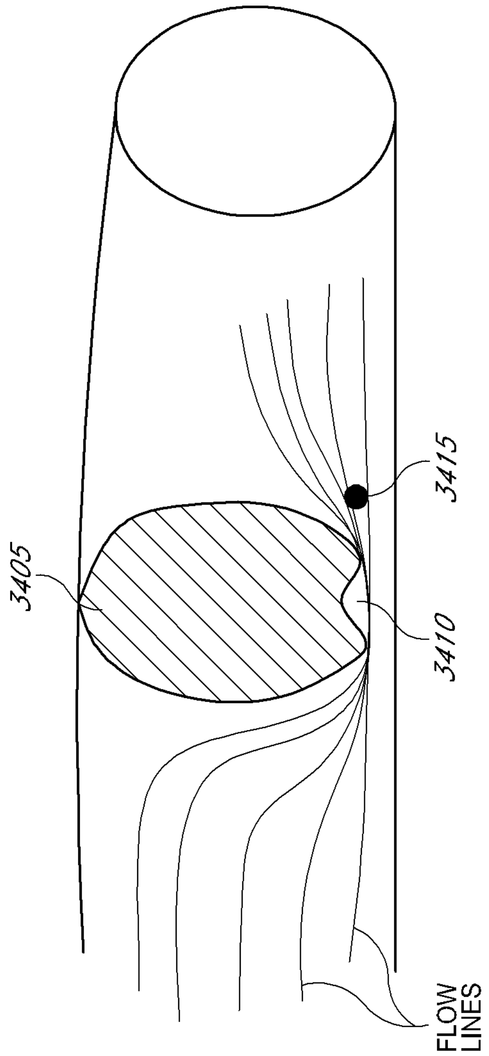

In one embodiment, the mass flow rate around the electrode and contacted tissue at the therapeutic target is increased, as illustrated, for example, in FIGS. 34A-34C. For example, by reducing the cross-sectional area around the electrode (e.g., by partially occluding a vessel using a plug or other obstruction or occlusion device), the average flow velocity increases and the peak velocity flow line is moved closer to the electrode and contacted tissue, as shown in the transverse cross-section in FIG. 34B and in FIG. 34C. The shading in FIGS. 34A and 34B illustrates fluid velocity—the darker the shading, the higher the flow velocity. As shown, by at least partially occluding flow, the blood flow adjacent to the electrode is increased over unobstructed or unoccluded flow. FIG. 34C illustrates a longitudinal cross-section view of an obstruction or occluding element 3405 within a blood vessel (e.g., hepatic artery). The obstruction or occluding element 3405 may have an opening or notch or indentation 3410 that is at least substantially aligned with an electrode 3415. The obstruction or occluding element 3405 with the aligned opening 3410 may cause flow line density downstream of the electrode 3415 to be more dense than upstream of the electrode 3415. The increased blood flow may result in increased cooling of the electrode 3415.

In one embodiment the obstruction element (e.g., balloon) is effective to apply a reaction force as close to the electrode as possible (in a direction perpendicular to the surface defined by the contact of the electrode and the tissue surface, in one embodiment). In one embodiment, the balloon is disposed directly opposite the electrode. In order to limit motion of a balloon within the artery as an artifact of diaphragmatic motion, the balloon may be comprised of materials having higher coefficients of friction between the balloon and arterial components, such as endothelial tissue. In one embodiment, the balloon is comprised of silicone.

In various embodiments, the balloon is configured to occlude at least 50% of the arterial cross-sectional area. Suitable ranges may include 50-60%, 50-70%, 50-80%, 60-80%, and 70-90% occlusion, or overlapping ranges thereof.

Figure 96B:
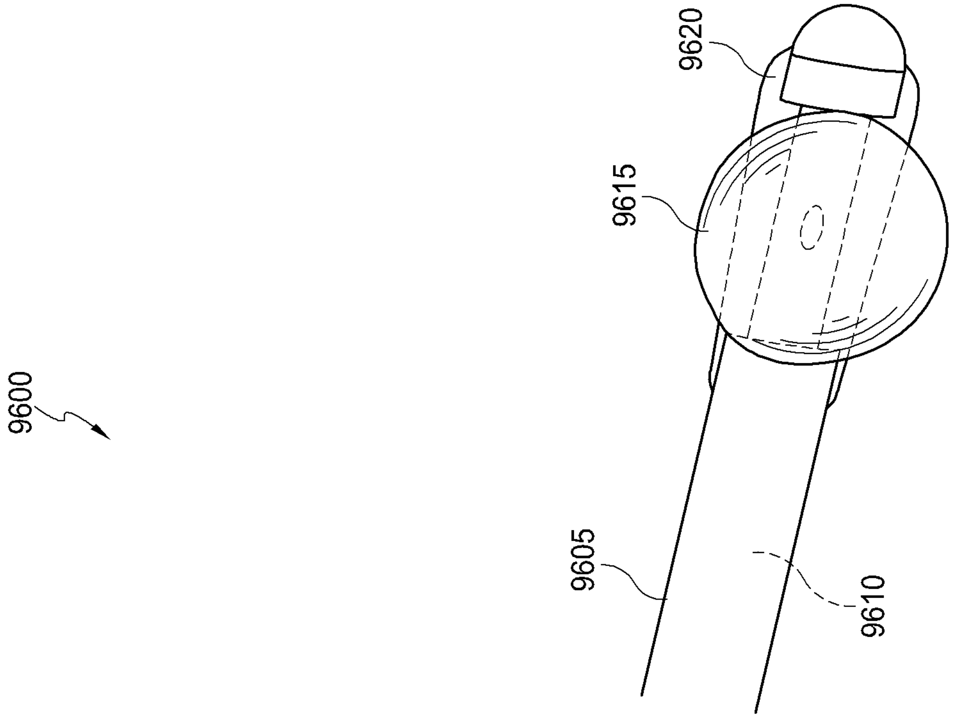
FIGS. 96A and 96B and FIGS. 97A and 97B illustrate various views of embodiments of balloon catheters.
Figure 96A:
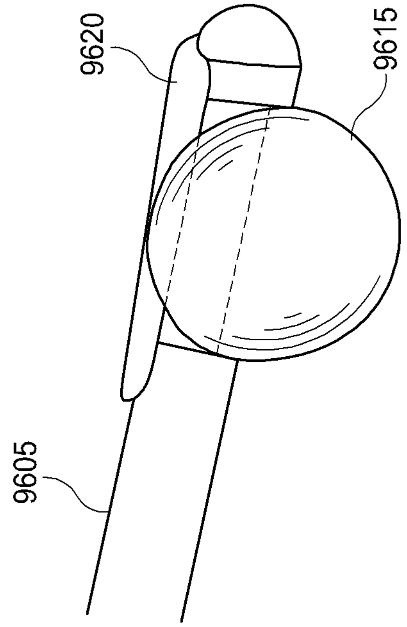

FIGS. 96A and 96B illustrate an embodiment of a balloon catheter 9600 configured to deliver RF energy. In one embodiment, the catheter is comprised of a polymeric shaft 9605 having a lumen 9610 disposed along a portion or substantially the entire length in communication at a proximal end portion with a pressure source (e.g., capable of creating between 0-600 mmHg within a balloon at a distal end of the catheter). In one embodiment, the lumen 9610 exits through a transverse surface of the shaft 9605 near the distal tip of the shaft 9605. As shown, a balloon 9615 is disposed about the lumen exit and a portion of the shaft. In various embodiments, the balloon 9615 is disposed about a substantial (e.g., greater than 30%, greater than 40%, greater than 50%, greater than 60%, about 40%, about 50%, about 60%, about 70%, about 80%, or about 90%, of the circumference of the shaft 9605.

In one embodiment, the balloon 9615 is disposed about the entire circumference of the shaft 9605 not covered by an electrode or other energy delivery member. In one embodiment, the balloon 9615 is expandable to a diameter of 1 mm-8 mm (e.g., 1 mm to 5 mm, 1 mm to 4 mm, 2 mm to 5 mm, 3 mm to 8 mm, 1 mm to 6 mm, 4 mm to 8 mm, or overlapping ranges thereof) and is disposed about a length of 5 mm to 30 mm (e.g., 5 mm to 20 mm, 5 mm to 15 mm, 10 mm to 20 mm, 10 mm to 30 mm, 5 mm to 25 mm, 15 mm to 25 mm, 20 mm to 30 mm, or overlapping ranges thereof) along a distal portion of the shaft 9605. In one embodiment, substantially opposite the balloon 9615 an electrode (e.g. half-cylindrical electrode) or other energy delivery member 9620 is bonded or otherwise affixed to the shaft and in electrical communication with a wire (e.g., thermocouple wire) through either the lumen or routed along an exterior surface of the catheter 9600, which is connected to an RF generator and a thermocouple (e.g., type T thermocouple)

reading circuit to permit the delivery of RF energy and assessment of electrode or tissue temperature. In one embodiment, the electrode 9620 is positioned within 1 cm of the distal tip of the catheter 9600. The electrode 9620 is advantageously flush or substantially flush with the catheter surface, in one embodiment.

In some embodiments, the power required to reach a target electrode temperature is higher when the vessel lumen is substantially occluded compared to the unoccluded configuration, increasing the efficiency of energy delivery.

Figure 35A:
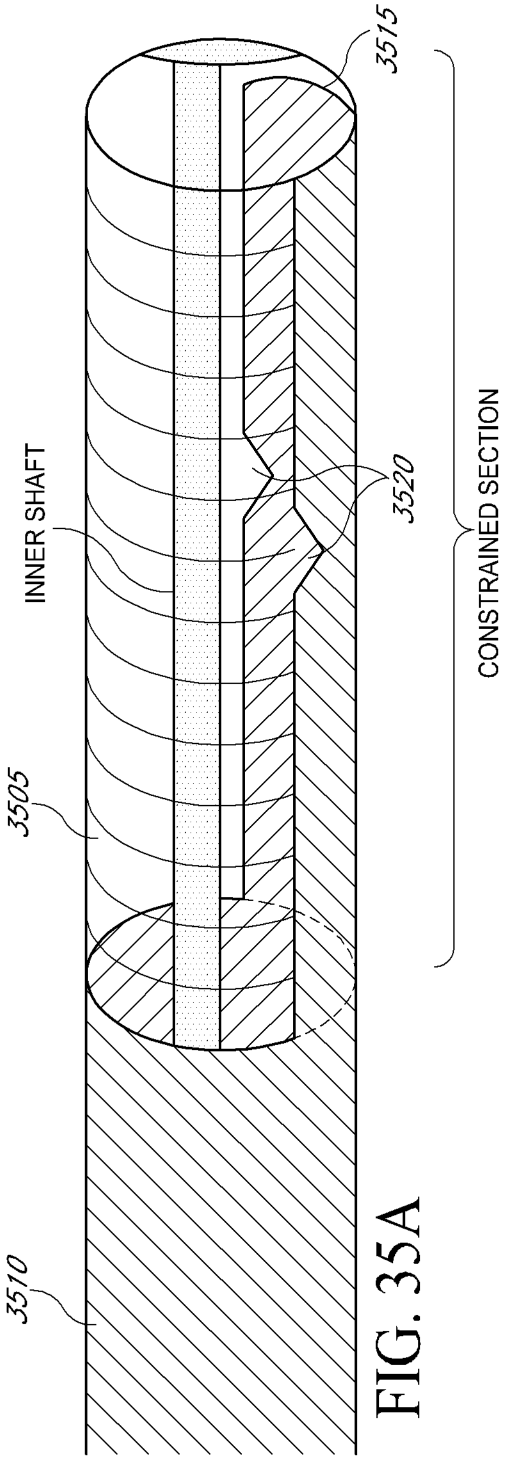
Figure 35B:
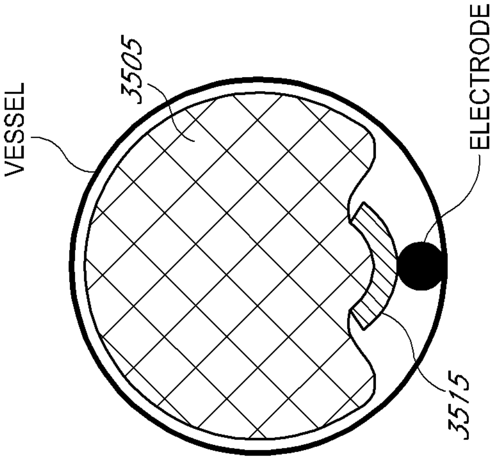
Figure 35C:
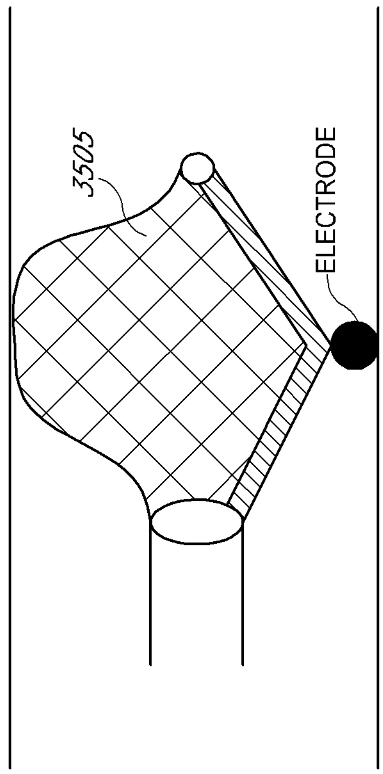

Referring now to FIGS. 35A-35C, one embodiment of an occlusive or obstruction element is a compliant balloon 3505 (e.g., made of silicone, polyurethane, or other suitable compliant material) bonded to a distal end of a catheter shaft 3510 and to a distal point of the overall catheter (e.g., which include an electrode or other activation member). In one embodiment, a portion of the balloon's circumferential arc 3515 is constrained by a less compliant material (e.g., PEBAX, Nylon, PE, Nitinol, stainless steel, or other suitably less compliant material) that spans a significant distance of the balloon's axial length. In some embodiments, the constrained section or portion of the catheter is an extension of the catheter shaft and may be constructed so that it can bend. In the illustrated embodiment, the constrained section incorporates physical design elements, such as notches or flexure-like regions 3520 to permit bending.

As shown in FIG. 35B, during inflation of the balloon 3505, the balloon material would expand evenly until it hit the vessel wall everywhere except near the constrained section. In some embodiments, although the constrained section would move out radially, the constrained section would still restrict the compliant balloon 3505, thereby creating a gap between the vessel (e.g., artery) wall and the balloon 3505 on either side of the constrained section arc 3515. The size of this gap may be pressure dependent (as it is related to the expansion of the compliant balloon). In some embodiments, the gap size is characterized as a function of balloon pressure by experimentation where the compliant balloon (with a constrained arc) is expanded within a semi-compliant tube and the cross-sectional area is measured visually or as a function of fluid resistance.

In various embodiments, the cross-section of the gap is advantageously smaller than the natural vessel cross-section, thereby increasing the fluid velocity at that cross-section. In some embodiments, the midpoint of the cross-section (e.g., region of highest velocity flow lines) would be moved closer to the constrained arc 3515.

In some embodiments, when the balloon 3505 is inflated, it expands evenly, except around the strip of catheter material, where it has to bend (requiring more pressure to stretch the material in that area). Through a range of pressures, the balloon 3505 may expand to press against the opposing vessel wall while leaving a gap around the electrode. In various embodiments, this pressure range could be experimentally defined.

In one embodiment, the balloon 3505 is inflated by a syringe at the proximal end of the catheter. The physician or other clinician may self-inflate the balloon, using his/her tactile sense (and potentially a pressure gauge in the syringe), and adjust the applied pressure. In one embodiment, the pressure is limited by a release valve or by a set volume placed in the syringe before inflating the balloon. In one embodiment, the balloon becomes the mechanism for applying the electrode force, and this mechanism has tactile feedback (e.g., the syringe). The balloon may be filled with cold fluid to enhance the overall cooling effect.

In various embodiments, the electrode(s) are bonded (e.g., physically with an overmold, chemically with adhesive, or other suitable bonding method) onto the constrained section. The wire(s) from the electrode(s) may run outside, within or inside the constrained section. In one embodiment, the constrained section is made of a thin, flexible circuit with wire(s) and electrode(s) embedded within the circuit encasing material.

Figure 36:
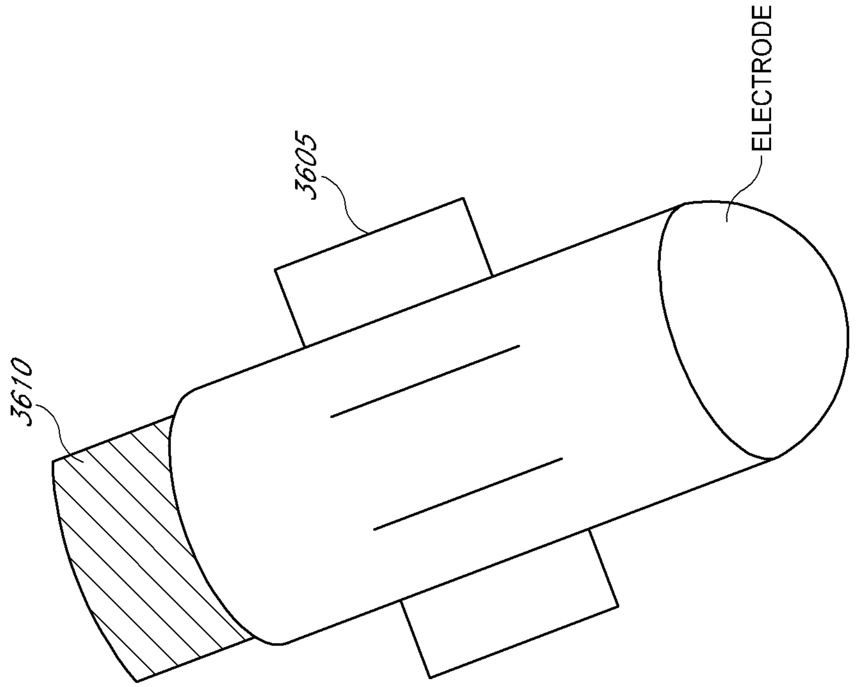

In accordance with several embodiments, the surface area of the electrode or a region in thermal proximity to the electrode can be increased. The increased temperatures can be achieved by increasing the length or diameter of the electrode, as convective cooling according to Newton's law is proportional to the surface area. In one embodiment, increasing the surface area of the electrode is achieved by adding fins 3605 or thermally connecting the electrode to another section of the catheter 3610 (as illustrated in FIG. 36). In various embodiments, the finned region of the catheter 3610 might either be in direct electrical communication with the electrode or electrically isolated from the electrode by means of a thin dielectric layer. In accordance with several embodiments, electric insulation (for example a thin 0.001" layer of polyimide) does not substantially reduce the thermal communication between the finned region and the electrode because the rate of thermal conduction through a thin material is greater than that through a thicker material.

In various embodiments, instead of fins, the surface of the electrode can also be microstructured, for example bead-blasted, microfractured, or etched. In some embodiments, small solder bumps are welded or riveted onto the surface of the electrode. In one embodiment, gold or other radiopaque material solder bumps are particularly advantageous to increase the radiopacity of the electrode.

Figure 37:
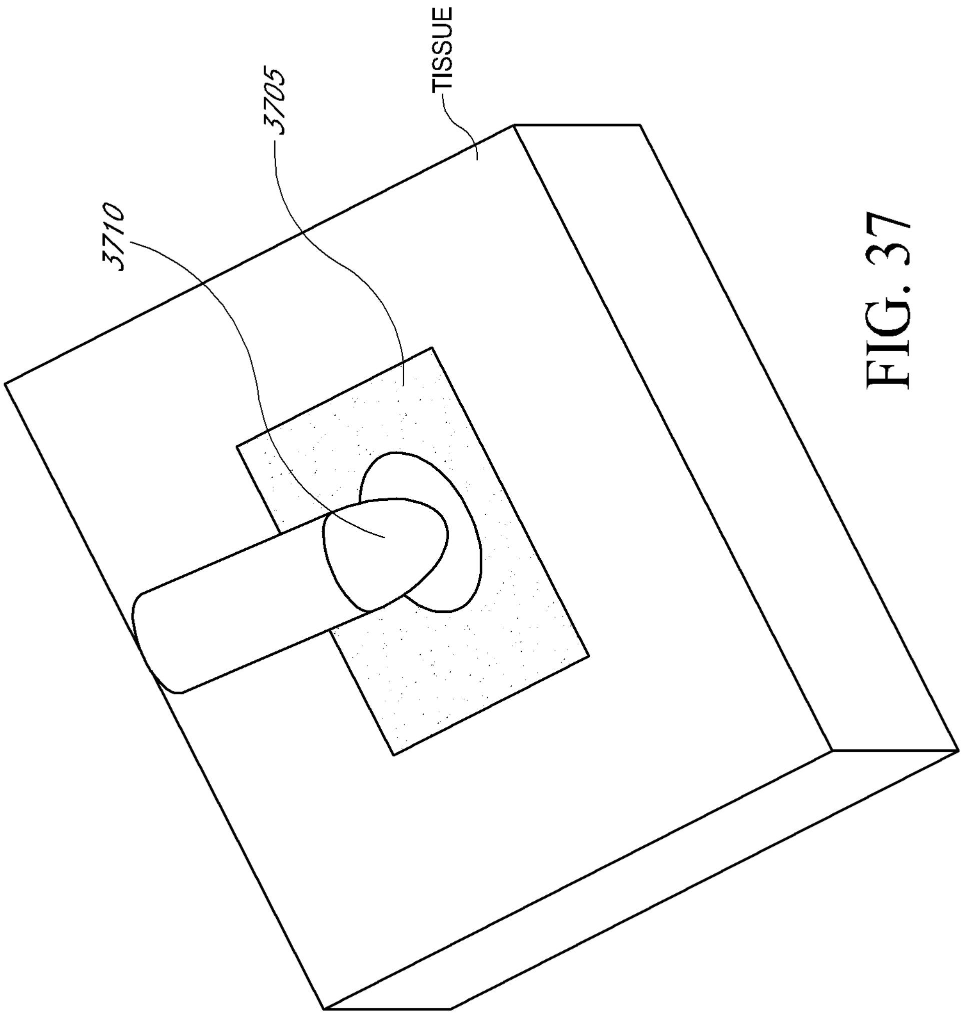

In one embodiment, electrode cooling is increased by effectively increasing the surface area of the lumen of the vessel (as opposed to increasing the surface area of the electrode), thereby increasing the heat transfer rate from the tissue to the blood. In an embodiment shown in FIG. 37, increasing the heat transfer rate from the tissue to the blood is achieved by placing a thermally conductive pad 3705 in contact with the tissue surrounding the electrode 3710. For example, a stent or ring may be deployed before the ablation energy dosage. The deployable stent or ring may place a thermally conductive structure (e.g., "pad") around the ablation site. In one embodiment, the pad 3705 is a pre-formed structure comprised of gelatin, hydrogel, or other high thermal conductivity material. In order to prevent non-targeted ablation of tissue, it may be necessary to electrically insulate the pad 3705 from the electrode. Electrical insulation may be achieved by leaving space between the electrode 3710 and the conductive pad 3705 (thereby preventing contact between the pad 3705 and the electrode 3710) through accurate placement of the electrode 3710 or a placement-guiding mechanism such as a funnel. Electrical insulation may also be achieved by placing a thin layer of an electrical insulator on the surface of the pad 3705 exposed to the electrode 3710. The layer of electrical insulation may also be attached to the catheter between the electrode 3710 and the pad 3705.

In accordance with various embodiments, it would be advantageous for the pad to have a large surface area. Fins, as shown and described in FIG. 36, are one way to increase the surface area and to increase heat dissipation.

In some embodiments, an ablation region is precooled using cold infusion techniques (e.g., iced saline infused directly into the vessel) or using a chilled balloon. In some embodiments, blood flow may also be restricted during pre-cooling to increase residence time and achieve desired heat transfer. The pre-cooling of the ablation region may advantageously lower the initial temperature for the ablation and allow more power to be delivered locally, thereby enabling steeper temperature gradients and deeper, tighter lesions. The pre-cooling may also result in lower conductivity in the cooled region, further concentrating power into locally heated regions. In one embodiment, a balloon having one or more electrodes is inserted to a target ablation site within a blood vessel or organ (e.g., within a common hepatic artery). Coolant may be circulated through the balloon for a period of time (e.g., 20-60 seconds, 30-50 seconds, 20-40 seconds, 30 seconds) prior to initiating ablation via the one or more electrodes. In some embodiments, the pre-cooling of the target ablation site may advantageously allow for delivery of ablative energy at a higher power level than if the target ablation site was not pre-cooled, thereby enabling deeper, more narrow lesions to be formed.

In one embodiment, electrode and/or tissue cooling is increased by decreasing the temperature of the blood in order to increase heat conduction by increasing the temperature delta between the blood and the electrode and surrounding tissue. In several embodiments, electrode and/or tissue cooling is achieved by placing thermoelectrics on the catheter and proximal to the electrode. Using the Peltier effect, a current driven through a junction of two different conductors can be used to remove heat from (cool) the junction. Because the catheter is inserted into the hepatic artery in an antegrade fashion, blood flows along the catheter towards the electrode (or ablation site). In one embodiment, the region of the catheter proximal to the electrode is upstream of the ablation (other site and the blood could be cooled along the catheter before it reaches the ablation site. In one embodiment, multiple thermoelectric coolers (e.g., the MD03 series or MDL06 series) are placed in the catheter proximal to the electrode and used to cool the blood. Since increasing the thermal conductance of the thermoelectric sites improves the efficiency of the thermoelectric elements, the thermoelectric elements may be placed to maximize surface area (e.g., fins), minimize wall thickness, and/or maximize location near the max velocity flow lines. In some embodiments, cold fluid injections upstream of the ablation site are used instead of thermoelectrics to achieve the same goal of reducing the blood temperature at the ablation site.

Figure 38A:
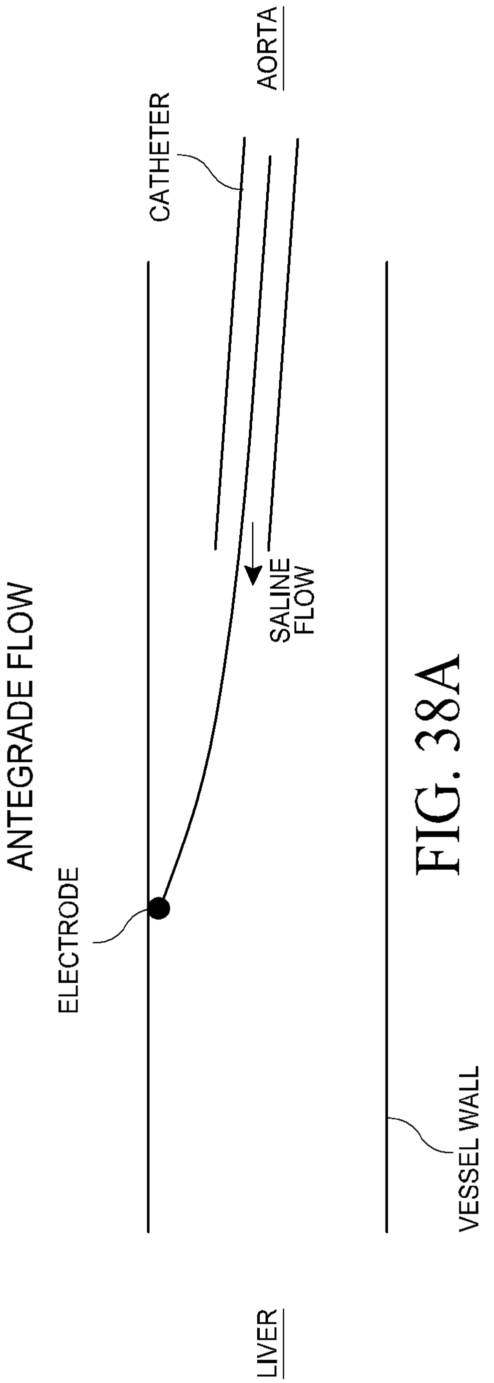
Figure 38B:
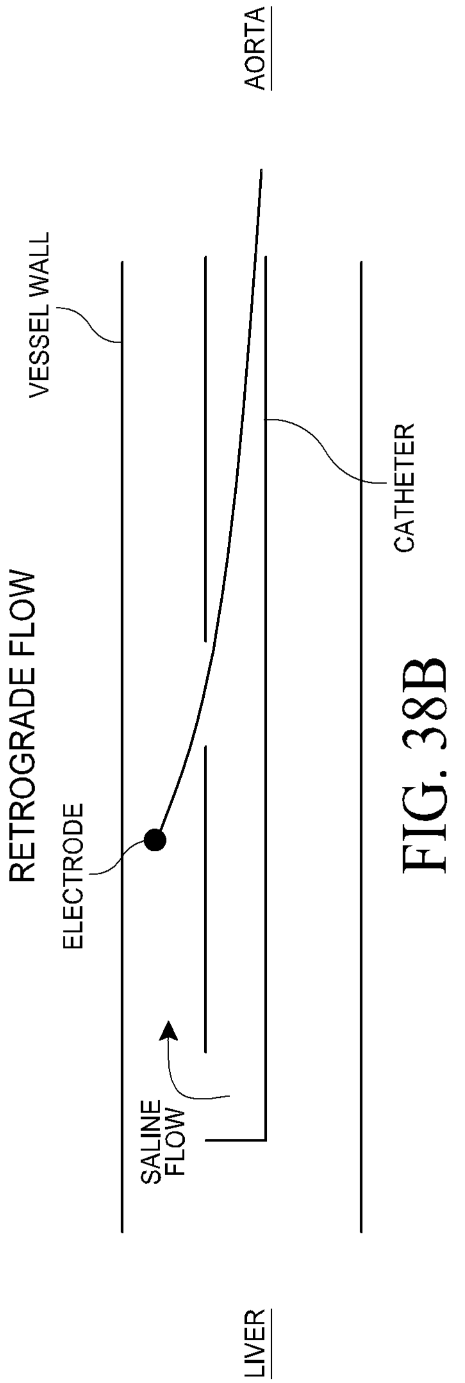
Figure 39:
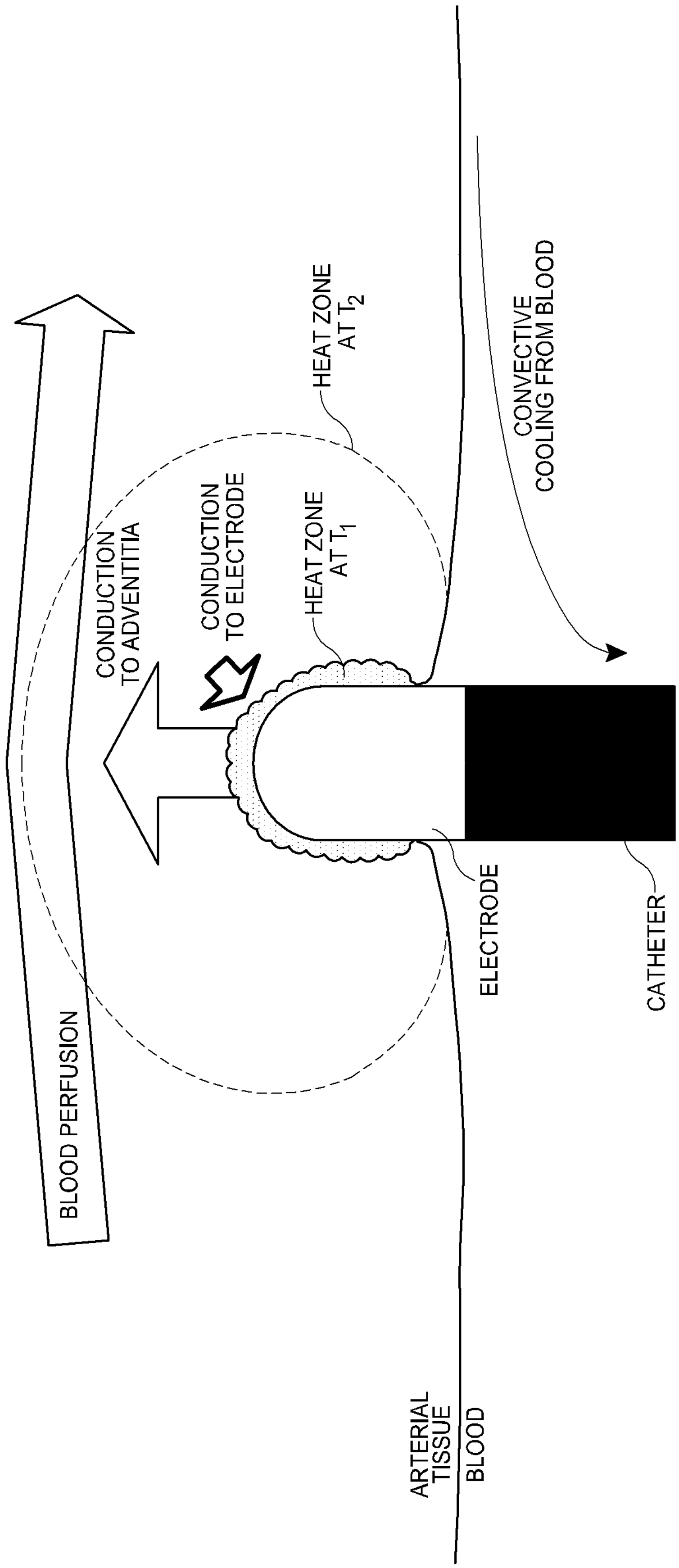

In some embodiments, a saline hyperphysiologic flow catheter is used to increase fluid flow within a target artery (e.g., common hepatic artery). FIGS. 38A and 38B illustrate schematic embodiments of a saline hyperphysiologic flow catheter. FIG. 38A illustrates an embodiment of a saline hyperphysiologic flow catheter configured to provide increased antegrade flow control at the electrode-vessel contact location (e.g., of about 500 mL/min). FIG. 38B illustrates an embodiment of a saline hyperphysiologic flow catheter configured to provide increased retrograde or reverse flow past the electrode-vessel contact location. In one embodiment, the vessel flow may be partially or completely stopped proximally or distally of the electrode and/or lower power can be used. The saline flow may cause flow within the vessel to be increase by two, three, four, five, six times or more. In one embodiment, a flow sensor is placed at a distal tip of the catheter to provide feedback of the convective cooling rate so that a desired temperature can be achieved.

Figure 108A:
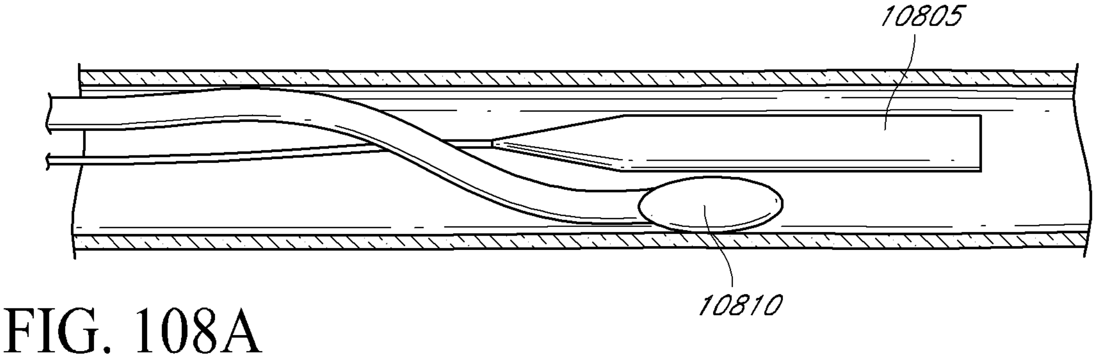
FIGS. 108A-108D Illustrate embodiments of devices configured to redirect or divert high velocity blood flow from the center of a vessel toward an electrode in contact with the vessel wall.
Figure 108B:
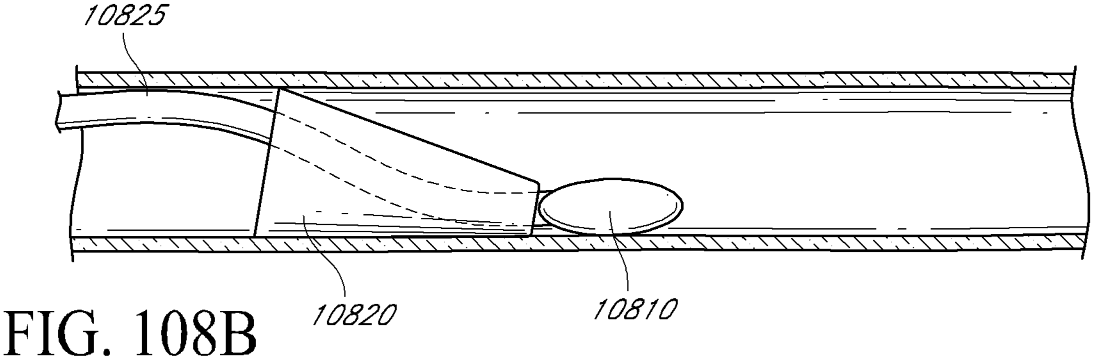
Figure 108C:
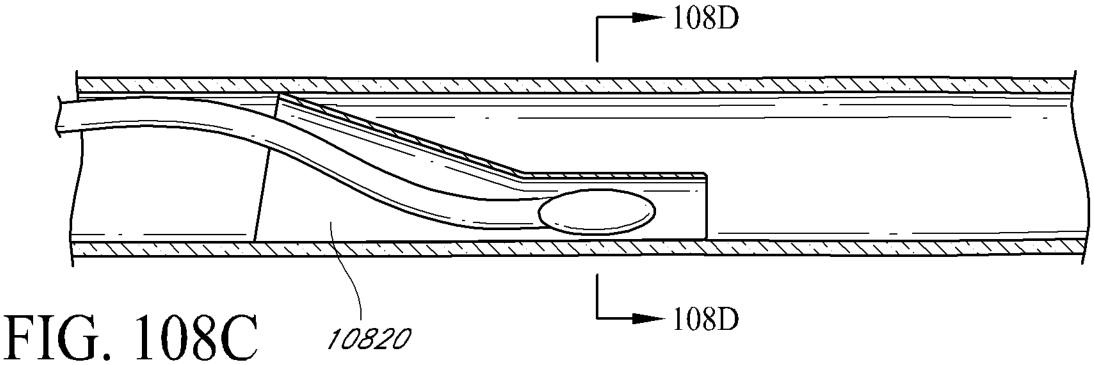
Figure 108D:
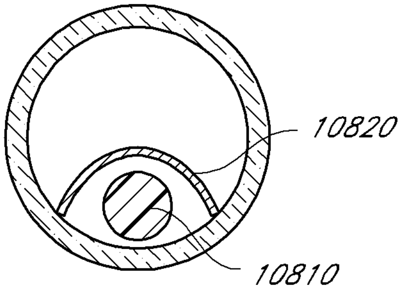

In accordance with several embodiments, redirecting high velocity blood flow from a higher-flow region (e.g., center) of the vessel to the vessel wall (or to an electrode in contact with the vessel wall) increases the removal of heat generated during ablation. FIGS. 108A-108D Illustrate embodiments of devices configured to redirect or divert high velocity blood flow from the center of a vessel toward an electrode in contact with the vessel wall. FIG. 108A illustrates an embodiment of an inflatable cone 10805, which can be placed above an electrode 10810 to redirect flow toward the electrode 10810. In one embodiment, the inflatable cone 10805 may be introduced into and delivered to the location through a separate catheter. The cone 10805 can be inflated to give room for blood flow around the cone 10805 and may be positioned in the center of the vessel, thereby resulting in a laminar high velocity flow along the walls of the vessel, and thereby cooling the electrode 10810 and vessel lumen. FIGS. 108B-108D illustrate an embodiment of a funnel 10820 configured to divert flow toward an electrode 10810 at a distal end of a catheter 10825 (e.g., probe or shaft). FIG. 108D is a cross-section view of FIG. 108C. The funnel 10820 may be affixed or coupled to the catheter 10825 by a joint or hinge at a location near the electrode 10810 (however, other coupling techniques may be used as desired and/or required). The funnel 10820 may be configured to collect higher blood flow at the center of the vessel and divert the flow directly across the electrode 10810. In some embodiments, the funnel 10820 comprises a flexible material. The cooling provided by the increased blood flow may facilitate formation of deeper lesions without causing charring or spasm, may reduce the likelihood of excessive superficial injury, and may provide more control over ablations. In one embodiment, flaps may capture and divert flow over the electrode to enhance cooling and direct the electrode toward an upstream location in the vessel (e.g., artery). The flaps may enable the electrode to be directed by the flow against the vessel wall, thereby enhancing or enabling wall contact. In one embodiment, a proximal catheter shaft can be extremely flexible to enable traversing extreme tortuosity. The flow-directed wall contact may enable electrode contact in situations where there is a desire to neuromodulate (e.g., ablate) on tight bends. In one embodiment, a "cup" may be created for blood capture, thereby enabling flow directed tracking and flow directed wall contact.

In accordance with several embodiments, branches of a main vessel other than those leading to a target vessel (e.g., the common hepatic artery) are partially or completely occluded to increase blood flow to the target vessel. For example, the left gastric artery and splenic artery (which branch off of the abdominal aorta upstream of the origin of the common hepatic artery) may be occluded temporarily during treatment of a common hepatic artery to increase blood flow through the common hepatic artery, thereby increasing electrode cooling and reducing the likelihood of spasms, notching and charring. In some embodiments, the partial or total occlusion of the branch vessels may be provided by a guide catheter. The guide catheter may be modified to add extensible and adjustable plates that may be retracted during insertion and removal of the guide catheter and deployed upon advancement of the guide catheter to an appropriate location adjacent a target vessel (e.g., within the abdominal aorta adjacent an origin of the common hepatic artery). Once the guide catheter is in position, the plates may be deployed and positioned to occlude a portion or the entire entrance to the branch arteries upstream of the target artery, thereby increasing flow into the target artery, which in turn increases the cooling of the electrode and of the arterial wall.

In accordance with some embodiments, buried and/or shielded electrode designs are used to prevent cooling. FIG.

39 illustrates an example of burying the electrode to substantially shield the electrode from cooling by blood flow within the artery, thereby increasing electrical aperture. In some embodiments, the electrode can be pushed against or into the media of the arterial wall to create a "false lumen" between the intima and the media to shield the electrode from blood flow. In one embodiment, a flat or substantially flat electrode can be used that is placed such that the electrode is parallel or substantially parallel to the vessel wall, thereby shielding the electrode from cooling due to blood flow. In one embodiment, the electrode comprises a finger-like electrode with a hemisphere covered with insulation to prevent blood cooling.

Figure 14A:
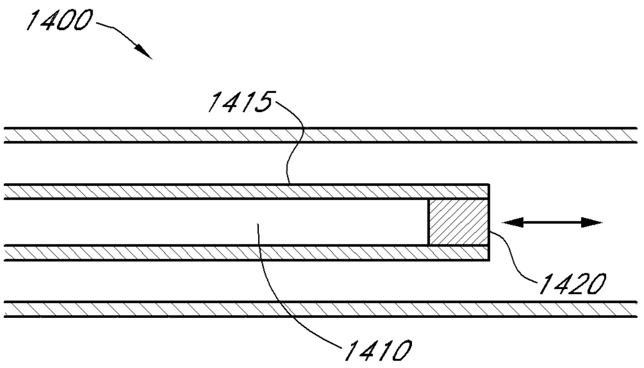
Figure 14B:
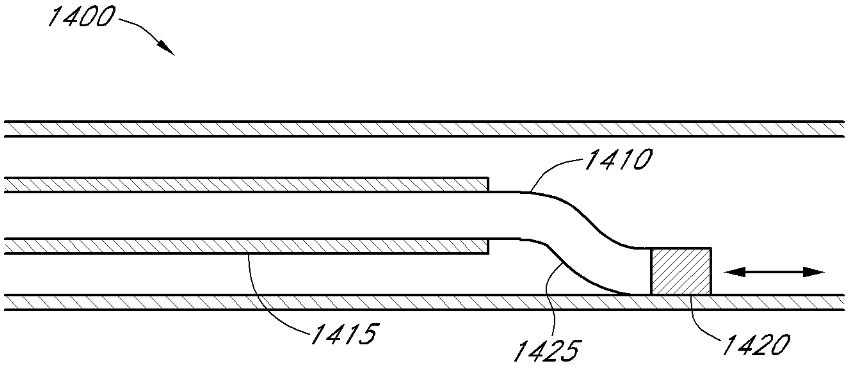

The hepatic artery anatomy is generally more tortuous and variable than anatomies of other vessels in other areas. Maintaining good contact of electrodes or other energy delivery elements in the tortuous hepatic artery anatomy can be difficult and may require the use of different catheter devices than existing catheter devices for nerve ablation. FIGS. 14A and 14B illustrate an embodiment of a low-profile ablation catheter 1400 that may advantageously facilitate contact of electrodes or other energy delivery elements with the inner walls of arteries of the tortuous hepatic vascular anatomy. The low-profile ablation catheter 1400 comprises an inner electrode member 1410 and an outer sheath 1415. The inner electrode member 1410 may comprise a reversibly deflectable, pre-shaped cylindrical shaft comprising resilient (e.g., shape memory) material and at least one electrode 1420. In one embodiment, the outer sheath 1415 comprises a guide catheter having a lumen. The inner electrode member 1410 may be configured to be delivered within the lumen of the outer sheath 1415 and to be translatable relative to the outer sheath 1415 such that the inner electrode member 1410 may be advanced out of a distal end of the outer sheath 1415 and retracted back in. In one embodiment, the inner electrode member 1410 assumes a generally deflected (e.g., off-axis) configuration when advanced out of the distal end of the outer sheath 1415, as shown in FIG. 14B. In this unconstrained state, the distal end of the inner electrode member 1410 deviates from a longitudinal axis defined by the proximal portion of the electrode. When the inner electrode member 1410 is retracted within the outer sheath 1415, the inner electrode member 1410 is resiliently deformed to assume a substantially straight shape defined by the substantially straight shape of the lumen of the outer sheath 1415, as shown in FIG. 14A. In some embodiments, when the inner electrode member 1410 is advanced out of the distal end of the outer sheath 1415, the distal end portion of the inner electrode member 1410 deflects to contact a vessel wall (e.g., arterial wall). The shape of the distal end of the inner electrode member 1410 in the unconstrained state may be pre-formed to ensure contact with the vessel wall.

In some embodiments, the outer sheath 1415 has a diameter of less than about 4 mm, less than about 3 mm, less than about 2 mm, or less than about 1 mm. In some embodiments, the inner electrode member 1410 comprises a shaft formed, at least partly, of memory material such as a nickel titanium alloy material. The inner electrode member 1410 may have an outer cross-sectional dimension that is substantially equal to the outside diameter of the outer sheath 1415 or may have an outer cross-sectional dimension that is smaller or larger than the outside diameter of the outer sheath 1415. In some embodiments, when the inner electrode member 1410 is slid out of the outer sheath 1415 past a pre-formed step 1425 at or near its distal end, the step 1425 at or near the distal end places the surface of the distal end of the inner electrode member 1410 away from the natural axis of the outer sheath 1415. In some embodiments, the step 1425 near the distal end of the inner electrode member 1410 places the surface of the inner electrode member 1410 between about the same plane as the outer surface of the outer sheath 1415 and about double the diameter from the center of the outer sheath 1415 to the outer surface of the outer sheath 1415. In some embodiments, the outer sheath 1415 is deflectable.

In some embodiments, the magnitude of the off-axis deflection created in the step 1425 near the distal end is tailored to satisfy varying anatomic requirements (e.g., larger step near the distal end for larger blood vessels and smaller step near the distal end for smaller blood vessels). In some embodiments, the inner electrode member 1410 is interchangeable and may be replaced with a different inner electrode member with different size parameters. The different sizes of inner electrode members or electrode members with different pre-formed shapes may be provided in a kit and an appropriate inner electrode member may be selected after evaluating patient anatomy (for example, by CT, fluoroscopy, or ultrasound imaging methods). In some embodiments, the inner electrode member 1410 is rotated within the catheter body.

In some embodiments, the at least one electrode 1420 of the inner electrode member 1410 comprises one or more monopolar, bipolar or multipolar electrodes (the addition of additional pre-shaped electrodes may enable bipolar and multi-polar RF energy delivery). Any combination of electrodes may be incorporated into the design of the inner electrode member 1410 to create a catheter with any desired properties.

In some embodiments, the shaft of the inner electrode member 1410 comprises an insulation member to prevent heat transfer away from or electrically insulate portions of the inner electrode member 1410. In some embodiments, the insulation member is a tubing, coating or heat shrink comprised of polyamide, polytetrafluoroethylene, polyetheretherketone, polyethylene, or any other high dielectric material. The insulation member may comprise one or more openings to expose portions of the distal end portion of the inner electrode member 1410. In some embodiments, the insulation member is used to define specific electrode geometries by selective removal of the insulation member in whatever geometry is desired. In other embodiments, the inner electrode member 1410 comprises a shape memory polymer or shape-biased polymer with one or more electrode leads disposed therein. In one embodiment, the low-profile ablation catheter comprises a catheter coextruded with a shape memory electrode spine, where the extruded catheter provides electrical insulation. In one embodiment, the at least one electrode 1420 comprises a spherical electrode. In one embodiment, the distal end of the inner electrode shaft comprises a series of electrodes.

In some embodiments, the low-profile ablation catheter 1400 comprises a radial window or slot in a side portion near the distal end of the ablation catheter. In one embodiment, the distal end of the inner electrode member 1410 is configured to be deployed out of the radial window or slot. In one embodiment, the lumen of the ablation catheter 1400 comprises a ramp leading up to the radial window or slot to direct the distal end of the inner electrode member out of the radial window or slot.

In accordance with several embodiments, the low-profile ablation catheter 1400 advantageously provides a device that comprises a low profile (e.g., small outer cross-sectional dimension) and uses the same mechanism to actuate the electrode deflection as well as the electrode itself, thereby reducing the number of distinct components. The inner electrode 1410 of the low-profile ablation catheter may also advantageously be at least partially deployed to facilitate navigation by providing a variety of tip curvature options for “hooking” vascular branches or navigating tortuous vessels during catheter insertion. In accordance with several embodiments, the low-profile ablation catheter 1400 advantageously facilitates solid and continuous contact with the vessel wall, thereby allowing for substantially constant voltage to maintain a desired electrode tip temperature.

FIGS. 14C-1, 14C-2, 14D, 14E, 14F, 14G, 14H-1, 14H-2, 14I-1, 14I-2, 14I-3, 14I-4, 14J-1, 14J-2 and 14K Illustrate various embodiments of energy delivery devices configured to facilitate maintained contact of an energy delivery member (e.g., an electrode) against a vessel wall (e.g., a wall of a common hepatic artery) despite motion due to respiration or blood flow.

Figures 1, 14C:
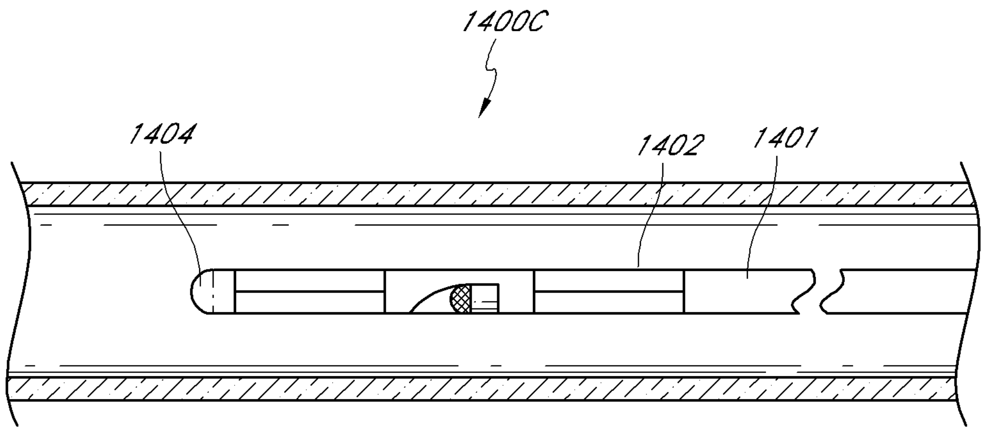
Figures 2, 14C:
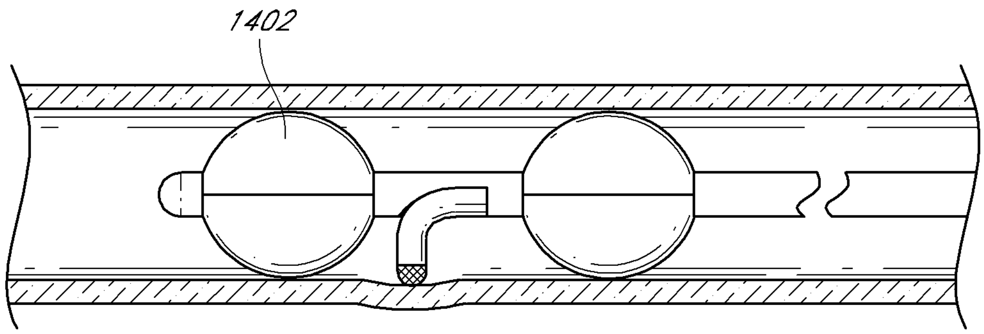

FIGS. 14C-1 and 14C-2 illustrate an embodiment of an ablation catheter system 1400C comprising a shaft 1401 having one or more expandable intravascular structures 1402 configured to expand into contact with a vessel wall upon expansion. The ablation catheter system 1400C may advantageously be used to provide vessel centering for embodiments involving an electrode-tipped catheter. In some embodiments, the expandable structures 1402 allow for minimal restriction to blood flow while supporting an electrode 1404 for a controlled vertical presentation to a desired treatment site. The expandable intravascular structures 1402 may comprise a scaffold, frame or basket formed of multiple lobes or tines constructed from a flexible, durable and/or flex resilient material (such as Nitinol, Inconel or other shape memory materials). In one embodiment, expansion of the structures 1402 from the unexpanded state to the expanded state involves compression, or foreshortening, by way of a pull wire being retracted. As shown in the illustrated embodiment, the shaft 1401 may comprise two expandable intravascular structures 1402. The electrode-tipped catheter may comprise a cylindrical probe or tube having an electrode tip 1404 that is advanced through a lumen of the shaft 1401 and out of a port or side opening 1403 of the shaft 1401. In one embodiment, the electrode tip 1404 is advanced through the lumen of the shaft 1401 until it reaches a deflection ramp positioned between (e.g., at the midpoint between) the expandable intravascular structures 1402 that forces the electrode tip 1404 out of the port or side opening 1403 of the shaft 1401 at a 90 degree angle relative to the longitudinal axis of the shaft 1401 until the electrode tip 1404 contacts the vessel wall.

Figure 14D:
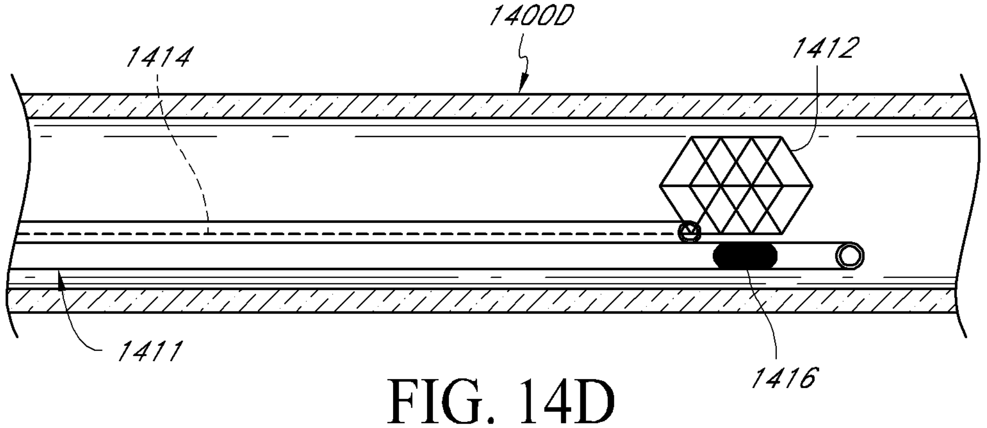

FIG. 14D illustrates an embodiment of an ablation catheter system 1400D comprising a dual-lumen catheter 1411. A distal end of the dual-lumen catheter 1411 comprises an expandable structure 1412 and an electrode 1416. In the illustrated embodiment, the expandable structure 1412 is mechanically expanded by a pull-wire 1414 extending from a proximal end of one of the lumens to the expandable structure 1412 at the distal end. The expandable structure 1412 may advantageously comprise a scaffold or basket having an open pattern that facilitates free, unrestricted flow of blood while the scaffold or basket is in an expanded state. The expandable structure 1412 may have a configuration that enables the structure 1412 to be deployed and secured within any of a number of target vessels having different diameters (e.g., for the purpose of creating a lesion) without the influence of movement due to respiration or blood flow (e.g., piston-like axial movement), thereby providing consistent and focused electrode wall contact during energy delivery. As an example embodiment of a method of use, an operator may place the dual-lumen catheter 1411 in a target vessel, advance it to a target site within the target vessel, and deploy the expandable structure 1412 using the mechanical pull-wire 1414. Energy may be delivered via the electrode 1416. Once the energy cycle is complete, the expandable structure 1412 may be retracted and the catheter 1411 may be withdrawn or moved to a different target site. In some ablative embodiments, the improved precision of lesion creation and minimization of axial lesion extension reduces likelihood of lesion overlap and improves vascular safety profile.

Figure 14E:
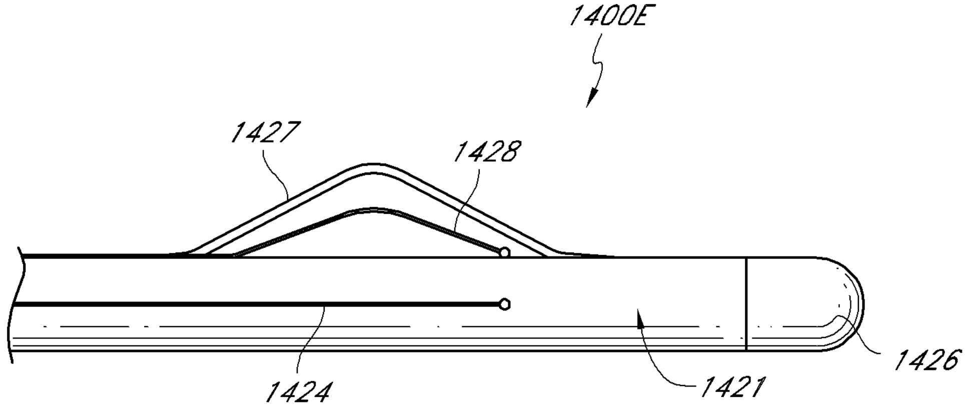

FIG. 14E illustrates an embodiment of a radiofrequency energy delivery catheter 1400E that is configured to harness the energy of blood flow through a vessel to facilitate maintained contact of an electrode against the vessel wall. The catheter 1400E comprises a deflectable shaft segment 1421, a pull wire 1424, a distal tip electrode 1426, an elastic membrane 1427 and a push wire 1428 configured to expand the elastic membrane 1427. As actuation of the deflectable shaft segment 1421 occurs upon pulling of the pull wire 1424, the same action pushes the push wire 1428, thereby expanding the elastic membrane 1427. The elastic membrane 1427 extends around a portion (e.g., 180 degrees of the shaft circumference) of the deflectable shaft segment 1421, and forms a “sail” that takes advantage of the force provided by blood flow to provide increased electrode contact force and stability. The design of catheter 1400E may minimize shaft profile by eliminating actuation structures. In some embodiments, the push wire 1428 and the pull wire 1424 are actuated independently.

In accordance with several embodiments, energy delivery devices (e.g., catheters) comprise a distal portion constructed of shape memory material and a lumen configured to receive a guidewire. The shape memory material may be heat or shape set so as to cause an electrode positioned on the distal portion of the energy delivery device to contact an inner wall of a target vessel. A guidewire may retain the distal portion of the energy delivery device in a straight or substantially straight alignment until the distal portion is positioned in a desired position within the target vessel. When the guidewire is withdrawn from the lumen of the energy delivery device, the shape-memory distal portion deforms to the heat- or shape-set configuration so as to cause an electrode of the energy delivery device to contact the inner wall of the target vessel. In some embodiments, energy delivery devices (e.g., catheters may have one or more pre-formed configuration portions configured to transition to a pre-formed configuration upon being advanced out of a sheath or introducer catheter and one or more pre-formed configuration portions configured to transition to a pre-formed configuration upon removal or withdrawal of a guidewire.

Figure 14F:
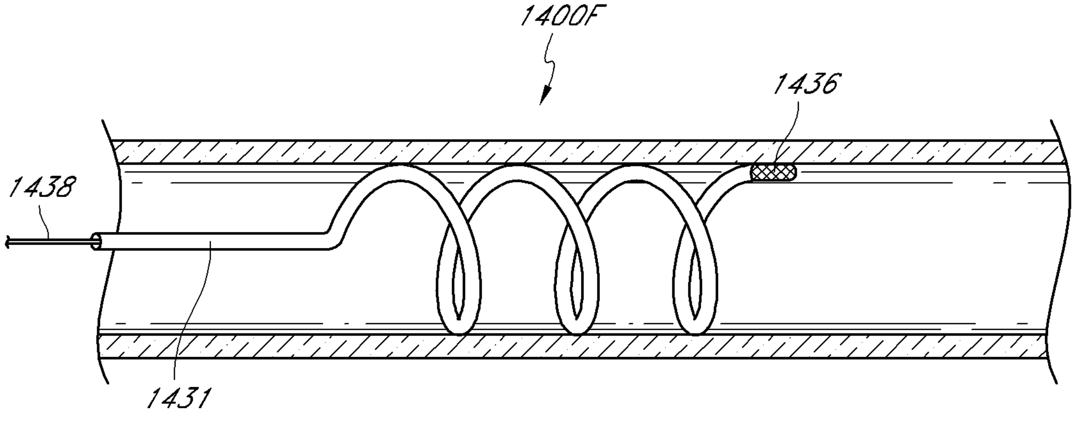

FIG. 14F illustrates an embodiment of an RF energy delivery system 1400F comprising a device (e.g., catheter) 1431 having a tip electrode 1436 and a guidewire 1438. The distal portion of the catheter 1431 is shape set during manufacture to have a pre-formed pigtail (e.g., spiral or corkscrew) shape. The distal portion of the catheter 1431 remains in a straight or substantially straight shape as it is advanced to a target location over the guidewire. Upon retraction of the guidewire, the distal portion of the catheter 1431 assumes the pre-formed pigtail shape, thereby causing contact of the distal portion of the catheter 1431 at multiple locations along the length and circumference of the vessel wall, including at the electrode tip 1436. Re-insertion of the guidewire straightens the distal portion of the catheter 1431 and facilitates removal of the catheter 1431.

In accordance with several embodiments, the electrode(s) may advantageously be positioned on a side of a low-profile catheter (e.g., probe or shaft), thereby providing a longer segment of electrode contact with the vessel wall than a tip electrode. The side placement may allow for reduced catheter dimensions for equivalent energy delivery.

Figure 14G:
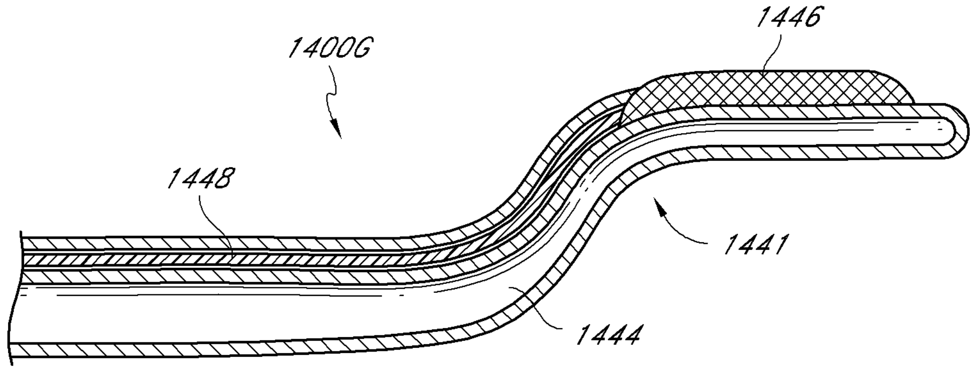

FIG. 14G illustrates an embodiment of an energy delivery catheter (e.g., shaft or probe) 1400G comprising a distal end portion 1441 having a pre-formed bend shape and comprising a side electrode 1446. The energy delivery catheter 1400G may comprise (1) a core wire 1444 having the pre-formed bend shape that is configured to transition to the pre-formed bend shape upon being advanced out of a sheath or catheter or (2) a hollow sheath having the pre-formed bend shape that is configured to be advanced over a guidewire and then "deployed" upon retraction of the guidewire. In some embodiments, the catheter 1400G comprises an insulating and/or protective layer between the core wire 1444 and the electrode 1446 and the electrode lead wire(s) 1448.

Figures 1, 14H:
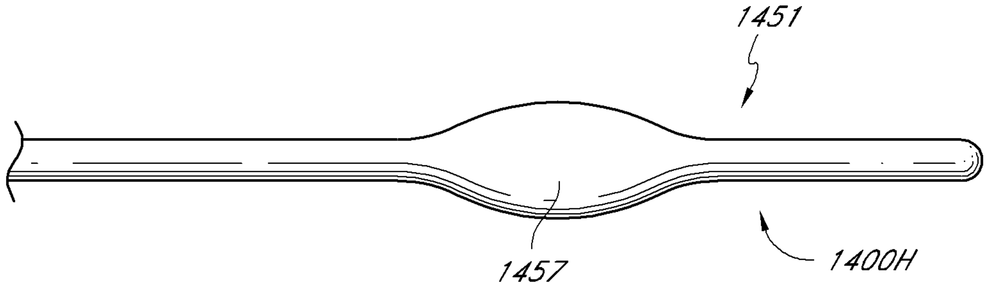
Figures 2, 14H:
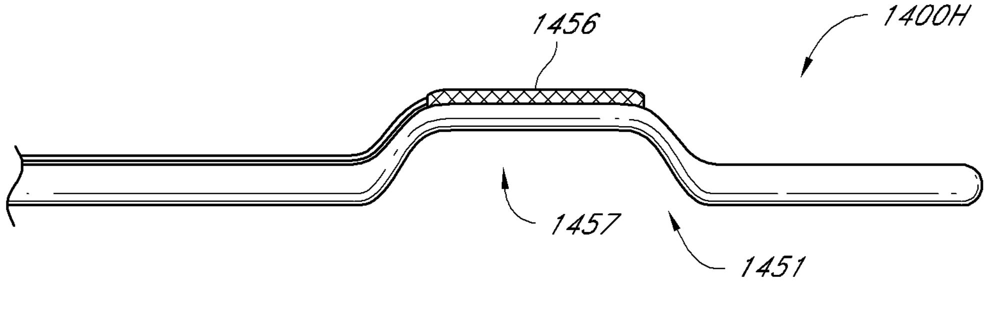

FIGS. 14H-1 and 14H-2 illustrate an embodiment of an energy delivery catheter (e.g., shaft, probe, or wire) 1400H comprising a distal end portion 1451 having a pre-formed bend shape and comprising a side electrode 1456. FIG. 14H-1 illustrates that a segment 1457 of the energy delivery catheter is flattened. The side electrode 1456 is positioned at a distance from a distal terminus of the distal end portion 1451 at the location of the flattened segment 1457. FIG. 14H-2 illustrates the pre-formed bend shape of the distal end portion 1451 that is heat- or shape-set during manufacture. The pre-formed bend shape facilitates contact of the side electrode 1456 with a vessel wall upon being advanced out of an outer sheath (e.g., guide extension catheter or guide catheter).

Figures 1, 14I:
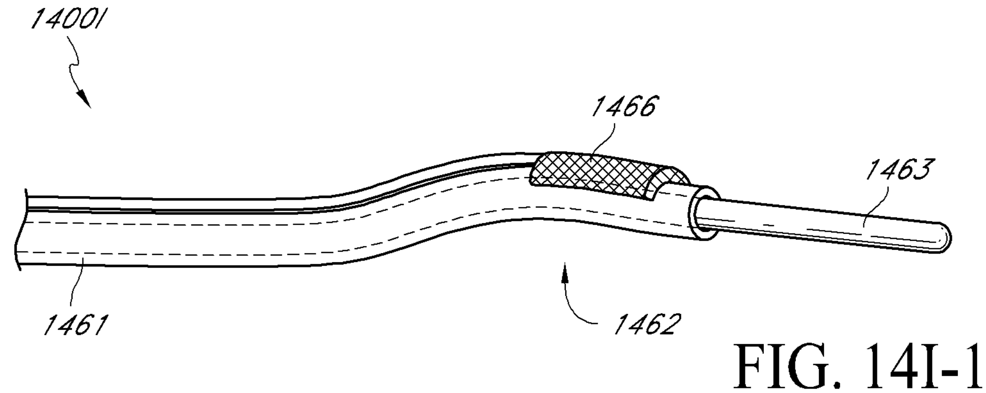
Figures 2, 14I:
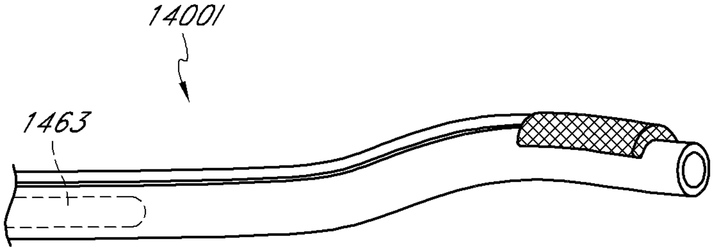
Figures 3, 14I:
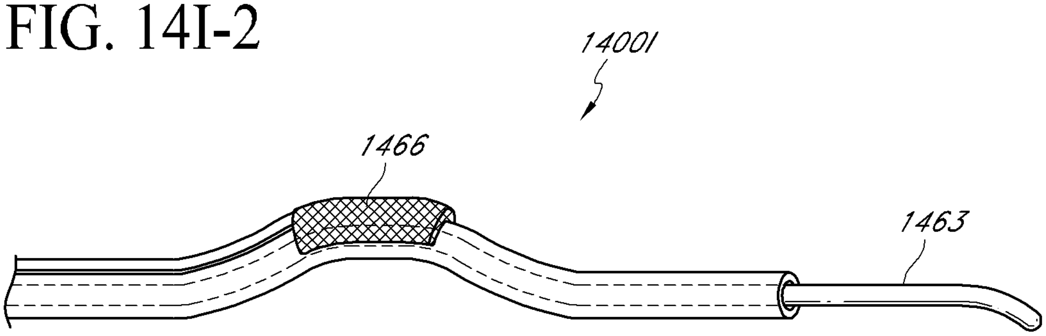
Figures 4, 14I:
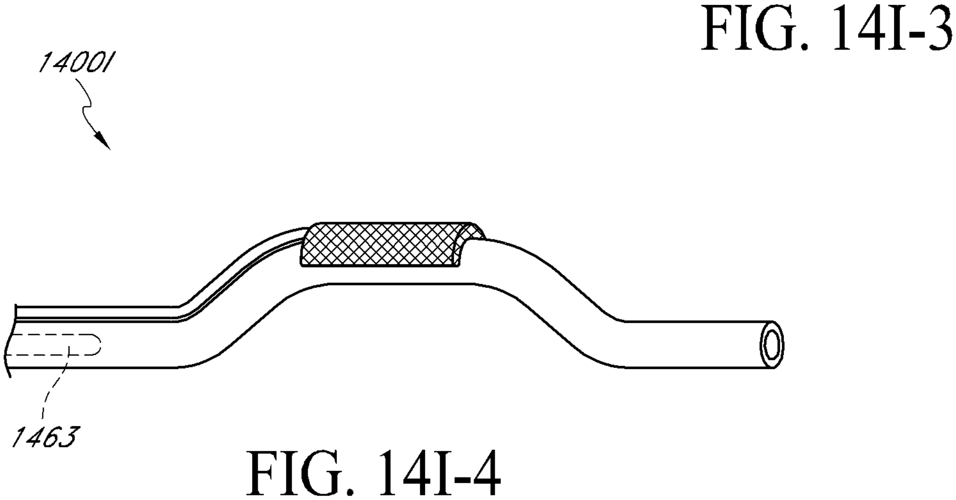

FIGS. 14I-1 to 14I-4 illustrate embodiments of an energy delivery system 14001 comprising a catheter 1461 having a distal end portion 1462 with a pre-formed bend shape or configuration and a side electrode 1466 and a guidewire 1463 (e.g., 0.014" wire). The distal end portion 1462 remains in a substantially straight configuration while being advanced over the guidewire 1463 and transitions to a "cobra-head" configuration upon retraction of the guidewire 1463, thereby causing the side electrode 1466 to contact the vessel wall. The side electrode 1466 is positioned at or near a distal terminus in FIGS. 14I-1 and 14I-2 and at a location spaced from the distal terminus in FIGS. 14I-3 and 14I-4. The guidewire 1463 can be re-advanced to straighten the distal end portion 1462 to facilitate removal of the catheter 1461.

Figures 1, 14J:
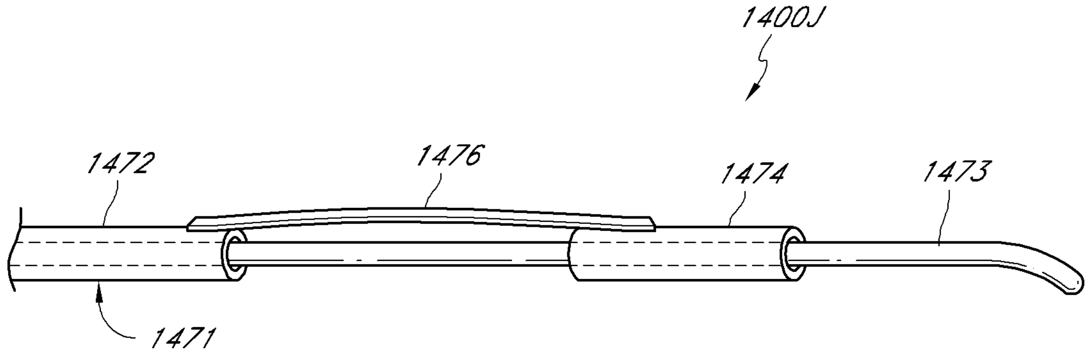
Figures 2, 14J:
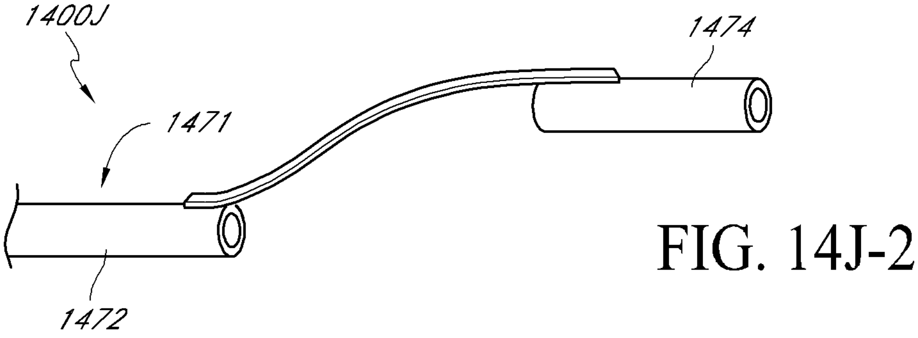

FIGS. 14J-1 and 14J-2 illustrate embodiments of an energy delivery system 1400J comprising a low-profile catheter 1471 and a guidewire 1473. The catheter 1471 comprises a main shaft 1472, a distal shaft tip 1474 and an electrode 1476. The proximal end of the electrode 1476 is coupled to the distal portion of the main shaft 1472 and the distal end of the electrode 1476 is coupled to the proximal portion of the distal shaft tip 1474. The catheter 1471 is advanced over the guidewire 1473 to a target treatment site within a target vessel. The guidewire 1473 may then be retracted, allowing the electrode 1476 to transition to a configuration in which the electrode 1476 contacts the vessel wall. The embodiment of the energy delivery system 1400J advantageously provides for lower profile at the electrode location.

Figure 14K:
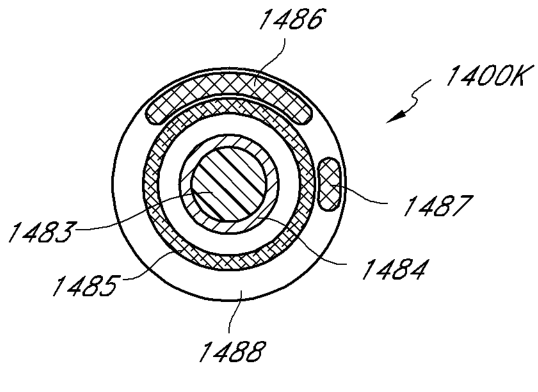

FIG. 14K illustrates a cross-section view of an embodiment of an energy delivery catheter 1400K. The catheter 1400K may be delivered over a guidewire 1483 such that at least a portion of the catheter 1400K having a shape-memory configuration remains in a substantially straight configuration. The catheter 1400K may comprise a central lumen 1484 configured to receive the guidewire 1483, a braided wall 1485 formed of shape-memory material (e.g., nitinol) extending along all or a portion of the catheter length, and an electrode 1486 and a temperature-measurement device 1487 (e.g., thermistor, thermocouple) embedded in an outer layer 1488 of the catheter 1400K.

Figure 15:
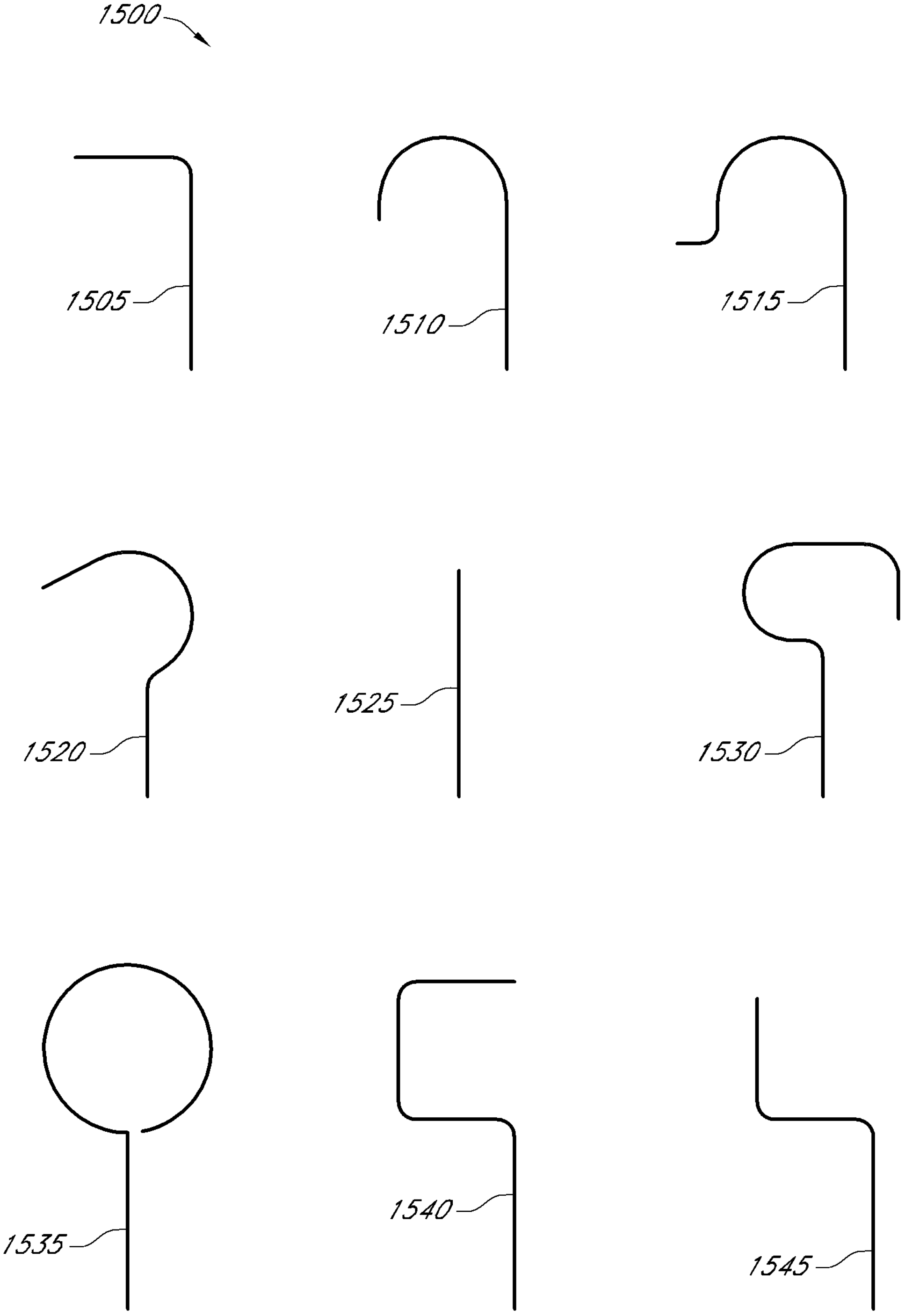
FIG. 15 illustrates several embodiments of catheter distal tip electrode and guide wire shapes.

FIG. 15 illustrates various embodiments of distal tip electrode and guide wire shapes 1500. The distal tip electrode and guide wire shapes 1500 may include an "L" shaped tip 1505, a "J" shaped tip 1510, a "shepherds crook"-shaped tip 1515, a "hook" shaped tip 1520, a "line" shaped tip 1525, a "key" shaped tip 1530, a "circle" shaped tip 1535, a "square hook" shaped tip 1540, or a "step" shaped hook 1545. A spiral-shaped tip (such as shown in FIG. 12A) may also be used. In one embodiment, a lasso-shaped tip is used. The lasso-shaped tip may have a similar configuration to the "circle" shaped tip 1535 but with the "circle"- or "lasso"-shaped tip portion being oriented substantially perpendicular to the straight line portion. The various shapes illustrated in FIG. 15 may advantageously be selected from and used in conjunction with the low-profile ablation catheter 1400 or other catheter devices to facilitate contact of electrodes or other energy delivery elements with the inner walls of arteries of the tortuous hepatic vascular anatomy (e.g., based on the particular vascular anatomy of the subject being treated or the particular vessels being treated). Any of the shapes 1500 shown in FIG. 15 may comprise a plurality of electrodes arranged in different patterns. The various distal tip shapes or designs may be provided in a kit and can increase the ability to treat the wide variety of hepatic artery anatomies or other target anatomies between subjects.

In some embodiments, the distal tip electrode itself, or a guide wire, may be partially or fully extended from an insertion catheter, to aid in navigation, thereby providing for a variety of tip curvature options for "hooking" vascular branches during catheter insertion. In some embodiments, shape-memory electrodes may be interchangeable by a clinician-user. For example, the clinician may select the most appropriate shape conformation for the patient's unique anatomy from a kit of different shaped devices, rather than being bound to a single device conformation or configuration. In one embodiment, the particular shape is selected based on angiography or other imaging modalities of the target treatment region. The various shaped tips may advantageously be selected to optimize the ability for the one or more electrodes or energy delivery elements to contact the target vessel due to the tortuosity and variability of the vascular anatomy at and/or surrounding the target vessel. The electrode assembly may also include a sensing element, such as a thermal sensing element (e.g., thermistor or thermocouple) to permit measurement of tissue temperatures and energy delivery during the treatment. The sensing element may provide feedback regarding confirmation of denervation or blocking of nerve conduction and/or regarding the contact force applied to the vessel wall and whether or not the contact force is sufficient to enable effective neuromodulation.

In accordance with several embodiments, once a particular shape is selected, forces (F) can be applied to the proximal end of the electrode to adjust the contact force F' against a vessel wall. In some embodiments, the degree of strain of the electrode distal portion is proportional to the force applied to the vessel wall. Radiopaque markers may be placed along the length of the inner electrode 1410 and the relative angle Φ between lines drawn between two of the radiopaque markers can be designed such that F'=f(Φ(F)). A clinician may then adjust the force on the proximal end of the electrode to achieve the desired contact force.

Figure 85A:
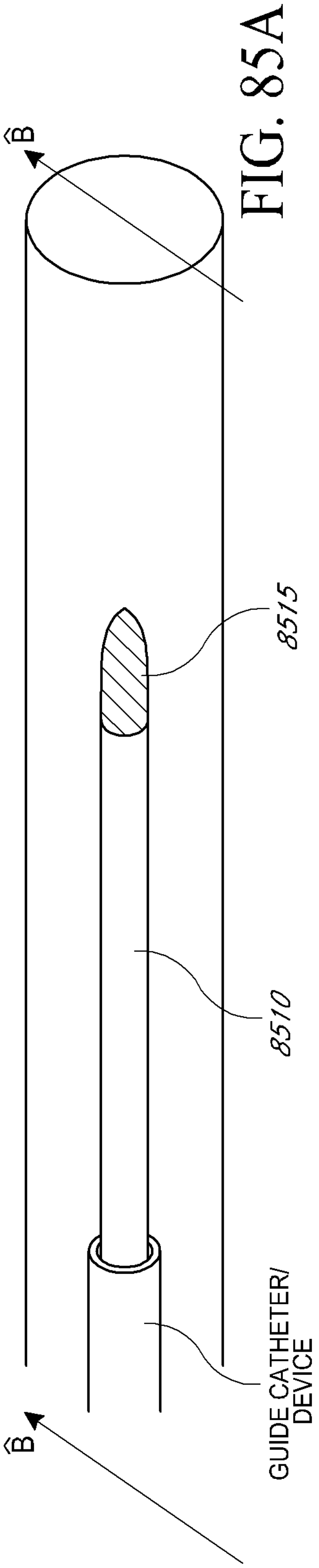
Figure 85B:
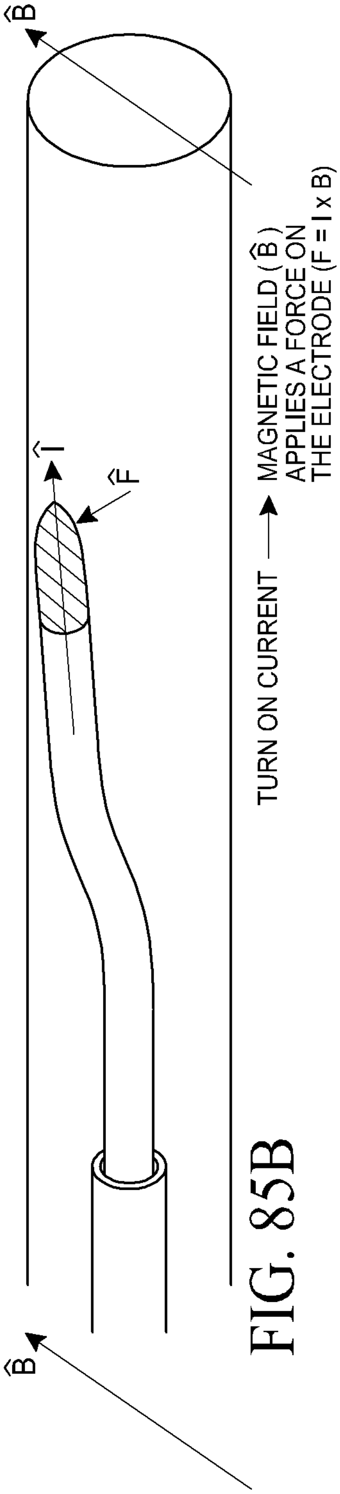

In some embodiments, electrode contact force and/or electrode articulation is provided through the use of electromagnetic elements disposed within the neuromodulation catheter (e.g., ablation catheter). As shown in FIGS. 85A and 85B, an embodiment of an ablation catheter device is comprised of at least an electrode 8515, a flexible shaft 8510, and a segment that is capable of carrying current and that is significantly close to the electrode to effect movement of the electrode in response to an applied magnetic field. In some embodiments, the ablation catheter device is positioned in a vessel and a magnetic field is applied through the vessel (for example, applied external to the patient). When the current is turned on, an electro-magnetic force is applied to the current-carrying segment per the Lorentz force law: F=I×B. The location of the magnetic field may be moved so that the direction of the force (and hence the location of the applied force within the vessel) can be adjusted. The magnitude and the current or magnetic field may be adjusted to adjust the magnitude of the force. The direction of the current and magnetic field can be used to adjust the magnitude of the force, as the magnitude of a cross product is dependent on direction of the crossed vectors. In various embodiments, one or more current-carrying segments, one or more electrodes and/or one or more flexible catheter segments may be used.

Figure 86A:
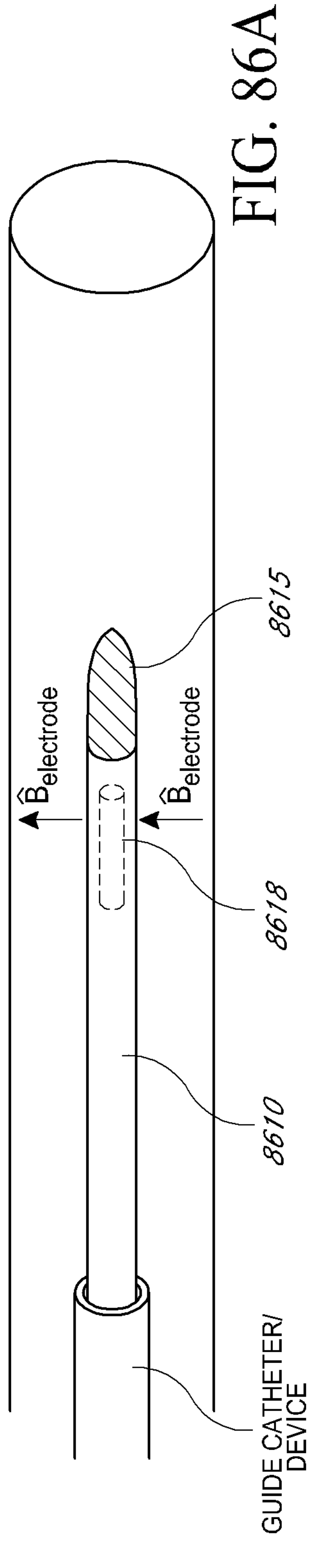
Figure 86B:
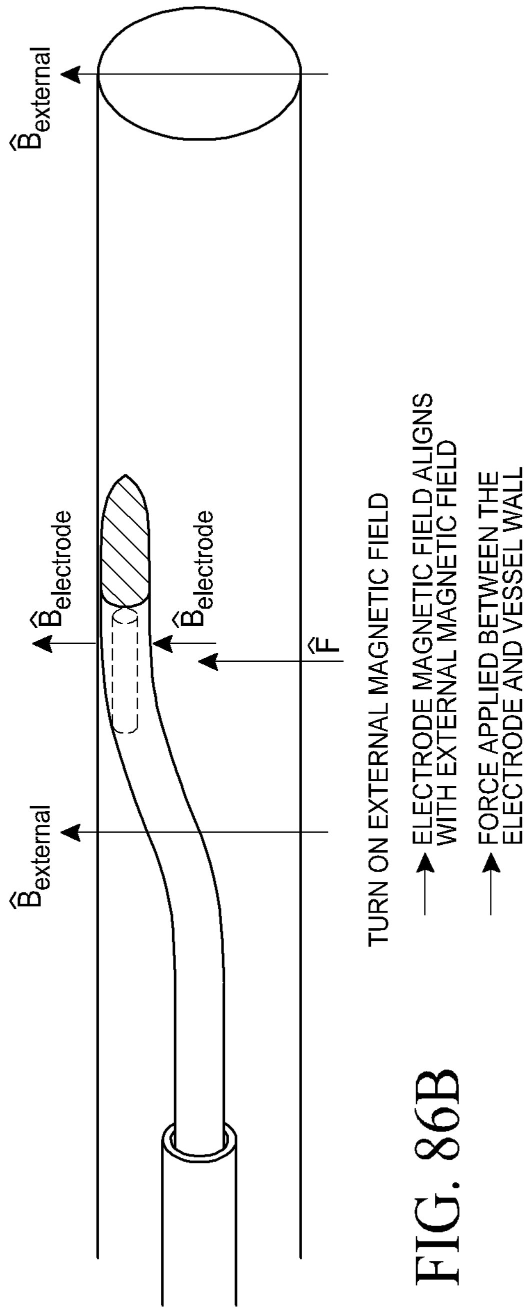

In one embodiment, shown in FIGS. 86A and 86B, a neuromodulation device (e.g., ablation catheter) is comprised of at least an electrode 8615, a flexible shaft 8610, and a segment or element 8618 that is capable of carrying a magnetic field (for example, a ferromagnetic material) and that is significantly close to the electrode to effect movement of the electrode in response to one or more applied magnetic fields. The ablation catheter device may be positioned in a vessel at a particular location and a magnetic field may then be applied through the vessel in conjunction with application of the magnetic field of the magnetic segment, thereby causing the opposite poles of the magnetic fields to attract. The location and/or direction of the magnetic fields may be moved to adjust the direction of the force. The magnitude of the magnetic fields may be adjusted to adjust the magnitude of the force. In various embodiments, the number of magnetic field-carrying segments may vary (e.g., one, two, three, four or more) and/or the number of electrodes and flexible catheter segments may vary (e.g., one, two, three, four or more). In some embodiments, the magnetic segment 8618 comprises a ferromagnet and/or electro-magnet.

Figure 87A:
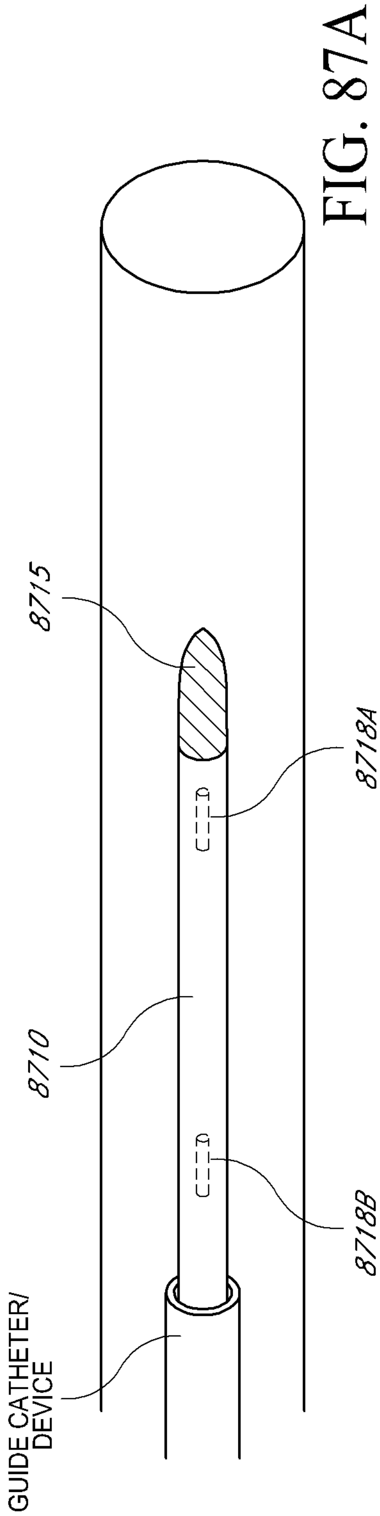
Figure 87B:
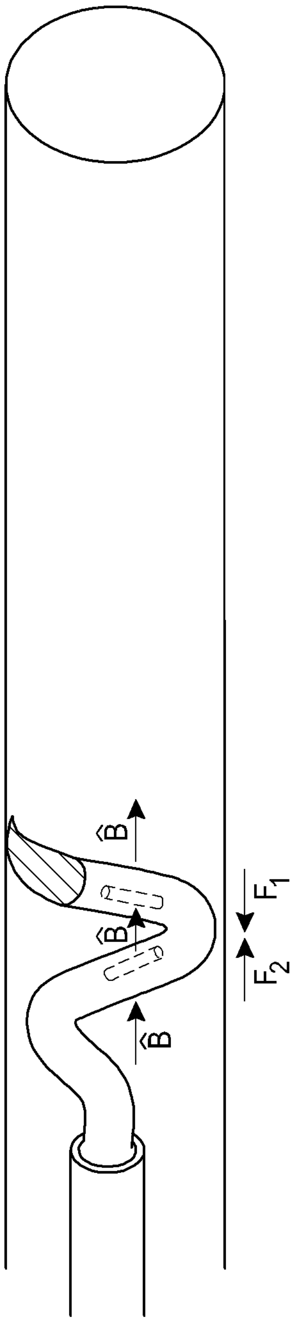

With reference to FIGS. 87A and 87B, in some embodiments, a neuromodulation device (e.g., ablation catheter) is comprised of at least an electrode 8715, a flexible shaft 8710, and two segments or elements 8718 that are capable of carrying a magnetic field and that are significantly close to the electrode to effect movement of the electrode in response to one or more applied magnetic fields. In some embodiments, the two magnetic segments are configured to generate magnetic fields having opposite poles. The device may be positioned in a vessel at a particular target location. Magnetic fields may be applied through the magnetic segments, causing the opposite poles of the magnetic fields of the two magnetic segments to attract (e.g., magnetic fields align), thereby leading to at least one bending moment in the flexible shaft. As shown in FIG. 87B, multiple bends can be created in the distal portion of the catheter. The location and/or direction of the magnetic fields may be moved to adjust the direction of the force and/or bending moment(s). The magnitude of the magnetic fields may be adjusted to adjust the magnitude of the force and/or bending moment(s). In various embodiments, the number of magnetic field-carrying segments may vary (e.g., one, two, three, four or more) and/or the number of electrodes and flexible catheter segments may vary (e.g., one, two, three, four or more). In some embodiments, one or more of the magnetic segment comprises a ferromagnet and/or electro-magnet.

The embodiments illustrated in and described in connection with FIGS. 85 through 87 may advantageously allow a force to be applied directly to a segment of the ablation catheter device that is significantly close to the electrode(s), thereby improving control of the electrode(s) and control of the electrode-vessel force when the ablation catheter device is placed in a tortuous or otherwise difficult-to-navigate anatomy.

In some embodiments, a catheter having an outer diameter substantially matching the target vessel's inner diameter is used, thereby minimizing mechanical and footprint requirements for precise targeting. A catheter may be selected from a kit of catheters having various outside diameter dimensions based on a measured inner diameter of the target vessel. In some embodiments, the outside diameter of a catheter can be modified using spacers provided in a procedure kit. The catheter may be advanced through the patient's vasculature (the inner diameter of which may decrease as the target location nears). Once the catheter is advanced to the target vessel location, it may then advantageously engage the vessel wall with substantially uniform contact pressure about its circumference. In some embodiments, because application of energy to the entire circumference of the vessel is undesirable (due to the risk of stenosis,) any of the designs herein disclosed that employ selective electrode placement or electrode "windows" are used, thereby allowing the delivery of energy in discrete locations about the vessel wall.

Figure 109A:
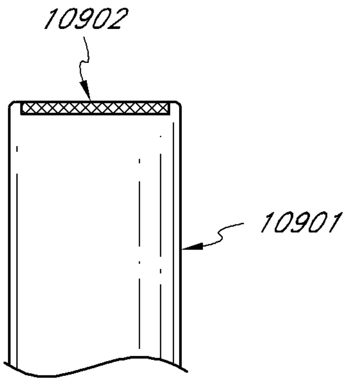
FIGS. 109A-109C illustrate embodiments of an RF electrode ablation catheter.
Figure 109B:
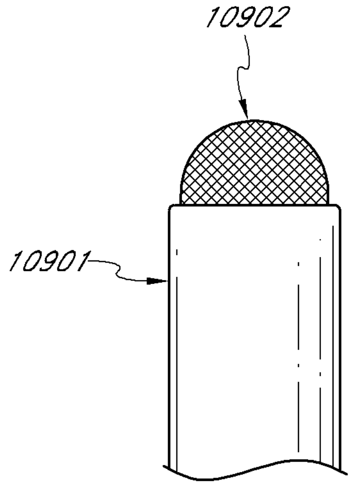
Figure 109C:
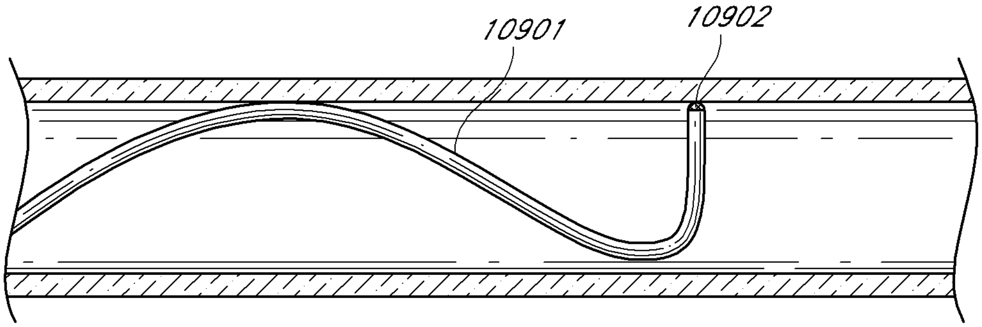

Turning to FIGS. 109A-109C, embodiments of an RF electrode ablation catheter (e.g., probe) 10900 are illustrated. The RF ablation catheter 10900 may comprise a tip electrode 10902 configured to contact a vessel wall provide more focused, more directed energy delivery to a target ablation site, thereby reducing circumferential heating of extraneous tissues and surrounding blood. The RF ablation catheter 10900 in FIG. 109A comprises a flat plate electrode and the RF ablation catheter 10900 in FIG. 109B comprises a semi-sphere electrode. With reference to FIG. 109C, the distal-most portion 10901 of the RF ablation catheter 10900 may be actuated to position a contact surface of the tip electrode flush or substantially flush with the vessel wall (e.g., such that the a longitudinal axis of the distal-most portion 10901 is perpendicular or substantially perpendicular to the vessel wall) by cantilevering off the opposite vessel wall (e.g., via one or more pull-wires and one or more flexible, steerable and/or shape-memory deformable portions of a main shaft 10902 of the RF ablation catheter 10900).

Figure 40:
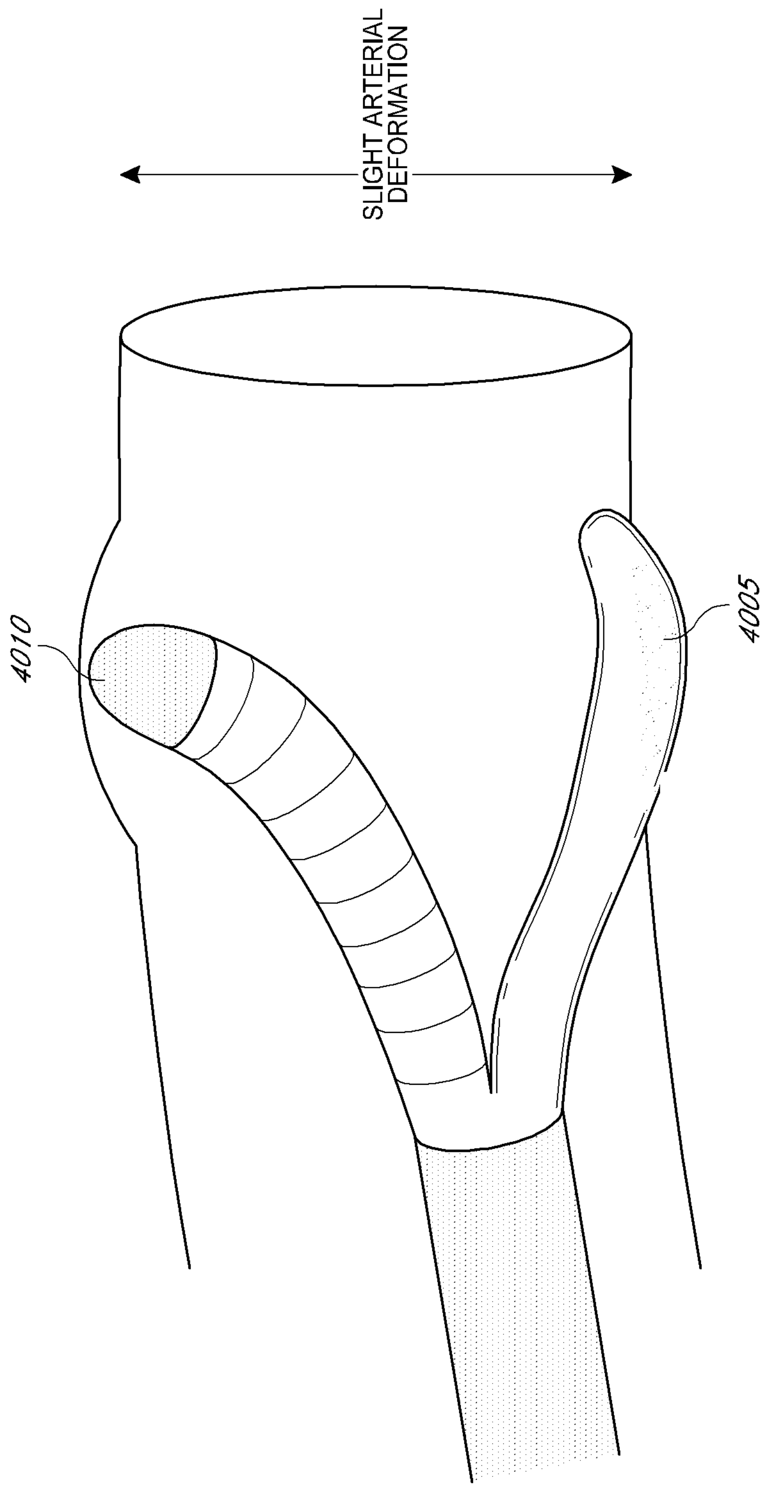
FIGS. 40-42, 43A, 43B, 44, 45, 46, 47A, 47B, 48A, 48B, 49A, 49B, 50, 51A, 51B, 52A, 52B, 53A, 53B and 54A-54C illustrate embodiments of devices and methods for increasing catheter and/or electrode stabilization of electrode catheters within target vessels.

FIGS. 40-42, 43A, 43B, 44A, 44B, 45, 46, 47A, 47B, 48A, 48B, 49A, 49B, 50, 51A, 51B, 52A, 52B, 53A, 53B, and 54A-54C illustrate embodiments of electrode catheters or catheter modifications configured to provide enhanced catheter stabilization and/or electrode contact with vessel walls at therapeutic target locations (e.g., within hepatic arteries). FIG. 40 illustrates one embodiment of an electrode catheter with a retractable stabilization segment 4005 configured to anchor to the inner wall of a vessel (e.g., artery), in the opposite direction of the electrode 4010. To provide friction, the stabilization segment 4005 may comprise an anti-slip surface. In one embodiment, the stabilization segment 4005 only protrudes or is deployed once in place so that the friction does not significantly affect the ability to insert the catheter. In one embodiment, the anti-slip surface is achieved by modifying the outer layer of silicone so that it is no longer smooth but has an array of longitudinal and transversal small size dents. The extensible stabilization segment 4005 presses into the arterial wall without poking a hole in it, as its tip extends parallel to the arterial wall, in order to distribute the stress on a larger surface. In one embodiment, the catheter with the stabilization segment causes at least a slight vessel (e.g., arterial) deformation as a result of the stabilization forces.

Because of the tortuous anatomy of the hepatic arteries or other vasculature, it may be difficult to apply a repeatable force to the electrode of an RF electrode catheter at various locations along the length of the artery. Cantilever flex catheters are catheters that apply a bending moment along a distal section of the catheter by compressing the inner arc with a pull wire. The bending moment moves the catheter tip towards the vessel wall. In order for the bending moment to apply a force through the catheter tip and into the vessel wall, a reactionary force must be applied at another section of the catheter. This reactionary force is likely between the catheter and vessel wall opposite of the catheter distal tip and through a segment of the catheter proximal to the distal tip. With tortuous anatomy and sharp bends, this "reaction force" may not be repeatable. Several embodiments of the devices, systems and methods described herein are configured to provide a repeatable and/or continuous contact force. In several embodiments of catheters and methods of use described herein, pulsatile contact is advantageously provided.

Figure 41:
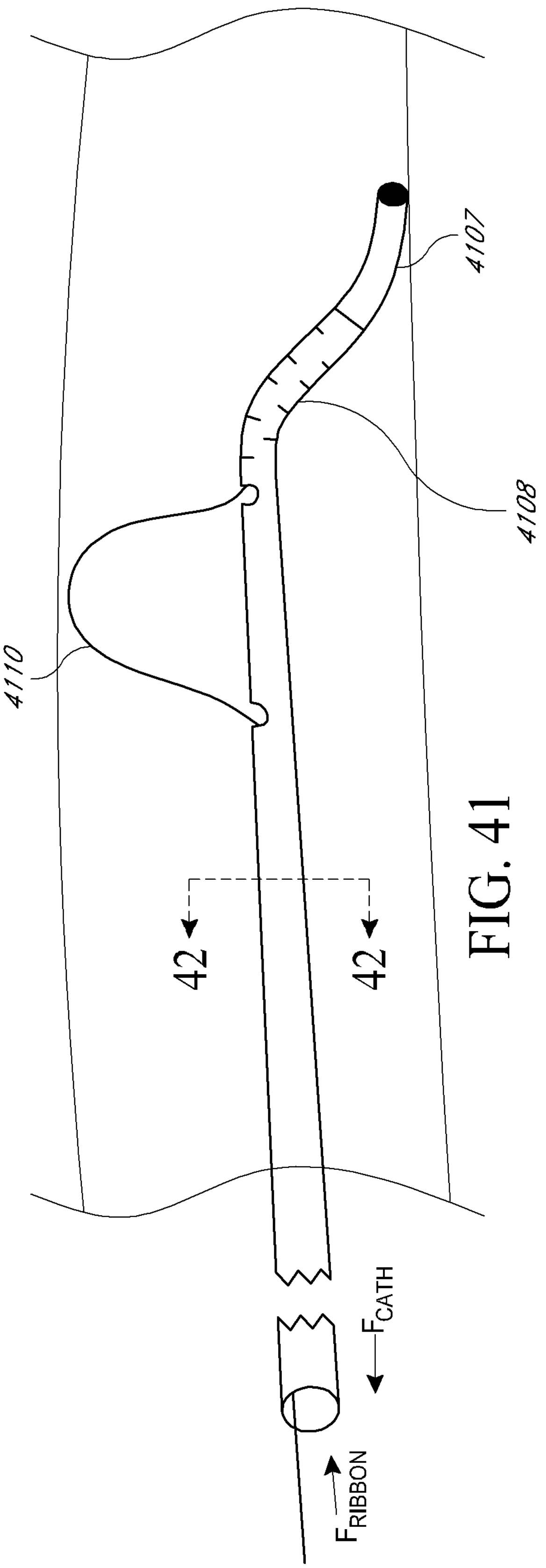
Figure 42:
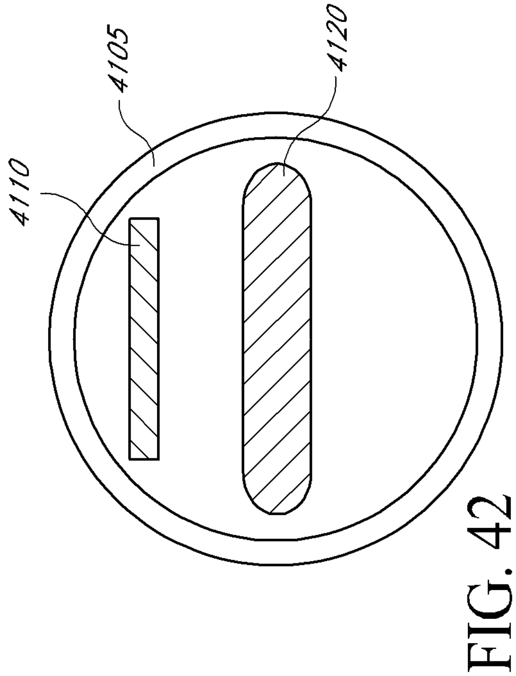

In one embodiment, instead of applying a moment at the distal tip and relying on a reaction force between the vessel and a proximal segment of the catheter, one could use a wire or ribbon to apply the reaction force closer to the bending moment and cantilevered tip. The objective is to create a reaction force (or multiple reaction forces) as close to the electrode contact as possible, thereby anchoring the distal region of the catheter relative to the vessel wall to provide a reaction moment against the flex mechanism (e.g., cantilever flex catheter) that applies the electrode into the vessel wall with a bending moment. Referring now to FIG. 41, two openings are made in a cantilever flex catheter 4105 opposite of the location where the bending moment is applied (e.g., where a pull wire is attached to the catheter shaft) and a ribbon 4110 is threaded through these openings so that the ribbon 4110 is outside of the catheter 4105 between these two openings. The ribbon may 4110 be fixed to a point in the catheter 4105 that is distal to the most distal opening and able to be pushed at the proximal end of the catheter. When the ribbon 4110 is pushed, it moves out of the proximal opening and creates a loop. This loop is enlarged until it presses against the wall of the vessel opposite of the bending moment. An optional additional feature that may be added to reduce slack in the system (since the ribbon is being pushed, it will want to fill all of the empty space in the catheter) is a divider 4120 that runs along the length of the catheter 4105 and rests near the midpoint of the cross-section, as shown in FIG. 42. Because the divider is at the cross-sectional midpoint in some embodiments, the divider would not significantly affect the catheter's flexibility towards and away from the ribbon 4110; therefore, the divider 4120 could run through the distal flex section 4108 without affecting the bending moment.

In various embodiments, modifications and improvements to the catheter of the sort described in connection with FIG. 41 may be made. For example, in one embodiment, instead of using a pull wire to create the bending moment at the catheter tip 4107, the ribbon 4110, which is pushed along the outer arc of the catheter 4105, could place the outer arc of the flex region in tension and create the bending moment. This embodiment would simplify the design by reducing the redundant pull wire.

Figure 43A:
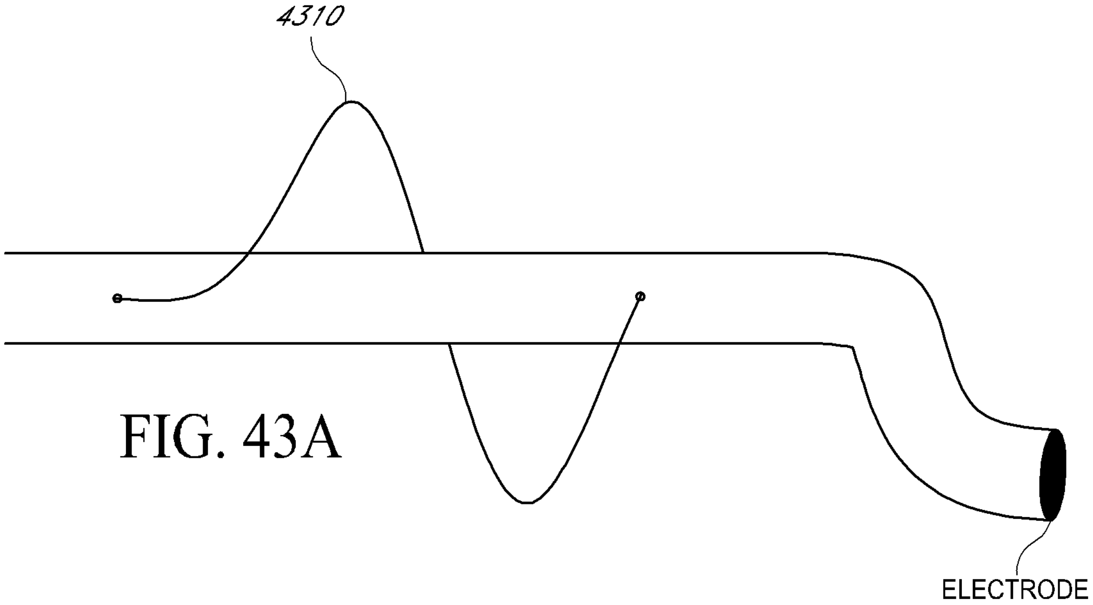
Figure 43B:
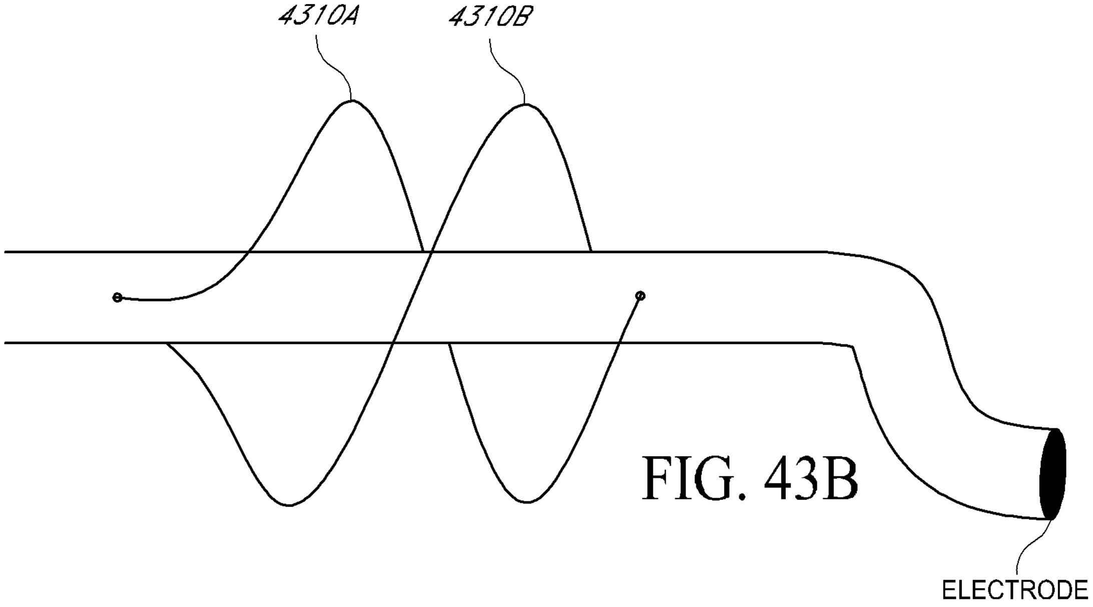

In some embodiments, multiple ribbons 4310 could be used as shown in FIGS. 43A and 43B. These embodiments increase the number of contact points and increase catheter stability. In one embodiment, a balloon could be used alone or in combination with the one or more ribbons.

In one embodiment, instead of providing multiple contact points in a line along the circumference, one could create contact points (also shown in FIGS. 43A and 43B) that contact the vessel at different locations along the vessel's length and/or circumference. Creating multiple points separated by a distance may enable these points to resist a torque (because their applied force is separated by a distance).

The "ribbon" is not limited to a specific material or geometric configuration. For example, metallic, polymer, or shape memory materials may be used. In some embodiments, flat wires (ribbons) could be replaced with wires or any other geometry (e.g., cylindrical, triangular, rectangular, diamond).

In accordance with several embodiments, applying the "reaction force" closer to the bending moment and cantilevered tip reduces the length required to apply the electrode force when compared to a standard cantilever flex catheter, which may advantageously improve the repeatability of the applied "electrode force" in tortuous vessels. Moving reaction forces or contact points towards the electrode may also increase the stability near the electrode and reduce electrode movement during use. Increasing the normal force applied to the vessel may also increase the stability of the catheter electrode in the target anatomy.

Figure 44:
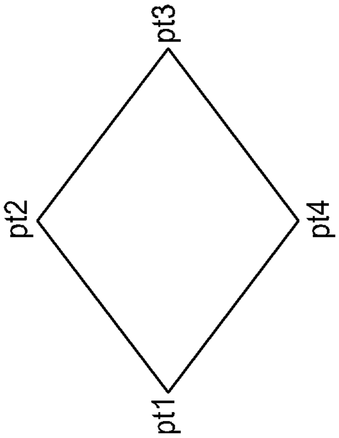
Figure 45:
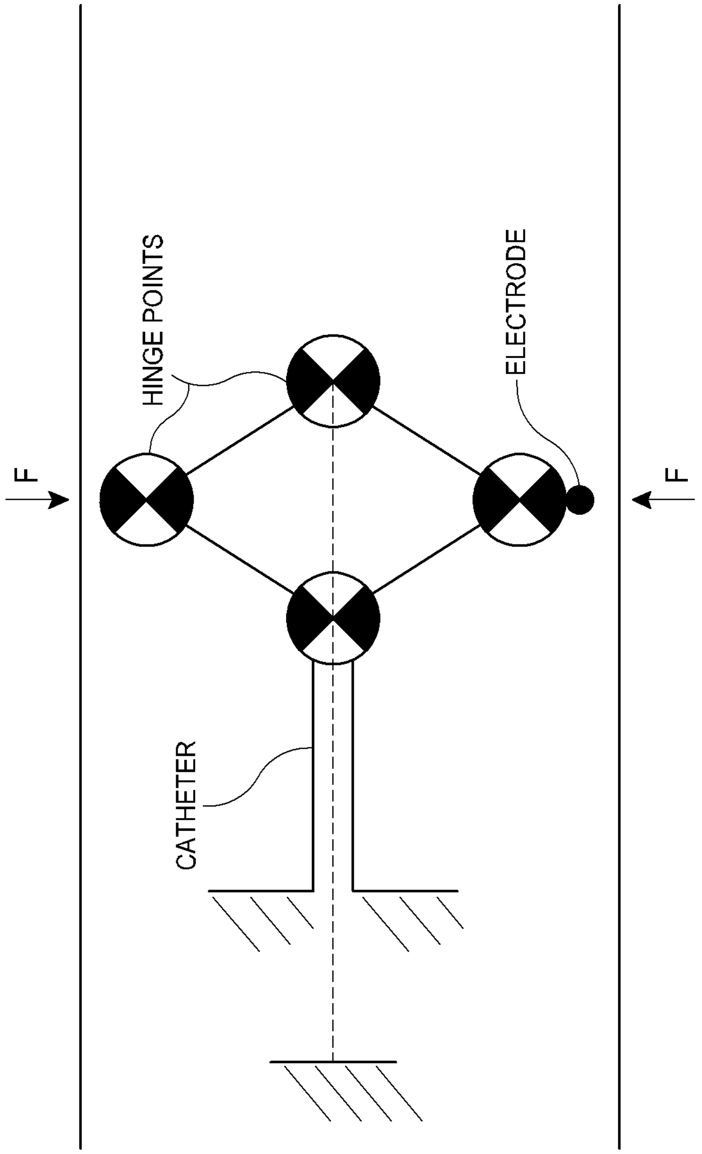

In some embodiments, instead of applying a moment at the distal tip of the catheter and relying on a reaction force between the vessel and a proximal segment of the catheter, one could apply the reaction force perpendicular to the electrode force (also interchangeably referred to as the catheter tip force). Referring now to FIG. 44, a structure comprising four hinge points connected by members resembling a square or parallelogram could be disposed at the distal end of a catheter. Assuming the members connecting these points have a constant length, if two opposite hinge points are pulled towards each other (e.g., pt1 and pt3) the other pair of opposite points will move away from each other (e.g., pt2 and pt4). In one embodiment, this opposing motion could be achieved by fixing pt1 against the distal end of a catheter and pulling pt3 towards pt1. The electrode can be placed at one of the other hinge points (pt2 or pt3) and both of these hinge points can apply a force against the vessel wall, as illustrated in FIG. 45.

Figure 46:
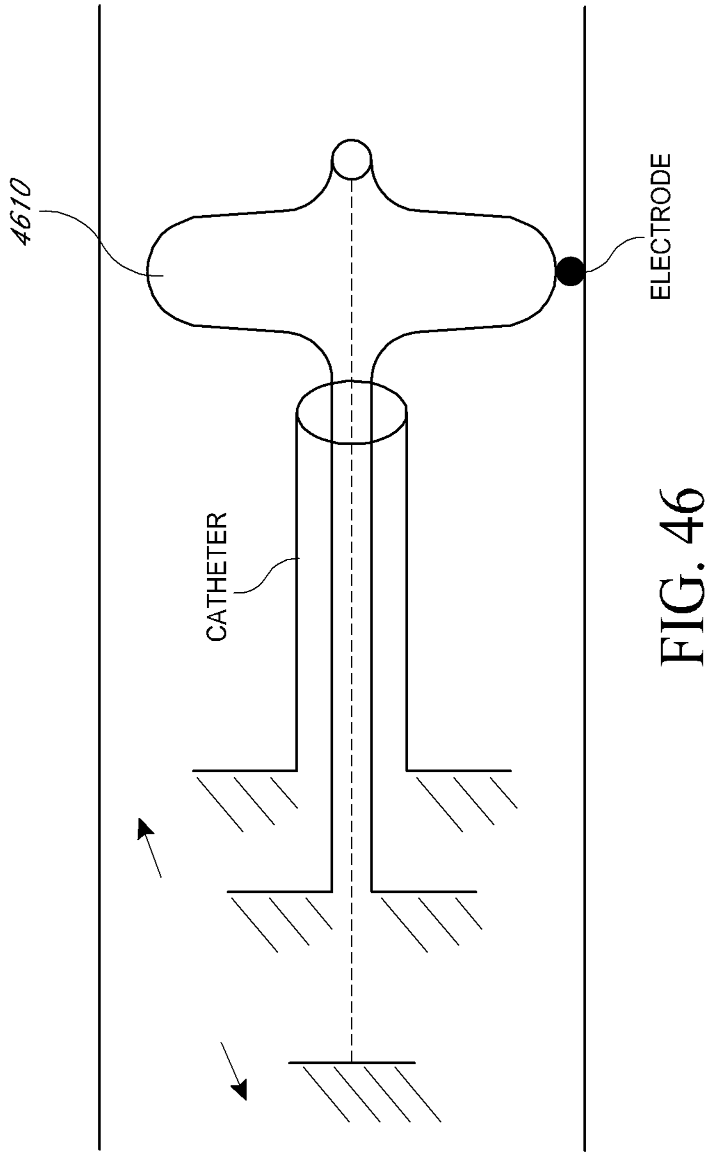

In one embodiment, as shown in FIG. 46, the hinge points comprise flexures (e.g., thin, flexible segments connecting larger segments) or the members and opposite hinge points (pt2 and pt4) could be replaced by a flexible, continuous length of wire or ribbon, forming "virtual" or "living" hinges. Using flexible ribbons 4610 may eliminate the need for explicit hinge points (pt2 and pt4) and it would also eliminate the need for explicit hinges at pt1 and pt3. Instead, pt1 could be an opening in the catheter and pt3 could be the bond point for the ribbons. In this embodiment, the electrode can be fixed on at least of one of the ribbons in a location substantially in contact with the vessel wall.

In accordance with several embodiments, the "reaction force" vector is opposite of (180 degrees from) the "electrode force" and the "reaction force" is applied at the same segment of the vessel as the "electrode force," thereby reducing the length required to apply the electrode force when compared to a cantilever flex catheter, and thereby improving the repeatability of the applied "electrode force" in tortuous vessels. Moving reaction forces or contact points towards the electrode may also increase the stability near the electrode and reduce electrode movement during use.

Figure 48A:
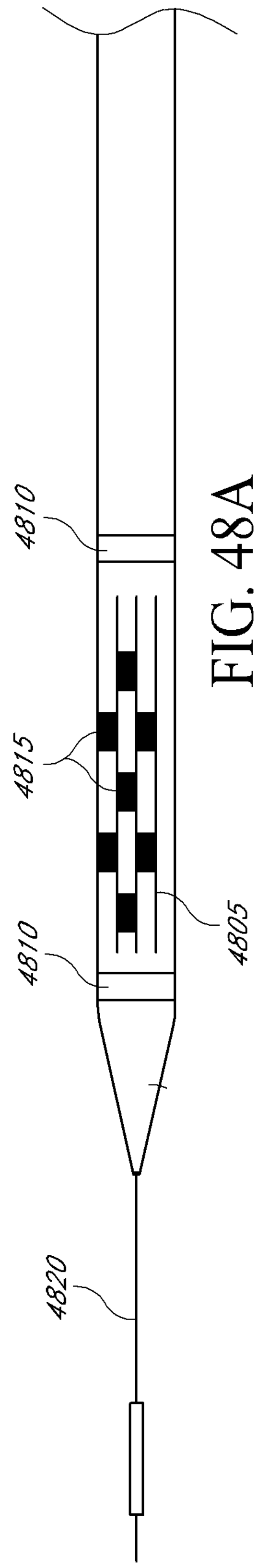
Figure 48B:
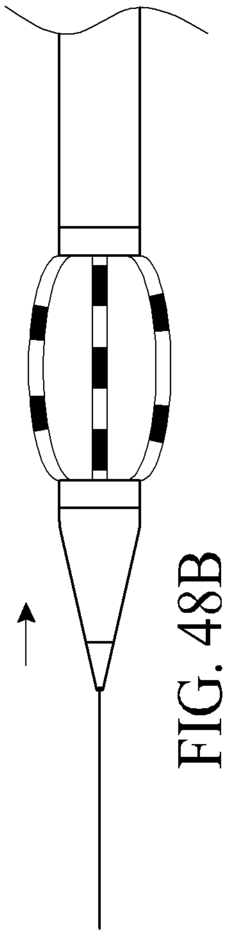

In another preferred embodiment illustrated in FIGS. 48A and 48B, a plurality of ribbons may be formed by cutting slits 4805 through the wall of a tube formed of flexible electronics, or electronic devices mounted on flexible plastic substrate, such as polyimide. For example, two layers of polyimide having a plurality of copper or silver leads (preferably at least one) embedded between the two layers can be rolled into a tube structure, defining a cylindrical structure. A plurality of openings (preferably at least one) can be cut into the polyimide layer comprising the outer surface of the cylinder to define individual electrodes 4815 that can be connected to a generator, including but not limited to an electrosurgical (RF) generator in either a monopolar or bipolar or multipolar fashion. To define the ribbons described previously, slits 4805 can be cut along substantially the longitudinal axis of the tube. The tube structure can be mounted on a catheter as shown in FIGS. 48A and 48B, with marker bands 4810 (e.g., radiopaque marker bands) defining the proximal and distal extents of the tube structure. In one embodiment, the ribbon or wire or like device (such as a thin nitinol ribbon) is jacketed with polyimide in a manner to provide the substrate to mount the flexible electronics. The nitinol or other higher modulus material, may provide integrity to an expandable structure while it is in the expanded and unexpanded states. In one embodiment, a guidewire housing is disposed at the distal end of the catheter, in communication with a lumen extending through substantially the entire length of the catheter. In one embodiment, the catheter device is passed or introduced over a locking guidewire 4820 containing a detent feature designed to interface with the guidewire housing, such that moving the guidewire and the catheter in opposite directions creates a compression force on the tube structure that causes expansion of the ribbons. The detent may be designed such that upon exceeding a maximum detent force, the locking guidewire 4820 is retracted into the guidewire housing. In this manner, this maximum contact force applied to tissue can be limited; for example, the detent force (and hence the force applied to tissue) can be controlled by varying the dimensional interference defined by an outer dimension of the detent feature and an inner dimension of the guidewire housing.

One particular advantage of the embodiment of the flexible circuit design described above is the ability to isolate the delivery of energy from the blood flow while still achieving the beneficial effects of convective cooling from the blood. Because of the high dielectric properties of flex circuit materials such as polyimide, polyether ether ketone (PEEK) or polyester, only a thin layer of material may be required to electrically isolate any one of the plurality of electrodes from the arterial blood flow, effectively limiting the amount of energy "lost" to the blood, and providing a more repeatable and measureable titration of electrical and thermal energy to the target tissues surrounding the artery. In some embodiments, the thin construction of the electrical isolation layer permits enhanced heat transfer from the electrode, through the isolation layer, and to the arterial blood to limit the temperature of the electrode, thereby advantageously allowing for higher power energy delivery, deeper ablations, and reduced treatment times, for example.

Figure 49B:
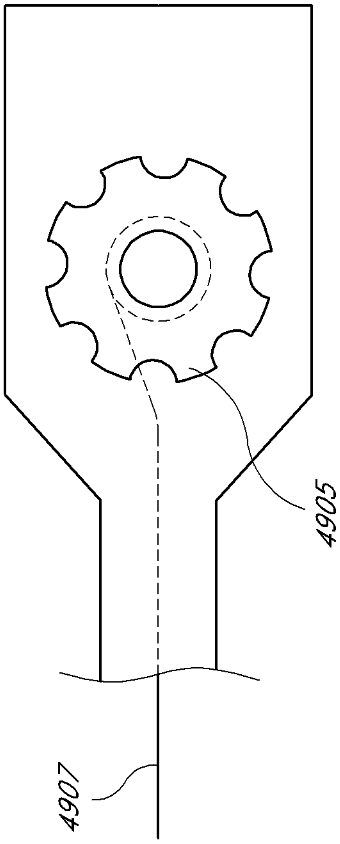
Figure 49A:
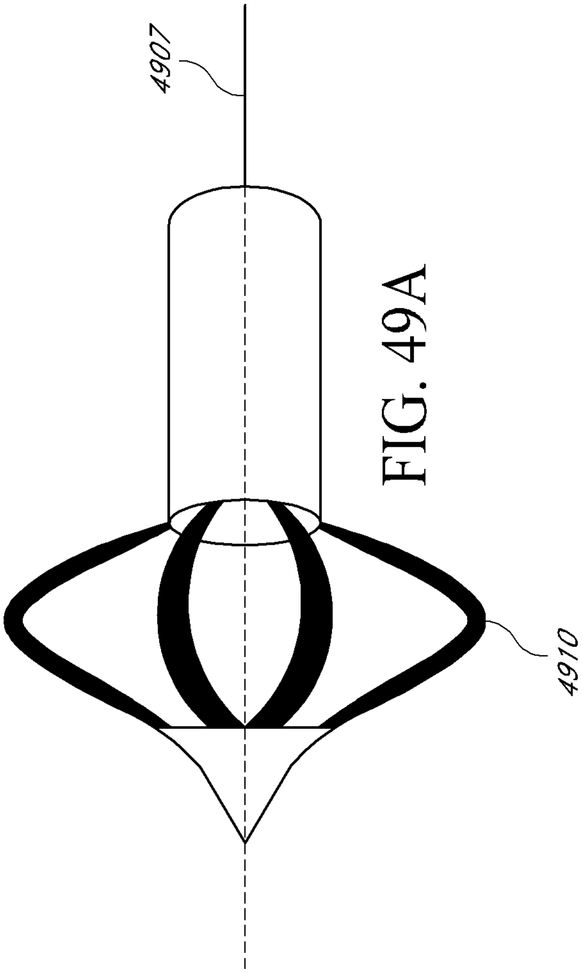

Referring now to FIGS. 49A and 49B, the force applied to the vessel wall may also be limited by a torque limiter 4905 in the handle of the catheter to deploy one or more ribbons of an expandable structure 4910. For example, the pull wire 4907 might be wrapped around the capstan of a torque-wrench mechanism having a pre-defined torque slip value.

In yet other embodiments, modifications and improvements to the catheter of the sort described in FIGS. 46-49 are provided. For example, in one embodiment, instead of using two ribbons (one to apply the electrode force, the other to apply the reaction force), multiple ribbons are used to apply the reaction force (e.g., 3, 4, 5, 6 or more contact points against the vessel wall). The "ribbon" is not limited to a specific material or geometric configuration. In various embodiments, metallic, polymer, or shape memory materials may be used. In some embodiments, flat wires (ribbons) could be replaced with wires or any other geometry (e.g., cylindrical, triangular, rectangular, diamond).

Figure 47A:
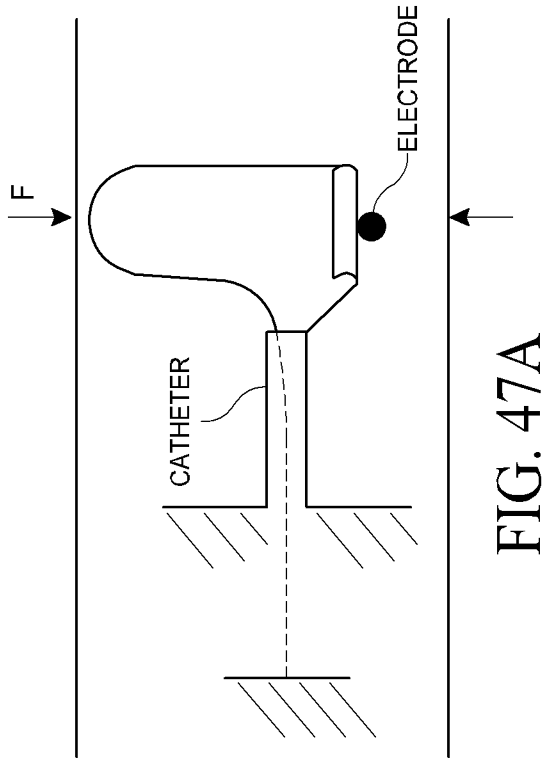
Figure 47B:
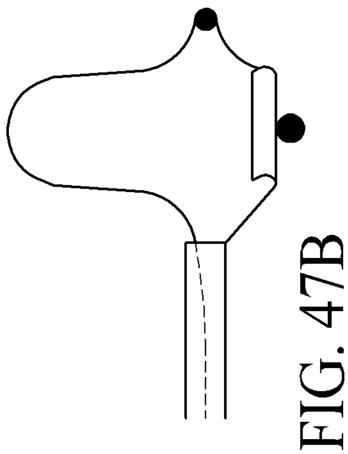

In various embodiments, a stage could be used to support the electrode, as illustrated in FIGS. 47A and 47B. The stage may be connected to pt1 (catheter end) with a flexible ribbon and it can act like pt3 (distal connection point for the other ribbon). In one embodiment, the stage could be connected to pt1 (catheter end) and a separate pt3 (distal connection point for the other ribbon) with a flexible ribbon.

Figure 50:
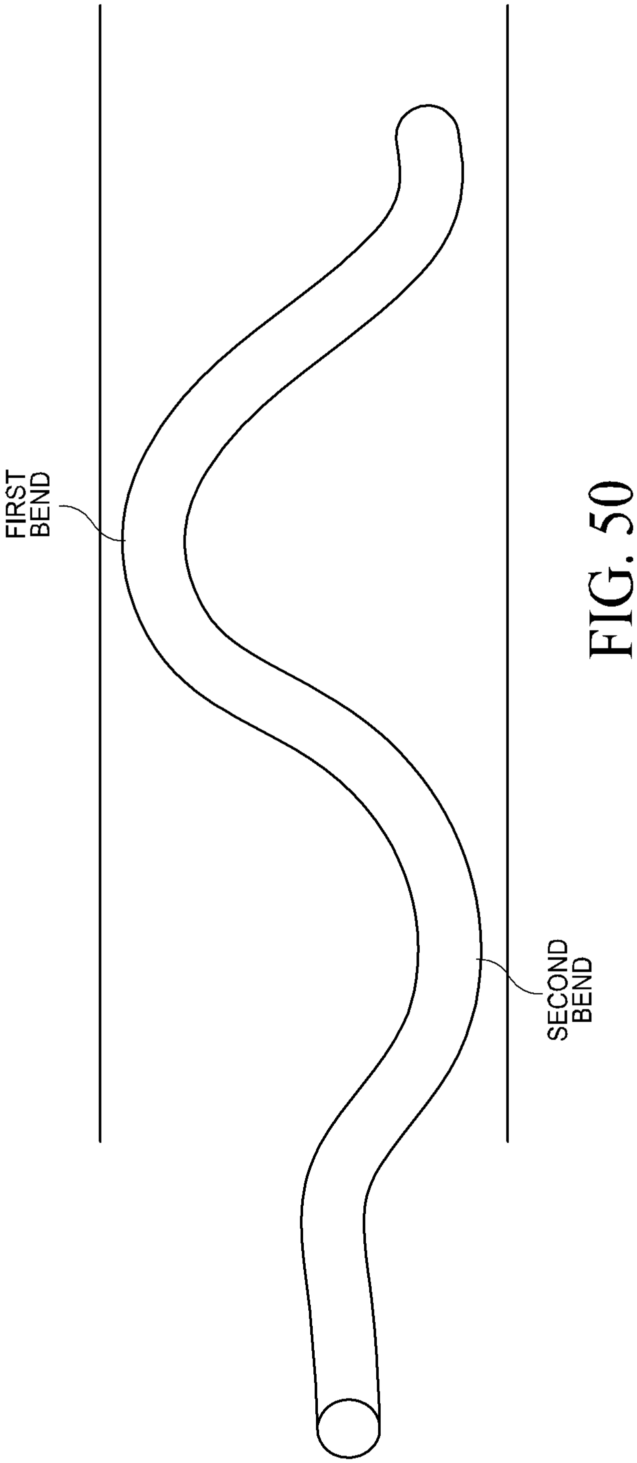
Figure 51A:
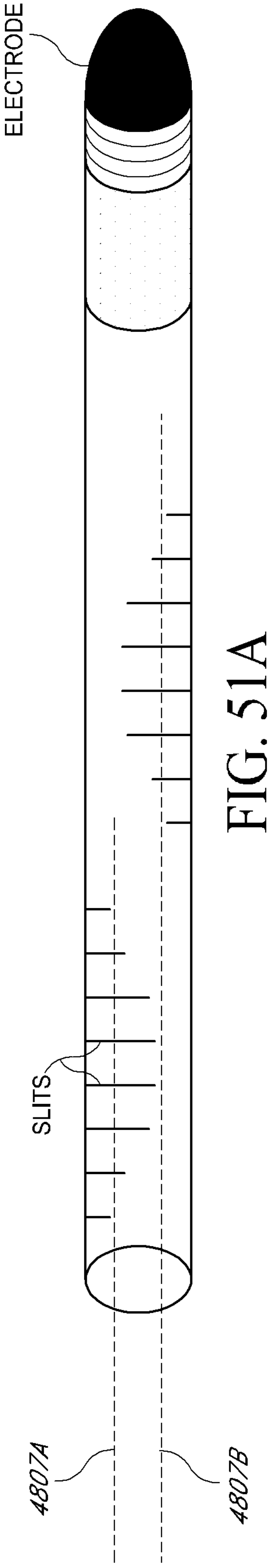
Figure 51B:
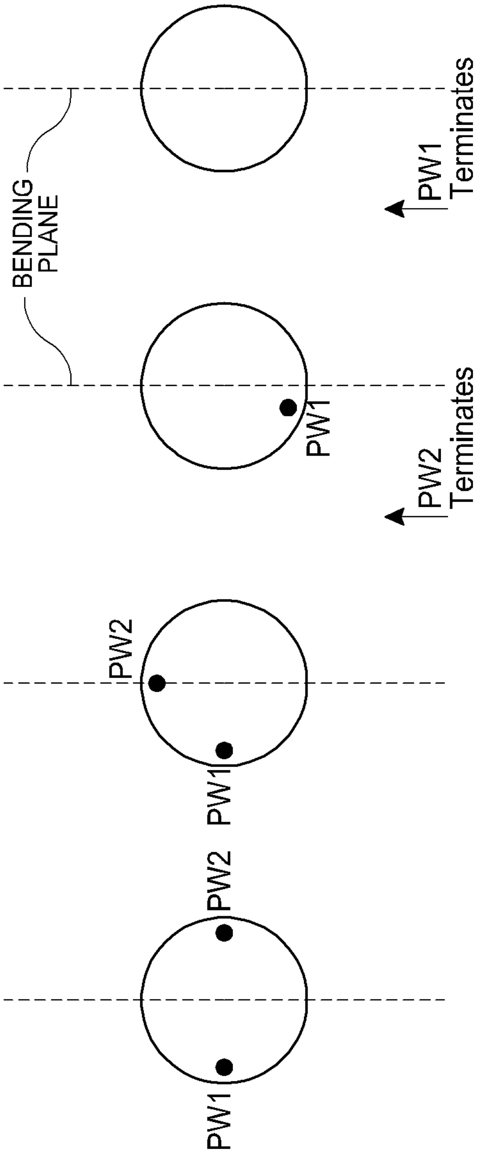
Figure 52A:
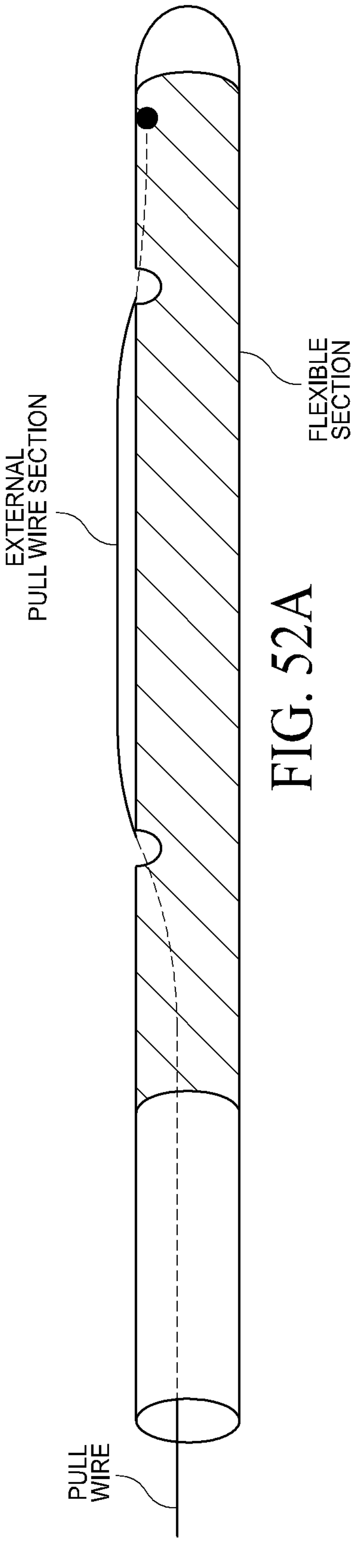
Figure 52B:
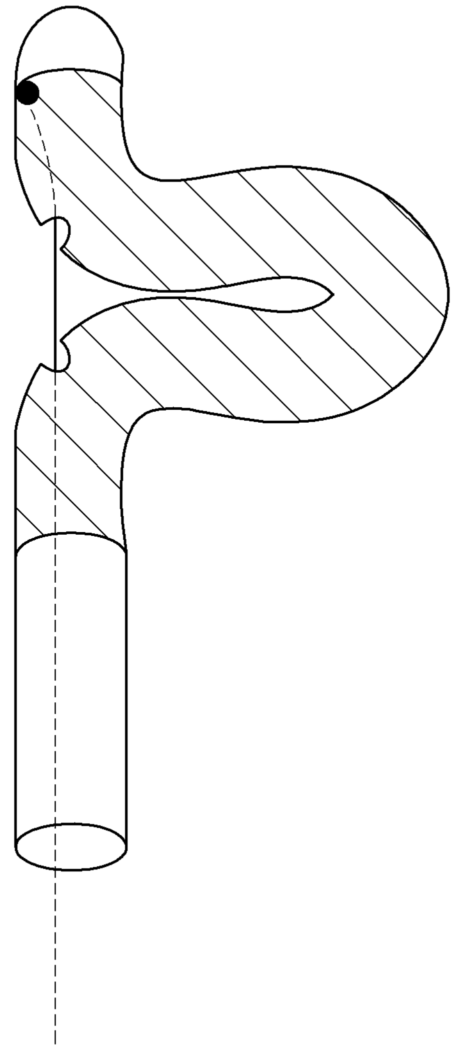

In one embodiment, instead of applying a moment at a distal tip of the steerable catheter 800 and relying on a reaction force between the vessel and a segment of the steerable catheter 800, one could force the catheter to bend at specific locations (e.g., creating an s-curve) and/or apply larger reaction forces at multiple locations. Referring now to FIG. 50, multiple bending moments can be provided that force the catheter into the vessel and apply a force through the electrode to the vessel wall. The electrode(s) may advantageously be disposed at locations in contact with the vessel wall. FIGS. 51A and 51B illustrate one embodiment of a catheter having an s-curve (e.g., having two bends). A hypotube-supported catheter may be laser cut (as shown in FIG. 51A) to create two highly flexible sections close to the distal tip and the electrode. In one embodiment, the two sections are separated by a distance and are offset by 180 degrees or about 180 degrees, such that the two sections bend opposite of each other and within the same plane. For example, the two sections can facilitate 180-degree articulation of the catheter. In one embodiment, two pull wires 5107A, 5107B run down the length of the catheter (see FIG. 51B), perpendicular to the bending plane until they each reach their corresponding flexible section. Through a pull wire's flex section, the pull wire runs in the bending plane and along the catheter wall with the flex cuts. The pull wire may then be bonded to the catheter shaft (e.g., just distal to its flex cuts). Orienting the pull wires in this manner may advantageously prevent opposing forces from each pull wire that would otherwise resist multi-segment, multi-direction flexing.

In various embodiments, modifications and improvements to the device (e.g., catheter) of the sort described in FIGS. 46-49 may be made. For example, some embodiments may comprise one or more of the following:

1. Instead of using two pull wires, one pull wire could be used to cause both bending moments (e.g., compression of the inner arc length of each bend). Causing both bending moments with a single pull wire can be performed, for example, by placing the pull wire in a spiral pattern along the inside of the catheter and orienting the pull wire with the flex cuts or, alternatively, one pull wire could run loosely within the catheter until the location of the flex cuts, where the pull wire would enter through loops connected to each of the flex cut sections.
2. Instead of using the single pull wire to compress the inner arc length of each bend, one pull wire could pass outside of the catheter through a hole, extend outside of the catheter lumen along a section of the catheter length, and then re-enter the catheter lumen through a second hole (see, for example, FIGS. 52A and 52B). In one embodiment, the pull wire is fixed distal to both holes and can be pulled by a mechanism proximal to both holes. The catheter may have a flexible region at least extending proximally and distally from the holes. Upon pulling the pull wire, the two holes may move towards each other, thereby causing the catheter to bend in an arc away from the holes.
3. Multiple flex sections (>1, >2, >3, >4) could be used to improve stability and apply force through the electrode with more repeatability.
4. Instead of bending in one plane (because the flex cuts are oriented 180 degrees apart), the catheter could bend in multiple (e.g., two, three, four or more) planes. In one embodiment, the catheter bends into a helical shape (e.g., a pigtail or corkscrew shape).
5. In one embodiment, the catheter could be cut or configured so that pulling a distal point of a pull wire would cause the catheter to elastically collapse into a coil or helical shape. Once the tension in the pull wire is released, the catheter may elastically straighten out.

Figure 98A:
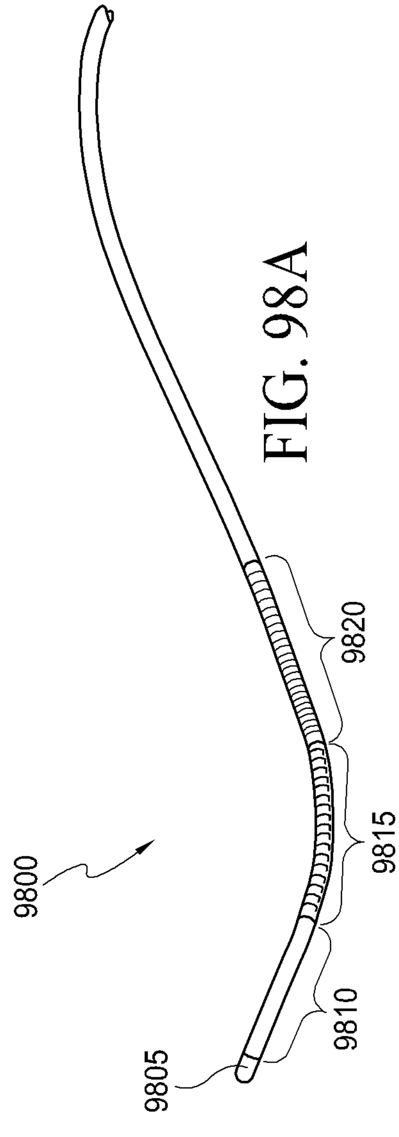
FIGS. 98A-98C illustrate an embodiment of a radiofrequency energy delivery catheter configured for hepatic denervation.
Figure 98B:
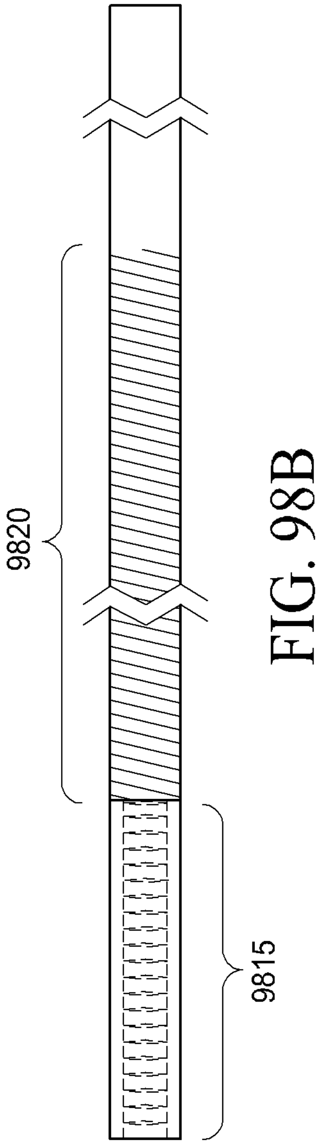
Figure 98C:
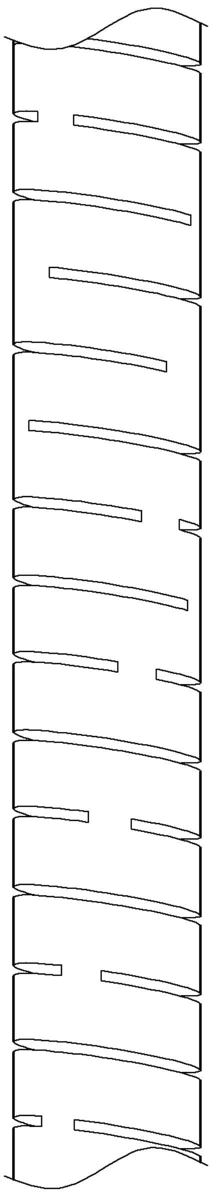

FIGS. 98A-98C illustrate embodiments of a catheter 9800 having a longitudinal axis and an internal lumen disposed about a substantial portion of the longitudinal axis. In the illustrated embodiment, an electrode 9805 is disposed at a distal tip or towards the distal end of the catheter 9800, with a resiliently deformable region 9810 disposed proximal to the electrode 9805, a deflectable or articulatable region 9815 disposed proximal to the resiliently deformable region 9810, and a torsionally-rigid but flexible region 9820 (torsionally rigid in at least one rotational direction) disposed proximal to the deflectable region 9815. The remaining length of the catheter 9800 (proximal solid tubing portion 9825) may be substantially torsionally and flexually rigid. The catheter 9800 may comprise a hypotube with the resiliently deformable region 9810 and the deflectable region 9815 having a spine cut pattern and the torsionally-rigid but flexible region 9820 having a spiral cut pattern (interrupted or continuous).

Figure 99:
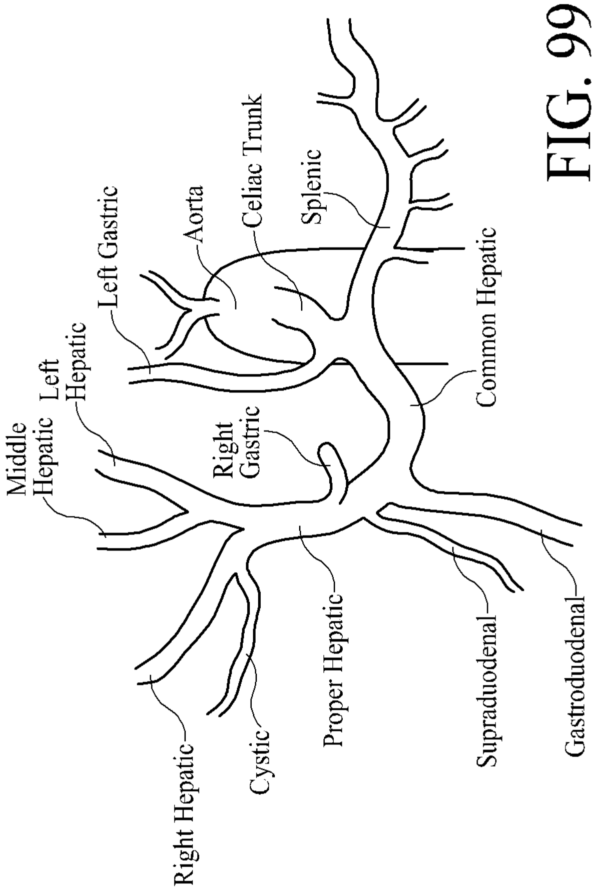
FIG. 99 is a schematic illustration of arterial branches that may be targeted by the methods, devices and systems described herein.

The dimensional characteristics of each catheter region may be tailored to the specific anatomy targeted for the neuromodulation. For example, the catheter 9800 may be used to access any portions of the arteries illustrated in FIG. 99. In one embodiment, the catheter 9800 is configured to access and modulate nerves surrounding (e.g. within a wall of, such as within the intima, media or adventitia of) the common hepatic artery. Treatment of the common hepatic artery can be particularly difficult due to the tortuosity and routing variance of the vasculature in this region. In one embodiment, the diameter of the electrode 9805 is 2 mm (6 Fr) with a length of 2 mm, though other combinations of electrode diameter (e.g., 0.5-1 mm, 1-1.25 mm 1-1.5 mm, 1.5-2 mm, 2-2.5 mm, 2.5-3 mm) and length (e.g., 0.5-1 mm, 1-1.25 mm, 1-1.5 mm, 1.5-2 mm, 2-2.5 mm, 2.5-3 mm) may be desirable. In order to provide and maintain an effective contact force (such as the contact forces and pressures described herein) and cantilever support, the length of the resiliently deformable region 9810, in one embodiment, is covered with a reflow polymer (e.g., 40D PEBAX of 35D hytrel, 0.042" OD×0.038" ID and between 0.250" and 0.350" in length (or alternatively, 30 mm+1 mm in length)). In one embodiment, the catheter 9800 is configured to repeatably apply an effective contact force or pressure (e.g., 0.1-100 g/mm$^2$, 0.1-10 g/mm$^2$, 5-20 g/mm$^2$) to the inner wall of the common hepatic artery. The resiliently deformable region 9810 may be designed to provide the cantilever support to provide a consistent and effective contact force or pressure. The catheter 9800 may be used to deliver 8-14 Watts of power (e.g., 8 W, 10 W, 12 W) for 1 to 4 minutes (e.g., 1 minute, 90 seconds, 2 minutes, 150 seconds, 3 minutes) to deliver energy between 480 J to 2520 J (e.g., about 1 kJ, about 1500 J, about 2000 J) at each ablation or heating location.

Figure 100:
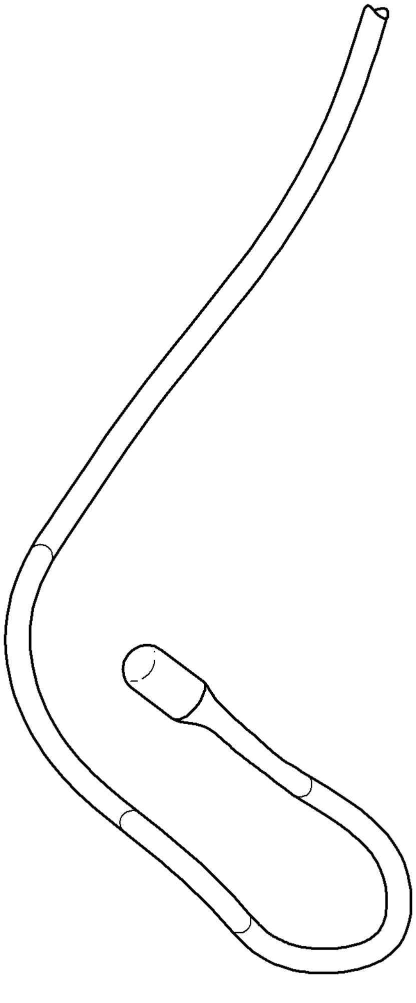
FIG. 100 illustrates an embodiment of a catheter configured to facilitate 180° articulation within vasculature.

In order to facilitate contact in the tortuous anatomy of the common hepatic artery or other arterial branches, increased ranges of deflection may be required in some embodiments, in contrast to relatively straight vascular beds such as the renal artery, where 90 degrees (by definition) is the minimum required deflection required to deflect a line off of its longitudinal axis to a point directly perpendicular to the longitudinal axis. In regions of increased vascular curvature or tortuosity (such as the vasculature proximate or within the common hepatic artery), the required deflection angle may be 90 degrees plus an amount proportional to the radius of curvature of the vessel. For example, in one embodiment, the deflectable or articulatable region 9815 is capable of 180 degrees of deflection, as shown in FIG. 100. The 180 degree deflection may advantageously improve the coupling of reaction forces between the electrode to tissue contact surface (defining an electrode to tissue contact force/pressure) and deflectable region segment to tissue contact surface. The coupling of reaction forces can serve to prevent motion of the distal catheter region within the hepatic artery during diaphragmatic motion. In some embodiments, in order to ensure that the deflectable region 9815 can reliably remain wholly within the length of the common hepatic artery, thereby providing the appropriate contact force or pressure, the length of the deflectable region 9815 plus the resiliently deformable region 9810 is less than 2 cm or other length corresponding to the mean common hepatic artery length (which, from studies has been determined to be 27 mm+8.5 mm) minus one standard deviation, thereby ensuring that the majority of common hepatic artery anatomies will be accessible by the catheter 9800. In some embodiments, this combined length is between 0.5 and 2 cm. The length of the deflectable region 9815, in some embodiments, is between about 0.4 inches and 0.5 inches. In one embodiment, a pull wire can be coupled to a distal end of the deflectable or articulatable region 9815 to effect deflection, articulation, or steerability.

One embodiment of the torsionally-rigid yet flexible or floppy section 9820 is shown in FIG. 98C. The section 9820 may advantageously include interrupted spiral cuts in a hypotube (e.g., stainless steel hypotube) to permit flexural bending for entrance into the tortuous anatomy of the celiac axis and common hepatic artery. In some embodiments, the length of the region 9820 is at least 5±3 cm in order to permit catheter access to a wide range of variable celiac and common hepatic anatomies found in human subjects. The embodiment illustrated in FIG. 98C, owing to its spiral cut hypotube design, is advantageously torsionally-rigid in at least one direction (or in a preferred direction), as the spiral is wound when rotated in the counter-clockwise direction and is measurably stiffer from a torsional perspective. Other tubing cut designs are possible, including continuous spiral cut and those with a) opposing double interrupted helix cuts (torsionally rigid in both directions), b) a pattern of holes drilled through a transverse axis of the tube, offset along the longitudinal axis of the tube by an angle (for example, 180 degrees), and other patterns. In one embodiment, the cut pattern is a spiral cut having a pitch or spine width of between 0.012" and 0.015" (e.g., 012", 0.013", 0.014", 0.015"). In one embodiment, the cut pattern is uniform along the entire length. In one embodiment, the cut pattern varies along its length, as shown in FIG. 98A. In one embodiment, the cut pattern includes a highly flexible interrupted spiral cut pattern along a first distal portion (e.g., 8.5 cm) and a transition (either an abrupt or gradual transition) to a less flexible, wider-pitch interrupted spiral cut pattern along a second proximal portion (11. 5 cm). For example, the pitch of the first distal portion can be 0.015" and then gradually transition to a 0.220" inch pitch. In some embodiments, the transition between the torsionally rigid yet flexible region 9820 and the solid tubing proximal region 9825 is supported by a thermoset heat shrink material (e.g., PET heat shrink tubing) to reduce the chance of kinking the catheter in this region. In one embodiment, the width of the cuts is 0.002"; however, the width may range from about 0.001" to about 0.005", from about 0.0015" to about 0.0025", from about 0.002" to about 0.004", or overlapping ranges thereof.

The catheter 9800 may advantageously be configured to have sufficient push efficiency to push the distal tip and electrode through at least two tight bends of about 0.5 cm radius. The catheter length of any of the catheters described herein (including the catheter 9800) may range from 50 cm to 150 cm (e.g., 50 cm to 100 cm, 80 cm to 120 cm, 90 cm to 130 cm, 100 cm, 110 cm, 120 cm) in various embodiments. In one embodiment, the catheter 9800 has a length of 110 cm. In one embodiment, the catheter 9800 comprises a smooth, low-friction material such as polytetrafluoroethylene (PTFE). The kink radius of the catheter 9800 may be less than 0.5 cm. The length of the electrode 9805 can be less than 0.25 inches. In various embodiments, the outer diameter of the catheter 9800 is less than 8 Fr, less than 7 Fr, 6 Fr or less, or less than 5 Fr. The electrode 9805 is advantageously flush or substantially flush with the catheter surface, in one embodiment. In some embodiments, the electrode 9805 has sufficient torque efficiency provided by the catheter 9800 to be configured to contact the inner wall of a vessel at four points (or fewer or more than four points as desired or required) around the circumference of the vessel (e.g., 4 points 90 degrees apart) after navigating through two or more tight (approximately 0.5 cm) bends. In various embodiments, the catheter 9800 is configured to deliver energy at multiple locations without having to reposition the catheter. The catheter 9800 may be introduced within vasculature through a vascular access system that includes a guide sheath or a guide catheter and (optionally) a guide extender. In some embodiments, a temperature-measurement device (e.g., thermocouple) is bonded to the electrode 9805 by soldering, spot welding and/or an adhesive.

In accordance with several embodiments, forcing the catheter to oppose the electrode force (the secondary s-bend) would reduce the length required to apply the electrode force and would improve the repeatability of the applied "electrode force" in tortuous vessels. Moving reaction forces or contact points towards the electrode may also increase the stability near the electrode and reduce electrode movement during use. Increasing the normal force applied to the vessel may also increase the stability of the catheter electrode in the target anatomy and increase the amount of energy delivered to target nerves surrounding (e.g., within a wall of, such as within the intima, media or adventitia of) the hepatic artery (e.g., common or proper hepatic artery or other arteries, veins or other vessels or organs). In accordance with several embodiments, directing the path of the pull wire as described herein provides a predictable bending direction for a given rotational catheter orientation.

In one embodiment, instead of applying a moment at the distal tip of the catheter and relying on a reaction force between the vessel and a segment of the catheter, one could apply the reaction force perpendicular to the electrode force (previously referred to as the catheter tip force), and instead of applying the force at one point, or multiple discrete points, it could be applied around the circumference of the vessel. For example, a balloon or stent-like member could be used to apply reaction forces and electrode forces to the circumference of the vessel. As an alternative, a "reverse" Tuohy Borst-type mechanism could be used. A Tuohy Borst is an example of a seal mechanism where a compressible polymer shaped like a thick hollow cylinder is placed within a cylindrical sleeve and compressed from either end of the sleeve. The compression can cause the compressible hollow cylinder to collapse on itself and reduce its inner diameter. Looking at the inverse, one could place a compressible hollow cylinder over a rod and compress it, thereby causing its outer diameter to expand. In one embodiment, creating longitudinal cuts in the material exaggerates this mechanism.

Figure 53B:
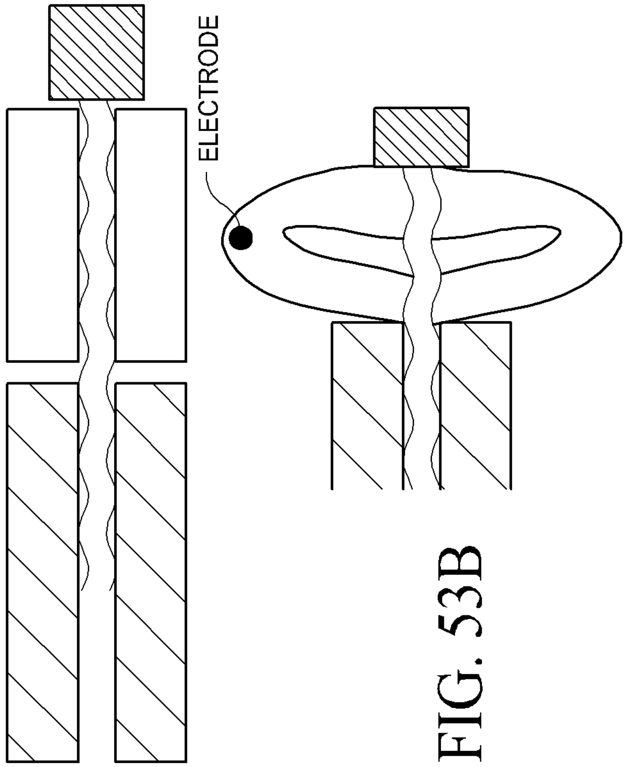
Figure 53A:
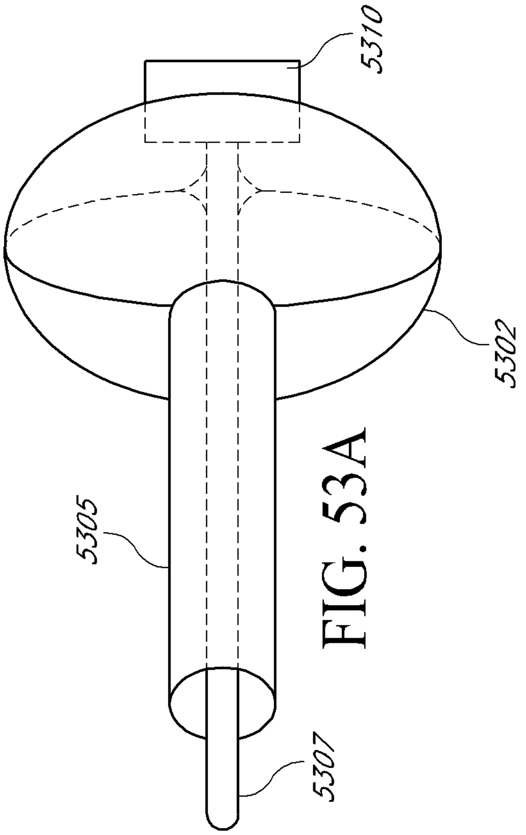

Referring now to FIGS. 53A and 53B, a cylinder 5302 of a soft and flexible material (e.g., low Young's modulus material such as silicone or polyurethane) is placed between a catheter shaft 5305 and a distal plug 5310, with a pull rod or pull wire 5307 running through the center of the material. In some embodiments, one or more electrodes are disposed near or at the mid-point of the longitudinal length of the cylinder such that the electrode(s) are exposed beyond the outer surface of the cylinder and are subsequently brought into contact with the vessel wall upon expansion of the cylinder. The electrode(s) may be fixed to the cylinder using an over-molding process or bonded to the cylinder with adhesive. In various embodiments, the wire(s) connected to the electrode(s) run along the outer surface of the cylinder, through the cylinder material (over-molded onto the wires), or inside the cylinder. In one embodiment, the wire(s) are replaced with a flexible, printed circuit. Pulling the distal plug 5310 relative to the catheter shaft 5305 causes the cylinder material to be deformed outward and brings the electrodes into contact with the vessel wall. In some embodiments, creating longitudinal cuts in the material exaggerates this mechanism.

Figure 54A:
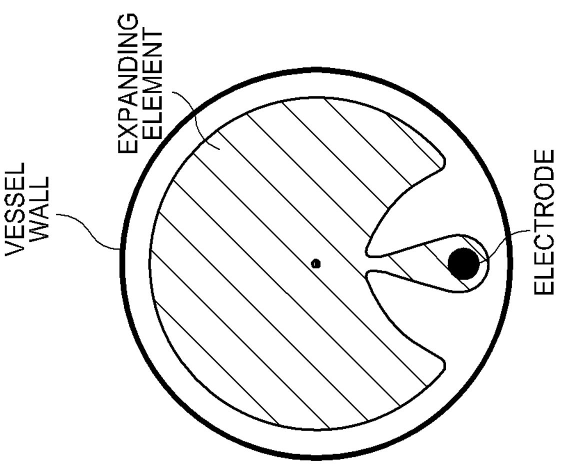
Figure 54B:
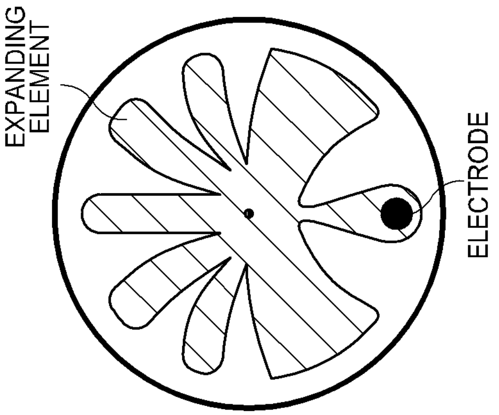
Figure 54C:
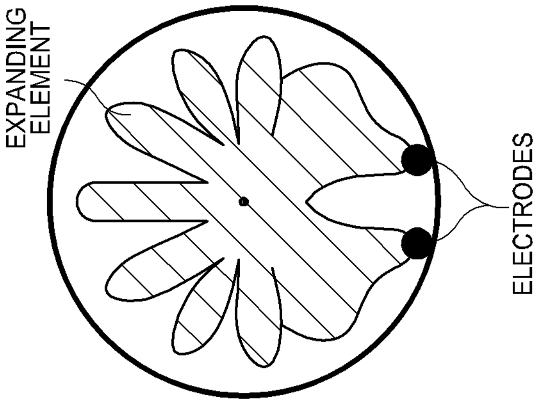

Applying the reaction force around a circumference in the same plane as the electrode force may reduce the length required to apply the electrode force and improve the repeatability of the applied "electrode force" in tortuous vessels. Moving reaction forces or contact points towards the electrode may also increase the stability near the electrode and reduce electrode movement during use. Increasing the normal force applied to the vessel may increase the stability of the catheter electrode in the target anatomy. As compared to the balloon or stent, a slit, "reverse Tuohy Borst" may enable the designer to direct blood flow to particular areas and control the mass flow rate through those areas, as illustrated in FIGS. 54A-54C.

In the case of denervating the common hepatic artery, unique vessel tortuosity (e.g., multiple acute turns or bends) can make force or torque transfer from the proximal end of the device to the distal end difficult. For example, torque may initially be lost due to translation of a catheter shaft until it contacts a tortuous vessel wall, and a pull wire locked in one plane of the catheter shaft can cause straightening or bending of the shaft through bends in that plane, leading to a loss of force along those bends prior to the flexing of the distal segment intended for articulation. Several embodiments described herein advantageously use a form of energy that does not experience a loss as it travels through tortuous bends.

Figure 88A:
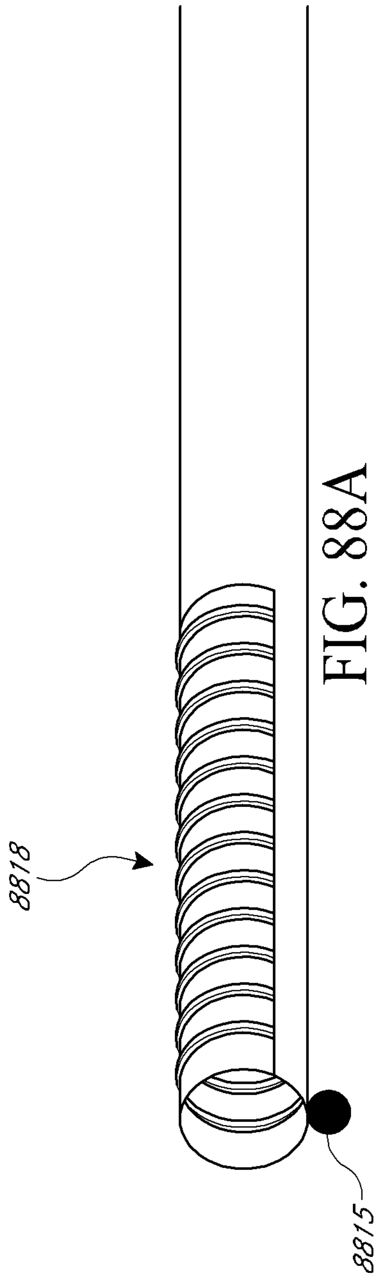
Figure 88B:
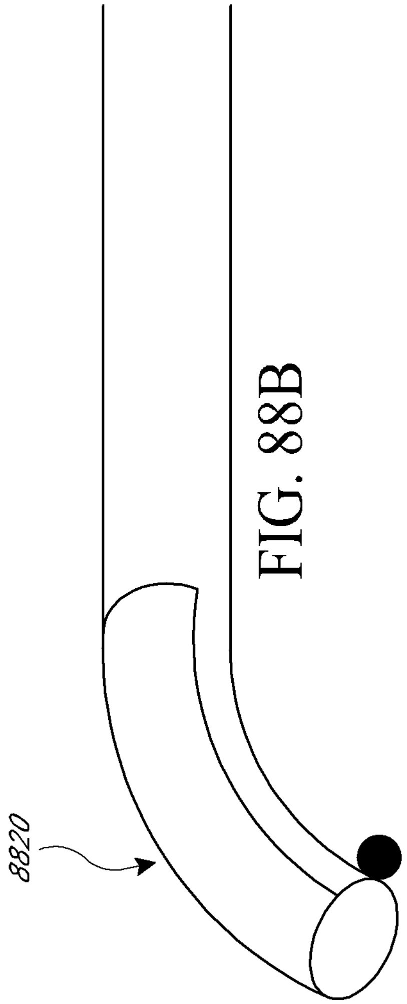

In some embodiments, mechanism other than pull wires can be used to actuate structures such as cantilever flex catheters as described herein. For example, hydraulic or pneumatic means can be utilized to effect bending of a flex catheter, as illustrated, for example, in FIGS. 88A and 88B. In some embodiments, a neuromodulation device (e.g., ablation catheter) is comprised of at least an electrode 8815, a flexible shaft, and a segment 8818 that is adjacent to the electrode (e.g., located at the distal end portion of the device) and that is exposed to a medium surrounding the shaft and/or to a fluid within the shaft. In one embodiment, the segment 8818 comprises a compliant balloon 8820 made of a material with a low elastic modulus (e.g., silicone or polyurethane) or a balloon made of a less compliant material (e.g., Nylon, PET, silicone, etc.) and processed to have circumferential ribs or folds (e.g., similar to a bendable straw). When the internal pressure is greater than the external pressure, the balloon may expand axially. If one side is constrained, the expansion can cause the balloon and constrained segment to bend towards the constrained segment or vessel wall.

Figures 89A, 89B:
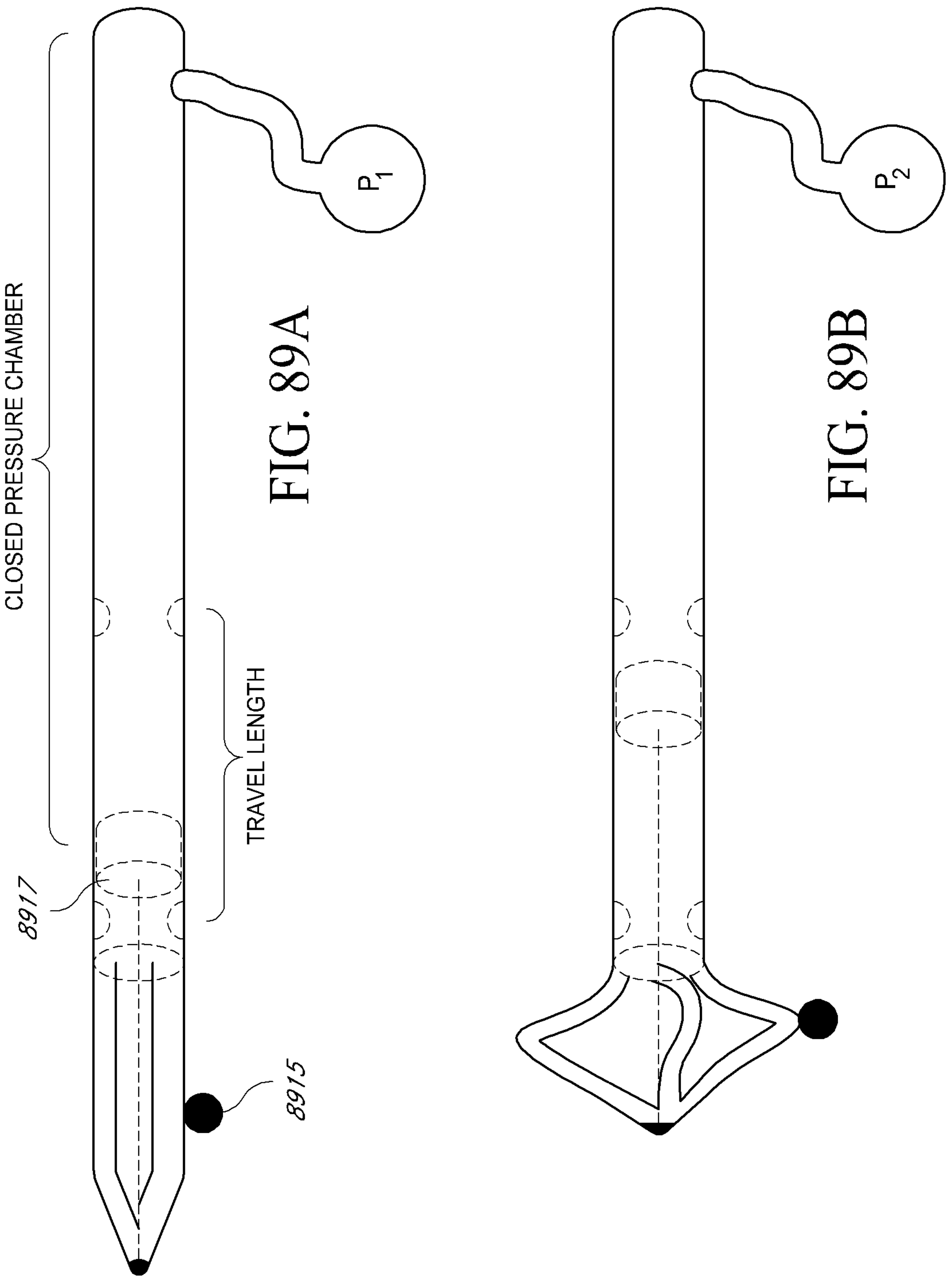

Referring now to FIGS. 89A and 89B, in one embodiment, a neuromodulation device (e.g., ablation catheter) is comprised of at least an electrode 8915, a flexible shaft, an articulating (e.g., expandable) section in communication with a plunger 8917, and two pressure chambers separated by a seal or plunger. In one embodiment, at least one chamber is filled with a compressible fluid or is filled with a non-compressible fluid and is also in communication with another chamber such as a syringe. In one embodiment, the plunger 8917 is driven by changing the pressure on either side of the plunger 8917, thereby transferring energy into the articulating section that is in communication with the plunger 8917. The articulating section illustrated in FIGS. 89A and 89B may be similar in structure and/or operation to the structure and/or operation of the expanding structure illustrated in and described in connection with FIGS. 48A, 48B, and 49A.

Figure 16A:
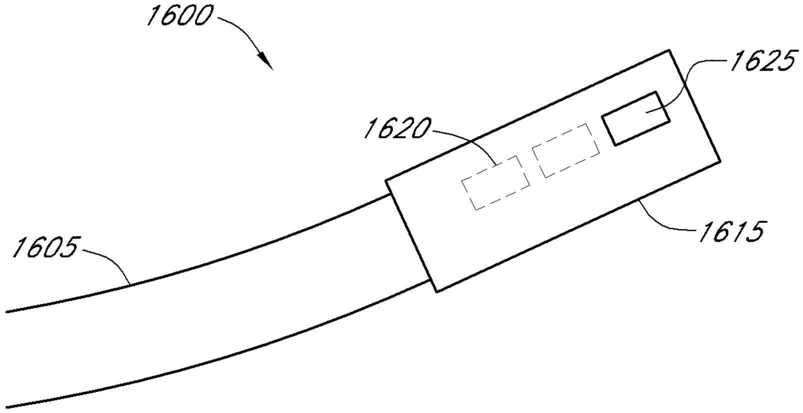
FIGS. 16A and 16B illustrate an embodiment of a windowed ablation catheter.
Figure 16B:
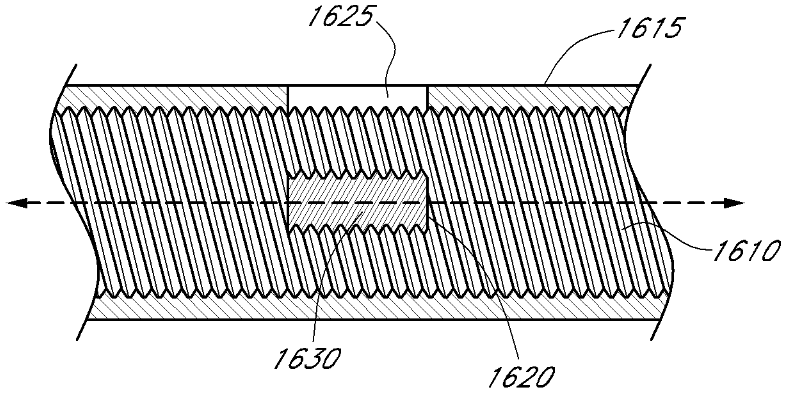

FIGS. 16A and 16B illustrate an embodiment of a windowed ablation catheter 1600. The windowed ablation catheter 1600 comprises a catheter body 1605, an inner sleeve 1610 having a first window 1620 and at least one ablation electrode 1630 and an outer sleeve 1615 having a second window 1625. FIG. 16A shows a view of the distal end of the windowed ablation catheter 1600 and FIG. 16B shows a detailed cut-away view of the distal end of the windowed ablation catheter 1600.

In some embodiments, the ablation electrode 1630 is disposed within a lumen of the inner sleeve 1610. The inner sleeve 1610 is rotatably received within the outer sleeve 1615 such that the outer sleeve 1615 is rotatable about the inner sleeve 1610. Energy can be delivered by the catheter by aligning the second window 1625 of the outer sleeve 1615 with the first window 1620 of the inner sleeve 1610 by rotating the inner sleeve 1610 with respect to the outer sleeve 1615, or vice-versa. In one embodiment, the inner sleeve 1610 comprises a dielectric covering to provide insulation.

In some embodiments, when the first window 1620 of the inner sleeve 1610 and the second window 1625 of the outer sleeve 1615 overlap, the ablating electrode 1630 is exposed to the outside of the outer sleeve 1615 (which may be placed against the wall of the target vessel). In one embodiment, energy only reaches the wall of the target vessel when the first window 1620 and the second window 1625 overlap, or are at least partially aligned. The degree of overlap may be controlled by the rotation or translation of the inner sleeve 1610 relative to the outer sleeve 1615. In one embodiment, the catheter is inserted by a user, the inner sleeve 1610 is turned based on user control, and the outer sleeve 1615 is turned based on user control, thereby allowing selective application of energy generated by the at least one ablation electrode to substantially any portion of the target vessel.

In some embodiments, the inner sleeve 1610 comprises multiple openings spaced along the length of the inner sleeve 1610 at different locations. For example, the inner sleeve 1610 may have openings spaced linearly along the axis of the inner sleeve 1610 and openings rotated about the axis of the inner sleeve 1610. In one embodiment, the openings of the inner sleeve 1610 define a spiral pattern. As shown in FIG. 16B, the external surface of the inner sleeve 1610 and the internal surface of the outer sleeve 1615 may be threaded such that the inner sleeve 1610 is translated with respect to the outer sleeve 1615 by rotation of the outer sleeve 1615 relative to the inner sleeve 1610. In some embodiments, relative rotation of the outer sleeve 1615 with respect to the inner sleeve 1610 serves to both translate and rotate window 1625 of the outer sleeve 1615, sequentially exposing vascular tissue to the ablation electrode 1635 through each of the openings of the inner sleeve 1610. In accordance with several embodiments, a windowed ablation catheter as described herein may facilitate creation of a spiral lesion along a length of the vessel wall. By selectively creating openings in the inner sleeve 1610, and rotating the outer sleeve 1615 with respect to the inner sleeve 1610, substantially any pattern of ablation along a helical path may be created.

To improve ablation catheter-vascular wall contact and thereby improve treatment efficacy, some embodiments include a window on the distal tip of the ablation catheter, or incorporated into one or more of the electrode windows, to provide suction (or vacuum pressure). The suction provided to the lumen wall places the artery in direct contact with the device to thereby achieve more efficient and less damaging ablation.

Figure 17:
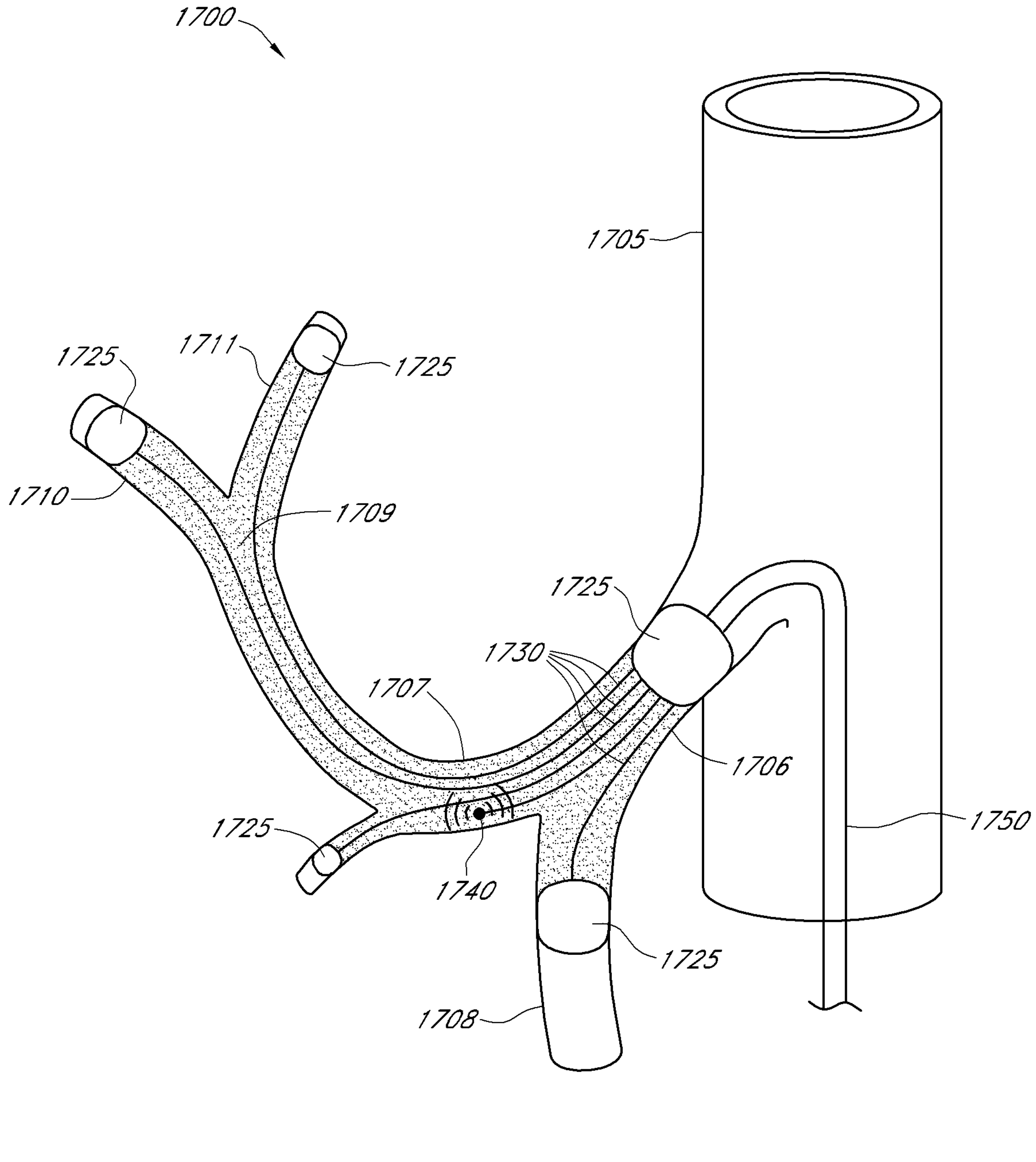
FIG. 17 illustrates an embodiment of a balloon-based volume ablation catheter system.

FIG. 17 is an embodiment of a balloon-based volume ablation system 1700, which can be used, for example, in the celiac, common hepatic, and proper hepatic arteries. In the illustrated embodiment, the balloon-based volume ablation system 1700 comprises a plurality of occlusive balloons 1725, a plurality of balloon guide wires 1730, a catheter 1750, and an electrode 1740. FIG. 17 also illustrates the abdominal aorta 1705, the celiac artery 1706, the common hepatic artery 1707, the splenic artery 1708, the proper hepatic artery 1709, the right hepatic artery 1710, and the left hepatic artery 1711 as an example of a target treatment site. In operation, the balloon-based volume ablation system 1700 may be inserted to the target treatment site through the abdominal aorta 1705 and into the celiac artery 1706.

Individual occlusive balloons 1725 may then be advanced into subsequent vessels, such as the splenic artery 1708, the right hepatic artery 1710 and the left hepatic artery 1711. When the appropriate occlusive balloons 1725 have been placed such that they define the desired volume of vasculature to be ablated, the occlusive balloons 1725 may be inflated, thereby occluding the vessels in which they have been placed. In one embodiment, the target volume is then filled with saline and the electrode 1740 is activated to deliver electrical energy to heat the entire target volume simultaneously. The electrode 1740 may be configured to deliver sufficient energy to the target volume to ablate all or at least a portion of the nerves of the vessels within the target treatment site. Upon completion, the occlusive balloons 1725 may be deflated and the entire balloon-based volume ablation system 1700 may be retracted.

In some embodiments, it may be advantageous to simultaneously ablate a region of nerves innervating a portion of all, or a subset of all, arteries arising from the celiac artery (such as the left gastric artery, the splenic artery, the right gastric artery, the gastroduodenal artery, and the hepatic artery). In some embodiments, ablation is achieved by using balloon catheters or other occlusion members deployed from a guide catheter within the celiac artery or abdominal aorta to block off or occlude portions of vessels not to be ablated (the target volume may be adjusted by inflating balloons or placing occlusion members upstream and downstream of the desired volume, thereby creating a discrete volume), filling the target volume with saline solution through a guide catheter, and applying RF or other energy to the saline to thereby ablate the tissues surrounding the target volume in a manner that maintains vessel patency with hydraulic pressure while also providing for direct cooling of the endothelial surfaces of the vessels through circulation of chilled saline. In some embodiments, the described "saline electrode" system is used to pressurize the target arteries with saline. The contact pressure of the saline electrode system against the arterial walls can be assessed by measurement of the arterial diameter on angiography and utilizing the pre-defined relationship between arterial diameter and fluid pressure or by using one or more pressure sensors, which in one embodiment, are included as a component of the saline electrode system. The saline electrode system may advantageously facilitate omnidirectional delivery of energy.

In some embodiments, hypertonic (e.g., hyperosmolar) saline is used in the ablation of the target volume. Using hypertonic saline may cause "loading" of the endothelial cells with ions, effectively increasing their conductivity. The loading of the endothelial cells with ions may have one or more of the following effects: decreasing ion friction in the endothelial lining (and other cells affected along the osmosis gradient, such as those in the media); reducing the heat deposited in the endothelial cell locations; preventing significant thermal damage to the endothelial cells; and increasing current density as a result of the increased conductivity in the region near the electrode, which may advantageously increase the efficiency of heating deeper in the vessel wall where the target nerves may be located. In one embodiment, "loading" of the vessel reduces the impact of the bile duct and/or portal vein structures on an ablation profile shape.

Saline slug electrodes, such as the embodiment described in FIG. 17, can be configured to circulate chilled fluid with constant infusion to maintain constant temperature at a lumen surface. In some embodiments, the difference between the inlet and outlet coolant flow can be measured to gauge the amount of energy delivered. Because a saline slug is by definition conformable to any shape or size lumen, the use of multiple compliant balloons (which may lead to delamination of the electrodes mounted on the respective balloons, is not required to accommodate variations in lumen size of various blood vessels. In accordance with several embodiments, the saline electrodes described herein advantageously provide improved electrode contact independent of device design, function, or operator variability. In several embodiments, the saline slug electrode employs catheter designs that interventional cardiologists are familiar with using in practice on a daily basis (e.g., balloons), whereas only electrophysiologists may be comfortable and trained using "point electrode" ablation catheters.

In several embodiments, by precisely controlling the convective heat transfer coefficient (h) in saline slug electrode (or metal electrode) configurations (e.g., by precisely controlling flow rate within the slug region), energy delivery can be interrupted, and by measuring the thermal decay (time constant) at a point within the slug, the depth of ablation can be assessed, where a longer time constant generally corresponds to a larger depth of ablation.

In various embodiments, capacitive coupling or resistive heating catheter devices are used to deliver thermal energy. In one embodiment, a capacitive coupling catheter device comprises a balloon comprising a bipolar electrode pair arranged in a capacitive coupling configuration with an insulation layer between the two electrodes. In one embodiment, the insulation layer coats the two electrodes. In one embodiment, the balloon comprises a non-conductive balloon filled with saline that is capacitively coupled to the target tissue through the dielectric layer formed by the substantially non-conductive balloon membrane. The capacitive coupling catheter device may advantageously not require direct electrode contact with the target tissue, thereby reducing current density levels and edge effects required by other devices. Capacitive coupling devices or methods similar to those described in U.S. Pat. No. 5,295,038, incorporated herein by reference, may be used. A return electrode path may also be provided.

In one embodiment, a resistive heating energy delivery catheter comprises a balloon catheter having a resistive heating element disposed thereon. For example, the balloon catheter may comprise spiral resistive heater that wraps around the balloon. Instead of inducing RF currents in the vascular tissue, DC or AC/RF currents can be used to generate heat in the balloon catheter itself and the heat can be transmitted to the surrounding vascular tissue (e.g., hepatic arterial tissue) by conduction.

In some embodiments, an RF energy delivery system delivers RF energy waves of varying duration. In some embodiments, the RF energy delivery system varies the amplitude of the RF energy. In other embodiments, the RF energy delivery system delivers a plurality of RF wave pulses. For example, the RF energy delivery system may deliver a sequence of RF pulses. In some embodiments, the RF energy delivery system varies the frequency of RF energy. In other embodiments, the RF energy delivery system varies any one or more parameters of the RF energy, including, but not limited to, duration, amplitude, frequency, and total number of pulses or pulse widths. For example, the RF energy delivery system can deliver RF energy selected to most effectively modulate (e.g., ablate or otherwise disrupt) sympathetic nerve fibers in the hepatic plexus. In some embodiments, the frequency of the RF energy is maintained at a constant or substantially constant level.

In some embodiments, the frequency of the RF energy is between about 50 KHz and about 20 MHz, between about 100 kHz and about 2.5 MHz, between about 400 kHz and about 1 MHz, between about 50 kHz and about 5 MHz, between about 100 kHz and about 10 MHz, between about 500 kHz and about 15 MHZ, less than 50 kHz, greater than 20 MHZ, between about 3 kHz and about 300 GHZ, or overlapping ranges thereof. Non-RF frequencies may also be used. For example, the frequency can range from about 100 Hz to about 3 kHz. In some embodiments, the amplitude of the voltage applied is between about 1 volt and 1000 volts, between about 5 volts and about 500 volts, between about 10 volts and about 200 volts, between about 20 volts and about 100 volts, between about 1 volt and about 10 volts, between about 5 volts and about 20 volts, between about 1 volt and about 50 volts, between about 15 volts and 25 volts, between about 20 volts and about 75 volts, between about 50 volts and about 100 volts, between about 100 volts and about 500 volts, between about 200 volts and about 750 volts, between about 500 volts and about 1000 volts, less than 1 volt, greater than 1000 volts, or overlapping ranges thereof.

In some embodiments, the current of the RF energy ranges from about 0.5 mA to about 500 mA, from about 1 mA to about 100 mA, from about 10 mA to about 50 mA, from about 50 mA to about 150 mA, from about 100 mA to about 300 mA, from about 250 mA to about 400 mA, from about 300 to about 500 mA, or overlapping ranges thereof. The current density of the applied RF energy can have a current density between about 0.01 $mA/cm^2$ and about 100 $mA/cm^2$, between about 0.1 $mA/cm^2$ and about 50 $mA/cm^2$, between about 0.2 $mA/cm^2$ and about 10 $mA/cm^2$, between about 0.3 $mA/cm^2$ and about 5 $mA/cm^2$, less than about 0.01 $mA/cm^2$, greater than about 100 $mA/cm^2$, or overlapping ranges thereof. In some embodiments, the power output of the RF generator ranges between about 0.1 mW and about 100 W, between about 1 mW and 100 mW, between about 1 W and 10 W, between about 1 W and 15 W, between 5 W and 20 W, between about 10 W and 50 W, between about 25 W and about 75 W, between about 50 W and about 90 W, between about 75 W and about 100 W, or overlapping ranges thereof. In some embodiments, the total RF energy dose delivered at the target location (e.g., at an inner vessel wall, to the media of the vessel, to the adventitia of the vessel, or to the target nerves within or adhered to the vessel wall) is between about 100 J and about 2000 J, between about 150 J and about 500 J, between about 300 J and about 800 J (including 500 J), between about 500 J and about 1000 J, between about 800 J and about 1200 J, between about 1000 J and about 1500 J, and overlapping ranges thereof. In some embodiments, the impedance ranges from about 10 ohms to about 600 ohms, from about 100 ohms to about 300 ohms, from about 50 ohms to about 200 ohms, from about 200 ohms to about 500 ohms, from about 300 ohms to about 600 ohms, and overlapping ranges thereof. In some embodiments, power is provided between 8 W and 14 W (e.g., 10 W, 12 W) for between 30 seconds and 3 minutes (e.g., 1 minute, 90 seconds, 2 minutes, 150 seconds) to provide a total energy delivery of between 240 J and 2520 J (e.g., 1200 J-10 W for 2 minutes, 1500 J-12 W for 2 minutes). Electrode(s) may be coupled (e.g., via wired or wireless connection) to an energy source (e.g., generator) even if the generator is not explicitly shown or described with each embodiment. The various treatment parameters listed herein (e.g., power, duration, energy, contact force/pressure, electrode size, pulsing, resistance, etc.) may be used for any of the embodiments of devices (e.g., catheters) or systems described herein.

In various embodiments, the generator comprises stored computer-readable instructions that, when executed, provide specific treatment (e.g., custom energy algorithm) to treat specific vessels selected by an operator. Accordingly, the generator facilitates delivery of RF energy having different treatment parameters using a single RF energy delivery device configured to provide similar or consistent performance across varying patient anatomy (e.g., one-size-fits-all). The generator may comprise safety controls tailored to environment: vessel size, flow, resistance, and/or other structures. The stored computer-readable instructions (e.g., software, algorithms) may be customized to deliver optimized lesion depth and/or may comprise pre-programmed operator-independent treatment algorithms. In some embodiments, a pre-programmed treatment course, which may include one or more parameters (such as power, treatment duration, number of target locations, spacing of target locations, energy, pulsed or non-pulsed, etc.) is provided. The pre-programmed treatment course may be based on vessel dimensions (e.g., diameter, segment length, wall thickness, age of patient, weight of patient, etc.). In one embodiment, a preconfigured or predetermined course of neuromodulation (e.g., ablation) may be performed (e.g., automatically or manually) to modulate (e.g., ablate) one or more nerves. The predetermined treatment course or profile may comprise a full or partial route of treatment or treatment points. The route may extend around a partial circumference of a blood vessel (e.g., 270 degrees, 220 degrees, 180 degrees, 90 degrees, or 60 degrees) or around the entire circumference.

For example, in some patients a target modulation (e.g., ablation) location (such as the common hepatic artery) may not be long enough to allow for complete modulation (e.g., ablation) of target nerves. In some embodiments, it may be desirable to treat multiple vessels adjacent to or that are portions of the hepatic artery vasculature (e.g., celiac, splenic, common hepatic, proper hepatic arteries) using a single energy delivery device. In some embodiments, an operator may select a vessel to be treated and the generator may automatically adjust the energy delivery parameters (e.g., select a pre-determined energy algorithm) based on the selected vessel. For example, different vessels may have different flow characteristics and different diameters. Accordingly, different energy profiles (e.g., varying power and/or time) may be associated with the different vessels to achieve a desired overall energy output. In ablation embodiments, the different energy profiles provide the same volume and/or circumferential arc of lesion for the various different vessels. The delivery of energy may be controlled manually or automatically according to a preconfigured energy profile determined by a controller, processor or other computing device (e.g., based on execution of instructions stored in memory) within the generator. For example, if the nominal vessel diameter (e.g., common hepatic artery) is greater than an adjacent vessel diameter, the power level and time can be adjusted lower as there will be a greater area of contact between the vessel wall and electrode surface. In some embodiments, the allowable temperature target or limit may be adjusted higher to compensate for a lower capacity of the blood flow to remove heat from the electrode. If the adjacent artery is larger, then power may be increased to modulate (e.g., ablation) a larger area in a single cycle. In some embodiments, a tendency towards more modulation (e.g., ablation) sites in the larger adjacent vessel may be employed.

The RF energy can be pulsed or continuous. The voltage, current density, frequencies, treatment duration, power, and/ or other treatment parameters can vary depending on whether continuous or pulsed signals are used. For example, the voltage or current amplitudes may be significantly increased for pulsed RF energy. The duty cycle for the pulsed signals can range from about 0.0001% to about 100%, from about 0.001% to about 100%, from about 0.01% to about 100%, from about 0.1% to about 100%, from about 1% to about 10%, from about 5% to about 15%, from about 10% to about 50%, from about 20% to about 60% from about 25% to about 75%, from about 50% to about 80%, from about 75% to about 100%, or overlapping ranges thereof. The pulse durations or widths of the pulses can vary. For example, in some embodiments, the pulse durations can range from about 10 microseconds to about 1 millisecond; however, pulse durations less than 10 microseconds or greater than 1 millisecond can be used as desired and/or required. In accordance with some embodiments, the use of pulsed energy may facilitate reduced temperatures, reduced treatment times, reduced cooling requirements, and/or increased power levels without risk of increasing temperature or causing endothelial damage due to heating. In some embodiments involving use of a catheter having a balloon, the balloon can be selectively deflated and inflated to increase lumen wall cooling and enhance the cooling function that pulsed energy provides.

Figure 55:
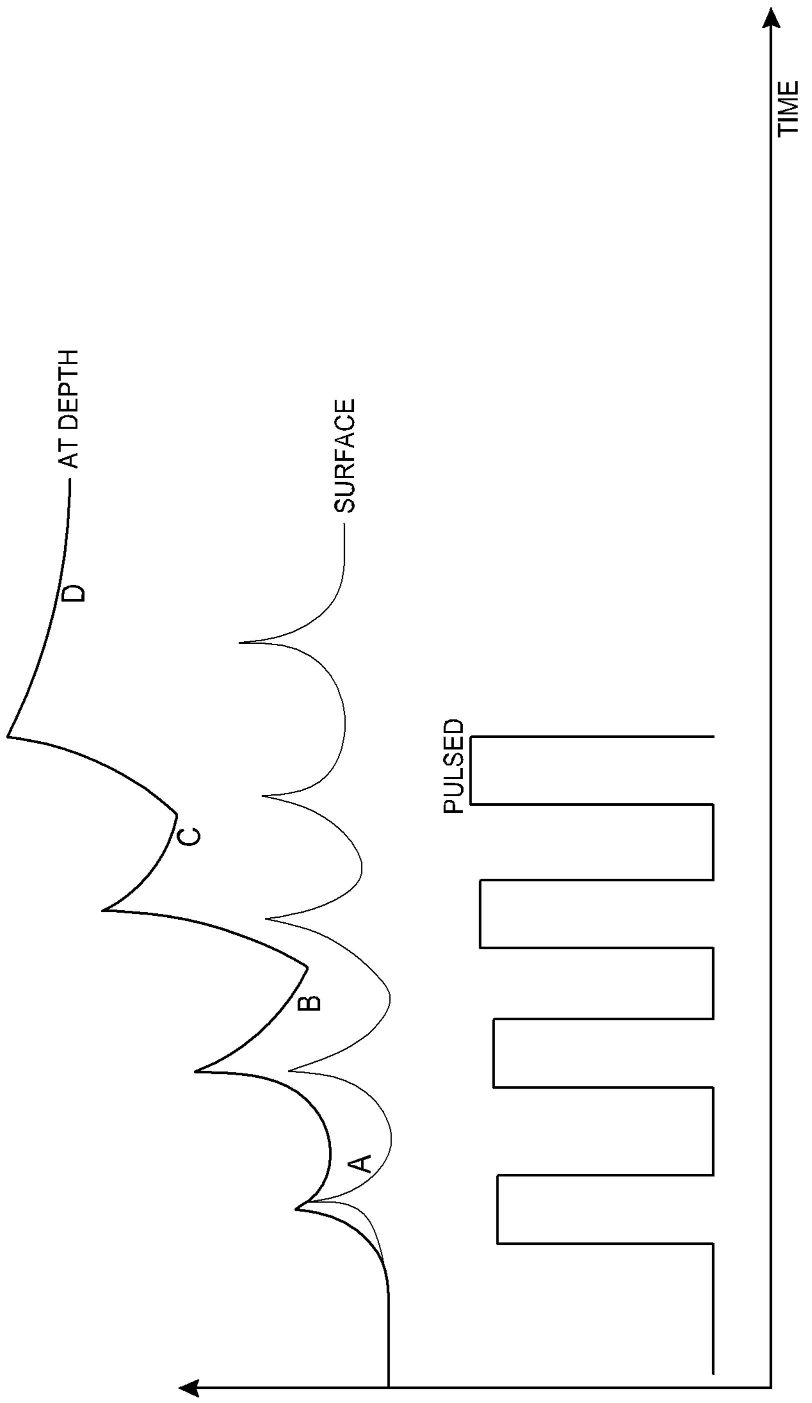
FIG. 55 illustrates a graph demonstrating the use of pulsed therapy, in accordance with an embodiment of the invention.

In some embodiments, the RF energy is pulsed based, at least in part, on the sensed tissue impedance or temperature, as shown, for example, in FIG. 55. For example, RF power can be delivered until a second temperature reaches a predefined value greater than a first temperature, at which point RF power may temporarily be interrupted. Because tissues near the arterial lumen cool faster than the target tissue (e.g., about 3, 3.5, 4, 4.5, 5 mm from the arterial lumen), in some embodiments, the temporary interruption tends to concentrate heat at the location of the target tissue, as shown in FIG. 55. In several embodiments, a similar result can be obtained by pulsing RF energy based, at least in part, on tissue impedance. In one embodiment, each subsequent cooling period (A, B, C, and then D) is longer than the previous cooling period (which may unexpectedly be particularly important in the hepatic artery, where flow rate is lower than other endovascular sites). Embodiments of this approach are described in U.S. Publ. No. 2010/0125268, which is incorporated by reference herein and may be used in conjunction with embodiments described herein. In some embodiments, pulsed energy is used to selectively deliver heat to nerves in the adventitia of the hepatic artery or other target vessels.

In several embodiments, the invention is particularly beneficial because it is unexpectedly useful for concentrating heat at the region of peripheral nerves (and particularly beneficial for treating the peripheral nerves about the hepatic artery). In several embodiments, substantially all of the target tissue treated is healthy tissue.

The treatment time durations can range from 1 second to 1 hour, from 5 seconds to 30 minutes, from 10 seconds to 10 minutes, from 30 seconds to 30 minutes, from 1 minute to 20 minutes, from 1 minute to 3 minutes, from 2 to four minutes, from 5 minutes to 10 minutes, from 10 minutes to 40 minutes, from 30 seconds to 90 seconds, from 5 seconds to 50 seconds, from 60 seconds to 120 seconds, overlapping ranges thereof, less than 1 second, greater than 1 hour, about 120 seconds, or overlapping ranges thereof. The duration may vary depending on various treatment parameters (e.g., amplitude, current density, proximity, continuous or pulsed, type of nerve, size of nerve). In some embodiments, the RF or other electrical energy is controlled such that delivery of the energy heats the target nerves or surrounding tissue in the range of about 50 to about 90 degrees Celsius (e.g., 60 to 75 degrees, 50 to 80 degrees, 70 to 90 degrees, 60 to 90 degrees or overlapping ranges thereof). In some embodiments, the temperature can be less than 50 or greater than 90 degrees Celsius. The electrode tip energy may range from 37 to 100 degrees Celsius. In some embodiments, RF ablation thermal lesion sizes range from about 0 to about 3 cm (e.g., between 1 and 5 mm, between 2 and 4 mm, between 5 and 10 mm, between 15 and 20 mm, between 20 and 30 mm, overlapping ranges thereof, about 2 mm, about 3 mm) or within one to ten (e.g., one to three, two to four, three to five, four to eight, five to ten) media thickness differences from a vessel lumen (for example, research has shown that nerves surrounding the common hepatic artery and other branches of the hepatic artery are generally within this range). In several embodiments, the media thickness of the vessel (e.g., hepatic artery) ranges from about 0.1 cm to about 0.25 cm. In some anatomies, at least a substantial portion of nerve fibers of the hepatic artery branches are localized within 0.5 mm to 1 mm from the lumen wall such that modulation (e.g., denervation) using an endovascular approach is effective with reduced power or energy dose requirements.

Figure 56:
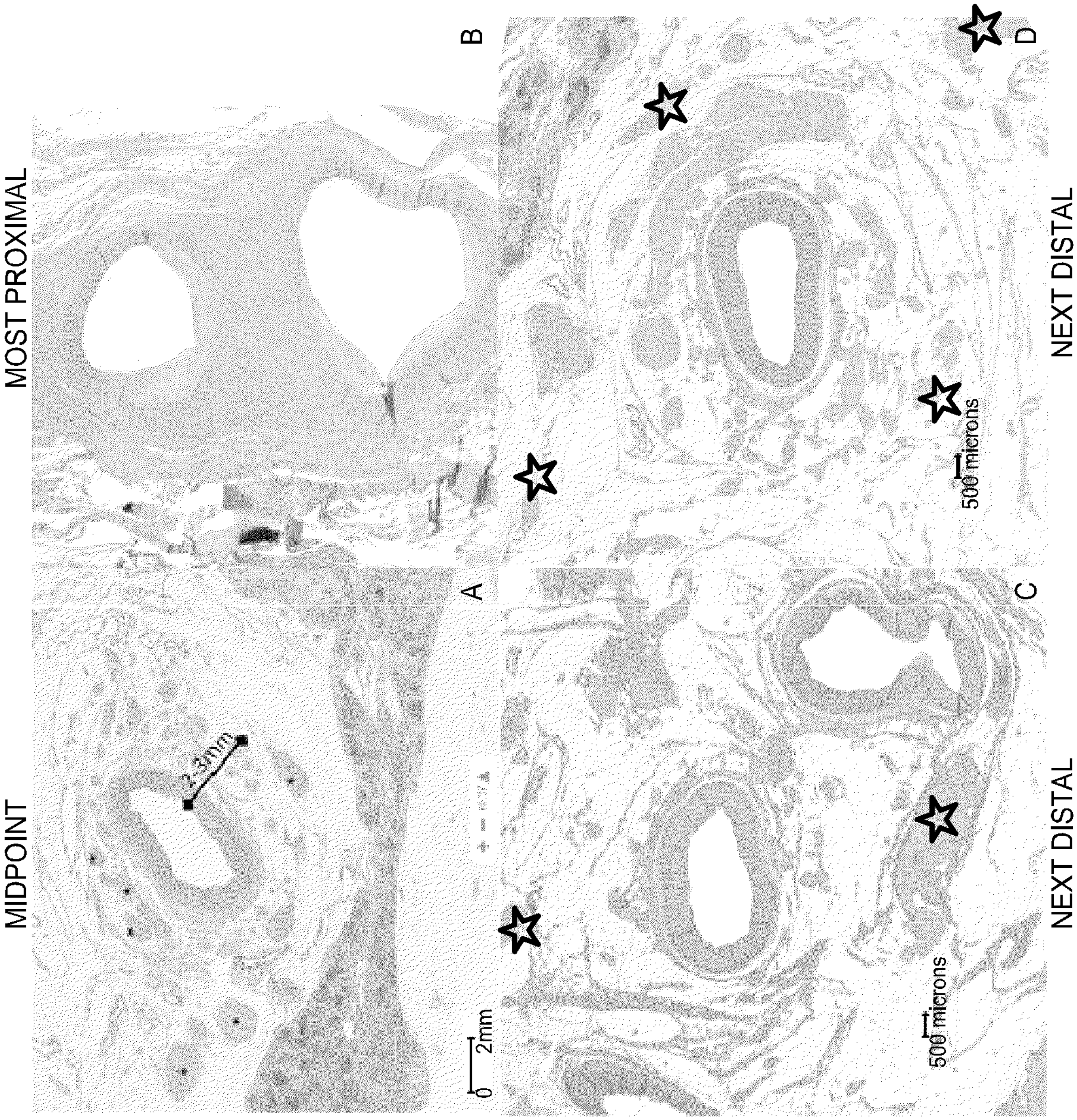
FIG. 56 illustrates images showing locations of nerves surrounding the common hepatic artery.

In some embodiments, an RF ablation catheter is used to perform RF ablation of sympathetic nerve fibers in the hepatic plexus at one or more locations. For example, the RF ablation catheter may perform ablation in a circumferential or radial pattern to ablate sympathetic nerve fibers in the hepatic plexus at one or more locations (e.g., one, two, three, four, five, six, seven, eight, nine, ten, six to eight, four to eight, more than ten locations). Referring now to FIG. 56, cadaver studies have shown that the hepatic nerves are generally focused in the region defined by the midpoint between the origin of the common hepatic artery and the origin of the gastroduodenal artery, as the nerves tend to approach the arterial lumen along non-branching regions of the artery, and diverge from the arterial lumen in regions of branching. The cadaver studies have also shown that the hepatic nerves predominantly reside within an annulus defined by the lumen of the artery and a concentric ring spaced approximately 4 mm from the arterial lumen. In some embodiments, the number of nerves and the proximity to the arterial lumen of the nerves increases towards the common hepatic artery midpoint. In some embodiments, the sympathetic nerve fibers are advantageously modulated (e.g., ablated) at the midpoint between the origin of the common hepatic artery and the origin of the gastroduodenal artery. In some embodiments, the sympathetic nerve fibers are modulated (e.g., ablated) up to a depth of 4-6 mm, 3-5 mm, 3-6 mm, 2-7 mm) from the lumen of the hepatic artery. In other embodiments, the sympathetic nerve fibers in the hepatic plexus are ablated at one or more points by performing RF ablation at a plurality of points that are linearly spaced along a vessel length. For example, RF ablation may be performed at one or more points linearly spaced along a length of the proper hepatic artery to ablate sympathetic nerve fibers in the hepatic plexus. In some embodiments, RF ablation is performed at one or more locations in any pattern to cause ablation of sympathetic nerve fibers in the hepatic plexus as desired and/or required (e.g., a spiral pattern or a series of linear patterns that may or may not intersect). The ablation patterns can comprise continuous patterns or intermittent patterns. In accordance with various embodiments, the RF ablation does not cause any lasting damage to the vascular wall because heat at the wall is dissipated by flowing blood, by cooling provided external to the body, or by increased cooling provided by adjacent organs and tissue structures (e.g., portal vein cooling and/or infusion), thereby creating a gradient with increasing temperature across the intimal and medial layers to the adventitia where the nerves travel. The adventitia is the external layer of the arterial wall, with the media being the middle layer and the intima being the inner layer. The intima comprises a layer of endothelial cells supported by a layer of connective tissue. The media is the thickest of the three vessel layers and comprises smooth muscle and elastic tissue. The adventitia comprises fibrous connective tissue.

In some embodiments, the energy output from the RF energy source may be modulated using constant temperature mode. Constant temperature mode turns the energy source on when a lower temperature threshold is reached and turns the energy source off when an upper temperature threshold is reached (similar to a thermostat). In some embodiments, an ablation catheter system using constant temperature mode requires feedback, which, in one embodiment, is provided by a temperature sensor. In some embodiments, the ablation catheter system comprises a temperature sensor that communicates with energy source (e.g., RF generator). In some of these embodiments, the energy source begins to deliver energy (e.g., turn on) when the temperature sensor registers that the temperature has dropped below a certain lower threshold level, and the energy source terminates energy delivery (e.g., turns off) when the temperature sensor registers that the temperature has exceeded a predetermined upper threshold level.

In some embodiments, the energy output from an energy delivery system may be modulated using a parameter other than temperature, such as tissue impedance. Tissue impedance may increase as tissue temperature increases. Impedance mode may be configured to turn the energy source on when a lower impedance threshold is reached and turn the energy source off when an upper impedance threshold is reached (in the same fashion as the constant temperature mode responds to increases and decreases in temperature). An energy delivery system using constant impedance mode may include some form of feedback mechanism, which, in one embodiment, is provided by an impedance sensor. In some embodiments, impedance is calculated by measuring voltage and current and dividing voltage by the current.

In some embodiments, a catheter-based energy delivery system comprises a first catheter with a first electrode and a second catheter with a second electrode. The first catheter is inserted within a target vessel (e.g., the common hepatic artery) and used to deliver energy to modulate nerves within the target vessel. The second catheter may be inserted within an adjacent vessel and the impedance can be measured between the two electrodes. For example, if the first catheter is inserted within the hepatic arteries, the second catheter can be inserted within the bile duct or the portal vein. In some embodiments, a second electrode is placed on the skin of the subject and the impedance is measured between the second electrode and an electrode of the catheter-based energy delivery system. In some embodiments, the second electrode may be positioned in other locations that are configured to provide a substantially accurate measurement of the impedance of the target tissues.

In some embodiments, the impedance measurement is communicated to the energy source (e.g., pulse generator). In some embodiments, the energy source begins to generate a pulse (i.e., turns on) when the impedance registers that the impedance has dropped below a certain lower threshold level, and the energy source terminates the pulse (i.e., turns off) when the impedance registers that the impedance has exceeded a predetermined upper threshold level.

In some embodiments, the energy output of the energy delivery system is modulated by time. In such embodiments, the energy source of the energy delivery system delivers energy for a predetermined amount of time and then terminates energy delivery for a predetermined amount of time. The cycle may repeat for a desired overall duration of treatment. In some embodiments, the predetermined amount of time for which energy is delivered and the predetermined amount of time for which energy delivery is terminated are empirically optimized lengths of time. In accordance with several embodiments, controlling energy delivery according to impedance and reducing energy delivery when impedance approaches a threshold level (or alternatively, modulating energy in time irrespective of impedance levels) advantageously provides for thermal energy to be focused at locations peripheral to the vessel lumen. For example, when the energy pulse is terminated, the vessel lumen may cool rapidly due to convective heat loss to blood, thereby protecting the endothelial cells from thermal damage. In some embodiments, the heat in the peripheral tissues (e.g., where the targeted nerves are located) dissipates more slowly via thermal conduction. In some embodiments, successive pulses tend to cause preferential heating of the peripheral (e.g., nerve) tissue. In accordance with several embodiments, when the impedance of tissue rises due to vaporization, electrical conductivity drops precipitously, thereby effectively preventing further delivery of energy to target tissues. In some embodiments, by terminating energy pulses before tissue impedance rises to this level (e.g., by impedance monitoring or time modulation), this deleterious effect may be avoided. In accordance with several embodiments, char formation is a consequence of tissue vaporization and carbonization, resulting from rapid increases in impedance, electrical arcing, and thrombus formation. By preventing impedance rises, charring of tissue may be avoided.

In some embodiments, total energy delivery is monitored by calculating the time integral of power output (which may be previously correlated to ablation characteristics) to track the progress of the therapy. In some embodiments, the relationship between temperature, time, and electrical field is monitored to obtain an estimate of the temperature field within the tissue surrounding the ablation electrode using the Arrhenius relationship. In some embodiments, a known thermal input is provided to the ablation electrode, on demand, in order to provide known initial conditions for assessing the surrounding tissue response. In some embodiments, a portion of the ablation region is temporarily cooled, and the resultant temperature is decreased. For example, for an endovascular ablation that has been in progress for a period of time, it may be expected that there is some elevated temperature distribution within the tissue. If a clinician wants to assess the progress of the therapy at a given time (e.g., to), the energy delivery can be interrupted, and cooled saline or gas can be rapidly circulated through the electrode to achieve a predetermined electrode temperature within a short period of time (e.g., about 1 second). In some embodiments, the resulting temperature rise (e.g., over about 5 seconds) measured at the electrode surface is then a representation of the total energy of the surrounding tissue. This process can be repeated through the procedure to track progress.

In some embodiments, a parameter, such as temperature, infrared radiation, or microwave radiation can be monitored to assess the magnitude of energy delivered to tissue, and thus estimate the degree of neuromodulation induced. Both the magnitude of thermal radiation (temperature), infrared radiation, and/or microwave radiation may be indicative of the amount of energy contained within a bodily tissue. In some embodiments, the magnitude is expected to decrease following the completion of the ablation as the tissue cools back towards body temperature, and the rate of this decrease, measured at a specific point (e.g., at the vessel lumen surface) can be used to assess the size of the ablation (e.g., slower decreases may correspond to larger ablation sizes). Any of the embodiments described herein may be used individually or in combination to indicate the actual size of the tissue lesion zone.

Electrode tip temperature control is often used as a control variable and treatment progress indicator for ablation procedures, particularly endovascular and/or cardiac ablation procedures. One potential problem with this approach is that although the goal is to treat tissue at a certain depth into the tissue, the temperature sensing element (thermocouple or thermistor) is generally only able to measure the surface temperature of the cardiac or vascular tissue. Furthermore, due to temperature gradients within the electrode itself, the temperature sensing element tends to measure the bulk temperature of the electrode, rather than precisely measure the surface temperature, which is often strongly influenced by the degree of convective blood flow about the electrode, which is typically about 37° C.

Figure 57:
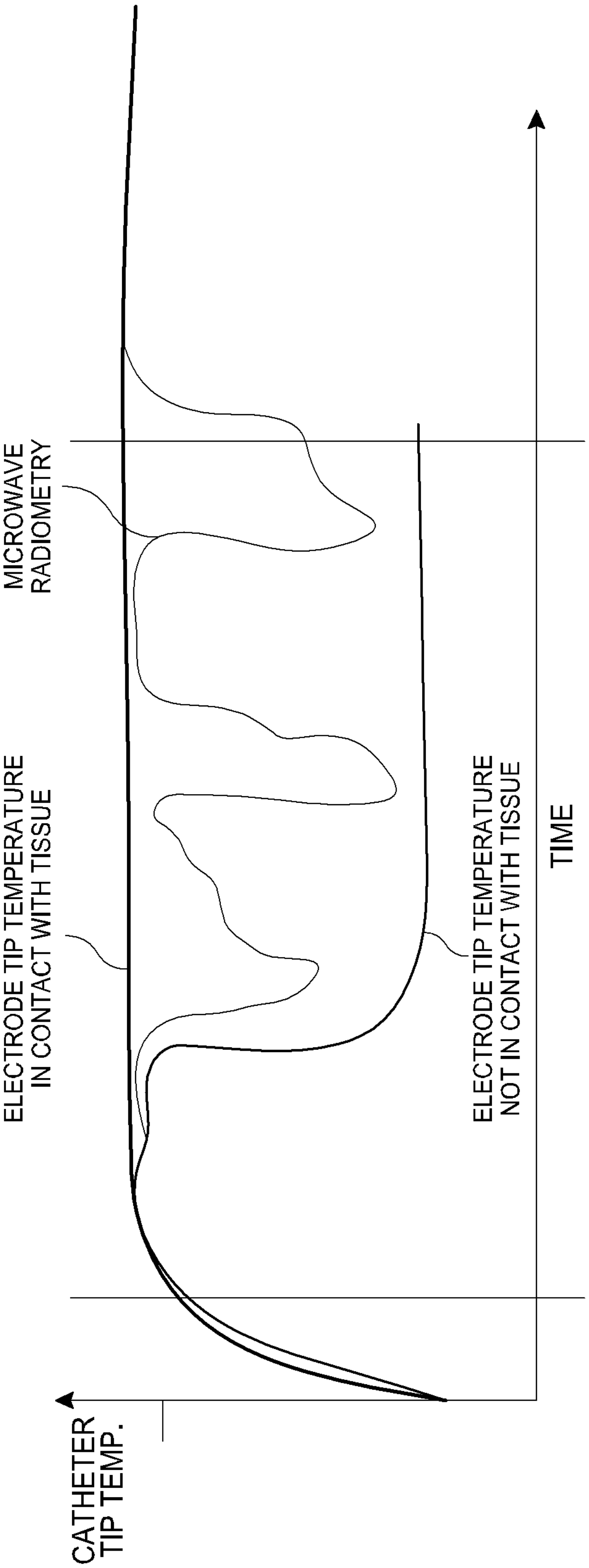
FIG. 57 illustrates a graph of motion of an electrode catheter tip indicated by a microwave radiometry sensor.

In one embodiment, microwave radiometry is used to measure tissue temperature at depth instead of at the electrode surface, such as described in US Publ. No. 2007/0299488 (the entire content of which is hereby expressly incorporated by reference). In addition to providing improved feedback on ablation progress and efficacy, microwave radiometry can also be used to estimate the stability of the treatment electrode within the target, in accordance with several embodiments. FIG. 57 illustrates an example of the effects of using microwave radiometry. FIG. 57 illustrates a base case with conventional electrode tip temperature measurements. Because the electrode tip temperature sensor measures the temperature of a small region of tissue around the electrode, the thermal mass of this tissue is limited. When the electrode is moved, the new tissue in contact with the electrode is heated rapidly, and variations in electrode tip temperature due to motion of the electrode are not significant, making this parameter potentially unreliable as an indicator of electrode and/or catheter motion. In accordance with several embodiments, because microwave radiometry measures the bulk thermal energy of a region of tissue, the temperature measurement corresponds to a region of tissue having a much larger thermal mass. Consequently, in accordance with several embodiments, temperature measurements using microwave radiometry will drop more significantly with motion of the electrode and/or catheter, as illustrated in FIG. 57. This fact can be used to control energy delivery (for example, an alarm can be generated when temperature drops below a certain threshold, indicating excessive catheter motion).

In several embodiments, by accurately measuring tissue temperature at depth using microwave radiometry lesion assessment, treatment efficacy and progress can be estimated more reliably. Excessive electrode and/or catheter motion can also be detected, thereby alerting a physician or other clinician to confirm good, or sufficient, electrode contact angiographically before proceeding with the treatment.

Some strategies for increasing lesion depth during ablation procedures have focused on actively cooling the surface of the electrode (e.g., using infused saline, internally circulated and/or chilled fluid). In some embodiments, electrode cooling allows deeper lesions to be formed without vaporizing the tissue adjacent to the electrode. In some applications, when cooling, it is difficult to have feedback about the peak temperature reached by the tissues, since the typical practice of placing a thermocouple within the electrode will measure a temperature that is biased by the cooling itself, and thus may not be representative of the peak temperature reached by the more distant tissues.

One embodiment for measuring the adventitia peak tissue temperature in an endovascular ablation of the hepatic artery is as follows. A thermocouple, thermistor or other temperature-measurement device may be placed at a location within the hepatic artery and used to measure the wall temperature at a distance of about 5 mm (as a shortest path) from the surface of the electrode, for electrode sizes between 1 mm and 2 mm in diameter. Studies have shown that measuring the wall temperature at such a distance is a fair approximation of the peak temperature reached within the adventitia.

With electrode cooling, the thermocouple within the electrode measures a temperature that is driven by the cooling itself, which may be much lower than the temperature reached by more distal tissues. Thus, for a temperature-controlled ablation, this measurement may not be useful in indicating the temperature reached by the adventitia, where the nerves are located. As a consequence, in one embodiment, the nerves can fail to be ablated if the heat provided is not sufficient to cause ablation within a certain time period, or there can be collateral damage if the heat is excessive. In accordance with several embodiments, a temperature-controlled neuromodulation (e.g., ablation) is desirable, as if one controls the electrical output (e.g., voltage, current, or power), the heat transferred to the tissues depends on a limited number of variables, such as contact force and impedance, thereby reducing the variability of the therapeutic effect. The placement of remote probes placed at discrete locations within the target tissue to address any shortcomings with cooled electrode strategies may be undesirable in several embodiments because they would require transvascular placement, thereby increasing the risk of the procedure.

Using a numerical model of hepatic arterial ablation, the Applicant has demonstrated that measuring the temperature at the arterial lumen at a shortest-path distance of 5 millimeters from the surface of the electrode provides a temperature that is reasonably close to the peak temperature reached at the media-adventitia interface. For the purposes of this analysis, the numerical model is based on the following assumptions, reflecting consolidated physiological knowledge of the hepatic arterial system:

1. artery with a diameter of 4 millimeters
2. thickness of the media is 2 millimeters
3. no external blood cooling (this assumption is appropriate because the electrode cooling dominates the thermal response near the electrode)
4. electrode diameter between 1 and 2 millimeters
5. the electrode is cooled and its surface is maintained around 37° C.

Figure 58:
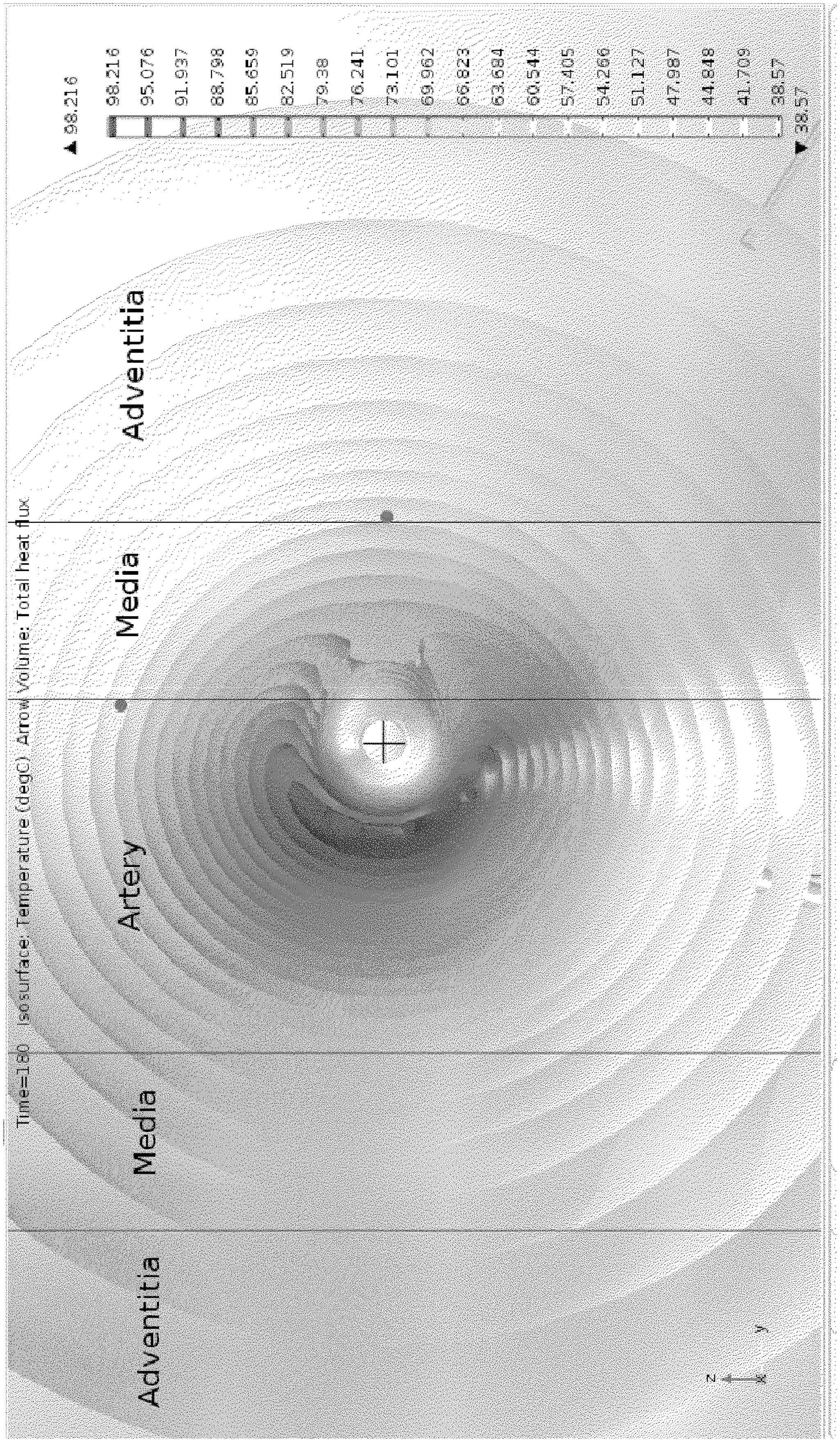
FIGS. 58 and 59 illustrate images obtained from a model of an endovascular ablation within the common hepatic artery.
Figure 59:
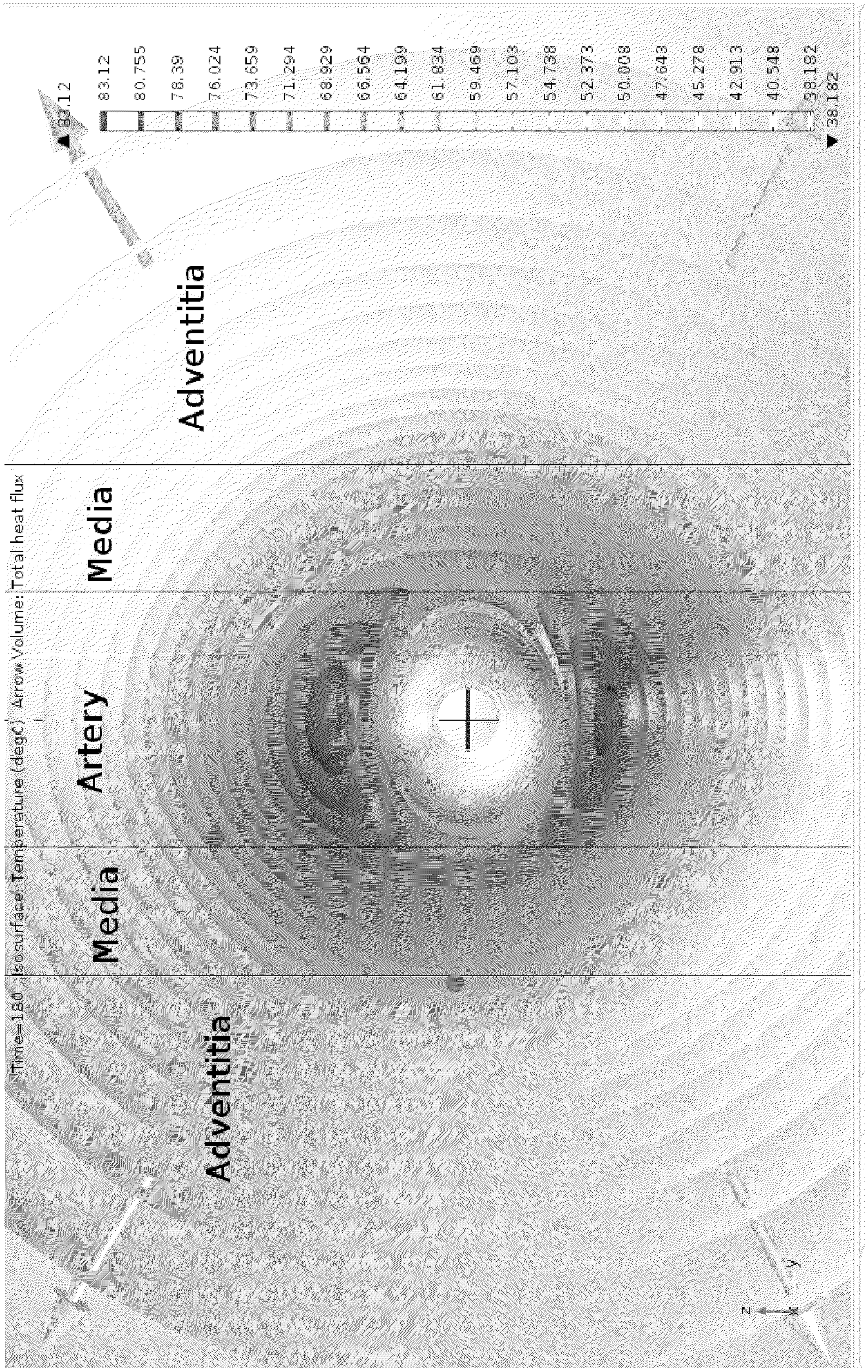

FIGS. 58 and 59 represent isothermal contours after a 3 minute ablation at 25 V. The figures are, respectively, the case of 1 and 2 millimeter diameter electrodes. In FIG. 58, the electrode is in contact with a right side of the artery, while in FIG. 59, the electrode is in contact with the bottom of the artery. The dots within the artery are at a distance of about 5 millimeters from the surface of the electrode. The dots within the adventitia represent the maximum temperature reached within the adventitia itself. In both cases, the pairs of dots belong to the same isothermal surface, and thus are, with good approximation, at the same temperature. In some embodiments, as the electrode gets smaller, the gradient of the temperature increases, and for sizes significantly smaller than 1 millimeter in diameter and for sizes significantly larger than 2 millimeters, the distance of 5 millimeter will likely change.

Figure 60A:
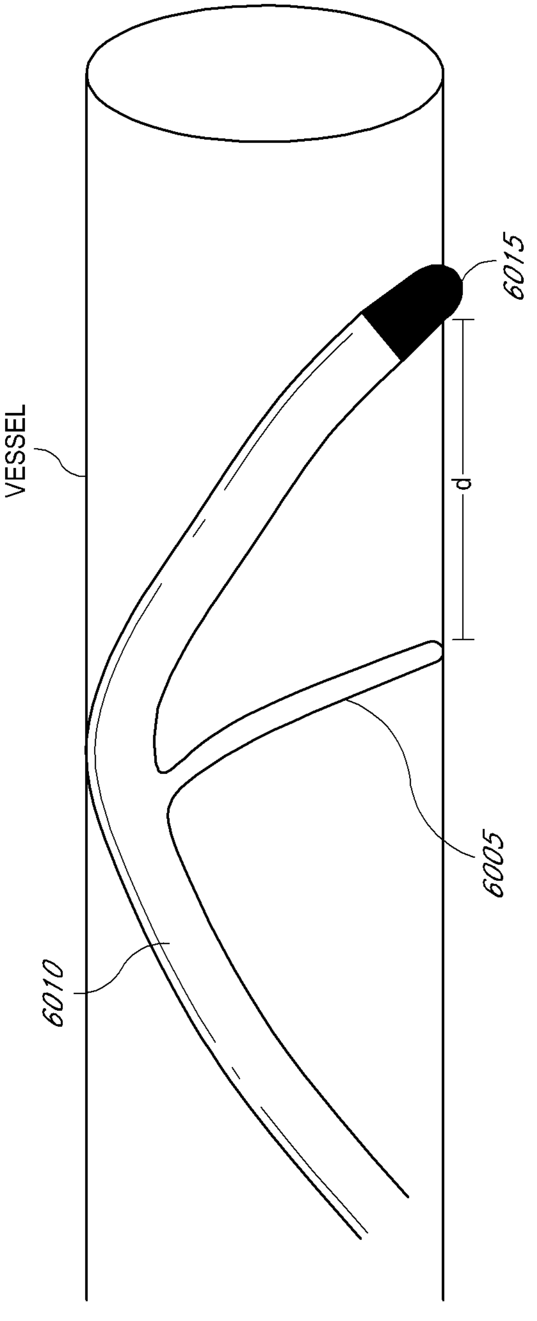
FIGS. 60A and 60B illustrate schematic embodiments of a catheter having a cooled electrode and a thermocouple to provide temperature feedback at a distance from the cooled electrode.
Figure 60B:
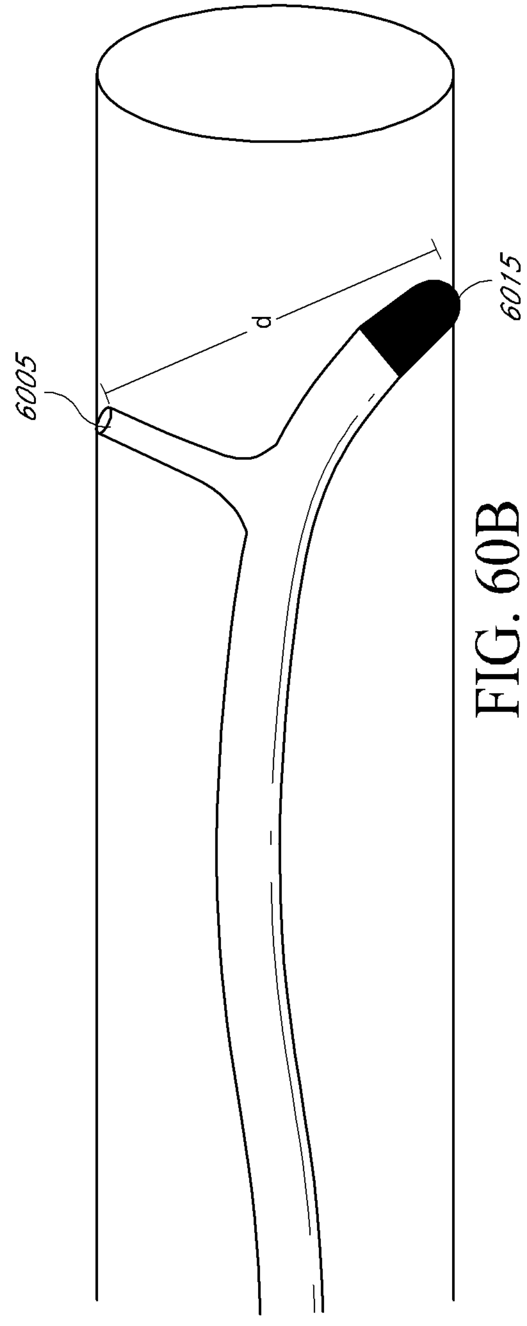

In several embodiments, the temperature at a distance d (e.g., 5 millimeters) from the electrode is measured using a temperature-sensing device 6005 (e.g., thermocouple) branching out of the catheter 6010, either on the same side of the electrode 6015, or on the opposite side (as shown in FIGS. 60A and 60B, respectively). The distance d between the electrode 6015 and the temperature-measurement device 6005 may be other than 5 millimeters (e.g., 2 mm, 2.5 mm, 3 mm, 3.5 mm, 4 mm, 4.5 mm, 5.5 mm, 6 mm, 6.5 mm, 7 mm, 7.5 mm, 8 mm, 8.5 mm, 9 mm, 9.5 mm, 10 mm or any distance between 2 mm and 10 mm, between 5 mm and 15 mm, between 10 mm and 20 mm or overlapping ranges thereof).

In various embodiments, the rate change of various treatment parameters (e.g., impedance, electrode temperature, tissue temperature, power, current, voltage, time, and/or energy) is monitored substantially in real time and displayed on a user interface. Treatment parameter data may be stored on a data store for later reporting and/or analysis. In some embodiments, an energy delivery system receives inputs transduced from physiologic signals such as blood glucose levels, norepinephrine levels, or other physiological parameters indicative of the status of the progress of treatment.

Other methods of observing the tissue ablation zone and the surrounding anatomy may include prior, concomitant, or subsequent imaging intravascularly by modalities including but not limited to: intravascular ultrasound, echo decorrelation, optical coherence tomography, confocal microscopy, infrared spectroscopy, ultraviolet spectroscopy, Raman spectroscopy, and microwave thermometry. All such imaging modalities may advantageously be adapted to the hepatic artery because of its unique tolerance to low flow. In some embodiments, ultrasound elastography is advantageously used for imaging. Ultrasound elastography may show areas of localized tissue stiffness resulting from the denaturing of collagen proteins during thermal ablation (ablated regions tend to stiffen compared to the native tissue); for example, stiff regions may correspond to ablated regions. Intravascular ultrasound may be used for example, to detect or monitor the presence and depth of ablation lesions. For example, if the lesions are in the range of 2 to 6 mm from the lumen wall, the clinician may be confident that the target nerves were destroyed as a result of thermal coagulation. Extravascular ultrasound imaging may also be used.

Figure 61:
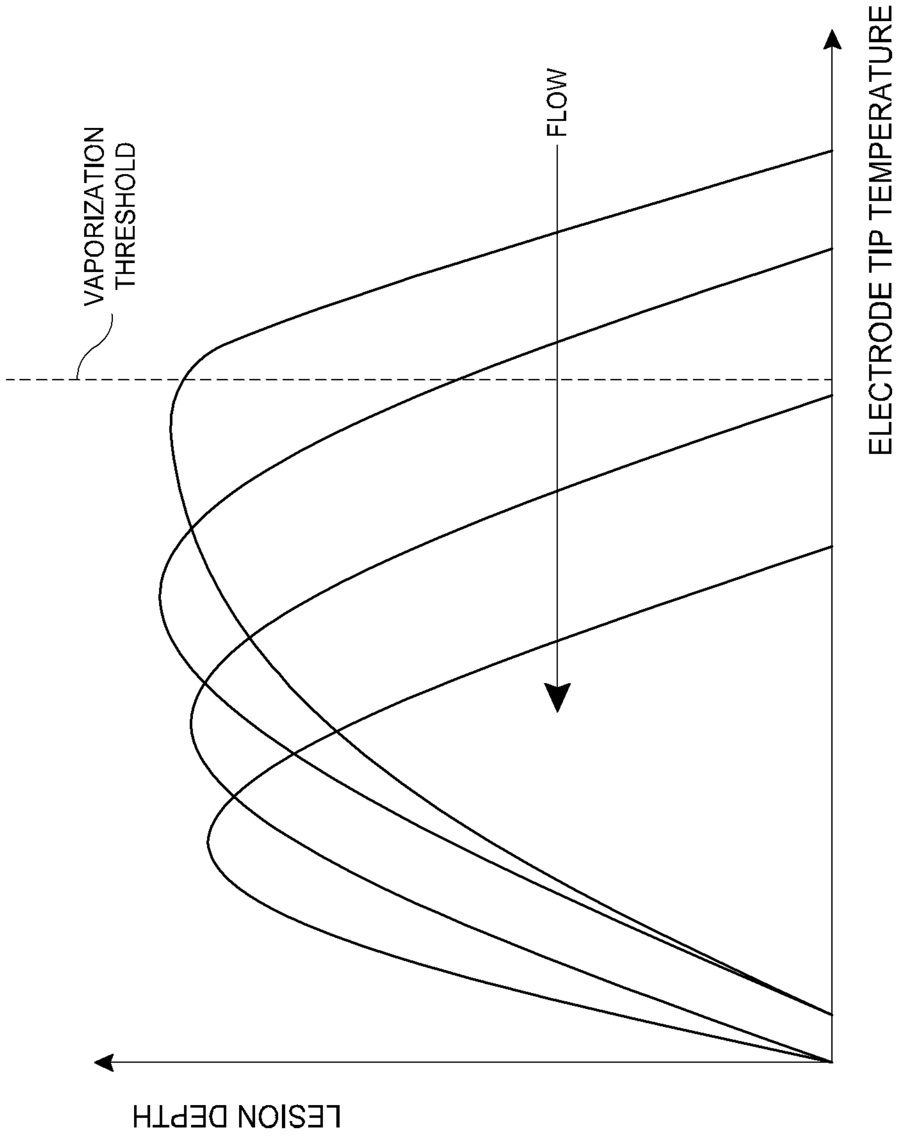
FIG. 61 illustrates a graph of electrode tip temperature and lesion depth as convective blood flow increases.

With respect to constant electrode tip temperature ablations (e.g., controlling RF generator output power to maintain a constant electrode tip temperature), in a physiologic situation, the degree of convective cooling effectively confounds the electrode temperature measurement-whereas for zero or limited convective cooling the temperature and time can be used to “set” the lesion size. In some embodiments, when there is significant convective cooling, the RF generator may end up outputting too much power to maintain a tip temperature, resulting in desiccation and vaporization at some depth (>0 mm from the electrode surface) within the tissue where the maximum temperatures are reached, thereby limiting ablation size. Electrode tip temperature and lesion size are related, as shown in FIG. 61, but there is always a maximum, and particularly, a maximum that shifts towards lower temperatures with increasing convective cooling. In order to assess which curve was applicable for a given physiologic boundary condition (e.g., blood flow velocity), a flow sensor could be added to the catheter to measure the degree of convective cooling. For a given convective cooling rate, the relationship between electrode tip temperature and lesion depth can be established using in vivo and ex vivo techniques to provide a valid look up table for specifying and assessing lesion size.

In one embodiment, electrode tip temperature can be used to prevent or limit thrombus formation, which can start to occur as a result of an edge effect as delivered power increases. As one example, RF power or other energy delivery (such as ultrasound, light, microwave, etc.) can be terminated as a threshold temperature (e.g., 75° C., 80° C., 90° C., etc.) is reached.

One method for assessing blood flow rate includes positioning an electrode within the blood flow stream, preferably in the center of the vessel (e.g., artery or other lumen). A set power (e.g., 2-10 W, 5 W) can be delivered for a set period of time, (e.g., 1-10 seconds, 3 seconds). The corresponding rise in electrode tip temperature measured during this time period may be inversely proportional to the blood flow rate in the target vessel (which is expected to range from 100 to 200 mL/min for the hepatic artery).

Figure 79:
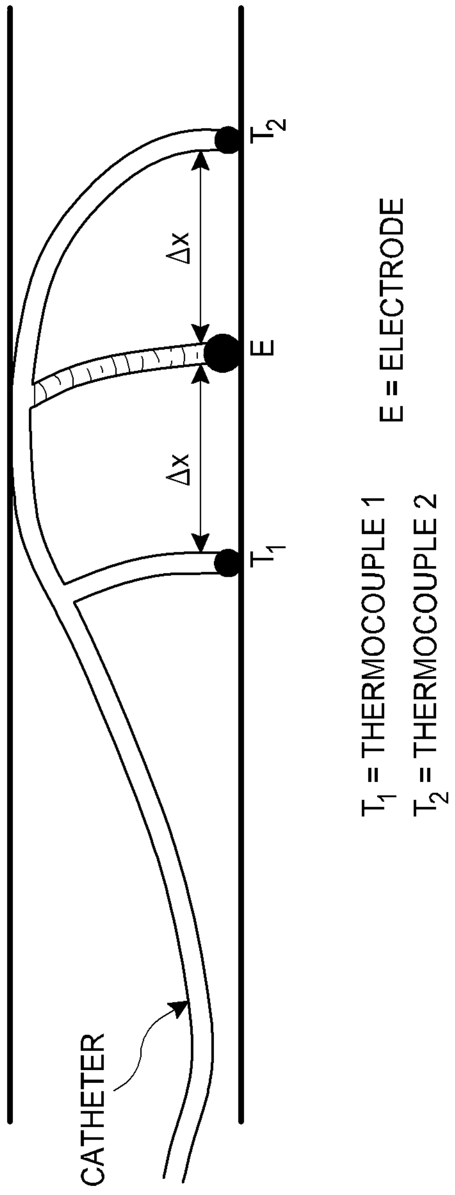
FIG. 79 illustrates an embodiment of a catheter having a thermal mass flow sensor.

One embodiment for measuring flow is shown in FIG. 79, depicting a catheter assembly configured to measure blood flow. In accordance with several embodiments described herein, catheter assemblies measure flow without impeding, or with minimal occlusion of, blood flow in the small lumen of the hepatic artery, thereby taking advantage of the potentially beneficial cooling action of the blood. The embodiment shown in FIG. 79 employs the fact that an RF heat source (e.g., an active electrode) is placed in the blood flow, which additionally may include a thermocouple or other temperature-measurement device in the electrode tip. As shown, two more thermocouples or other temperature-measurement devices may be added to the catheter, one upstream and one downstream from the electrode, thereby allowing for the measurement of the heat transferred by the flow. In one embodiment, measurement of the heat transferred by the flow is performed using consolidated technology for thermal mass flow in liquids, such as the LIQUI-FLOW® controller (Bronkhorst High-Tech, Amsterdam, Netherlands). As illustrated in FIG. 79, the two thermocouples may be added to the catheter assembly at discrete locations, for example one at a distance (e.g., 3 millimeters) downstream from the electrode, and one at a distance (e.g., 3 millimeters) upstream from the electrode. Other distances may be used. In some embodiments, the thermocouples may be disposed at the end of bending segments in order to achieve stable and precise positioning of the thermocouples in the vicinity of the electrode.

Figure 80:
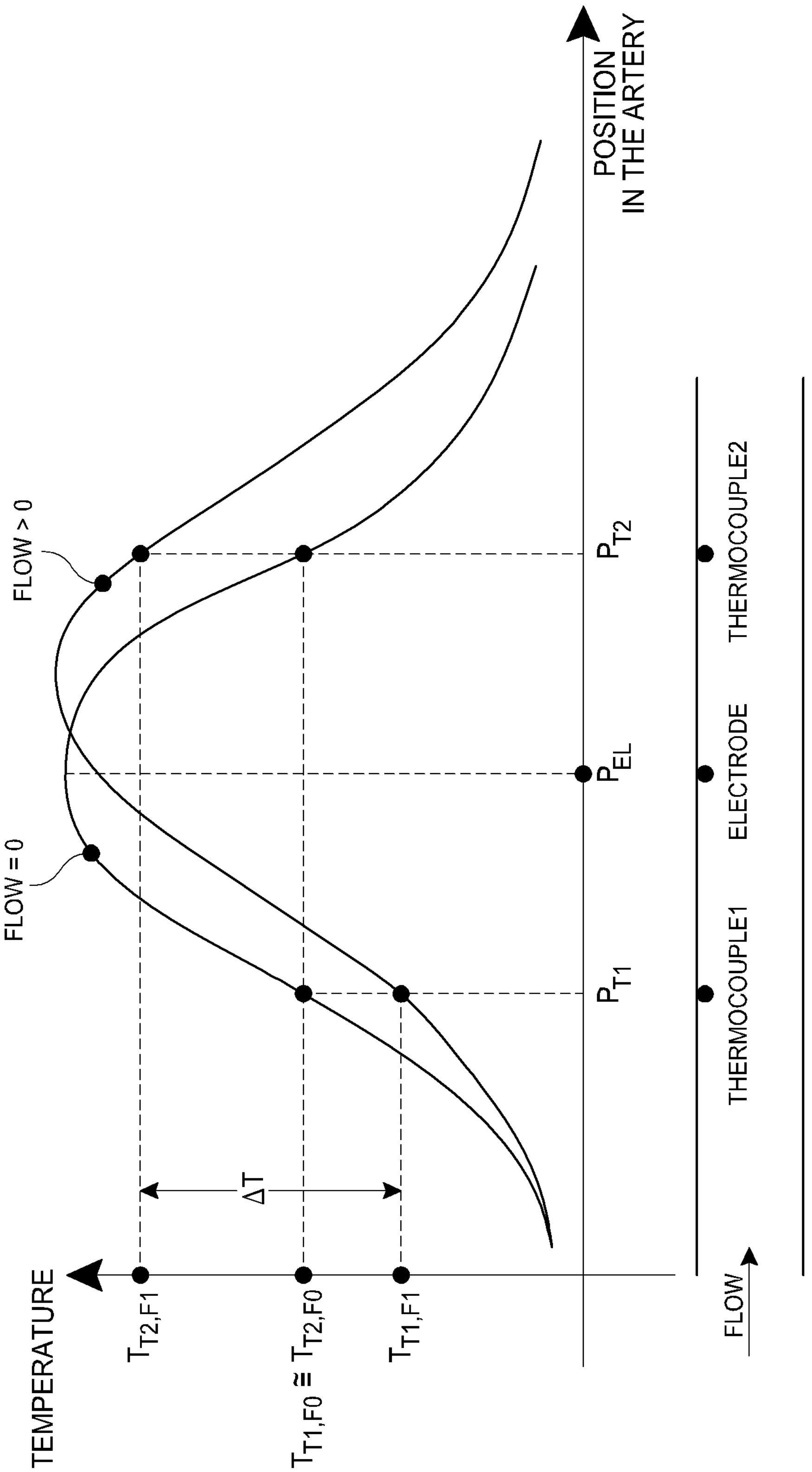
FIG. 80 is a graph illustrating a principle of operation of the thermal mass flow sensor of FIG. 79.

FIG. 80 illustrates the principle of a thermal flow sensor. In some embodiments, the electrode heats the surrounding tissues (e.g., blood and arterial wall) through the application of RF energy. When the arterial flow is zero, the two thermocouples sense the same temperature, as the heat generated in the tissues is conducted symmetrically from the electrode in the proximal and distal directions. When the blood flow is greater than zero, instead, the temperature profile shifts in the direction of the flow (to the right in FIG. 80) due to convective heat transfer, thereby resulting in a difference, ΔT, between the temperatures detected by the two thermocouples as a result of the heat transported by the flowing blood. ΔT is generally proportional to the magnitude of the flow rate, in some embodiments. By connecting the output of the thermocouples to an A/D converter and microprocessor, the precise flow can be determined from a previously-determined calibration relating ΔT to flow rate values under known, controlled conditions, which can be approximated as a linear relationship.

Figure 81:
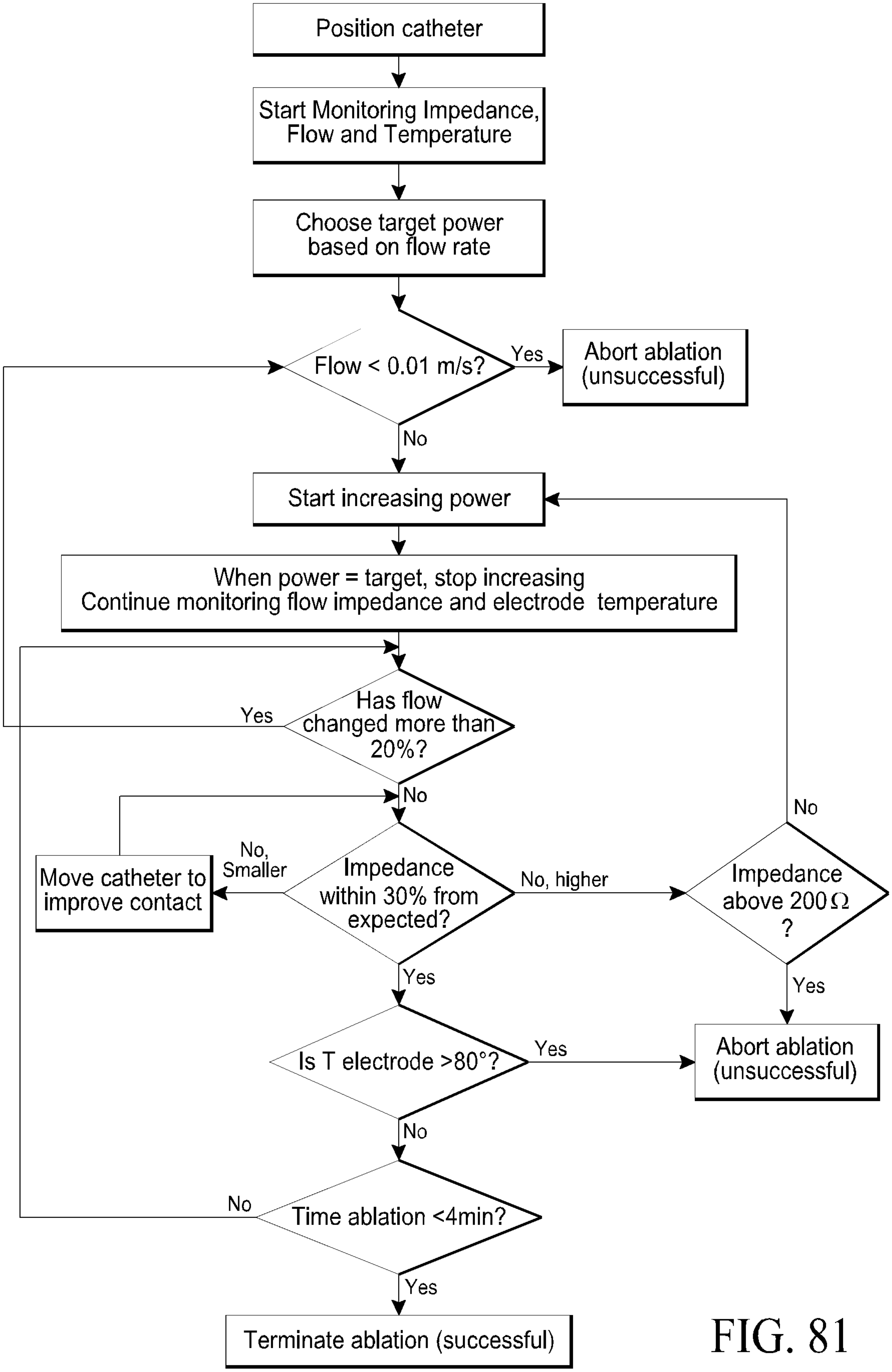
FIG. 81 illustrates a flow chart of an embodiment of an ablation control process.

Referring now to FIG. 81, an embodiment of an ablation control process is provided for achieving successful endovascular ablation of a common hepatic artery. Once the catheter is positioned, flow, impedance and electrode temperature can start being monitored in real time, utilizing any of the various embodiments previously described herein configured to do so. The blood flow rate value determines the target power according to the values previously described herein (see, for example, Table 1). If the value of the flow rate is below the minimum that is needed for a safe and successful ablation (e.g., at least 0.01 m/s), the ablation procedure is immediately terminated.

During application of RF energy, the change in impedance as the tissue temperature increases should be close (e.g., within a 30% tolerance range) to the impedance-temperature curve (see, for example, FIG. 74), where an increase in tissue temperature should correspond to a slight decrease in impedance. If the impedance decreases too much (e.g., >30% from the curve described in FIG. 74), the electrode may not be in contact with the arterial wall and instead may be in substantial direct communication with the blood, which has a significantly lower resistivity. In this situation, the catheter is repositioned to ensure good contact with the arterial wall.

If the impedance remains higher than expected (e.g., per FIG. 74), the tissue may need to be heated further by increasing the RF power level. Alternatively, if the impedance is much higher than expected (e.g., higher than about 200-300Ω), this is likely to indicate formation of thrombus. In such case, the ablations are immediately aborted, as tissue thrombus causes the ablation to become unpredictable and unsafe.

In general, according to the ablation control process in FIG. 81, the power is increased linearly (e.g., at a rate of 0.5 watts per second) until the target power level is reached. After increase of power, the power level is kept steady if the flow rate does not change by more than 20%. If flow rate has changed by more than 20%, the power is adjusted to the new flow rate, as long as the flow rate is above 0.01 m/s or some other threshold.

At any time during the ablation, flow, impedance and electrode temperature are monitored as real time feedback signals, and the power is adjusted (or stopped) according to their values. After 4 minutes, or other suitable time period (e.g., according to the power and time combinations listed in Table 1), RF energy delivery is terminated and the ablation is completed.

In the ablation control process described in FIG. 81, a power-controlled ablation algorithm may be employed instead of a temperature-controlled algorithm because the temperature at the electrode is not always a good indicator of the maximum temperature reached within the tissue. Since the electrode is in contact with the blood, its temperature is not expected to rise significantly beyond 37° C., and may be considerably lower than the temperature within the tissues. Electrode temperature can be used to detect complications during RF ablation treatments of the hepatic artery. For example, if the electrode temperature rises too much (for example, above 80° C.), this may be a sign that something unexpected has happened (for instance, a hole has been formed in the arterial wall and the electrode is inserted directly in the tissue, or alternatively, thrombus formation). In several embodiments, electrode temperature monitoring provides an additional layer of control redundancy to ensure procedure safety, but it may not be used as a primary feedback variable to control RF energy.

Figure 62A:
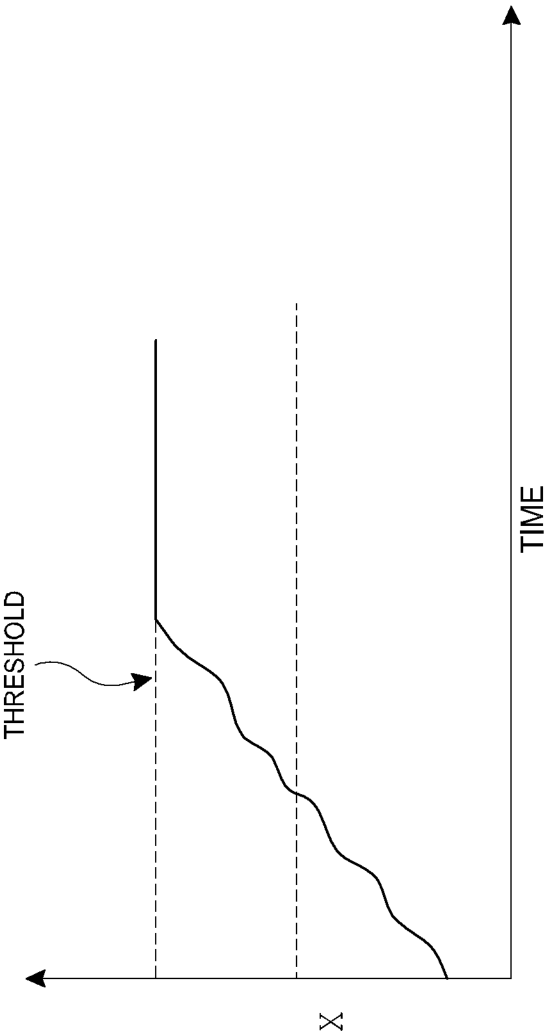
FIGS. 62A and 62B illustrate embodiments of an energy delivery algorithm based on blood flow measurement.
Figure 62B:
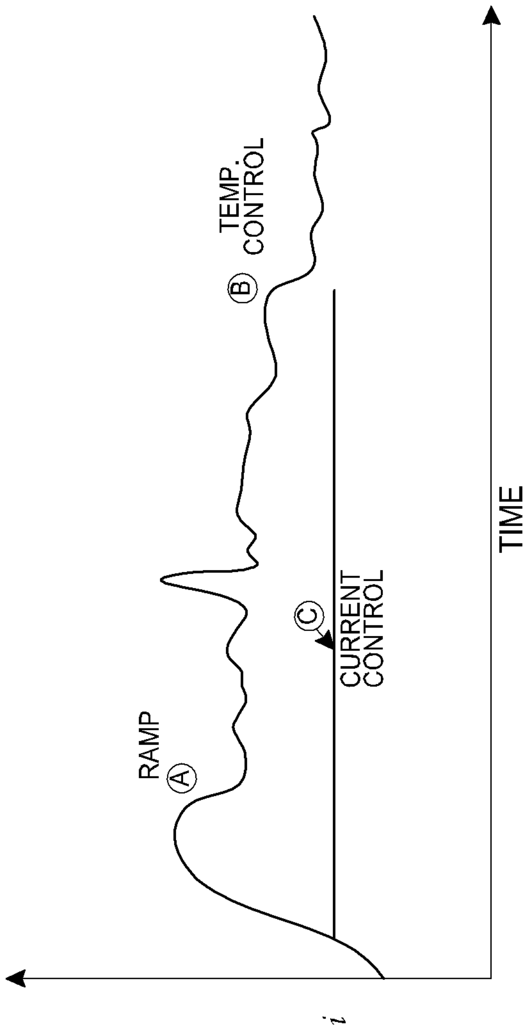

FIG. 62A illustrates an embodiment of an energy delivery algorithm based on blood flow measurement. The energy delivery algorithm utilizes the blood flow velocity or rate (or alternatively, generic control variable "X," such as impedance) as a control variable. In some embodiments, the generator conducts a checksum before applying RF energy to assess the initial value of the control variable, for example blood flow rate. Based at least in part on the value of the measured control variable, the proportional-integral-derivative (PID) controller gain values may be adjusted to ensure a stable control feedback loop throughout the duration of the energy application procedure. RF energy delivery may then be delivered for a first period in a manner that adjusts output power to maintain a constant first-derivative of the electrode tip temperature (or other control variable, for example impedance) until a set threshold value (e.g., 75° C.) is reached. RF energy may then be delivered for a second period in a manner that maintains a constant electrode tip temperature (or other control variable). The output power or current output (as shown in the current (i) graph in FIG. 62B) by the generator during time periods 1 and 2 is also shown in FIGS. 62A and 62B for illustrative purposes.

In accordance with several embodiments, the common hepatic artery is a target of ablation using an RF electrode catheter. For some subjects, a length of the common hepatic artery may limit the number of possible ablation sites. In some embodiments, minimizing the size of the lesions created along the longitudinal length of the common hepatic artery increases the number of ablation sites available within the vessel. In order to decrease the width of the lesions parallel to the vessel longitudinal axis while maintaining sufficient depth of the lesions and maximizing a surface of the electrode exposed to blood flow or cooling fluid for cooling, the electrode(s) of the RF electrode catheter may be constructed to have a diameter that is greater than or equal to its length. For example, if the electrode is generally 6 French in diameter (0.080 inches), then the length of the electrode may be 0.080 inches or less.

In accordance with several embodiments, consistency in lesion size is desired without being dependent on variations in vessel size, which may vary for the same target vessel across different subjects. For example, the inner diameter of the common hepatic artery may vary from 3 mm to 7 mm. In addition, overlap in lesion formation may be undesirable. Overlap in lesion formation can be difficult to avoid or prevent if a target treatment length is sufficiently short (e.g., due to patient anatomy) and multiple spaced-apart lesions are required to be formed along the vessel length.

For situations where there is an intrinsic limit in the number of ablations that can be performed at a defined spacing due to patient-specific anatomy limitations, a target vessel may be stretched out while being ablated. In one embodiment, the target vessel may be stretched by placing a spring in the vessel during ablation to stretch the vessel to a desired length and then may be removed upon completion of ablation. In one embodiment, a balloon is inserted within the vessel and expanded to straighten and thus stretch the vessel. The balloon may be a balloon of a balloon ablation catheter. In some embodiments, the length and the area of the vessel may be increased by the balloon, resulting in no increase in resistance of the vessel. In accordance with several embodiments, stretching of the vessel enables more lesions to be formed across the length of the target vessel or a portion of the target vessel at a given spacing, thereby resulting in potential greater effectiveness of therapy. In some embodiments, because cells are stretched by the vessel stretching while tissue conductivity remains constant, the energy plume or cone targets fewer cells within the vessel wall while still reaching the same density of nerve fibers within or surrounding the vessel wall (e.g., within the adventitia).

Figure 110A:
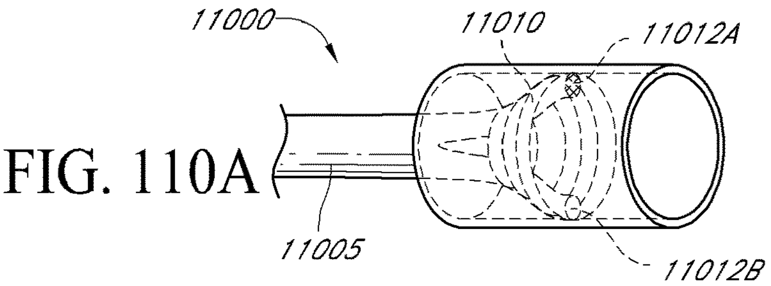
FIGS. 110A and 110B and 111-114 illustrate embodiments of systems and methods configured to control lesion formation.
Figure 110B:
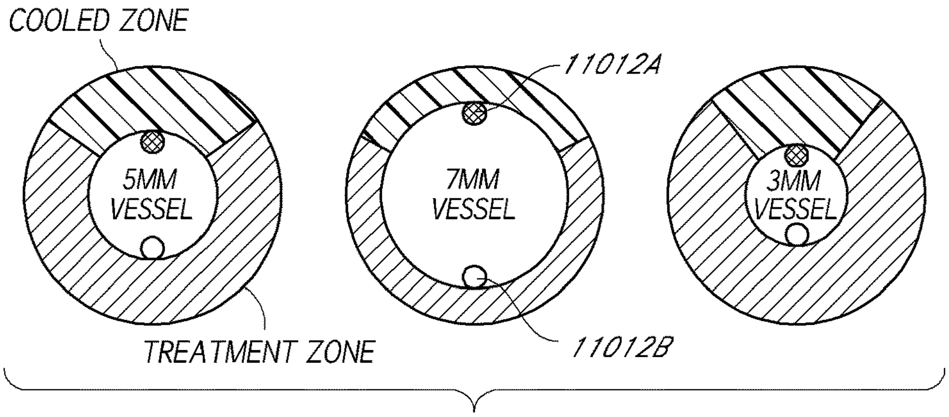

Turning to FIGS. 110A and 110B, a metabolic neuromodulation system 11000 configured to provide consistency in lesion size regardless of vessel diameter while utilizing a single energy protocol is illustrated. In one embodiment, the metabolic neuromodulation system 11000 advantageously allows for a single ablation protocol to be developed for a full range of vessel diameters that ensures a desired circumferentiality (e.g., 60-80% of vessel circumference) while reducing the risk of lesion tail overlap between spaced-apart lesions (e.g., reduces the risk of complete circumferentiality due to overlapping lesion zones). In some embodiments, the metabolic neuromodulation system 11000 may allow for reduction in the number of lesions necessary to ensure full circumferential treatment in multiple different planes. The metabolic neuromodulation system 11000 comprises a single disposable catheter 11005 with a mechanically-deployable scaffold 11010 having two opposing contact points 11012A and 11012B. The scaffold 11010 may be mechanically expanded and retracted by a mechanical pull wire (not shown). In one embodiment, the scaffold 11010 comprises a funnel-shaped basket. An electrode may be positioned at the second contact point 11012B to deliver energy for the purpose of ablation and a cooling tip may be positioned at the first contact point 11012A 180 degrees opposed to the second contact point 11012B to facilitate creation of a cooled tissue zone for the purpose of preventing lesion circumferentiality. In accordance with several embodiments, the size of the cooled tissue zone would differ based upon vessel diameter, but would be sufficient to prevent full circumferentiality of the lesion. In one embodiment, the cooling tip may be facilitated by continuously infusing cooled liquid through a lumen of the catheter 11005. The cooling tip may be directed toward the vessel wall adjacent to the electrode contact area. In this manner, the tissues adjacent to the electrode contact point may be cooled before, during, and/or after the electrode is energized or activated. In embodiments that employ modalities other than RF, the cooling tip may also be used. In embodiments that employ cryotherapy (such as cryoablation), warming elements/fluids may be introduced instead.

In some embodiments, the cooling tip of the catheter 11005 advantageously creates a cooled zone that is 180 degrees in opposition to the site of ablation during energy delivery to ensure that the “tails” of the C-shaped lesions do not touch or overlap, regardless of vessel diameter. The circumferential extent of the cooled zone can be variable as long as it is cool enough to prevent lesion formation across the entire vessel circumference regardless of vessel size. In some embodiments, the cooled zone prevents at least 10% of the vessel circumference from being ablated regardless of vessel diameter. In some embodiments, the cooled zone prevents at least 20% of the vessel circumference from being ablated regardless of vessel diameter. FIG. 110B schematically illustrates treatment zones 11025 and cooled zones 11030 for vessels having diameters of 3 mm, 5 mm and 7 mm.

Figure 111:
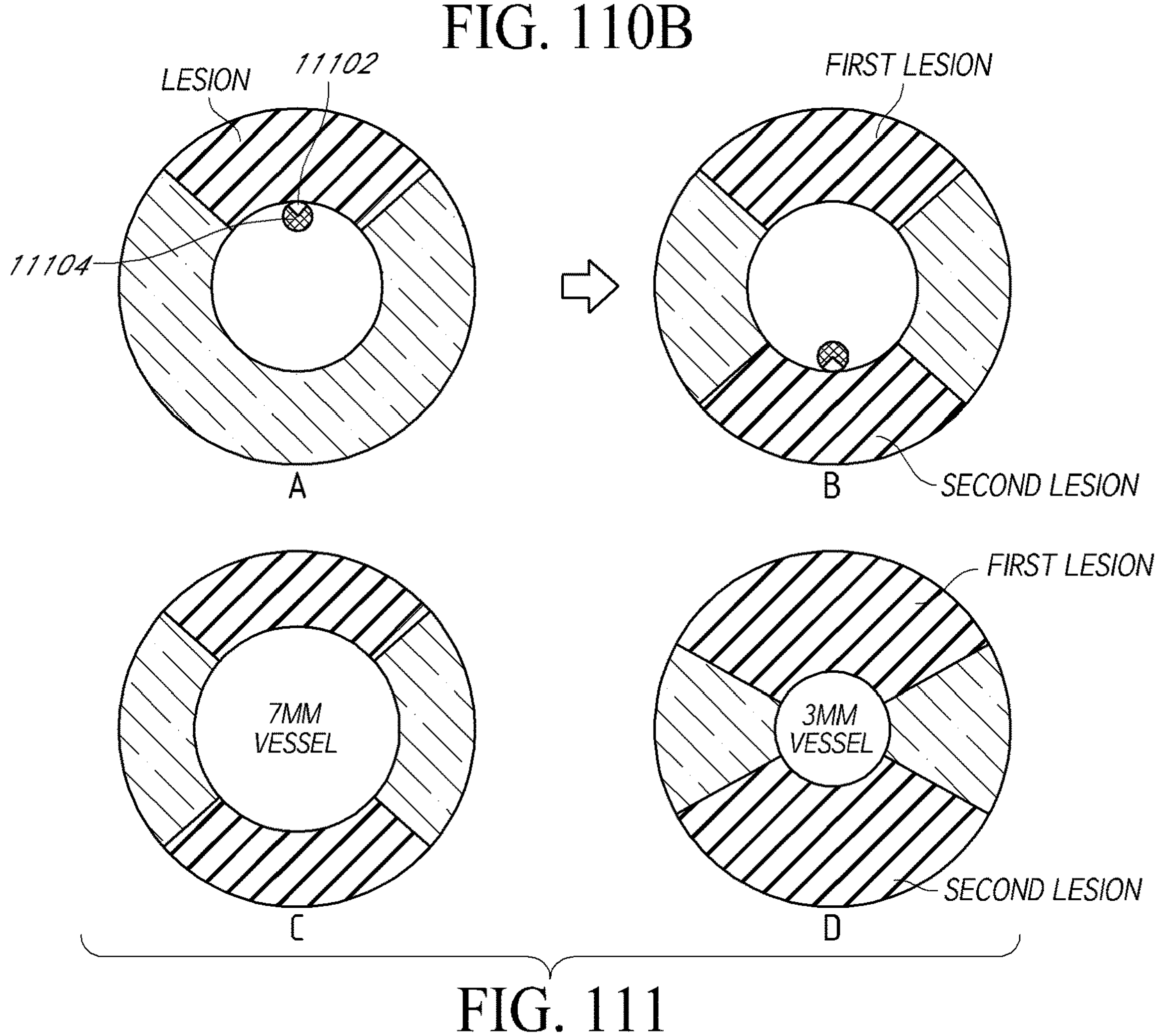

FIG. 111 schematically illustrates a metabolic neuromodulation system configured to provide controlled circumferentiality of lesions, thereby allowing for creation of two opposing lesions in the same plane while preventing or reducing the likelihood of circumferentiality or overlap of the two lesions. The neuromodulation system may comprise a single disposable catheter having an energy source 11102 (e.g., electrode) surrounded by shielding material or a shielding structure 11104 configured to cause directional energy delivery that creates an asymmetric lesion. The neuromodulation system may include instructions stored on a non-transitory computer-readable medium that, upon execution by a processor or other computing device, cause delivery of an energy protocol that allows for the creation of two opposing lesions in the same plane while ensuring that lesion borders do not touch or overlap across a range of representative vessel inner diameters (e.g., 3 mm-7 mm). FIG. 111 schematically illustrates examples of lesions formed for vessels having inner diameters of 3 mm (FIG. 111D), 5 mm (FIG. 111B) and 7 mm (FIG. 111C).

The embodiments illustrated in FIGS. 110 and 111 may allow for (1) increased lesion-to-length ratio without increase in risk, (2) a single ablation protocol to be developed for a full range of vessel diameters that ensures optimal (e.g., 50-80%) circumferentiality while eliminating or reducing the likelihood of risk of lesion tail overlap, (3) improved predictability of lesion circumferentiality regardless of vessel diameter, and (4) patients with smaller vessel (e.g., common hepatic artery) lengths to be treatment candidates. Other devices may also be configured to provide like performance across variable patient anatomy.

Figure 112:
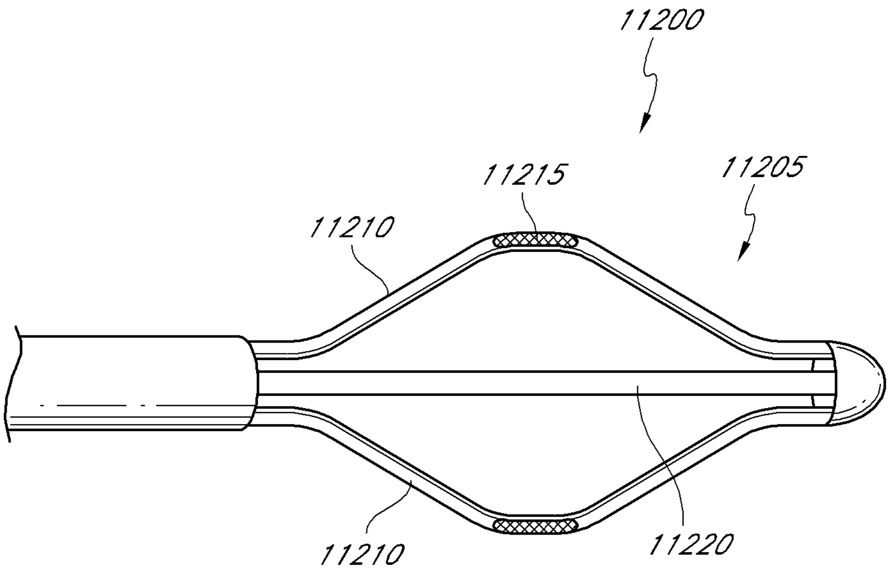

FIG. 112 illustrates an embodiment of an intravascular RF ablation catheter 11200 configured to prevent or reduce the likelihood of circumferentiality due to formation of multiple lesions within a single cross-sectional slice around a vessel wall. In one embodiment, the RF ablation catheter 11200 may provide assurance that energy is delivered in a manner that does not involve heating or ablation of more than 75% of the adventitia in any cross-sectional slice of the vessel. The RF ablation catheter 11200 comprises an expandable frame or scaffold 11205 configured to contact the vessel wall at spaced-apart locations around a circumference of the vessel. The expandable frame or scaffold 11205 comprises two treatment members or loops 11210 spaced 180 degrees apart from each other having electrodes 11215 positioned at vessel contact points along the members and two cooling members or loops 11220 spaced 180 degrees apart from each other and spaced 90 degrees apart from the two treatment members or loops 11210 having the electrodes 11215. The total number of members or loops of the expandable frame or scaffold 11205 may vary (e.g., 2, 4, 8) and the number of treatment members or loops 11210 and the number of cooling members or loops 11220 may vary. For example, the expandable frame or scaffold 11205 may comprise three treatment members or loops 11210 and one cooling member or loop 11220. The members or loops may comprise flexible splines, tines, arms, or the like. The expandable frame or scaffold may form a basket-like scaffold. The members or loops may be spaced in a uniform manner or a non-uniform manner. The treatment members and cooling members may alternate consecutively or may not alternate consecutively. In some embodiments, the catheter 11200 comprises one or more expandable members. The expandable member may be constructed of members that expand in a basket form. In the expanded form, the members may contact the vessel wall. The individual members of the basket can include at least one cooling channel configured to cool the vessel wall and at least one member with one or more RF electrodes that transfer RF energy into the vessel wall via contact. Multiple cooling members or electrode members can be configured to effect the desired ablation result. In one embodiment, the expandable member comprises a balloon that is expanded with cooling fluid and electrodes mounted on the surface of the balloon or an expandable basket that include RF electrodes mounted thereon. In various embodiments, the cooling fluid may be contained within the cooling members or released from the cooling members toward the vessel wall.

In accordance with several embodiments, lesions may be coordinated and positioned to provide continuous oblique circumferential lesions without creating a circumferential lesion at any one location or cross-sectional slice. In some embodiments, both the position and the extent of the lesions are controlled. The lesions may be placed 180 degrees apart and displaced axially along the vessel length. In some embodiments, the circumferential and axial extent of the lesion are controlled so that the margins of the lesions just intersect at a location 90 degrees on either side of the energy delivery element (e.g., electrode) positions. In some embodiments, a reference electrode may be positioned between the lesions to measure temperature or impedance to detect lesion intersection. In some embodiments, lesions are spaced between 1-50 mm apart (e.g., 1, 5, 10, 12, 15, 20, 25, 50 mm, and overlapping ranges thereof). Lesions may be overlapping or non-overlapping. In one embodiment, multiple foci or ablation sites, which may or may not overlap, are created to generate lines of thermal injury. The foci or sites can be spaced at 0.2 mm to 20 mm apart (e.g., 0.2 mm to 2 mm, 5 mm to 15 mm, 10 mm to 20 mm, 1 mm to 12 mm, or overlapping ranges thereof). In some embodiments, lesions are non-circumferential. In some embodiments, lesions are circumferential, including off-set circumferential, partially circumferential, and fully circumferential. In various embodiments, lesions may be spaced between 1 to 15 times the electrode diameter. For example, for electrodes having diameters of 1 or 2 mm, the electrodes may be spaced from 1 mm to 30 mm apart (e.g., 1 to 12 mm, 5 to 15 mm, 10 to 20 mm, and overlapping ranges thereof). Lesion spacing may be adjusted based on vessel diameter. The number of ablations may also vary based on vessel diameter.

Because catheter tip temperature and impedance alone may be poor indicators of tissue temperature or lesion size, tip temperature and impedance may both be measured during ablation in order to monitor lesion development and/or to confirm lesion formation, thereby providing confirmation of denervation of target nerves.

Initially, tip temperature increases and impedance decreases. Tissue conductivity increases with temperature up to a certain threshold (e.g., approximately 80 degrees Celsius). Above this threshold temperature, tissue may begin to contract and desiccate and impedance may start to increase instead of decrease. The decoupling of temperature and impedance may be used as an indication of lesion formation to confirm denervation. If impedance begins to increase without a corresponding decrease in tip temperature, this may be used as an end point or as confirmation of lesion formation. The time of decoupling of temperature and impedance may also be used as feedback to trigger other changes in an energy delivery protocol, such as decreasing power or increasing cooling.

Figure 113:
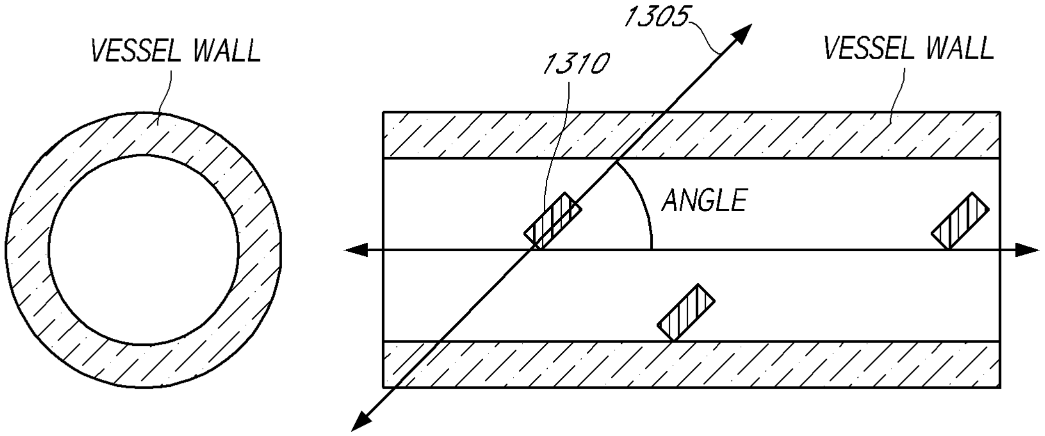

Turning to FIG. 113, a shaft or frame of an RF ablation catheter may be configured to ensure that a longitudinal axis 11305 of an electrode 11310 is not in the same plane as the vessel longitudinal axis 11315. For such a configuration, the longest dimension of the lesion created by the electrode may not be parallel to the vessel longitudinal axis 11315, as schematically illustrated in FIG. 113. In one embodiment, in order to orient an electrode 11310 off the vessel longitudinal axis 11315 for a catheter having a single distal electrode, a shaft of the catheter may be configured to form a spiral on the distal end, which may tilt the electrode 11310 out of the vessel's longitudinal plane. Alternatively, a pre-shaped shaft can be employed that shifts from a relatively straight to a non-straight orientation with the insertion or removal of a mandrel or guidewire. For multiple electrode catheter approaches, a basket or scaffold comprising a plurality of electrodes disposed around the basket or scaffold may, when actuated, be configured to hold the electrodes off axis.

Figure 114:
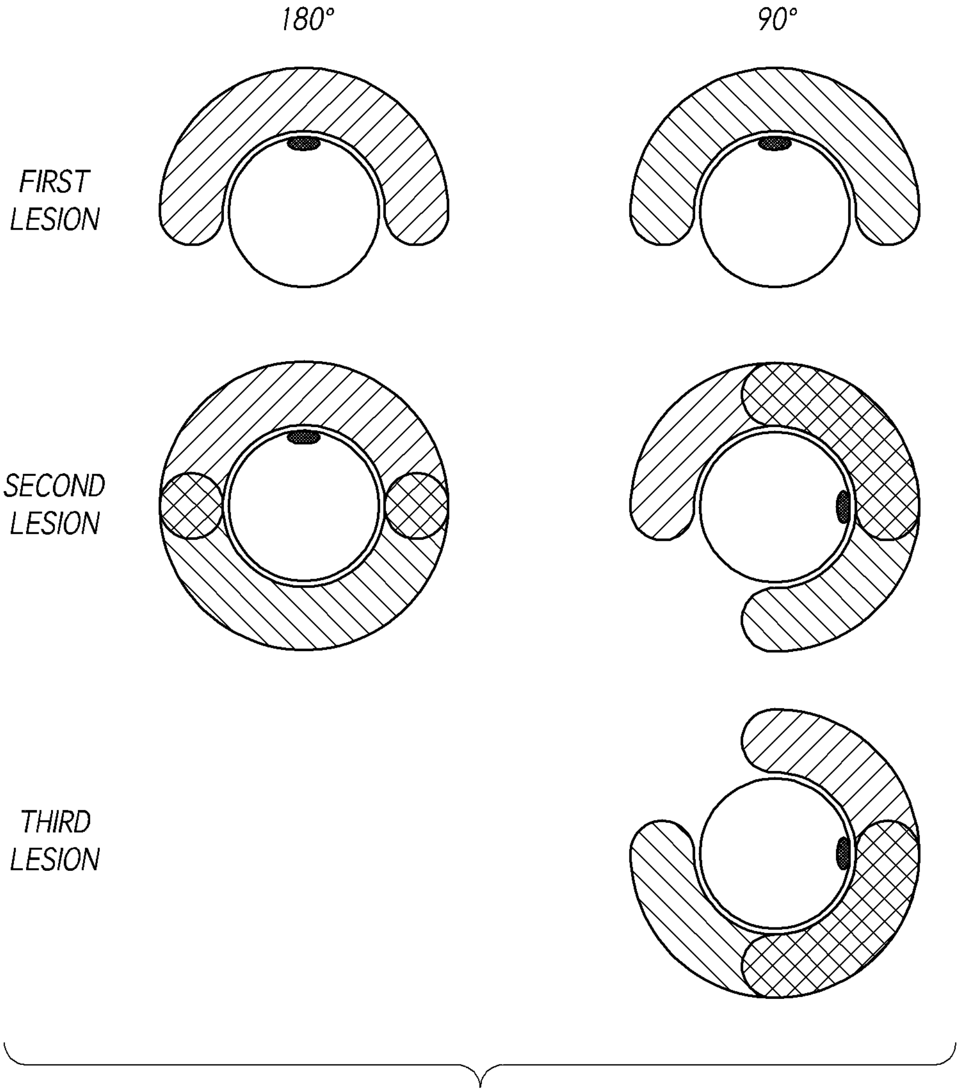

In some embodiments, complete circumferential ablation of a vessel may be prevented by spacing ablation sites radially at 90 degree intervals as opposed to at 180 degree intervals. FIG. 114 schematically illustrates ablation performed at 180 degree intervals and at 90 degree intervals. As shown, even if the 180 degree intervals are spaced apart axially along the length of the vessel, the "tails" of the ablation lesions could potentially overlap on both sides of the vessel (assuming that each ablation forms a lesion that extends around 180 degrees of the vessel circumference), thereby forming a complete circumferential lesion. When 90 degree intervals are used, there may potentially be overlap between adjacent lesions but the risk of complete vessel circumferentiality of the overall lesion composed of the multiple lesions is reduced. A single or multi-point RF ablation catheter may facilitate radial spacing of ablation sites by approximately 90 degrees and longitudinal spacing of at least one electrode length. In some embodiments, radial spacing of the ablation sites by 90 degrees causes less than complete circumferential ablation of the vessel (e.g., 75%-95%, 70%-90%, 65%-80%, 75%-90%, or overlapping ranges thereof).

2. Ultrasound

In some embodiments, an energy delivery system delivers ultrasonic energy to modulate (e.g., ablate, stimulate) sympathetic nerve fibers in the hepatic plexus. For example, the energy delivery system can employ focused ultrasonic energy such as high-intensity focused ultrasonic (HIFU) energy or low-intensity focused ultrasonic (LIFU) energy to ablate sympathetic nerve fibers. In some embodiments, the energy delivery system includes a neuromodulation device (e.g., ablation catheter) connected to one or more ultrasound transducers. For example, the ultrasound transducer(s) can deliver ultrasonic energy to one or more target sites to modulate (e.g., ablate) sympathetic nerve fibers in the hepatic plexus or other nerves described herein (e.g., celiac plexus or nerves innervating, surrounding or in proximity to the liver, pancreas or duodenum. The ultrasonic energy can be controlled by dosing, pulsing, or frequency selection. In some embodiments, HIFU energy can advantageously be focused at a distant point to reduce potential disturbance of the tissue of the blood vessel (e.g., the intima and the media layers) or surrounding tissues. HIFU energy can advantageously reduce the precision required for positioning of the neuromodulation device. The one or more ultrasound transducers can be refocused during treatment to increase the number of treatment sites or to adjust the depth of treatment. In some embodiments, the use of HIFU energy can result in increased concentrations of heat for a shorter duration and can simultaneously focus energy at multiple focal points, thereby reducing the total time required to administer the neuromodulation procedure.

In some embodiments, the energy delivery system comprises a focused ultrasound (e.g., HIFU) ablation catheter and an acoustic frequency generator. The ablation catheter can be steerable from outside of the subject using a remote mechanism. The distal end of the ablation catheter can be flexible to allow for deflection or rotational freedom about an axis of the catheter shaft to facilitate positioning within a hepatic or other artery. For example, the one or more ultrasound transducers, which may be single element or multiple element transducers, against the intima of the artery or spaced at a distance from the intimal layer. In some embodiments, the ablation catheter comprises focusing (e.g., parabolic) mirrors or other reflectors, gas-filled or liquid-filled balloons, and/or other structural focusing elements to facilitate delivery of the ultrasonic energy. The one or more transducers can be cylindrical, rectangular, elliptical, or any other shape. The ablation catheter can comprise sensors and control circuits to monitor temperature and prevent overheating or to acquire other data corresponding to the one or more ultrasound transducers, the vessel wall and/or the blood flowing across the ultrasound transducer. In some embodiments, the sensors provide feedback to control delivery of the ultrasonic energy. In some embodiments, the ultrasound energy is controlled such that delivery of the ultrasound energy heats the arterial tissue in the range of about 40 to about 90° C. (e.g., 40° C. to 60° C., 60° C. to 75° C., 65° C. to 80° C., 60° C. to 90° C., or overlapping ranges thereof. In some embodiments, the temperature can be less than 40° C. or greater than 90° C.

The frequencies used to ablate the sympathetic nerves can vary based on expected attenuation, the containment of the beam both laterally and axially, treatment depths, type of nerve, and/or other parameters. In some embodiments, the frequencies used range from about 20 KHz to about 20 MHZ, from about 500 kHz to about 10 MHz, from about 1 MHz to about 5 MHZ, from about 2 MHz to about 6 MHZ, from about 3 MHz to about 8 MHZ, less than 20 kHz, greater than 20 MHz or overlapping ranges thereof. However, other frequencies can be used without limiting the scope of the disclosure. In some embodiments, the HIFU catheter can also transmit frequencies that can be used for imaging purposes or for confirmation of successful ablation or denervation purposes. In some embodiments, the HIFU catheter delivers energy having parameters such that cavitation does not occur. The average ultrasound intensity for ablation of sympathetic nerve fibers in the hepatic plexus, celiac plexus or other sympathetic nerve fibers can range from about 1 W/cm$^2$ to about 10 kW/cm$^2$, from about 500 W/cm$^2$ to about 5 kW/cm$^2$, from about 2 W/cm$^2$ to about 8 kW/cm$^2$, from about 1 kW/cm$^2$ to about 10 kW/cm$^2$, from about 25 W/cm$^2$ to about 200 W/cm$^2$, from about 200 W/cm$^2$ to about 1 MW/cm$^2$, less than 1 W/cm$^2$, greater than 10 KW/cm$^2$, or overlapping ranges thereof. Power levels may range from about 25 W/cm$^2$ to about 1 MW/cm$^2$ (depending on the intensity of the ultrasound energy and/or other parameters). The ultrasound energy can be continuous or pulsed. The power levels or energy density levels used for pulsed ultrasound energy may be higher than the power levels used for continuous ultrasound energy. In some embodiments, ultrasound energy delivery devices or systems may deliver energy from outside the body (e.g., extracorporeally or transcutaneously), extravascularly but within the body, or intravascularly.

The treatment time for each target site (e.g., ablation site) can range from about 5 seconds to about 120 seconds, from about 10 seconds to about 60 seconds, from about 20 seconds to about 80 seconds, from about 30 seconds to about 90 seconds, less than 10 seconds, greater than 120 seconds, one minute to fifteen minutes, ten minutes to one hour, or overlapping ranges thereof. In accordance with several embodiments, the parameters used are selected to disable, block, cease or otherwise disrupt conduction of sympathetic nerves (e.g., of the hepatic plexus) for at least several months while creating minimal damage of the arterial walls or surrounding tissues or organs.

Figure 115A:
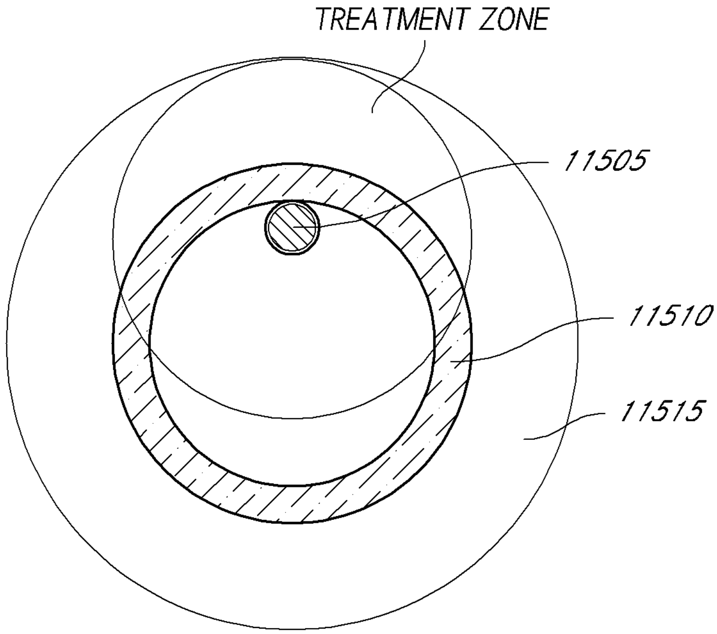
FIGS. 115A and 115B schematically illustrate embodiments of intravascular ablation catheters configured to prevent vessel circumferentiality during ablation therapy.
Figure 115B:
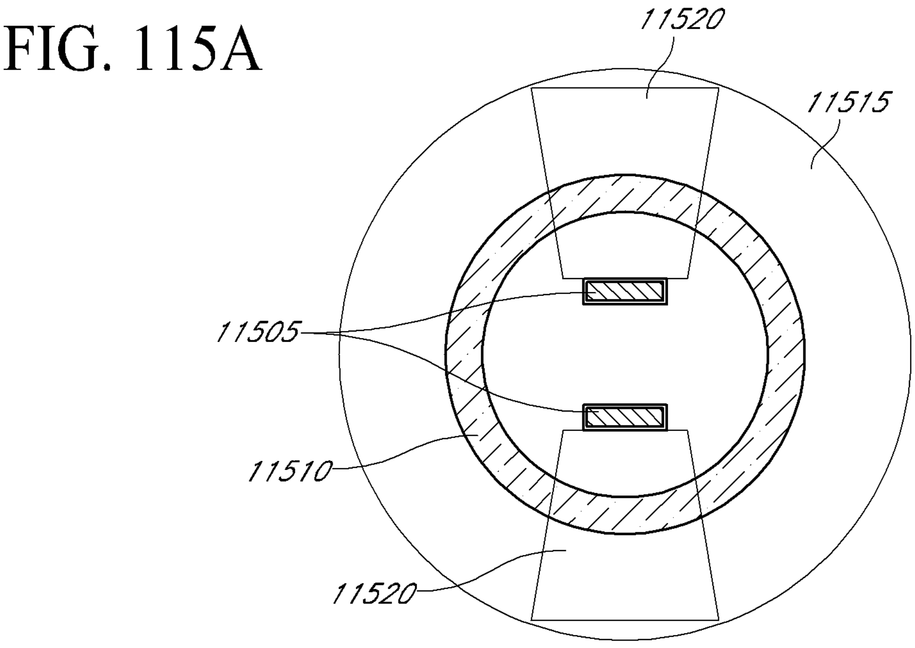

Ultrasound energy delivery devices may also be used to reduce the likelihood of forming a complete circumferential lesion around a target vessel. FIGS. 115A and 115B schematically illustrate embodiments of components of intravascular ablation catheters configured to prevent vessel circumferentiality during ablation therapy. FIG. 115A schematically illustrates that an intravascular ablation catheter may comprise a transducer 11505 configured to radially emit ultrasound energy near the distal tip of the ablation catheter. The construction of the ablation catheter may be such that the transducer 11505 is always held off the center of the vessel, similar to the RF ablation catheter approach described in connection with FIG. 113. In some embodiments, the radial emission primarily involves an arc of the vessel wall 11510 and adventitia 11515 (which may be considered an outer layer of the vessel wall 11510) closest to the transducer 11505. Optimization of energy level can occur such that the wall opposite of where the transducer 11505 is located is not involved in the ablation arc. In some embodiments, the intravascular ablation catheter comprises a balloon that positions the transducer 11505 off the center axis of the balloon and vessel. Other embodiments include a concentric balloon that is smaller than the vessel diameter or a catheter comprising a deflectable shaft that holds the transducer off axis. In one embodiment, the catheter comprises a pre-shaped distal shaft that orients the transducer off axis. For example, the shaft could be held straight by a guide wire or mandrel and, once removed, the shaft may deflect off axis. As another example, a removable pre-shaped mandrel could be utilized.

FIG. 115B schematically illustrates an embodiment of an intravascular ablation catheter comprising one or more flat transducers 11505 configured to emit ultrasound energy near the distal tip of the catheter. The transducers 11105 may be placed radially and/or longitudinally along the shaft of the catheter in manner that ensures the ablation pattern formed by all of the transducers does not involve more than 75% of the vessel circumference at any vessel cross-section. FIG. 115B schematically illustrates energy cones 11520 formed by emission of ultrasound energy from the two transducers 11505. In various embodiments, tilted ultrasound transducers may be used to create a narrow oblique circumferential lesion to prevent negative remodeling from occurring in any one circumferential plane. The ultrasound energy may be beam-shaped or intensity-modulated to maintain lesion depth.

3. Lasers

In several embodiments, lasers may be used to modulate (e.g., ablate) sympathetic nerve activity of the hepatic plexus or other nerves innervating the liver. Although lasers are not generally used for arterial nerve ablation in other arteries, the wall thickness of the hepatic arteries is substantially less than the thickness of other arterial structures, thereby rendering laser energy delivery possible. In some embodiments, one or more lasers are used to ablate nerves located within about 2 mm of the intimal surface, within about 1.5 mm of the intimal surface, within about 1 mm of the intimal surface, or within about 0.5 mm of the intimal surface of a hepatic artery. In some embodiments, chromophore staining of sympathetic fibers is performed to selectively enhance sympathetic nerve absorption of laser energy. In some embodiments, balloons are used to stretch the hepatic artery, thereby thinning the arterial wall and decreasing the depth from the intimal surface to the sympathetic nerve fibers, and thereby improving the delivery of the laser energy.

Other forms of optical or light energy may also be used. The light source may include an LED light source, an electroluminescent light source, an incandescent light source, a fluorescent light source, a gas laser, a chemical laser, a dye laser, a metal-vapor laser, a solid state laser, a semiconductor laser, a vertical cavity surface emitting laser, or other light source. The wavelength of the optical or laser energy may range from about 300 nm to about 2000 nm, from about 500 nm to about 1100 nm, from about 600 nm to about 1000 nm, from about 800 nm to about 1200 nm, from about 1000 nm to about 1600 nm, or overlapping ranges thereof.

4. Externally-Initiated

Figure 18:
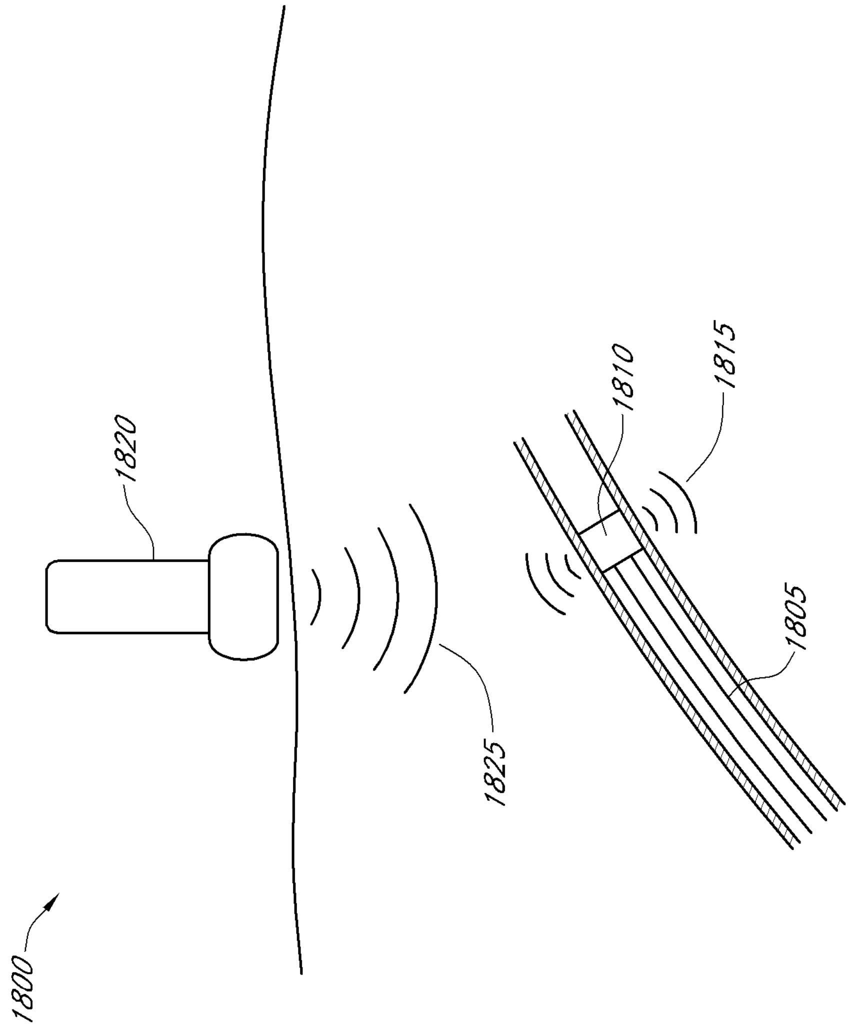
FIG. 18 illustrates an embodiment of a microwave-based ablation catheter system.

In accordance with various embodiments, energy delivery is initiated from a source external to the subject (e.g., extracorporeal activation). FIG. 18 illustrates an embodiment of a microwave-based energy delivery system 1800. The microwave-based energy delivery system 1800 comprises an ablation catheter 1805 and a microwave generating device 1820. In some embodiments, other energy sources may also be delivered externally.

In some embodiments, the ablation catheter 1805 comprises a high conductivity probe 1810 disposed at its distal end. In operation, the ablation catheter 1805 may be inserted into a target vessel and positioned such that the high conductivity probe 1810 is proximate to the site targeted for ablation. The microwave generating device 1820 is located outside a subject's body and positioned such that focused microwaves 1825 are delivered towards the target vessel and the high conductivity probe 1810. In several embodiments, when the delivered focused microwaves 1825 contact the high conductivity probe 1810, they induce eddy currents within the high conductivity probe 1810, thereby heating the high conductivity probe 1810. The thermal energy 1815 generated from the heating of the high conductivity probe can heat the target tissue through conductive heat transfer. In some embodiments, the thermal energy 1815 generated is sufficient to ablate nerves within or disposed on the target tissue (e.g., vessel wall). In various embodiments, the high conductivity probe 1810 has a conductivity greater than 10^3 Siemens/meter.

Figure 19:
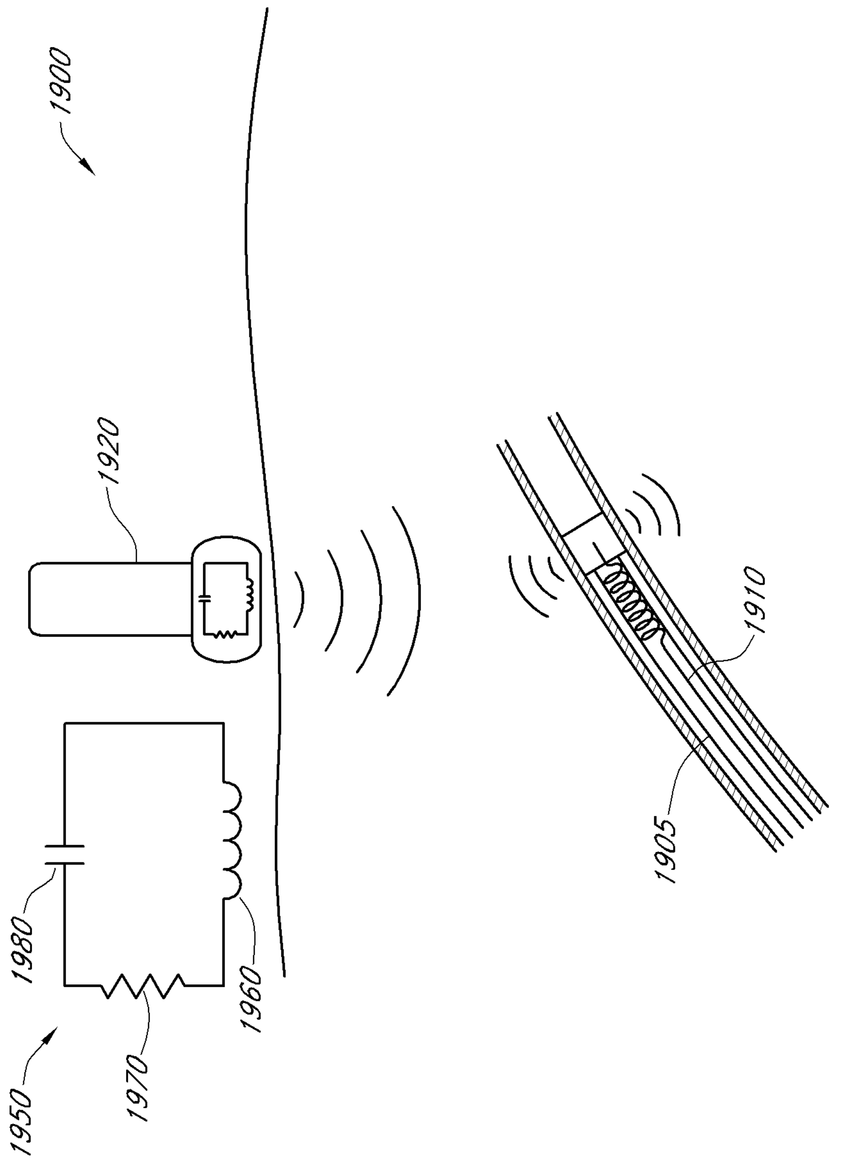
FIG. 19 illustrates an embodiment of an induction-based ablation catheter system.

FIG. 19 illustrates an embodiment of an induction-based energy delivery catheter system 1900. In the illustrated embodiment, the induction-based energy delivery system 1900 comprises a catheter 1905, an induction coil 1910, an external inductor power circuit 1950, an inductor 1960, a resistor 1970, and a capacitor 1980. In one embodiment, the induction coil 1910 is disposed at the distal end of the catheter 1905. In operation, the induction coil 1910 may act as an inductor to receive energy from the external inductive power circuit 1950. In some embodiments, the external inductive power circuit 1950 is positioned such that the inductor 1960 is adjacent the induction coil 1910 within a sufficient induction range. In some embodiments, current is delivered through the external inductive power circuit 1950, thereby causing current to flow in the induction coil 1910 and delivering subsequent ablative energy to surrounding tissues. In one embodiment, an induction coil is used in combination with any of the windowed catheter devices described herein (such as the windowed catheter devices described in connection with FIGS. 16A and 16B). For example, the induction coil may be placed within a lumen of a catheter or sleeve having one or more windows configured to permit the selective delivery of energy to the target tissue.

In some embodiments, one or more synthetic emboli may be inserted within a target vessel and implanted or lodged therein (at least temporarily). The synthetic emboli may advantageously be sized to match the anatomy of the target vessel (e.g., based on angiography of the target location and vessel diameter). The synthetic emboli may be selected based on a measured or estimated dimension of the target vessel. In one embodiment, an energy delivery catheter is coupled to the one or more synthetic emboli inserted within a target vessel to deliver energy. In some embodiments, energy is delivered transcutaneously to the synthetic emboli using inductive coupling as described in connection with FIG. 21, thereby eliminating the need for an energy delivery catheter. The synthetic emboli may comprise an induction coil and a plurality of electrodes embedded within an insulating support structure comprised of high dielectric material. After appropriate energy has been delivered to modulate nerves associated with the target vessel, the one or more emboli may be removed.

In several embodiments of the invention, the energy-based delivery systems comprise cooling systems that are used to, for example, reduce thermal damage to regions surrounding the target area. For example, cooling may lower (or maintain) the temperature of tissue at below a particular threshold temperature (e.g., at or between 40 to 50 degrees Celsius), thereby preventing or reducing cell necrosis. Cooling balloons or other expandable cooling members are used in some embodiments. In one embodiment, ablation electrodes are positioned on a balloon, which is expanded using cooling fluid. In some embodiments, cooling fluid is circulated through a delivery system (e.g., a catheter system). In some embodiments, cooling fluid (such as pre-cooled saline) may be delivered (e.g., ejected) from a catheter device in the treatment region. In further embodiments, cooling fluid is continuously or intermittently circulated internally within the catheter device to cool the endothelial wall in the absence of sufficient blood flow.

Extracorporeal neuromodulation may include delivery of ultrasound energy (e.g., high-intensity focused ultrasound energy or low-intensity ultrasound energy) or other forms of radiative energy other than microwave (e.g., X-ray or gamma radiation). In some embodiments, an ultrasound system is configured to deliver ultrasound at a frequency between about 200 kHz and about 20 MHZ (e.g., between 200 kHz and 2 MHZ, between 400 kHz and 4 MHZ, between 1 MHz and 10 MHZ, between 5 MHz and 20 MHZ, or overlapping ranges thereof). The parameters of the ultrasound energy may include any of the parameters and ranges of parameters described elsewhere herein. In various embodiments, ultrasound energy may be directed towards the target tissue by means of a single transducer or a plurality of transducers, which may or may not be placed in contact with skin of a patient. The one or more transducers are configured to focus energy at a desired location. In some embodiments the desired, or target, location is defined by external imaging means. The foci or other target locations may be determined by any of the image-guided techniques described herein. In some embodiments, an internal catheter or other devices (e.g., sensors, beacons or emitters) positioned at or in the proximity of the foci or other target locations may be provided to assist in targeting or defining the target locations. The target catheter may directly sense the transmitted energy. In other embodiments, the target catheter may respond to the transmitted energy by reflecting or retransmitting energy to an external transducer. The external transducer may be the transmitting transducer or a second transducer.

The focus or foci of the ultrasound system may be focused on one or more nerves innervating a liver, pancreas, duodenum or other organ (e.g., nerves of the hepatic plexus, celiac plexus, celiac ganglion). The delivery of energy may be controlled manually or automatically according preconfigured treatment parameters determined by a controller, processor or other computing device (e.g., based on execution of instructions stored in memory).

In addition to external treatment, several embodiments disclosed herein (both internal and external treatment) can be used with imaging (for example, as described elsewhere herein). In some embodiments of the invention, image guidance is provided by external ultrasound imaging. External imaging may provide direct representation of a target device (e.g. catheter) and the surrounding tissues. External imaging may also be used to measure the temperature of tissues. Energy delivery may be adjusted or controlled based on tissue temperature. In some embodiments, the target catheter may be configured to improve visualization. In some embodiments, materials, coatings or surface treatments are provided to increase diffuse reflection of ultrasound waves. In other embodiments, transducers are provided to detect and/or retransmit ultrasound energy to an external transducer. In some embodiments, transducers on the target device (e.g., catheter) transmit or detect ultrasound waves transmitted to or from reference transducers. References may be internal or external. The position of the target device can be reconstructed and compared to reference images or maps. In other embodiments, the catheter may increase the intensity of the externally transmitted energy by resonating and retransmitting energy, or the catheter may transmit energy directly to augment of modify the intensity of external energy delivery. In various embodiments, imaging may be provided via an endoscope or other body-inserted imaging device placed in the stomach, esophagus, colon or intestine. In some embodiments, the target device comprises polymer coatings or surface texture that facilitate scattering. The transducers or transponders may resonate at a different frequency from an excitation wave.

In some embodiments, image guidance is provided by external magnetic resonance (MR) imaging or X-ray imaging. External imaging may provide direct representation of the target device (e.g., catheter) and surrounding tissues. External imaging may also measure the temperature of tissues. Energy delivery may be adjusted or controlled based on tissue temperature. In some embodiments, the target device may be configured to improve visualization. In some embodiments, materials, coatings or surface treatments are provided to alter the relaxation of adjacent tissues in a manner that is visible in an MR or X-ray image. In some embodiments, antennas or coils are provided to detect or alter locally emitted energy (e.g., RF energy) that is used to reconstruct the image. In some embodiments, local emissions (such as RF) detected by coils or antennas on the target device (e.g., catheter) are used to calculate the position of the device. In some embodiments, T1 agents accelerate relaxation of polarized hydrogen nuclei, which may appear bright on T1 images, and T2 agents provide magnetic inhomogeneities that may accelerate T2 relaxation (dephasing), which may appear as dark areas on images. Imaging effects may be facilitated by coatings or inherent properties of components (e.g., materials such as metal) of a target device to be visualized (e.g., catheter).

D. Steam/Hot Water Neuromodulation

Figure 20:
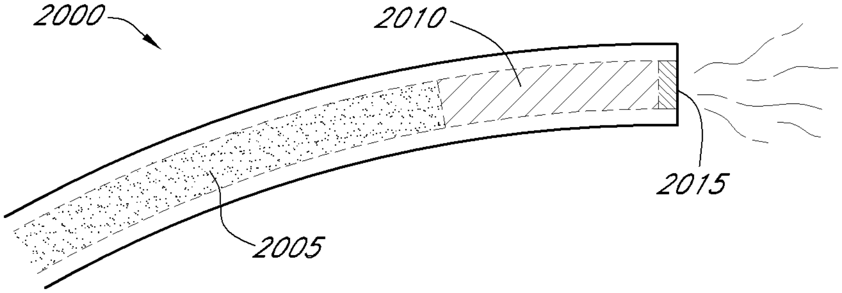
FIG. 20 illustrates an embodiment of a steam ablation catheter.

FIG. 20 illustrates an embodiment of a steam ablation catheter 2000. In the illustrated embodiment, the steam ablation catheter 2000 comprises a water channel 2005, a steam generating head 2010, and a steam outlet 2015. In operation, water may be forced through the water channel 2005 and caused to enter the steam generating head 2010. In one embodiment, the steam generating head 2010 converts the water into steam, which exits the steam ablation catheter 2000 through the steam outlet 2015.

In some embodiments, steam is used to ablate or denervate the target anatomy (e.g., hepatic arteries and nerves associated therewith). In accordance with several embodiments, water is forced through the ablation catheter 2000 and out through the steam generating head 2010 (which converts the water into steam) and the steam is directed to an ablation target. The steam ablation catheter 2000 may comprise one or more window along the length of the catheter body.

Figure 21:
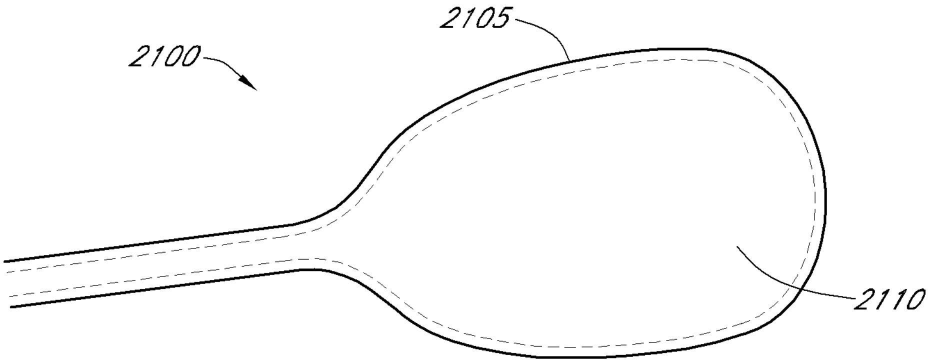
FIG. 21 illustrates an embodiment of a hot water balloon ablation catheter.

FIG. 21 illustrates an embodiment of a hot fluid balloon ablation catheter 2100. In the illustrated embodiment, the hot fluid balloon ablation catheter 2100 comprises an inflatable balloon 2105. In some embodiments, the inflatable balloon 2105 is filled with a temperature variable fluid 2110. In accordance with several embodiments, hot water is the temperature variable fluid 2110 used to fill the inflatable balloon 2105. The heat generated from the hot fluid within the inflatable balloon may be sufficient to ablate or denervate the target anatomy (e.g., hepatic arteries and nerves associated therewith). In some embodiments, the inflatable balloon 2105 is inserted to the ablation site and inflated with scalding or boiling fluid (e.g., water), thereby heating tissue surrounding the inflatable balloon 2105 sufficient to ablate or denervate the tissue. In some embodiments, the hot fluid within the balloon 2105 is within the temperature range of about 120° F. to about 212° F., from about 140° F. to about 212° F., from about 160° F. to about 212° F., from about 180° F. to about 212° F., about 200° F. to about 212° F., or overlapping ranges thereof. In some embodiments, the balloon ablation catheter 2100 comprises a temperature sensor and fluid (e.g., water) at different temperatures may be inserted and withdrawn as treatment dictates. In some embodiments, the inflatable balloon 2105 is made out of polyurethane or any other heat-resistant inflatable material.

E. Chemical Neuromodulation

In some embodiments, drugs are used alone or in combination with another modality to cause neuromodulation of any of the nerves described herein. Drugs include, but are not limited to, muscarinic receptor agonists, anticholinesterase agents, nicotinic receptor agonists, and nicotine receptor antagonists. Drugs that directly affect neurotransmission synthesis, degradation, or reuptake are used in some embodiments.

In some embodiments, drugs (either alone or in combination with energy modalities) can be used for neuromodulation. For example, a delivery device (e.g., catheter) may have one or more internal lumens. In some embodiments, one or more internal lumens are in fluid communication with a proximal opening and with a distal opening of the delivery catheter. In some embodiments, at least one distal opening is located at the distal end of the delivery catheter. In some embodiments, at least one proximal opening is located at the proximal end of the delivery catheter. In some embodiments, the at least one proximal opening is in fluid communication with at least one reservoir.

In some embodiments, at least one reservoir is a drug reservoir that holds drugs or therapeutic agents capable of modulating sympathetic nerve fibers in the hepatic plexus. In some embodiments, a separate drug reservoir is provided for each drug used with the delivery catheter system. In other embodiments, at least one drug reservoir may hold a combination of a plurality of drugs or therapeutic agents. Any drug that is capable of modulating nerve signals may be used in accordance with the embodiments disclosed herein. In some embodiments, neurotoxins (e.g., botulinum toxins) are delivered to the liver, pancreas, or other surrounding organs or nerves associated therewith. In some embodiments, neurotoxins (e.g., botulinum toxins) are not delivered to the liver, pancreas, or other surrounding organs or nerves associated therewith.

In some embodiments, a delivery catheter system includes a delivery device that delivers one or more drugs to one or more target sites. For example, the delivery device may be a pump. Any pump, valve, or other flow regulation member capable of delivering drugs through a catheter may be used. In some embodiments, the pump delivers at least one drug from the at least one drug reservoir through the at least one internal lumen of the catheter delivery system to the one or more target sites.

In some embodiments, the pump selects the drug dosage to be delivered from the reservoir to the target site(s). For example, the pump can selectively vary the total amount of one or more drugs delivered as required for neuromodulation. In some embodiments, a plurality of drugs is delivered substantially simultaneously to the target site. In other embodiments, a plurality of drugs is delivered in series. In other embodiments, a plurality of drugs is delivered substantially simultaneously and at least one other drug is delivered either before or after the plurality of drugs is delivered to the target site(s). Drugs or other agents may be used without delivery catheters in some embodiments. According to several embodiments, drugs may have an inhibitory or stimulatory effect.

In some embodiments, an ablation catheter system uses chemoablation to ablate nerve fibers (e.g., sympathetic nerve fibers in the hepatic plexus). For example, the ablation catheter may have one or more internal lumens. In some embodiments, one or more internal lumens are in fluid communication with a proximal opening and with a distal opening. In some embodiments, at least one distal opening is located in the distal end of an ablation catheter. In some embodiments, at least one proximal opening is located in the proximal end of the ablation catheter. In some embodiments, at least one proximal opening is in fluid communication with at least one reservoir.

In some embodiments, at least one reservoir holds and/or stores one or more chemicals capable of disrupting (e.g., ablating, desensitizing, destroying) nerve fibers (e.g., sympathetic nerve fibers in the hepatic plexus). In some embodiments, a separate reservoir is provided for each chemical used with the ablation catheter system. In other embodiments, at least one reservoir may hold any combination of chemicals. Any chemical that is capable of disrupting nerve signals may be used in accordance with the embodiments disclosed herein. For example, one or more chemicals or desiccants used may include phenol or alcohol, guanethidine, zinc sulfate, nanoparticles, radiation sources for brachytherapy, neurostimulants (e.g., methamphetamine), and/or oxygen radicals (e.g., peroxide). However, any chemical that is capable of ablating sympathetic nerve fibers in the hepatic plexus may be used in accordance with the embodiments disclosed herein. In some embodiments, chemoablation is carried out using a fluid delivery needle delivered percutaneously, laparascopically, or via an intravascular approach.

F. Cryomodulation

In some embodiments, the invention comprises cryotherapy or cryomodulation. In one embodiment, the ablation catheter system uses cryoablation techniques for neuromodulation. In one embodiment, cryoablation is used to ablate sympathetic nerve fibers in the hepatic plexus. For example, the ablation catheter may have one or more internal lumens. In some embodiments, one or more internal lumens are in fluid communication with a proximal opening. In some embodiments, at least one proximal opening is located in the proximal end of the ablation catheter. In some embodiments, at least one proximal opening is in fluid communication with at least one reservoir (e.g., a cryochamber). In some embodiments, the at least one reservoir holds one or more coolants including but not limited to liquid nitrogen. The ablation catheter can comprise a feed line for delivering coolant to a distal tip of the ablation catheter and a return line for returning spent coolant to the at least one reservoir. The coolant may reach a temperature sufficiently low to freeze and ablate sympathetic nerve fibers in the hepatic plexus. In some embodiments, the coolant can reach a temperature of less than 75 degrees Celsius below zero, less than 80 degrees Celsius below zero, less than 90 degrees Celsius below zero, or less than 100 degrees Celsius below zero.

In some embodiments, the ablation catheter system includes a delivery device that controls delivery of one or more coolants through one or more internal lumens to the target site(s). For example, the delivery device may be a pump. Any pump, valve or other flow regulation member that is capable of delivering coolants through a catheter may be used. In some embodiments, the pump delivers at least one coolant from at least one reservoir, through at least one proximal opening of the catheter body, through at least one internal lumen of the catheter body, and to the distal end of the ablation catheter (e.g., via a feed line or coolant line).

In some embodiments, the target nerves may be irreversibly cooled using an implantable Peltier cooling device. In some embodiments, an implantable cooling device is configured to be refilled with an inert gas that is injected at pressure into a reservoir within the implantable device and then released selectively in the vicinity of the target nerves, cooling them in an adiabatic fashion, thereby slowing or terminating nerve conduction (either temporarily or permanently). In some embodiments, local injections or infusion of ammonium chloride is used to induce a cooling reaction sufficient to alter or inhibit nerve conduction. In some embodiments, delivery of the coolant to the distal end of the ablation catheter, which may comprise one or more ablation electrodes or a metal-wrapped cylindrical tip, causes denervation of sympathetic nerve fibers in the hepatic plexus. For example, when the ablation catheter is positioned in or near the proper hepatic artery or the common hepatic artery, the temperature of the coolant may cause the temperature of the surrounding area to decrease sufficiently to denervate sympathetic nerve fibers in the hepatic plexus. In some embodiments, cryoablation is performed using a cryocatheter. Cryoablation can alternatively be performed using one or more probes alone or in combination with a cryocatheter.

The treatment time for each target ablation site can range from about 5 seconds to about 100 seconds, 5 minutes to about 30 minutes, from about 10 minutes to about 20 minutes from about 5 minutes to about 15 minutes, from about 10 minutes to about 30 minutes, less than 5 seconds, greater than 30 minutes, or overlapping ranges thereof. In accordance with several embodiments, the parameters used are selected to disable, block, cease or otherwise disrupt conduction of, for example, sympathetic nerves of the hepatic plexus. The effects on conduction of the nerves may be permanent or temporary. One, two, three, or more cooling cycles can be used.

In some embodiments, any combination of drug delivery, chemoablation, and/or cryoablation is used for neuromodulation of any of the nerves described herein, and may be used in combination with an energy modality. In several embodiments, cooling systems are provided in conjunction with energy delivery to, for example, protect tissue adjacent the nerve fibers.

III. Image Guidance, Mapping and Selective Positioning

Image guidance techniques may be used in accordance with several of the embodiments disclosed herein. For example, a visualization element (e.g., a fiber optic scope) may be provided in combination with a catheter-based energy or fluid delivery system to aid in delivery and alignment of a neuromodulation catheter. In other embodiments, fluoroscopic, ultrasound, Doppler or other imaging is used to aid in delivery and alignment of the neuromodulation catheter. In some embodiments, radiopaque markers are located at the distal end of the neuromodulation catheter or at one or more locations along the length of the neuromodulation catheter. For example, for catheters having electrodes, at least one of the electrodes may comprise a radiopaque material. Computed tomography (CT), fluorescence, radiographic, thermography, Doppler, optical coherence tomography (OCT), intravascular ultrasound (IVUS), and/or magnetic resonance (MR) imaging systems, with or without contrast agents or molecular imaging agents, can also be used to provide image guidance of a neuromodulation catheter system. In some embodiments, the neuromodulation catheter comprises one or more lumens for insertion of imaging, visualization, light delivery, aspiration or other devices.

In accordance with some embodiments, image or visualization techniques and systems are used to provide confirmation of disruption (e.g., ablation, destruction, severance, denervation) of the nerve fibers being targeted. In some embodiments, the neuromodulation catheter comprises one or more sensors (e.g., sensor electrodes) that are used to provide confirmation of disruption (e.g., ablation, destruction, severance, denervation) of communication of the nerve fibers being targeted.

In some embodiments, the sympathetic and parasympathetic nerves are mapped prior to modulation. In some embodiments, a sensor catheter is inserted within the lumen of the vessel near a target modulation area. The sensor catheter may comprise one sensor member or a plurality of sensors distributed along the length of the catheter body. After the sensor catheter is in place, either the sympathetic nerves or the parasympathetic nerves may be stimulated. In some embodiments, the sensor catheter is configured to detect electrical activity. In some embodiments, when the sympathetic nerves are artificially stimulated and parasympathetic nerves are left static, the sensor catheter detects increased electrical activity and the data obtained from the sensor catheter is used to map the sympathetic nervous geometry. In some embodiments, when the parasympathetic nerves are artificially stimulated and sympathetic nerves are left static, the sensor catheter detects increased electrical activity and the data obtained from the sensor catheter is used to map the parasympathetic nervous geometry. In some embodiments, mapping the nervous geometry using nervous stimulation and the sensor catheter advantageously facilitates improved or more informed selection of the target area to modulate, leaving select nerves viable while selectively ablating and disrupting others. As an example of one embodiment, to selectively ablate sympathetic nerves, the sympathetic nerves may be artificially stimulated while a sensor catheter, already inserted, detects and maps areas of increased electrical activity. To disrupt the sympathetic nerves, only the areas registering increased electrical activity may need to be ablated.

In one embodiment, a method of targeting sympathetic nerve fibers involves the use of electrophysiology mapping tools. While applying central or peripheral nervous signals intended to increase sympathetic activity (e.g., by administering noradrenaline or electrical stimulation), a sensing catheter may be used to map the geometry of the target vessel (e.g., hepatic artery) and highlight areas of increased electrical activity. An ablation catheter may then be introduced and activated to ablate the mapped areas of increased electrical activity, as the areas of increased electrical activity are likely to be innervated predominantly by sympathetic nerve fibers. In some embodiments, nerve injury monitoring (NIM) methods and devices are used to provide feedback regarding device proximity to sympathetic nerves located perivascularly. In one embodiment, a NIM electrode is connected laparascopically or thorascopically to sympathetic ganglia.

In some embodiments, to selectively target the sympathetic nerves, local conductivity may be monitored around the perimeter of the hepatic artery. Locations corresponding to maximum impedance are likely to correspond to the location of the sympathetic nerve fibers, as they are furthest away from the bile duct and portal vein, which course posterior to the hepatic artery and which are highly conductive compared to other tissue surrounding the portal triad. In some methods, to selectively disrupt sympathetic nerves, locations with increased impedance are selectively modulated (e.g., ablated). In some embodiments, one or more return electrodes are placed in the portal vein and/or bile duct to enhance the impedance effects observed in sympathetic nervous tissues. In some embodiments, return electrodes are placed on areas of the skin perfused with large veins and having decreased fat and/or non-vascular tissues (such as the neck or wrist, etc.). The resistance between the portal vein and other veins may be very low because of the increased electrical conductivity of blood relative to other tissues. Therefore, the impedance effects may be enhanced because comparatively small changes in resistance between various positions on the hepatic artery and the portal vein are likely to have a relatively large impact on the overall resistance registered.

In some embodiments, impedance and/or temperature may be measured with a reference transducer placed near the midpoint between adjacent lesions in order to help form continuous lesions with minimal overlap. In some embodiments, impedance is measured with reference to a ground electrode or a local bipolar reference electrode. Impedance changes as the lesion approaches the reference electrode. As one example, if two lesions are placed 5-10 mm apart axially and/or circumferentially along a vessel, a reference transducer may be positioned along a shaft of an ablation catheter at position corresponding to the desired extent of the lesion (e.g., approximately 2.5 mm-5 mm). The reference transducer may be configured to be placed in contact with the vessel wall. In some embodiments, impedance is measured at a different frequency than the ablation frequency. The reference transducer may be filtered to selectively measure the reference signal. In some embodiments, the reference transducer has high input impedance to avoid distorting the ablation field. In other embodiments, the reference transducer is gated so that impedance measurements are interleaved with an ablation signal.

In some embodiments, the sympathetic nerves are targeted locationally. It may be observed in some subjects that sympathetic nerve fibers tend to run along a significant length of the proper hepatic artery while the parasympathetic nerve fibers tend to join towards the distal extent of the proper hepatic artery. In some embodiments, sympathetic nerves are targeted by ablating the proper hepatic artery towards its proximal extent (e.g., generally half-way between the first branch of the celiac artery and the first branch of the common hepatic artery or about one centimeter, about two centimeters, about three centimeters, about four centimeters, or about five centimeters beyond the proper hepatic artery branch). Locational targeting may be advantageous because it can avoid damage to critical structures such as the bile duct and portal vein, which generally approach the hepatic artery as it courses distally towards the liver.

Figure 63:
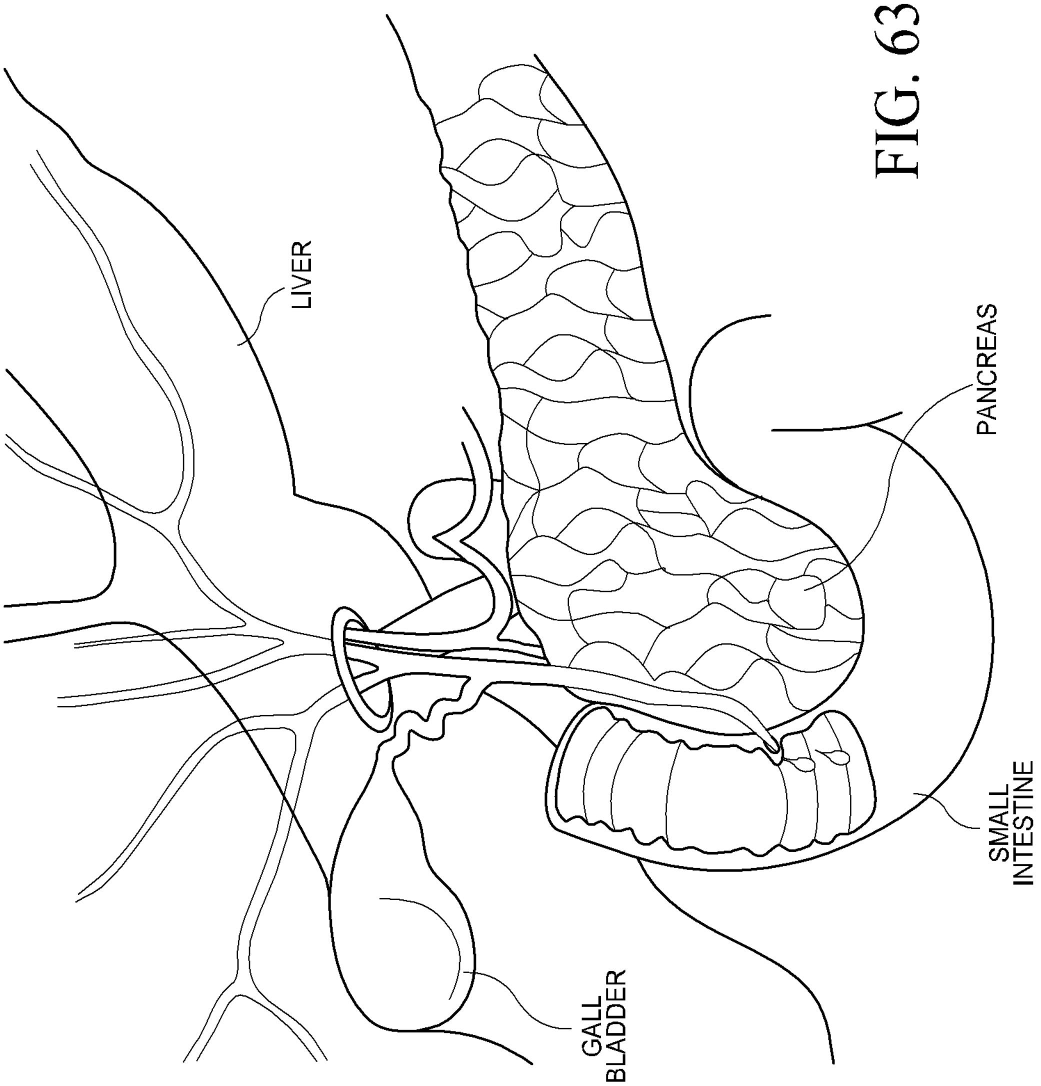
FIG. 63 illustrates a portion of a human anatomy surrounding the liver.

FIG. 63 illustrates a schematic representation of organs adjacent to the liver (e.g., gall bladder, pancreas, stomach). In accordance with several embodiments of the invention, the catheters and procedures described herein may prevent or reduce the likelihood of collateral damage to organs or tissue surrounding the liver (e.g., bile duct, portal vein, pancreas, stomach) during neuromodulation (e.g., RF electrode ablation) of the nerves within or surrounding the hepatic arteries. In various embodiments, the catheters and methods of use described herein can prevent or reduce the likelihood of biliary stenosis, portal vein thrombosis, or pancreatitis. In some embodiments, energy is directed away from the bile duct, portal vein, pancreas, and/or other organs or tissues using bipolar energy delivery devices and methods. In some embodiments, bipolar devices and methods limits the impact of adjacent structures (e.g., bile duct and portal vein) on an ablation region and prevents energy from tracking towards the adjacent structures.

In one embodiment, biliary protectant (e.g., a nonconductive, insulating substance) is injected percutaneously into the gall bladder or via endoscopic retrograde cholangiopancreatography (ERCP). In one embodiment, a cooled solution is injected into the biliary tree by the same means. In one embodiment, an insulating "ring" around the artery is injected, similar to hydrodissection but with a non-conductive biocompatible substance (e.g., a polyethylene glycol (PEG) hydrogel).

One method of decreasing likelihood of collateral damage to the gall bladder or other organs in the proximity of the hepatic arteries is to administer a bile acid inhibitor drug to a patient systemically before the neuromodulation procedure or to request that the patient not eat a fatty meal before the procedure in order to minimize bile secretion. Other precautionary steps could involve inducing vomiting to drain bile or administering ethanol to the patient prior to the procedure in order to cause "fatty" live protection and/or less conductivity. In one embodiment, protection of the stomach against possible collateral damage may be facilitated by having the patient swallow air or inflating the stomach to provide an air barrier to conduction in the stomach. For protection of the gall bladder, an intra-arterial catheter (e.g., having one or more magnetic portions) can be inserted within a hepatic artery or adjacent artery to "pull" the hepatic artery away from the gall bladder. External magnets may also be used to "pull" the hepatic artery away from the gall bladder.

In some embodiments, neuromodulation location is selected by relation to the vasculature's known branching structure (e.g., directly after a given branch). In some embodiments, neuromodulation location is selected by measurement (e.g., insertion of a certain number of centimeters into the target vessel). Because the relevant nervous and vessel anatomy is highly variable in humans, it may be more effective in some instances to select neuromodulation location based on a position relative to the branching anatomy, rather than based on a distance along the hepatic artery. In some subjects, nerve fiber density is qualitatively increased at branching locations.

In some embodiments, a method for targeting sympathetic nerve fibers comprises assessing the geometry of arterial structures distal of the celiac axis using angiography. In one embodiment, the method comprises characterizing the geometry into any number of common variations and then selecting neuromodulation (e.g., ablation) locations based on the expected course of the parasympathetic nerve fibers for a given arterial variation. Because arterial length measurements can vary from subject to subject, in some embodiments, this method for targeting sympathetic nerve fibers is performed independent of arterial length measurements. The method may be used for example, when it is desired to denervate or ablate a region adjacent and proximal to the bifurcation of the common hepatic artery into the gastroduodenal and proper hepatic arteries.

In the absence of nerve identification under direct observation, nerves can be identified based on their physiologic function. In some embodiments, mapping and subsequent modulation is performed using glucose and norepinephrine ("NE") levels. In some embodiments, glucose and NE levels respond with fast time constants. Accordingly, a clinician may stimulate specific areas (e.g., in different directions or circumferential clock positions or longitudinal positions) in a target artery or other vessel, monitor the physiologic response, and then modulate (e.g., ablate) only in the locations that exhibited the undesired physiologic response. Sympathetic nerves tend to run towards the anterior portion of the hepatic artery, while the parasympathetic nerves tend to run towards the posterior portion of the hepatic artery. Therefore, one may choose a location not only anterior, but also (using the aforementioned glucose and NE level measurements) a specific location in the anterior region that demonstrated the strongest physiologic response to stimulation (e.g., increase in glucose levels due to sympathetic stimulation). In some embodiments, stimulation with 0.1 s-on, 4.9 s-off, 14 Hz, 0.3 ms, 4 mA pulsed RF energy is a sympathetic activator and stimulation with 2 s-on, 3 s-off, 40 Hz, 0.3 ms, 4 mA pulsed RF energy is a parasympathetic activator. However, other parameters of RF energy or other energy types may be used.

In some embodiments, using electrical and/or positional selectivity, a clinician could apply a stimulation pulse or signal and monitor a physiologic response. Some physiologic responses that may indicate efficacy of treatment include, but are not limited to, the following: blood glucose levels, blood and/or tissue NE levels, vascular muscle tone, blood insulin levels, blood glucagon levels, blood C peptide levels, blood pressure (systolic, diastolic, average), and heart rate. In some cases, blood glucose and tissue NE levels may be the most accurate and readily measured parameters. The physiologic responses may be monitored or assessed by arterial or venous blood draws, nerve conduction studies, oral or rectal temperature readings, or percutaneous or surgical biopsy. In some embodiments, transjugular liver biopsies are taken after each incremental ablation to measure the resultant reduction in tissue NE levels and treatment may be titrated or adjusted based on the measured levels. For example, in order to measure tissue NE levels in the liver, a biopsy catheter may be inserted by a TIPS approach or other jugular access to capture a sample of liver parenchyma. In some embodiments, the vein wall of the portal vein may safely be violated to obtain the biopsy, as the vein is surrounded by the liver parenchyma, thereby preventing blood loss.

In some embodiments, ablation is performed using an ablation catheter with radiopaque indicators capable of indicating proper position when viewed using fluoroscopic imaging. Due to the two-dimensional nature of fluoroscopic imaging, device position can only be determined along a single plane, providing a rectangular cross-section view of the target vasculature. In order to overcome the difficulty of determining device position along a vessel circumference without repositioning the fluoroscopic imaging system, rotational positioning indicators that are visible using fluoroscopic imaging may advantageously be incorporated on an endovascular ablation device to indicate the circumferential position of ablation components (e.g., electrodes) relative to the vessel anatomy.

In one embodiment, an ablation catheter having an ablation electrode comprises three radiopaque indicators positioned along the longitudinal axis of the ablation catheter. In one embodiment, the first radiopaque indicator is positioned substantially adjacent to the electrode on the device axis; the second radiopaque indicator is positioned proximal to the electrode on the device axis; and the third radiopaque indicator is positioned off the device axis. In one embodiment, the third radiopaque indicator is positioned between the first and second radiopaque indicators. In embodiments with three radiopaque indicators, the ablation electrode is configured to contact the vessel wall through deflection from the central axis of the catheter. In one embodiment, alignment of the first and second radiopaque indicators means that the ablation electrode is located in a position spaced from, and directly perpendicular to, the imaging plane (e.g., either anteriorly or posteriorly assuming a coronal imaging plane). In one embodiment, the position of the third radiopaque indicator indicates the anterior-posterior orientation. For example, position of the third radiopaque indicator above, on, or below the line formed between the first and second radiopaque indicators may provide the remaining information necessary to allow the user to infer the position of the ablation catheter.

In accordance with several embodiments, methods of specific neural chemical targeting for labeling and destruction are provided. Nerves within or surrounding the hepatic arteries may be closer to the arterial lumen than for the renal artery. In some instances, the nerves converge towards the arterial lumen at a midpoint of a common hepatic artery segment and diverge thereafter. Nerves innervating the common hepatic artery may be predominantly sympathetic efferent nerves. As shown in FIG. 56, the nerves innervating the common hepatic artery may be embedded mostly in fat tissue In some embodiments, a method of targeting nerves comprises injecting a drug specific to efferent fibers (e.g., a TH inhibitor that spares afferent nerves while destroying efferent). In some embodiments, a chemical solution (e.g., potassium hydroxide) is used to dissolve nerves while leaving fat intact. In one embodiment, fat-specific dissolving drugs are injected to skeletonize nerves, thereby bringing the nerves even closer to the arterial lumen or vascular wall.

In some embodiments, the nerves are targeted mechanically instead of chemically (e.g., by taking advantage of different stiffness properties of nerves versus soft fat. Vibrational energy (e.g., sound, ultrasound) may be used, for example to target nerves. In one embodiment, fluorescent markers are injected in specific lobes of the liver to determine where they innervate around the hepatic artery. In one embodiment, a midpoint specific ablation pattern is used to ablate the common hepatic artery.

In accordance with several embodiments, monitoring lesion growth during ablation can provide a method to produce consistent lesions. In addition, overtreatment can be avoided knowing lesion size and severity during ablation. In some embodiments, echo decorrelation of ultrasound images may be used to map tissue changes during ablation. Echo decorrelation is performed by measuring changes in the local ultrasound signal frame to frame. Degradations in the signal are recorded to produce a cumulative decorrelation map. These resulting images can visualize tissue changes due to injury severity. In some embodiments, an intravascular ultrasound probe is positioned at the site of ablation. In other embodiments, the intravascular ultrasound probe is positioned in a parallel vein or artery or other structure. Echo decorrelation can be performed in real time to monitor the growth of one or more ablation lesions formed in the wall (e.g., intima, media and/or adventitia) of the vessel. In some embodiments, echo decorrelation uses thresholds defined from in vitro empirical tissue ablation data to visualize one or more growing lesions. The monitoring may advantageously be used to stop ablative energy delivery (e.g., from an electrode or ultrasound transducer) when the lesion has reached a sufficient size or if the lesion severity approaches unsafe levels.

Various systems and methods are provided herein to provide the ability to detect (acutely and/or chronically) whether nerves have been ablated or denervated and the neural connections to the end-organ (e.g., liver, pancreas, duodenum, etc.) thus disrupted. In accordance with several embodiments, it may be desirable to detect in real-time the actual energy being delivered. Since nerves carry electrical signals, and denervated or ablated nerves can no longer carry these signals, it may be possible to measure conduction along the length of the nerve fibers. In some embodiments, a binary signal (e.g., on/off) or a quantitative signal correlating with degree of nerve disruption could be determined. In some embodiments, expected physiological responses (e.g., glucose changes, insulin or glucagon changes, GI motility, etc.) to stimulation of the target nerves (e.g., nerves surrounding the hepatic arteries) may be monitored directly after a denervation or nerve ablation procedure to determine whether or not the expected physiological responses occur, thereby leading to the possibility of a real-time intra-procedural diagnostic. In some embodiments, real-time feedback during the ablation procedure may facilitate delivery of only enough energy (or formation of only enough lesions) as needed for successful denervation, thereby opening up a wider population to the procedure due to anatomic constraints (e.g. vessel length, tortuosity, etc.) that may limit the number of possible ablations and/or reducing the likelihood of any safety effects (e.g. vascular or adjacent structure injury) due to excessive energy delivery.

In accordance with several embodiments, the catheter used for energy delivery (e.g., ablation) comprises sensing electrodes proximal and/or distal to the site of ablation. The sensing electrodes may be configured to be placed in contact with a vessel wall in order to detect conduction in the targeted nerve fibers (e.g., nerve fibers in the adventitia surrounding a common hepatic artery). Any of the structures and features described herein for facilitating contact of electrodes with vessel walls may be used. For example, a balloon ablation catheter may comprise ablation electrodes in the middle of the balloon and sensing electrodes on the same balloon proximal and distal of the ablation electrodes. In some embodiments, the same electrodes are configured to provide ablation and sensing functions. In some embodiments, a balloon ablation catheter may comprise multiple balloons, with sensing balloons (e.g., balloons with sensing electrodes) on either side of an ablation balloon (or balloon with ablation electrodes).

Similar technologies could be employed on a separate catheter from the ablation catheter, and a diagnostic procedure could be performed with the separate sensing catheter immediately after or within a certain time (e.g., 5 minutes, 10 minutes, 15 minutes, 20 minutes, 30 minutes, 45 minutes, 60 minutes) following the ablation or on some other diagnostic or treatment session in the future. In some embodiments, non-catheter-based diagnostic systems and methods are used. For example, the proximal and distal sensing electrodes may be positioned on cuffs, needles, patches, and/or the like. Access could be percutaneous, placed on the skin outside of the body, placed in adjacent structures (e.g. portal vein, bile duct, inferior vena cava), or placed in organ tissue (e.g., liver tissue) itself. In accordance with several embodiments, the methods advantageously involve monitoring at the physiology that is being targeted (e.g. neural electrical conduction), which provides the most direct measurement conceivable.

In various embodiments, a signal or response detected by a circuit comprised of sensing electrodes or other diagnostic members on both sides of the ablation or denervation site could be (1) impedance (e.g., a change in dynamic resistance or conductance of the circuit created) and/or (2) action potentials (e.g., the circuit could be probed with a brief voltage impulse and then electrical response monitored, since nerve fibers conduct physiologically using such action potentials). In some embodiments, physiologic responses are monitored, leading to several possibilities depending on the organ and physiology interrogated. Examples of physiologic responses include the following: (1) Liver/glucose: since stimulation of the hepatic sympathetic nerves increases net hepatic glucose production and thus systemic glucose levels, a lesser increase in blood glucose levels may be observed after denervation or ablation; (2) pancreas/insulin-glucagon: since stimulation of the pancreatic sympathetic nerves could increase insulin secretion and decrease glucagon secretion, both of these hormone levels could be measured pre and post denervation; and (3) duodenum-stomach/motility: since stimulation of the GI sympathetics may lead to decreased motility, direct observation of motility or via a number of motility tests could be measured pre and post denervation or ablation. The systems and methods described above may be universally applicable to intravascular denervation regardless of the end organ (e.g., may apply to any organ innervated by nerves around an artery). The measurements (whether electrical or physiologic or other type) may be conducted serially during an ablation procedure, or chronically (e.g., at some period of time after the procedure), to assess success of denervation.

In embodiments involving liver, or hepatic, denervation, confirmation of denervation may be assessed by tissue norepinephrine levels. For example, the tissue norepinephrine levels may be reduced by more than 90%. In some embodiments involving hepatic denervation by ablating the common hepatic artery or other adjacent vessels, there may be a corresponding "dose-response" in the pancreas and duodenum. In other words, in some embodiments, the pancreas and/or duodenum may be sufficiently denervated (e.g., >90%) in addition to the liver being denervated, by ablating the common hepatic artery and/or surrounding vessels as described herein. Accordingly, physiologic assessments (e.g., established clinical tests or measurements) of the pancreas or duodenum that suggest impact of denervation may be used to confirm success of liver denervation. In some embodiments, ablations could be continued until an intended or expected clinical change is detected.

Clinical measurements for measuring pancreatic response affected by denervation may include oral glucose challenges and subsequent insulin response. Denervation of the pancreas in theory should lead to greater insulin secretion, and evidence of this has been observed in dog studies. Thus, multiple oral glucose challenges could be given, and blood insulin levels measured, and if the insulin levels increased, denervation success could be inferred. Clinical measurements for measuring pancreatic response may also include spot insulin measurements without glucose challenge. In some embodiments, glucagon measurements, which is a hormone secreted from the pancreas that may be affected by denervation) may be taken to confirm denervation of the liver.

Clinical measurements for measuring duodenal response may include GI motility testing, since with sympathetic denervation of the duodenum, there may be increased duodenal motility and decreased transit time. Several clinically validated tests exist to measure motility changes, including nuclear medicine tests looking at transit of radioactive food ingested, and C-acetate breath testing. In some embodiments, an endoscopy could be performed and the duodenum visualized directly to look at signs of motility changes.

In some embodiments, system-wide responses (due to possibility that afferent neural connections could be disrupted by ablating the common hepatic artery) may be measured to facilitate confirmation of liver denervation upon ablation of the common hepatic artery. Sympathetic outflow to other organs may be reduced via a reflex path from the liver to the brain to other organs. Parameters that could be affected and measured include, but are not limited to, blood pressure, heart rate and muscle sympathetic nerve activity (MSNA).

As mentioned above, diagnostic probes may be inserted within structures adjacent to the common hepatic artery to be used as a monitoring site to detect formation of ablation lesions or other penetration of ablation. For example, the stomach and duodenum may be accessed via en endoscopic approach using probes placed at the time of the procedure. Diagnostic devices may be inserted into the portal vein through a percutaneous approach directly from outside the abdomen or through venous access crossing the liver tissue from the vena cava. Diagnostic devices may be inserted into the bile duct, which may be accessed, for example, percutaneously from outside the abdomen. Diagnostic devices may be inserted into the inferior vena cava through standard venous approaches. In some embodiments, diagnostic elements are placed external to the patient on the skin of the abdomen. The various diagnostic devices (e.g., probes) may measure temperature using thermocouples, thermistors, microwave detection, volumetric heat mapping, or mechanical changes in tissue (e.g., using ultrasound or optical coherence tomography (OCT) probes). In accordance with several embodiments, the diagnostic devices (e.g., probes) inserted into the adjacent structures may advantageously give the operator confidence that energy was actually delivered to the intended sites (thus suggesting efficacy) and provide assurance that adjacent sensitive structures that were not intended to be ablated (such as the bile duct) were not impacted (thus ensuring safety).

IV. Alternative Catheter Delivery Methods

In addition to being delivered intravascularly through an artery, the neuromodulation systems described herein (e.g., ablation catheter systems and other access/delivery systems) can be delivered intravascularly through the venous system. For example, an ablation catheter system may be delivered through the portal vein. In other embodiments, an ablation catheter system is delivered intravascularly through the inferior vena cava. Any other intravascular delivery method or approach may be used to deliver neuromodulation systems, e.g., for modulation of sympathetic nerve fibers in the hepatic plexus.

In some embodiments, the neuromodulation systems (e.g., catheter and other access/delivery systems) are delivered transluminally to modulate nerve fibers. For example, catheter systems may be delivered transluminally through the stomach. In other embodiments, the catheter systems are delivered transluminally through the duodenum, or transluminally through the biliary tree via endoscopic retrograde cholangiopancreatography (ERCP). Any other transluminal or laparoscopic delivery method may be used to deliver the catheter systems according to embodiments described herein.

In some embodiments, the catheter systems are delivered percutaneously to the biliary tree to ablate sympathetic nerve fibers in the hepatic plexus. Any other minimally invasive delivery method may be used to deliver neuromodulation systems for modulation or disruption of sympathetic nerve fibers in the hepatic plexus as desired and/or required.

In some embodiments, an open surgical procedure is used to modulate sympathetic nerve fibers in the hepatic plexus. Any open surgical procedure may be used to access the hepatic plexus. In conjunction with an open surgical procedure, any of the modalities described herein for neuromodulation may be used. For example, RF ablation, ultrasound ablation, HIFU ablation, ablation via drug delivery, chemoablation, cryoablation, ionizing energy delivery (such as X-ray, proton beam, gamma rays, electron beams, and alpha rays) or any combination thereof may be used with an open surgical procedure. In one embodiment, nerve fibers (e.g., in or around the hepatic plexus) are surgically cut in conjunction with an open surgical procedure in order to disrupt sympathetic signaling, e.g., in the hepatic plexus.

In some embodiments, a non-invasive procedure or approach is used to ablate sympathetic nerve fibers in the hepatic plexus and/or other nerve fibers. In some embodiments, any of the modalities described herein, including, but not limited, to ultrasonic energy, HIFU energy, electrical energy, magnetic energy, light/radiation energy or any other modality that can effect non-invasive ablation of nerve fibers, are used in conjunction with a non-invasive (e.g., transcutaneous) procedure to ablate sympathetic nerve fibers in the hepatic plexus and/or other nerve fibers.

V. Stimulation

According to some embodiments, neuromodulation is accomplished by stimulating nerves and/or increasing neurotransmission. Stimulation, in one embodiment, may result in nerve blocking. In other embodiments, stimulation enhances nerve activity (e.g., conduction of signals).

In accordance with some embodiments, therapeutic modulation of nerve fibers is carried out by neurostimulation of autonomic (e.g., sympathetic or parasympathetic) nerve fibers. Neurostimulation can be provided by any of the devices or systems described above (e.g., ablation catheter or delivery catheter systems) and using any of the approaches described above (e.g., intravascular, laparoscopic, percutaneous, non-invasive, open surgical). In some embodiments, neurostimulation is provided using a temporary catheter or probe. In other embodiments, neurostimulation is provided using an implantable device. For example, an electrical neurostimulator can be implanted to stimulate parasympathetic nerve fibers that innervate the liver, which could advantageously result in a reduction in blood glucose levels by counteracting the effects of the sympathetic nerves.

In some embodiments, the implantable neurostimulator includes an implantable pulse generator. In some embodiments, the implantable pulse generator comprises an internal power source. For example, the internal power source may include one or more batteries. In one embodiment, the internal power source is placed in a subcutaneous location separate from the implantable pulse generator (e.g., for easy access for battery replacement). In other embodiments, the implantable pulse generator comprises an external power source. For example, the implantable pulse generator may be powered via an RF link. In other embodiments, the implantable pulse generator is powered via a direct electrical link. Any other internal or external power source may be used to power the implantable pulse generator in accordance with the embodiments disclosed herein.

In some embodiments, the implantable pulse generator is electrically connected to one or more wires or leads. The one or more wires or leads may be electrically connected to one or more electrodes. In some embodiments, one or more electrodes are bipolar. In other embodiments, one or more electrodes are monopolar. In some embodiments, there is at least one bipolar electrode pair and at least one monopolar electrode. In some embodiments, one or more electrodes are nerve cuff electrodes. In other embodiments, one or more electrodes are conductive anchors.

In some embodiments, one or more electrodes are placed on or near parasympathetic nerve fibers that innervate the liver. In some embodiments, the implantable pulse generator delivers an electrical signal to one or more electrodes. In some embodiments, the implantable pulse generator delivers an electrical signal to one or more electrodes that generates a sufficient electric field to stimulate parasympathetic nerve fibers that innervate the liver. For example, the electric field generated may stimulate parasympathetic nerve fibers that innervate the liver by altering the membrane potential of those nerve fibers in order to generate an action potential.

In some embodiments, the implantable pulse generator recruits an increased number of parasympathetic nerve fibers that innervate the liver by varying the electrical signal delivered to the electrodes. For example, the implantable pulse generator may deliver a pulse of varying duration. In some embodiments, the implantable pulse generator varies the amplitude of the pulse. In other embodiments, the implantable pulse generator delivers a plurality of pulses. For example, the implantable pulse generator may deliver a sequence of pulses. In some embodiments, the implantable pulse generator varies the frequency of pulses. In other embodiments, the implantable pulse generator varies any one or more parameters of a pulse including, but not limited to, duration, amplitude, frequency, and total number of pulses.

In some embodiments, an implantable neurostimulator chemically stimulates parasympathetic nerve fibers that innervate the liver. For example, the chemical neurostimulator may be an implantable pump. In some embodiments, the implantable pump delivers chemicals from an implanted reservoir. For example, the implantable pump may deliver chemicals, drugs, or therapeutic agents to stimulate parasympathetic nerve fibers that innervate the liver.

In some embodiments, the implantable neurostimulator uses any combination of electrical stimulation, chemical stimulation, or any other method to stimulate parasympathetic nerve fibers that innervate the liver.

In some embodiments, non-invasive neurostimulation is used to stimulate parasympathetic nerve fibers that innervate the liver. For example, transcutaneous electrical stimulation may be used to stimulate parasympathetic nerve fibers that innervate the liver. In other embodiments, any method of non-invasive neurostimulation is used to stimulate parasympathetic nerve fibers that innervate the liver.

In accordance with the embodiments disclosed herein, parasympathetic nerve fibers other than those that innervate the liver are stimulated to treat diabetes, hypertension and/or other conditions, diseases, disorders, or symptoms related to metabolic conditions. For example, parasympathetic nerve fibers that innervate the pancreas, parasympathetic nerve fibers that innervate the adrenal glands, parasympathetic nerve fibers that innervate the small intestine, parasympathetic nerves that innervate the stomach, parasympathetic nerve fibers that innervate the kidneys (e.g., the renal plexus) or any combination of parasympathetic nerve fibers thereof may be stimulated in accordance with the embodiments herein disclosed. Any autonomic nerve fibers can be therapeutically modulated (e.g., disrupted or stimulated) using the devices, systems, and methods described herein to treat any of the conditions, diseases, disorders, or symptoms described herein (e.g., diabetes or diabetes-related conditions). In some embodiments, visceral fat tissue of the liver or other surrounding organs is stimulated. In some embodiments, intrahepatic stimulation or stimulation to the outer surface of the liver is provided. In some embodiments, stimulation (e.g., electrical stimulation) is not provided to the outer surface of the liver or within the liver (e.g., to the liver parenchyma), is not provided to the vagal or vagus nerves, is not provided to the hepatic portal vein, and/or is not provided to the bile ducts.

Stimulation may be performed endovascularly or extravascularly. In one embodiment, a stimulation lead is positioned intravascularly in the hepatic arterial tree adjacent parasympathetic nerves. The main hepatic branch of the parasympathetic nerves may be stimulated by targeting a location in proximity to the proper hepatic artery or multiple hepatic branches tracking the left and right hepatic artery branches and subdivisions. In one embodiment, the stimulation lead is positioned within a portion of the hepatoesophageal artery and activated to stimulate parasympathetic nerves surrounding the hepatoesophageal artery, as both vagal branches travel along the hepatoesophageal artery.

In one embodiment, the stimulation lead is positioned in the portal vein and activated to stimulate nerve fibers surrounding the portal vein, which may have afferent parasympathetic properties. In one embodiment, the stimulation lead is positioned across the hepatic parenchyma from a central venous approach (e.g., via a TIPS-like procedure) or positioned by arterial access through the hepatic artery and then into the portal vein. In one embodiment, the portal vein is accessed extravascularly through a percutaneous approach. The stimulation lead may be longitudinally placed in the portal vein or wrapped around the portal vein like a cuff. Extravascular stimulation of the portal vein may be performed by placing the stimulation lead directly on the parasympathetic fibers adhered to or within the exterior vessel wall. In various embodiments, the stimulation lead is placed percutaneously under fluoroscopy guidance, using a TIPS-like approach through the wall of the portal vein, by crossing the arterial wall, or by accessing the biliary tree.

In some embodiments, the stimulation lead is stimulated continuously or chronically to influence resting hepatic glucose product and glucose uptake. In various embodiments, stimulation is performed when the subject is in a fasting or a fed state, depending on a subject's glucose excursion profile. In some embodiments, stimulation may be programmed to occur automatically at different times (e.g., periodically or based on feedback). For example, a sensory lead may be positioned in the stomach or other location to detect food ingestion and trigger stimulation upon detection. In some embodiments, the stimulation is controlled or programmed by the subject or remotely by a clinician over a network.

In some embodiments, stimulation with 0.1 s-on, 4.9 s-off, 14 Hz, 0.3 ms, 4 mA pulsed RF energy is used for sympathetic nerve stimulation and stimulation with 2 s-on, 3 s-off, 40 Hz, 0.3 ms, 4 mA pulsed RF energy is used for parasympathetic activation. However, other parameters of RF energy or other energy types may be used.

Parasympathetic stimulation may also cause afferent effects along the vagus nerve, in addition to efferent effects to the liver resulting in changes in hepatic glucose production and uptake. The afferent effects may cause other efferent neurally mediated changes in metabolic state, including, but not limited to one or more of the following: an improvement of beta cell function in the pancreas, increased muscle glucose uptake, changes in gastric or duodenal motility, changes in secretion or important gastric and duodenal hormones (e.g., an increase in ghrelin in the stomach to signal satiety, and/or an increase in glucagon-like peptide-1 (GLP-1) from the duodenum to increase insulin sensitivity).

VI. Examples

Examples provided below are intended to be non-limiting embodiments of the invention.

A. Example 1

Figures 1, 64A:
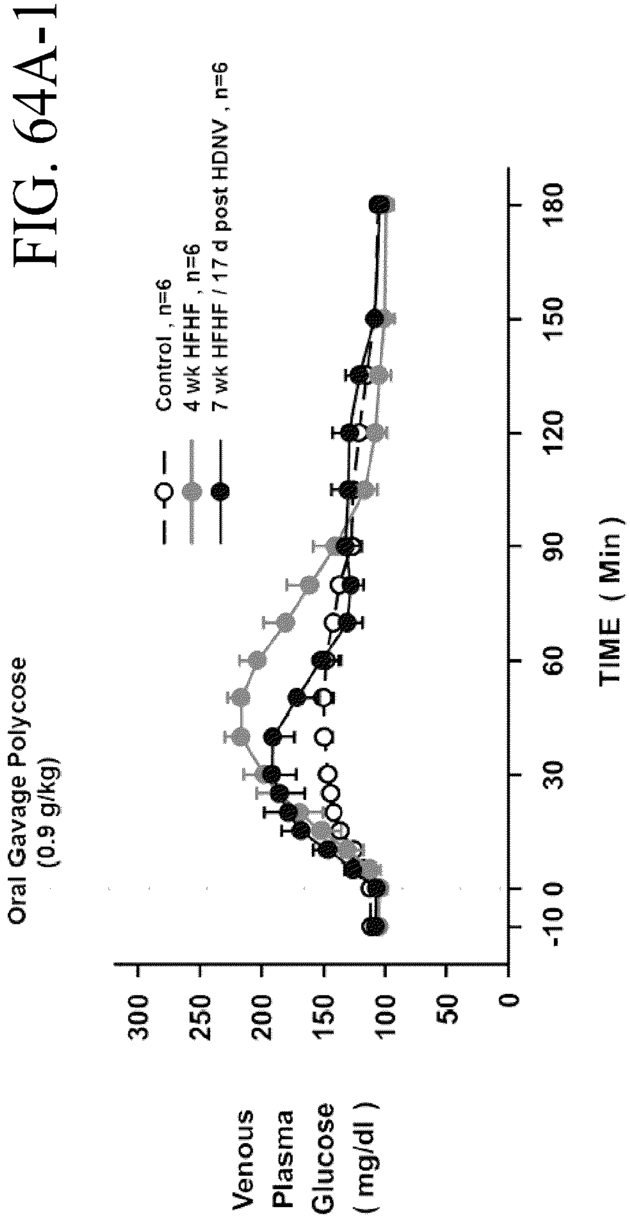
Figures 2, 64A:
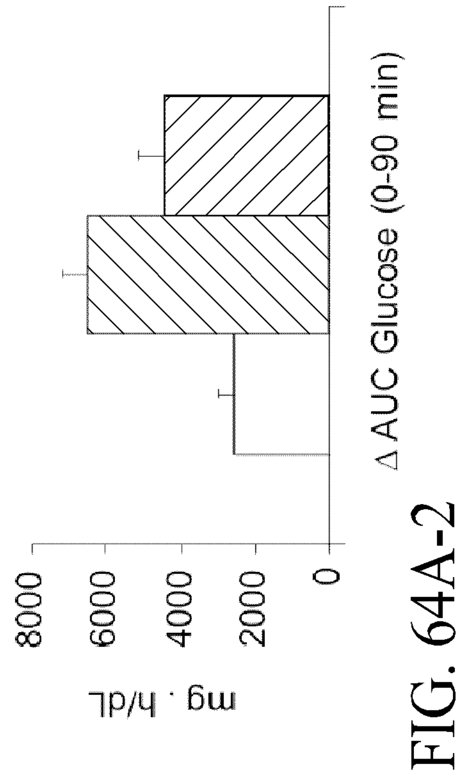
Figure 64B:
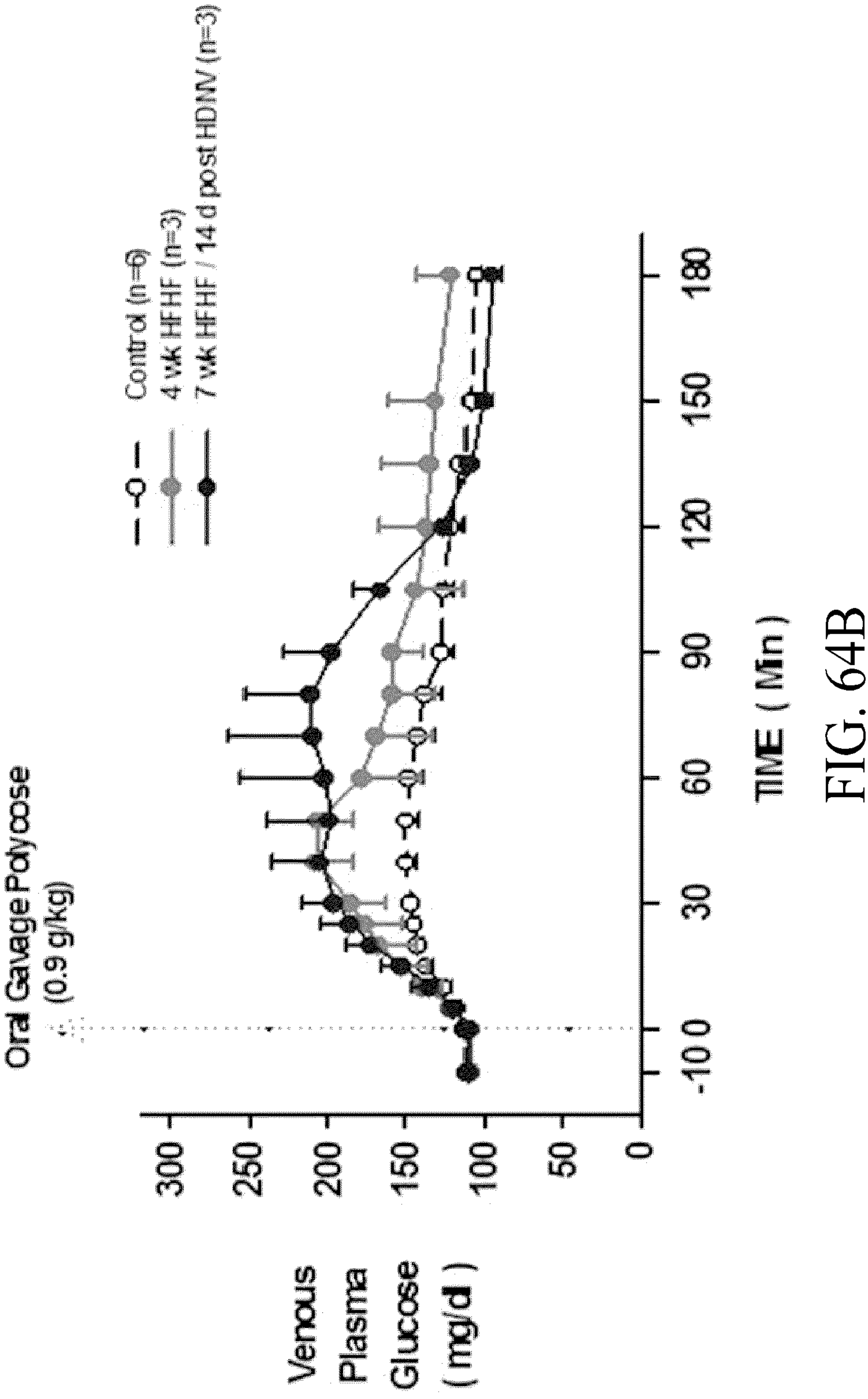

Nine dogs were put on a high fat, high fructose diet for four weeks, thereby rendering the dogs insulin resistant. As controls, a 0.9 g/kg oral gavage polycose dose was administered prior to initiation of the diet and at four weeks after initiation of the diet after an overnight fast and oral glucose tolerance tests were performed at various time intervals to track glucose levels. The common hepatic arteries of six dogs were then surgically denervated, and three dogs underwent a sham operation. Another 0.9 g/kg oral gave polycose dose was administered after an overnight fast about two to three weeks following hepatic denervation. Oral glucose tolerance tests were performed at various time intervals after administration of the polycose. FIG. 64A-1 illustrates a graph of the average venous plasma glucose over time for the six denervated dogs reported by the three oral glucose tolerance tests (OGTTs). The curve with data points represented by open circles represents the average of glucose measurements from the OGTT testing of the six dogs prior to high fat, high fructose diet feeding, and the curve with the data points represented by gray circles represents the average of the glucose measurements from the OGTT testing of the six dogs after the four weeks of high fat, high fructose diet before hepatic denervation. The oral gavage polycose doses were administered at time zero (as shown in FIG. 64A-2). The curve with the data points represented as black circles represents the average of the glucose measurements from the OGTT testing of the same six dogs seventeen days after hepatic denervation. As can be seen in FIG. 64A, the glucose values after hepatic denervation peaked at lower glucose concentrations and dropped much more rapidly than the glucose values prior to hepatic denervation, and the areas under the curve of the OGTTs improved by approximately 50% back to normal, chow fed levels. Interestingly, insulin levels during the OGTT actually increased after denervation, suggesting a beneficial effect on beta cell function. FIG. 64B illustrates a graph of the three sham operated dogs at the same time points, showing an increase over time of glucose area under the curve. The sham operated dogs also had no increase in insulin levels. In accordance with several embodiments, the results of the study provide strong evidence of the efficacy of hepatic denervation for controlling blood glucose levels. In some embodiments, insulin levels may remain constant or not increase or decrease by more than 5%.

B. Example 2

Figure 65:
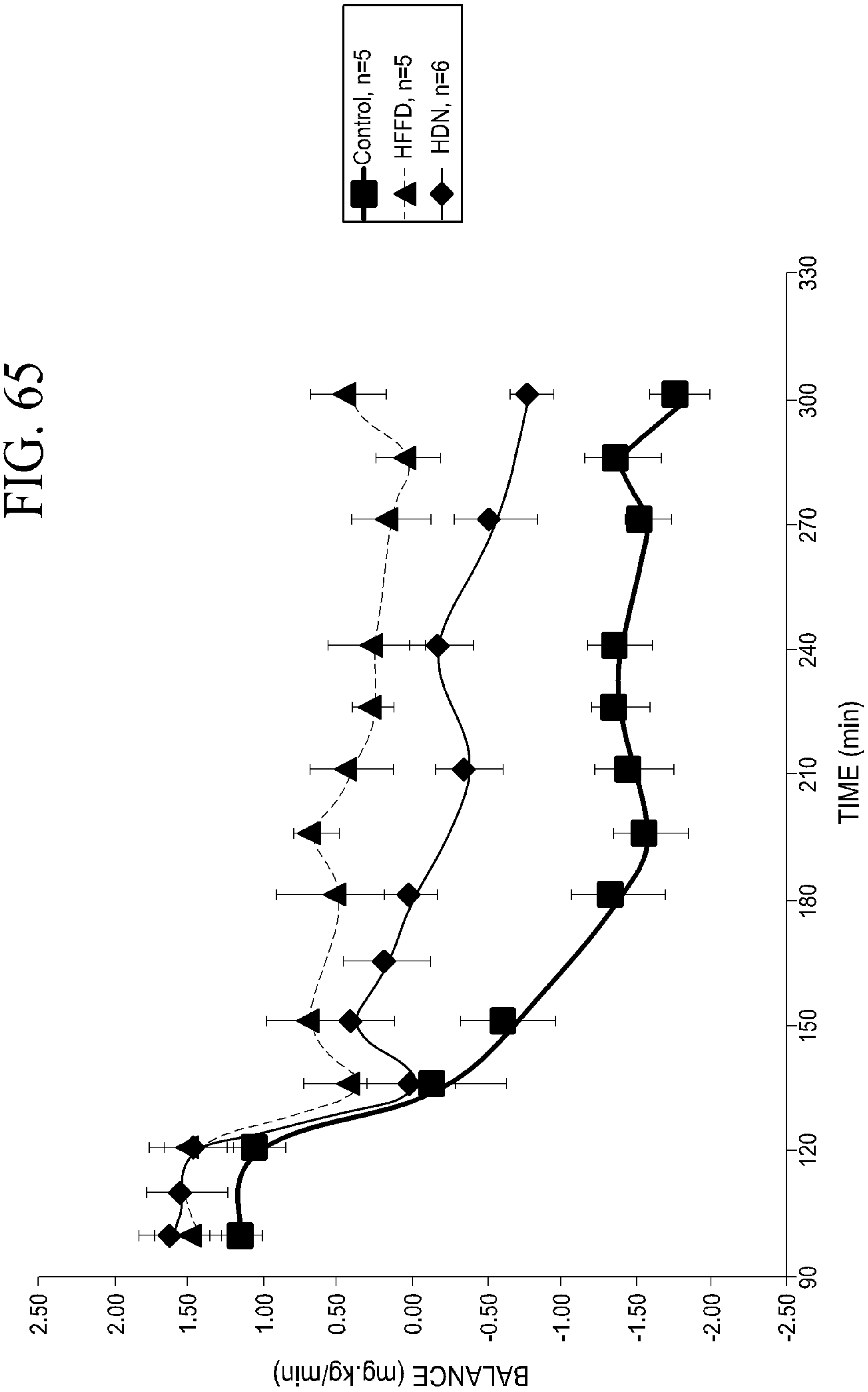

FIG. 65 illustrates the net hepatic glucose balance obtained during a hyperglycemic-hyperinsulinemic clamp study. The data represented with diamond indicators (HDN) represents the average net hepatic glucose levels of the same 6 dogs from Example 1 four weeks after denervation. The data represented with triangle indicators (HF/HF) represents the average net hepatic glucose levels of 5 dogs that were fed a high fat, high fructose diet. The data represented with the square indicators (Control) represents the average net hepatic glucose levels of 5 dogs fed a normal diet. The data shows that toward the end of the curves, hepatic denervation can restore net hepatic glucose balance to about 50% back to baseline, which suggests insulin resistance in the liver in the HF/HF dog model is largely corrected by hepatic denervation, and which indicates that hepatic denervation has an effect on hepatic glucose uptake and/or hepatic glucose production, in accordance with embodiments of the invention.

C. Example 3

A hepatic artery was harvested from a porcine liver as far proximal as the common hepatic artery and as far distal as the bifurcation of the left hepatic artery and the right hepatic artery. The arterial plexus was sandwiched between two sections of liver parenchyma (a “bed” and a “roof”), and placed in a stainless steel tray to serve as a return electrode. A total of 3 arteries were ablated using a RADIONICS RFG-3C RF generator using a NiTi/dilator sheath, having an exposed surface of approximately 1⁄16" to 3⁄32" in length. RF energy was applied for 117 seconds in each case, with the generator power setting at 4 (generally delivering 2-3 W into 55-270Ω). For the first 2 sample arteries, a K-type thermocouple was used to monitor extravascular temperatures, which reached 50-63° C. The first ablation was performed in the left hepatic artery, the second ablation was performed in the right hepatic artery, and the third ablation was performed in the proper hepatic artery. For the first ablation in the left hepatic artery having a lumen diameter of 1.15 mm, two ablation zone measurements were obtained (0.57 mm and 0.14 mm). A roughly 3 mm coagulation zone was measured. The electrode exposure distance was 3⁄32". For the second ablation in the right hepatic artery, an electrode exposure distance of 1⁄16" was used. The generator impeded out due to high current density and no ablation lesion was observed. For the third ablation of the proper hepatic artery having a lumen diameter of 2 mm and using an electrode exposure distance was 3⁄32", three ablation zone widths of 0.52 mm, 0.38 mm and 0.43 mm were measured. The measured ablation zone widths support the fact that nerves surrounding the proper hepatic artery (which may be tightly adhered to or within the arterial wall) can be denervated using an intravascular approach. Histological measurements of porcine hepatic artery segments have indicated that hepatic artery nerves are within 1-10 medial thicknesses (approximately 1-3 mm) from the lumen surface, thereby providing support for modulation (e.g., denervation, ablation, blocking conduction of, or disruption) of nerves innervating branches of the hepatic artery endovascularly using low-power RF energy (e.g., less than 10 W and/or less than 1 kJ) or other energy modalities. Nerves innervating the renal artery are generally within the 4-6 mm range from the lumen of the renal artery.

D. Example 4

An acute animal lab was performed on a common hepatic artery and a proper hepatic artery of a porcine model. The common hepatic artery was ablated 7 times and the proper hepatic artery was ablated 3 times. According to one embodiment of the invention, temperature-control algorithms (e.g., adjusting power manually to achieve a desired temperature) were implemented at temperatures ranging from 50° C. to 80° C. and for total ablation times ranging from 2 to 4 minutes. According to one embodiment of the invention, the electrode exposure distance for all of the ablations was 3⁄32". Across all ablations the ablation parameters generally ranges as follows, according to various embodiments of the invention: resistance ranged from about 0.1 ohms to about 869 ohms (generally about 100 ohms to about 300 ohms), power output ranged from about 0.1 W to about 100 W (generally about 1 Watt to about 10 Watts), generator voltage generally ranged from about 0.1 V to about 50 V, current generally ranged from about 0.01 A to about 0.5 A, and electrode tip temperature generally ranged from about 37° C. to about 99° C. (generally +/−5° C. from the target temperature of each ablation). Energy was titrated on the basis of temperature and time up to approximately 1 kJ or more in many ablations. Notching was observed under fluoroscopy in locations corresponding to completed ablations, which may be a positive indicator of ablative success, as the thermal damage caused arterial spasm.

It was observed that, although separation of ablation regions by 1 cm (in accordance with one embodiment) was attempted, the ablation catheter skipped distally during the ablation procedure, which is believed to have occurred due to the movement of the diaphragm during the ablation procedure, thereby causing movement of the anatomy and hepatic arterial vasculature surrounding the liver (which may be a unique challenge for the liver anatomy).

Unlike previous targets for endovascular ablation (e.g., renal arteries, which course generally straight toward the kidneys), the hepatic arterial vasculature is highly variable and tortuous. It was observed during the study that catheters having a singular articulated shape may not be able to provide adequate and consistent electrode contact force to achieve ablative success. For example, in several ablation attempts using an existing commercially-available RF ablation catheter, with energy delivered according to a manually-implemented constant-temperature algorithm, the power level was relatively high with low variability in voltage output required to maintain the target temperature. This data is generally indicative of poor vessel wall contact, as the electrode is exposed to higher levels of cooling from the blood (thereby requiring higher power output to maintain a particular target temperature). Additionally, tissue resistivity is a function of temperature. Although the tissue within the vessel wall is spatially fixed, there is constant mass flux of "refreshed" blood tissue in contact with the electrode at physiologic temperatures. Consequently, in one embodiment, when the electrode is substantially in contact with "refreshed" blood at physiologic temperatures, the electrode "sees" substantially constant impedance. Due to the correlation between impedance and voltage (e.g., $P=V^2/R$), the substantially constant impedance is reflected in a substantially constant (less variable) voltage input required to maintain a target electrode tip temperature. Therefore, particular embodiments (such as those described, for example, in FIGS. 14 and 15) advantageously enable adequate electrode contact in any degree of hepatic artery tortuosity that may be encountered clinically.

In a follow-up hepatic artery denervation procedure, it was demonstrated that the ability to reduce liver norepinephrine levels by ablating using a monopolar catheter, the results of which are shown in FIG. 66. Compared to historical liver norepinephrine drops observed in dogs following surgical hepatic arterial denervation, the endovascular ablation denervation procedure was estimated to be 72-95% effective at destroying sympathetic communication with the liver.

E. Example 5

A numerical model representing the hepatic artery and surrounding structures was constructed in COMSOL Multiphysics 4.3. using anatomical, thermal, and electrical tissue properties. Thermal and electrical properties are a function of temperature. Electrical conductivity (sigma, or σ) generally varies according to the equation $\sigma=\sigma_0 e^{0.015(T-T_0)}$, where $\sigma_0$ is the electrical conductivity measured at physiologic temperatures ($T_0$) and T is temperature. With reference to FIGS. 22A-22D, model geometry was assessed and included regions representing the hepatic artery lumen, bile duct 2205, and portal vein 2210. The bile 2205 duct and portal vein 2210 were modeled as grounded structures, highlighting the effect of these structures on current flow. By calculating liver blood flow and the relative contributions from the hepatic artery and portal vein 2210, we determined the flow in the hepatic artery was significantly lower than flow rates in other arteries (e.g., renal arteries). In one embodiment, the estimated flow rate was 139.5 mL/min. for the hepatic artery. Using the model described above, independent solutions were first obtained for monopolar and bipolar electrode configuration. A geometric model corresponding to the common hepatic artery was created and a time-dependent solution was calculated in COMSOL using the bioheat equation, $$\rho_b c_{pb}\frac{\partial T}{\partial t}=\nabla(k\nabla T_t)+\rho_b u c_{pb}(T_B-T)+q_m,$$

which, in one embodiment, relates the temperature at any point in the model as a function of the temperature gradient in the tissue, blood perfusion, blood temperature entering the geometric region of interest, and the heat generated ($q_m$) as a function of RF energy deposition.

Figure 22A:
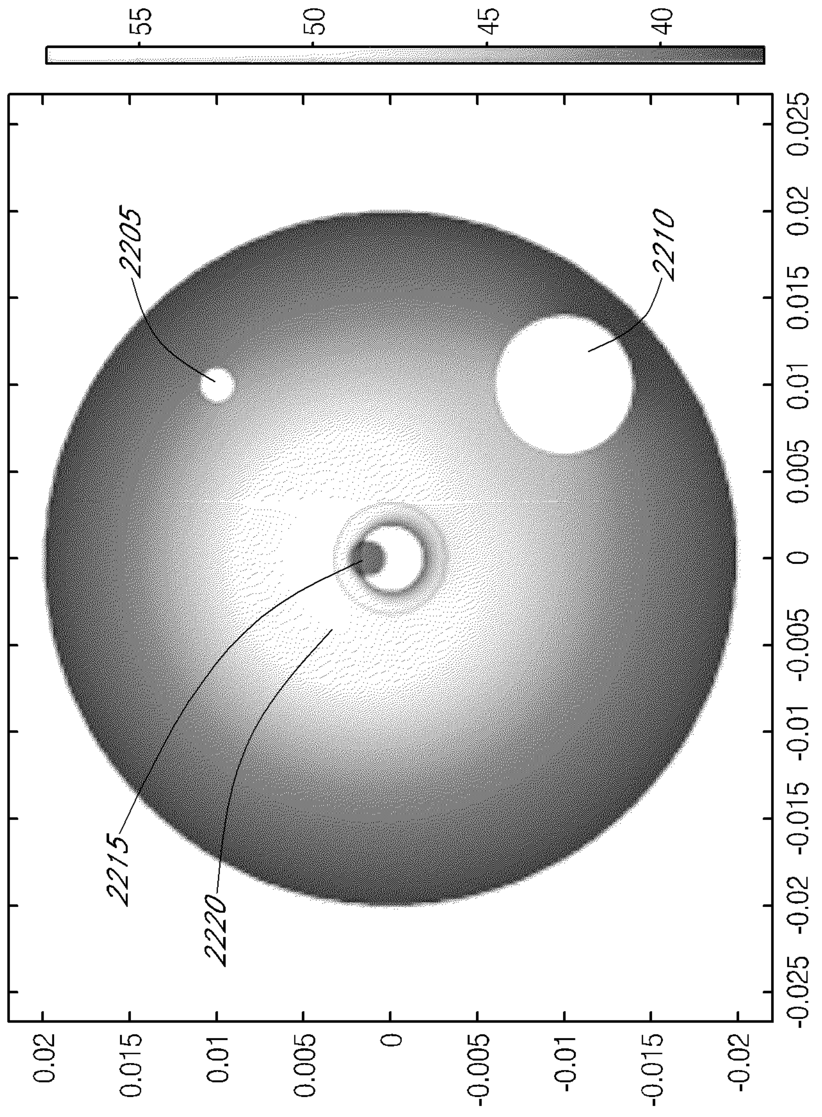
FIGS. 22A-22D illustrate geometric models.
Figure 22B:
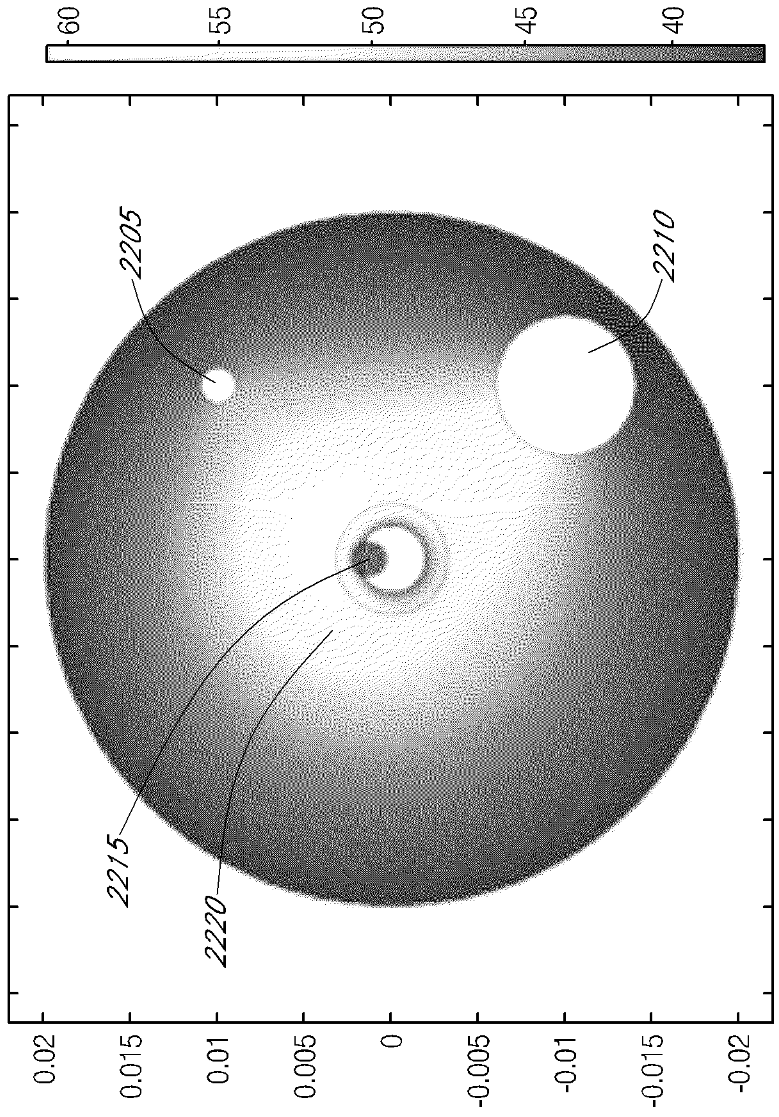
Figure 22C:
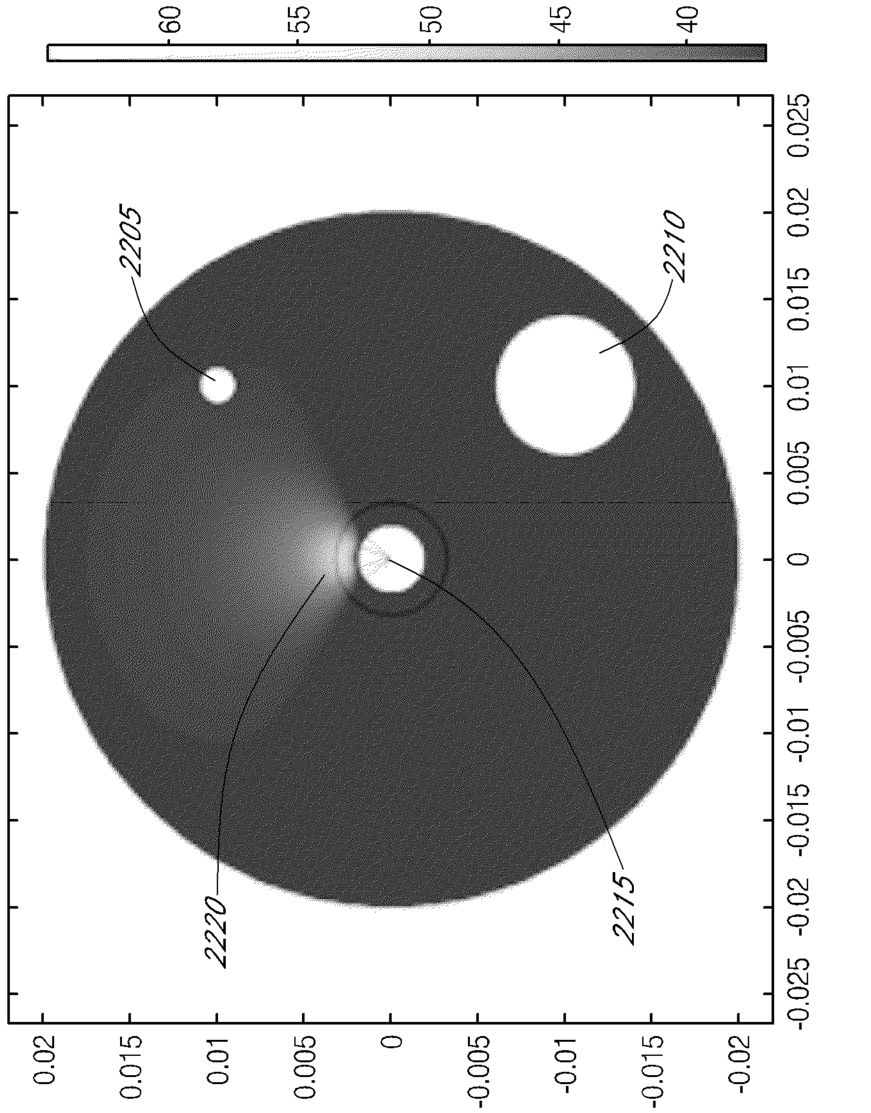
Figure 22D:
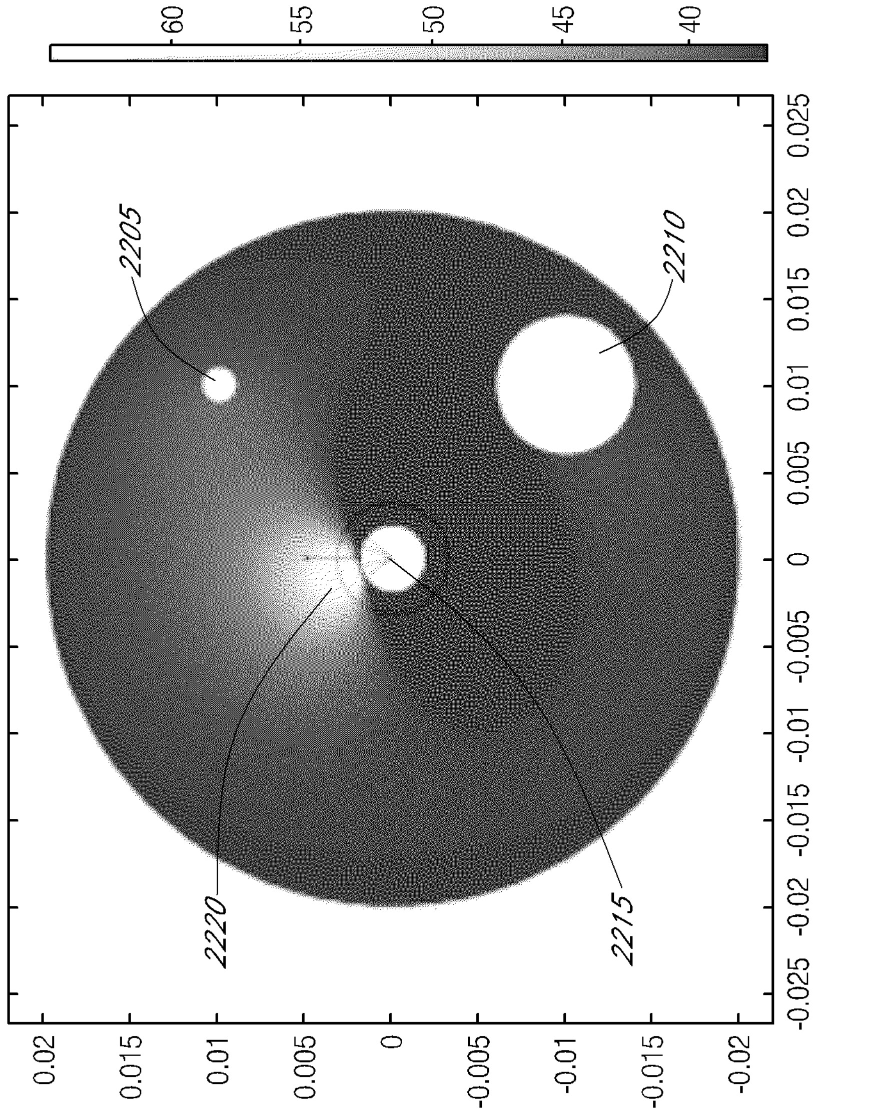

FIGS. 22A and 22B illustrate a geometric model of RF energy deposition in the common hepatic artery using a single electrode, with the conductivity of the bile duct 2205 and the portal vein 2210 grounded (FIG. 22A) and accounted for (FIG. 22B). As shown in FIG. 22B, biliary and portal vein conductivity can influence where ablation energy travels when a single electrode 2215 is used. FIGS. 22C and 22D illustrate a geometric model of RF energy deposition in the common hepatic artery for a bipolar electrode configuration 2215, with the conductivity of the bile duct 2205 and the portal vein 2210 grounded (FIG. 22C) and accounted for (FIG. 22D).

In accordance with an embodiment of the invention, the shape of the electric field and resulting thermal ablation 2220 was significantly affected in the monopolar ablation model due to biliary and portal vein conductivity (as shown in FIGS. 22A and 22B). Minimal effects due to biliary and portal vein conductivity (e.g., shaping effects) were observed in the shape of the electric field and resulting thermal ablation 2220 for the bipolar ablation model (shown in FIGS. 22C and 22D). FIGS. 22A and 22B were obtained when the pair of bipolar electrodes were modeled, according to one embodiment, as disposed at a location that is substantially tangent to the inner lumen of the artery, with each individual electrode having an arc length of 20 degrees and with an inter-electrode spacing of 10 degrees. In one embodiment, the edges of the electrodes have radii sufficient to reduce current concentrations (less than 0.001"). In several embodiments, the bipolar configuration advantageously provides effective ablation (e.g., thermal ablation of the hepatic artery) without significant effect on shaping of the ablation zone, despite the effects of biliary and portal vein conductivity due to proximity of the bile duct and portal vein to the common hepatic artery.

F. Example 6

Independent modeling solutions were obtained for an ablation with convective cooling (e.g., provided by blood flow alone) and for an ablation incorporating active cooling (e.g., 7° C. coolant) using the same bipolar configuration model described above in Example 5. The models showed significantly decreased temperatures at the location corresponding to the lumen (endothelial) interface. Higher power (45% higher power) was delivered to the active cooling model. Even with higher power delivered (e.g., 45% higher power) to the active cooling model, the endothelial region of the common hepatic artery remained cool (e.g. less than hyperthermic temperatures up to 1 mm from the lumen). The effective shaping of the thermal ablation zone was also directed into a more linear shape directed radially in the active cooling model. It was observed, that, in accordance with several embodiments, as cooling power is increased and RF power is increased, the linear shaping effect was magnified, thereby rendering the ablation zone capable of being directed or "programmed" (e.g., toward a more targeted location).

G. Example 7

Using a COMSOL model similar to the one described previously in connection with FIGS. 22A and 22B, the cooling effect of blood flow is observed to play a major role in the success of an ablation procedure, as the cooling effect allows the ablation procedure to achieve greater depth without vaporizing any tissue. The literature reports a considerable variation of the flow rate in the common hepatic artery. Moreover, a sudden constriction of the artery may occur during the procedure, which could considerably change the outcome of the ablation. In the following example, the importance of knowing the blood flow rates in the hepatic artery in real time is quantitatively shown. To do so, results that link the ablation parameters (e.g., maximum temperature reached within the tissue and temperature at 6 millimeters from the lumen) with the flow rates in the common hepatic artery are presented, in accordance with an embodiment of the invention. Measuring the flow rates in real time allows for adjustment of the power during the ablation.

In accordance with several embodiments, one criterion for the definition of a successful ("effective") ablation is one where the maximum temperature reached anywhere in the tissue is less than 98° C. at any time during the application of energy to the tissue. This temperature threshold can advantageously avoid tissue vaporization, which may cause collateral damage, as well as increase the tissue impedance, thereby potentially causing the lesion size to become unpredictable. Moreover, for the ablation to be successful in accordance with several embodiments, a temperature of at least 50° C. at a distance of 6 millimeters from the lumen, and for a period of at least 2 minutes must be achieved. These parameters may provide increased confidence in cellular death at the location of the majority of the nerves around the hepatic artery (e.g., at a distance of about 4 mm from the arterial lumen).

Figure 67:
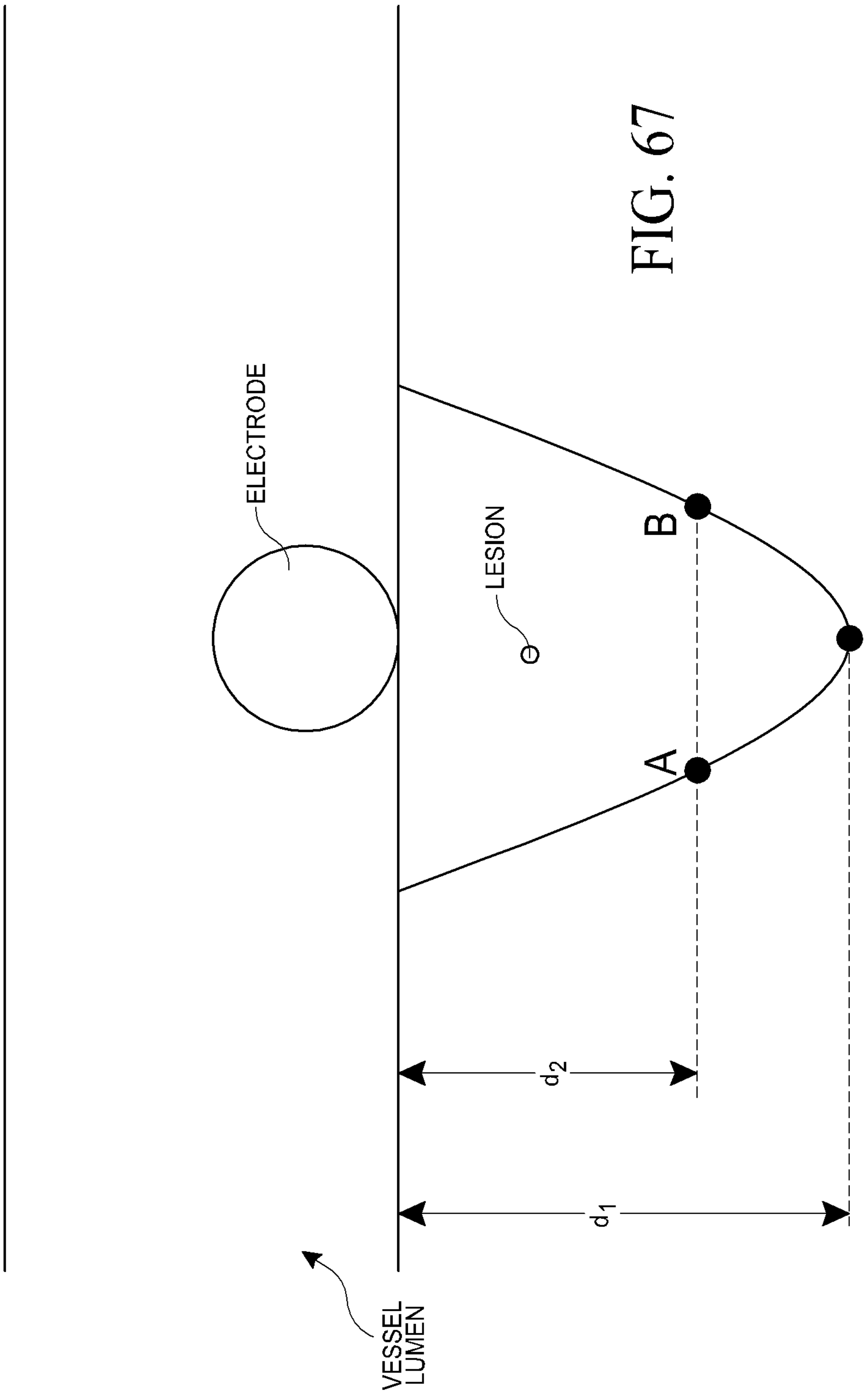
FIG. 67 illustrates a schematic two-dimensional representation of lesion depth, in accordance with an embodiment of the invention.

In accordance with several embodiments, a successful ablation of hepatic nerves is defined as one having a depth of 6 mm, even though the nerves are predominantly located 4 mm from the lumen, because the lesion (in some embodiments) has a conical or frustoconical shape. If we were to take the maximum at exactly 4 mm, the diameter of the lesion at such depth may be very small. By considering the maximum temperature at 6 mm, it can be assured that at 4 mm such temperature is reached for a relatively wide area (as shown in FIG. 67).

Data from simulations allows one to estimate what the power should be, in order to have a desired lesion size of 4 mm in depth, for a given value of flow rate. In accordance with several embodiments, there are two main strategies to achieve a lesion: 1) maximum power–minimum time, and 2) minimum power–maximum time. The first strategy pushes the temperature near the maximum that the tissues can reach without being vaporized, thereby minimizing the total time of ablation. With the second strategy, the temperature at the edge of the lesion is maintained relatively low, but the ablation takes a long time for the cumulative effect of the heat to cause tissue death (according to the Arrhenius equation). Since one of the problems during ablation of the common hepatic artery is movement due to breathing, employing the first strategy (maximum power and minimum time) may be advantageous, as it is reasonable to want to minimize the risk of electrode movements. In addition, clinicians generally prefer a shorter procedure time in order to reduce patient risk.

In some embodiments, energy or power delivery may be gated based on respiration using temperature or impedance measurements due to the asymmetric motion of the electrode during a respiratory cycle. The electrode may remain relatively stationary for about two-thirds of the respiratory cycle (expiration) and during this time period the tissue in contact with the electrode increases in temperature. When the electrode is in motion during the other third of the respiratory cycle (inspiration), the tissue may cool down. The changes in temperature may be monitored and used to gate the delivery of RF energy to the electrode so that energy is only delivered when the electrode is stationary (e.g., during expiration) or power is increased during this period to maintain a desired average power level (e.g., 10 Watts). Because tissue impedance varies with temperature, impedance measurements could be monitored (either alternatively or in combination with temperature) and used to start and stop the energy delivery. In situations where variation in temperature and/or impedance measurements is not detected, power may be delivered at a constant rate.

In such embodiments in which power output is synchronized with respiration, the ramp of the RF generator may be adjusted to achieve an almost instantaneous climb of power. The adjustment may be performed by modifying a ramping algorithm of the generator. In some embodiments, the generator may be programmed to ramp up from a power output below 1 W to a peak power output in less than half a second. In accordance with several embodiments, synchronization of power output with respiration takes advantage of the time frame when blood flow in the vessel (e.g., common hepatic artery) is at a maximum, thereby providing enhanced cooling to the electrode and vessel wall, which may reduce charring, notching and vessel spasm.

Figure 68:
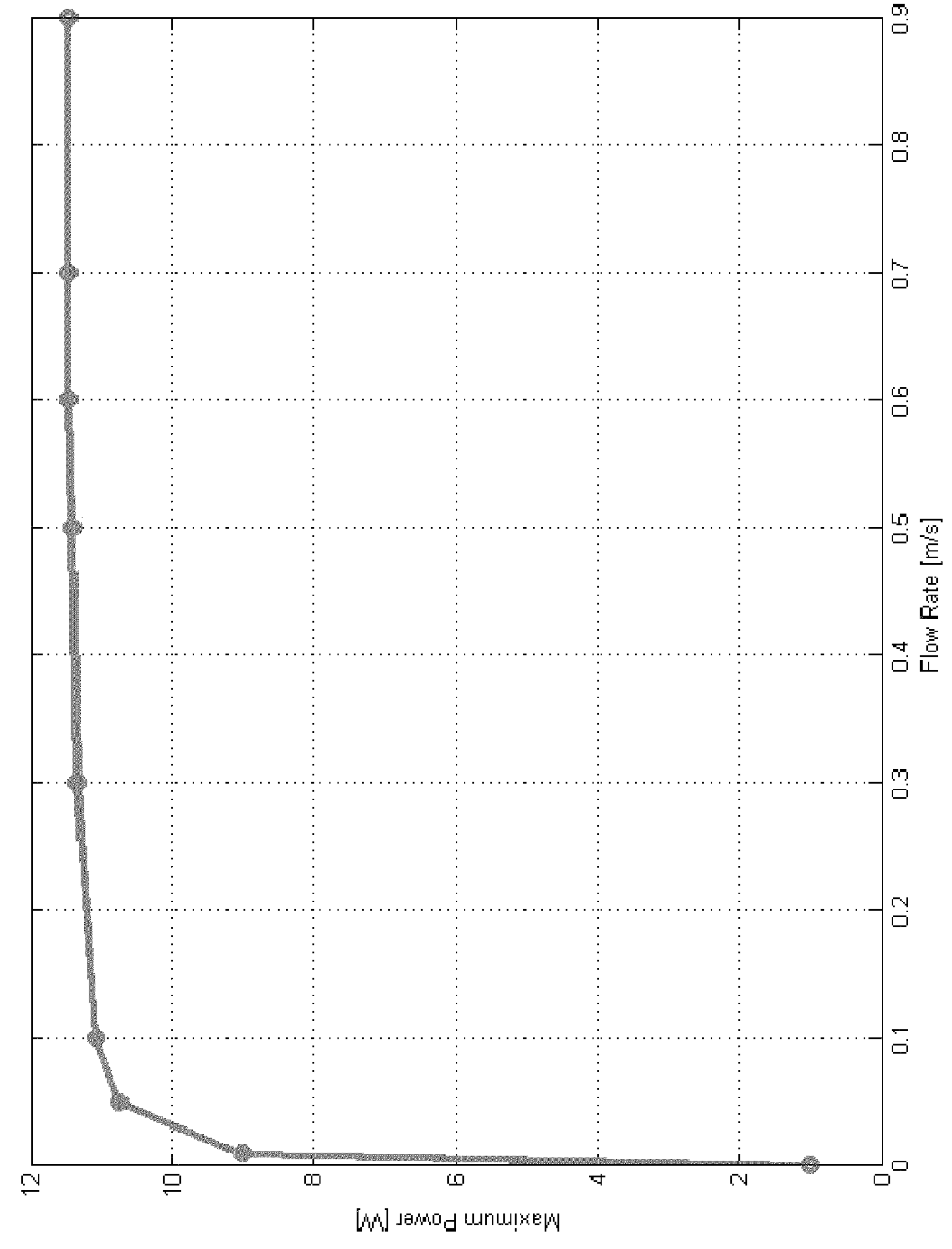
FIG. 68 is a graph illustrating maximum power as a function of arterial flow rate, in accordance with an embodiment of the invention.

FIG. 68 represents the maximum power that can be applied without resulting in vaporization as a function of arterial flow rate. The curve is generated based on the assumption of a 4 to 5 minute ablation, with a 2 millimeter diameter electrode. In several embodiments, to avoid vaporization temperature is maintained below about 97° C. and the lesion temperature is maintained at a minimum temperature of 47° C. for at least two minutes. In certain cases, tissue death may also be caused with a temperature of about 60° C. for a few seconds. In accordance with several embodiments, temperatures significantly higher than 50° C. cannot be reached throughout the lesion without causing tissue vaporization.

As shown in FIG. 68, as the flow rate increases, the maximum power increases rapidly for very low levels of flow rate and plateaus at a flow rate of about 0.6 m/s. The plateau is based at least in part on the fact that cooling capability of the blood reaches a saturation point. Thus, even for higher levels of flow rate, the power cannot be increased. Typical flow rates in the hepatic artery are generally no higher than 0.5 m/s. The flow rate value can easily be lowered unpredictably during an ablation (for example, if the catheter obstructs some of the blood flow).

This means that in reality, hepatic arterial ablation is conducted based on the conditions represented by the left part of the curve in FIG. 68. In this area of the curve, the maximum power varies considerably with small variations of the flow rate. In several embodiments, monitoring the flow is vital to avoid excessive or insufficient power, both of which may cause the ablation to be unsuccessful.

Figure 69:
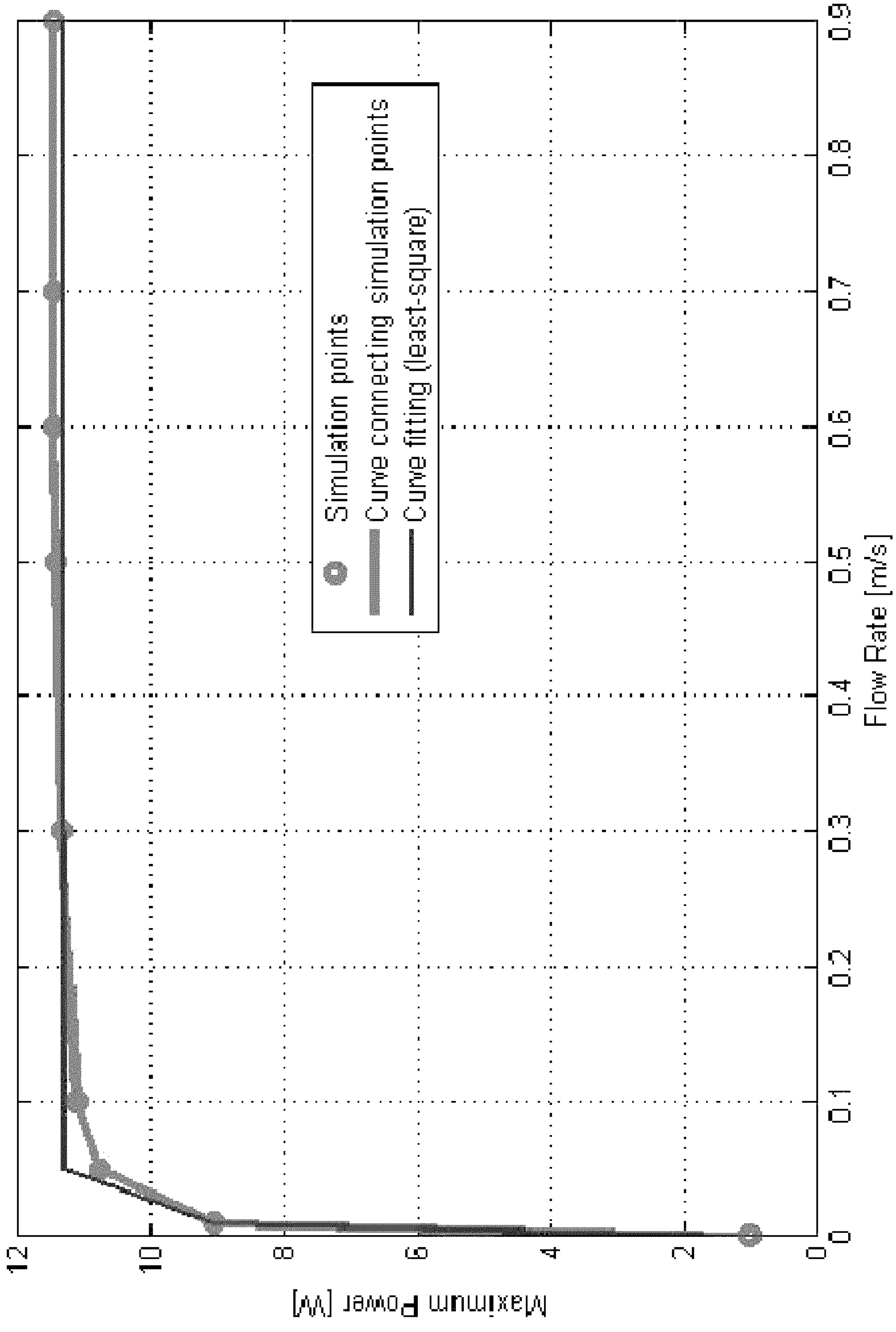
FIG. 69 is a graph of a least-square curve fitting for the relation between maximum power and arterial flow rate, in accordance with an embodiment of the invention.

The curve linking maximum power and flow rate can be approximated (for example, as shown in FIG. 69) with a non-linear least-square curve fitting having the following formula:

$$Power = K_1 - K_2 e^{(-K_3 * FlowRate)},$$

where $K_1 = 11.27$, $K_2 = 10.28$ and $K_3 = 151.59$

The table below shows the variation in temperature, for some embodiments, for different durations of RF power applications, both at the peak temperature (typically at about 1 mm from the surface of the electrode) and at about 6 millimeters from the arterial lumen. In some embodiments, the variation of temperature between 120 and 300 seconds is minimal, however, since the temperature at the edge of the lesion is relatively low (slightly less than 50° C.), an ablation lasting at least 240 seconds in order to cause tissue death may be used, in accordance with several embodiments.

TABLE 1

Acceptable power and time combinations for various degrees of hepatic artery blood flow

| Time [s] | Peak Temperature [deg C.] | Temp, at 6 mm from the lumen [deg C.] |
|---|---|---|
| Flow Rate = 0 (free convection); Power = 0.99059 | | |
| 120 | 93.888 | 39.61 |
| 180 | 96.021 | 40.35 |
| 240 | 97.065 | 40.77 |
| 300 | 97.612 | 40.94 |
| Flow Rate = 0.1 m/s; Power = 11.08679 W | | |
| 120 | 96.111 | 47.29 |
| 180 | 96.963 | 48.67 |
| 240 | 97.279 | 49.01 |
| 300 | 97.428 | 49.49 |
| Flow Rate = 0.3 m/s; Power = 11.32912 W | | |
| 120 | 95.831 | 47.14 |
| 180 | 96.718 | 47.98 |
| 240 | 97.09 | 49.28 |
| 300 | 97.291 | 49.66 |
| Flow Rate = 0.5 m/s; Power = 11.40233 W | | |
| 120 | 95.858 | 47.33 |
| 180 | 96.711 | 48.74 |
| 240 | 97.052 | 49.2 |
| 300 | 97.23 | 49.67 |
| Flow Rate = 0.7 m/s; Power = 11.45126 W | | |
| 120 | 95.955 | 47.2 |
| 180 | 96.838 | 48.63 |
| 240 | 97.2 | 49.35 |
| 300 | 97.386 | 49.6 |

From the non-limiting simulations described above, the minimum flow rate that allows a 4 mm deep lesion (e.g., using the criteria of no vaporization and a minimum temperature of about 50° C. at a location 6 mm from the vessel lumen) and avoids vaporization is about 0.01 m/s. Therefore, it may be advantageous to measure flow in the hepatic artery before the procedure to ensure flow is adequate before initiating treatment. Below such a flow rate, other forms of cooling may need to be added, such as internal electrode cooling or irrigation of the artery.

H. Example 8

The hepatic artery has an average estimated diameter of 4 mm in adult humans. In an endovascular ablation, this diameter restricts the size of the electrode(s) that can be used. A study was performed to investigate the optimal size of the electrode to reach a lesion approximately 4 mm deep within the adventitia of the hepatic artery.

Figure 70:
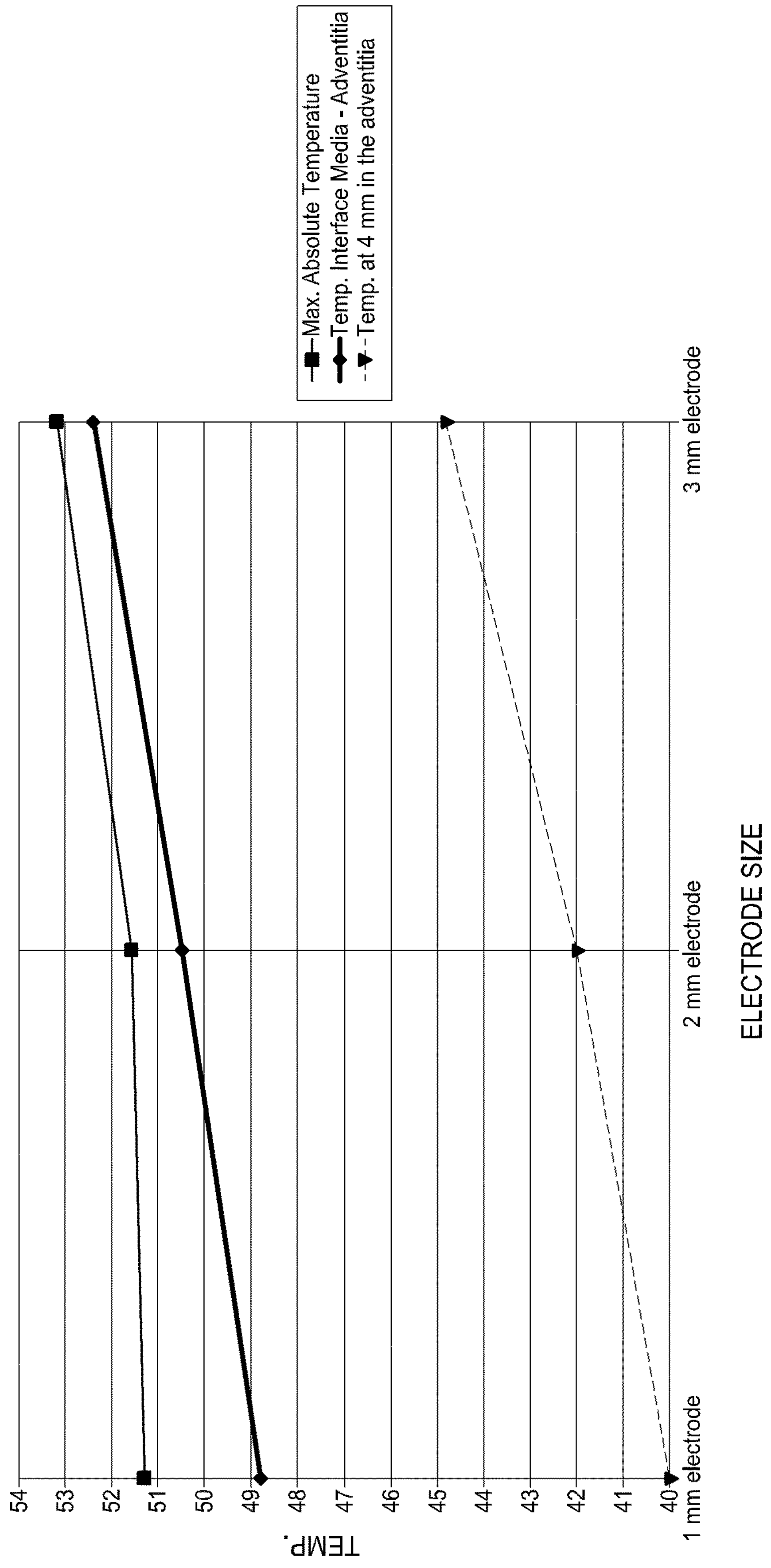
FIG. 70 is a graph illustrating change in lesion temperature as electrode size changes, in accordance with an embodiment of the invention.

In accordance with embodiments of the invention, the models assume an ablation performed in a monopolar setting, with an active spherical electrode of respectively 1, 2, and 3 millimeters diameter. The models also assume that the electrode is externally cooled by a blood flow having a speed of 0.1 m/s, that the media has a thickness of 2 millimeters, and that 25 V are applied with minimal contact force, for 3 minutes, in one embodiment. FIG. 70 shows the trend of the temperature changes with electrode size.

In several embodiments, there are two factors influencing the lesion size, when electrode size changes. The first factor is the electric field lines, which tend to become denser in the region adjacent to the electrode, which may cause a higher temperature near a smaller electrode and a more rapid decrease with distance from the electrode. If this effect was dominating, as the electrode size grows, the temperature would decrease for a given power level.

The second factor is the cooling action of the blood flow. In some embodiments, the electrode diameter is comparable in size with the artery diameter, and thus a bigger electrode blocks or occludes some of the blood flow, thereby causing an increase in temperature as the electrode size increases.

In the case of the common hepatic artery, the second factor may slightly dominate the first factor: there may be a slight increase in temperature as the electrode size increases.

The study was limited to electrodes of 3 millimeters in diameter. The diameter was selected based on the diameter of the hepatic artery to avoid complete occlusion. In various embodiments, the electrode diameter is selected so as to prevent complete occlusion by the electrode itself and/or to reduce peak temperature and thereby prevent against obtaining the reaching of the vaporization point.

In accordance with several embodiments, systems and methods described herein control neuromodulation (e.g., nerve destruction) over a wide range of anatomical and physiologic conditions (e.g., arterial lumen diameter, blood flow velocity, tissue composition, etc.), which impacts lesion geometry. In accordance with several embodiments, for hepatic artery denervation, it is particularly advantageous to define an energy delivery strategy that is insensitive (e.g., robust) to initial and boundary conditions (e.g., blood flow velocity, arterial lumen diameter, breathing motion). This may be particularly true for hepatic denervation, where anatomy and physiology can vary more significantly than in the renal artery, both patient-to-patient and intraoperatively. For example, the hepatic artery can move up to 5 cm during each ventilated breathing cycle, leading to variations in electrode position and arterial blood flow. It has been observed that only about 60-75% of patients present with normal hepatic arterial anatomy, and pathology studies in human cadavers have indicated that tissue composition (especially the degree of visceral fat in the hepatic arterial region) can vary significantly between subjects.

In several embodiments, means for assessing the progress of an endovascular ablation procedure are provided. Ablations controlled using electrode tip temperature control can vary based on the amount of convective cooling in the treatment region—for high cooling environments, more energy may be delivered to the target tissue, resulting in larger lesions, and for low cooling environments, less energy may be delivered to the target tissue, resulting in smaller lesions. In various embodiments, it may be desirable to employ open-loop energy control as a primary control method, including the appropriate safety-monitoring features and temperature, impedance, or other feedback control schemes as secondary control means. The open-loop control algorithm, by virtue of being developed on the basis of historical in vitro and in vivo studies (e.g., using data mining techniques), can ensure a safe and effective starting point for the treatment that can then be adjusted on the basis of feedback signals.

In one embodiment, a specific power and temperature control algorithm is described that safely, quickly, and reliably achieves hepatic denervation. Based on in vitro and/or in vivo testing, the temperature response of the target tissue to known levels of constant RF power applications is characterized. Energy may then first be delivered at a maximum initial power for a first set time period, followed by a second set time period where power is decremented by a set amount, and so on, until a steady-state tissue temperature is achieved at a given steady-state power. Using the known relationship between impedance and temperature, any marked increases in tissue impedance can be used to decrease applied power or terminate energy delivery in order to prevent unpredictable, highly non-linear results. In several embodiments, the power can be applied such that a defined drop in impedance is achieved and maintained throughout the duration of the procedure.

In some embodiments, electrode tip temperature measurements are employed as a power shut-off limit and/or used to provide estimates of blood flow velocity, adjusting target power and impedance levels accordingly.

Figure 71:
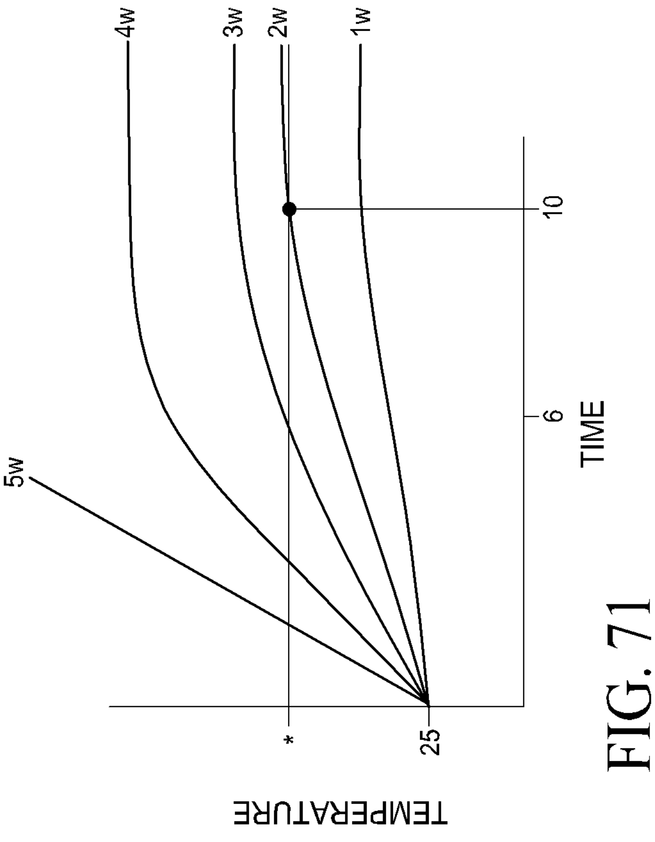
FIG. 71 is a graph illustrating change in temperature over time for different power levels of RF energy, in accordance with an embodiment of the invention.

An idealized tissue response to a range of RF power levels (1 W-5 W) at a given point location is shown in FIG. 71. For some period of time, $t<t_{ss}$, the temperature increases linearly as a function of time, with dT/dt defined by the delivered power. In biological tissues, heat losses due to conduction to surrounding tissues, blood flow, and perfusion causes tissue temperatures to generally approach steady-values over time. Ideally, one would simply increase power in order to achieve higher steady-state temperatures faster. However, because biological tissues have temperature-dependent properties that are highly non-linear at temperatures near vaporization temperatures (e.g., ~100° C.), the temperature progression and resulting lesion size is highly variable and unpredictable (see, for example, FIG. 74).

Figure 75:
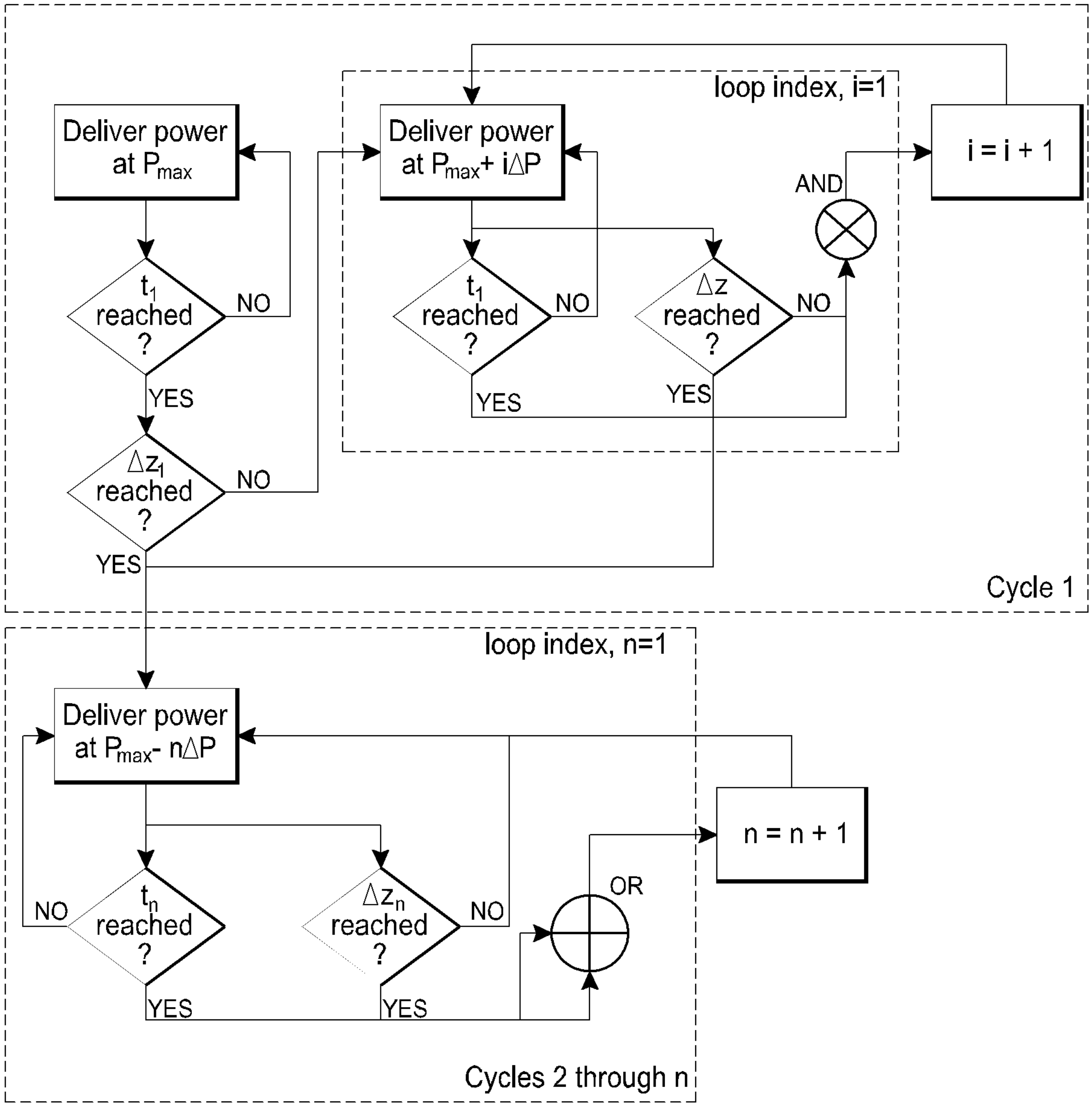
FIG. 75 illustrates an embodiment of a power control process incorporating impedance feedback control.

In accordance with several embodiments, a decremented power delivery algorithm (shown, for example, in FIG. 75) is provided to maximize steady-state temperatures and increase the speed at which they are reached. In cycle 0 (n=0), a maximum power $P_{max}$ is applied for a time period $t_1$, where $P_{max}$ is the maximum power that can be delivered in a controllable time period without causing tissue vaporization and $t_1$ is the maximum time for which $P_{max}$ can be delivered without causing vaporization. In cycle 1 (n=1), corresponding to $t=t_1$, the applied power is decremented to $P_{max}-\Delta P$ and applied for a period $t_2$, corresponding to the maximum time for which $P_{max}-\Delta P$ can be delivered without causing vaporization. This decrement algorithm may continue for n cycles, where the delivered power in each cycle n is $P_{max}-n\Delta P$, and the power application time $t_n$ corresponds to the maximum time for which $P_{max}-n\Delta P$ can be delivered without causing vaporization.

$P_{max}$, $\Delta P$ and $t_1, \ldots, t_n$ can be determined empirically using suitable in vitro and in vivo models and data reported in the literature, with statistical methods employed to choose levels for these parameters that will generally ensure tissue vaporization is avoided (e.g., 99% reliability, 95% confidence lower-bound values for $P_{max}$, $\Delta P$ and $t_1, \ldots, t_n$ to avoid vaporization.)

$\Delta P$ might vary in subsequent cycles and is described here as a single variable for brevity (it may be two, three, four or more variables). In some embodiments, $\Delta P$ decreases (and t, increases) with each subsequent cycle as the steady-state power is approached asymptotically. The algorithm described in FIG. 75 has the effect of delivering the maximum sustainable heating power to tissue without causing vaporization or inducing unpredictable, non-linear tissue responses, in one embodiment.

While, in some embodiments, the open-loop approach provides a good empirical approach based on historically obtained data, it may not account for the anatomic and physiologic variations encountered clinically. Some degree of feedback control may be desired to tailor the core or primary energy deliver algorithm described above to each unique clinical situation. For example, in high cooling environments, less energy may be delivered to the target tissue (since more of the energy is carried away through convection), and alternatively, in low cooling environments, more energy may be delivered to the target tissue. Due to variations in tissue composition, some tissue might reach vaporization or desiccate faster than other tissues, leading to non-linear effects.

Figure 73:
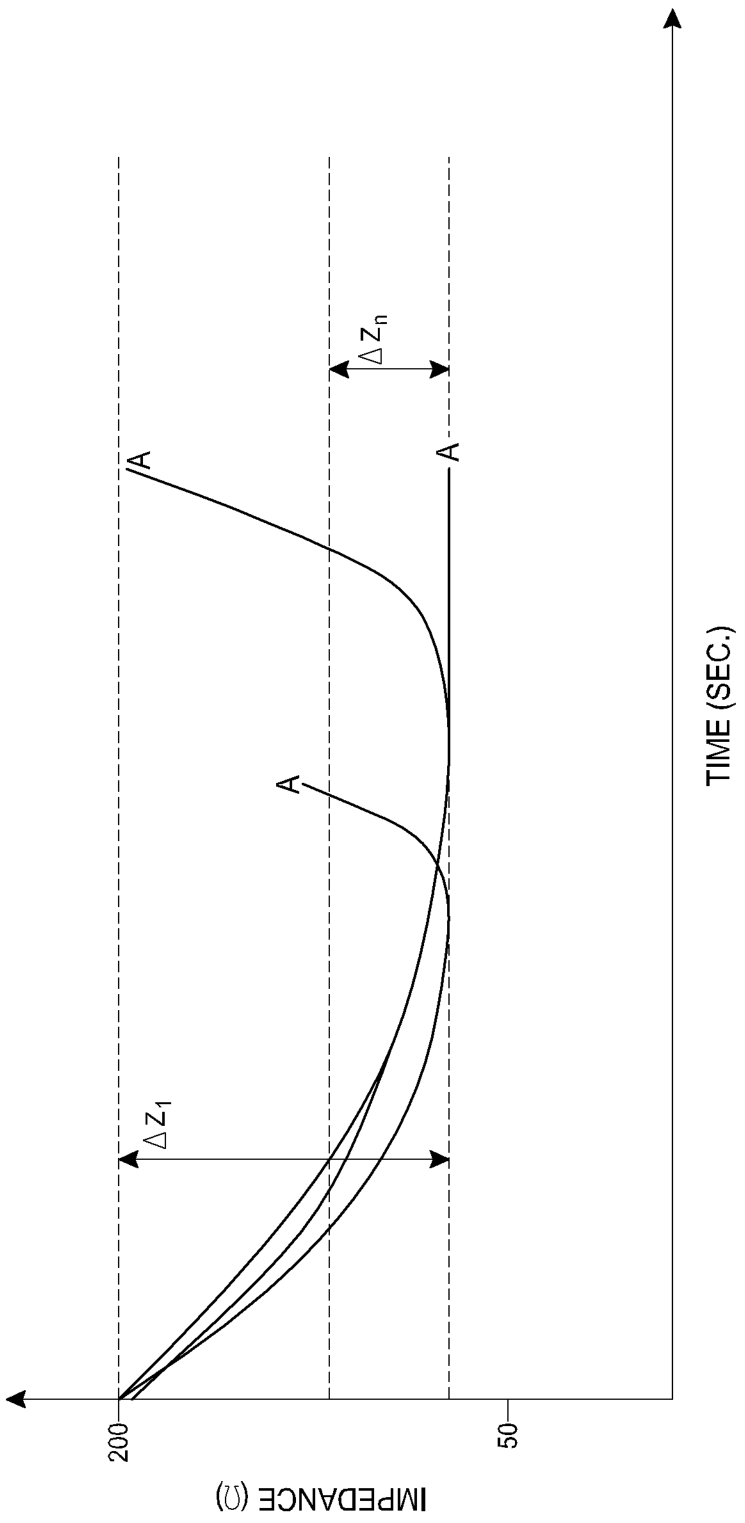

Because impedance is generally related to temperature (as shown, for example, in FIG. 74), impedance can be used as a proxy for the bulk temperature of the tissue surrounding the electrode. A characteristic drop, $\Delta z_1$ in impedance (shown in FIG. 73) during the initial heating period may be indicative of effective heating, whereas impedance increases $\Delta z_n$ after this initial period may be indicative of non-linear effects and vaporization. In some embodiments, non-linear effects and vaporization are avoided.

Figure 72:
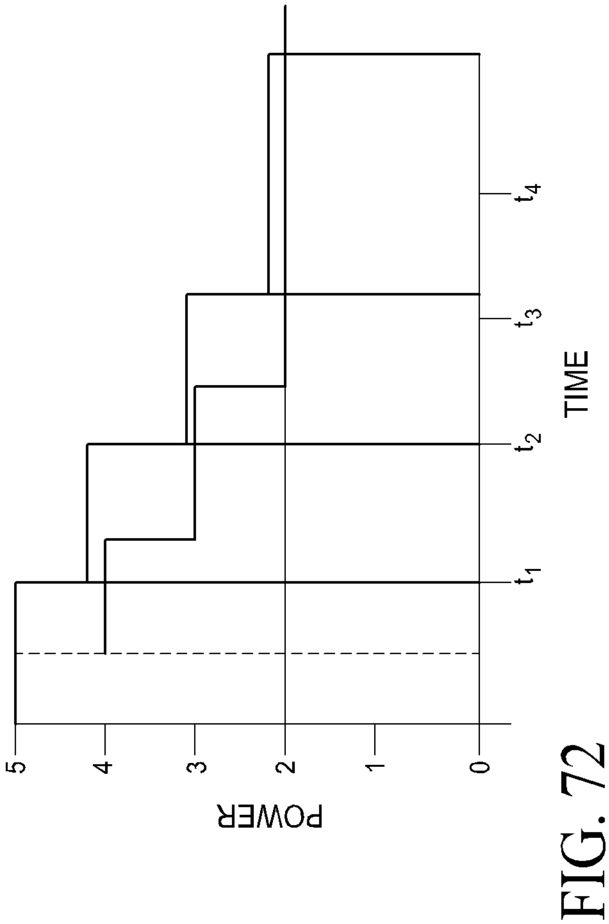
FIGS. 72-74 are graphs illustrating relationships between various treatment parameters, in accordance with embodiments of the invention.
Figure 74:
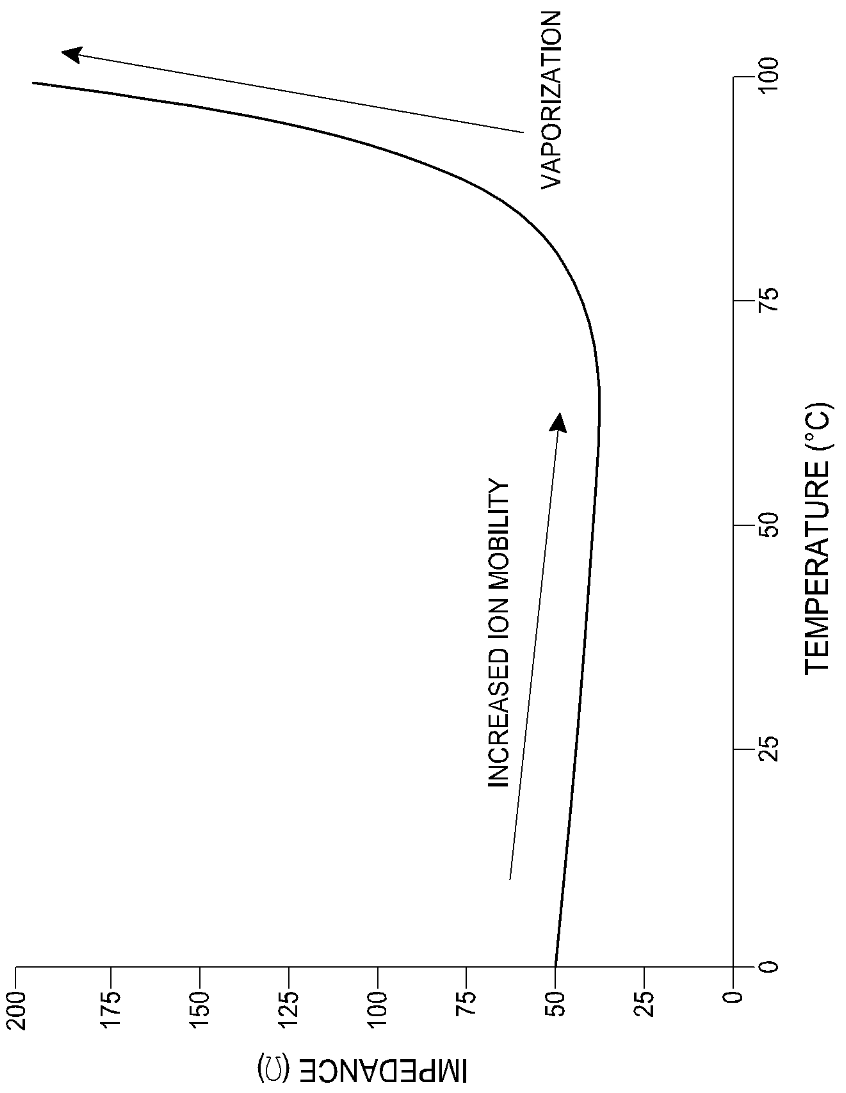

An embodiment of an algorithm for overlaying impedance-based feedback control with the open-loop power control algorithm is illustrated in FIG. 74. In some embodiments, the effect of this algorithm is generally to shift $P_{max}$ (the curve represented in FIG. 72) upwards in order to achieve the desired drop in impedance in the first cycle. In subsequent cycles, power may be decremented after the prescribed time period ($t_n$) defined by the open loop algorithm is reached or until a threshold impedance rise ($\Delta z_n$) is detected, after which power may further be decremented to avoid vaporization. In some embodiments, RF power delivery is interrupted or otherwise terminated upon detection of a threshold impedance rise.

$\Delta z_1$ can be variably defined as a target impedance relative to a reference impedance value (e.g., for a target impedance of 150Ω and initial impedance of 210Ω, $\Delta z_1$=60Ω), or alternatively, can be strictly defined relative to the impedance measured at the beginning of energy delivery to tissue (e.g., a fixed value of $\Delta z_1$=50Ω from the impedance measurement at the start of a treatment or procedure). Similarly, $\Delta z_n$ can be defined as an absolute value or can be scaled relative to the target impedance value (e.g., 10% deviation from the target impedance value).

In order to improve the fidelity of the impedance measurement in some embodiments, it may be desirable to implement a filtering or averaging calculation (e.g., a windowed average or other filter) in order to avoid noise in the impedance measurement triggering false positive control signals.

RF generator designs commonly calculate power and impedance by measuring voltage and current (P=VI, and V/I=R). Due to reactance in the system, this measurement can be erroneous, leading to inadequate treatment (e.g., ablation) of the nerves surrounding the hepatic artery or other target artery, vessel or tissue.

Figure 76:
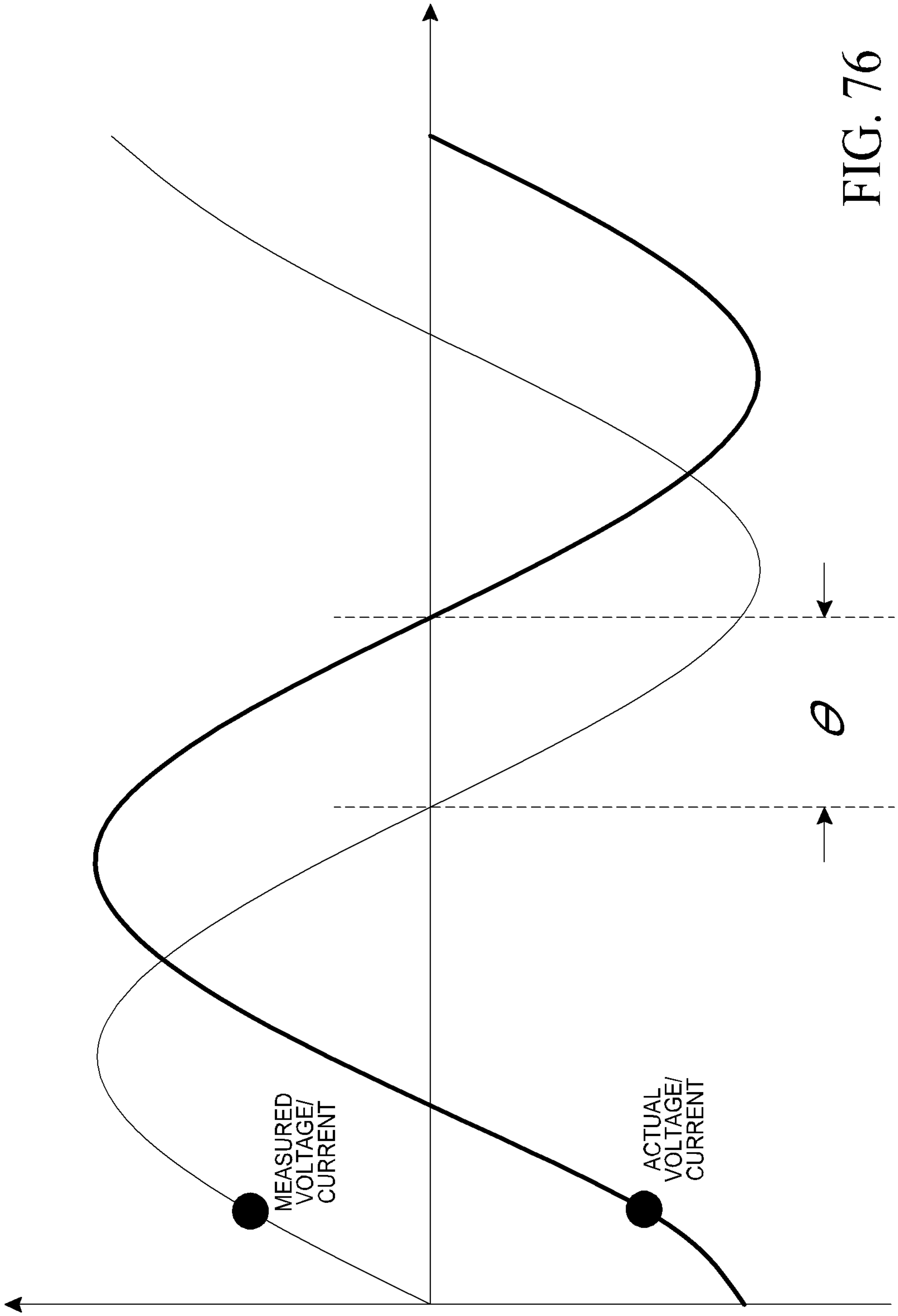
FIG. 76 illustrates how phase shifts can cause inaccurate measurement of current and/or voltage.

Reactance, a result of capacitance and inductance in the RF circuit can lead to a phase shift (as illustrated in FIG. 76), where the voltage and/or current in the target tissue is offset from the voltage and/or current measured by the RF generator. When the measured and actual voltage and current are different, the progress of the therapy is unknown and can lead to unpredictable results, since power and impedance are used as control variables for a wide range of energy control algorithms. Measured power and impedance can often differ by as much as 10% from the actual values.

Inductance is generally a result of the tortuosity of the electrode lead, and for ablation procedures, is generally ignored. In biological tissue, capacitance may be a result of capacitive coupling between the electrode shaft (alternatively, the "electrode leads") and the tissue across the insulating dielectric generally disposed about the non-therapeutic portions of the electrode shaft or electrode leads. Ions in the tissue move in response to changes in the electrode polarity, but the capacitance leads to discrete delays in the flow of ions relative to the driving voltage of the RF generator, manifested as a phase shift. At the tissue level, capacitance may arise due to the variable composition of tissue—for example, lipids, fats, and other non-conducting tissues disposed in the hilus sheath surrounding the hepatic artery can lead to local capacitance causing discrete delays in the flow of ions through the tissue, which may also contribute to the phase shift. In one embodiment, the phase shift may be accounted for by employing a bi-linear transform such as the bi-linear transform described in U.S. Publ. No. 2012/0095461 (e.g., paragraphs [0050] through [0089]), which is incorporated by reference herein. By accurately accounting for phase and magnitude changes at the load, power and impedance can be measured more accurately, leading to more efficacious treatment, e.g., ablation, of the nerves surrounding the hepatic artery.

Referring now again to FIG. 75, not shown is the ability to monitor tip temperature throughout the treatment. The tip temperature measurement can also be used as a feedback signal, for example, to terminate RF power delivery once a threshold temperature is reached. In some embodiments, leveraging the fact that at a given power level, the tip temperature is a function of blood flow velocity, P max can similarly be adjusted up or down to increase (e.g., maximize) effective energy delivery on the basis of the available convective cooling power, which effectively converts the electrode into a hot wire anemometer flow sensor.

Figure 77:
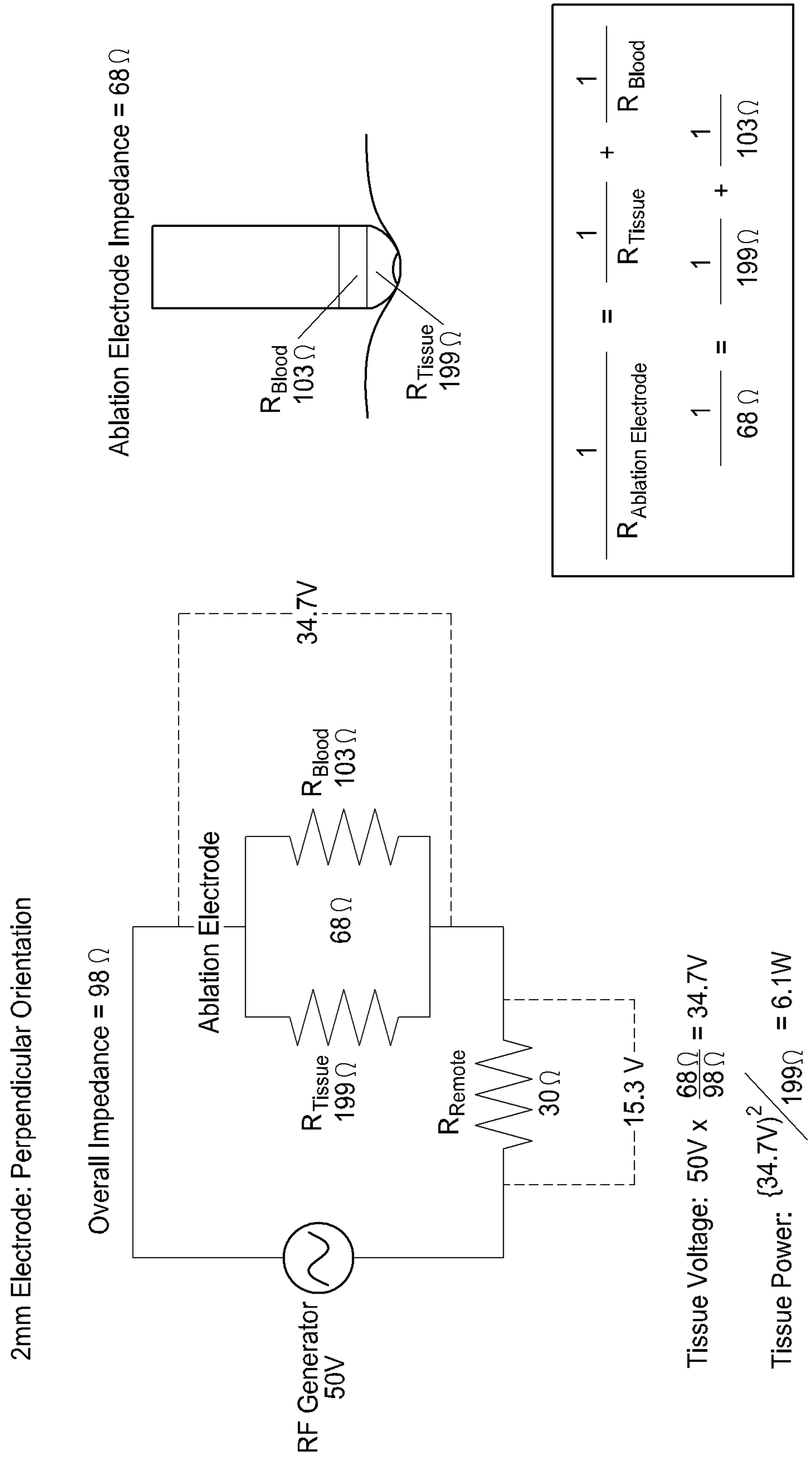
FIG. 77 illustrates components of impedance in an embodiment of an endovascular ablation procedure.

The ability to monitor impedance changes for monopolar configurations has not been previously appreciated, and for endovascular ablation, it was generally believed that impedance control algorithms were only useful for bipolar electrode configurations. Because the region of tissue heated in a bipolar configuration is confined to a relatively limited region, the impedance of the system is generally regarded as the impedance of the heated region. However, the impedance of the heated region can be determined for monopolar configurations as well. Although the resistance pathway through biological tissue is generally regarded as a bulk property, it can be resolved into three components for a monopolar configuration, with representative values for each component highlighted in FIG. 77:

1) The resistance of the blood ($R_{blood}$)
2) The "background" or "remote" resistance of the bulk tissue ($R_{remote}$)
3) The resistance of the tissue in the vicinity of the monopolar electrode (the target tissue), $R_{tissue}$.

In some embodiments, by subtracting out the components of impedance contributed by the background tissue and blood, a more sensitive impedance measurement treated tissue region can be obtained, thereby improving the accuracy and applicability of impedance control in a monopolar configuration. By subtracting the power deposited in non-target tissues, a more reliable estimate of the energy delivered to the target tissue can be obtained.

Figure 78:
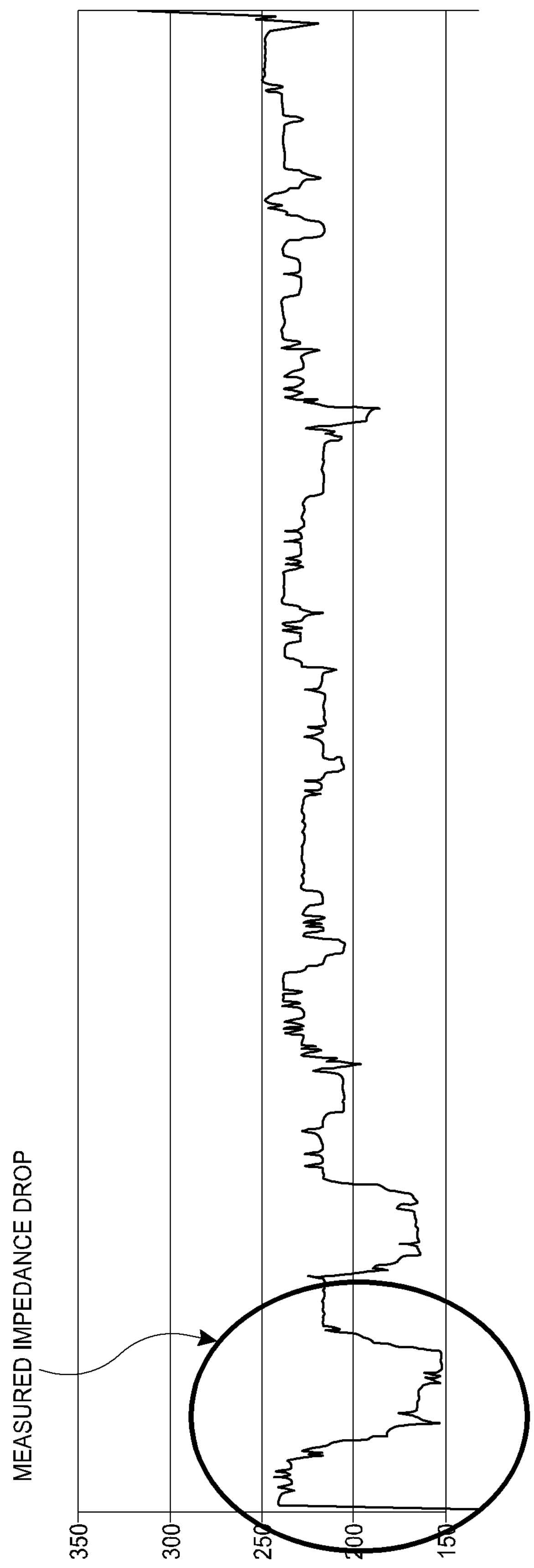
FIG. 78 illustrates an effect on impedance measurements by subtracting a background impedance signal, in accordance with an embodiment of the invention.

As illustrated in FIG. 78, measurable changes in tissue impedance have been demonstrated during hepatic arterial ablation by subtracting out the largely "DC" components of resistance and focusing on the variable component driven by the local tissue response.

In accordance with several embodiments, the treatment control approaches described above unexpectedly provide the effective "decoupling" of the electrode tip temperature measurement from variations in blood flow. Using electrode tip temperature control algorithms, output power may be adjusted to maintain a generally constant electrode tip temperature. Power may then become a de facto measurement of convective cooling due to blood flow, but a lagging indicator as it is the controlled output. By implementing the power control algorithm described above, the electrode tip temperature sensor may be "freed" to perform other functions, such as 1) providing a safety signal to shut-off power in the event excessive temperatures are reached, to avoid thrombus or eschar formation or 2) the steady-state temperature reached for a given power application can be used as a leading indicator of blood flow, which can also be used to generally increase or decrease the overall level of power delivered to the tissue (e.g., increase or decrease $P_{max}$).

In some embodiments, the neuromodulation catheter (e.g., ablation catheter) designs described herein (e.g., the balloon catheters of FIGS. 13A-13C) advantageously provide effective modulation of nerves innervating branches of the hepatic artery without causing, or at least minimizing endothelial damage, if desired. For example, the catheters described herein can occlude the hepatic artery (e.g., using a balloon) and then circulate coolant in the region of the ablation (e.g., within the lumen of the balloon). In some embodiments, the catheters provide the unique advantage of both higher power net energy offered through larger electrode surface area (which may be enabled by the larger electrode sizes that can be manufactured on a balloon) and increased deposition time (which may be permitted by the ability to occlude flow to the hepatic artery for longer periods of time). In accordance with several embodiments, the increase in energy density through higher power mitigates the risk of damage to the endothelial wall by the flow of coolant within the balloon.

While the devices, systems and methods described herein have primarily addressed the treatment of diabetes (e.g., diabetes mellitus), other conditions, diseases, disorders, or syndromes can be treated using the devices, systems and methods described herein, including but not limited to ventricular tachycardia, atrial fibrillation or atrial flutter, inflammatory diseases, endocrine diseases, hepatitis, pancreatitis, gastric ulcers, gastric motility disorders, irritable bowel syndrome, autoimmune disorders (such as Crohn's disease), obesity, Tay-Sachs disease, Wilson's disease, NASH, NAFLD, leukodystrophy, polycystic ovary syndrome, gestational diabetes, diabetes insipidus, thyroid disease, and other metabolic disorders, diseases, or conditions.

The various illustrative logical blocks, modules, and circuits described in connection with the embodiments disclosed herein (e.g., generators) can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In one embodiment, one or more tasks of the embodiments of methods and/or systems described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. In one embodiment, a network (wired or wireless) connection is provided. A display and/or a user input device (such as a keyboard, mouse, touchscreen, user-actuatable inputs, trackpad) may optionally be provided.

Although certain embodiments and examples have been described herein, aspects of the methods and devices shown and described in the present disclosure may be differently combined and/or modified to form still further embodiments. Additionally, the methods described herein may be practiced using any device suitable for performing the recited steps. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure (including the figures) herein of any particular feature, aspect, method, property, characteristic, quality, attribute, element, or the like in connection with various embodiments can be used in all other embodiments set forth herein.

For purposes of this disclosure, certain aspects, advantages, and novel features of the inventions are described herein. Embodiments embodied or carried out in a manner may achieve one advantage or group of advantages as taught herein without necessarily achieving other advantages. The headings used herein are merely provided to enhance readability and are not intended to limit the scope of the embodiments disclosed in a particular section to the features or elements disclosed in that section. The features or elements from one embodiment of the disclosure can be employed by other embodiments of the disclosure. For example, features described in one figure may be used in conjunction with embodiments illustrated in other figures.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as “delivering a neuromodulation catheter within a hepatic artery” include “instructing the delivery of a neuromodulation catheter within a hepatic artery.”

Various embodiments of the invention have been presented in a range format. It should be understood that the description in range format is merely for convenience and brevity and should not be construed as an inflexible limitation on the scope of the invention. The ranges disclosed herein encompass any and all overlap, sub-ranges, and combinations thereof, as well as individual numerical values within that range. For example, description of a range such as from about 5 to about 30 minutes should be considered to have specifically disclosed subranges such as from 5 to 10 degrees, from 10 to 20 minutes, from 5 to 25 minutes, from 15 to 30 minutes etc., as well as individual numbers within that range, for example, 5, 10, 15, 20, 25, 12, 15.5 and any whole and partial increments therebetween. Language such as “up to,” “at least,” “greater than,” “less than,” “between,” and the like includes the number recited. Numbers preceded by a term such as “about” or “approximately” include the recited numbers (for example, “about 3 mm” includes “3 mm”). The terms “approximately”, “about”, and “substantially” as used herein represent an amount close to the stated amount that still performs a desired function or achieves a desired result.

What is claimed:

1. A neuromodulation system comprising:

a catheter including a balloon and a therapeutic element at a distal portion of the catheter, wherein the therapeutic element is configured to deliver energy to one or more nerves proximate a hepatic blood vessel, the hepatic blood vessel having a blood vessel wall;

a fluid delivery device; and a controller configured to:

control the fluid delivery device to deliver a fluid to the balloon to expand the balloon within the hepatic blood vessel, and control the fluid delivery device to circulate, when the balloon is expanded within the hepatic blood vessel, the fluid through the balloon to maintain a continuous contact pressure of the balloon against the blood vessel wall while the therapeutic element delivers energy to the one or more nerves proximate the hepatic blood vessel, wherein the circulated fluid cools the blood vessel wall while the therapeutic element delivers energy to the one or more nerves proximate the hepatic blood vessel.

2. The neuromodulation system of claim 1, wherein to control the fluid delivery device to circulate the fluid through the balloon, the controller is configured to control the fluid delivery device to continuously circulate the fluid through the balloon during delivery of the energy by the therapeutic element.

3. The neuromodulation system of claim 1, wherein the controller is configured to control the fluid delivery device to circulate the fluid through the balloon for a period of time prior to delivery of energy by the therapeutic element.

4. The neuromodulation system of claim 1, wherein the circulated fluid cools a surface of the therapeutic element while the therapeutic element delivers energy to the one or more nerves proximate the hepatic blood vessel.

5. The neuromodulation system of claim 1, wherein to control the fluid delivery device to deliver the fluid, the controller is configured to control the fluid delivery device to pump the fluid into the balloon via an inlet into the balloon, and wherein the fluid exits the balloon via an outlet tube.

6. The neuromodulation system of claim 1, wherein a time duration of the delivery of the energy by the therapeutic element is 1 second to 120 seconds.

7. The neuromodulation system of claim 1, wherein the hepatic blood vessel includes a hepatic artery.

8. The neuromodulation system of claim 1, wherein the fluid is saline or water.

9. The neuromodulation system of claim 1, wherein the fluid is nonconductive.

10. The neuromodulation system of claim 1, wherein the continuous contact pressure is 1 $g/mm^2$ to about 50 $g/mm^2$.

11. The neuromodulation system of claim 1, wherein the continuous contact pressure is sufficient to fully occlude a portion of the hepatic blood vessel.

12. The neuromodulation system of claim 1, wherein a flow rate of the fluid is less than 500 mL/minute.

13. The neuromodulation system of claim 12, wherein a range of drive pressures within the balloon to provide the flow rate is 25 psi to 150 psi.

14. The neuromodulation system of claim 1, wherein the therapeutic element comprises an ultrasound transducer, and wherein the energy comprises ultrasound energy sufficient to ablate the one or more nerves proximate the hepatic blood vessel.

15. The neuromodulation system of claim 14, wherein the ultrasound transducer is cylindrical.

16. A method comprising:

delivering, by a therapeutic element at a distal portion of a catheter, energy to one or more nerves proximate a hepatic blood vessel, the hepatic blood vessel having a blood vessel wall;

delivering, by a fluid delivery device, a fluid to a balloon at the distal portion of the catheter to expand the balloon within the hepatic blood vessel; and circulating, by the fluid delivery device and when the balloon is expanded within the hepatic blood vessel, the fluid through the balloon to maintain a continuous contact pressure of the balloon against the blood vessel wall and to cool the blood vessel wall while the therapeutic element delivers energy to the one or more nerves proximate the hepatic blood vessel.

17. The method of claim 16, wherein circulating, by the fluid delivery device, the fluid through the balloon includes continuously circulating the fluid through the balloon during delivery of the energy by the therapeutic element.

18. The method of claim 16, further comprising cooling a surface of the therapeutic element by circulating the fluid through the balloon.

19. The method of claim 16, wherein the fluid is saline or water.

20. The method of claim 16, wherein the continuous contact pressure is sufficient to fully occlude a portion of the hepatic blood vessel.

21. The method of claim 16, wherein the hepatic blood vessel includes a hepatic artery.

22. The method of claim 16, wherein the one or more nerves proximate the hepatic blood vessel include one or more hepatic nerves.

* * * * *